United States Patent
Philippou et al.

(10) Patent No.: US 12,336,991 B2
(45) Date of Patent: Jun. 24, 2025

(54) FACTOR XIIA INHIBITORS

(71) Applicant: UNIVERSITY OF LEEDS, Leeds (GB)

(72) Inventors: Helen Philippou, Leeds (GB); Richard Foster, Leeds (GB); Colin Fishwick, Leeds (GB); Charlotte Revill, Leeds (GB); Ian Yule, Leeds (GB); Roger Taylor, Leeds (GB); Alan Naylor, Harston (GB); Philip Spencer Fallon, Saffron Walden (GB); Stuart Crosby, Saffron Walden (GB); Anna Hopkins, Saffron Walden (GB); Lucie Juliette Guetzoyan, Saffron Walden (GB); Alistair James Macnair, Saffron Walden (GB); Mark Richard Stewart, Saffron Walden (GB); Natalie Louise Winfield, Saffron Walden (GB)

(73) Assignee: University of Leeds (GB)

( * ) Notice: Subject to any disclaimer, the term of this patent is extended or adjusted under 35 U.S.C. 154(b) by 214 days.

(21) Appl. No.: 17/040,604

(22) PCT Filed: Mar. 28, 2019

(86) PCT No.: PCT/GB2019/050883
§ 371 (c)(1),
(2) Date: Sep. 23, 2020

(87) PCT Pub. No.: WO2019/186164
PCT Pub. Date: Oct. 3, 2019

(65) Prior Publication Data
US 2022/0305011 A1   Sep. 29, 2022

(30) Foreign Application Priority Data
Mar. 29, 2018 (GB) .................................. 1805174

(51) Int. Cl.
| | | |
|---|---|---|
| *A61K 31/506* | (2006.01) | |
| *A61K 31/40* | (2006.01) | |
| *A61K 31/4192* | (2006.01) | |
| *A61K 31/437* | (2006.01) | |
| *A61K 31/4439* | (2006.01) | |
| *A61K 31/454* | (2006.01) | |
| *A61P 7/02* | (2006.01) | |
| *C07D 207/16* | (2006.01) | |

(Continued)

(52) U.S. Cl.
CPC ............ *A61K 31/506* (2013.01); *A61K 31/40* (2013.01); *A61K 31/4192* (2013.01); *A61K 31/437* (2013.01); *A61K 31/4439* (2013.01); *A61K 31/454* (2013.01); *A61P 7/02* (2018.01); *C07D 207/16* (2013.01); *C07D 401/06* (2013.01); *C07D 401/14* (2013.01); *C07D 403/12* (2013.01); *C07D 403/14* (2013.01); *C07D 405/14* (2013.01); *C07D 409/14* (2013.01); *C07D 471/04* (2013.01)

(58) Field of Classification Search
CPC .. A61K 31/506; A61K 31/40; A61K 31/4192; A61K 31/437; A61K 31/4439; A61K 31/454; A61K 31/4025; A61K 31/416; A61K 31/4355; A61K 31/4725; A61K 31/496; A61K 31/4995; A61K 31/5386; A61P 7/02; C07D 207/16; C07D 401/06; C07D 401/14; C07D 403/12; C07D 403/14; C07D 405/14; C07D 409/14; C07D 471/04
USPC ........................................................ 514/256
See application file for complete search history.

(56) References Cited

U.S. PATENT DOCUMENTS

2003/0130270 A1* 7/2003 Boeckel ................ A61P 7/02
548/428
2005/0281746 A1* 12/2005 Melton ............. A61K 49/0438
424/9.34

(Continued)

FOREIGN PATENT DOCUMENTS

EP  0 672 658 A1  9/1995
JP  2004-516286 A  6/2004

(Continued)

OTHER PUBLICATIONS

Schafer et al. Drug Discovery Today 2008, 13 (21/22), 913-916.*

(Continued)

*Primary Examiner* — Ana Z Muresan
(74) *Attorney, Agent, or Firm* — Shackelford, Mckinley & Norton, LLP

(57) ABSTRACT

This invention relates to compounds of formula (I) and methods of treatment using the compounds. The invention also relates to processes and methods for producing the compounds of the invention. The compounds of the invention are modulators of Factor XII (e.g. Factor XIIa). In particular, the compounds are inhibitors of Factor XIIa and may be useful as anticoagulants.

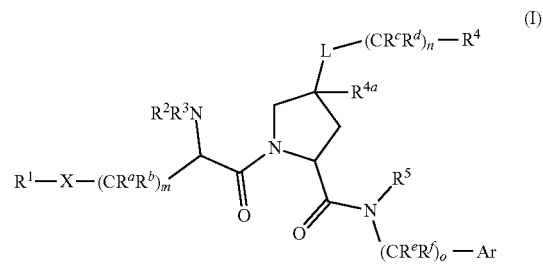

20 Claims, 1 Drawing Sheet

(51) Int. Cl.
*C07D 401/06* (2006.01)
*C07D 401/14* (2006.01)
*C07D 403/12* (2006.01)
*C07D 403/14* (2006.01)
*C07D 405/14* (2006.01)
*C07D 409/14* (2006.01)
*C07D 471/04* (2006.01)

(56) References Cited

U.S. PATENT DOCUMENTS

| | | |
|---|---|---|
| 2008/0176901 A1 | 7/2008 | Tully et al. |
| 2012/0252743 A1 | 10/2012 | Herold et al. |

FOREIGN PATENT DOCUMENTS

| | | |
|---|---|---|
| JP | 2014-500280 A | 1/2014 |
| WO | WO 02/50056 A1 | 6/2002 |
| WO | WO 2008/085608 | 7/2008 |
| WO | WO 2012/083436 A1 | 6/2012 |
| WO | WO 2017/035360 A1 | 3/2017 |

OTHER PUBLICATIONS

International Search Report and Written Opinion of the International Searching Authority of PCT/GB2019/050883 dated Jun. 17, 2019018; 14 pages.
Feng et al., "Discovery of a Novel, Selective, and Orally Bioavailable Class of Thrombin Inhibitors Incorporating Aminopyridyl Moieties at the P1 Position", J. Med. Chem., 1997, vol. 40, No. 23, pp. 3726-3733.
Great Britain Search Report for patent application No. GB 1805174.8 dated Nov. 12, 2018; 5 pages.
Korean Office Action issued in corresponding Korean Patent Application No. 10-2020-7030475 on Feb. 3, 2023.
Chinese Office Action issued in corresponding Chinese Patent Application No. 201980035935.4 on Feb. 13, 2023.
European Office Action issued in corresponding European Patent Application No. 19 716 228.2-1112 on Mar. 13, 2023.
Laveena Muley et al., "Enhancement of Hydrophobic Interactions and Hydrogen Bond Strength by Cooperativity: Synthesis, Modeling, and Molecular Dynamics Simulations of a Congeneric Series of Thrombin Inhibitors", Journal of Medicinal Chemistry 2010, vol. 53, No. 5, 2126-2135, DOI: 10.1021/jm9016416, Published on Web Feb. 11, 2010, pubs.acs.org/jmc, 10 pages.
Office Action for Japanese Pat. App. No. 2020-552703, mailed on Mar. 22, 2023.
Office Action for Korean Pat. App. No. 1020207030475, mailed on Jul. 1, 2023.

* cited by examiner

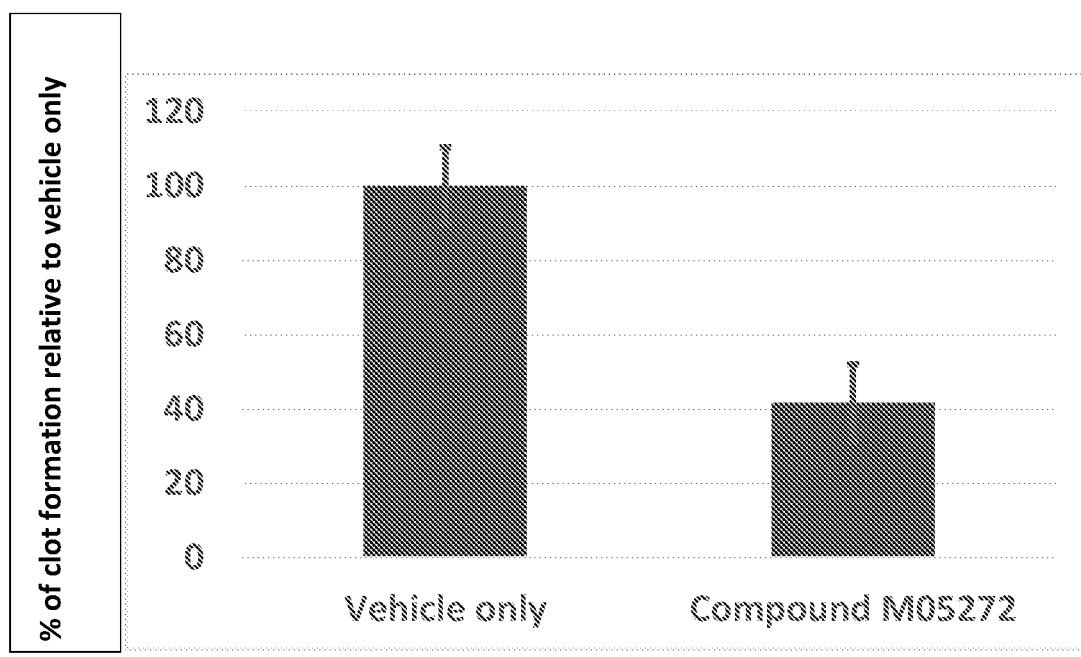

FACTOR XIIA INHIBITORS

This invention relates to compounds and methods of treatment (or prevention) using the compounds. The invention also relates to processes and methods for producing the compounds of the invention. The compounds of the invention are modulators of Factor XII (e.g. Factor XIIa). In particular, the compounds are inhibitors of Factor XIIa and may be useful as anticoagulants.

BACKGROUND

Cardiovascular disease is the leading cause of death in the developed world, affecting millions of people worldwide every year. The disease is generally caused by atherosclerosis of the arterial wall, which develops over many years and is characterised by inflammation of the endothelium, sub-endothelial lipid deposition, macrophage infiltration and plaque development. In the acute phase of the disease, the atherosclerotic plaque becomes unstable and ruptures, triggering thrombosis. The development of a thrombus (blood clot) that occludes the blood vessel and consequently deprives the tissue of oxygen constitutes the main precipitating event leading to morbidity and mortality. Blood clot formation is initiated by activation and aggregation of platelets. The platelet plug is consolidated by the activation of coagulation and formation of a fibrin network. Arterial occlusion by the thrombus leads to tissue death downstream, and, depending upon where this occurs, is associated with the development of myocardial infarction, stroke or claudication.

Thrombosis in the venous circulation has a different aetiology as it does not depend on atherosclerosis, but is triggered by circulatory stasis due to immobilisation and is often associated with naturally occurring deficiencies of coagulation inhibitors (e.g. antithrombin, protein C and S) and with surgical procedures. Venous thrombosis usually occurs in the leg or arm (deep vein thrombosis, DVT) and can lead to emboli (thrombus fragments) blocking downstream smaller vessels particularly in the lung (pulmonary embolism, PE). Other triggers of DVT include cancer, nephrotic syndrome, antiphospholipid syndrome and heart failure.

Thrombosis is a very serious condition and is associated with up to 25,000 and 200,000 fatalities in the UK alone on an annual basis for venous and arterial thrombosis respectively. In January 2010, the UK National Institute for Health and Clinical Excellence (NICE) published new guidelines to increase screening for early signs of thrombosis in patients admitted to hospital.

Current medications to treat or prevent thrombosis target either platelets or coagulation. Generally, antiplatelet drugs are used in the prevention of arterial disease, whereas anticoagulants are used in the prevention of stroke in patients with atrial fibrillation, deep venous thrombosis (DVT) and pulmonary embolism (PE). The largest clinical problem associated with current anticoagulant use is the risk of bleeding. As many as 1 to 3% of patients experience major bleeding or 15-18% patients experience minor bleeding whilst on anticoagulation therapy, dependent upon patient group and choice of anticoagulation.

Warfarin and heparin (encompassing all of its derivatives) are the most commonly used anticoagulant drugs. Warfarin, the oldest approved long-term oral anticoagulant, requires regular monitoring via prothrombin time (PT) clotting assays to determine optimal dosage, which places a major burden on the healthcare system and patient quality of life. Warfarin is non-specific and targets several coagulation enzymes, whereas heparin, which is administered subcutaneously or intravenously, targets activated factor X (FXa) and/or thrombin depending on its molecular weight. Furthermore, the new oral anticoagulants (NOACs) on the market or in development that target thrombin or FXa, also carry a significant risk of bleeding which is comparable to that of heparin and warfarin with the exception of intracranial haemorrhage where NOACs have better outcome than warfarin. However, gastrointestinal bleeding is increased with NOACs compared with low-molecular-weight heparin and vitamin K antagonist that encompasses warfarin [New Oral Anticoagulants Increase Risk for Gastrointestinal Bleeding: A Systematic Review and Meta-analysis Holster IL, Valkhoff V E, Kuipers E J, Tjwa E T Gastroenterology. 2013 July; 145(1):105-112].

Therefore, there is a large unmet clinical need for a novel anticoagulant that is not associated with bleeding. This goal has been an aspiration for the field for more than 6 decades. However, it was always assumed that anticoagulation leads to an unavoidable risk of bleeding because the mechanisms involved in thrombosis were considered the same as those involved in haemostasis.

Factor XII (FXII) was identified 50 years ago as a coagulation protein in the intrinsic pathway of blood coagulation as FXII deficient patients had marked prolongation of the in vitro surface-activated coagulation time. However, series of investigations have convincingly shown that FXII has no role in normal haemostasis. Evidence within the last decade has identified FXII as essential for thrombus formation in vivo (Renne T, Pozgajova M, Gruner S, Schuh K, Pauer H U, Burfeind P, Gailani D, Nieswandt B. Defective thrombus formation in mice lacking coagulation factor XII. J Exp Med 2005; 202:271-281; Kleinschnitz C, Stoll G, Bendszus M, Schuh K, Pauer H U, Burfeind P, Renne C, Gailani D, Nieswandt B, Renne T. Targeting coagulation factor XII provides protection from pathological thrombosis in cerebral ischemia without interfering with hemostasis. J Exp Med 2006; 203:513-518; Renne T, Nieswandt B, Gailani D. The intrinsic pathway of coagulation is essential for thrombus stability in mice. Blood Cells Mol Dis 2006; 36:148-151; Hagedorn I, Schmidbauer S, Pleines I, Kleinschnitz C, Kronthaler U, Stoll G, Dickneite G, Nieswandt B. Factor XIIa inhibitor recombinant human albumin Infestin-4 abolishes occlusive arterial thrombus formation without affecting bleeding. Circulation 2010; 121:1510-1517 and Matafonov A, Leung P Y, Gailani A E, Grach S L, Puy C, Cheng Q, Sun M F, McCarty O J, Tucker E I, Kataoka H, Renne T, Morrissey J H, Gruber A, Gailani D. Factor XII inhibition reduces thrombus formation in a primate thrombosis model. Blood. 2014; 13; 123(11):1739-46). A unique characteristic of FXII is that its deficiency does not incur bleeding, unlike deficiencies in all other coagulation factors. Therefore, FXIIa is a highly attractive target for the discovery of an anticoagulant with the potential for a greatly improved safety profile.

Recent studies have challenged dogma in the haemostasis and thrombosis field by demonstrating novel mechanisms in thrombosis involving FXII. These studies provide clear evidence that FXII is necessary for thrombus development whilst not playing a role in haemostasis. FXII deficient mice were remarkably protected against thrombosis when challenged with collagen and epinephrine infusion, whilst showing no prolongation of bleeding time during surgery or tail-clipping. Similar protection against thrombosis was observed in mesenteric arterioles exposed to $FeCl_3$ and in the aorta after mechanical injury. Infusion of human FXII in these models restored the development of thrombi. The ground breaking nature of these findings is illustrated by the debate on FXII function and the role of the contact coagulation pathway activated by FXIIa that, until recently, dominated the field. This debate was fueled by the fact that FXII deficiency does not lead to bleeding whereas deficiency in every other coagulation protease does, which led to the belief that FXII was not required for physiological coagulation and that FXII activation was an in vitro phenomenon.

However, recent studies have shown that FXII is activated by negatively charged surfaces and the surface of activated platelets (Zakharova et al, PLoS One. 2015 Feb. 17; 10(2): e0116665). These in vivo and in vitro studies demonstrate that FXII plays a hitherto unrecognized role in thrombosis. The generation of FXIIa stabilises the thrombus through enhanced thrombin generation, fibrin deposition and direct prothrombotic effects on fibrin structure. This mechanism does not appear to play a role in normal haemostasis, since FXII deficiency is phenotypically silent in humans as well as mice, making FXII an ideal target for the development of a new anticoagulant to treat thrombosis.

The effectiveness of FXII deficiency in reducing thrombosis has been shown in several different in vivo thrombosis models. In addition to the models mentioned above, the role of FXII in thrombosis has been demonstrated in a murine model of thrombosis induced by ligation of the carotid artery and a murine model of cerebral microvascular thrombosis secondary to transient occlusion of the middle cerebral artery. Brain infarct sizes were significantly reduced in FXII deficient mice and restored to large infarcts by the infusion of human FXII. Inhibition of FXII has also been shown to reduce risk of venous thrombosis. One study has demonstrated that a Kunitz-type inhibitor of contact activation isolated from the tick salivary glands (Ir-CPI) effectively reduces thrombosis in mouse and rat models of venous thrombosis induced by vessel ligation. This inhibitory protein was also effective in reducing PE in a murine model induced by infusion with collagen and epinephrine, and in a murine model of dorsal skin arteriole thrombosis. Again, there was no effect on bleeding time in the animals treated with Ir-CPI. Inhibition of FXIIa with H-D-Pro-Phe-Arg-chloromethylketone (PCK) has also been shown to protect against thrombosis. These studies provide preclinical proof of concept that inhibition of FXIIa is efficacious in the treatment of thrombosis.

More recently, Magnus Larsson et al., "A Factor XIIa Inhibitory Antibody Provides Thromboprotection in Extracorporeal Circulation Without Increasing Bleeding Risk" *Sci Transl Med* 6, 222ra17 (2014); demonstrated that recombinant fully human antibody 3F7 binds into the FXIIa enzymatic pocket. 3F7 interfered with FXIIa-mediated coagulation, abolished thrombus formation under flow, and blocked experimental thrombosis in mice and rabbits. In rabbits 3F7 provided thromboprotection as efficiently as heparin, but unlike heparin, 3F7 treatment did not impair the haemostatic capacity and did not increase bleeding from wounds. Larsson et al conclude that targeting of FXIIa is a safe mode of thromboprotection in bypass systems, and provides a clinically relevant anticoagulation strategy that is not complicated by excess bleeding.

Dabigatran, apixaban, rivaroxaban, edoxaban and betrixaban are approved for short-term use as oral FXa/thrombin inhibitors, respectively. Dabigatran is 3-({2-[(4-carbamimidoyl-phenylamino)-methyl]-1-methyl-1H-benzoimidazole-5-carbonyl}-pyridin-2-yl-amino)-propionic acid;

Dabigatran is also approved for long term prevention of stroke in patients with atrial

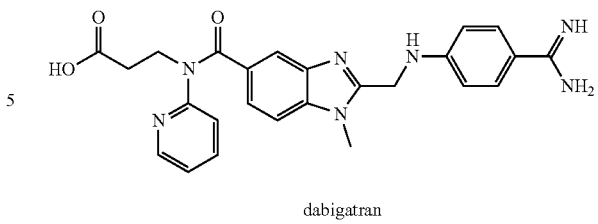

dabigatran fibrillation (AF) and is described in U.S. Pat. No. 6,087,380.

Rivaroxaban is (S)-5-chloro-N-{[2-oxo-3-[4-(3-oxomorpholin-4-yl)phenyl]oxazolidine-5-yl]methyl} thiophene-2-carboxamide;

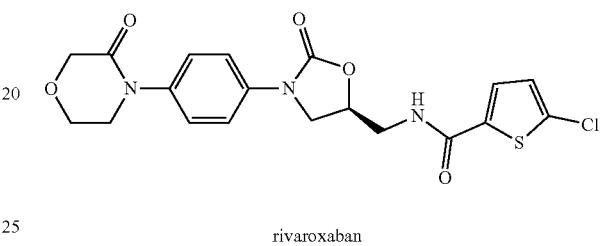

rivaroxaban

Rivaroxaban is also approved for reducing stroke risk in patients with nonvalvular AF. Rivaroxaban has shown superiority of once-daily rivaroxaban over warfarin in protecting AF patients from stroke and non-CNS systemic embolism. Rivaroxaban also demonstrates comparable major and non-major clinically relevant bleeding, as well as significantly lower rates of intracranial haemorrhage vs. warfarin. Rivaroxaban, is described in U.S. Pat. No. 7,157,456.

Apixaban is also factor Xa inhibitor approved for use in preventing stroke and systemic embolism in patients with nonvalvular atrial fibrillation.

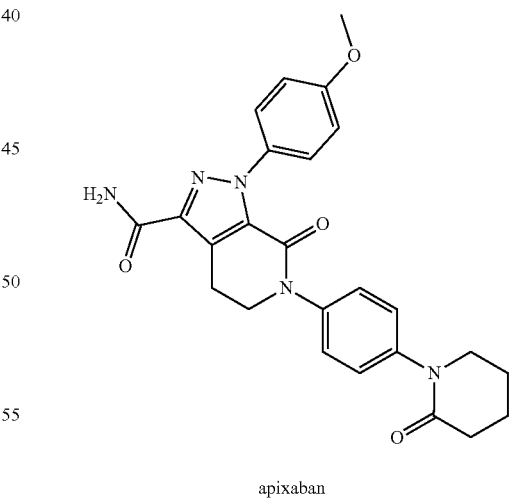

apixaban

Apixaban is 1-(4-methoxyphenyl)-7-oxo-6-[4-(2-oxopiperidin-1-yl)phenyl]-4,5-dihydropyrazolo[5,4-c]pyridine-3-carboxamide:

Apixaban is described in U.S. Pat. No. 6,413,980.

Edoxaban is N'-(5-chloropyridin-2-yl)-N$^2$-((1S,2R,4)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

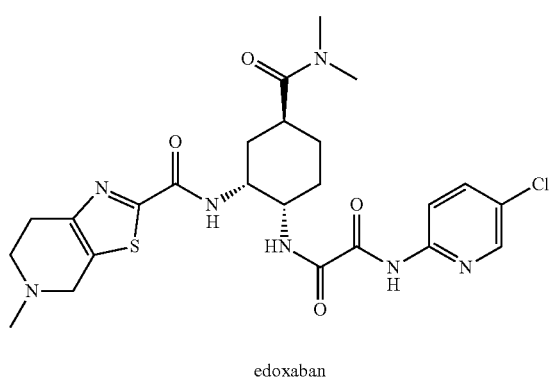

edoxaban

Edoxaban is another factor Xa inhibitor approved for use in preventing stroke and systemic embolism in patients with nonvalvular atrial fibrillation and for the treatment of deep vein thrombosis. Edoxaban is described in U.S. Pat. No. 7,365,205.

Betrixaban is N-(5-chloropyridin-2-yl)-2-[4-(N,N-dimethylcarbamimidoyl)benzamido]-5-methoxybenzamide:

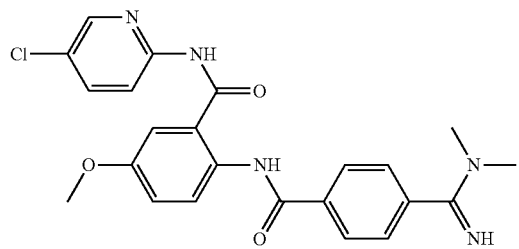

betrixaban

Betrixaban is a factor Xa inhibitor approved for use in preventing venous thromboembolism in patients with moderate to severe restricted mobility. Betrixaban is described in U.S. Pat. No. 6,376,515.

Recent surveys of the cardiovascular pipelines of major pharmaceutical companies have not revealed any oral inhibitors of FXIIa in development. Infestin-4 is a biological agent produced by CSL Behring that targets FXIIa, and shows efficacy in a $FeCl_3$-induced model of thrombosis in mice and rabbits. Other antibody approaches targeting FXII(a) have also shown in vivo efficacy. However, if infestin-4 or the antibody approaches were successful, they would require intravenous administration, which makes them less suitable for long term anticoagulation.

As FXII deficiency in humans is asymptomatic, unlike other coagulation factor deficiencies that cause bleeding and that deficiency or inhibition of the activity of FXII show an anticoagulant effect; a selective FXIIa inhibitor, has the potential to reduce bleeding risk associated with currently available anticoagulant therapies.

European Patent application No. EP0672658 (Eli Lilly) describes phenylalanine proline derivatives that are useful as thrombin inhibitors.

International Patent application No. WO 2002/064559 (Merck) also describes phenylalanine proline derivatives that are useful as thrombin inhibitors. The compounds are selective inhibitors of cyclooxygenase-2 inhibition over cyclooxygenase-1.

International Patent application No. WO 02/50056 (Merck) describes benzylamine and cyclohexylamine derivatives that are useful as thrombin inhibitors.

It is an aim of aspects of the present invention to at least partially mitigate the problems associated with the prior art.

It is an aim of certain embodiments of the present invention to provide compounds that inhibit FXII activity, in particular FXIIa activity, for example the serine protease activity of FXIIa.

It is an aim of certain embodiments of the present invention to provide compounds that possess physicochemical and pharmacokinetic properties consistent with the potential for oral bioavailability It is an aim of certain embodiments of this invention to provide compounds which exhibit reduced cytotoxicity or increased solubility relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

It is an aim of certain embodiments of this invention to provide a modulator of a target, where the embodiment selectively modulates the target over other targets. It is an aim of certain embodiments of the present invention to provide compounds that are selective FXIIa inhibitors. In particular, an aim of certain embodiments of the invention is to provide compounds that selectively inhibit FXIIa over thrombin and FXa.

Certain embodiments of the present invention satisfy some or all of the above aims.

BRIEF SUMMARY OF THE DISCLOSURE

In accordance with the present invention there is provided a compound according to formula (I) and pharmaceutically acceptable salts thereof:

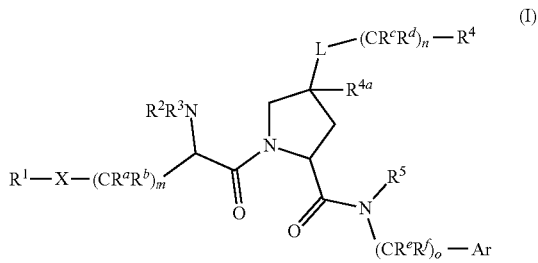

wherein
X is either a bond, —C(O)NH—, —C(O)O— or —C(O)—;
L is selected from: bond, —O—, —$NR^6$—, and —$NR^7$C(O)—;
Ar is selected from a substituted or unsubstituted 5 to 10 membered heteroaryl group having 1, 2 or 3 heteroatoms selected from O, N or S, or a substituted or unsubstituted 6 to 10 membered aryl group, wherein, when substituted, the heteroaryl or aryl groups are substituted with 1, 2, or 3 substituents selected from: halo, $C_{1-6}$ alkyl, —$OR^g$, —$NR^gR^h$ or $C_{1-4}$ alkyl substituted by —$NR^gR^h$;

m is selected from 0, 1, 2, or 3;
n is selected from 0, 1, 2, 3, or 4;
is selected from 1 or 2;
$R^1$ is selected from substituted or unsubstituted: —$NR^8R^9$, 5 to 10 membered carbocyclic ring system or a 5 to 10 membered heterocyclic ring system;
  wherein when substituted $R^1$ is substituted with 1, 2, or 3 groups selected from: =O, CN, —OH, or —O—$C_{1-6}$ alkyl, halo, $C_{1-6}$ alkyl and $C_{1-6}$ haloalkyl;
$R^2$ is selected from: H, $C_{1-6}$ alkyl, $C_{1-6}$ haloalkyl, phenyl, benzyl, —$C(O)R^{2a}$, and —$S(O_2)R^{2a}$;
  wherein $R^{2a}$ is selected from: $C_{1-6}$ alkyl, phenyl, and benzyl;
$R^3$ is:
  (a) H or $C_{1-6}$ alkyl; or
  (b) $R^3$ together with one of $R^a$ or $R^b$ forms a bond, —$CH_2$— or —$CH_2CH_2$— group resulting in a 4, 5 or 6 membered heterocycloalkyl ring comprising the —$CH_2$— or —$CH_2CH_2$— group, the N atom to which $R^3$ is attached, the C atom to which $R^a$ or $R^b$ are attached, and any intervening atoms; or
  (c) $R^3$ forms a bond, —$CH_2$— or —$CH_2CH_2$— group with an atom of $R^1$ when $R^1$ is a carbocyclic ring system or a heterocyclic ring system;
$R^4$ is selected from: H, =$CH_2$, —CN, halo, $C_{1-4}$ alkyl, $C_{1-4}$ haloalkyl, —$OR^{10}$, —$NR^{10}R^{11}$, 6 to 10 membered aryl, $C_{3-8}$ cycloalkyl, 3 to 6 membered heterocycloalkyl, 5 to 10 membered heteroaryl, wherein the $C_{3-8}$ cycloalkyl, 3 to 6 membered heterocycloalkyl, 6 to 10 membered aryl or heteroaryl group is unsubstituted or substituted with 1, 2 or 3 $R^{12}$;
$R^{4a}$ is selected from: H, —OH, halo or $C_{1-4}$ alkyl;
$R^5$ is H or $C_{1-6}$ alkyl;
$R^6$ is H, $C_{1-6}$ alkyl or —$C(O)C_{1-6}$ alkyl;
$R^7$ is H or $C_{1-6}$ alkyl;
$R^8$ and $R^9$ are independently at each occurrence selected from: H, $C_{1-6}$ alkyl, $C_{3-6}$ cycloalkyl, phenyl, $C_{1-4}$ alkyl substituted with —$OR^i$, or $C_{1-4}$ alkyl substituted with phenyl, or $R^8$ and $R^9$ taken together with the atom to which they are attached form 3 to 8 membered heterocycloalkyl ring, which is unsubstituted or substituted with: CN, halo, $C_{1-6}$ alkyl or —$OR^i$;
$R^{12}$ is independently at each occurrence selected from: halo, $C_{1-4}$ alkyl, $C_{1-4}$ haloalkyl, —$OR^{13}$, —CN, —$C(O)R^{10}$, =O, $SO_2R^{10}$, benzyl, phenyl, unsubstituted 5 or 6 membered heteroaryl, or methyl substituted 5 or 6 membered heteroaryl;
$R^{10}$ and $R^{11}$ are independently at each occurrence selected from: H and $C_{1-4}$ alkyl;
$R^{13}$ is selected from: H, $C_{1-4}$ alkyl, $C_{1-4}$ haloalkyl, phenyl or benzyl;
$R^a$ and $R^b$ are independently at each occurrence selected from: H, $C_{1-4}$ alkyl, —$OR^j$ or one of $R^a$ or $R^b$ together with $R^3$ forms a bond, —$CH_2$— or —$CH_2CH_2$— group resulting in a 4, 5 or 6 membered heterocycloalkyl ring comprising the —$CH_2$— or —$CH_2CH_2$— group, the N atom to which $R^3$ is attached, the C atom to which $R^a$ or $R^b$ are attached, and any intervening atoms; and
$R^c$, $R^d$, $R^e$, $R^f$, $R^g$, $R^h$, $R^i$ and $R^j$ are independently at each occurrence selected from: H and $C_{1-4}$ alkyl.

In accordance with the present invention there is provided a compound according to formula (I) and pharmaceutically acceptable salts thereof:

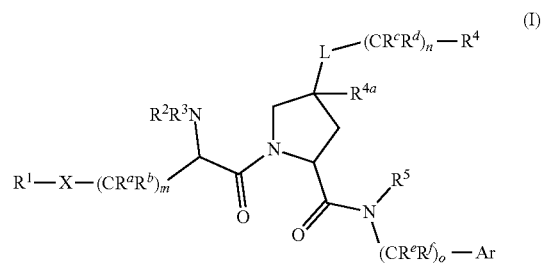

wherein
X is either a bond, —C(O)NH—, —C(O)O— or —C(O)—;
L is selected from: bond, —$NR^6$—, and —$NR^7C(O)$—;
Ar is a substituted or unsubstituted 9 to 10 membered bicyclic heteroaromatic ring system (preferably 9 membered) having 1, 2 or 3 heteroatoms selected from O, N or S, wherein, when substituted, the bicyclic heteroaromatic ring system is substituted with 1, 2, or 3 substituents selected from: halo, $C_{1-6}$ alkyl, —$OR^g$, —$NR^gR^h$ or $C_{1-4}$ alkyl substituted by —$NR^gR^h$;
m is selected from 0, 1, 2, or 3;
n is selected from 0, 1, 2, 3, or 4;
is selected from 1 or 2;
$R^1$ is selected from substituted or unsubstituted: —$NR^8R^9$, 5 to 10 membered carbocyclic ring system or a 5 to 10 membered heterocyclic ring system;
  wherein when substituted $R^1$ is substituted with 1, 2, or 3 groups selected from: =O, CN, —OH, or —O—$C_{1-6}$ alkyl, halo, $C_{1-6}$ alkyl and $C_{1-6}$ haloalkyl;
$R^2$ is selected from: H, $C_{1-6}$ alkyl, $C_{1-6}$ haloalkyl, phenyl, benzyl, —$C(O)R^{2a}$, and —$S(O_2)R^2$;
  wherein $R^{2a}$ is selected from: $C_{1-6}$ alkyl, phenyl, and benzyl;
$R^3$ is:
  (a) H or $C_{1-6}$ alkyl; or
  (b) $R^3$ together with one of $R^a$ or $R^b$ forms a bond, —$CH_2$— or —$CH_2CH_2$— group resulting in a 4, 5 or 6 membered heterocycloalkyl ring comprising the —$CH_2$— or —$CH_2CH_2$— group, the N atom to which $R^3$ is attached, the C atom to which $R^a$ or $R^b$ are attached, and any intervening atoms; or
  (c) $R^3$ forms a bond, —$CH_2$— or —$CH_2CH_2$— group with an atom of $R^1$ when $R^1$ is a carbocyclic ring system or a heterocyclic ring system;
$R^4$ is selected from: =$CH_2$, —$NR^{10}R^{11}$, 6 to 10 membered aryl, 3 to 6 membered heterocycloalkyl, 5 to 10 membered heteroaryl, wherein the 3 to 6 membered heterocycloalkyl, 6 to 10 membered aryl or heteroaryl group is unsubstituted or substituted with 1, 2 or 3 $R^{12}$
$R^{4a}$ is selected from: H, —OH, halo or $C_{1-4}$ alkyl;
$R^5$ is H or $C_{1-6}$ alkyl;
$R^6$ is H, $C_{1-6}$ alkyl or —$C(O)C_{1-6}$ alkyl;
$R^7$ is H or $C_{1-6}$ alkyl;
$R^8$ and $R^9$ are independently at each occurrence selected from: H, $C_{1-6}$ alkyl, $C_{3-6}$ cycloalkyl, phenyl, $C_{1-4}$ alkyl substituted with —$OR^i$, or $C_{1-4}$ alkyl substituted with phenyl, or $R^8$ and $R^9$ taken together with the atom to which they are attached form 3 to 8 membered heterocycloalkyl ring, which is unsubstituted or substituted with: CN, halo, $C_{1-6}$ alkyl or —$OR^i$;
$R^{12}$ is independently at each occurrence selected from: halo, $C_{1-4}$ alkyl, $C_{1-4}$ haloalkyl, —$OR^{13}$, —CN, —$C(O)R^{10}$, =O, $SO_2R^{10}$, benzyl, phenyl, unsubstituted 5 or 6 membered heteroaryl, or methyl substituted 5 or 6 membered heteroaryl;

$R^{10}$ and $R^{11}$ are independently at each occurrence selected from: H and $C_{1-4}$ alkyl;

$R^{13}$ is selected from: H, $C_{1-4}$ alkyl, $C_{1-4}$ haloalkyl, phenyl or benzyl;

$R^a$ and $R^b$ are independently at each occurrence selected from: H, $C_{1-4}$ alkyl, —$OR^j$ or one of $R^a$ or $R^b$ together with $R^3$ forms a bond, —$CH_2$— or —$CH_2CH_2$— group resulting in a 4, 5 or 6 membered heterocycloalkyl ring comprising the —$CH_2$— or —$CH_2CH_2$— group, the N atom to which $R^3$ is attached, the C atom to which $R^a$ or $R^b$ are attached, and any intervening atoms; and $R^c$, $R^d$, $R^e$, $R^f$, $R^g$, $R^h$, $R^i$ and $R^j$ are independently at each occurrence selected from: H and $C_{1-4}$ alkyl.

In embodiments where $R^3$ is option (a) or option (b) then m is not 0 when X is a bond. In embodiments where $R^3$ is option (c) then m may be 0 when X is a bond.

The compound according to formula (I) may be a compound of formula (a) and pharmaceutically acceptable salts thereof:

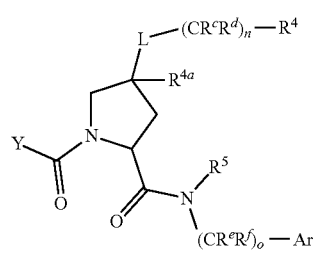

(Ia)

wherein
Y is selected from:

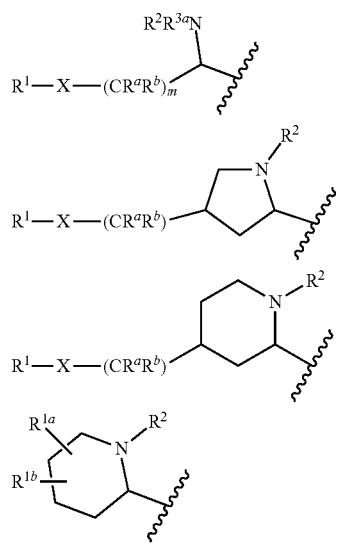

and $R^{1a}$ and $R^{1b}$ taken together form a substituted or unsubstituted: 5 or 6 membered heteroaromatic ring or a phenyl ring;
wherein when the ring formed from $R^{1a}$ and $R^{1b}$ is substituted it is substituted with 1, 2, or 3 $R^z$ groups wherein $R^z$ is independently selected at each occurrence from: =O, CN, —OH, or —O—$C_{1-6}$ alkyl, halo and $C_{1-6}$ alkyl;

$R^{3a}$ is H or $C_{1-6}$ alkyl; and m is selected from 1, 2, or 3.

In embodiments $R^{1a}$ and $R^{1b}$ are substituted on adjacent atoms. Accordingly, Y may be selected from:

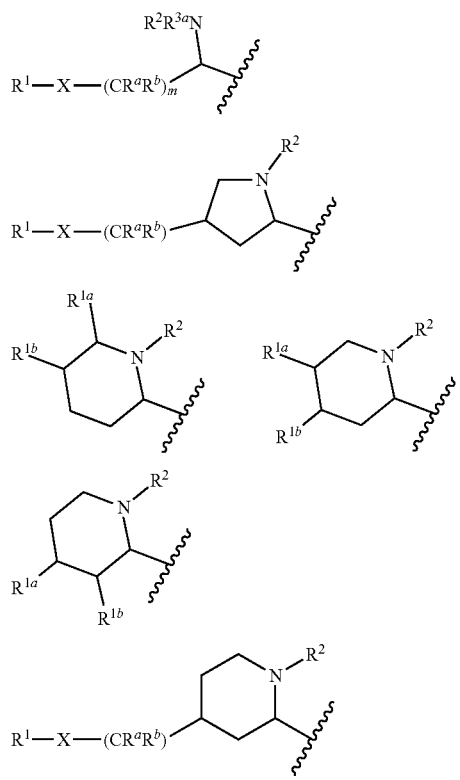

In embodiments Y is selected from:

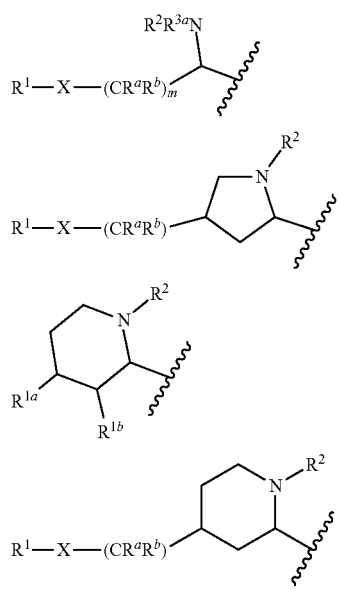

In embodiments $R^{1a}$ and $R^{1b}$ form a phenyl ring substituted with 1, 2, or 3 $R^z$ groups.

In embodiments Y is selected from:

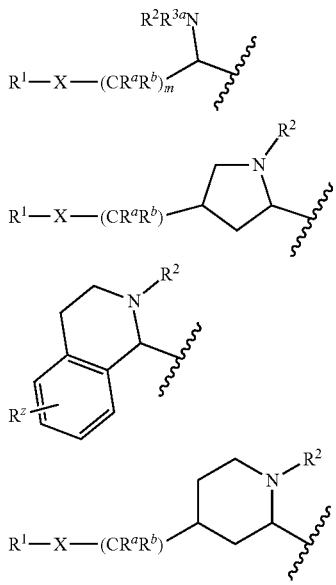

wherein $R^z$ is selected from =O, CN, —OH, or —O—$C_{1-6}$ alkyl, halo, $C_{1-6}$ alkyl and $C_{1-6}$ haloalkyl.

In embodiments m is 2 or 3. Alternatively m is 1 or 2.

In embodiments X is either a bond, —C(O)NH—, or —C(O)—. In embodiments X is a bond or —C(O)—.

In an embodiment the compound of formula (I) is a compound according to formulae (IIa), (IIb), (IIc) or (IId):

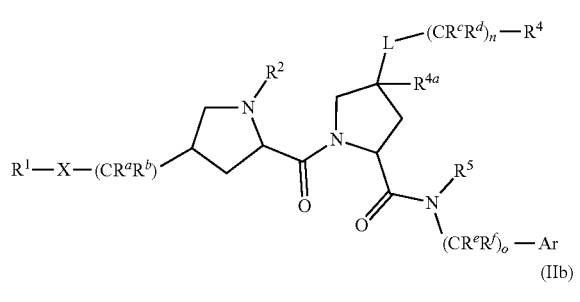

(IIa)

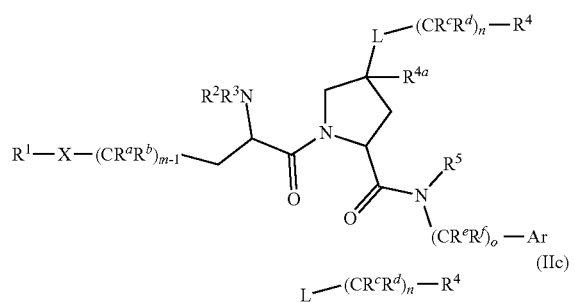

(IIb)

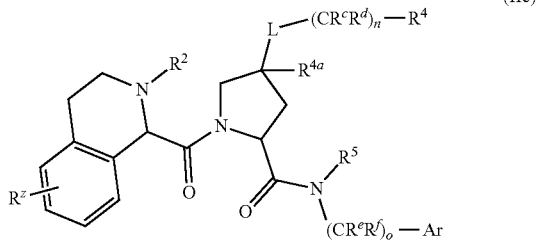

(IIc)

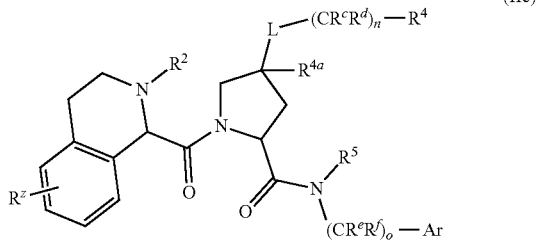

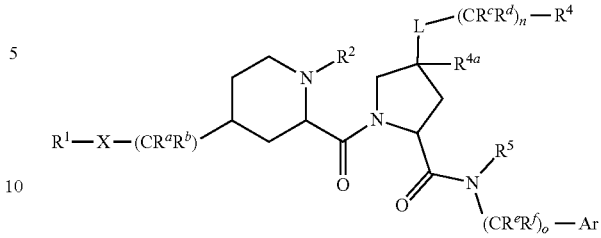

(IId)

In embodiments of formula (IIa) m is 2 or 3. In embodiments of formula (IIa) X is a bond. Accordingly, in embodiments the compound of formula (I) is a compound according to formula (IIIa) or (IIIb):

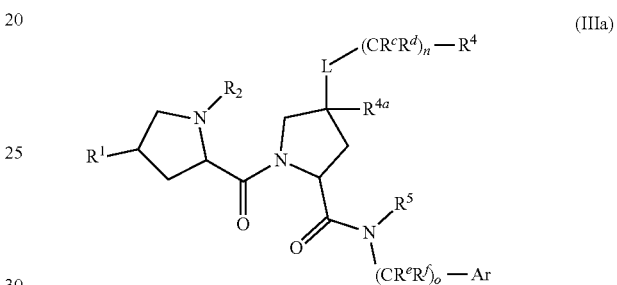

(IIIa)

(IIIb)

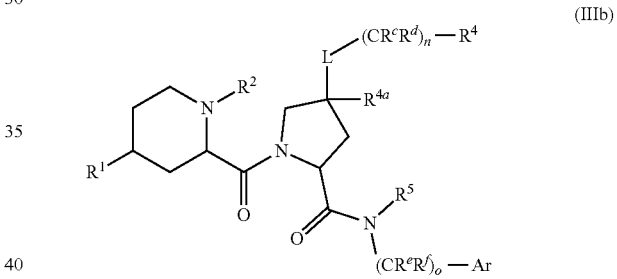

In embodiments of formula (IIb) m is 1 or 2. In embodiments of formula (IIb) X is either a bond, —C(O)NH—, or —C(O)—, preferably X is —C(O)—.

In embodiments $R^z$ is selected from H, OH, C or OMe. Accordingly, in embodiments the compound of formula (I) may be a compound according to formula (IV):

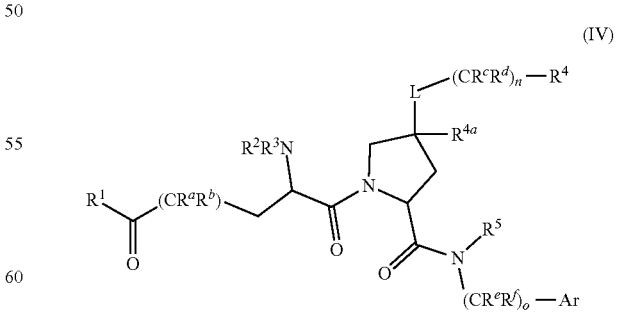

(IV)

In embodiments o is 1. In embodiments $R^e$ and $R^f$ are H.

In preferred embodiments o is 1 and $R^e$ and $R^f$ are H. Accordingly, in an embodiment the compound of formula (I) is a compound according to formula (V) or (Va):

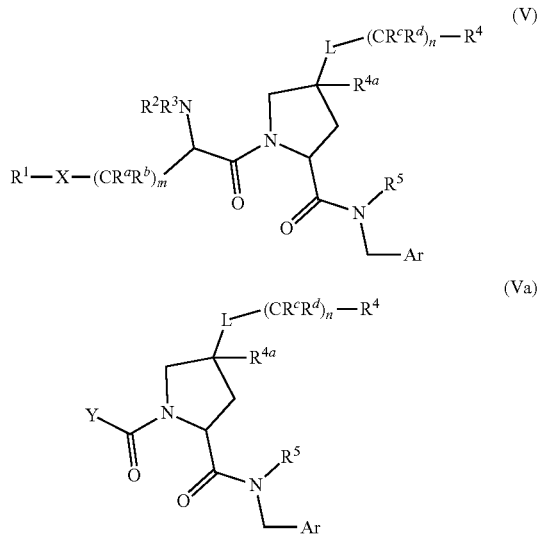
(V)

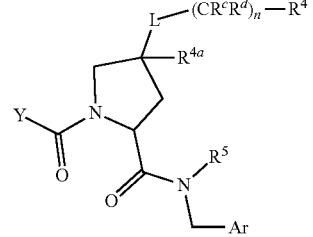
(Va)

In embodiments $R^2$ is H. In embodiments $R^3$ is H. In embodiments $R^5$ is H. In embodiments $R^2$, $R^3$ and $R^5$ are each H. In embodiments $R^a$ and $R^b$ are each H. In embodiments $R^2$, $R^3$, $R^5$, $R^a$ and $R^b$ are each H.

In embodiments the compound of formula (I) may be a compound according to formulae (VIa), (VIb), (VIc) or (VId):

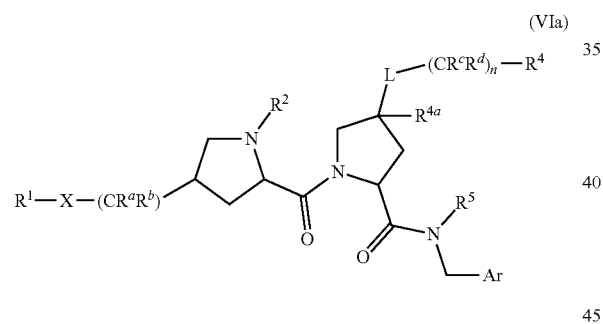
(VIa)
(VIb)
(VIc)

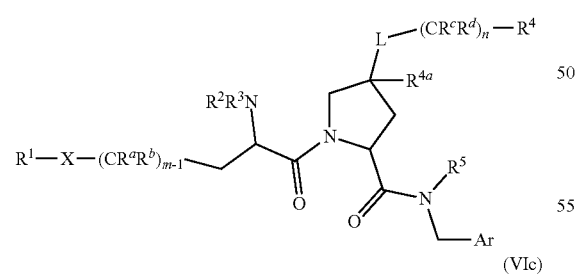
(VId)

In embodiments of compounds of formulae (VIa) or (VIb) $R^2$, $R^3$ and $R^5$ are each H. In embodiments of compounds of formulae (VIc) or (VId) $R^2$ and $R^5$ are each H. In embodiments of compounds of formulae (VIa) or (VIb) $R^a$ and $R^b$ are each H. In embodiments of compounds of formulae (VIa) or (VIb) $R^2$, $R^3$, $R^5$, $R^a$ and $R^b$ are each H.

In embodiments the compound of formula (I) may be a compound according to formulae (VIIa), (VIIb), (VIIc) or (VIId):

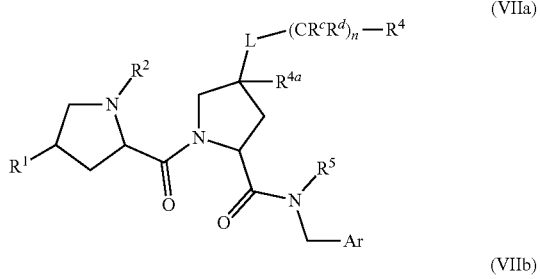
(VIIa)

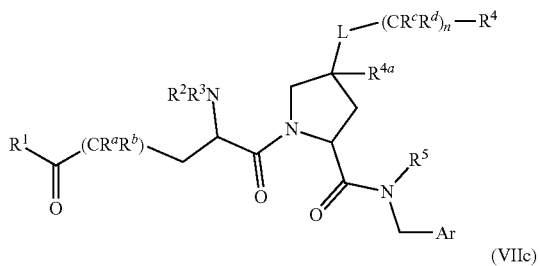
(VIIb)

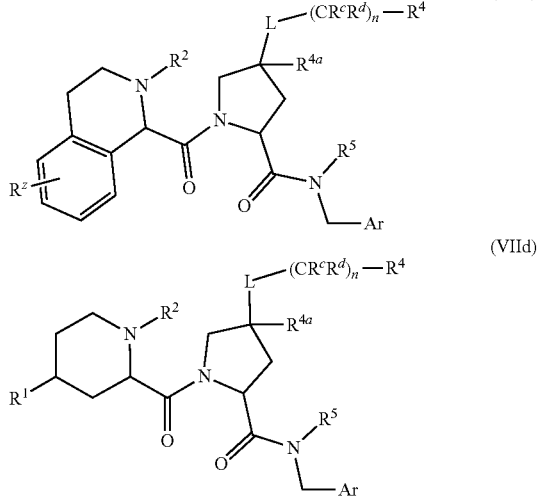
(VIIc)
(VIId)

In embodiments of compounds of formulae (VIIa) or (VIIb) $R^2$, $R^3$ and $R^5$ are each H. In embodiments of compounds of formulae (VIIc) or (VId) $R^2$ and $R^5$ are each H. In embodiments of compounds of formulae (VIa) or (VIIb) $R^a$ and $R^b$ are each H. In embodiments of compounds of formulae (VIa) or (VIIb) $R^2$, $R^3$, $R^5$, $R^a$ and $R^b$ are each H.

In embodiments $R^{4a}$ may be selected from H, OH or F. Preferably, $R^{4a}$ is H.

In embodiments the compound of formula (I) is a compound according to formulae (VIIIa), (VIIIb), (VIIIc) or (VIIId):

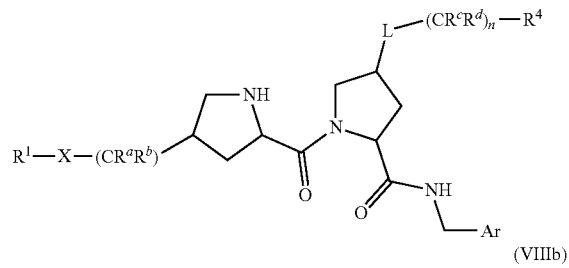

(VIIIa)

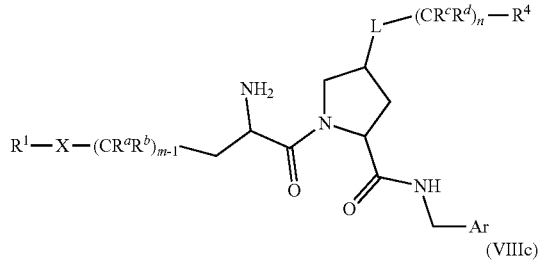

(VIIIb)

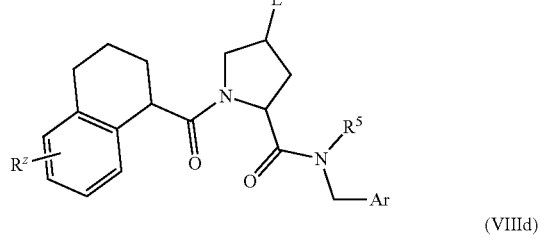

(VIIIc)

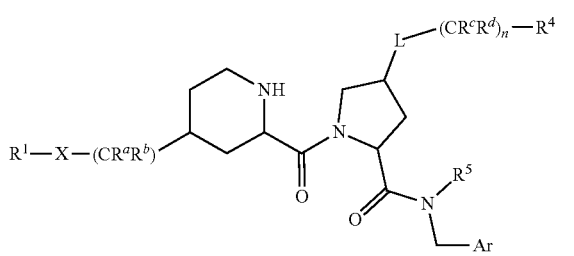

(VIIId)

In embodiments Ar is selected from phenyl, 6 membered heteroaryl or 9 to 10 membered bicyclic heteroaromatic ring system (preferably 9 membered), wherein Ar is unsubstituted or substituted with $C_{1-6}$ alkyl, —$OR^g$, —$NR^gR^h$ or $C_{1-4}$ alkyl substituted by —$NR^gR^h$. Optionally, Ar is unsubstituted or substituted with methyl, chloro, —OMe, —$NH_2$ or —$CH_2NH_2$.

In embodiments Ar is selected from 9 to 10 membered bicyclic heteroaromatic ring system (preferably 9 membered), wherein Ar is unsubstituted or substituted with $C_{1-6}$ alkyl, —$OR^g$, —$NR^gR^h$ or $C_{1-4}$ alkyl substituted by —$NR^gR^h$. Optionally, Ar is unsubstituted or substituted with methyl, chloro, —OMe, —$NH_2$ or —$CH_2NH_2$.

$R^g$ and $R^h$ may be independently at each occurrence selected from: H and methyl.

In embodiments Ar is selected from phenyl, pyridyl, benzotriazole, imidazopyridine, pyridofuran, azaindole, benzopyrazole, pyridoazathiophene, benzoxazole, quinoline, thiophenyl, and isoquinoline wherein Ar is unsubstituted or substituted with methyl, chloro, —OMe, —$NH_2$ or —$CH_2NH_2$.

In embodiments Ar is selected from benzotriazole, imidazopyridine, pyridofuran, azaindole, benzopyrazole, pyridoazathiophene, benzoxazole, quinoline, and isoquinoline wherein Ar is unsubstituted or substituted with methyl, chloro, —OMe, —$NH_2$ or —$CH_2NH_2$.

In embodiments Ar is selected from phenyl, pyridyl, benzotriazole, imidazopyridine, pyridofuran, azaindole, benzopyrazole, pyridoazathiophene, benzoxazole, thiophenyl, wherein Ar is unsubstituted or substituted with methyl, chloro, —OMe, —$NH_2$ or —$CH_2NH_2$.

In embodiments Ar is selected from benzotriazole, imidazopyridine, pyridofuran, azaindole, benzopyrazole, pyridoazathiophene, benzoxazole, wherein Ar is unsubstituted or substituted with methyl, chloro, —OMe, —$NH_2$ or —$CH_2NH_2$.

In embodiments Ar is selected from:

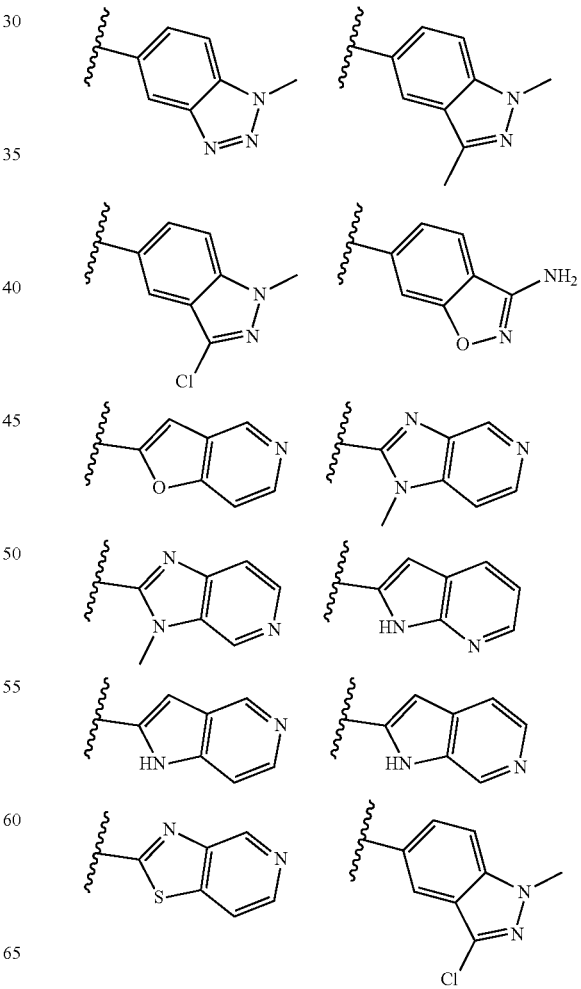

-continued
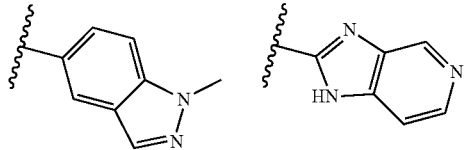
In embodiments Ar is not substituted or unsubstituted phenyl.
In preferred embodiments Ar is azaindole, benzotriazole or N-methyl benzotriazole.
In preferred embodiments Ar is:
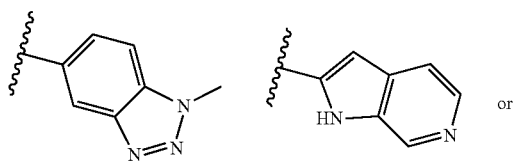 or
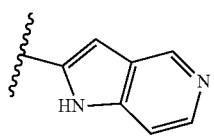
In embodiments the compound of formula (I) is a compound according to formulae (IXa), (IXb), (IXc) or (IXd):
In embodiments Ar is selected from:
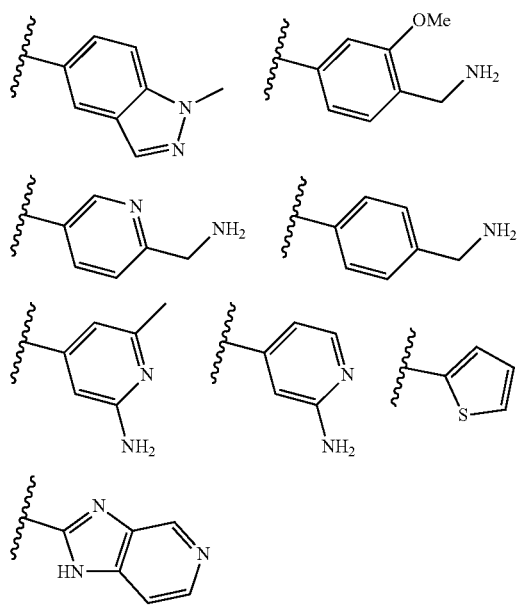
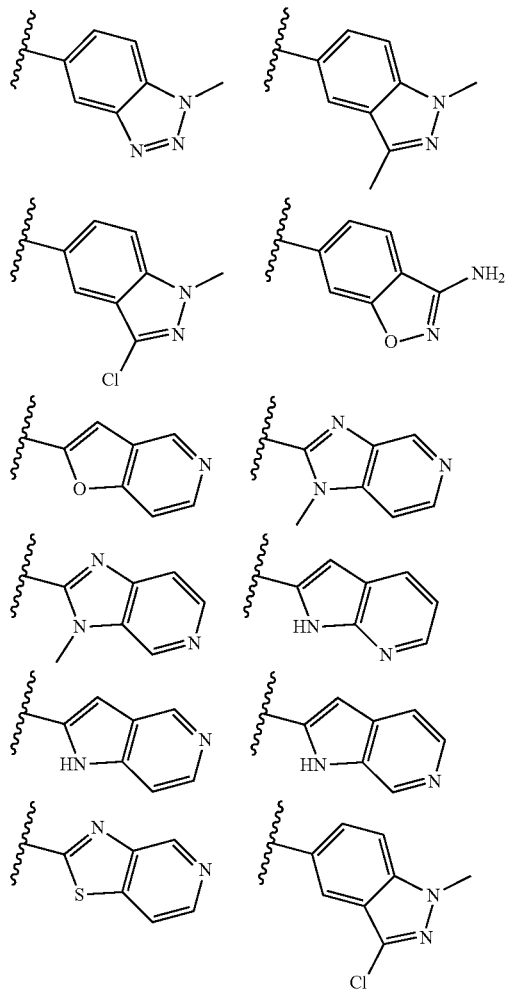
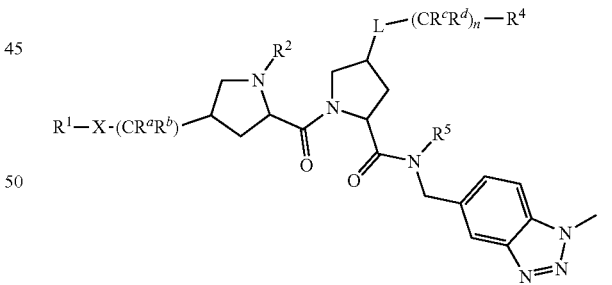
(IXa)
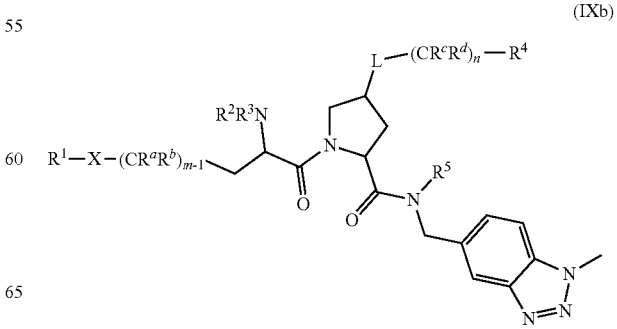
(IXb)

-continued

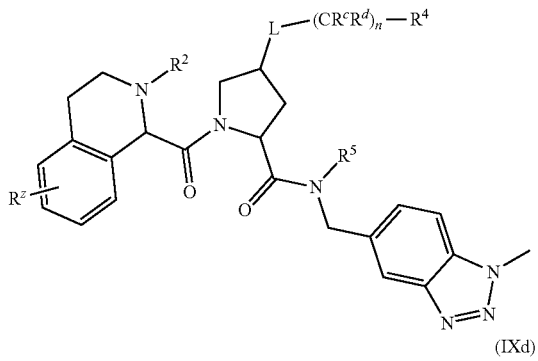
(IXc)

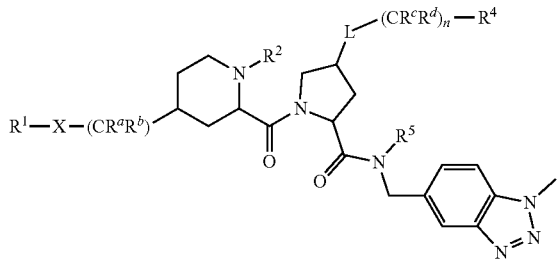
(IXd)

In embodiments of compounds of formulae (IXa) or (IXb) $R^2$, $R^3$ and $R^5$ are each H. In embodiments of compounds of formulae (IXa) or (IXb) $R^a$ and $R^b$ are each H. In embodiments of compounds of formulae (IXc) or (IXd) $R^2$ and $R^5$ are each H. In embodiments of compounds of formulae (IXa) or (IXb) $R^2$, $R^3$, $R^5$, $R^a$ and $R^b$ are each H.

In embodiments L is selected from: bond, —$NR^6$—, and —$NR^7C(O)$—.

$R^6$ may be H, Me or —C(O)Me. $R^7$ may be H. In embodiments $R^6$ is H.

In embodiments L is selected from: bond, —NH—, —NMe—, —N(C(O)Me)—, and —NHC(O)—.

In embodiments n is 0, 1, 2 or 3. In embodiments n is 0 or 1.

$R^c$ and $R^d$ are independently at each occurrence selected from H and methyl. Preferably, $R^c$ and $R^d$ are H.

In embodiments -L-$(CR^cR^d)_n$— is selected from: a bond, $CH_2$, —NH—, —$NHCH_2$—, —$NH(CH_2)_2$—, —$NH(CH_2)_3$—, —N(Me)—, —N(C(O)Me)$CH_2$—, —NHC(O)—, —NHC(O)$CH_2$—, —NHC(O)$(CH_2)_2$—, or NHC(O)$(CH_2)_3$—.

In embodiments -L-$(CR^cR^d)_n$— is selected from: a bond or $CH_2$.

$R^4$ may be selected from: =$CH_2$, —CN, halo, $C_{1-4}$ alkyl, $C_{1-4}$ haloalkyl, —$OR^{10}$, —$NR^{10}R^{11}$, 6 to 10 membered aryl, $C_{3-8}$ cycloalkyl, 3 to 6 membered heterocycloalkyl, 5 to 10 membered heteroaryl, wherein the $C_{3-8}$ cycloalkyl, 3 to 6 membered heterocycloalkyl, 6 to 10 membered aryl or heteroaryl group is unsubstituted or substituted with 1, 2 or 3 $R^{12}$.

$R^4$ may be selected from: =$CH_2$, —$NR^{10}R^{11}$, 6 to 10 membered aryl, 3 to 6 membered heterocycloalkyl, 5 to 10 membered heteroaryl, wherein the 3 to 6 membered heterocycloalkyl, 6 to 10 membered aryl or heteroaryl group is unsubstituted or substituted with 1, 2 or 3 $R^{12}$.

The 6 to 10 membered aryl of $R^4$ may be selected from phenyl or napthalenyl. The $C_{3-8}$ cycloalkyl of $R^4$ may be selected from cyclopropyl, cyclobutyl, cyclopentyl, and cyclohexyl. The 3 to 6 membered heterocycloalkyl of $R^4$ may be selected from tetrahydropyranyl, tetrahydrofuranyl, piperidinyl, piperazinyl, morpholinyl, pyrrolidinyl, pyrazolidinyl, or imidazolidinyl (preferably tetrahydropyranyl or piperazinyl). The 5 to 10 membered heteroaryl of $R^4$ may be selected from pyridinyl, pyrazinyl, pyrazolyl, imidazolyl, dihydrobenzofuran, benzodioxolanyl or isoindolinyl (optionally pyridinyl, pyrazinyl, pyrazolyl, imidazolyl, dihydrobenzofuran, benzodioxolanyl or isoindolinyl). Any of the $C_{3-6}$ cycloalkyl, 3 to 6 membered heterocycloalkyl, 6 to 10 membered aryl or heteroaryl groups may be unsubstituted or substituted with 1, 2, or 3 $R^{12}$.

The 6 to 10 membered aryl of $R^4$ may be selected from phenyl or napthalenyl. The 3 to 6 membered heterocycloalkyl of $R^4$ may be selected from tetrahydropyranyl, tetrahydrofuranyl, piperidinyl, piperazinyl, morpholinyl, pyrrolidinyl, pyrazolidinyl, or imidazolidinyl (preferably tetrahydropyranyl or piperazinyl). The 5 to 10 membered heteroaryl of $R^4$ may be selected from pyridinyl, pyrazinyl, pyrazolyl, imidazolyl, dihydrobenzofuran, benzodioxolanyl or isoindolinyl (optionally pyridinyl, pyrazinyl, pyrazolyl, imidazolyl, dihydrobenzofuran, benzodioxolanyl or isoindolinyl). Any of the 3 to 6 membered heterocycloalkyl, 6 to 10 membered aryl or heteroaryl groups may be unsubstituted or substituted with 1, 2, or 3 $R^{12}$.

In embodiments $R^4$ is selected from: =$CH_2$, —CN, halo, $C_{1-4}$ alkyl, $C_{1-4}$ haloalkyl, —$OR^{4b}$, —$NR^{4b}R^{4c}$, phenyl or napthalenyl, cyclopropyl, cyclobutyl, cyclopentyl, cyclohexyl, tetrahydropyranyl, tetrahydrofuranyl, piperidinyl, piperazinyl, morpholinyl, pyrrolidinyl, pyrazolidinyl, imidazolidinyl, pyridinyl, pyrazinyl, pyrazolyl, imidazolyl, dihydrobenzofuran, benzodioxolanyl or isoindolinyl; wherein any group that is cyclic is unsubstituted or substituted with 1, 2, or 3 $R^{12}$.

In embodiments $R^4$ is selected from: =$CH_2$, —$NR^{4b}R^{4c}$, phenyl or napthalenyl, tetrahydropyranyl, tetrahydrofuranyl, piperidinyl, piperazinyl, morpholinyl, pyrrolidinyl, pyrazolidinyl, imidazolidinyl, pyridinyl, pyrazinyl, pyrazolyl, imidazolyl, dihydrobenzofuran, benzodioxolanyl or isoindolinyl; wherein any group that is cyclic is unsubstituted or substituted with 1, 2, or 3 $R^{12}$.

In embodiments $R^{12}$ is independently selected from: halo, $C_{1-4}$ alkyl, $C_{1-4}$ haloalkyl, —$OR^{13}$, —CN, —$C(O)R^{10}$, =O, $SO_2R^{10}$, benzyl, phenyl, unsubstituted 5 or 6 membered heteroaryl, or methyl substituted 5 or 6 membered heteroaryl. Optionally, $R^{12}$ is independently selected from: Cl, Br, F, $CF_3$, OMe, OEt, OPh, CN, $SO_2Me$, methyl, pyridinyl, or methylpyrazole.

In embodiments $R^{4a}$ is H, OH or F (preferably H) and -L-$(CR^cR^d)_n$—$R^4$ is selected from: —$CF_3$, —OH, —$NH_2$, =$CH_2$, —CN, —NHC(O)Me, —NHC(O)Ph, —NHC(O)Bn, —NHC(O)$CH_2CH_2Ph$, —NHC(O)$(CH_2)_3Ph$, —NHC(O)OMe, —NHC(O)NHMe, —N(C(O)Me)benzyl, —N(C(O)Me)$CH_2$pyridinyl, —N(Me)cyclohexyl, phenyl, isoindoline, piperazine, benzyl, —$CH_2$phenyl, —$CH_2$pyridinyl, —$CH_2$cyclopentyl, —$CH_2$tetrahydropyranyl, —$CH_2$pyrazolyl, —$CH_2$dihydrobenzofuran, —$CH_2$imidazolyl, —$CH_2$benzodioxolanyl, —NHcyclohexane, —NHpyrazinyl, —$NHCH_2Ph$, —$NHCH_2$cyclohexane, —$NHCH_2CH_2Ph$, and —$NHCH_2CH_2CH_2Ph$;
wherein any of the above cyclic groups is unsubstituted or substituted with 1, 2 or 3 groups selected from: Cl, Br, F, $CF_3$, OMe, OEt, —O-phenyl, —O-benzyl, CN, $SO_2Me$, methyl, pyridinyl, or methylpyrazole.

In embodiments $R^{4a}$ is H, OH or F (preferably H) and -L-$(CR^cR^d)_n$—$R^4$ is selected from: =$CH_2$, —NHC(O)Ph, —NHC(O)Bn, —NHC(O)$CH_2CH_2Ph$, —NHC(O)

(CH$_2$)$_3$Ph, —NHC(O)NHMe, —N(C(O)Me)benzyl, —N(C(O)Me)CH$_2$pyridinyl, phenyl, isoindoline, piperazine, benzyl, —CH$_2$phenyl, —CH$_2$pyridinyl, —CH$_2$tetrahydropyranyl, —CH$_2$pyrazolyl, —CH$_2$dihydrobenzofuran, —CH$_2$imidazolyl, —CH$_2$benzodioxolanyl, —NHpyrazinyl, —NHCH$_2$Ph, —NHCH$_2$CH$_2$Ph, and —NHCH$_2$CH$_2$CH$_2$Ph; wherein any of the above cyclic groups is unsubstituted or substituted with 1, 2 or 3 groups selected from: Cl, Br, F, CF$_3$, OMe, OEt, —O-phenyl, —O-benzyl, CN, SO$_2$Me, methyl, pyridinyl, or methylpyrazole.

In embodiments $R^{4a}$ is H and -L-(CR$^c$R$^d$)$_n$—R$^4$ is:

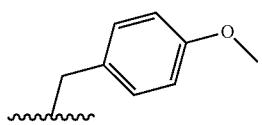 [SMILES: *Cc1ccc(OC)cc1]

In embodiments the compound of formula (I) is a compound according to formula (Xa) or (Xb):

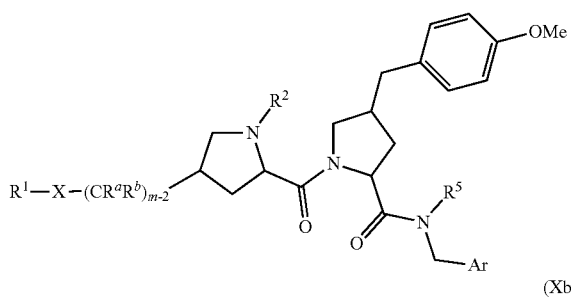

In embodiments the compound of formula (I) is a compound according to formula (XIa) or (XIb):

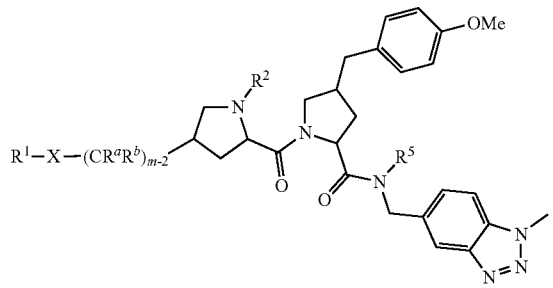

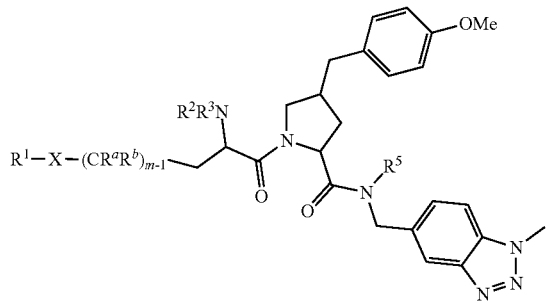

In embodiments R$^1$ is selected from substituted or unsubstituted: —NR$^8$R$^9$, 5 to 10 membered carbocyclic ring system or a 5 to 6 membered heterocyclic ring system; wherein when substituted R$^1$ is substituted with 1, 2, or 3 groups selected from: =O, CN, —OH, or —O—C$_{1-6}$ alkyl, halo, C$_{1-6}$ alkyl and C$_{1-6}$ haloalkyl.

In embodiments R$^1$ is selected from substituted or unsubstituted: —NR$^8$R$^9$, 5 to 10 membered cycloalkyl or a 5 to 6 membered heterocycloalkyl; wherein when substituted R$^1$ is substituted with 1, 2, or 3 groups selected from: =O, CN, —OH, or —O—C$_{1-6}$ alkyl, halo, C$_{1-6}$ alkyl and C$_{1-6}$ haloalkyl.

In embodiments R$^1$ is selected from substituted or unsubstituted: —NR$^8$R$^9$, 5 or 6 membered carbocyclic group or a 5 or 6 membered heterocyclic group; wherein when substituted R$^1$ is substituted with 1, 2, or 3 groups selected from: =O, CN, —OH, or —O—C$_{1-6}$ alkyl, halo, C$_{1-6}$ alkyl and C$_{1-6}$ haloalkyl.

In embodiments R$^1$ is selected from substituted or unsubstituted: —NR$^8$R$^9$, 6 or 10 membered aryl, 5, 6 or 9 membered heteroaryl, 3 to 7 membered heterocycloalkyl; wherein when substituted R$^1$ is substituted with 1, 2, or 3 groups selected from: =O, CN, —OH, or —O—C$_{1-6}$ alkyl, halo and C$_{1-6}$ alkyl.

In embodiments R$^1$ is selected from substituted or unsubstituted: —NR$^8$R$^9$, 6 or 10 membered aryl, 5 or 6 membered heteroaryl, 3 to 7 membered heterocycloalkyl; wherein when substituted R$^1$ is substituted with 1, 2, or 3 groups selected from: =O, CN, —OH, or —O—C$_{1-6}$ alkyl, halo and C$_{1-6}$ alkyl.

In embodiments R$^1$ is not a 10 membered aryl group or a 8, 9, 10 or 13 membered heteroaryl group. In embodiments R$^1$ is not a 10 membered aryl group. In embodiments R$^1$ is not a 9 membered heteroaryl group. In embodiments R$^1$ is not a 8, 10 or 13 membered heteroaryl group.

In embodiments R$^1$ is not indole. In embodiments R$^1$ is not pyrazole.

R$^1$ may be selected from: —NMe$_2$, —N(Me)i-Pr, —NH-cyclopropyl, cyclopropyl, phenyl, pyridinyl, pyridinonyl, pyrimidinyl, imidazolyl, oxazolyl, pyrollidinyl, methylpyrollidinyl, fluoropyrollidinyl, azetidinyl, piperidinyl, piperazinyl, azepanyl, indoline, tetrahydronapthalenyl, or

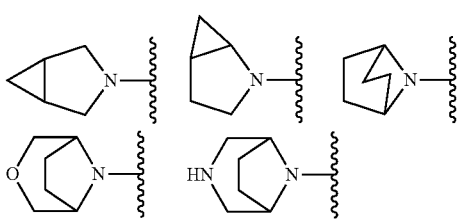

R[1] may be substituted with a group selected from: F, CN, =O, —OH, —OCF$_3$, —OMe, Me, i-Pr, or —CF$_3$.
Preferably R[1] may be selected from: phenyl, pyridinyl, piperidinyl, pyrollidinyl, or methylpyrrolidinyl wherein R[1] is unsubstituted or substituted with a group selected from: F, CN, —OH, —OCF$_3$, —OMe, Me, i-Pr, or —CF$_3$.
In embodiments the compounds of formula (I) are selected from:
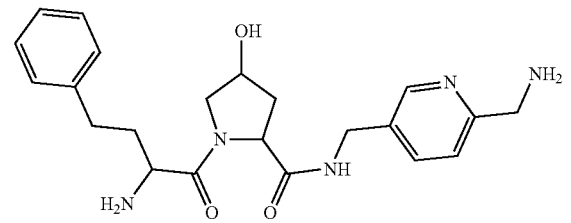
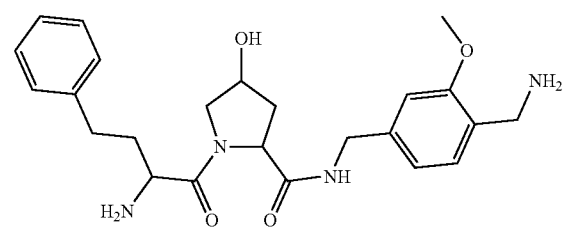
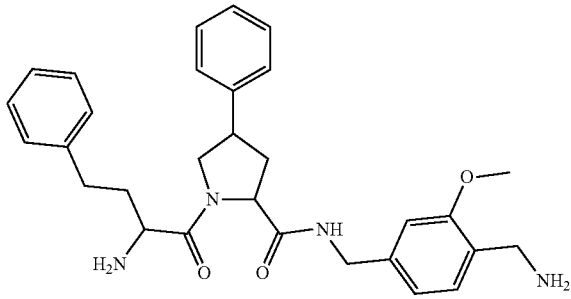
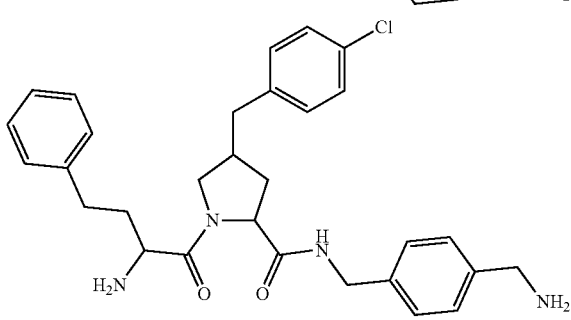
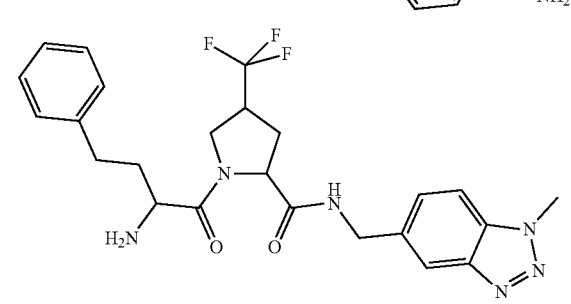
-continued
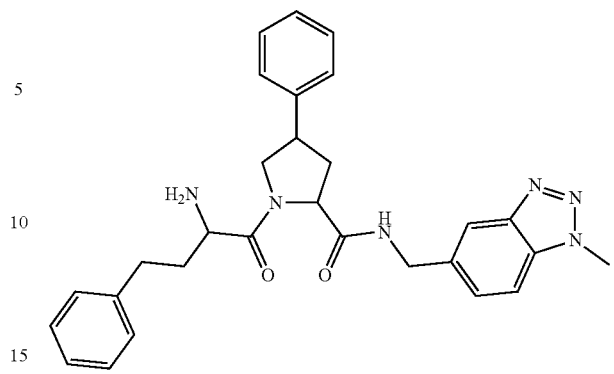
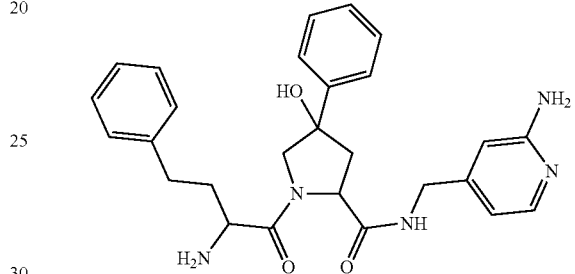
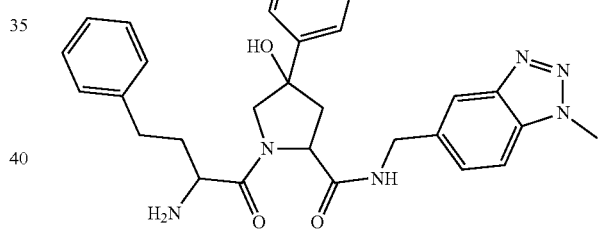
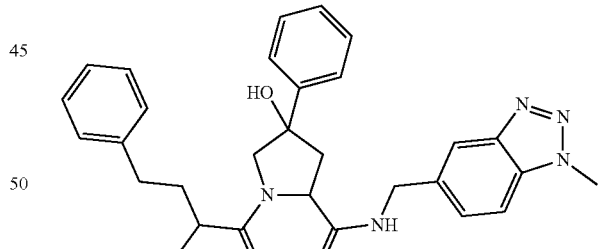
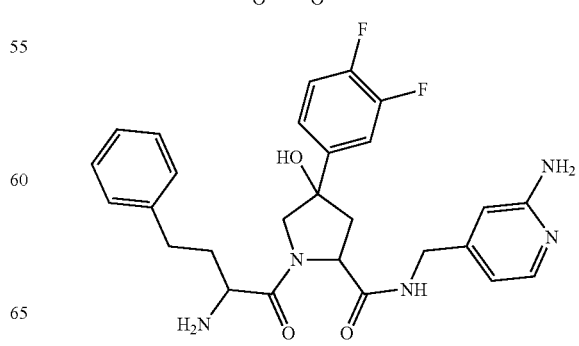

25
-continued
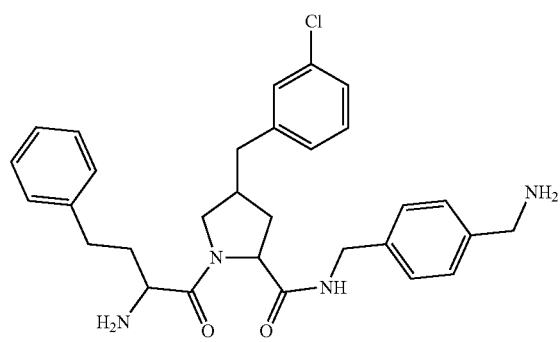
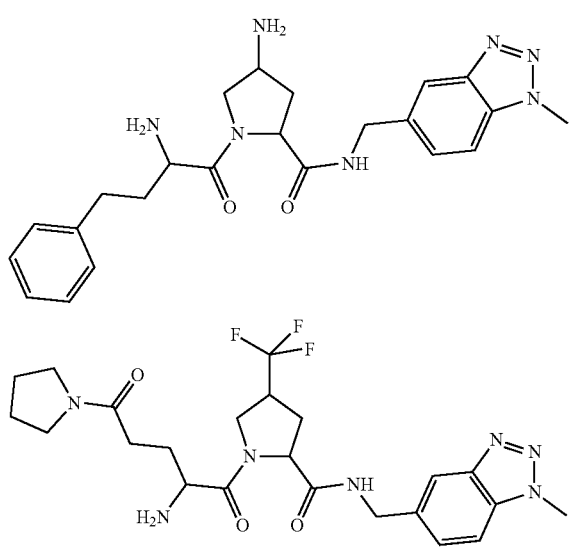
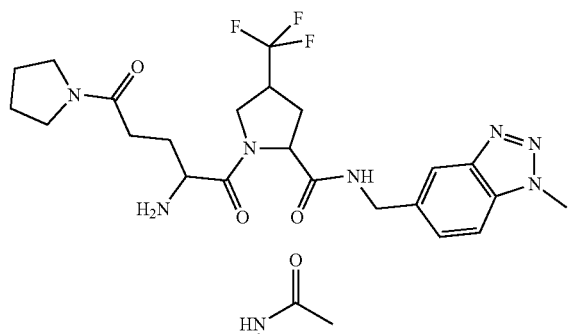
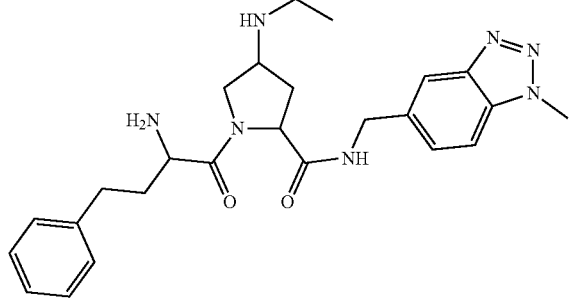
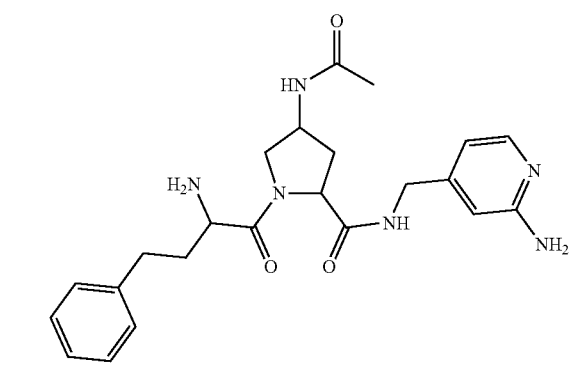
26
-continued
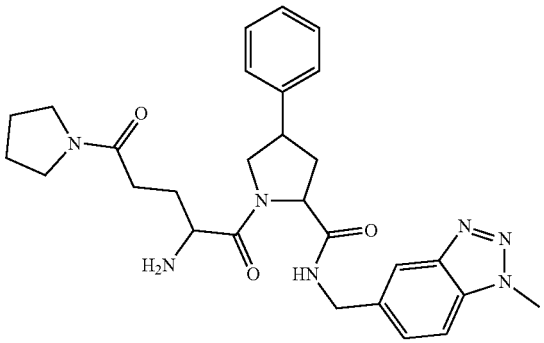
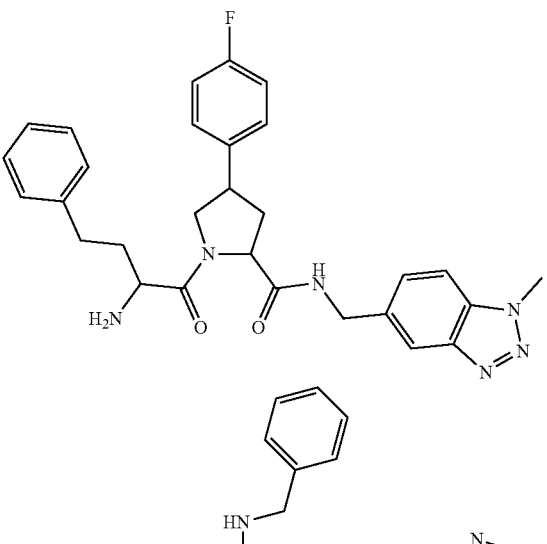
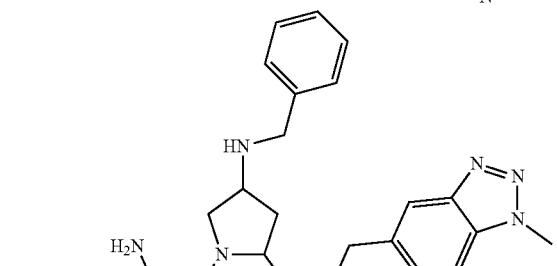
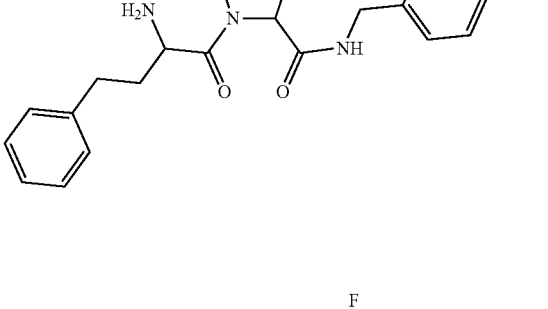
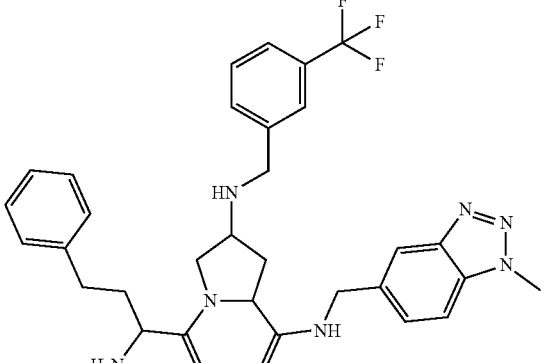

27
-continued
28
-continued
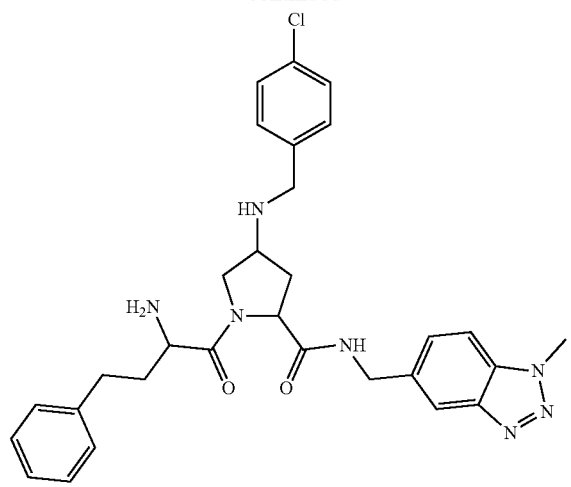
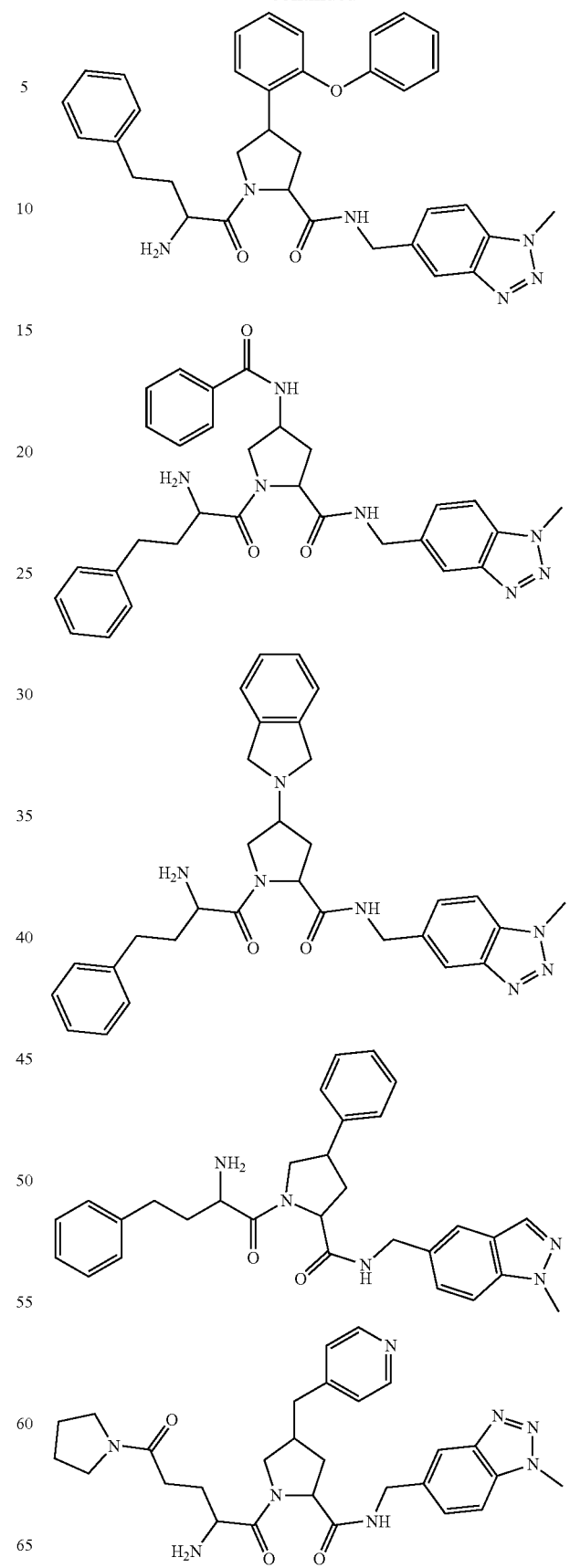

29
-continued
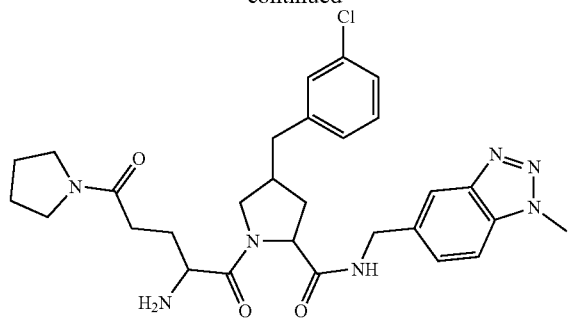
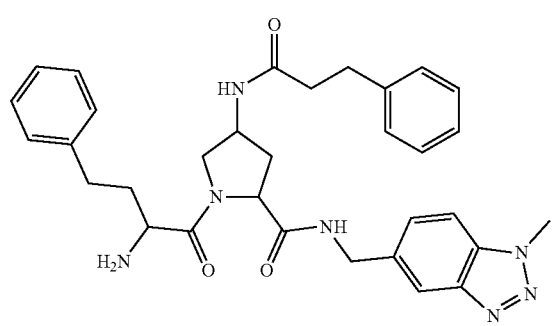
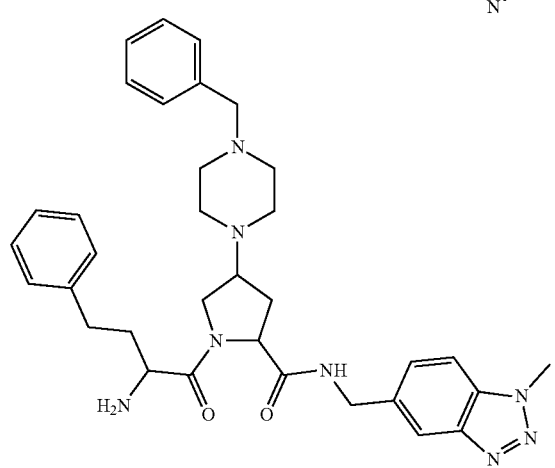
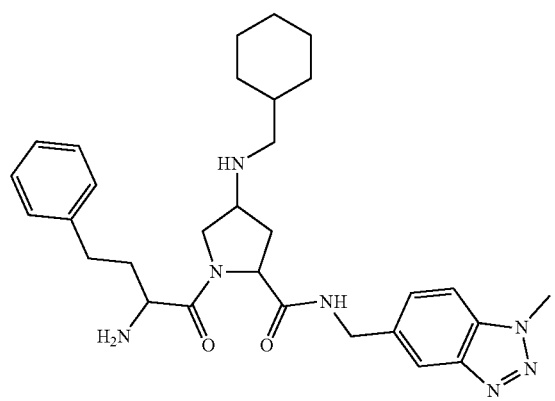
30
-continued
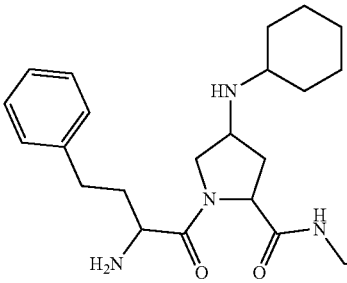
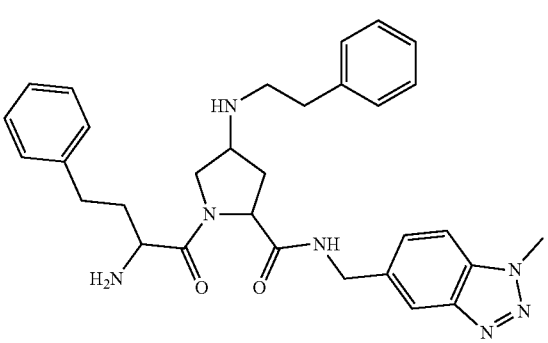
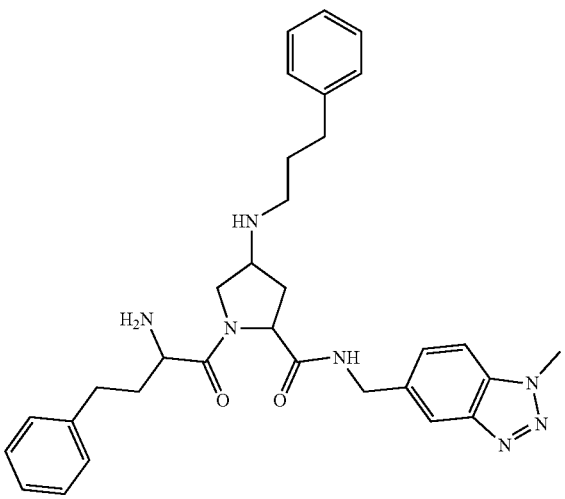
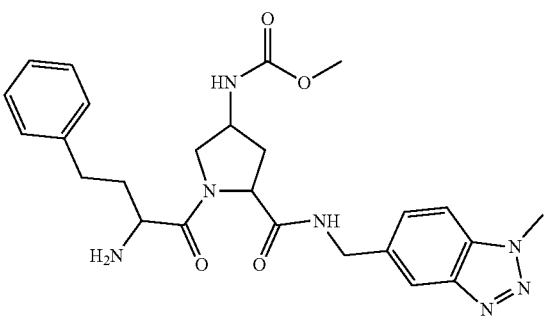

31
-continued
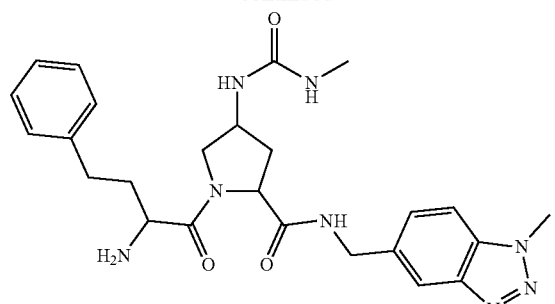
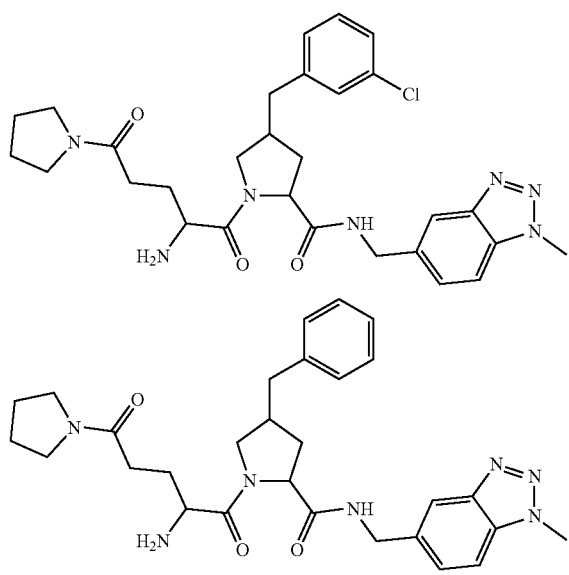
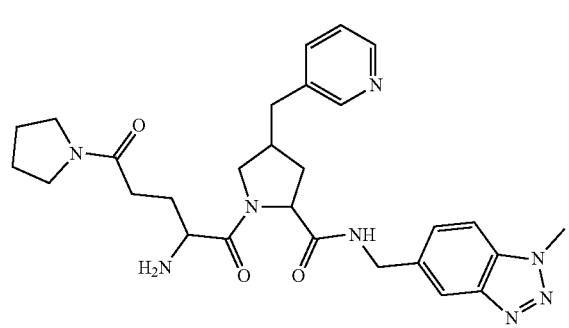
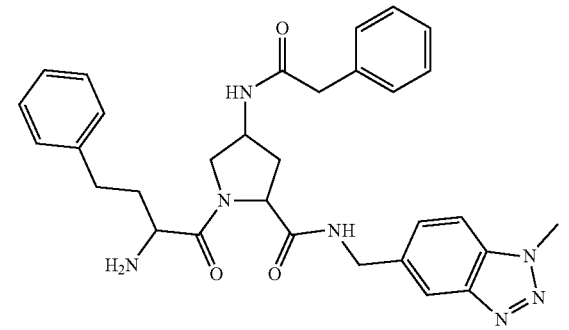
32
-continued
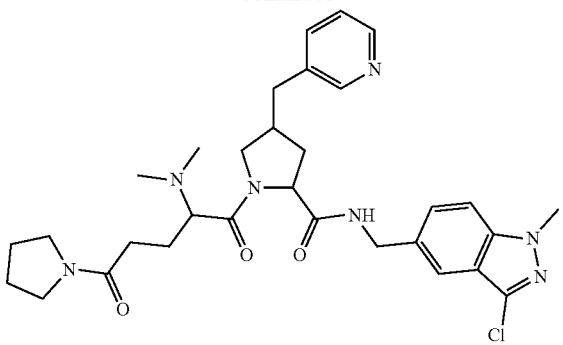
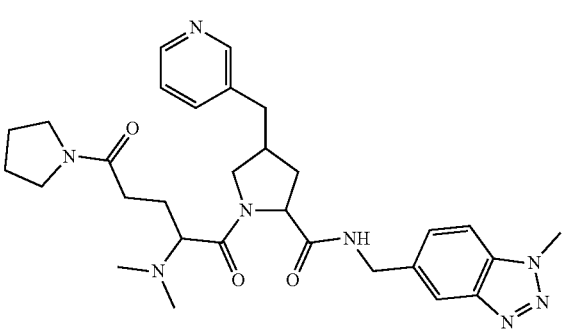
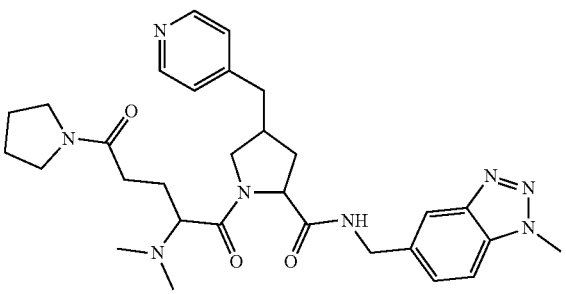
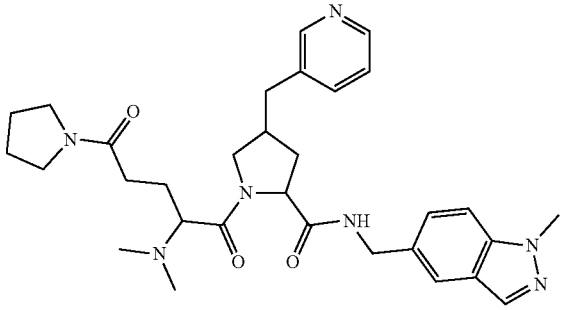
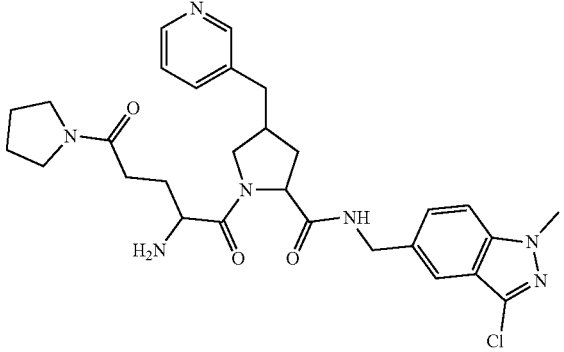

33
-continued

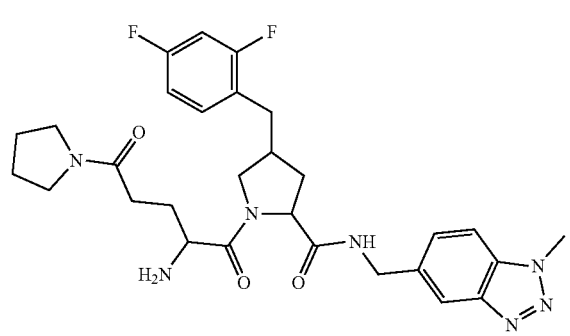
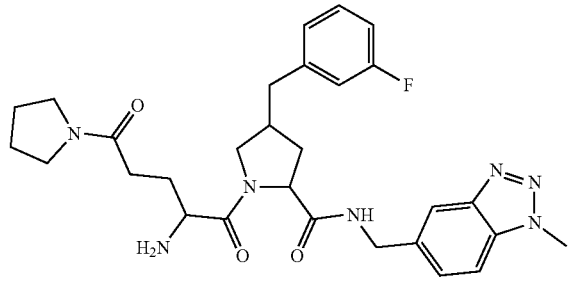
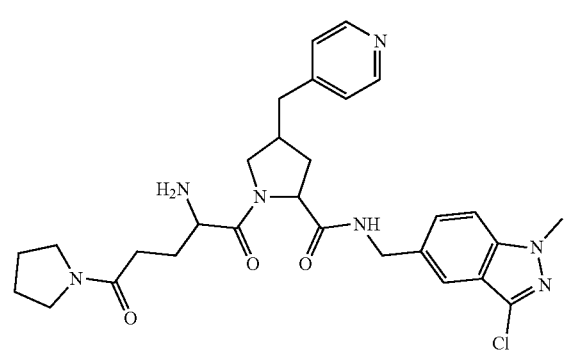
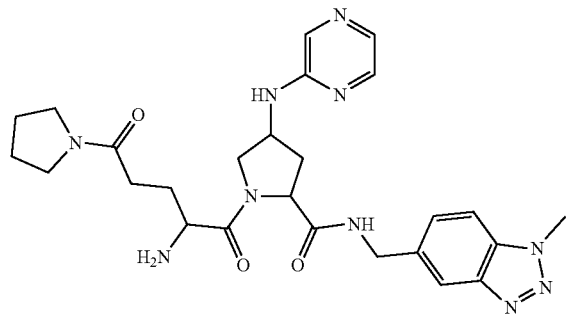
34
-continued
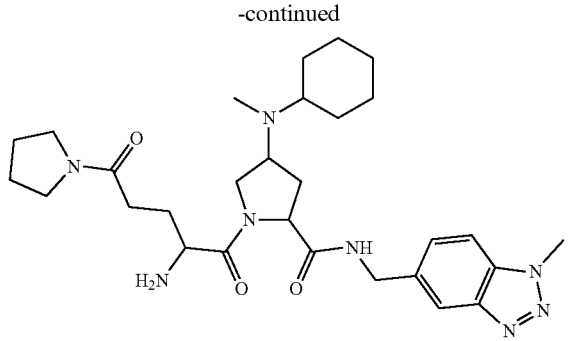
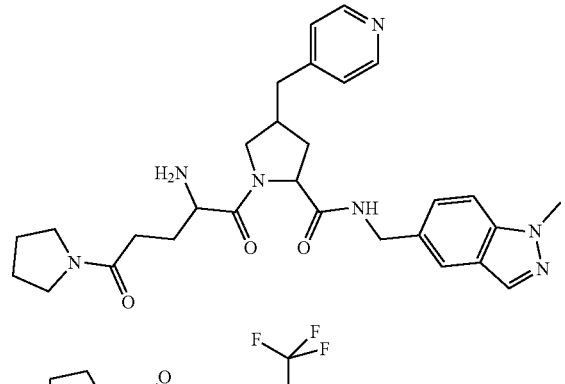
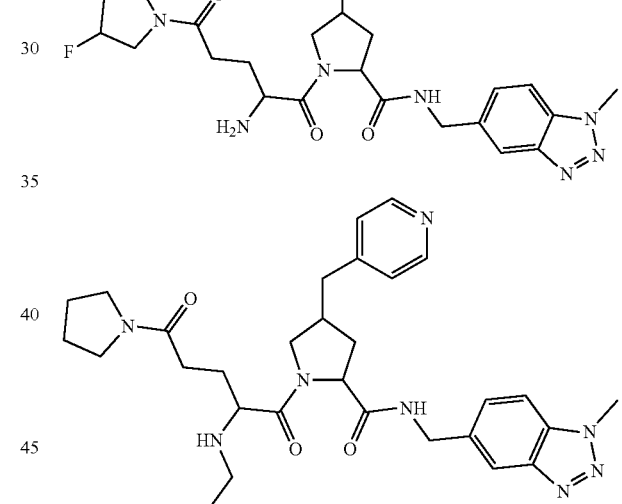
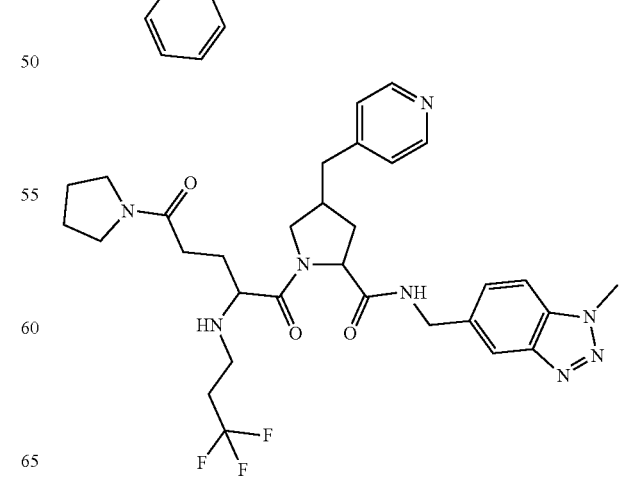

35
-continued
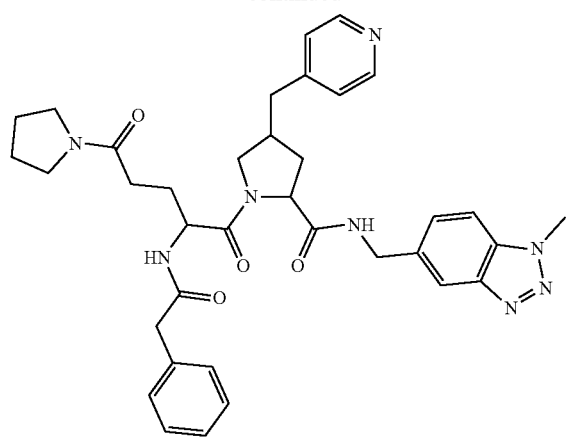
36
-continued
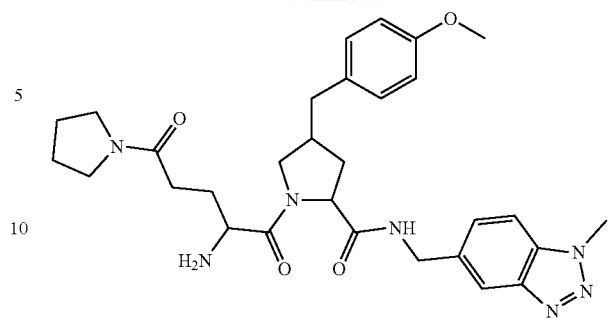
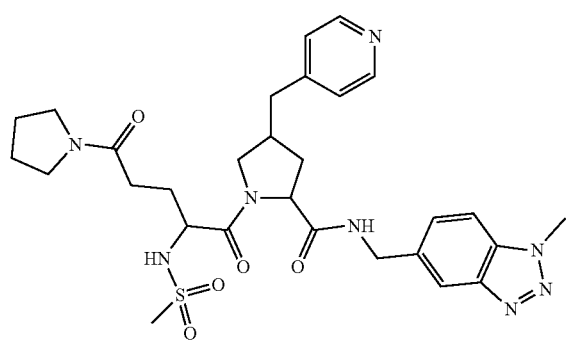
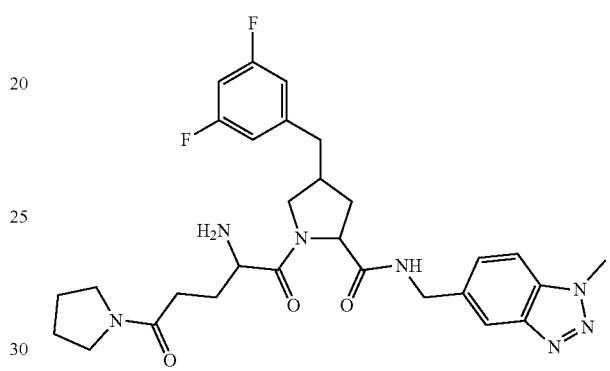
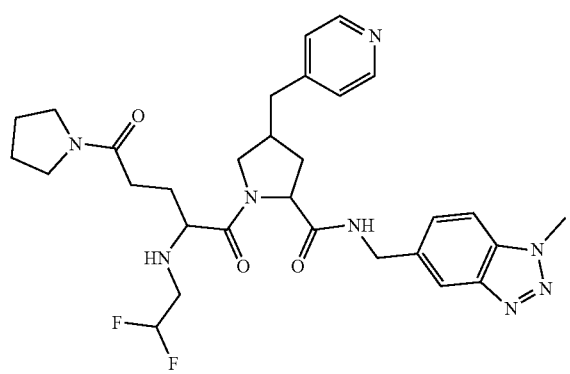
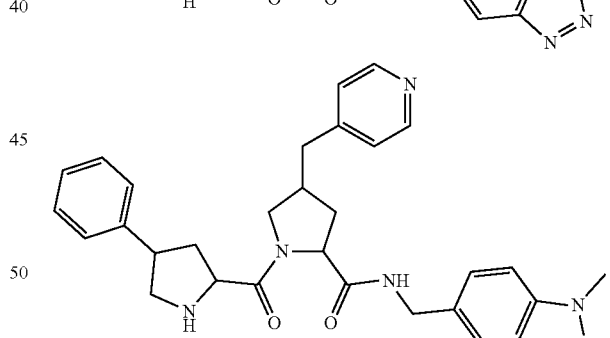
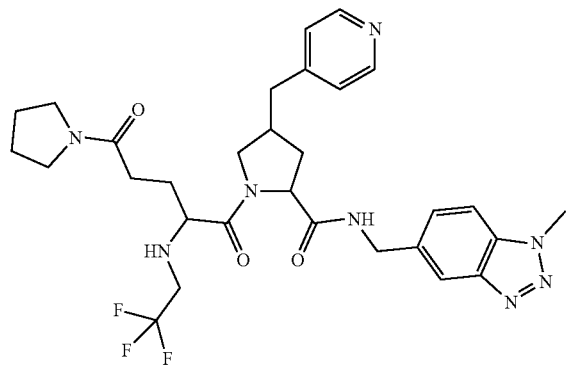
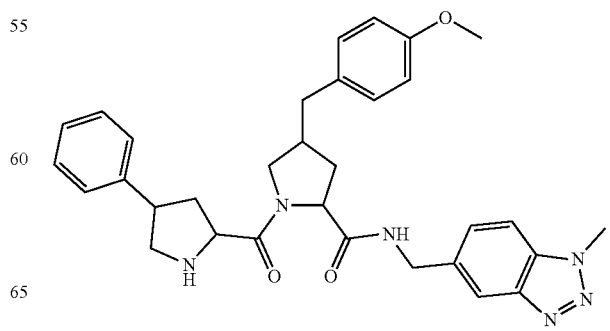

37
-continued
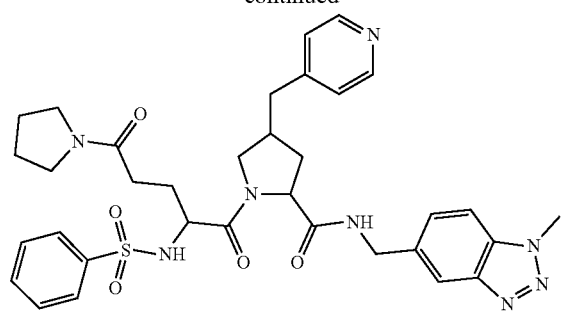
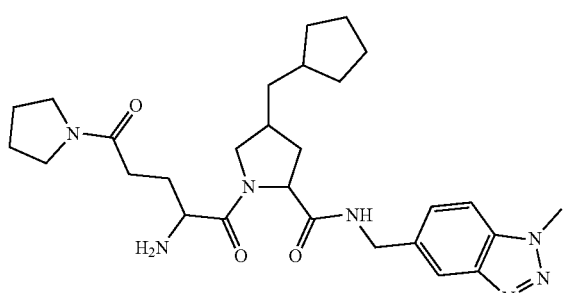
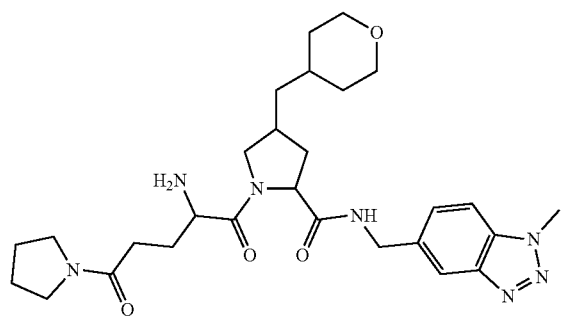
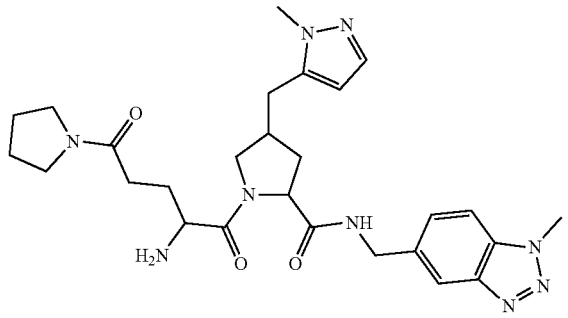
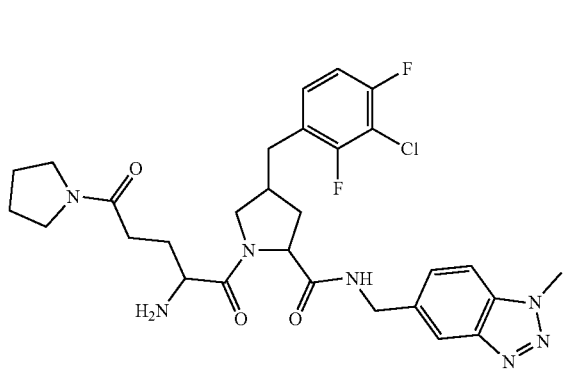
38
-continued
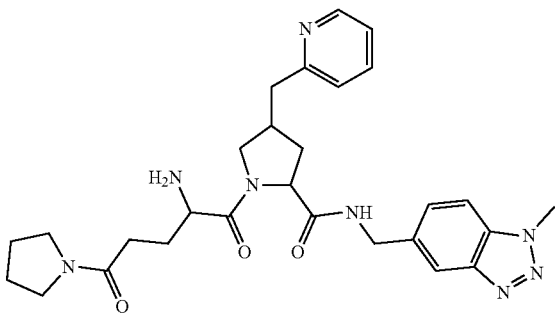
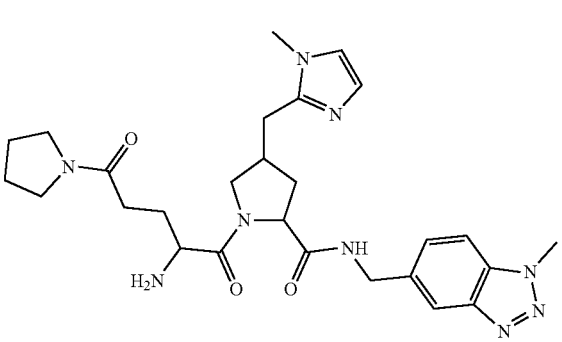
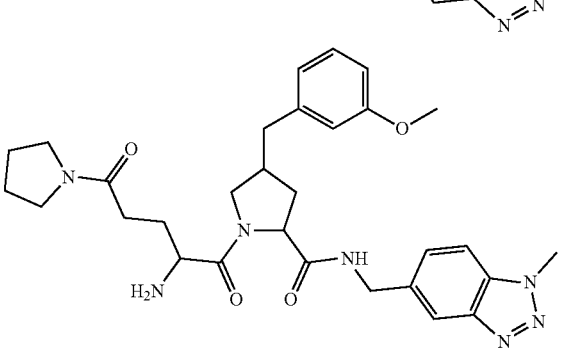
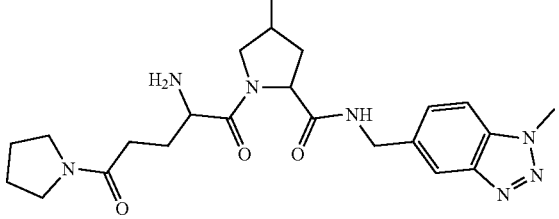
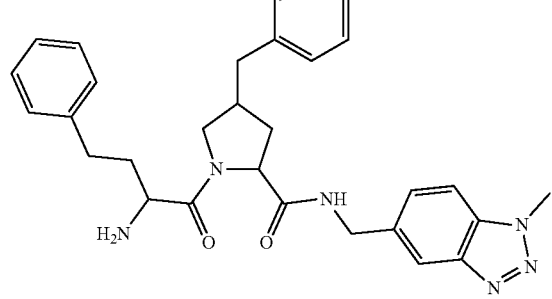

-continued

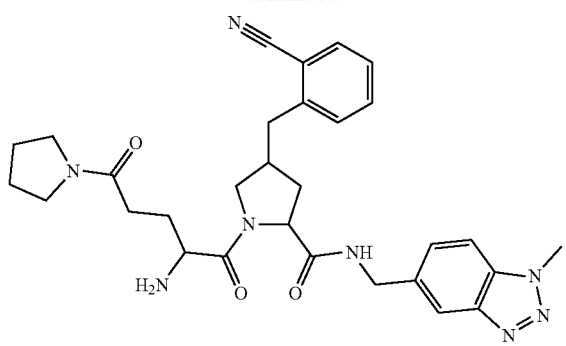
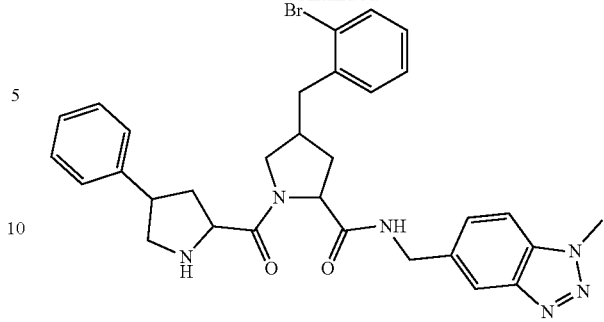
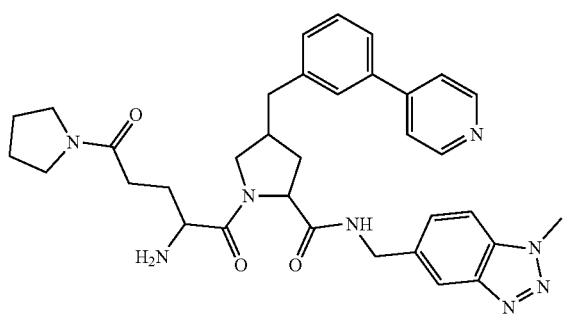
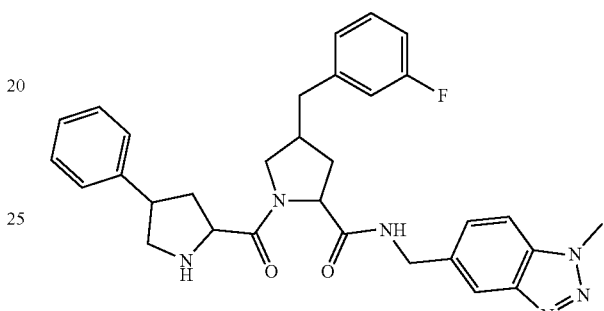
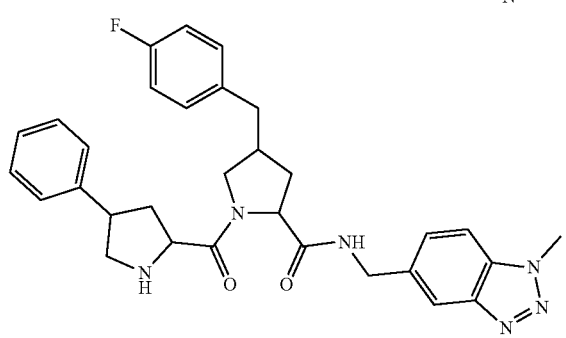
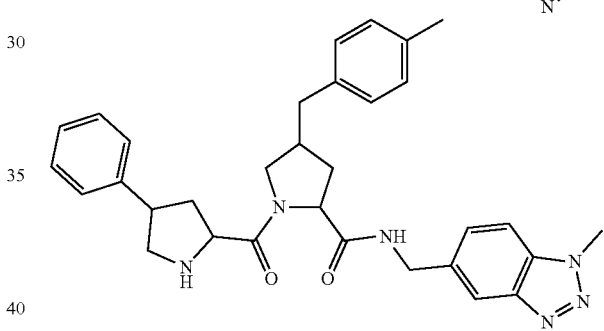
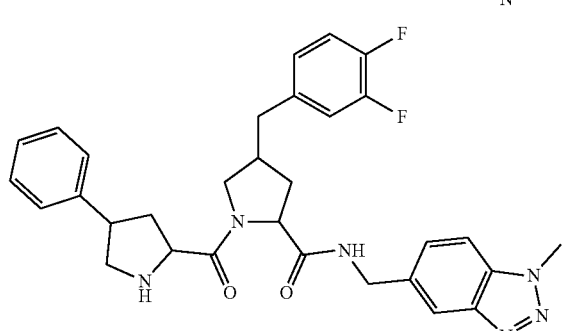
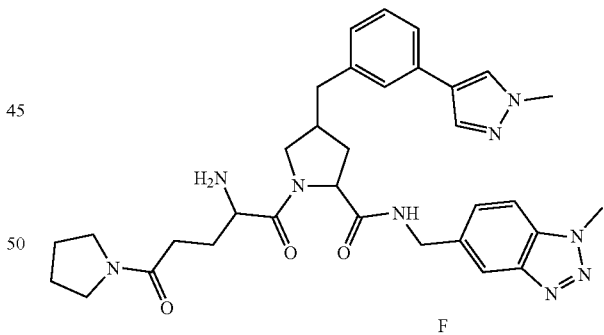
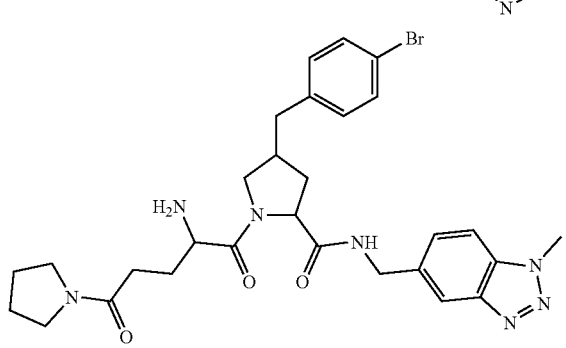
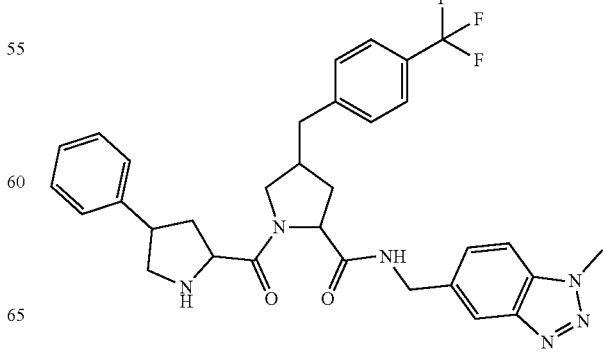

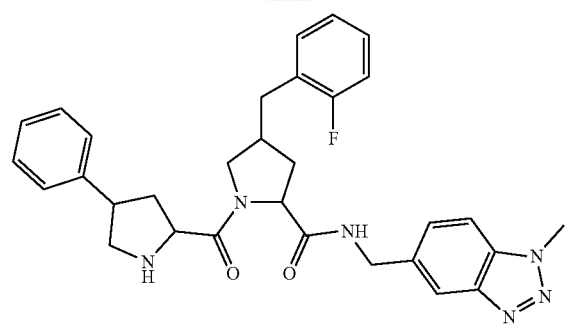
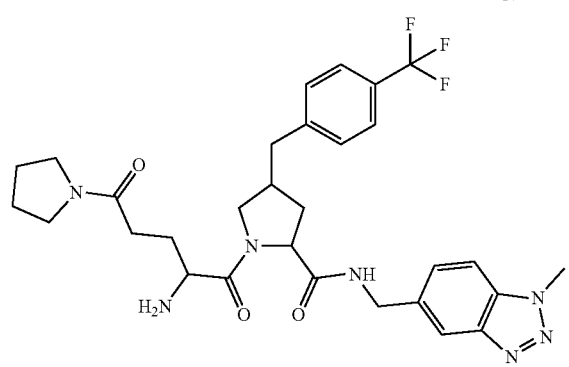
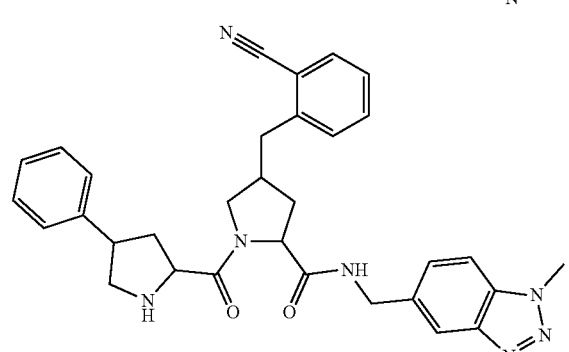
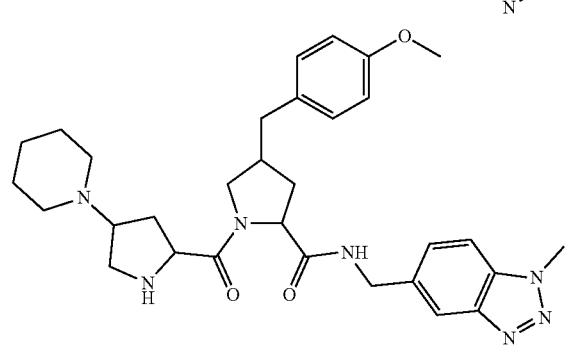
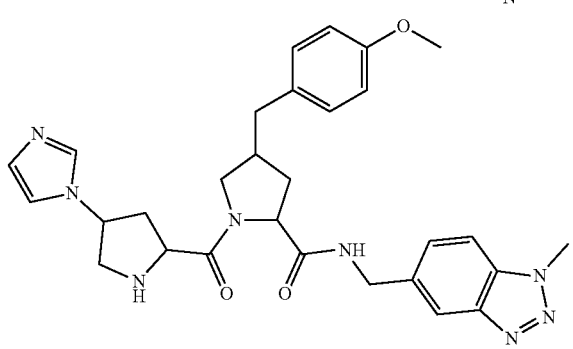
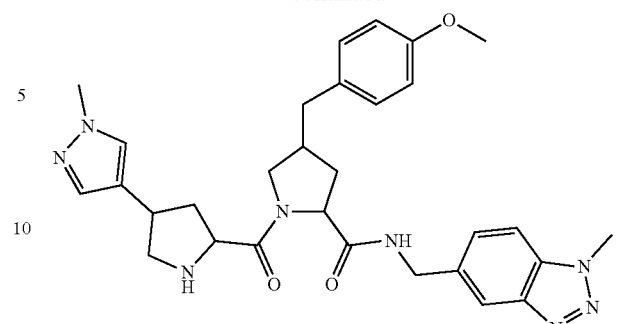
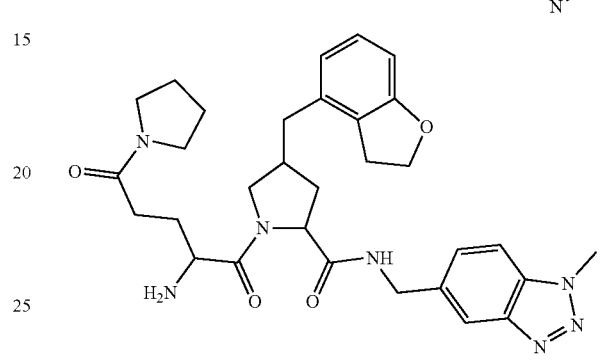
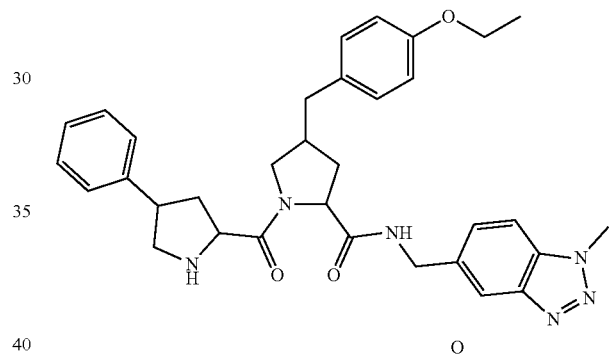
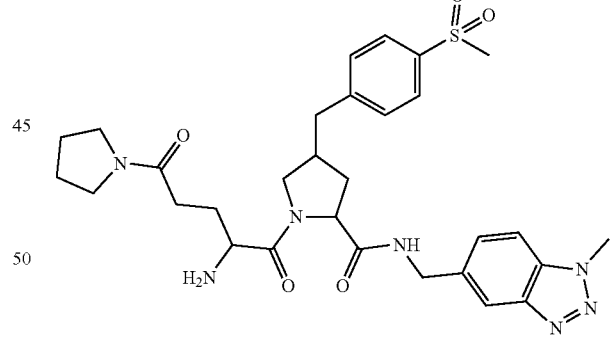
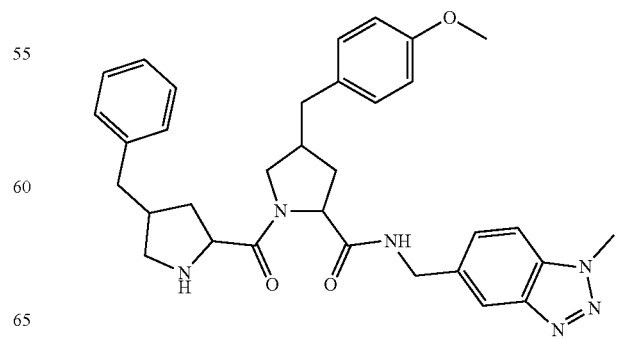

45
-continued
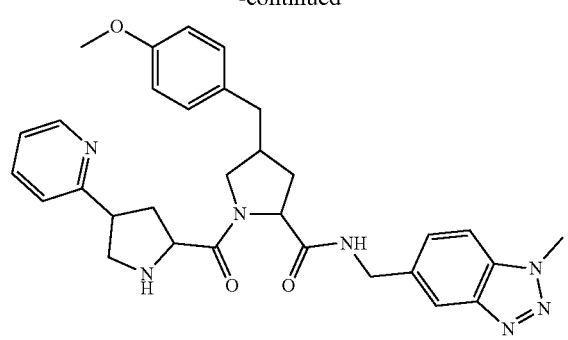
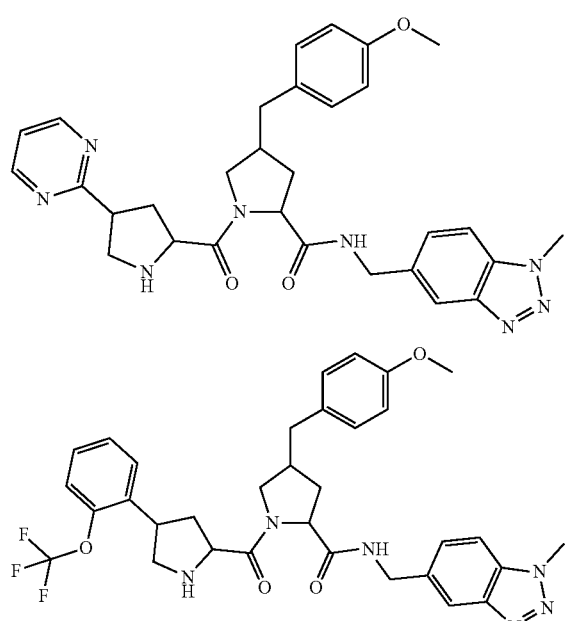
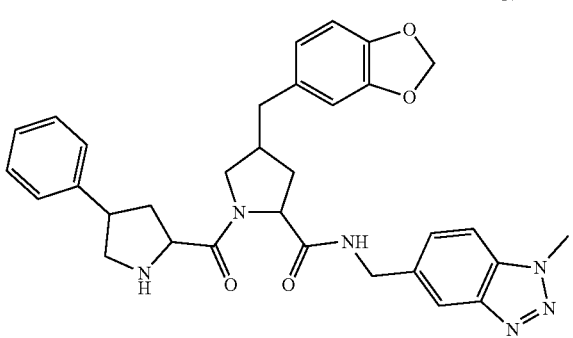
46
-continued
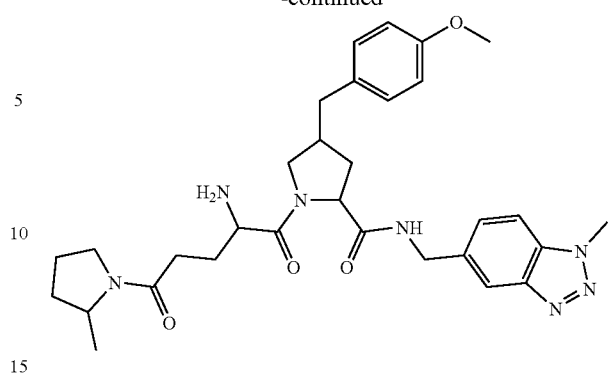
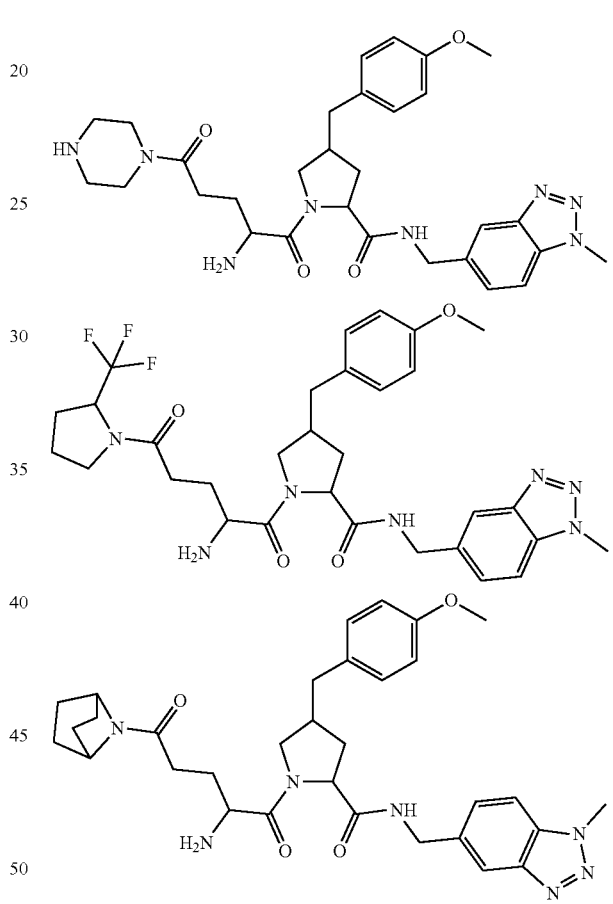
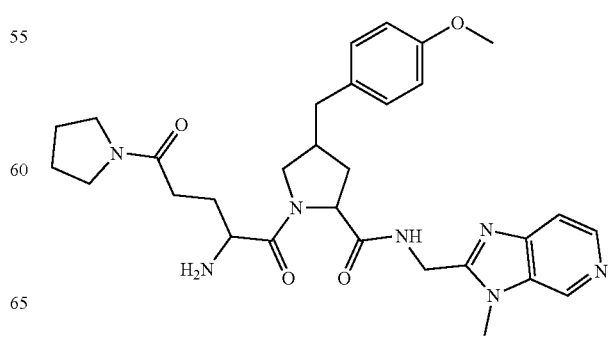

47
-continued
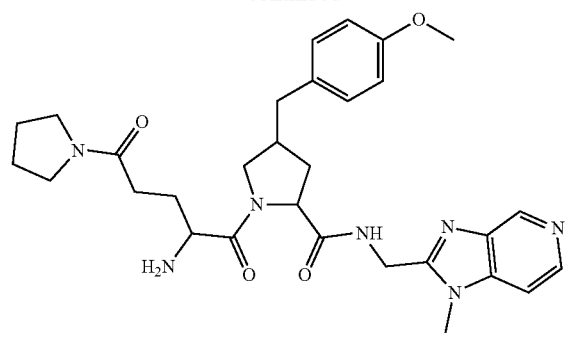
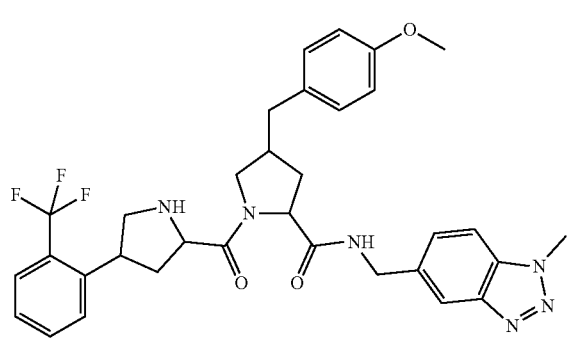
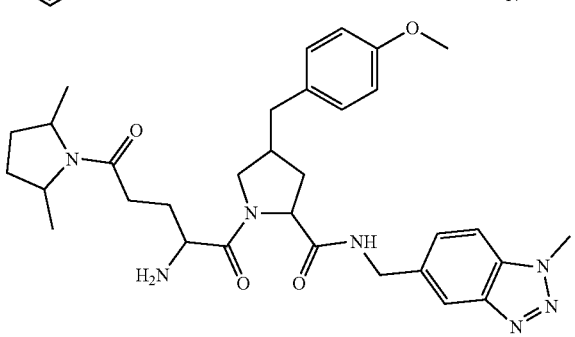
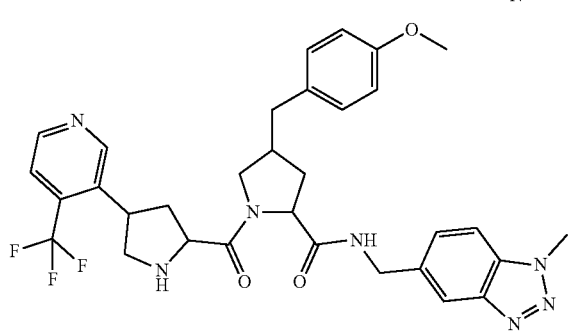
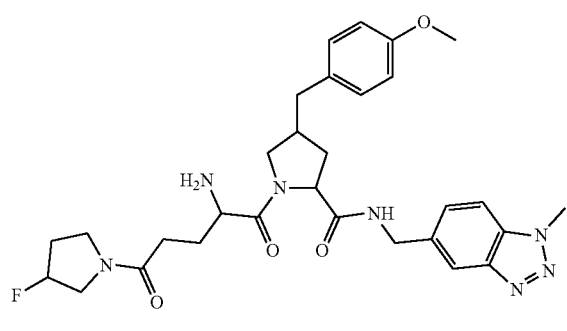
48
-continued
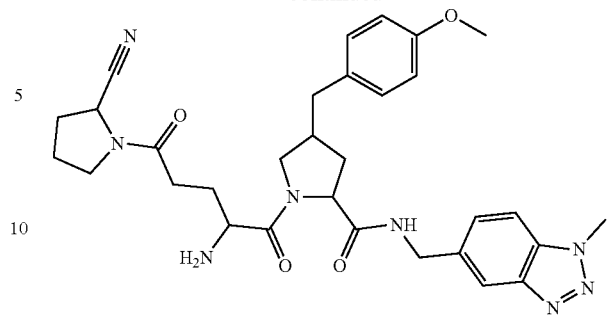
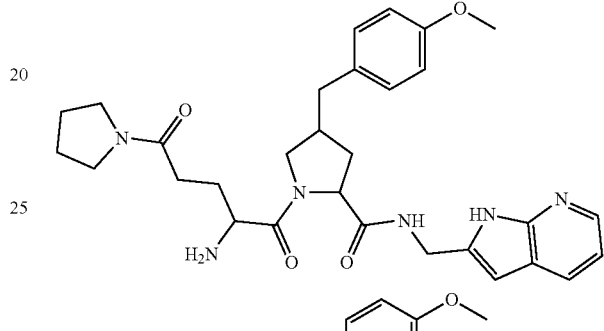
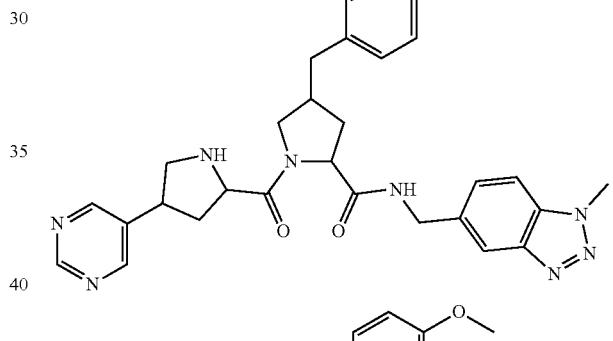
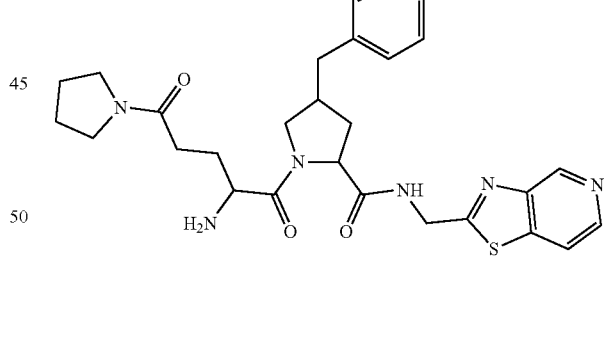
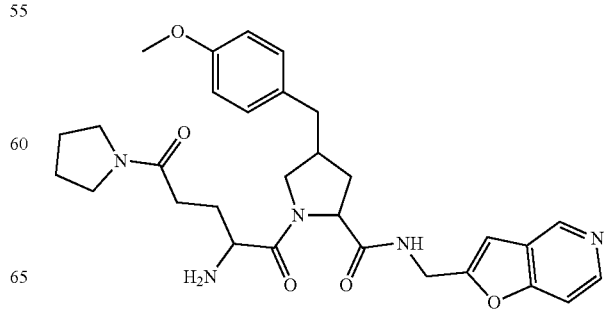

49
-continued

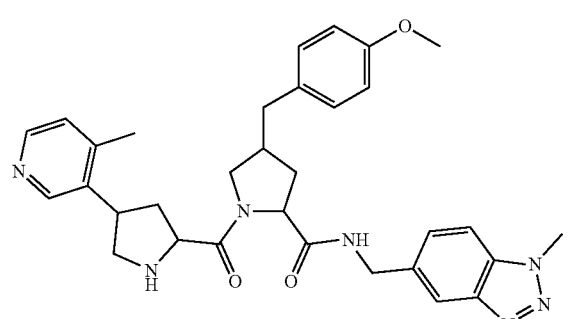
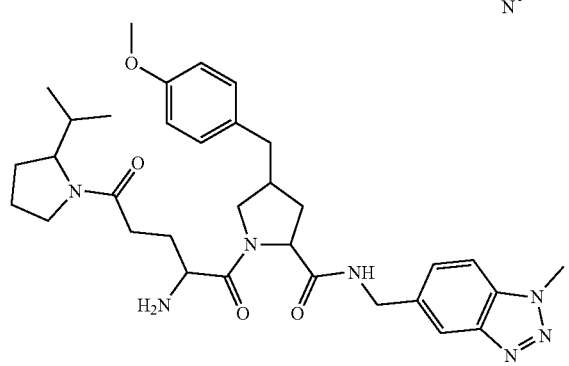
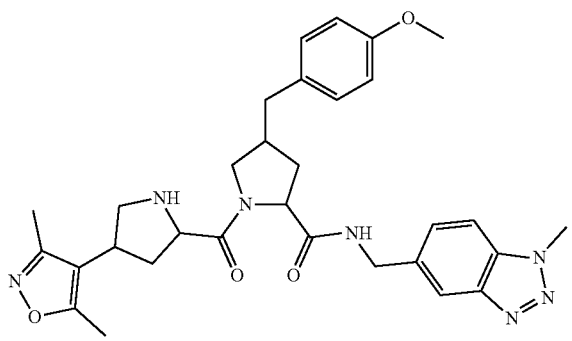
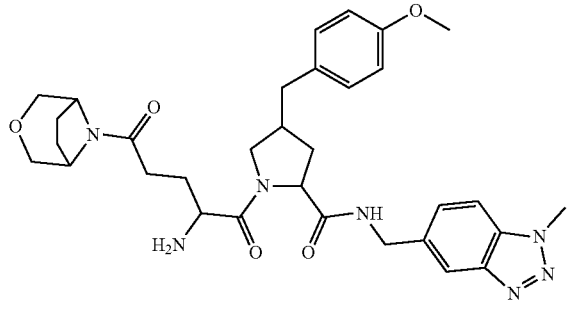
50
-continued
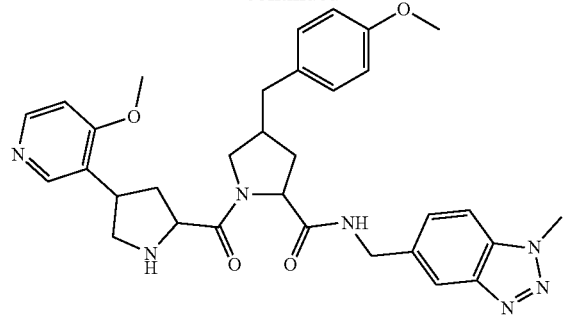
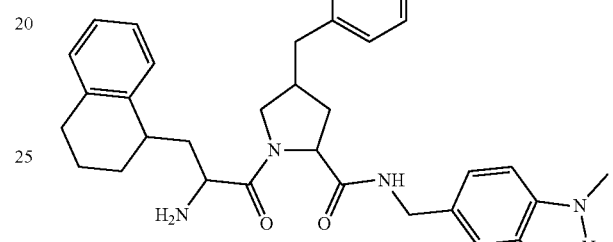
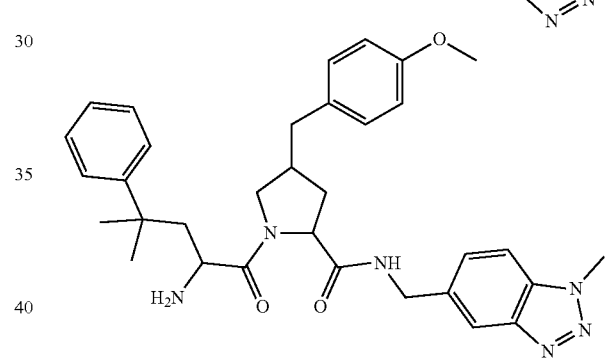
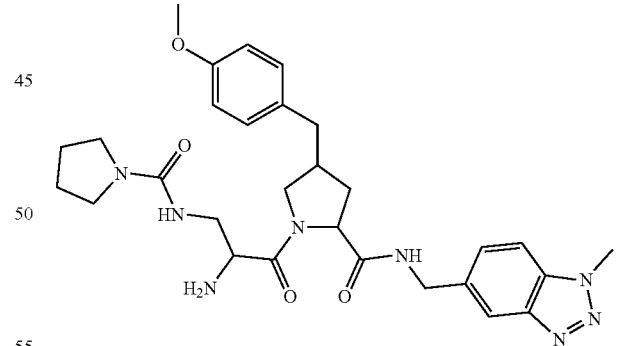
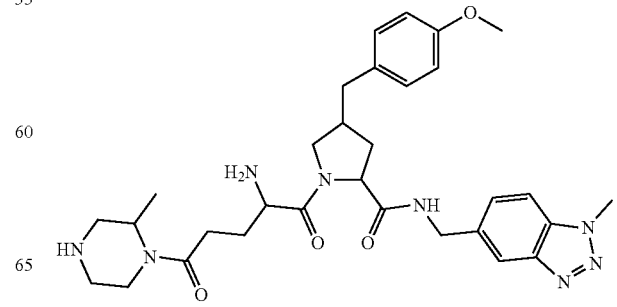

51
-continued
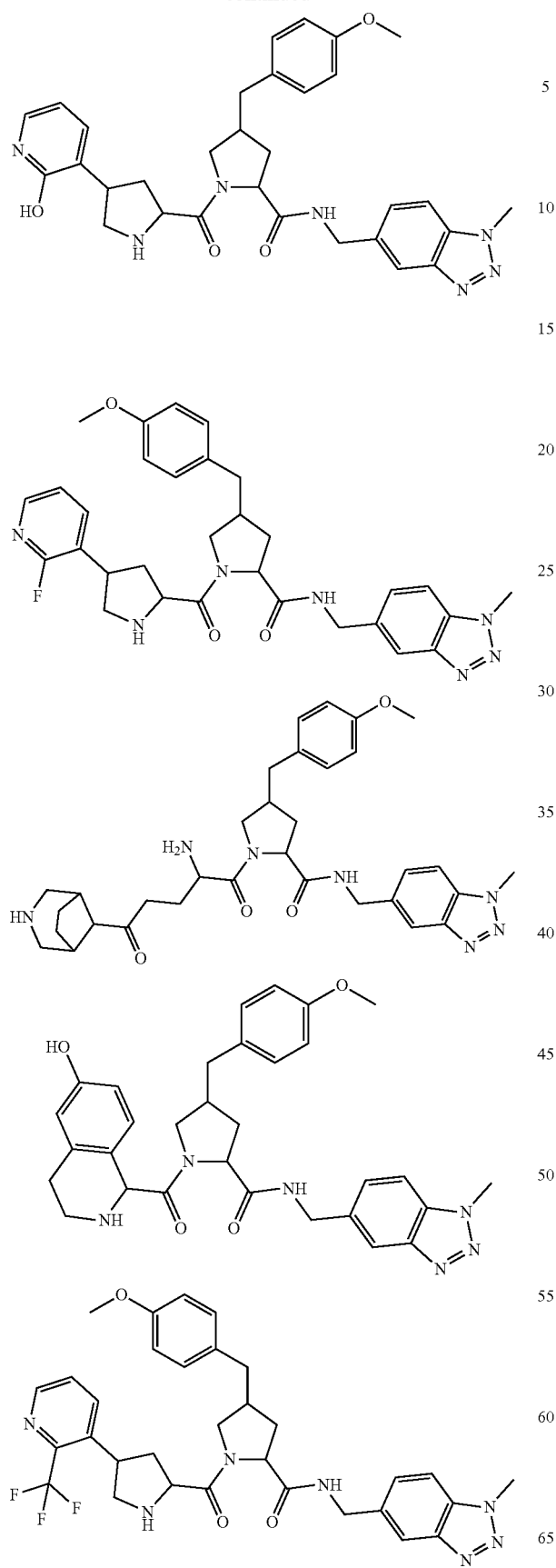
52
-continued
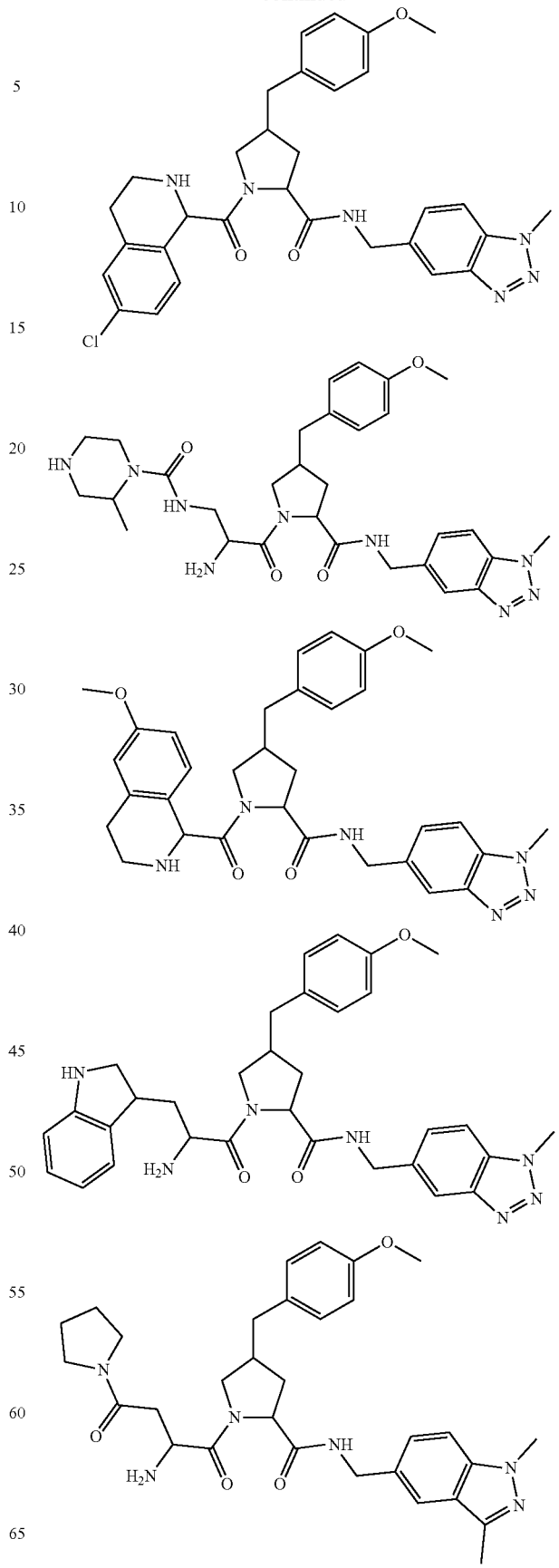

53
-continued
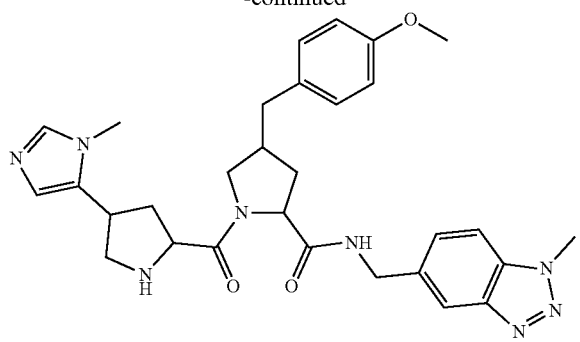
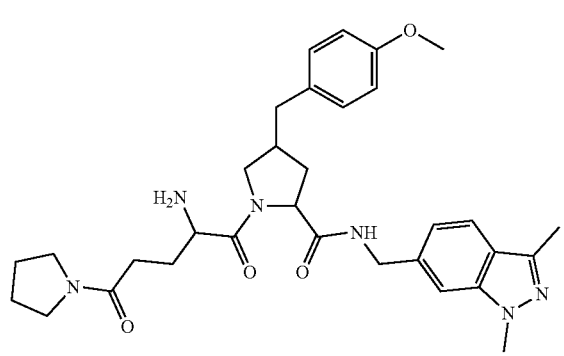
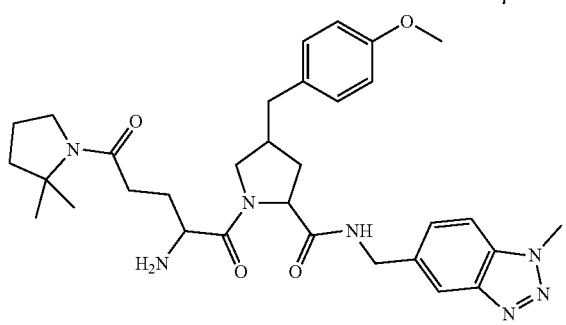
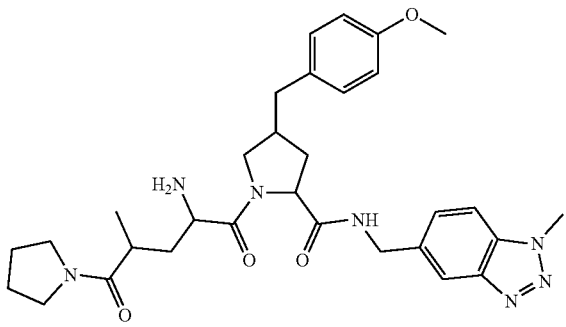
54
-continued
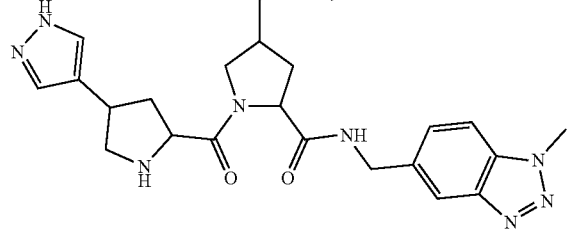
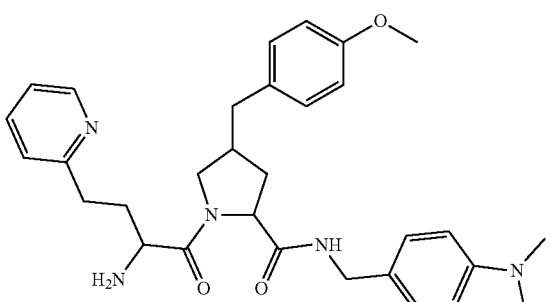
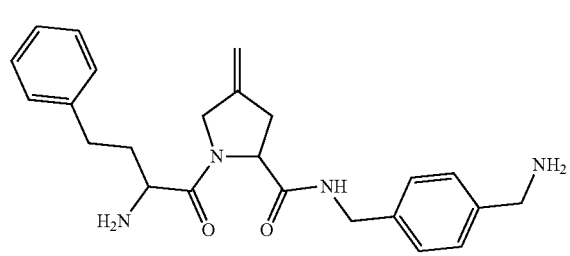
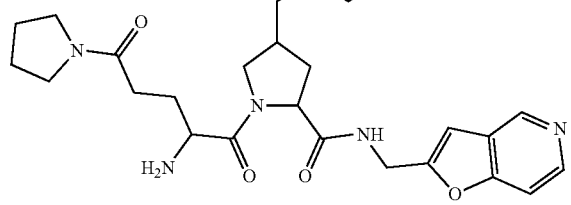

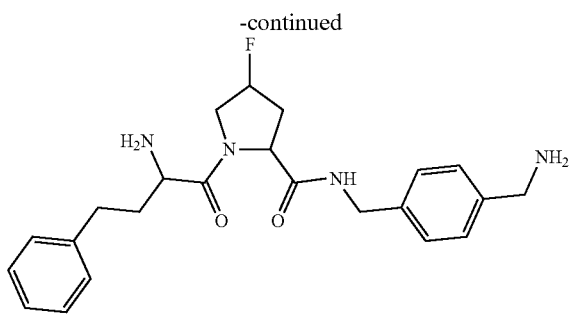
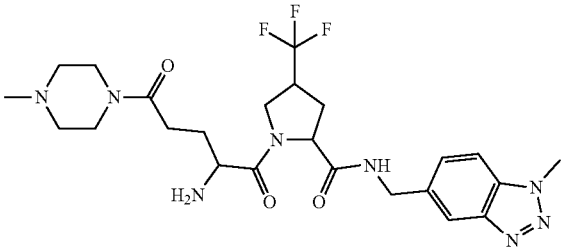
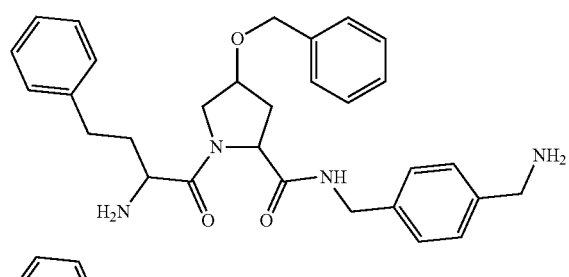
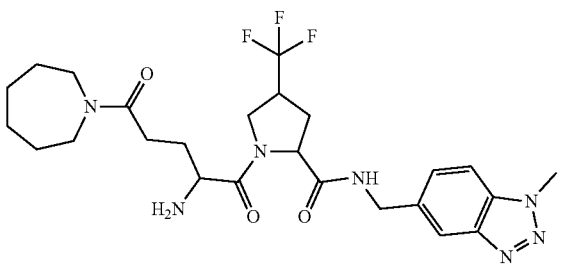
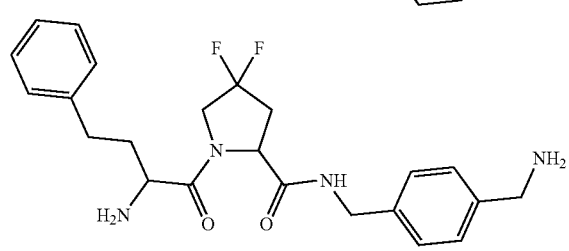
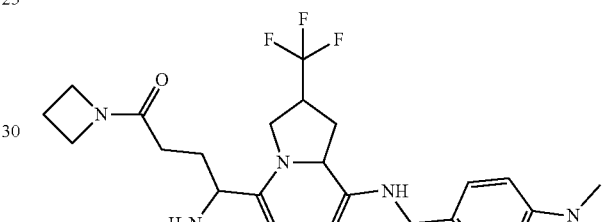
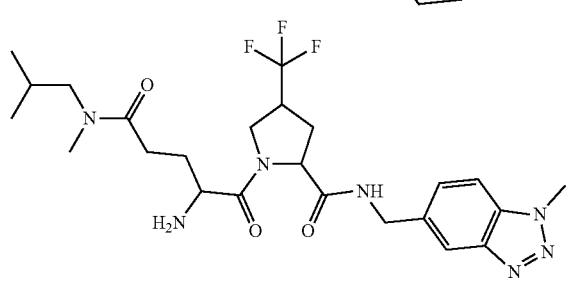
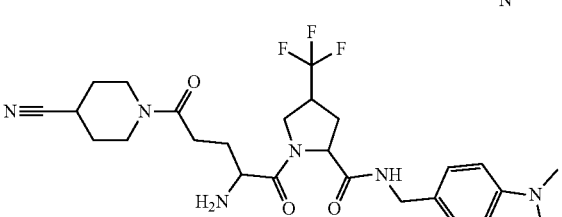
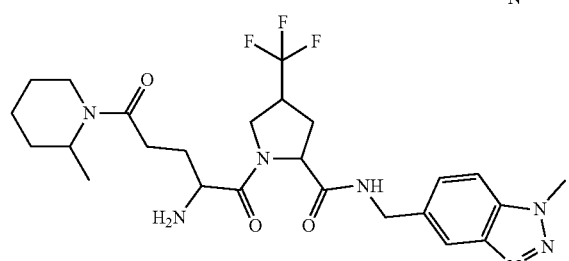
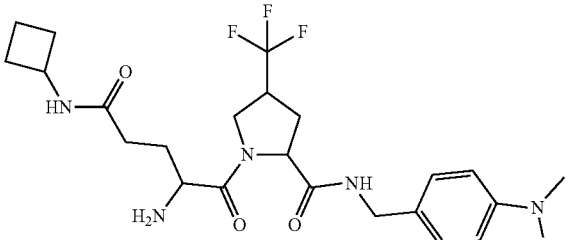
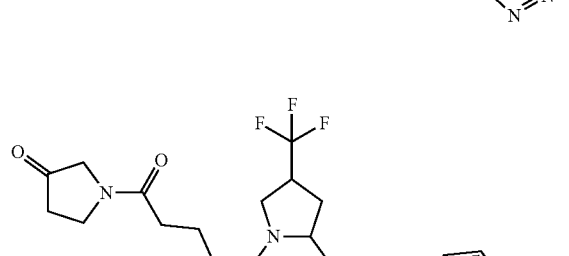
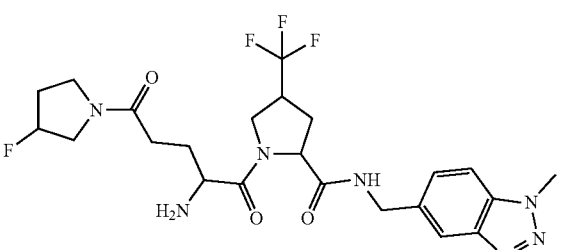

57
-continued
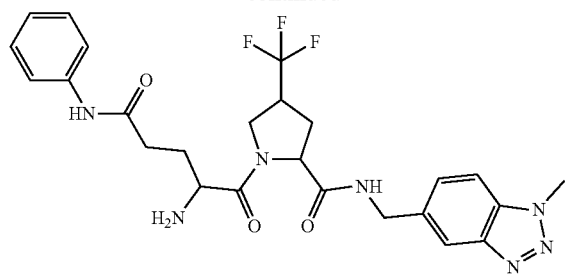
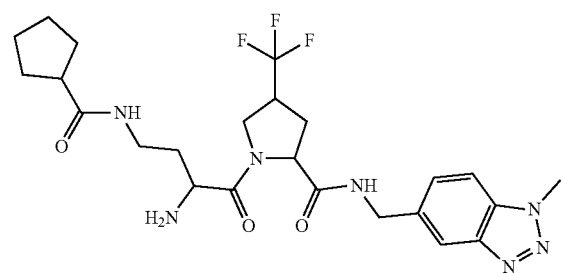
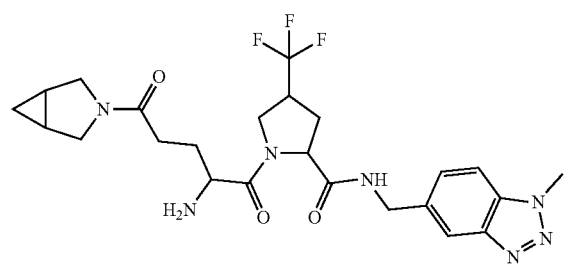
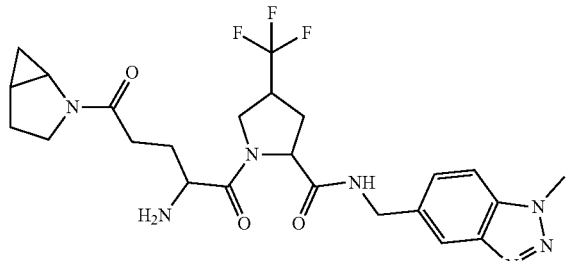
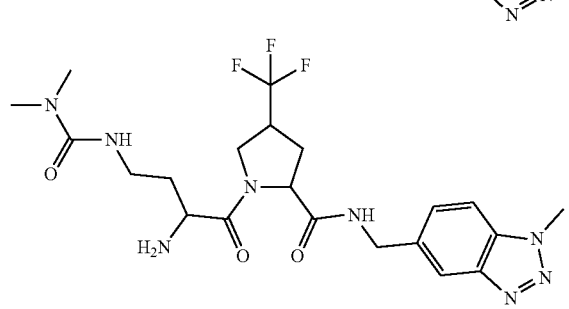
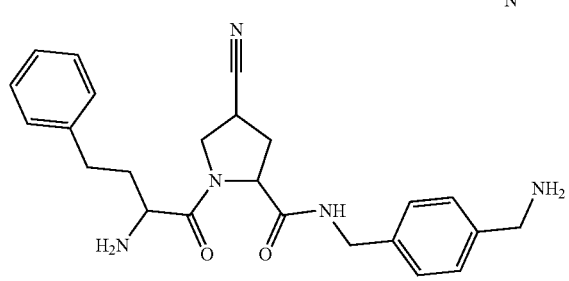
58
-continued
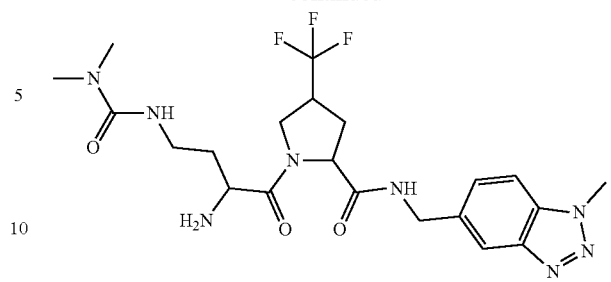
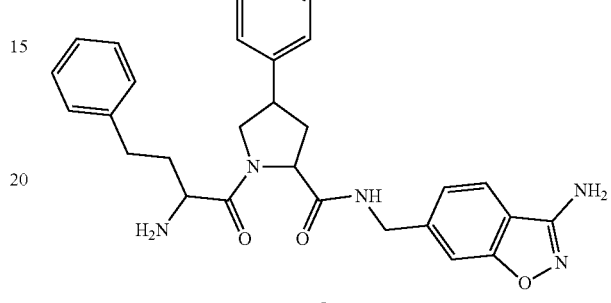
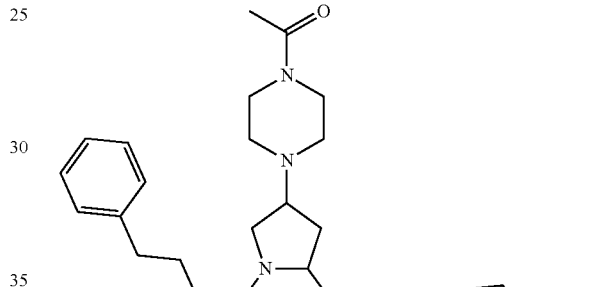
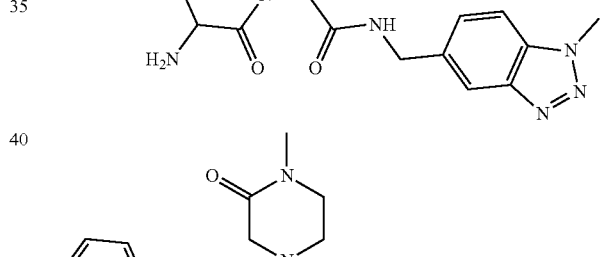
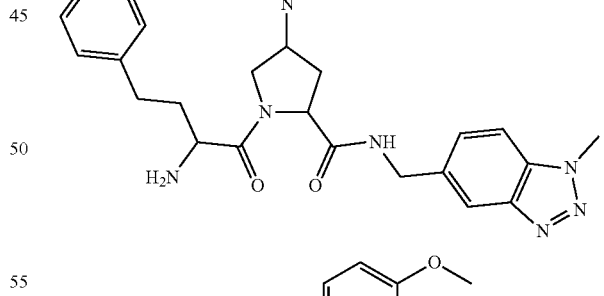
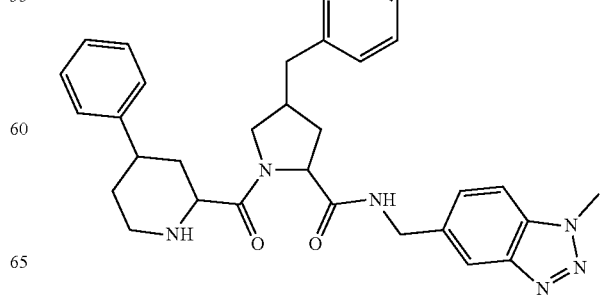

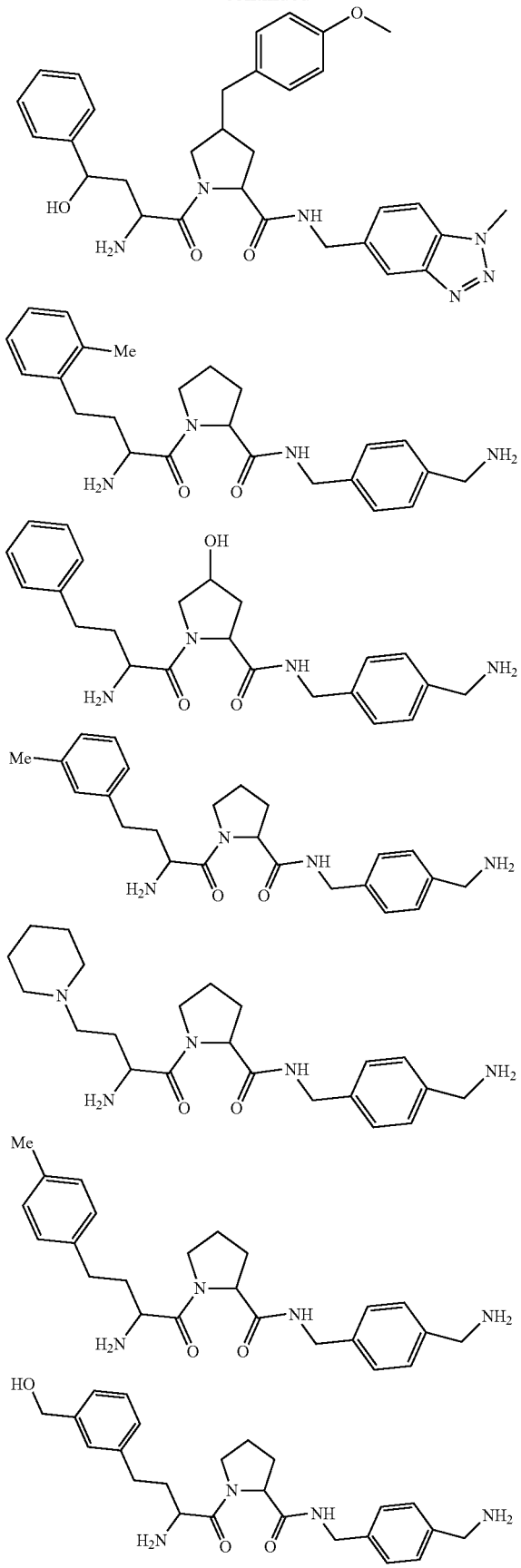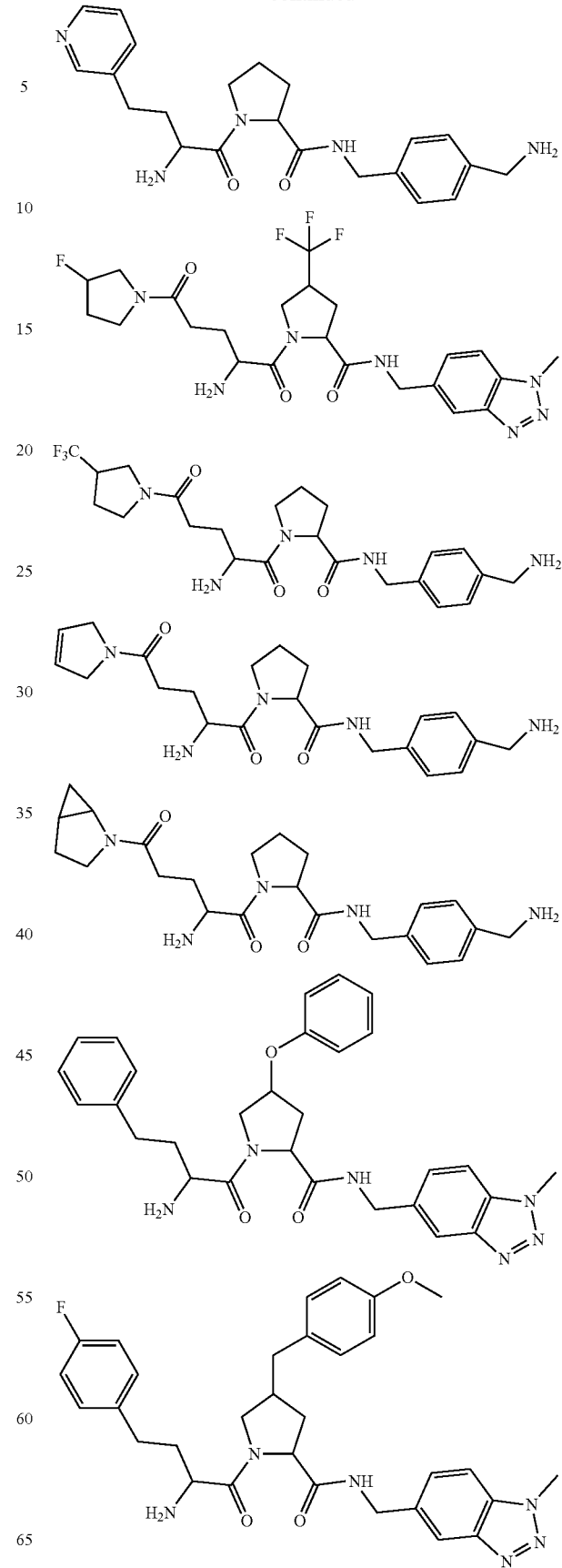

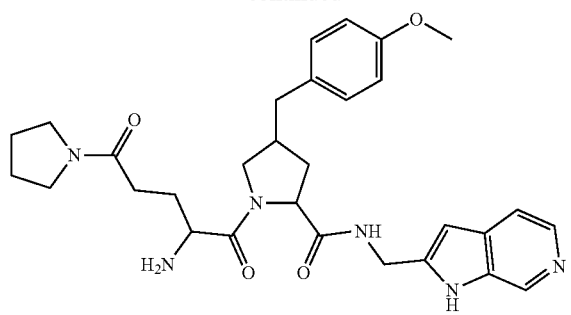
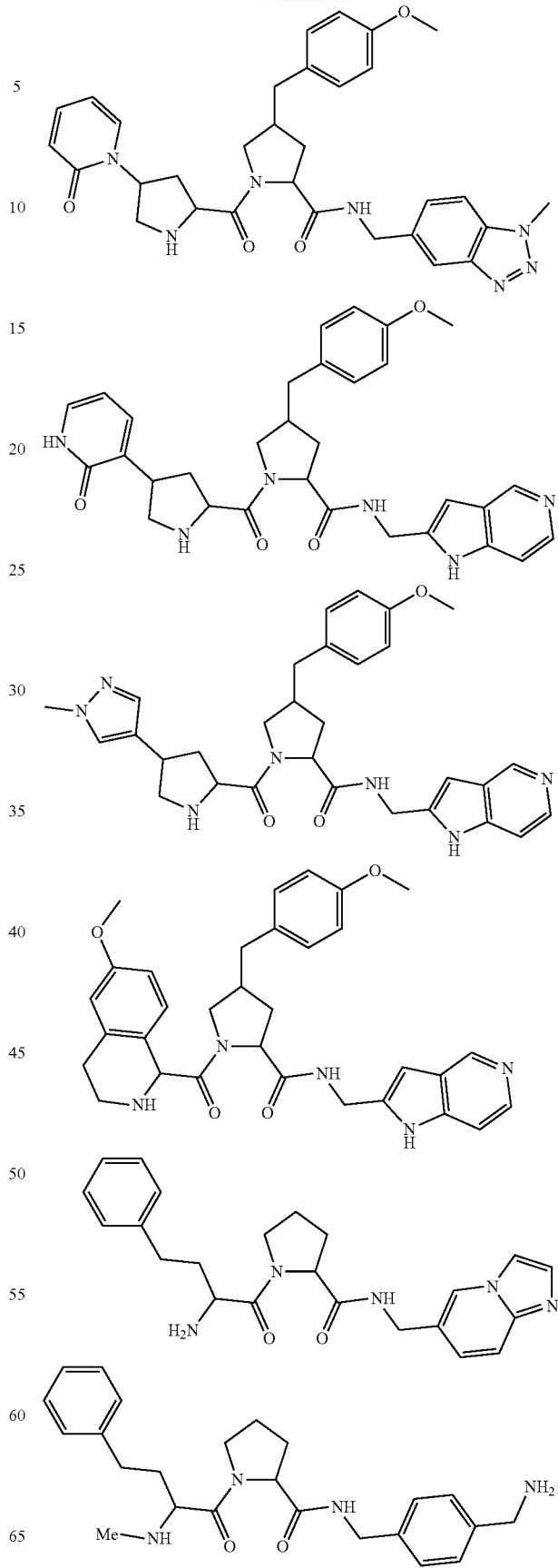

63
-continued
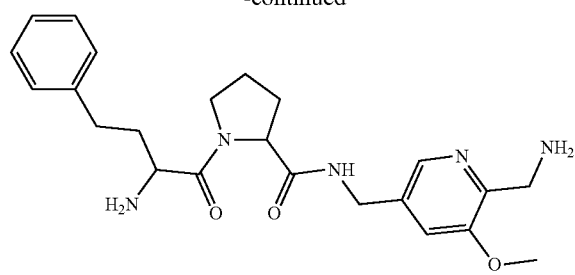
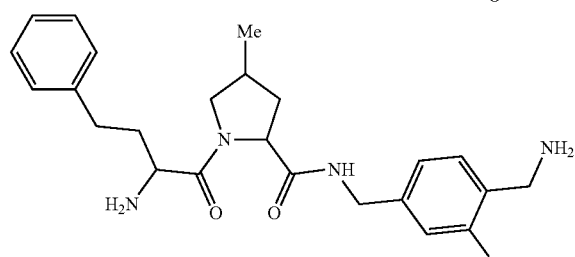
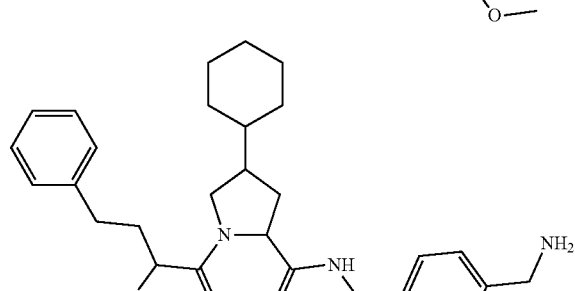
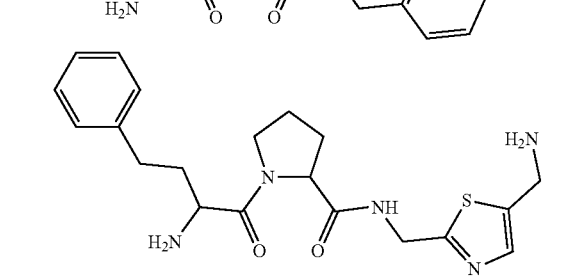
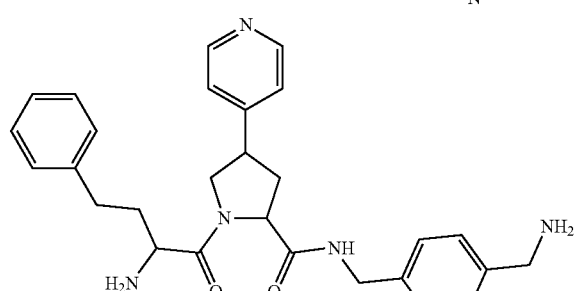
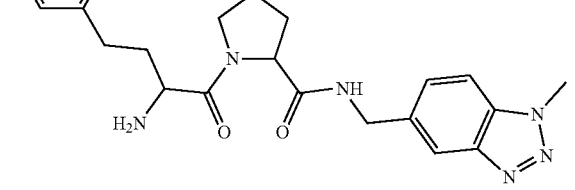
64
-continued
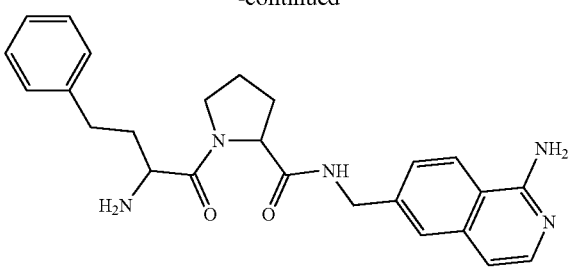
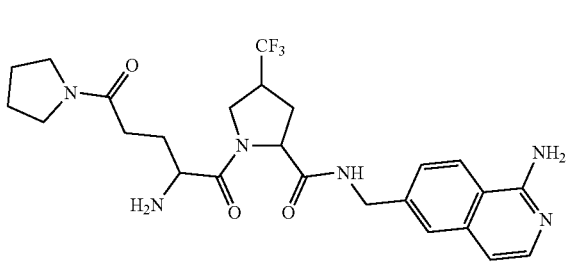
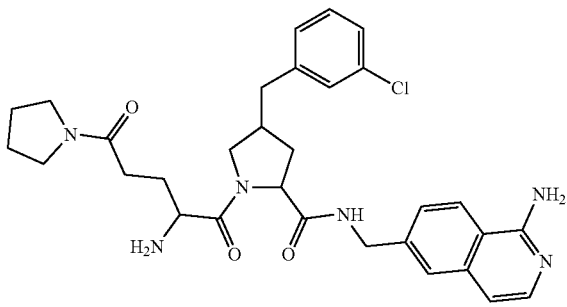
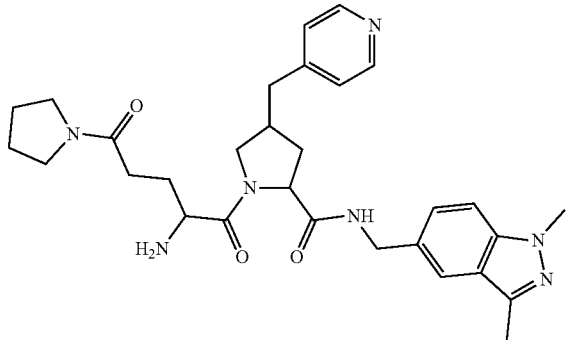
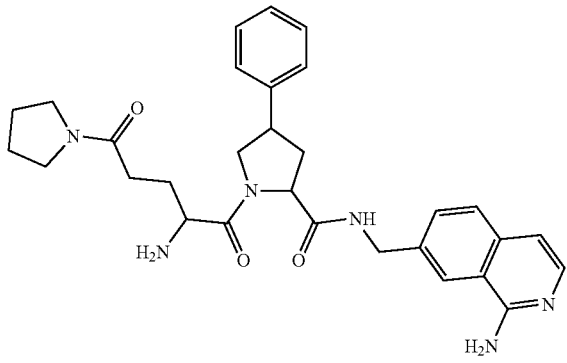

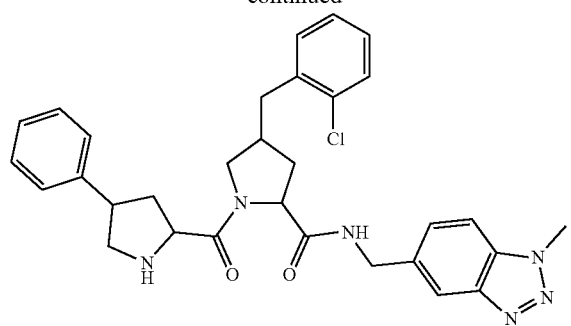
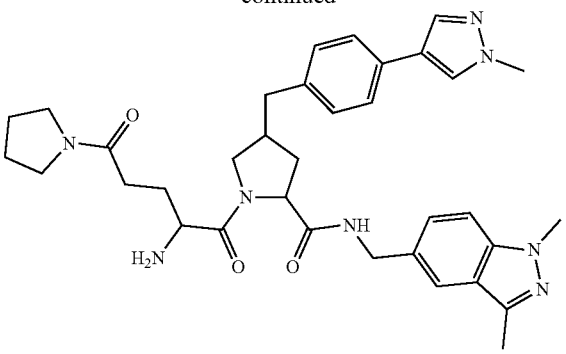
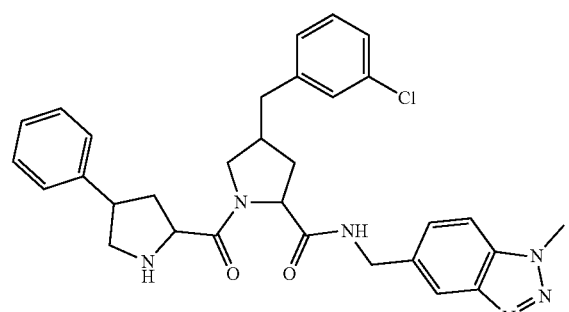
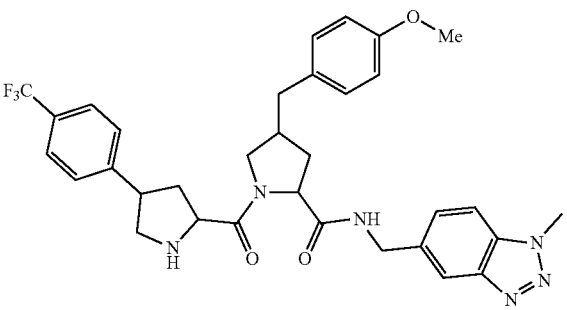
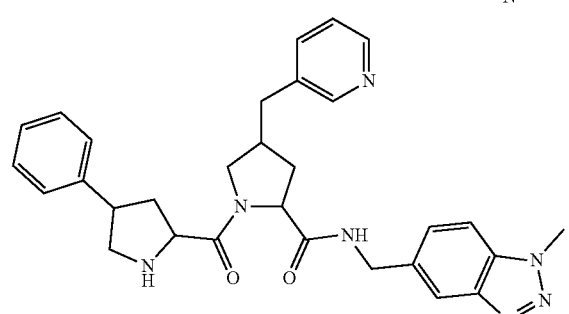
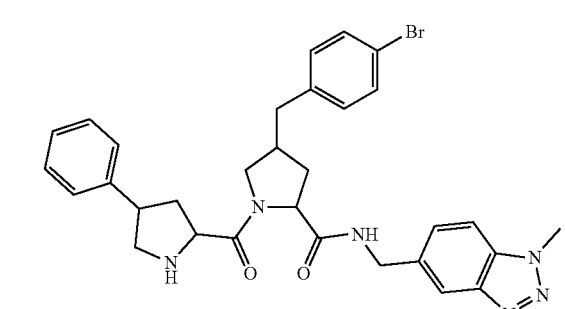
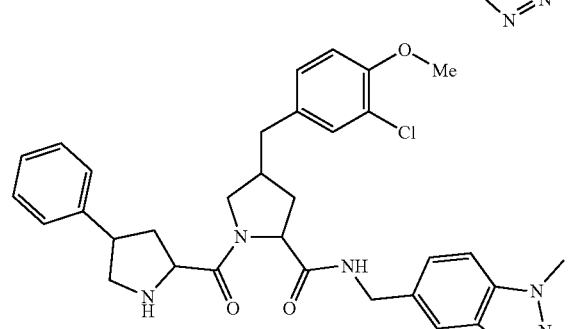
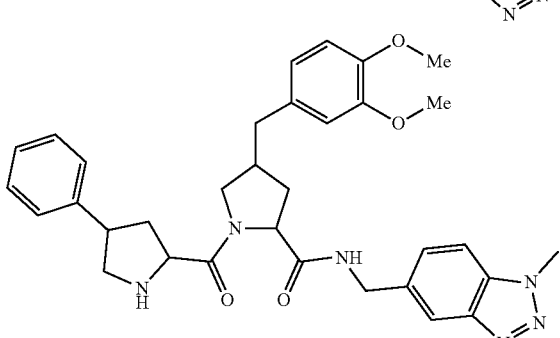
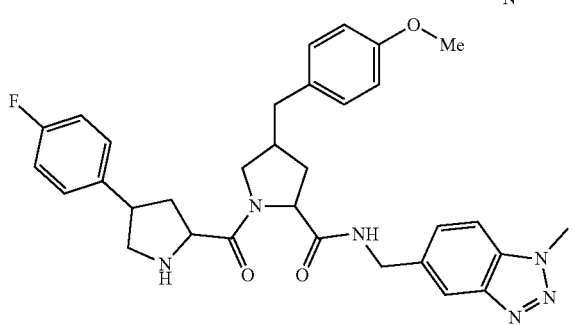
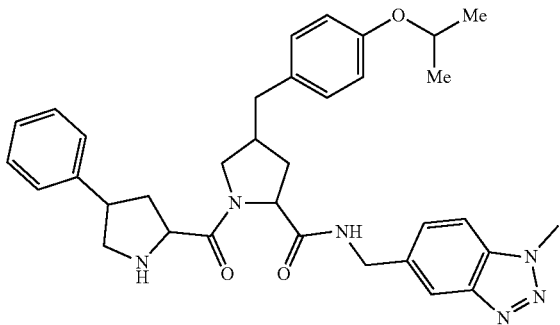

67
-continued
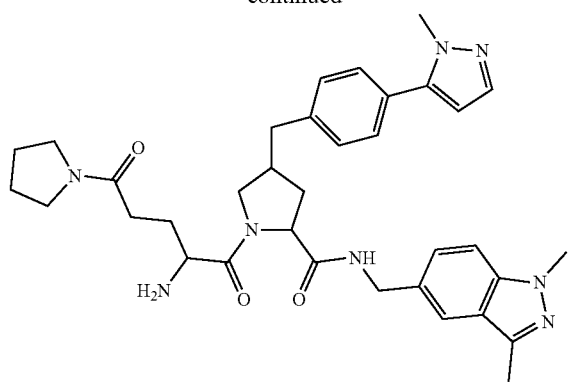
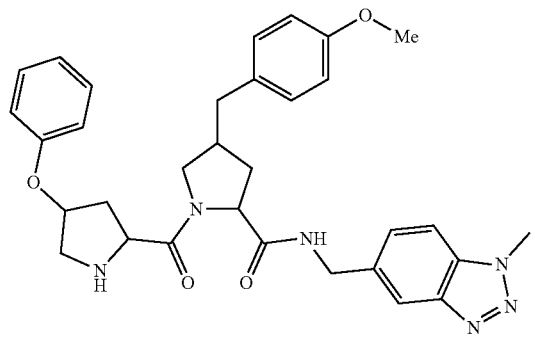
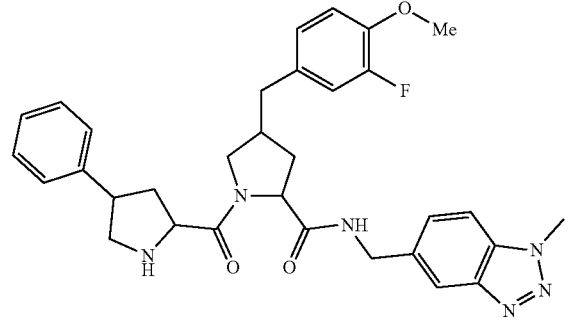
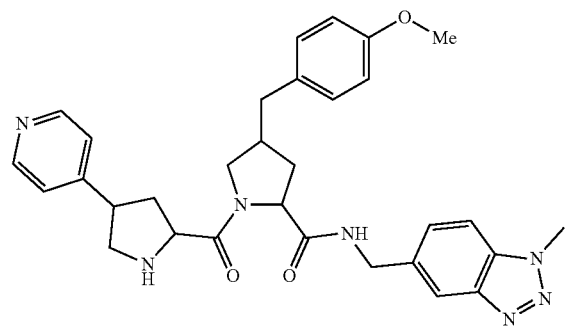
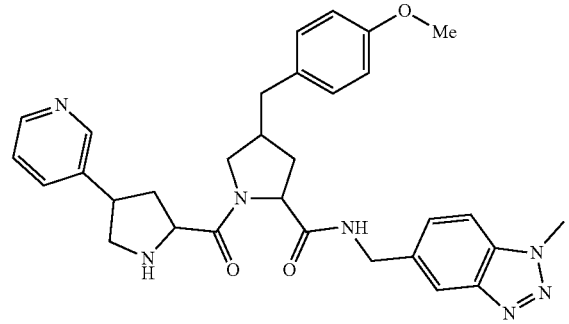
68
-continued
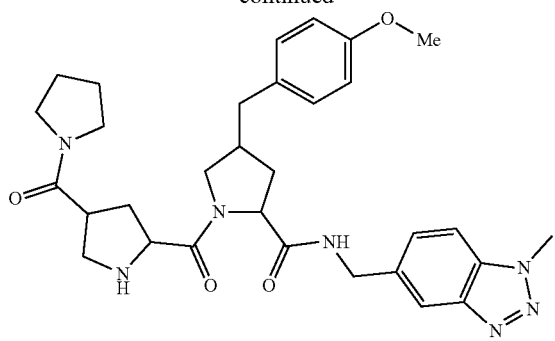
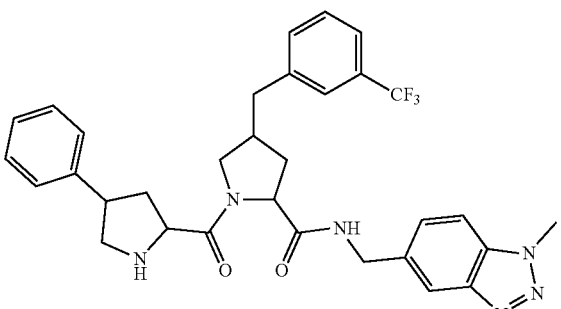
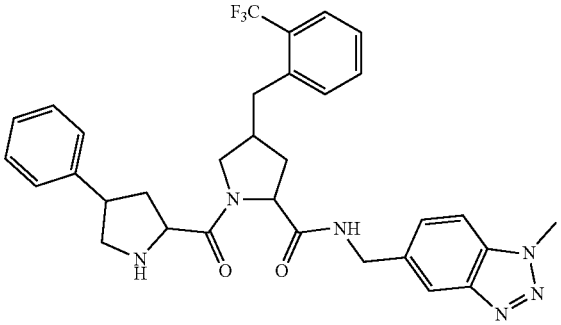
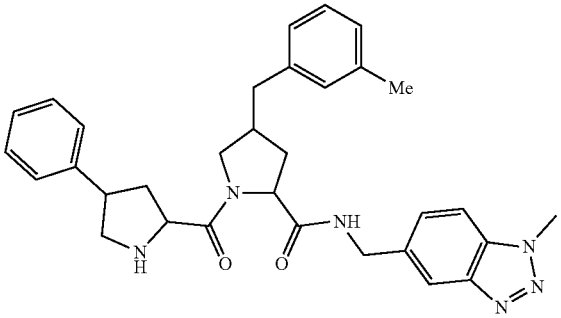
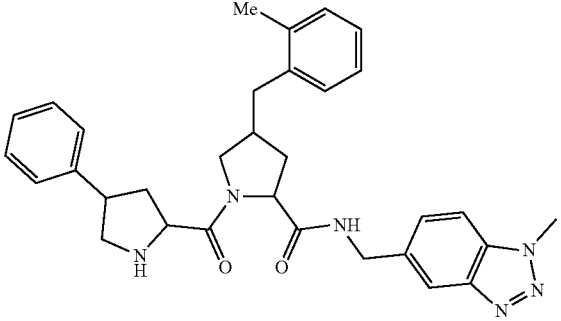

69
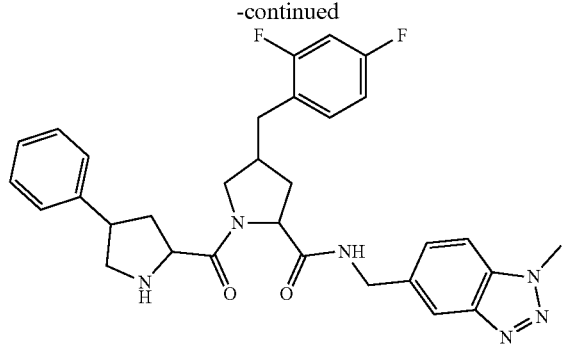
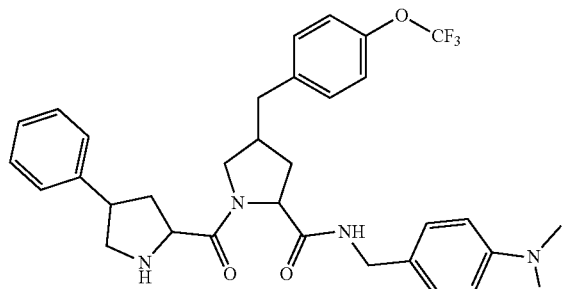
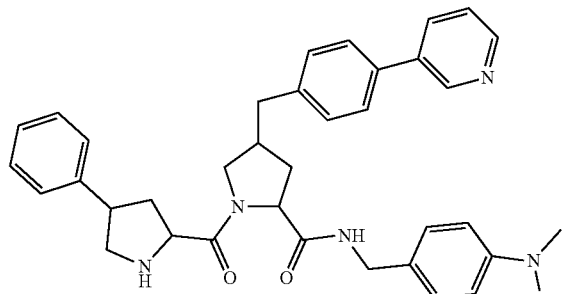
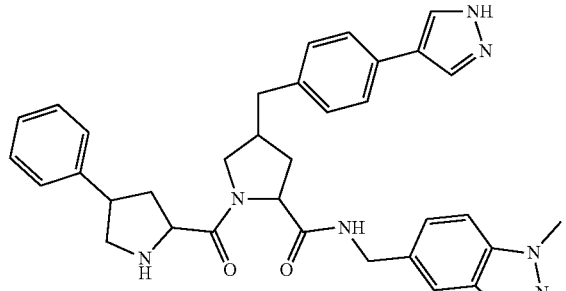
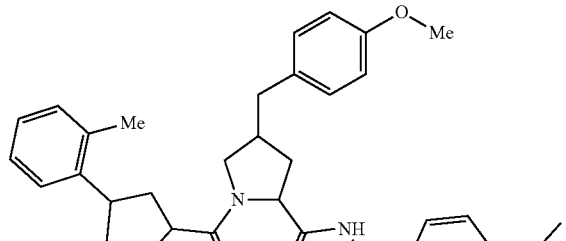
70
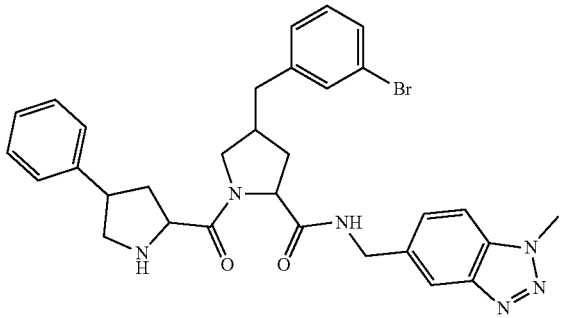
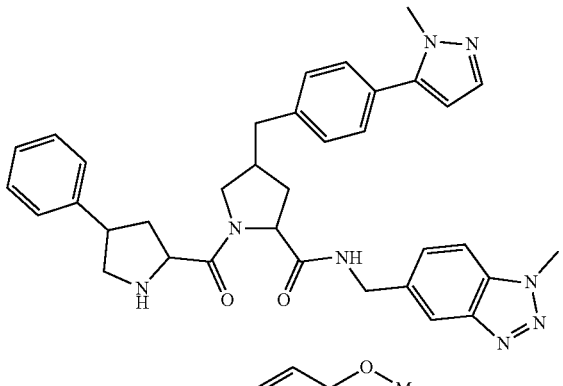
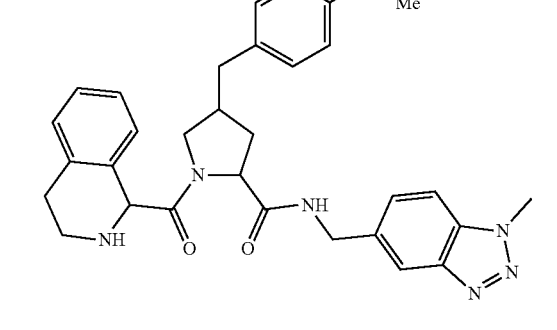
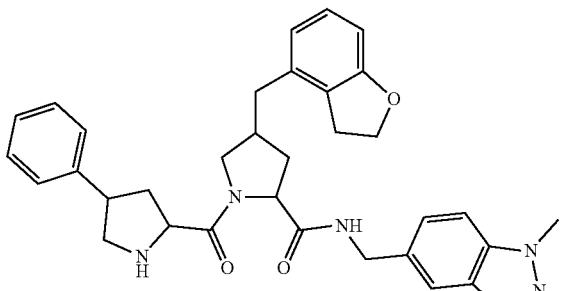
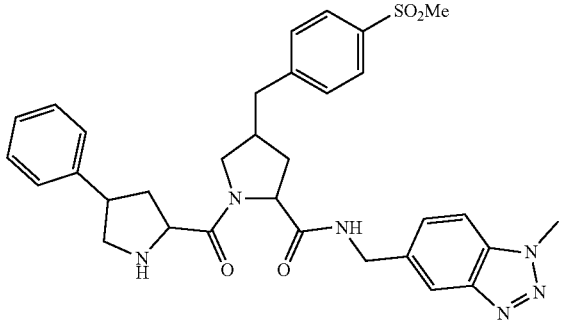

71
-continued
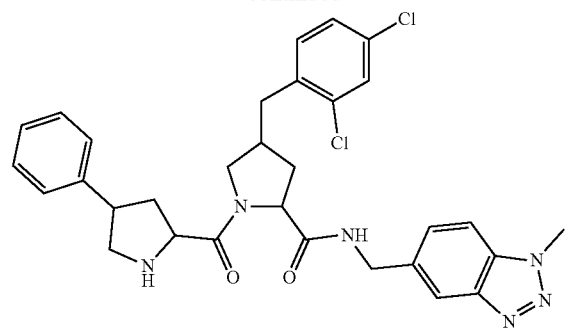
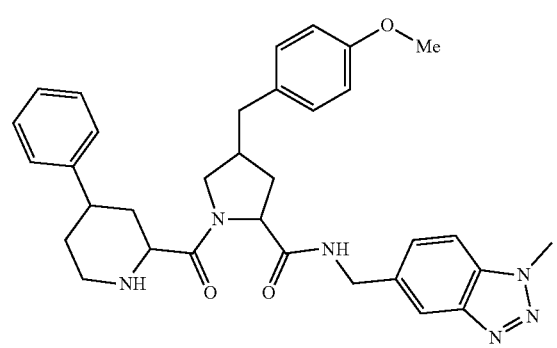
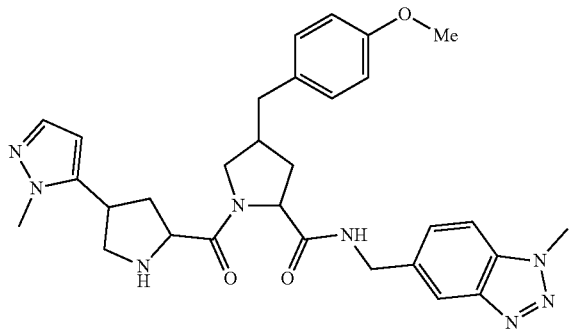
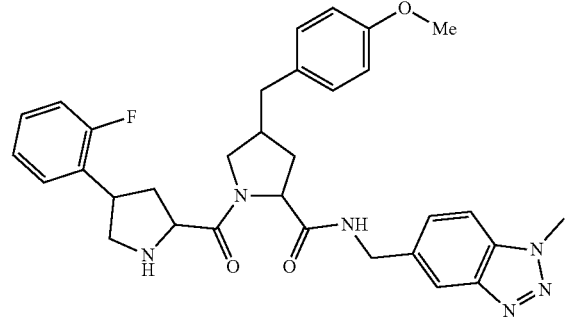
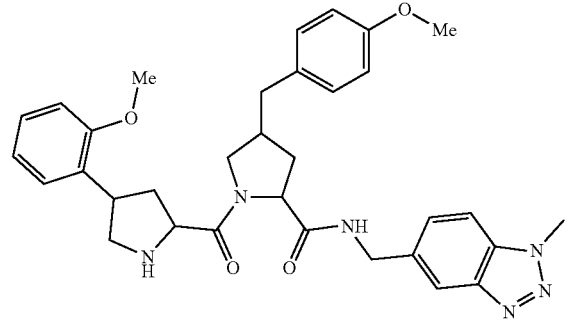
72
-continued
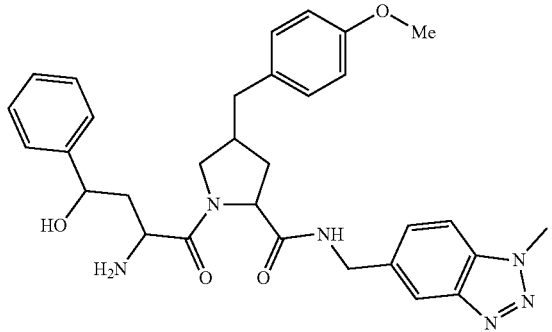
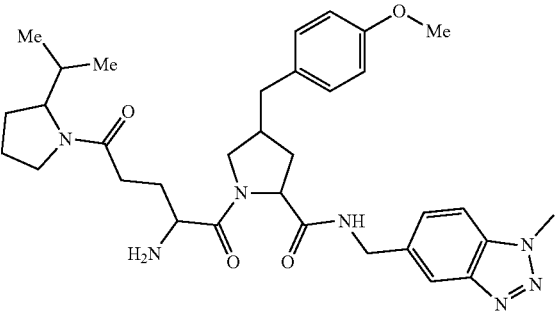
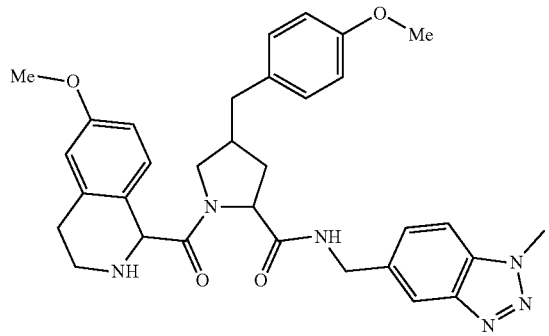
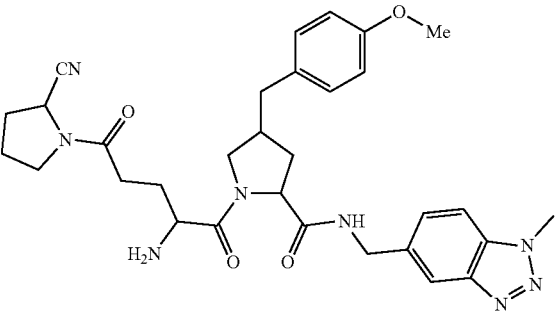
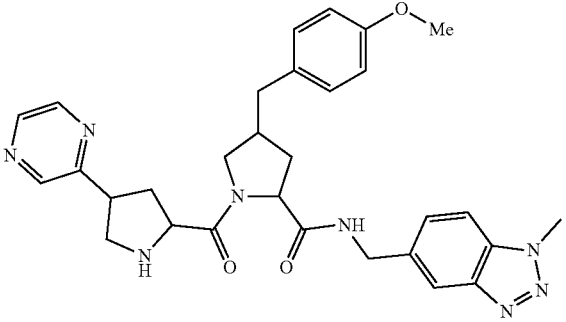

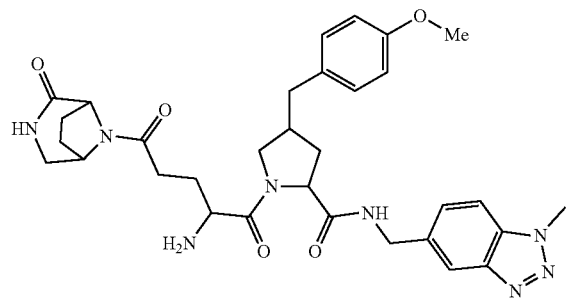
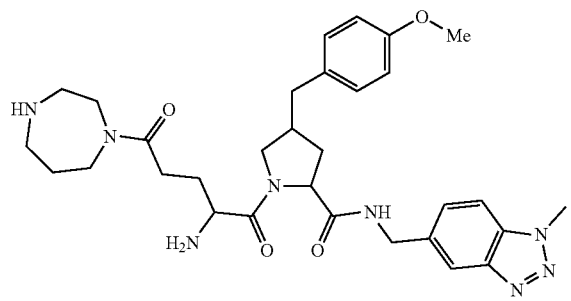
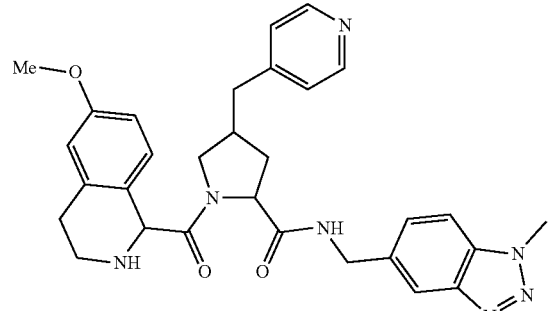
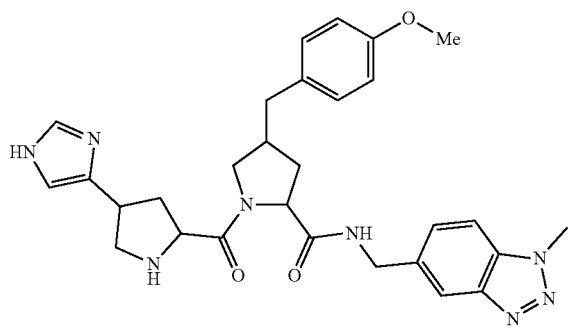
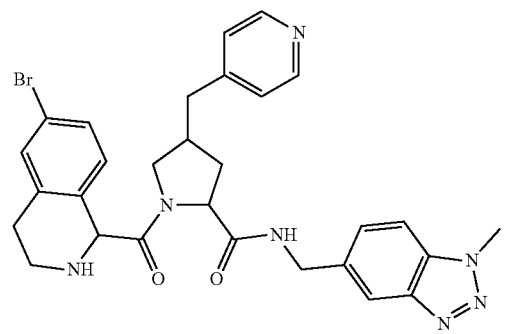
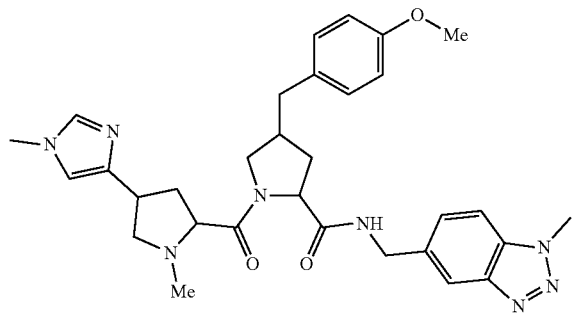
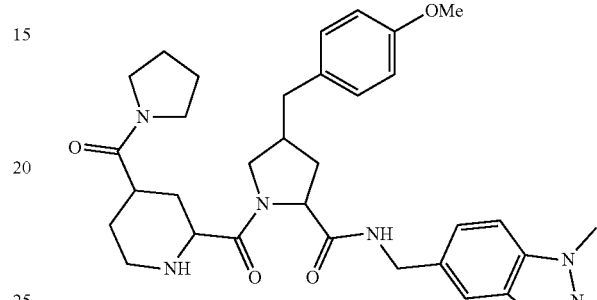
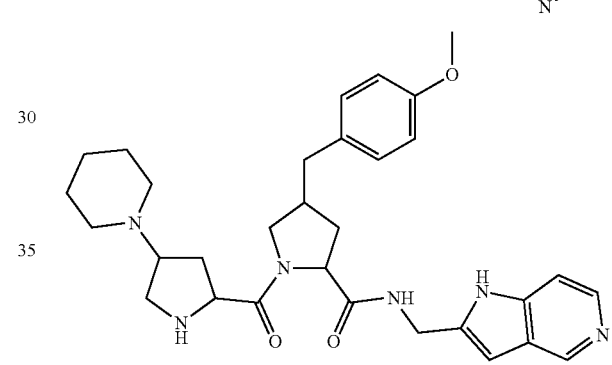
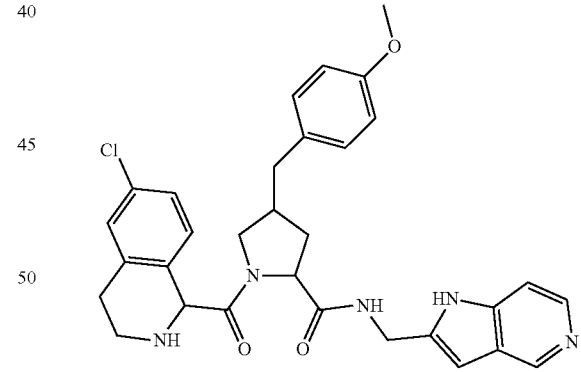
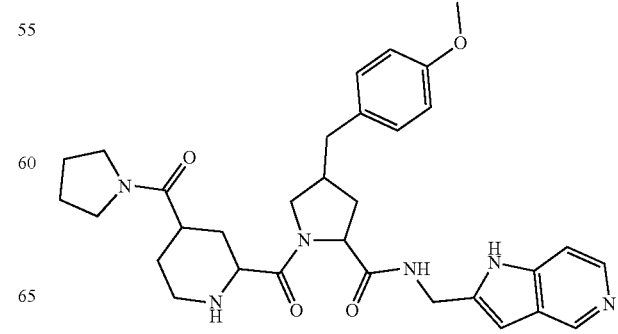

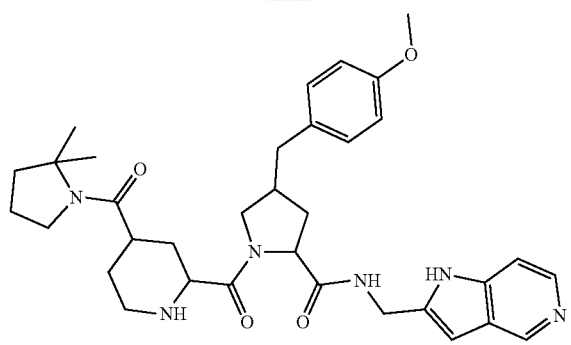

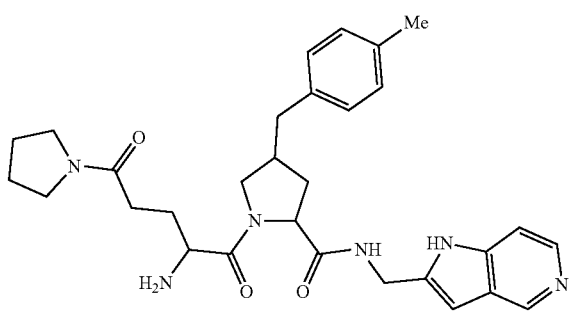 [SMILES: Cc1ccc(CC2CC(C(=O)NCc3cc4cnccc4[nH]3)N(C(=O)C(N)CCC(=O)N3CCCC3)C2)cc1]

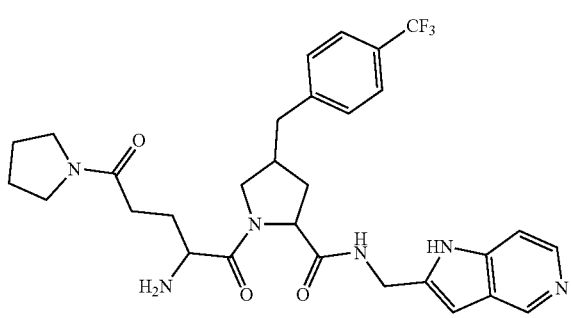

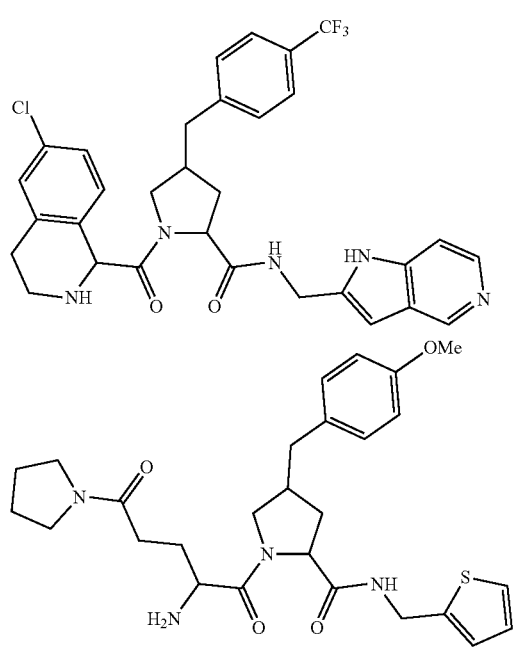

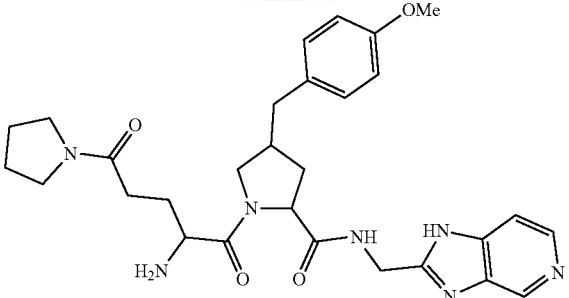

As will be evident to the skilled person the compounds of the present invention contain a number of stereocentres. The present invention encompasses all possible stereoisomers of the present invention whether in a single stereoisomeric form or a mixture thereof. A preferred stereoisomer is the S enantiomer at the 2 position of the pyrrolidine ring. For example:

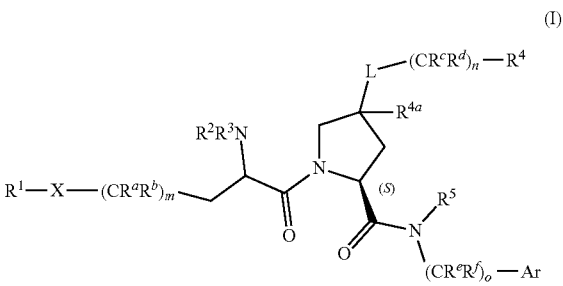
(I)

The preferred stereochemistry of the —NR$^2$R$^3$ group is R. For example:

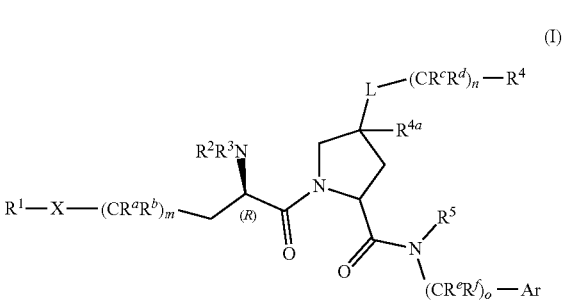
(I)

Accordingly, in an embodiment the compound of the invention is a diastereomer with S configuration at the 2 position of the pyrrolidine and a R configuration at the —NR$^2$R$^3$ group. As such, the compound of formula (I) may be:

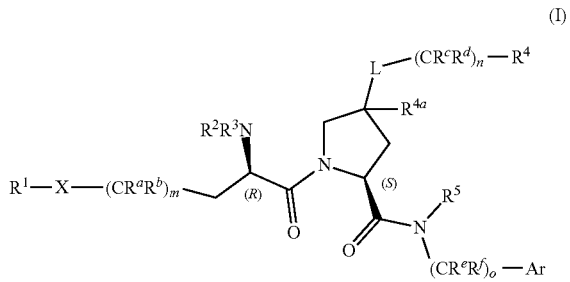

(I)

In an embodiment, the -L-(CR$^c$R$^d$)$_n$—R$^4$ group on the pyrrolidine has a trans relationship with the group at the 2 position, when the 2 position is in the S configuration. For example:

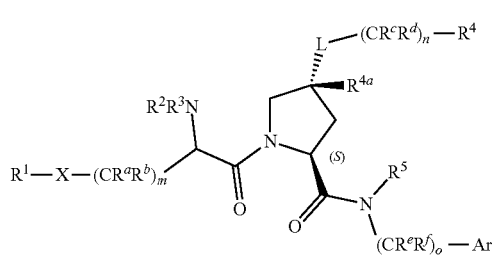

(I)

In an embodiment, compounds of the invention have the stereochemistry shown below.

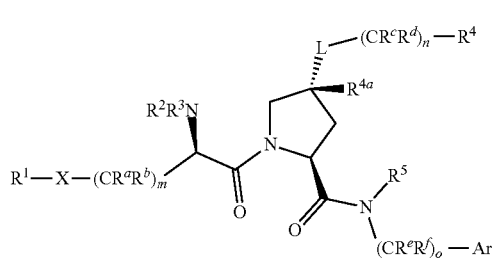

(I)

In an embodiment, the —(CR$^a$R$^b$)—X—R$^1$ group substituted onto a pyrrolidine of compounds such as formula (IIa) has a cis relationship with the —C(=O)— group at the 2 position. For example:

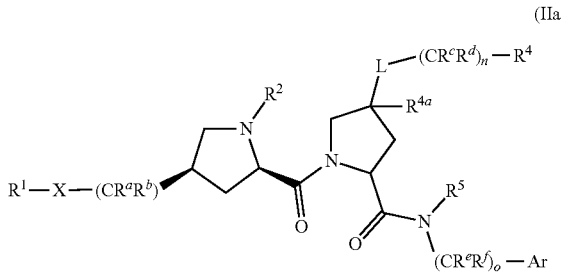

(IIa)

In an embodiment R$^1$ is not indoline. In embodiments R$^1$ is not a 9 membered bicyclic heteroaromatic group.

In an aspect of the invention there is provided the compounds of the present invention for use as a medicament.

In accordance with another aspect, the present invention provides a pharmaceutical formulation comprising a compound of the present invention and a pharmaceutically acceptable excipient.

In an embodiment the pharmaceutical composition may be a combination product comprising an additional pharmaceutically active agent.

In a preferred aspect of the invention, the compounds are selective FXIIa inhibitors. By the term "selective FXIIa inhibitors" is meant compounds that selectively inhibit FXIIa over thrombin and FXa. Generally, a compound of the present invention may have a selectivity for FXIIa over thrombin of at least >10 fold, preferably at least >100 fold.

In accordance with another aspect of the invention, there is provided a compound of the present invention for use in the prevention or treatment of a condition which is modulated by Factor XIIa. Conditions preventable or treatable by modulation of Factor XIa would ordinarily be conditions that are preventable or treatable by the inhibition of Factor XIa. Accordingly, the compounds of the present invention may be for use in the prevention or treatment of a condition preventable or treatable by the inhibition of Factor XIIa.

The compound of the present invention may be for use in the prevention or treatment of a condition selected from the following or as a co-therapy in a treatment or prevention of a condition selected from: thrombosis, deep venous thrombosis, complex left-sided ablation (pulmonary vein isolation; VT ablation), reperfusion injury also know as ischaemia-reperfusion injury, transcatheter aortic valve replacement (TAVR) also known as transcatheter aortic valve implantation (TAVI), spinal or epidural anaesthesia, lumbar diagnostic puncture, thoracic surgery, abdominal surgery, major orthopaedic surgery, liver biopsy, transurethral prostate resection, kidney biopsy, renal insufficiency, liver diseases, endoscopy with biopsy, prostate or bladder biopsy, electrophysiological study or radiofrequency catheter ablation for supraventricular tachycardia (including left-sided ablation via single trans-septal puncture), angiography, pacemaker or implantable cardioverter defibrillator (ICD) implantation (unless complex anatomical setting, e.g. congenital heart disease), mechanical valve implantation, prosthetic valve implantation, myocardial infarction, angina pectoris (including unstable angina), reocclusions and restenoses after angioplasty or aortocoronary bypass, stroke, patients with atrial fibrillation to reduce their risk of stroke, patients with atrial fibriliation and chronic kidney disease, transitory ischaemic attacks, peripheral arterial occlusion disorders, pulmonary embolisms, deep venousmicrovascular disease, patients requiring extra corporeal membrane oxygenation (ECMO), patients requiring extra corporeal circulation such as coronary artert bypass grafting (CABG), disseminated intravascular coagulation (DIC), atherosclerosis, arthritis, thrombosis in patients with cancer, silent brain ischaemia, stroke, neurotraumatic disorder, neurological inflammatory disorders, medical procedures comprising contact with artificial surfaces including renal dialysis, other conditions where inhibition of FXIIa could be beneficial such as Alzheimer's disease, vascular dementia, macular degeneration, diabetic retinopathy, diabetic macular oedema, cerebral oedema in stroke, other causes of oedema, hereditary angioedema or acquired angioedema.

The condition preventable or treatable by the inhibition of Factor XIIa may be a condition associated with blood thickening, blood coagulation, or blood clot formulation for example the condition may be thrombosis.

In embodiments of the invention, compounds are provided for use in the prevention or treatment of or as a co-therapy for conditions associated with a high risk of bleeding, a low risk of bleeding, or thromboembolic disorders.

In embodiments of the invention, compounds are provided for use in the prevention or treatment of or as a co-therapy for conditions associated with a high risk of bleeding.

In embodiments of the invention, compounds are provided for use in the prevention or treatment of or as a co-therapy for conditions associated with a low risk of bleeding.

In embodiments of the invention, compounds are provided for use in the prevention or treatment of or as a co-therapy for conditions associated with thromboembolic disorders.

In embodiments of the invention, the compound of the invention is for use as part of a prevention or treatment for a condition associated with a high risk of bleeding, wherein the treatment is selected from complex left-sided ablation (pulmonary vein isolation; VT ablation), spinal or epidural anaesthesia, lumbar diagnostic puncture, thoracic surgery, abdominal surgery, major orthopaedic surgery, liver biopsy, transurethral prostate resection, kidney biopsy, liver diseases or renal insufficiency.

In embodiments of the invention, the compound of the invention is for use as part of a prevention or treatment for a condition associated with a low risk of bleeding, wherein the treatment is selected from endoscopy with biopsy, prostate or bladder biopsy, electrophysiological study or radiofrequency catheter ablation for supraventricular tachycardia (including left-sided ablation via single trans-septal puncture), angiography, pacemaker or implantable cardioverter defibrillator (ICD) implantation (unless complex anatomical setting, e.g. congenital heart disease), mechanical valve implantation, or prosthetic valve implantation.

In an embodiment, compounds of the present invention are for use to avoid or mitigate the contraindications of existing anticoagulant therapies, such as Dabigatran, Rivaroxaban, Apixaban, warfarin, Edoxaban and Betrixaban.

In an aspect of the invention there is provided a use of a compound of the invention to avoid or mitigate the contraindications of existing anticoagulant therapies, such as Dabigatran, Rivaroxaban, Apixaban, warfarin, Edoxaban and Betrixaban.

In an embodiment, the compounds of the present invention are for use in mitigating the contraindications of therapies using Rivaroxaban; wherein the contraindication may include: an estimated Glomerular Filtration Rate (eGFR) of less than 15 mL/minute/1.73 m$^2$, active bleeding, a significant risk of major bleeding from: current or recent gastrointestinal ulcer, oesophageal varices, recent brain or spinal injury, recent brain, spine, or ophthalmic surgery, recent intracranial haemorrhage, malignant neoplasm, vascular aneurysm, prosthetic heart valve, liver disease associated with coagulopathy and clinically relevant bleeding risk, as well as people who have cirrhosis with Child Pugh B and C or people who are taking any other anticoagulants, except when switching to or from warfarin treatment; and people who are taking strong inhibitors of cytochrome P 3A4 enzyme and P-glycoprotein, such as ketoconazole, or HIV protease inhibitors such as ritonavir.

In an embodiment, the compounds of the present invention are for use in mitigating the contraindications of therapies using Apixaban; wherein the contraindication may include: creatinine clearance (CrCl) of less than 15 mL/min, or eGFR <15 mL/minute/1.73 m$^2$, active bleeding, a significant risk of major bleeding such as: current or recent gastro-intestinal ulcer, oesophageal varices, recent brain or spinal injury, recent brain, spine, or ophthalmic surgery, recent intracranial haemorrhage, malignant neoplasm, vascular aneurysm, liver disease associated with coagulopathy and clinically relevant bleeding risk, a prosthetic heart valve, people who are taking any other anticoagulants, except when switching to or from warfarin treatment, or people who are taking strong inhibitors of cytochrome P3A4 enzyme and P-glycoprotein, such as ketoconazole, or HIV protease inhibitors such as ritonavir.

In an embodiment, the compounds of the present invention are for use in mitigating the contraindications of therapies using Edoxaban; wherein the contraindication includes Edoxaban not being used in NVAF patients with CrCl>95 mL/minute because of an increased risk of ischemic stroke compared to warfarin.

In an embodiment, the compounds of the present invention are for use in mitigating the contraindications of therapies using Dabigatran; wherein the contraindication includes stroke prophylaxis with atrial fibrillation (Prevention of stroke and systemic embolism associated with nonvalvular atrial fibrillation), renal impairment CrCl <15 mL/min or dialysis, DVT or PE treatment (Indicated for treatment of deep vein thrombosis (DVT) and pulmonary embolus (PE) in patients who have been treated with a parenteral anticoagulant for 5-10 days) CrCl 530 mL/min or on dialysis, DVT or PE prophylaxis (Indicated for the prophylaxis of deep vein thrombosis (DVT) and pulmonary embolism (PE) following hip replacement surgery), Dabigatran is contraindicated with defibrotide, mifepristone and human prothrombin complex concentrate, dabigatran should not be used with the following: antithrombin alfa, antithrombin iii, apixaban, carbamazepine, dalteparin, dexamethasone, doxorubicin, doxorubicin liposomal, dronedarone, edoxaban, enoxaparin, fondaparinux, fosphenytoin, heparin, ketoconazole, lepirudin, nefazodone, phenobarbital, phenytoin, primidone, rifampin, st john's wort, tenofovir df, tipranavir, vinblastine and warfarin.

In an embodiment, the compounds of the present invention are for use in mitigating the contraindications of therapies using Dabigatran; wherein the contraindication includes: renal impairment (CrCl <15 mL/min), hemodialysis, hypersensitivity, ctive pathologic bleeding, impairment of hemostasis, mechanical or prosthetic heart valves, thromboembolic events (eg, valve thrombosis, stroke, TIAs, MI), excessive major bleeding (predominantly postoperative pericardial effusions requiring intervention for hemodynamic compromise), increased bleeding risk during labor and delivery, anticoagulants for active bleeding, elective surgery, or invasive procedures, patients at an increased risk of stroke, additive risk of bleeding when coadministered with antiplatelet agents, warfarin, heparin, fibrinolytic therapy, and long-term NSAIDs or aspirin, congenital or acquired coagulation disorders, ulcerative GI diseases and other gastritis like symptoms, recent haemorrhage, recent brain, spinal, or ophthalmic surgery, patients undergoing neuraxial anesthesia (spinal/epidural anesthesia), patients undergoing spinal puncture at risk of developing an epidural or spinal hematoma which can result in long-term or permanent paralysis, coadministration with P-gp inducers and inhibitors, P-gp inducers (eg, rifampin) or any combination thereof.

In an embodiment, the compounds of the present invention are for use in mitigating the contraindications of therapies using Betrixaban; wherein the contraindication includes: patients taking P-gp inhibitor, pateints who have severe renal impairment, patients with hepatic impairment, patients with intrinsic coagulation abnormalities, or patients with prosthetic heart valves, coadministration with drugs affecting hemostasis (thereby increasing bleeding risk), coadministration with aspirin, coadministration with other antiplatelet agents, coadministration with other anticoagulants, coadministration with heparin, coadministration with thrombolytic agents, coadministration with selective serotonin reuptake inhibitors (SSRIs), coadministration with serotonin-norepinephrine reuptake inhibitors (SNRIs), and coadministration with non-steroidal anti-inflammatory drugs (NSAIDs).

In an embodiment, compounds of the invention may be used as anticoagulants for the prophylaxis and/or therapy of thromboembolic disorders; wherein the disorder is one of: myocardial infarction, angina pectoris (including unstable angina), reocclusions and restenoses after angioplasty or aortocoronary bypass, stroke, patients with atrial fibrillation to reduce their risk of stroke, patients with atrial fibriliation and chronic kidney disease, transitory ischaemic attacks, peripheral arterial occlusion disorders, reperfusion injury also know as ischaemia-reperfusion injury, transcatheter aortic valve replacement (TAVR) also known as transcatheter aortic valve implantation (TAVI), pulmonary embolisms, deep venousmicrovascular disease or patients requiring extra corporeal membrane oxygenation (ECMO).

In an embodiment, compounds according to the invention may be suitable for preventing and/or treating disseminated intravascular coagulation (DIC).

In an embodiment, the compounds of the invention are also suitable for the prophylaxis and/or treatment of atherosclerosis and arthritis, and additionally also for the prophylaxis and/or treatment of thrombosis in patients with cancer.

In an embodiment the compounds of the present invention is for use in a method of preventing and/or treating thrombosis.

In an aspect of the invention the compound disclosed herein may be for use as an anticoagulant.

In an aspect of the invention there is provided a method for prevention of thrombosis or deep venous thrombosis, prevention and/or treatment of a condition selected from: thrombosis, complex left-sided ablation (pulmonary vein isolation; VT ablation), spinal or epidural anaesthesia, lumbar diagnostic puncture, thoracic surgery, abdominal surgery, major orthopaedic surgery, liver biopsy, transurethral prostate resection, kidney biopsy, renal insufficiency, liver diseases, endoscopy with biopsy, prostate or bladder biopsy, electrophysiological study or radiofrequency catheter ablation for supraventricular tachycardia (including left-sided ablation via single trans-septal puncture), angiography, pacemaker or implantable cardioverter defibrillator (ICD) implantation (unless complex anatomical setting, e.g. congenital heart disease), mechanical valve implantation, prosthetic valve implantation, myocardial infarction, angina pectoris (including unstable angina), reocclusions and restenoses after angioplasty or aortocoronary bypass, stroke, patients with atrial fibrillation to reduce their risk of stroke, patients with atrial fibriliation and chronic kidney disease, transitory ischaemic attacks, peripheral arterial occlusion disorders, pulmonary embolisms, deep venousmicrovascular disease, patients requiring extra corporeal membrane oxygenation (ECMO), patients requiring extra corporeal circulation such as coronary artert bypass grafting (CABG), disseminated intravascular coagulation (DIC), atherosclerosis, arthritis, thrombosis in patients with cancer, silent brain ischaemia, stroke, neurotraumatic disorder, neurological inflammatory disorders, medical procedures comprising contact with artificial surfaces including renal dialysis, other conditions where inhibition of FXIIa could be beneficial such as Alzheimer's disease, vascular dementia, macular degeneration, diabetic retinopathy, diabetic macular oedema, cerebral oedema in stroke, other causes of oedema, hereditary angioedema or acquired angioedema, wherein the method comprises administering a therapeutically effective amount of a compound of the invention or administering a therapeutically effective amount of a compound of the present invention as a co-therapy.

In an aspect of the invention there is provided a method of preventing coagulation, wherein the method comprises the administration of a therapeutically effective amount of a compound of the invention.

In an aspect of the invention there is provided a method of preventing and/or treating thrombosis, wherein the method comprises the administration of a therapeutically effective amount of a compound of the invention.

In an aspect of the invention there is provided a use of a compound of the invention in the manufacture of a medicament for use in the prevention and/or treatment of conditions preventable and/or treatable by the inhibition of Factor XII (optionally Factor XIIa), for example the condition may be thrombosis.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent. The additional pharmaceutically active agent may be one disclosed elsewhere herein.

The compounds of the present invention may be used for the prevention and/or treatment of any of the conditions disclosed above. Alternatively, the compounds of the present invention may be used as a co-therapy in a prevention and/or treatment of a condition disclosed above. Where the compound of the present invention is used as a co-therapy with respect to a particular condition, it is meant that the compound of the invention could be used in combination with another art known therapy for the condition. For example a FXII(a) inhibitor may be used in combination with anti-platelet therapy with the aim of providing enhanced anti-thrombotic efficacy without incurring an increased risk of bleeding compared with the anti-platelet therapy alone. Furthermore, a FXII(a) inhibitor is likely to be used in combination with other treatments.

BRIEF DESCRIPTION OF THE DRAWINGS

FIG. 1 shows that anticoagulant efficacy of compound M05272 using a standard dose of intravenous administration in a femoral vessel ferric chloride induced thrombosis model. The percentage inhibition of clot formation is calculated relative to mice administered vehicle only for the 60 minute time point. A minimum of 4 mice were employed in each group.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular, the term refers to fluorine, chlorine, bromine and iodine. Preferably, the term refers to bromine or iodine.

The term "alkyl" refers to a linear or branched hydrocarbon chain. For example, the term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "alkoxy" refers to an alkyl group which is attached to a molecule via oxygen. For example, the term "$C_{1-6}$ alkoxy" refers to a group where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "haloalkyl" refers to a hydrocarbon chain substituted with at least one halogen atom independently chosen at each occurrence, for example fluorine, chlorine, bromine and iodine.

For example, the term "$C_{1-6}$ haloalkyl" refers to a linear or branched hydrocarbon chain containing 1, 2, 3, 4, 5 or 6 carbon atoms substituted with at least one halogen. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "alkenyl" refers to a branched or linear hydrocarbon chain containing at least one double bond. For example, the term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "alkynyl" refers to a branched or linear hydrocarbon chain containing at least one triple bond. For example, the term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "heteroalkyl" refers to a branched or linear hydrocarbon chain containing at least one heteroatom selected from N, O and S positioned between any carbon in the chain or at an end of the chain. For example, the term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term cycloalkyl refers to a saturated hydrocarbon ring system. For example "$C_{3-8}$ cycloalkyl" refers to a ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "heterocycloalkyl" refers to a saturated hydrocarbon ring system containing carbon atoms and at least one heteroatom within the ring selected from N, O and S. For example there may be 1, 2 or 3 heteroatoms, optionally 1 or 2. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be a "$C_{3-8}$ heterocycloalkyl". The term "$C_{3-8}$ heterocycloalkyl" refers to a saturated hydrocarbon ring system containing 3, 4, 5, 6, 7 or 8 atoms at least one of the atoms being a heteroatom within the ring selected from N, O and S. The "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "heterocycloalkenyl" refers to an unsaturated hydrocarbon ring system, that is not aromatic, containing carbon atoms and at least one heteroatom within the ring selected from N, O and S. For example there may be 1, 2 or 3 heteroatoms, optionally 1 or 2. The "heterocycloalkenyl" may be bonded to the rest of the molecule through any carbon atom or heteroatom. The "heterocycloalkenyl" may have one or more, e.g. one or two, bonds to the rest of the molecule: these bonds may be through any of the atoms in the ring. For example, the "heterocycloalkenyl" may be a "$C_{3-8}$ heterocycloalkenyl". The term "$C_{3-8}$ heterocycloalkenyl" refers to a saturated hydrocarbon ring system containing 3, 4, 5, 6, 7 or 8 atoms at least one of the atoms being a heteroatom within the ring selected from N, O and S. The "heterocycloalkenyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups. The term "aryl" also includes bicyclic or tricyclic ring systems that are not completely aromatic but contain an aromatic ring within the ring system, for example, indane or tetralin.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole. The term "heteroaryl" also includes bicyclic or tricyclic ring systems that are not completely aromatic but contain an aromatic ring. The heteroatoms may be present within the ring system in the aromatic ring or in a non-aromatic ring. For example heteroaryl also encompasses chromene, chromane, indoline, tetrahydroquinoline, The term "halogen" herein includes reference to F, Cl, Br and I. Halogen may be Br. Halogen may be I.

A bond terminating in a "⌒" represents that the bond is connected to another atom that is not shown in the structure. A bond terminating inside a cyclic structure and not terminating at an atom of the ring structure represents that the bond may be connected to any of the atoms in the ring structure where allowed by valency.

A bond drawn as a solid line and a dotted line represents a bond which can be either a single bond or a double bond, where chemically possible. For example, the bond drawn below could be a single bond or a double bond.

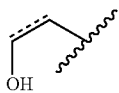

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, NHR, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. R may be selected from H, $C_{1-6}$ alkyl, $C_{3-8}$ cycloalkyl, phenyl, benzyl or phenethyl group, e.g. R is H or $C_{1-3}$ alkyl. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌒".

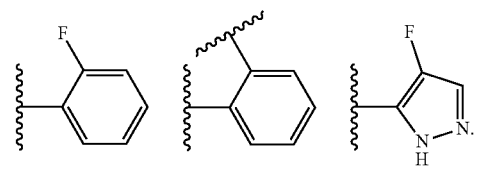

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

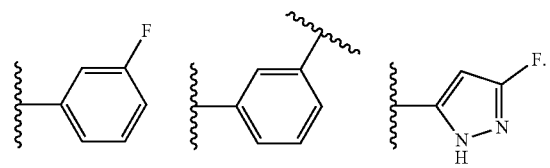

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

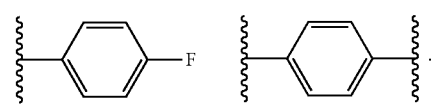

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocenter, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%, at least 60% or less. For example, the e.e. or d.e. may be 90% or more, 90% or more, 80% or more, 70% or more, 60% or more, 50% or more, 40% or more, 30% or more, 20% or more, or 10% or more.

The invention contemplates pharmaceutically acceptable salts of the compounds of the invention. These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labelled compounds of the invention.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

One or more compounds of the invention may be combined with one or more pharmaceutical agents, for example anti-inflammatory agents, anti-fibrotic agents, chemotherapeutics, anti cancer agents, immunosuppressants, anti-tumour vaccines, cytokine therapy, or tyrosine kinase inhibitors, for the treatment of conditions modulated by the inhibition of ROCK, for example fibrotic diseases, autoimmune, inflammatory-fibrotic conditions, inflammatory conditions, central nervous system disorders, or cancer.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

The compounds of the invention can be administered in vivo either alone or in combination with other pharmaceutically active agents, e.g. agents effective in particular for the treatment and/or prophylaxis of the aforementioned diseases. A suitable combination consists of a compound of the present invention with one or more active substances which may be mentioned by way of example and preferably are: lipid-lowering agents, in particular HMG-CoA-(3-hydroxy-3-methylglutaryl-coenzyme A)-reductase inhibitors; coronary therapeutics/vasodilators, in particular ACE (angiotensin converting enzyme) inhibitors; AII (angiotensin II) receptor antagonists; β-adrenoceptor antagonists; alpha-1-adrenoceptor antagonists; diuretics; calcium channel blockers; substances which bring about an increase in cyclic guanosine monophosphate (cOMP), such as, for example, stimulators of soluble guanylate cyclase; plasminogen activators (thrombolytics/fibrinolytics) and thrombolysis/fibrinolysis-increasing compounds such as inhibitors of the plasminogen activator inhibitor (PAI inhibitors) or inhibitors of the thrombin-activated fibrinolysis inhibitor (TAFI); substances having anticoagulatory activity (anticoagulants); substances inhibiting platelet aggregation (platelet aggregation inhibitors, thrombocyte aggregation inhibitors); and fibrinogen receptor antagonists (glycoprotein IIb/IIIa antagonists).

The compounds of the invention may be advantageous in the treatment of cancer since cancer patients have a prothrombotic state and may need anticoagulants. This normally has to be balanced with risk of bleeding, therefore, the compounds described herein offer a safer anticoagulant in cancer patients because of the reduced risk of bleeding. For the treatment of cancer the compounds of the invention may be administered in combination with known cancer treating therapies.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. The skilled person within the field of drug dosage would readily identify a suitable dosage, for example the dosage may be a standard dosage amount.

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention may be any length of time. For example, the treatment duration may be days, weeks, months or years. The treatment may be indefinite. It may be that the treatment may be for between one and seven months for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

Examples and Synthesis

1H-NMR: Spectra are obtained on a Bruker DRX 400 MHz or Jeol ECS 400 MHz spectrometer. Spectra are measured at 294K (unless otherwise stated) and chemical shifts (δ-values) are reported in parts per million (ppm), referenced to either TMS (0.0 ppm), DMSO-d6 (2.50 ppm), CDCl3 (7.26 ppm). Coupling constants (J) are reported in Hertz (Hz), spectra splitting pattern are designated as singlet (s), doublet (d), triplet (t), quadruplet (q), multiplet or more overlapping signals (m), broad signal (br); solvent is given in parentheses.

Abbreviations

The following abbreviations are used in the Examples and other parts of the description.

ABCN: azobis cyclohexanecarbonitrile; Boc: tert-butyloxycarbonyl; Cbz: Carbobenzyloxy; DavePhos: 2-dicyclohexylphosphino-2'-(N,N-dimethylamino)biphenyl; dba: tris (dibenzylideneacetone); DBU: 1,8-diazabicyclo[5.4.0] undec-7-ene; DCE: 1,2-dichloroethane; DCM: dichloromethane; DIAD: diisopropyl azodicarboxylate; dioxane: 1,4-dioxane; DIPEA: Diisopropyl ethylamine; DMA: dimethyl acetamide; DMAP: 4-(dimethylamino)pyridine; DMF: N,N-dimethylformamide; DMS: Dimethylsulfide; DMSO: dimethylsulfoxide; Dppf: 1,1'-bis(diphenylphosphino)ferrocene; dtbpf: ([1,1'-bis(di-tert-butylphosphino)ferrocene]; EtOAc: ethyl acetate; Fmoc: 9-Fluorenylmethoxycarbonyl; h: hour(s); HATU: 2-(7-aza-1H-benzotriazole-1-yl)-1,1,3,3-tetramethyluronium. Hexafluorophosphate; HBTU: (2-(1H-benzotriazol-1-yl)-1,3,3-tetramethyluronium hexafluorophosphate; HPLC: High-performance liquid chromatography; MIDA: N-methyliminodiacetic acid; min: minute(s); LCMS: Liquid chromatography—mass spectrometry; MS: mass spectroscopy; Ms: Mesyl; Pet-ether: petroleum ether (b.p. 60-80° C.); quant.: quantitative (conversion); Rt: retention time; RT: room temperature; SCX: strong cation exchange; TEA: triethylamine; TFA: trifluoroacetic acid; THF: tetrahydrofuran; TsCl: p-toluenesulfonyl chloride; XPhos: 2-dicyclohexylphosphino-2',4',6'-triisopropylbiphenyl; XantPhos: 4,5-bis(diphenylphosphino)-9,9-dimethylxanthene Analytical Methods Analysis of products and intermediates has been carried out using reverse phase analytical HPLC-MS using the parameters set out below.

HPLC Analytical Methods:

AnalpH2_MeOH_4 min: Phenomenex Luna C18 (2) 3 μm, 50×4.6 mm; A=water+0.1% formic acid; B=MeOH+ 0.1% formic acid; 45° C.; % B: 0.0 min 5%, 1.0 min 37.5%, 3.0 min 95%, 3.5 min 95%, 3.51 min 5%, 4.0 min 5%; 2.25 mL/min.

AnalpH2_50-95MeOH_4 min: Phenomenex Luna C18 (2) 3 μm, 50×4.6 mm; A=water+0.1% formic acid; B=MeOH+0.1% formic acid; 45° C.; % B: 0.0 min 50%, 1.5 min 95%, 3.5 min 95%, 3.51 min 5%, 4.0 min 5%; 2.25 mL/min.

AnalpH9_MeOH_4 min: Phenomenex Luna C18 (2) 3 μm, 50×4.6 mm; A=water pH 9 (Ammonium Bicarbonate 10 mM); B=MeOH+0.1% formic acid; 45° C.; % B: 0.0 min 5%, 1.0 min 37.5%, 3.0 min 95%, 3.5 min 95%, 3.5 min, 5%, 4.0 min 5%; 2.25 mL/min.

AnalpH2_MeOH_QC_V1: Phenomenex Gemini NX C18 5 μm, 150×4.6 mm; A=water+0.1% formic acid; B=MeOH+ 0.1% formic acid; 40° C.; % B: 0.0 min 5%, 0.5 min, 5%, 7.5 min 95%, 10.0 min 95%, 10.1 min 5%, 13.0 min 5%; 1.5 mL/min.

AnalpH9_MeOH_QC_V1: Phenomenex Gemini NX C18 5 μm, 150×4.6 mm; A=water+pH 9 (Ammonium Bicarbonate 10 mM); B=MeOH; 40° C.; % B: 0.0 min 5%, 0.50 min 5%, 7.5 min 95%, 10.0 min 95%, 10.1 min 5%, 13.0 min 5%; 1.5 mL/min.

Agilent_MeCN_HPLC_3 min: Phenomenex Luna C18, 50×2 mm: A=water+0.1% formic acid; B=MeCN+0.1% formic acid; 5-95% B 0-3 min; 1 mL/min UPLC Analytical Methods AnalpH2_MeCN_UPLC_3.8 min: Acquity UPLC BEH C-18 1.7 um, 2.1×50 mm, A=water+0.05% formic acid; B: acetonitrile+0.05% formic acid; 35° C.; % B: 0.0 min 10%, 0.5 min 10%, 1 min 35%, 1.5 min 45%, 2.3 min 90%, 3.2 min 90%, 3.8 min 10%; 0.55 mL/min AnalpH2_MeCN_UPLC_4.0 min: Acquity UPLC BEH C-18 1.7 um, 2.1×50 mm, A=water+0.05% formic acid; B: acetonitrile+0.05% formic acid; 35° C.; % B: 0.0 min 10%, 0.5 min 10%, 1 min 35%, 1.5 min 45%, 2.3 min 90%, 3.2 min 90%, 3.6 min 10%, 4.0 min 10%; 0.55 mL/min AnalpH2_MeCN_UPLC_4.2 min: Acquity UPLC BEH C-18 1.7 um, 2.1×50 mm, A=water+0.05% formic acid; B: acetonitrile+0.05% formic acid; 40° C.; % A: 0.0 min 95%, 0.3 min 95%, 2 min 5%, 3.5 min 5%, 3.6 min 95%, 4.2 min 95%; 0.6 mL/min AnalpH2_MeCN_UPLC_5.0 min: Acquity UPLC BEH C-18 1.7 um, 2.1×50 mm, A=water+0.05% formic acid; B: acetonitrile+0.05% formic acid; 40° C.; % A: 0.0 min 50%, 3.0 min 90%, 5.0 min 90%, 5.1 min 50%; 0.4 mL/min AnalpH2_MeCN_UPLC_6.1 min: Acquity UPLC BEH C-18 1.7 um, 2.1×100 mm, A=water+0.05% formic acid; B:

acetonitrile+0.05% formic acid; 40° C.; % A: 0.0 min 60%, 2.0 min 90%, 6.0 min 90%, 6.1 min 60%; 0.3 mL/min AnalpH9_MeCN_UPLC_10 min: Acquity UPLC BEH C-18 1.7 um, 2.1×50 mm, A=5 mM ammonium acetate in water; B: acetonitrile; 40° C.; % B: 0.0 min 3%, 1.0 min 3%, 7.0 min 100%, 7.5 min 100%, 9.0 min 3%, 10 min 3%; 0.5 mL/min Thermo_MeOH_UHPLC_1.2 min: Phenomenex Kinetex, 2.6 uM, 50×2.1 mm, A=water+0.1% formic acid; B=MeOH+0.1% formic acid; 2-95% B 0-1.0 min; 1.3 mL/min General Methods General Method 1 (GM1): Amide Coupling A mixture of carboxylic acid (1.0 eq), amine (1.0-1.5 eq), N,N-diisopropylethylamine or triethylamine (1.5-3.0 eq) and a coupling agent such as HBTU (2-(1H-benzotriazol-1-yl)-1,1,3,3-tetramethyluronium hexafluorophosphate), HATU (1-[Bis(dimethylamino)methylene]-1H-1,2,3-triazolo[4,5-b]pyridinium 3-oxidhexafluorophosphate) or HCTU (O—(1H-6-Chlorobenzotriazole-1-yl)-1,1,3,3-tetramethyluronium hexafluorophosphate (1.0-1.5 eq) in anhydrous solvents such as DMF or DCM was stirred at room temperature for 1-72 h. The product was isolated and purified using one of the following methods:

The reaction mixture was diluted with a mixture of water and aqueous sat. NaCl solution and extracted with EtOAc. The organic phase was dried over $Na_2SO_4$ or $MgSO_4$, filtered and concentrated in vacuo to yield the crude material which was either used without further purification, or purified by column chromatography.

The solvent was removed in vacuo and the residue dissolved in EtOAc, and the organic phase washed with $NaHCO_3$(aq) solution, $H_2O$ then brine. The organic phase was dried over $Na_2SO_4$ or $MgSO_4$, filtered and the filtrate concentrated in vacuo to yield the crude material which was either used without further purification, or purified by column chromatography.

The reaction was diluted with water or aqueous sat. NaC solution and extracted with DCM. The organic phase was dried over $MgSO_4$ and filtered, or passed through a hydrophobic frit and concentrated in vacuo. Crude material was either used without further purification, or purified by column chromatography.

The reaction was cooled in an ice bath and diluted with water and extracted with EtOAc. The organic phase was washed sequentially with $NaHCO3_3$ (aq) solution, $NH_4Cl$ (aq) and brine, then dried over $Na_2SO_4$, filtered and the filtrate concentrated in vacuo to yield the crude material which was purified by column chromatography.

General Method 2 (GM2): Boc Deprotection

Method Boc deprotection 2A: Boc-protected amine was stirred in a mixture of DCM:TFA (in a ratio from 10:1 to 1:1) for 1-18 h.

Method Boc deprotection 2B: Boc-protected amine was dissolved in EtOAc or DCM and either 4M HCl in dioxane, 2M HCl in $Et_2O$ or 1 M HCl in $Et_2O$ added. The reaction mixture was stirred at room temperature for 0.25-18 h.

Method Boc deprotection 2C: The crude Boc-protected amine in DCM was passed through a MP-TsOH cartridge, washed with MeOH (up to 5 column volumes) and eluted with 2M $NH_3$-MeOH.

The reaction mixture (or product-containing fractions: Method 2C) were concentrated in vacuo to yield the crude material which was either used crude, or purified by one of the following methods:

SCX-2 followed by prep HPLC

Basified by addition of 1M $NH_3$ in MeOH, concentrated in vacuo and purified by prep HPLC Diluted with 0.5N $HCl_{(aq)}$ and EtOAc and the layers separated. The aqueous phase may be washed with EtOAc then basified (pH≈10) and extracted with EtOAc. The combined organic extracts dried ($MgSO_4$), filtered and the solvent evaporated in vacuo.

Reverse-Phase Chromatography

Water and sat. aq. $NaHCO_3$ added. The product was extracted into EtOAc, and the organic extract dried ($MgSO_4$) and the solvent removed in vacuo.

Prep HPLC optionally followed by SCX-2.

SCX-2 followed by addition of 4 M HCl in dioxane and the solvent removed to give the HCl salt.

General Method 3 (GM3): Hydrogenation

General Method 3A (hydrogenation with $H_2$ balloon): The alkene or Cbz/benzyl protected species (1 eq) was dissolved in EtOH or methanol, placed under $N_2$ atmosphere, and Pd/C or $Pd(OH)_2$/C (10 wt %) added. A $H_2$ atmosphere was introduced and the reaction mixture stirred at room temperature for 1-72 h. The mixture was filtered through celite and the filtrate concentrated to give the crude product which was used with no further purification.

Optionally additional aliquots of Pd/C may be added during the course of the reaction.

General Method 3B (hydrogenation with ammonium formate): The alkene (1 eq) was dissolved in EtOH and Pd/C (0.5 eq), and $NH_4HCO_2$ (10 eq) added. The mixture was stirred at reflux for 1-72 h. The solution was cooled to room temperature and filtered through celite, washing with MeOH or EtOAc. The solvent were evaporated in vacuo and the residue partitioned between EtOAc and sat. aq. $NaHCO_3$. The organic phase was dried ($MgSO_4$), filtered and the solvent removed to yield the crude product which was used without further purification.

Optionally additional aliquots of Pd/C and/or $NH_4HCO_2$ may be added during the course of the reaction.

General Method 3C (hydrogenation with H-Cube): The alkene was dissolved in a protic solvent and passed through a H-cube reactor (Pd/C cartridge), typical conditions: 30° C., 20 bar, 1 mL/min. The solvent was evaporated in vacuo and the material used without further purification.

General Method 4 (GM4): Ester Hydrolysis

Method Ester Hydrolysis 4A: The ester (1.0 eq) was dissolved in MeOH or 1,4-dioxane, and 1M LiOH (1-2 eq) added and stirred at room temperature for 1-64 h.

Optionally additional equivalents of 1M LiOH (aq) may be added during the reaction.

Method Ester Hydrolysis 4B: The ester (1.0 eq) was dissolved in a 1:1:1 solution of 1M NaOH/MeOH/THF and stirred at room temperature for 1-18 h.

Method Ester Hydrolysis 4C: The ester (1.0 eq) was dissolved in 10M NaOH (5 equiv) in MeOH, and stirred at 60° C. for 1-18 h.

The solvent was removed in vacuo and the product isolated using one of the following methods:

Crude product used without further purification.

Diluted with water and acidified to pH1-4, then extracted with EtOAc or DCM. The organic extracts were dried over $MgSO_4$, filtered and the solvent removed to yield the product which was used without further purification.

The crude product was dissolved in water and the aqueous layer washed with EtOAc or DCM. The aqueous layer was acidified with 1M HCl and the product extracted into EtOAc or DCM.

The combined organic extracts were dried (MgSO$_4$), filtered and the solvent removed to yield the product which was used without further purification.

2N HCl added, adjusting to pH 7. The solvent was evaporated in vacuo and the residue dissolved in DCM. The solution was filtered and the filtrate concentrated under reduced pressure, and the resulting solid residue dried in vacuo.

The crude mixture was diluted with water and extracted with Et$_2$O. The organic phase was extracted with water. The combined aqueous phases were concentrated in vacuo, the crude product dissolved in toluene and concentrated in vacuo to give the carboxylic acid as the lithium salt.

General Method 5 (GM5): Fmoc Deprotection

Fmoc-protected amine was stirred in a 10:1 mixture of piperidine and either DCM or DMF at room temperature for 1-18 h. The solvent was removed under reduced pressure, and the residue either used without further purification, or was purified by column chromatography or prep HPLC.

General Method 6 (GM6): Nitrile Reduction with NaBH$_4$/NiCl$_2$.6H$_2$O

Method NaBH$_4$/NiCl$_2$.6H$_2$O 6A: To the benzonitrile (1 eq) in MeOH at 0° C. was added NiCl$_2$.6H$_2$O (0.1 eq), followed by portionwise addition of NaBH$_4$ (10 eq). Reaction temperature was maintained <5° C. Stirred for 1-3 h.

Method NaBH$_4$/NiCl$_2$.6H$_2$O in situ Boc protection 6B: To the benzonitrile (1 eq) in MeOH at 0° C. was added NiCl$_2$.6H$_2$O (0.1 eq) and Boc$_2$O(2 eq), followed by portionwise addition of NaBH$_4$ (10 eq). Reaction temperature was maintained <5° C. Stirred for 1-2 h.

The reaction mixture was concentrated in vacuo, then suspended in sat. NaHCO$_{3(aq)}$ sol. and water and extracted with EtOAc. Organic phases were dried over Na$_2$SO$_4$, filtered and concentrated in vacuo. The crude product was purified using column chromatography.

General Method 7 (GM7): Alkylation of Methyl N-(Diphenylmethylene)Glycinate

To a solution of methyl N-(diphenylmethylene)glycinate (1 eq) in anhydrous DMF and toluene (1:1) under N$_2$ was added potassium tert-butoxide (1 eq) and the reaction mixture stirred at RT. After 20 min, the appropriate phenethyl bromide (1 eq) in anhydrous DMF was added dropwise and the reaction was stirred at RT for (18-24 h). The reaction mixture was then diluted with water and extracted with EtOAc. The combined organic phases were washed with brine, dried over Na$_2$SO$_4$, filtered and concentrated in vacuo. The crude product was purified using column chromatography.

General Method 8 (GM8): Benzophenone Deprotection and In Situ Boc Protection

To a solution of methyl N-(diphenylmethylene)glycinate derivative (1.0 eq) in DCM was added 2M HCl in diethyl ether (approx. 20 eq) and the reaction stirred at RT for (24-72 h) and the reaction mixture was concentrated in vacuo. To a solution of the crude mixture in DCM was added Boc$_2$O(1.2 eq) and DIPEA (3.0 eq). On complete consumption of the crude intermediate (1-23 h), the reaction mixture was diluted with DCM and washed with water, sat. NH$_4$Cl$_{(aq)}$, and brine. The organic phase was dried over Na$_2$SO$_4$, filtered and concentrated in vacuo. The crude product was purified using column chromatography.

General Method 9 (GM9): Aryl Iodine to Alkyl Iodine Coupling

To an oven dried, N$_2$ purged flask was added sequentially zinc dust (6.0 eq), anhydrous DMF and 1,2-dibromoethane (0.3 eq). The reaction mixture was heated to 60° C. for 30 min, then cooled to RT. Trimethylsilyl chloride (0.06 eq) was added and the reaction stirred vigorously for 30 min. Benzyl (2R)-2-{[(tert-butoxy)carbonyl]amino}-4-iodobutanoate (1.0 eq) in anhydrous DMF was added and the reaction heated to 35° C. for 30 min, then cooled to RT. Pd$_2$dba$_3$ (0.02 eq), P(o-tol)$_3$ (0.08 eq) and the appropriate aryl iodine species (0.75 eq) were added sequentially before stirred the reaction for 18-48 h. The reaction was then diluted with EtOAc and washed with brine. The organic solution was then dried over Na$_2$SO$_4$, filtered and concentrated in vacuo. The crude product was purified by column chromatography.

General Method 10 (GM10): Iodine Displacement with Amines

To a solution of iodo species (1.0 eq) in anhydrous DMF was added amine (2.5 eq) and the reaction heated to 50° C. After 1 h the reaction mixture was cooled to RT and diluted with water. The aqueous solution was extracted with EtOAc and the combined organic phases were sequentially washed with LiCl$_{(aq)}$ solution (10% w/v) and brine, dried over Na$_2$SO$_4$ and concentrated in vacuo. Crude products were purified by column chromatography if required.

General Method 11 (GM11): Mesylation and Displacement

To a solution of alcohol (1.0 eq) in anhydrous DCM under nitrogen was added Et$_3$N (1.2 eq). The reaction mixture was cooled to 0° C. and methane sulfonyl chloride (1.2 eq) was added dropwise. Temperature was maintained at 0° C. under complete conversion to mesylated species (1-17 h). The reaction mixture was then diluted with DCM, and washed sequentially with 1M HCl, sat. NaHCO$_3$ solution and brine before drying over Na$_2$SO$_4$ and concentrated in vacuo. Used immediately in one of the following reactions without further purification.

Displacement with cyclic amines 11A: To mesylate (1.0 eq) in anhydrous DMF was added cyclic amine (10 eq) and the reaction heated to 90° C. for 17-24 h. The reaction was cooled to RT and diluted with water. The aqueous solution was extracted with EtOAc (3×) and the combined organic phase was washed with brine (1×), dried over Na$_2$SO$_4$ and concentrated in vacuo. Residual starting material removed using SCX column, using only fractions eluted with methanoic ammonia (2M). Crude products were purified using reverse phase column chromatography.

Displacement with cyclic amides 11B: To a solution of cyclic amide (10 eq) in anhydrous DMF under N$_2$ was added cautiously NaH (60% in mineral oil) (10 eq). After 30 min a solution of mesylate (1.0 eq) in anhydrous DMF was added to the flask and the reaction heated to 90° C. On complete consumption of mesylate (19 h) the reaction was cooled to RT and diluted with water. The aqueous solution was extracted with EtOAc and the combined organic phase was washed with brine, dried over Na$_2$SO$_4$ and concentrated in vacuo. Crude products were purified by column chromatography if required.

General Method 12 (GM12):—Amide Coupling with T3P

To a stirred suspension of acid (1.0-1.1 eq dependant on whether acid or amine is limiting reagent), amine (1.0-1.1 eq dependant on whether acid or amine is limiting reagent) and Et$_3$N (4.0-5.0 eq) was added dropwise T3P (50% in EtOAc) (2.0 eq) at 0° C. Suspension was warmed to RT and stirred for until starting material fully consumed, then cooled to 0° C., diluted with water and stirred for a further 30 min. The aqueous solution was extracted with EtOAc (×3) and the combined organic phases were washed with water (×1) and brine (×1), dried over Na$_2$SO$_4$ and concentrated in vacuo. Crude product purified using column chromatography if required.

97
Synthesis of RgA

Synthesis of (4-Aminomethyl-benzyl)-carbamic acid 9H-fluoren-9-ylmethyl ester

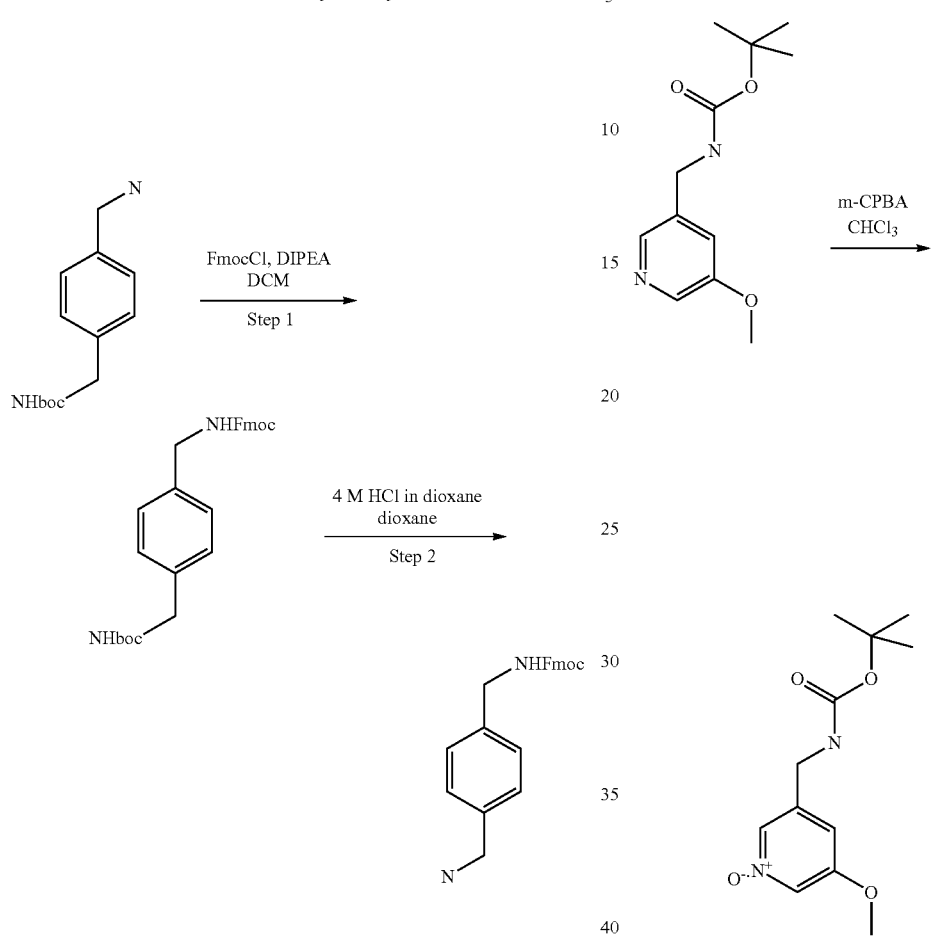

Step 1: 1-(N-boc-aminomethyl)-4-(aminomethyl) benzene (3.80 g, 16.1 mmol) was dissolved in DCM (100 mL) and DIPEA (5.0 mL, 29 mmol), followed by FmocCl (5.0 g, 19 mmol) were added. The reaction mixture was stirred at room temperature for 1 hour, after which a precipitate appeared. Water (100 mL) was added and the precipitate filtered and dried to give [4-(tert-butoxycarbonylamino-methyl)-benzyl]-carbamic acid 9H-fluoren-9-ylmethyl ester (6.32 g, 86%) as a white solid.

AnalpH2_MeOH_4MIN: Rt: 3.52 min, m/z 481.3 [M+H]$^+$

Step 2: [4-(tert-Butoxycarbonylamino-methyl)-benzyl]-carbamic acid 9H-fluoren-9-ylmethyl ester (6.32 g, 13.2 mmol) was suspended in dioxane (50 mL) and HCl solution (4 M in dioxane, 20 mL) was added slowly. The reaction mixture was stirred overnight at room temperature, then a further aliquot of 4 M HCl in dioxane (10 mL) was added and the mixture stirred for a further 2 hours at room temperature. The reaction mixture was diluted with ihexane (150 mL), the product collected by filtration and dried in vacuo to give (4-aminomethyl-benzyl)-carbamic acid 9H-fluoren-9-ylmethyl ester (4.0 g, 73%) as an off-white solid.

AnalpH2_MeOH_4MIN: Rt: 2.32 min, m/z 359.3 [M+H]$^+$

98
5-Aminomethyl-3-methoxy-pyridine-2-carbonitrile (for GS7)

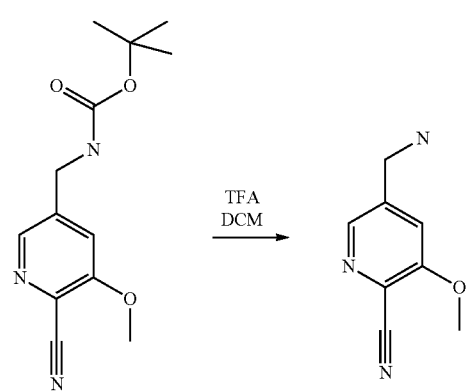

(5-Methoxy-1-oxy-pyridin-3-ylmethyl)-carbamic acid tert-butyl ester

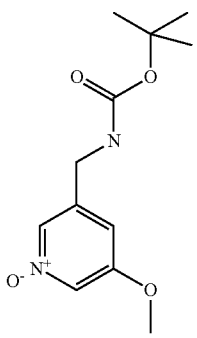

tert-Butyl (5-methoxypyridin-3-yl)methyl carbamate (1 eq) was dissolved in chloroform (5 mL). meta-Chloroperoxybenzoic acid (1.9 eq) was added and the reaction mixture stirred at RT overnight. The reaction mixture was diluted with dichloromethane and washed with a 2M aqueous solution of sodium hydroxide. The organic layer was dried over MgSO$_4$, filtered and concentrated in vacuo to afford (5-methoxy-1-oxy-pyridin-3-ylmethyl)-carbamic acid tert-butyl ester (208 mg, 92%) as a white solid.

AnalpH2_MeOH_4MIN: Rt: 2.26 min, m/z 255.3 [M+H]$^+$

(6-Cyano-5-methoxy-pyridin-3-ylmethyl)-carbamic acid tert-butyl ester

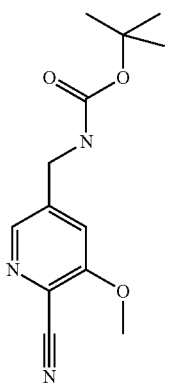 [SMILES: COc1cc(CNC(=O)OC(C)(C)C)cnc1C#N]

Acetonitrile (2 mL) was added to (5-methoxy-1-oxy-pyridin-3-ylmethyl)-carbamic acid tert-butyl ester (1 eq), followed by dimethylcarbamyl chloride (1.56 eq). The reaction mixture was heated at 40° C. for 4 h. The reaction mixture was then cooled to 0° C. and a solution of sodium cyanide (3.3 eq) in water (2 mL) was added. The reaction mixture was stirred at RT overnight. A 2 M aqueous solution of sodium hydroxide (5 mL) was added and the reaction mixture stirred at RT for 3 h. More 2M aqueous sodium hydroxide (10 mL) was added and the mixture extracted with ethyl acetate (×3). The organic layers were combined, dried over MgSO$_4$, filtered and concentrated in vacuo. The crude material was purified by preparative HPLC to afford (6-cyano-5-methoxy-pyridin-3-ylmethyl)-carbamic acid tert-butyl ester (86 mg, 40%) as a white solid.

AnalpH2_MeOH_4MIN: Rt: 2.60 min, m/z 264.3 [M+H]$^+$

5-Aminomethyl-3-methoxy-pyridine-2-carbonitrile

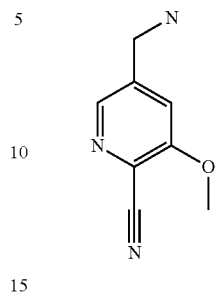

(6-Cyano-5-methoxy-pyridin-3-ylmethyl)-carbamic acid tert-butyl ester (1 eq) was treated with a 1:1 mixture of TFA:DCM. The reaction mixture was monitored by LCMS. Once the starting material had been consumed the reaction mixture was concentrated in vacuo. The crude material was purified by SCX-2 ion exchange column to afford 5-aminomethyl-3-methoxy-pyridine-2-carbonitrile (55 mg, quant.) as an off white solid.

AnalpH9_MeOH_4MIN: Rt: 1.50 min, m/z 164.3 [M+H]$^+$

Scheme. Synthesis of 1-Amino-isoquinoline-6-carbonitrile

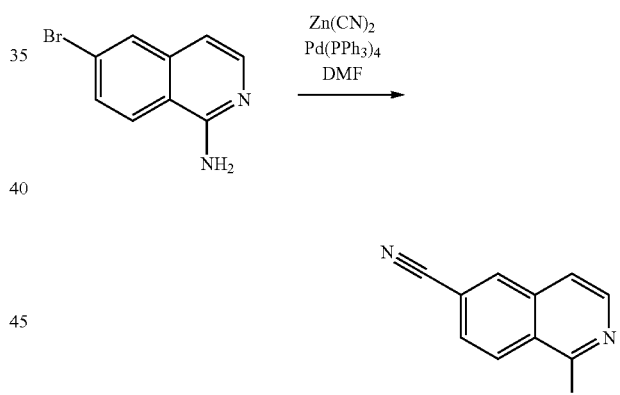

1-Amino-6-bromoisoquinoline (500 mg, 2.24 mmol) was dissolved in DMF (5 mL), Pd(PPh$_3$)$_4$ (260 mg, 0.22 mmol) added and N$_2$ bubbled through the solution for 10 mins. Zn(CN)$_2$ (157 mg, 1.34 mmol) was added and the reaction mixture heated in the microwave for 1 hour at 120° C. Water and EtOAc were added, the layers separated and the aqueous layer extracted with EtOAc twice. The combined organic layers were washed with brine, passed through a phase separator and solvent removed in vacuo. The crude product was purified by column chromatography (biotage, 25 g SNAP cartridge, 0-100% EtOAc in hexane followed by 0-20% MeOH in EtOAc). The solvent was removed to give 1-amino-isoquinoline-6-carbonitrile (293 mg, 77%) as a yellow solid.

AnalpH9_MeOH_4MIN: Rt: 2.12 min, m/z 170.1 [M+H]$^+$

The following compounds were made by analogous methods:

| Example No. | Structure & conditions | Analytical Data | Mass, % yield, state |
|---|---|---|---|
| 1,3-Dimethyl-1H-indazole-5-carbonitrile | Using 5-bromo-1,3-dimethyl-1H-indazole | AnalpH2_MeOH_4MIN: Rt: 2.42 min, m/z 172.3 [M + H]+ | 144 mg, 63%, solid |
| 1,3-Dimethyl-1H-indazole-6-carbonitrile | Using 6-bromo-1,3-dimethyl-1H-indazole | AnalpH2_MeOH_4MIN: Rt: 2.58 min, m/z 172.2 [M + H]+ | 12g, 73%, yellow solid |
| 1-Methyl-1H-indazole-6-carbonitrile | Using 6-bromo-1-methyl-1H-indazole | AnalpH2_MeCN_UPLC_4.2 min: Rt: 1.67 min, m/z 158.0 [M + H]+ | 18g, 95%, white solid |

3-chloro-1-methyl-1H-indazole-6-carbonitrile

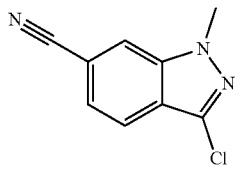

To a stirred solution of 1-methyl-1H-indazole-6-carbonitrile, (20.0 g, 105 mmol) in dry acetonitrile (250 ml) was added N-chlorosuccinimide (18.0 g, 150 mmol) at room temperature. After completion of the reaction (monitored by thin layer chromatography), the reaction mixture was concentrated and purified by silica gel flash column chromatography using ethyl acetate and petroleum ether (10-30%) solution to afford 3-chloro-1-methyl-1H-indazole-6-carbonitrile (13.0 g, 59%) as a white solid.

AnalpH2_MeCN_UPLC_4.2 min: Rt: 1.96 min, m/z 192.1 [M+H]+

C-(1-Methyl-1H-benzotriazol-5-yl)-methylamine

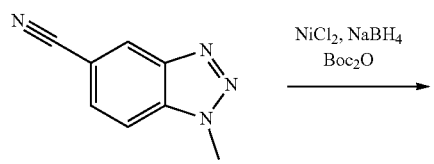

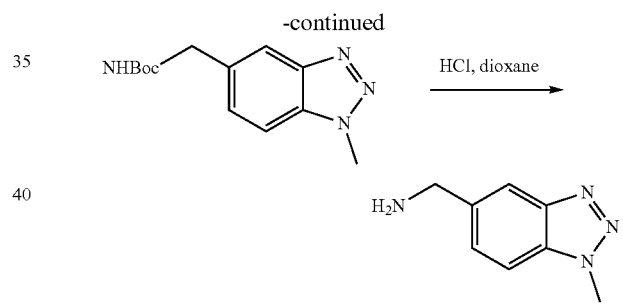

Step-1: tert-butyl (1-methyl-1H-benzo[d][1,2,3]triazol-5-yl)methylcarbamate

To a stirred solution of 1-methyl-1H-benzotriazole-5-carbonitrile (5.0 g, 32 mmol) in dry methanol (200 mL) were added Boc$_2$O(13.8 g, 63.0 mmol) and NiCl$_2$.6H$_2$O(0.41 g, 3.2 mmol) at 0° C. Then NaBH$_4$ (8.4 g, 220 mmol) was added portionwise over 20 minutes and the reaction mixture was allowed to warm to room temperature overnight. Diethylenetriamine (3.4 mL, 32 mmol) was added at room temperature and mixture stirred for a further 30 minutes. EtOAc and saturated aqueous NaHCO$_3$(300 mL) were added and the layers separated. The aqueous layer was extracted with EtOAc and the combined organic extracts were washed with sat. aq. NaHCO$_3$ and brine, dried and concentrated under reduced pressure. The crude product was purified by column chromatography (biotage, 100 g, 0-100% EtOAc/ihex) to afford (1-methyl-1H-benzotriazol-5-ylmethyl)-carbamic acid tert-butyl ester (5.05 g, 61%) as a brown solid.

Step-2: (1-methyl-1H-benzo[d][1,2,3]triazol-5-yl)methanamine hydrochloride (1-Methyl-1H-benzotriazol-5-ylmethyl)-carbamic acid tert-butyl ester (5.05 g, 19.2 mmol) was dissolved in 4M HCl in dioxane (100 mL) and stirred at room temperature for 45 mins. The reaction mixture was filtered and dried in vacuo to afford (1-methyl-1H-benzo[d][1,2,3]triazol-5-yl)methanamine hydrochloride (2.67 g, 53%) as a white solid.

AnalpH2_MeOH_4MIN: Rt: 0.38 min, m/z 163.2 [M+H]$^+$

The following compounds were made by analogous methods:

| Example No. | Structure & conditions | Analytical Data | Mass, state |
|---|---|---|---|
| 6-Aminomethyl-isoquinolin-1-ylamine | From 1-Amino-isoquinoline-6-carbonitrile | AnalpH2_MeOH_4MIN: Rt: 1.57 min, m/z 174 [M + H]$^+$ | 505 mg, solid |
| C-(1,3-Dimethyl-1H-indazol-5-yl)-methyl-amine hydrochloride | From 1,3-Dimethyl-1H-indazole-5-carbonitrile | AnalpH9_MeCN_UPLC_10 min: Rt: 1.99 min, m/z 176.1 [M + H]$^+$ | 6.5 g, white solid |
| C-(1,3-Dimethyl-1H-indazol-6-yl)-methyl-amine hydrochloride | From 1,3-Dimethyl-1H-indazole-6-carbonitrile | AnalpH2_MeOH_4MIN: Rt: 1.23 min, m/z 176.2 [M + H]$^+$ | 7.1 g, white solid |
| C-(3-Chloro-1-methyl-1H-indazol-6-yl)-methyl-amine hydrochloride | From 3-chloro-1-methyl-1H-indazole-6-carbonitrile | AnalpH9_MeCN_UPLC_10 min: Rt: 2.71 min, m/z 196.1 [M + H]$^+$ | 6.1 g, white solid |

Synthesis of (5-Aminomethyl-thiazol-2-ylmethyl)-carbamic acid tert-butyl ester

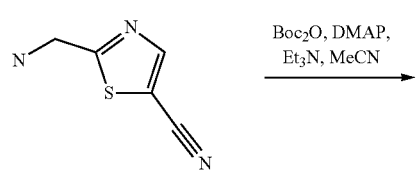

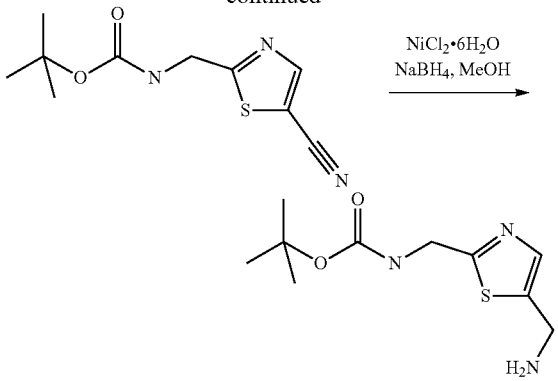

Step 1: Di-tert-butyl dicarbonate (746 mg, 3.42 mmol) was added to 2-aminomethyl-thiazole-5-carbonitrile (5.0 g, 2.9 mmol) in MeCN(10 mL). DMAP (355 mg, 0.29 mmol) was added followed by Et$_3$N (0.4 mL, 2.8 mmol) and the reaction mixture stirred at room temperature overnight. The reaction mixture was diluted with EtOAc and washed with sat. aq. NaHCO$_3$ solution. The organic layer was dried over MgSO$_4$, filtered and concentrated in vacuo to give (5-cyano-thiazol-2-ylmethyl)-carbamic acid tert-butyl ester which was used without further purification.

Step 2: (5-Cyano-thiazol-2-ylmethyl)-carbamic acid tert-butyl ester was dissolved in MeOH (20 mL) and cooled to 0° C. NiCl$_2$.6H$_2$O (135 mg, 0.57 mmol) was added, followed by NaBH$_4$ (1.08 g, 28.5 mmol) portionwise. The reaction mixture was allowed to warm to room temperature for 2 h, then diluted with EtOAc and washed with sat. aq. NaHCO$_3$ solution. The organic layer was dried over MgSO$_4$, filtered through celite and purified by SCX-2 (washing with MeOH and eluting with 0.5 M NH$_3$ in MeOH). The solvent was removed and the crude product purified by prep HPLC to give (5-aminomethyl-thiazol-2-ylmethyl)-carbamic acid tert-butyl ester (33.3 mg, 5%) as a yellow oil.

AnalpH2_MeOH_4MIN: Rt: 0.82-1.34 min, m/z 244.4 [M+H]$^+$

Synthesis of c-Furo[2,3-c]pyridin-2-yl-methylamine

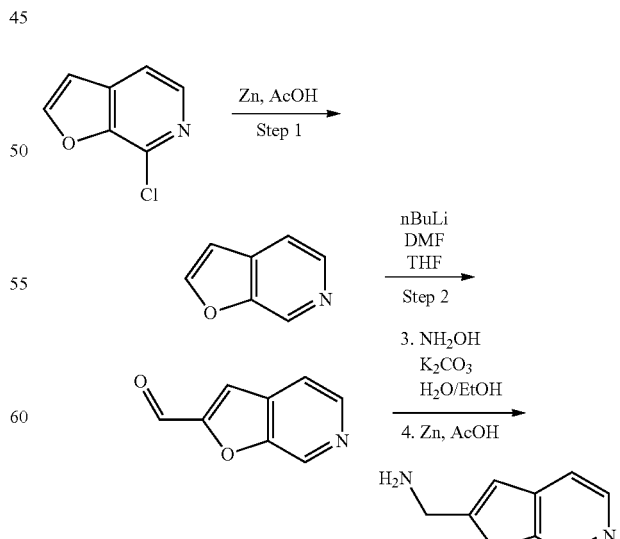

Step 1: 7-Chlorofuro[2,3-c]pyridine (433 mg, 2.82 mmol) was dissolved in acetic acid (6 mL) and zinc powder (1.03 g, 15.8 mmol) was added. The reaction mixture was heated at reflux for 2 hours before cooling to room temperature. The mixture was then filtered and the filtrate was concentrated in vacuo. The resulting solid was dissolved in water, basified using 2M NaOH and extracted using DCM (×3). The combined organics were dried using MgSO₄ and concentrated in vacuo to produce furo[2,3-c]pyridine (206 mg, 62%) as an orange oil.

ANALPH2_MEOH_4 min, Rt: 0.36 min, m/z 120.2 [M+H]+

Step 2: Furo[2,3-c]pyridine (206 mg, 1.72 mmol) was dissolved in anhydrous THF (8 mL) and cooled to −78° C. whereupon n-butyllithium (0.87 mL, 2.15 mmol) was added. The reaction mixture was stirred for 30 minutes before DMF (0.27 mL, 3.44 mmol) was added. The reaction mixture was allowed to warm to room temperature and stirred for 18 hours. The reaction was quenched with 1M HCl and neutralised using NaHCO₃ before extraction using DCM (×3). The combined organics were dried using MgSO₄ and concentrated in vacuo to produce furo[2,3-c]pyridine-2-carbaldehyde (165 mg, 65%) as an orange solid.

ANALPH2_MEOH_4 min, Rt: 0.36 min, m/z 148.1 [M+H]+

Step 3: Furo[2,3-c]pyridine-2-carbaldehyde (165 mg, 1.12 mmol) was dissolved in ethanol (2.5 mL) with warming. Solutions of hydroxylamine hydrochloride (164 mg, 2.36 mmol) in water (0.33 mL), and potassium carbonate (164 mg, 1.19 mmol) in water (0.83 mL) were added and the reaction mixture was allowed to cool to room temperature and stirred for 18 hours. The mixture was filtered and the residue dried under reduced pressure to afford furo[2,3-c]pyridine-2-carbaldehyde oxime (130 mg, 72%) as an off-white solid.

ANALPH2_MEOH_4 min. Rt: 0.37 min. m/z 163.1 [M+H]+

Step 4: Furo[2,3-c]pyridine-2-carbaldehyde oxime (130 mg, 0.80 mmol) was dissolved in acetic acid (2 mL) and zinc powder (293 mg, 4.48 mmol) was added. The reaction mixture was stirred at room temperature for 30 minutes. The mixture was then filtered and the filtrate concentrated in vacuo to produce c-furo[2,3-c]pyridin-2-yl-methylamine (123 mg, quant.) as an orange oil which was used 'as is' in subsequent reactions.

ANALPH2_MEOH_4 min, Rt: 0.27 min, m/z 149.1 [M+H]+

Synthesis of RgB

General Schemes for RgB Cores

Scheme: Synthesis of 4-(bromomethyl)-2,3-dihydrobenzofuran (2,3-Dihydro-benzofuran-4-yl)-methanol

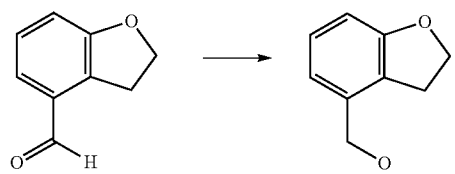 [SMILES: O=Cc1cccc2c1CCO2 ; OCc1cccc2c1CCO2]

2,3-dihydrobenzofuran-4-carbaldehyde (2.00 g, 13.5 mmol) was dissolved in dry MeOH (30 mL) and the solution cooled to 0° C. NaBH₄ (510 mg, 13.5 mmol) was added and the solution stirred at room temperature for 1 hour. Ice water was added and the layers separated. The organic phase was evaporated in vacuo to yield the title compound as colourless crystalline solid (1.90 g, 94

AnalpH2_MeOH_4MIN: Rt: 2.00 min, m/z 151.3 [M+H]+

4-Bromomethyl-2,3-dihydro-benzofuran

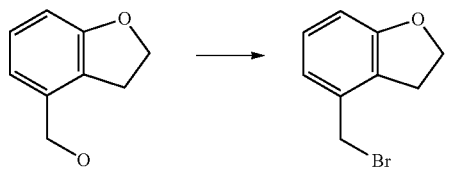 [SMILES: OCc1cccc2c1CCO2 ; BrCc1cccc2c1CCO2]

2,3-dihydrobenzofuran-4-ylmethanol (1.90 g, 12.6 mmol) was dissolved in dry DCM (30 mL) and the mixture cooled to 0° C. PBr₃ (2.40 mL, 25.4 mmol) was added dropwise over 10 minutes and the mixture stirred at room temperature for 1 hour. The mixture was cooled to 0° C. and sat. NaHCO₃(aq) (50 mL) was added portionwise. The mixture was stirred at 0° C. for 10 minutes then diluted with DCM (30 mL). The layers were separated and the organic phase washed with sat. NaHCO₃(aq) (50 mL) then saturated brine solution (50 mL). The organic phase was dried (MgSO₄), filtered and the solvent evaporated in vacuo to afford the title compound (2.35 g, 87%) as a pale yellow oil.

AnalpH2_MeOH_4MIN: Rt: 2.99 min, m/z gave no identifiable ionisation

Scheme 2A (Acids)

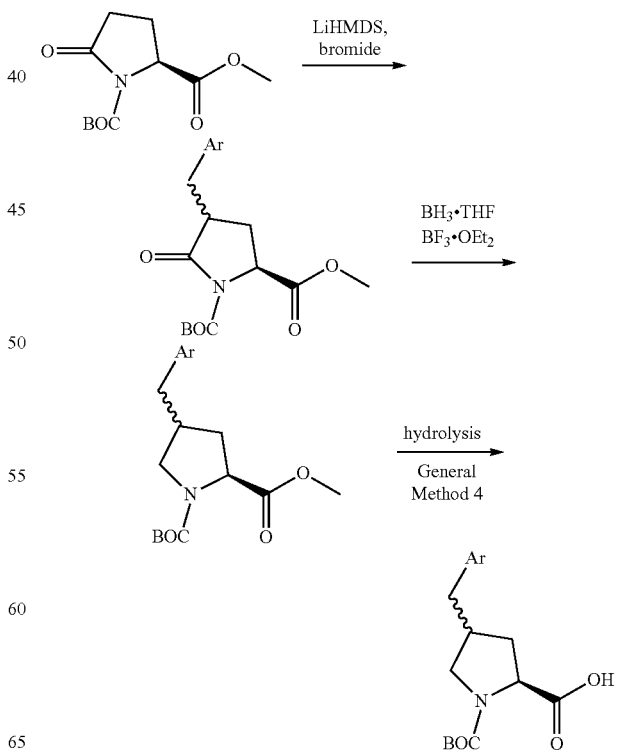

Route 1: Synthesis of (2S)-4-(1,3-benzodioxol-5-ylmethyl)-1-tert-butoxycarbonyl-pyrrolidine-2-carboxylic acid

(S)-4-Benzo[1,3]dioxol-5-ylmethyl-5-oxo-pyrrolidine-1,2-dicarboxylic acid 1-tert-butyl ester 2-methyl ester

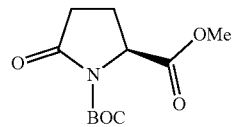

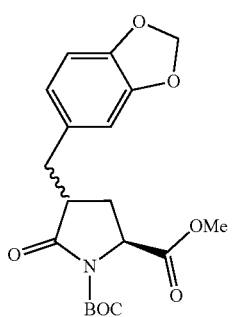

Boc-L-Pyroglutamic acid methyl ester (1.05 g, 4.32 mmol) was dissolved in dry THF (20 mL). The mixture was cooled to −78° C. LiHMDS (1M in THF, 4.40 mL, 4.40 mmol) was added dropwise at −78° C. over 10 minutes. The solution was stirred at −78° C. for 1 hour. A solution of 5-(bromomethyl)-1,3-benzodioxole (0.975 g, 4.53 mmol) in dry THF (5 mL) was then added dropwise at −78° C. over 30 minutes. The solution was stirred at −78° C. for 2 hours. Sat. NaHCO₃ (aq) (40 mL) was added dropwise with continual stirring until the solution reached room temperature. The mixture was diluted with EtOAc (50 mL) and the layers separated. The organic phase was washed with sat. brine (aq) (40 mL) then dried (MgSO₄), filtered and the solvent evaporated in vacuo. The crude product was purified by flash chromatography (Biotage Isolera; 50 g SNAP cartridge) eluting with isohexane→40% EtOAc—isohexane to yield the title compound (1.08 g, 66%) as a white solid.

AnalpH2_MeOH_4MIN: Rt: 3.03 min, m/z 378.3 [M+H]+

Optionally after addition of the requisite benzyl bromide the reaction may be stirred for up to 18 hours at room temperature.

Optionally after reaction completion the mixture may be warmed to room temperature and quenched with sat. NH₄Cl (aq) or sat. brine (aq).

(2S,4R)-4-Benzo[1,3]dioxol-5-ylmethyl-pyrrolidine-1,2-dicarboxylic acid 1-tert-butyl ester 2-methyl ester

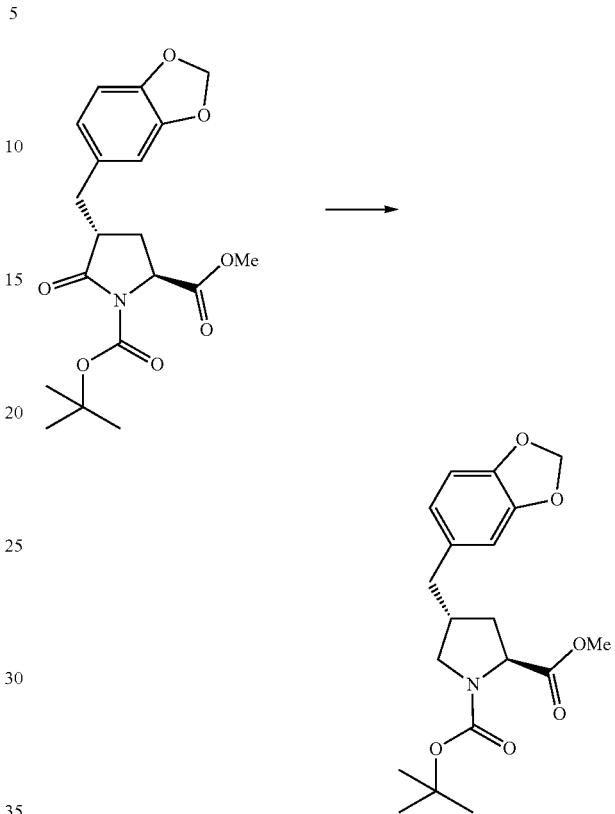

(S)-4-Benzo[1,3]dioxol-5-ylmethyl-5-oxo-pyrrolidine-1,2-dicarboxylic acid 1-tert-butyl ester 2-methyl ester (550 mg, 1.46 mmol) was dissolved in dry DCM (15 mL). The mixture was cooled to 0° C. and 1M BH₃-THF (1.80 mL, 1.80 mmol) added dropwise over 5 minutes under N₂ followed by the dropwise addition of BF₃-Et₂O (200 μL, 1.62 mmol) over 5 minutes at 0° C. under N₂. 1M BH₃-THF (1.80 mL, 1.80 mmol) and BF₃-Et₂O (200 μL, 1.62 mmol) were then added dropwise successively over 5 minutes at 0° C. The mixture was stirred at 0° C. for 1 hour then stirred at room temperature for 1 hour. Sat. NH₄Cl (aq) (30 mL) and EtOAc (40 mL) were added at 0° C. and the mixture stirred vigorously for 15 minutes. The layers were separated and the organic phase washed with sat. brine (aq) (40 mL) then dried (MgSO₄), filtered and the solvent evaporated in vacuo. The crude product was purified by flash chromatography (Biotage Isolera; 25 g SNAP cartridge) eluting with isohexane→40% EtOAc-isohexane to yield the title compound (352 mg, 66%) as a pale yellow oil.

AnalpH2_MeOH_4MIN: Rt: 3.26 min, m/z 364.3 [M+H]+

Optionally 1M BH₃-THF was added in one portion followed by BF₃-Et₂O at 0° C. under N₂ and the solution then warmed to room temperature immediately afterwards and stirred for up to 3 hours.

Optionally incomplete reactions may have an additional aliquot of 1M BH₃-THF (10 mol %) and/or BF₃·Et₂O (20 mol %) and the mixture stirred at room temperature for an additional 16 hours. Incomplete reactions may then have further additions of BH₃-THF & BF₃·Et₂O as required and stirred up to 24 hours.

Optionally the product may be purified by reversed phase HPLC.

(2S,4R)-4-Benzo[1,3]dioxol-5-ylmethyl-pyrrolidine-1,2-dicarboxylic acid 1-tert-butyl ester

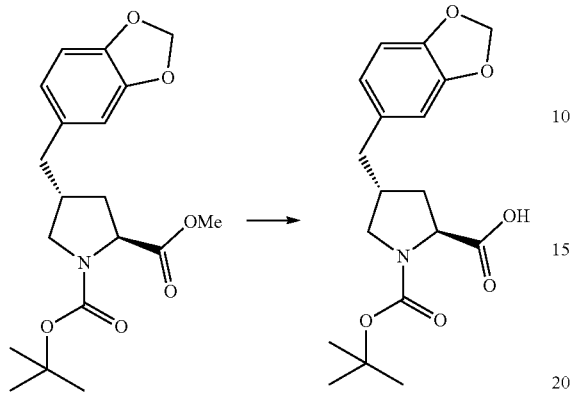

(2S,4R)-4-Benzo[1,3]dioxol-5-ylmethyl-pyrrolidine-12-dicarboxylic acid 1-tert-butylester 2-methyl ester (352 mg, 0.969 mmol) was dissolved in MeOH (7.5 mL) LiOH (1M in H$_2$O, 2.50 mL, 2.50 mmol) was added and the mixture stirred at room temperature for 16 hours. The solvent was evaporated in vacuo and the residue partitioned between EtOAc (50 mL) and 0.25M HCl(aq) (40 mL). The aqueous phase was extracted with EtOAc (40 mL) and the combined organic layers dried (MgSO$_4$), filtered and the solvent evaporated in vacuo to afford (2S,4R)-4-Benzo[1,3]dioxol-5-ylmethyl-pyrrolidine-12-dicarboxylic acid 1-tert-butyl ester (262 mg, 78%) as a colourless gum.

AnalpH2_MeOH_4MIN: Rt: 3.10 min m/z 350.3 [M+H]+

The following compounds were made by analogous methods:

| Structure | Method | Analytical data | Mass, state |
|---|---|---|---|
| 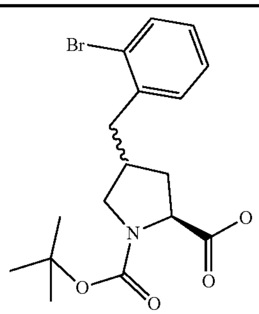 | Route 1 using 2-bromobenzyl Bromide and hydrolysis using GM4A | AnalpH2_MeOH_4MIN: Rt: 3.41 min,m/z 384.1/386.1 [M + H]+ | 450 mg, white solid |
| 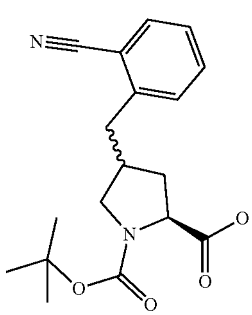 | Route 1 using 2-(bromomethyl)benzonitrile and hydrolysis using GM4A | AnalpH2_MeOH_4MIN: Rt: 2.87 min, m/z 329.2 [M − H]− | 500 mg, colourless oil |

M05337-int & M05320-int

| Structure | Method | Analytical data | Mass, state |
|---|---|---|---|
| 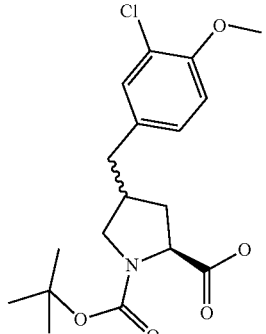 M05339-int | Route 1 using 4-bromomethyl-2-chloromethoxybenzene and hydrolysis using GM4A | AnalpH2_MeOH_4MIN: Rt: 3.17 min, m/z 368.1 [M − H]− | 647 mg, white solid |
| 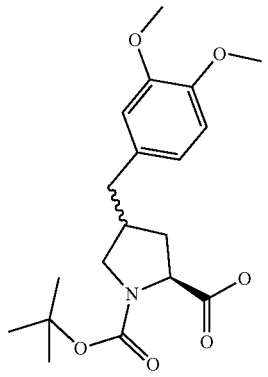 M05348-int | Route 1 using 4-(bromomethyl)-1,2-dimethoxybenzene and hydrolysis using GM4A | AnalpH2_MeOH_4MIN: Rt: 2.93, 2.96 min, m/z 364.1 [M − H]− | 245 mg, used crude in subsequent reaction |
| 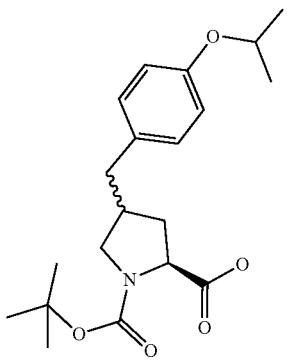 M05349-int | Route 1 using 1-(bromomethyl)-4-(propan-2-yloxy)benzene and hydrolysis using GM4A | AnalpH2_MeOH_4MIN: Rt: 3.31 min, m/z 364.3 [M + H]+ | 94 mg used crude in subsequent reaction |
| 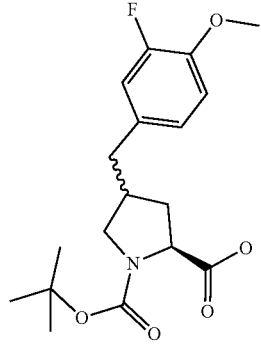 M05352-int | Route 1 using 3-fluoro-4-methoxybenzyl bromide and hydrolysis using GM4A with purification method B | AnalpH2_MeOH_4MIN: Rt: 3.11 min, m/z 354.3 [M + H]+ | 675 mg, Colourless oil |

-continued

| Structure | Method | Analytical data | Mass, state |
|---|---|---|---|
| M05361-int & M05274-int | Route 1 using 3,5-difluorobenzyl bromide and hydrolysis using GM4A | AnalpH9_MeOH_4MIN: Rt: 2.82 min, m/z 340.1 [M − H]− | 215 mg, colourless oil |
| M05362-int | Route 1 using 4-trifluoromethoxybenzyl-bromide and hydrolysis using GM4A | AnalpH2_MeOH_4MIN: Rt: 3.33 min, m/z 388.1 [M − H]− | 423 mg, colourless oil |
| M05371-int & M05380-int | Route 1 using 4-(bromomethyl)-2,3-dihydrobenzofuran and hydrolysis using GM4A | AnalpH9_MeOH_4MIN: Rt: 2.58 min, m/z 346.2 [M − H]− | 340 mg, white solid |
| M05372-int & M05384-int | Route 1 using 4-methylsulfonebenzyl bromide and hydrolysis using GM4A | AnalpH2_MeOH_4MIN: Rt: 2.63 min, m/z 382.1 [M − H]− | 393 mg, white solid |

| Structure | Method | Analytical data | Mass, state |
|---|---|---|---|
| M05382-int | Route 1 using 4-ethoxybenzyl bromide and hydrolysis using GM4A | AnalpH2_MeOH_4MIN: Rt: 3.24 min, m/z 348.3 [M − H]− | 197 mg, colourless oil |
| M05319-int | Route 1 using 3-(bromomethyl)benzonitrile and hydrolysis using GM4A | AnalpH2_MeOH_4MIN: Rt: 2.87 min, m/z 329.2 [M − H]− | 96 mg, white solid |
| M05235-int | Route 1 using 2,4-difluorobenzyl bromide and hydrolysis using GM4A | AnalpH2_MeOH_4MIN: Rt: 3.19 min, m/z 342.3 [M + H]+ | 300 mg, colourless oil |

Scheme 2B (Carboxylic Acids):

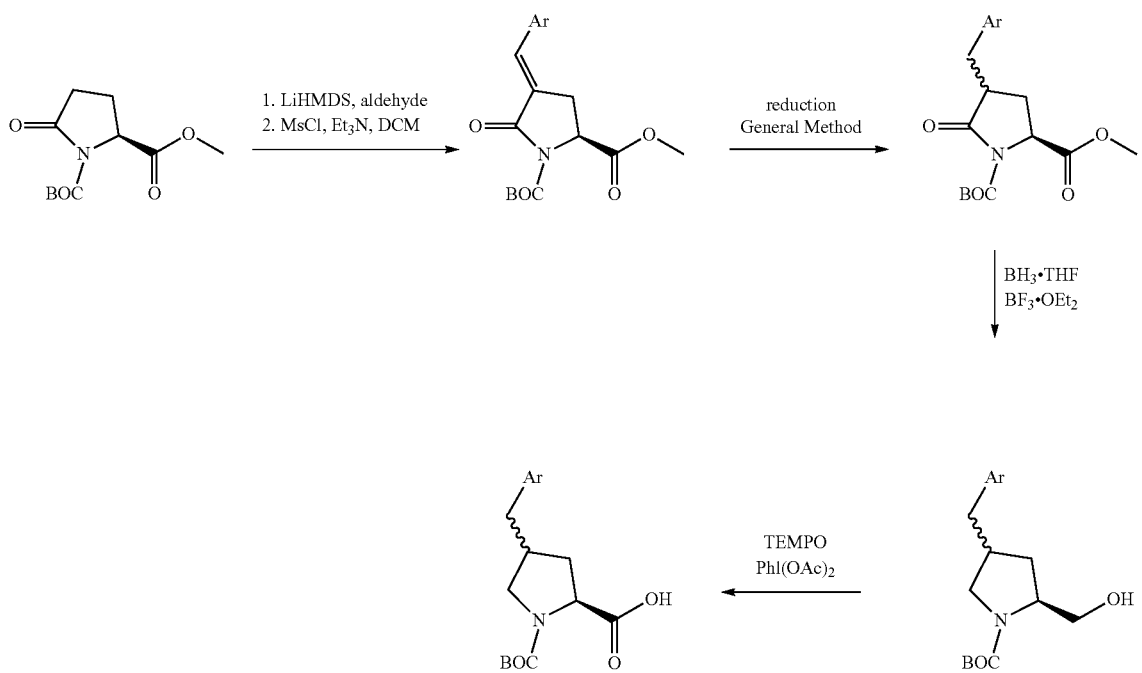

Route 2: Synthesis of (S)-4-(2-Trifluoromethyl-pyridin-4-ylmethyl)-pyrrolidine-1,2-dicarboxylic acid 1-tert-butyl ester

(S)-5-Oxo-4-[1-(2-trifluoromethyl-pyridin-4-yl)-methylidene]-pyrrolidine-1,2-dicarboxylic acid 1-tert-butyl ester 2-methyl ester

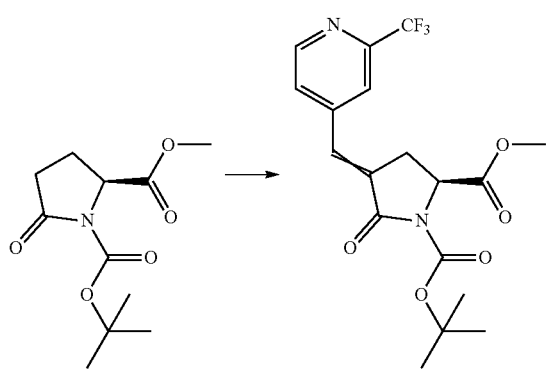 [SMILES: COC(=O)[C@@H]1CCC(=O)N1C(=O)OC(C)(C)C ; COC(=O)[C@@H]1CC(=Cc2ccnc(C(F)(F)F)c2)C(=O)N1C(=O)OC(C)(C)C]

Boc-L-Pyroglutamic acid methyl ester (1.00 g, 4.11 mmol) was dissolved in dry THF (20 mL). The mixture was cooled to −78° C. and LiHMDS (1M in THF, 4.30 mL, 4.30 mmol) was added dropwise over 10 minutes. The solution was stirred at −78° C. for 1 hour. A solution of 2-(trifluoromethyl) isonicotinaldehyde (0.720 g, 4.11 mmol) in dry THF (5 mL) was then added dropwise at −78° C. over 30 minutes. The resulting solution was then stirred at −78° C. for 2.5 hours. H₂O(10 mL) was added dropwise with continual stirring at approx. −40° C. then EtOAc (50 mL) added. The solution was warmed to room temperature with continual stirring. The layers were separated and the organic phase washed with sat. brine (aq) (30 mL), dried (MgSO₄), filtered and the solvent evaporated under reduced pressure. The crude product was obtained as a yellow gum (918 mg) which was dissolved in dry DCM (20 mL). TEA (750 μL, 5.38 mmol) was added followed by MsCl (200 μL, 2.58 mmol) and the mixture stirred at room temperature for 3 hours. The mixture was diluted with DCM (30 mL) and the solution washed with sat. NaHCO₃(aq) followed by sat. aq. brine (30 mL), dried (MgSO₄), filtered and the solvent evaporated in vacuo. The title compound was obtained as a pale yellow gum (0.800 g, 48%).

AnalpH2_MeOH_4MIN: Rt: 2.92 min, m/z 401.2 [M+H]+

Optionally TsCl may be used, in place of MsCl, to achieve the dehydration.

(S)-5-Oxo-4-(2-trifluoromethyl-pyridin-4-ylmethyl)-pyrrolidine-1,2-dicarboxylic acid 1-tert-butyl ester 2-methyl ester

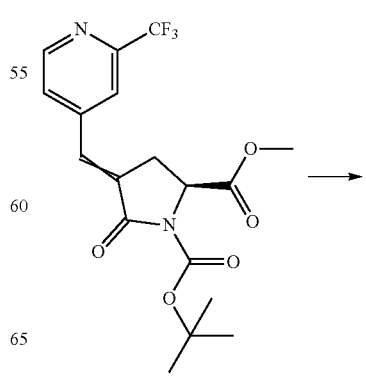

119

-continued

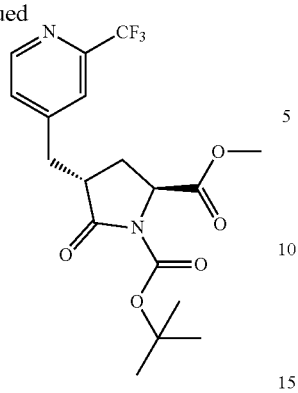

120

-continued

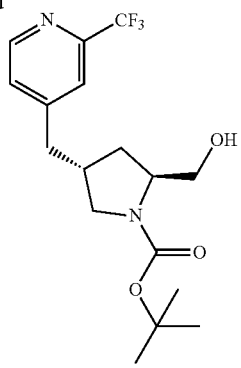

(S)-5-Oxo-4-[1-(2-trifluoromethyl-pyridin-4-yl)-methylidene]-pyrrolidine-1,2-dicarboxylic acid 1-tert-butyl ester 2-methyl ester (0.800 g, 2.00 mmol) and NH₄OAc (1.26 g, 20.0 mmol) were dissolved in EtOH (20 mL). Pd/C (10% wt., 64 mg, 0.60 mmol) was added and the reaction mixture stirred at reflux for 1 hour. The reaction mixture was filtered through celite washing the residue with EtOAc (50 ml). The filtrate was evaporated in vacuo and the resulting residue dissolved in EtOAc (60 mL). The organic phase was washed with sat. NaHCO₃(aq) followed by sat. brine (aq) (40 mL), then dried (MgSO₄), filtered and the solvent evaporated in vacuo. The crude product was purified by flash chromatography (Biotage; 25 g SNAP cartridge) eluting with 8:2 isohexane-EtOAc→2:8 isohexane-EtOAc to yield the title compound as a pale yellow gum (0.328 g, 41%).

AnalpH2_MeOH_4MIN: Rt: 2.82 min, m/z 403.2 [M+H]+

(S)-2-Hydroxymethyl-4-(2-trifluoromethyl-pyridin-4-ylmethyl)-pyrrolidine-1-carboxylic acid tert-butyl ester

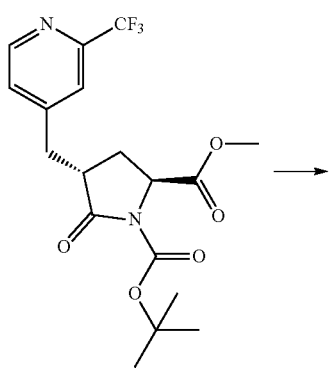

(S)-5-Oxo-4-(2-trifluoromethyl-pyridin-4-ylmethyl)-pyrrolidine-1,2-dicarboxylic acid 1-tert-butyl ester 2-methyl ester (270 mg, 0.671 mmol) was dissolved in dry DCM (15 mL). 1M BH₃-THF (3.40 mL, 3.40 mmol) and BF₃·Et₂O (1.25 mL, 1.01 mmol) were added and the mixture stirred at 80° C. in the microwave for 30 minutes. The mixture was diluted with DCM (30 mL) and the solution washed with sat. NaHCO₃(aq) then dried (MgSO₄), filtered and the solvent evaporated in vacuo. The title compound was obtained as a yellow solid (217 mg, 90%).

AnalpH2_MeOH_4MIN: Rt: 3.00 min, m/z 361.2 [M+H]+

Optionally BF₃·Et₂O may be added up to 1 hour after the addition of BH₃-THF.

(S)-4-(2-Trifluoromethyl-pyridin-4-ylmethyl)-pyrrolidine-1,2-dicarboxylic acid 1-tert-butyl ester

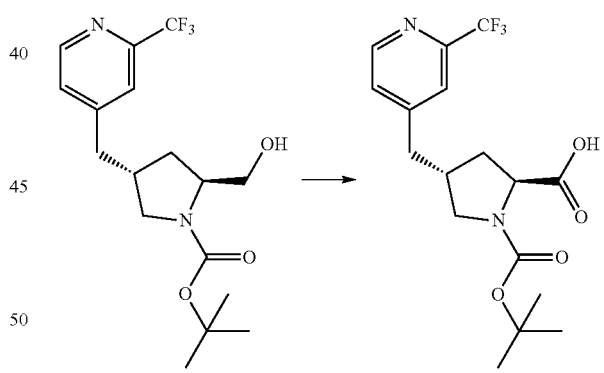

((S)-2-Hydroxymethyl-4-(2-trifluoromethyl-pyridin-4-ylmethyl)-pyrrolidine-1-carboxylicacid tert-butyl ester (217 mg, 0.602 mmol), TEMPO (28 mg, 0.179 mmol) and PhI(OAc)₂ (427 mg, 1.33 mmol) were dissolved in 1:1 MeCN—H₂O (8 mL) and the reaction mixture stirred at room temperature for 6 hours. The mixture was diluted with H₂O(20 mL) and the solution extracted with EtOAc (3×30 mL). The combined organics were washed with sat. brine (aq) (30 mL) then dried (MgSO₄), filtered and the solvent evaporated in vacuo to yield the title compound as an off-white solid (50 mg, 22%).

AnalpH2_MeOH_4MIN: Rt: 3.17 min, m/z 375.4 [M+H]+

The following compound was made by analogous methods:

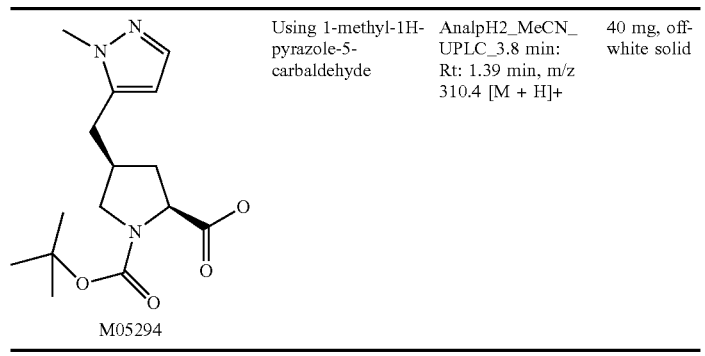

| | | | |
|---|---|---|---|
| M05294 | Using 1-methyl-1H-pyrazole-5-carbaldehyde | AnalpH2_MeCN_UPLC_3.8 min: Rt: 1.39 min, m/z 310.4 [M + H]+ | 40 mg, off-white solid |

Scheme 2C (Esters)

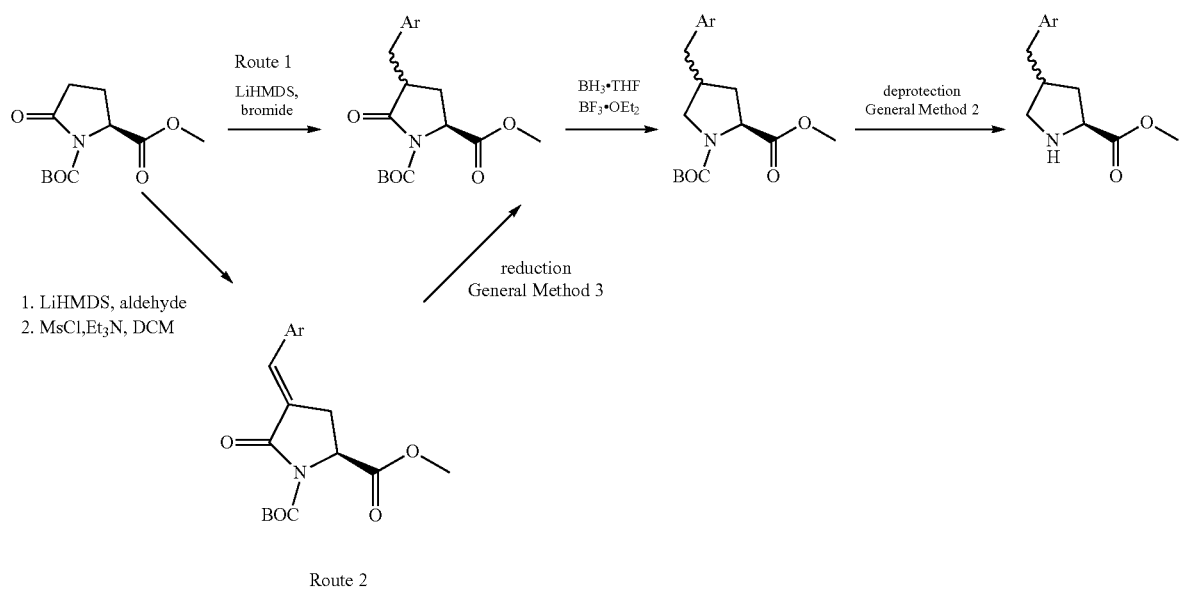

The following compounds were synthesised in an analogous fashion to the sequence depicted in Scheme 2A &2B. The difference being the final deprotection step which has been switched from a saponification to Boc deprotection, the general BOO deprotection methodology of which is described in General Method 2. Example synthetic procedures for the preceding steps have also been discussed in the previous section (Scheme 2A &2B).

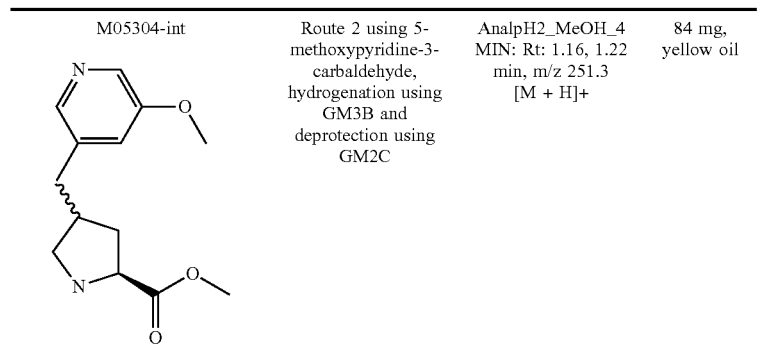

| M05304-int | Route 2 using 5-methoxypyridine-3-carbaldehyde, hydrogenation using GM3B and deprotection using GM2C | AnalpH2_MeOH_4 MIN: Rt: 1.16, 1.22 min, m/z 251.3 [M + H]+ | 84 mg, yellow oil |
|---|---|---|---|

| | | | |
|---|---|---|---|
| M05306-int 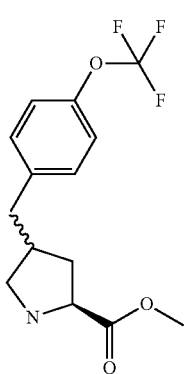 [SMILES: COC(=O)[C@@H]1CC(Cc2ccc(OC(F)(F)F)cc2)CN1] | Route 1 using 4-(trifluoromethoxy) benzyl bromide and deprotection using GM2A | AnalpH2_MeOH_4 MIN: Rt: 1.99 min, m/z 304.2 [M + H]+ | 300 mg, yellow oil |
| M05295-int 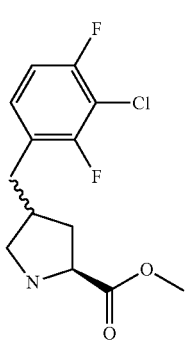 [SMILES: COC(=O)[C@@H]1CC(Cc2ccc(F)c(Cl)c2F)CN1] | Route 1 using 3-chloro-2,4-difluoro-benzyl bromide and deprotection using GM2A | AnalpH2_MeOH_4 MIN: Rt: 1.82 min, m/z 290.2 [M + H]+ | 224 mg, yellow oil |
| M05297-int 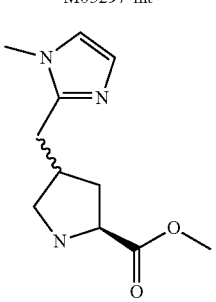 | Route 2 using 1-methyl-2-imidazole carboxaldehyde, hydrogenation using GM3B and deprotection using GM2C | AnalpH9_MeOH_4 MIN: Rt: 1.80 min, m/z 224.1 [M + H]+ | 157 mg, Used crude in subsequent reaction |
| M05300-int 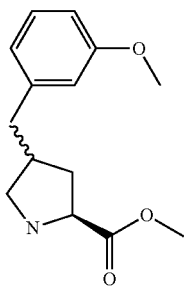 [SMILES: COC(=O)[C@@H]1CC(Cc2cccc(OC)c2)CN1] | Route 2 using m-anisaldehyde, hydrogenation using GM3B and deprotection using GM2A | AnalpH2_MeOH_4 MIN: Rt: 1.52 min, m/z 250.3 [M + H]+ | 221 mg, yellow oil |

-continued

| | | | |
|---|---|---|---|
| M05298-int 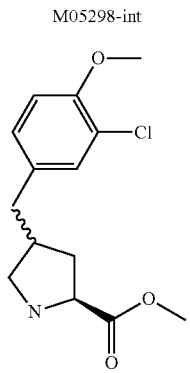 | Route 1 using 4-bromomethyl-2-chloro-1-methoxybenzene and deprotection using GM2A | AnalpH2_MeOH_4 MIN: Rt: 1.66 min, m/z 284.2 [M + H]+ | 274 mg, colourless oil |
| M05309-int 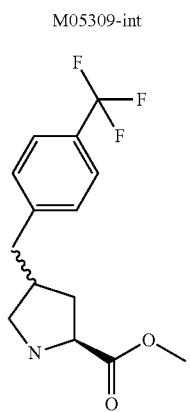 | Route 2 using 4-(trifluoromethyl) benzaldehyde, hydrogenation using GM3B and deprotection using GM2A | AnalpH2_MeOH_4 MIN: Rt: 1.93 min, m/z 288.2 [M + H]+ | 54 mg, off-white solid |
| M05312-int 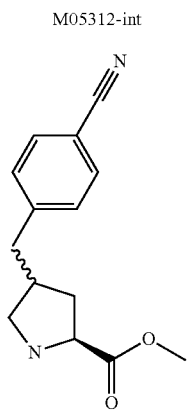 | Route 1 using 4-cyanobenzyl bromide, and deprotection using GM2A | AnalpH9_MeOH_4 MIN: Rt: 2.42 min, m/z 245.2 [M + H]+ | Colourless oil, 83 mg |
| from M05314-int & M05315-int 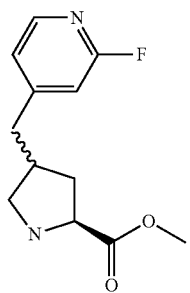 [SMILES: COC(=O)[C@@H]1CC(Cc2ccnc(F)c2)CN1] | Route 2 using fluoropyridine-4-carboxaldehyde, hydrogenation using GM3B and deprotection using GM2A | AnalpH2_MeOH_4 MIN: Rt: 0.98 min, m/z 239.2 [M + H]+ | Yellow oil, 294 mg |

Scheme. Synthesis of (2S,4R)-4-Pyridin-2-ylm-ethyl-pyrrolidine-1,2-dicarboxylic acid 1-tert-butyl ester)

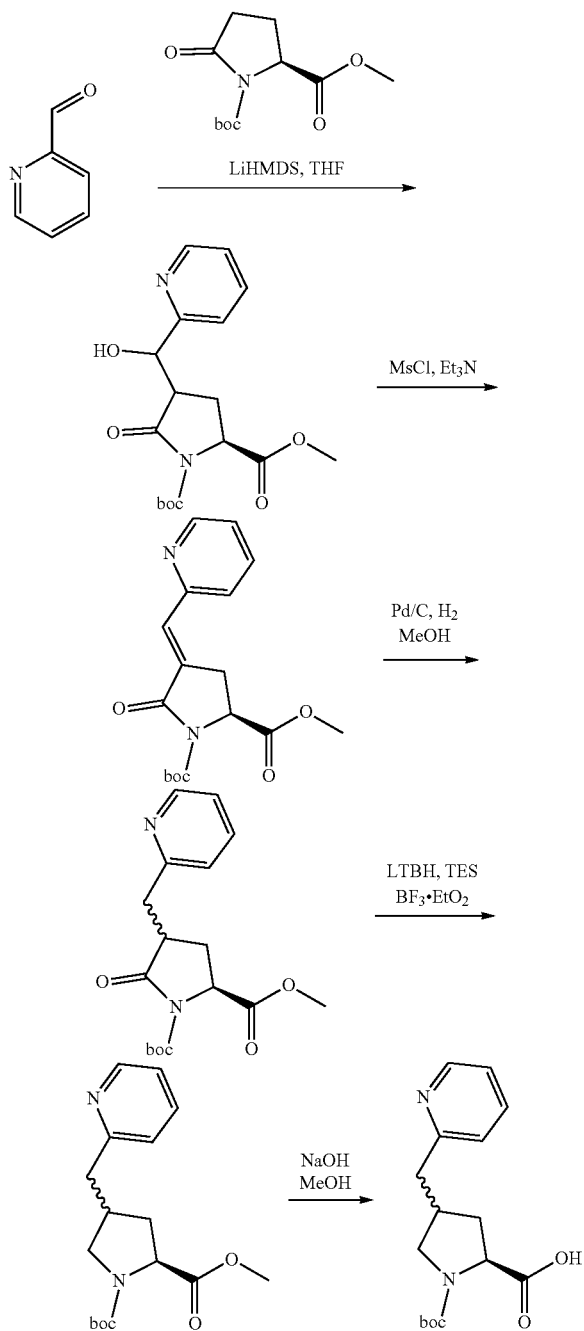

Step 1: To a solution of Boc-L-Pyroglutamic acid methyl ester (10.0 g, 41.2 mmol) in dry THF (200 mL), LiHMDS was added dropwise (1M in THF, 45.2 ml, 45.2 mmol, 1.1 eq) under nitrogen at −78 C. Then the reaction mixture was stirred for 2 h at −78 C. 2-pyridinecarboxaldehyde (4.8 g, 45.2 mmol) was added to reaction mixture at −78 C & stirred at −78° C. for another 4 h. The reaction was quenched with saturated ammonium chloride (100 ml). The crude product was extracted with EtOAc (3×200 ml) and the combined extract was dried over anhydrous magnesium sulphate and concentrated in vacuo. The crude product was purified by flash column (15% EtOAc/Hexane) chromatography to obtain (S)-4-(hydroxy-pyridin-2-yl-methyl)-5-oxo-pyrrolidine-1,2-dicarboxylic acid 1-tert-butyl ester 2-methyl ester (6.5 g, 45%) as off white solid.

AnalpH2_MeCN_UPLC_4.0 min: Rt: 1.38 min, m/z 351.5 [M+H]+

Step 2: To a solution of (S)-4-(hydroxy-pyridin-2-yl-methyl)-5-oxo-pyrrolidine-1,2-dicarboxylic acid 1-tert-butyl ester 2-methyl ester (6.50 g, 18.6 mmol) in DCM (65 ml) at 0° C. were added TEA (25.8 ml, 186 mmol) and methane sulfonyl chloride (2.3 g, 20.4 mmol). The reaction mixture was stirred at RT for 3 days. The reaction mixture was poured into ice cold water and extracted with ethyl acetate (2×500 mL). The combined organic extract was dried over anhydrous $Na_2SO_4$, concentrated under reduced pressure to afford (S)-5-oxo-4-[1-pyridin-2-yl-methyl-idene]-pyrrolidine-1,2-dicarboxylic acid 1-tert-butyl ester 2-methyl ester (3.5 g, 58%) as brown oil.

AnalpH2_MeCN_UPLC_4.0 min: Rt: 1.94 min, m/z 333.4 [M+H]+

Step 3: To a solution of (S)-5-oxo-4-[1-pyridin-2-yl-methylidene]-pyrrolidine-1,2-dicarboxylic acid 1-tert-butyl ester 2-methyl ester (3.5 g, 10.5 mmol) in methanol (35 ml) was added 10% palladium carbon (1.75 g, 16.8 mmol) under nitrogen atmosphere. The mixture was hydrogenated at 60 psi for 3 h. The reaction mixture was filtered through celite, washed with methanol and concentrated under reduced pressure to afford crude (S)-5-oxo-4-pyridin-2-ylmethyl-pyrrolidine-1,2-dicarboxylic acid 1-tert-butyl ester 2-methyl ester as off white solid (3.5 g, 100%). LCMS shows the compound as mixture of diastereomers.

AnalpH2_MeCN_UPLC_4.0 min: Rt: 1.23 min, m/z 335.5 [M+H]+

Step 4: To a solution of (S)-5-oxo-4-pyridin-2-ylmethyl-pyrrolidine-1,2-dicarboxylic acid 1-tert-butyl ester 2-methyl ester (2.8 g, 8.38 mmol) in THF (28 ml) at −78 C was added lithium triethyl borohydride (1.1 ml, 10 mmol) and the reaction mixture was stirred for 1 h. It was quenched with saturated sodium bicarbonate and warmed to 0 C. 35% $H_2O_2$ was added at 0 C, the mixture stirred for another 20 minutes at RT. The reaction mixture was concentrated under reduced pressure and extracted with DCM and dried. The residue was dissolved in DCM, triethylsilane (2.6 ml, 16.8 mmol) and $BF_3 \cdot EtO_2$ (2.1 ml, 16.8 mmol) were added at RT. The mixture was stirred for 30 minutes and quenched with saturated sodium bicarbonate solution. The aqueous layer was extracted with DCM and concentrated to give a crude product which was purified by flash column (35% EtOAc/isohexane) chromatography over silica-gel to obtain (S)-4-pyridin-2-ylmethyl-pyrrolidine-1,2-dicarboxylic acid 1-tert-butyl ester 2-methyl ester (950 mg, 36.5%) as white solid.

AnalpH2_MeCN_UPLC_4.0 min: Rt: 1.28 min, m/z 321.5 [M+H]+

Step 5: To a solution of (S)-4-pyridin-2-ylmethyl-pyrrolidine-1,2-dicarboxylic acid 1-tert-butyl ester 2-methyl ester (650 mg, 2.05 mmol) in MeOH (10 ml) and THF (10 ml), was added 1N sodium hydroxide solution (10 ml) at 0° C. The reaction mixture was stirred at RT for 1 h. The reaction mixture was concentrated under reduced pressure and acidified with 1N HCl, adjusting to ~pH 4-5. The aqueous layer was extracted with ethyl acetate and the combined organic extracts concentrated under reduced pressure to afford a crude product was purified by SFC to afford (2S,4R)-4-pyridin-2-ylmethyl-pyrrolidine-1,2-dicarboxylic acid 1-tert-butyl ester (276 mg, 44%) as a white solid.

AnalpH2_MeOH_4MIN: Rt: 1.78 min, m/z 307.3 [M+H]+

Scheme. Synthesis of (2S,4R)-4-Cyclopentylmethyl-pyrrolidine-1,2-dicarboxylic acid 1-tert-butyl ester

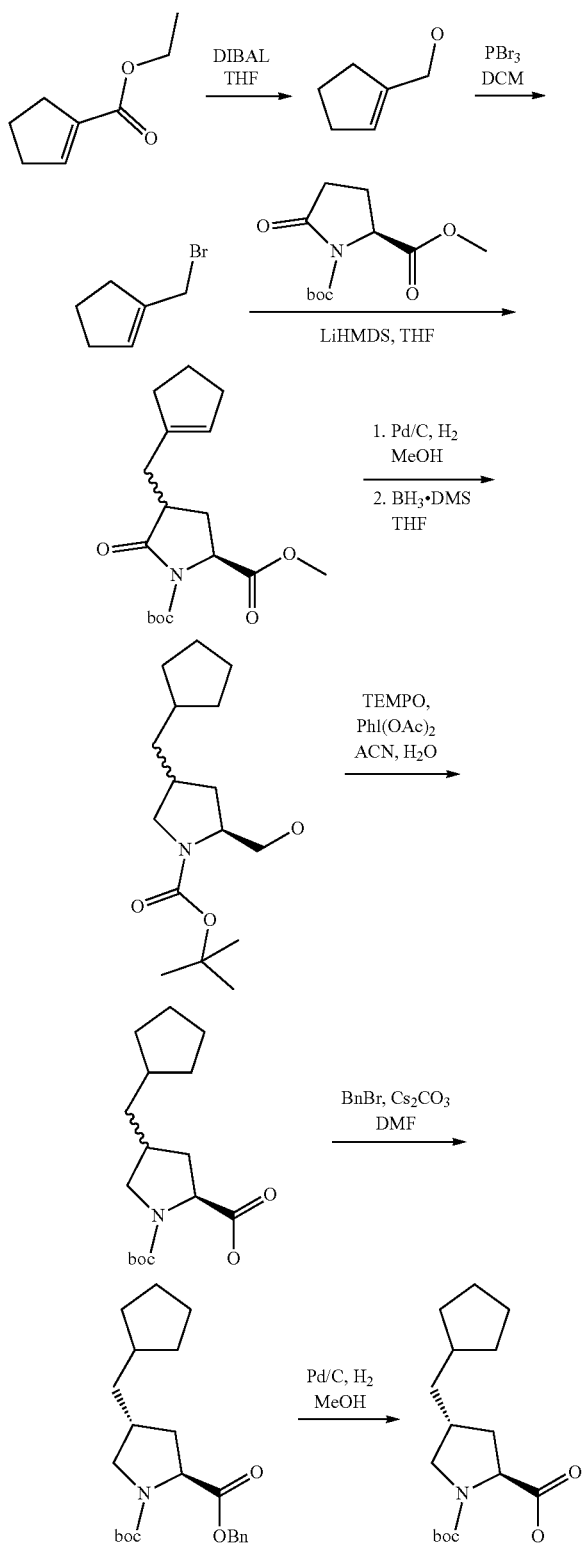

Step 1: To a solution of cyclopent-1-enecarboxylic acid ethyl ester (9.5 g, 75.3 mmol) in hexane (100 ml) at −78 C, was added DIBAL (1M in THF, 82 mL, 83 mmol) dropwise under nitrogen atmosphere. The reaction mixture was stirred at −78° C. for 3 h. The reaction mixture was quenched with saturated ammonium chloride (100 mL). The crude product was extracted with diethyl ether (3×200 mL) and the combined organic extracts were dried over anhydrous magnesium sulphate and concentrated in vacuo to obtain cyclopent-1-enyl-methanol (5.5 g, 75%) as a yellow oil.

$^1$H NMR (400 MHz, CDCl$_3$) δ 5.62 (1H, br s), 4.20 (2H, s), 2.37 (4H, m), 1.92 (2H, J=7.6 Hz, q), 1.36 (1H, br s)

Step 2: To a stirred solution of cyclopent-1-enyl-methanol (5.5 g, 56 mmol) in diethyl ether (230 ml) was added PBr$_3$ (2.3 mL, 28 mmol) at −78° C. The reaction mixture stirred at −78° C. under N$_2$ for 2 h, allowed to warm to room temperature and stirred for 10 h. The reaction was quenched with saturated sodium bicarbonate solution and extracted with diethyl ether (2×100 ml). The combined organic layers were washed with water (2×50 ml) followed by brine (100 ml), dried over anhydrous Na$_2$SO$_4$ and concentrated under reduced pressure. The crude product was purified by column chromatography on silica gel (100-200 mesh) using 5-10% EA/Pet ether as an eluent to afford 1-bromomethyl-cyclopentene (6.0 g, 66%) as a yellow liquid.

$^1$H NMR (400 MHz, CDCl$_3$) δ 5.80 (1H, br s), 4.09 (2H, s), 2.39 (4H, m), 1.95 (2H, J=7.2 Hz, q)

Step 3: (S)-5-Oxo-pyrrolidine-1,2-dicarboxylic acid 1-tert-butyl ester 2-methyl ester (4.0 g, 16.4 mmol) was dissolved in dry THF (40 ml). The mixture was cooled at −78 C and LiHMDS (1M in THF, 18 mL, 18 mmol) was added dropwise under nitrogen atmosphere. The reaction mixture was stirred for 2 h and a solution of 1-bromomethyl-cyclopentene (2.91 g, 18.1 mmol) was added drop-wise. The mixture was further stirred at −78° C. for 3 h. The reaction was quenched with saturated ammonium chloride (100 ml). The crude product was extracted with EtOAc (3×200 ml) and the combined extract was dried over anhydrous magnesium sulphate and concentrated in vacuo. The crude product was purified by flash column (0-5% EtOAc/is hexane) chromatography to obtain (S)-4-cyclopent-1-enyl-methyl-5-oxo-pyrrolidine-1,2-dicarboxylic acid 1-tert-butyl ester 2-methyl ester (mixture of diastereomers) (2.8 g, 53%) as a white solid.

$^1$H NMR (400 MHz, CDCl$_3$) δ 5.39 (1H, br s), 4.65 (1H, J=9.6, 1.2 Hz, dd), 3.78 (3H, s), 2.81-2.70 (2H, m), 2.33-2.11 (7H, m), 1.97-1.82 (3H, m), 1.50 (9H, s)

Step 4: To a solution of (S)-4-cyclopent-1-enylmethyl-5-oxo-pyrrolidine-1,2-dicarboxylic acid 1-tert-butyl ester 2-methyl ester (3.0, 9.3 mmol) in methanol, 10% palladium-carbon (1.48 g, 13.9 mmol) was added under nitrogen atmosphere. The reaction mixture was hydrogenated under balloon pressure for 3 h. The reaction mixture was filtered through celite, washed with hot methanol and concentrated under reduced pressure to afford crude (S)-4-cyclopentylmethyl-5-oxo-pyrrolidine-1,2-dicarboxylic acid 1-tert-butyl ester 2-methyl ester (2.7 g, 96%) as yellow liquid which was used crude in the subsequent reaction.

Step 5: To a stirred solution of (S)-4-cyclopentylmethyl-5-oxo-pyrrolidine-1,2-dicarboxylic acid 1-tert-butyl ester 2-methyl ester (2.7 g, 8.3 mmol) in THF (30 ml) under argon was added BH$_3$·DMS (946 mg, 12.5 mmol) at 0C. The mixture was heated at 90 C for 12 h. The reaction was quenched with methanol (10 mL) and extracted with ethyl acetate (50 ml). The organic layer was washed with brine, dried over MgSO$_4$ and concentrated to obtain crude product as an oil. The crude product was purified by column chromatography over silica gel (100-200 mesh) using 30% EA/Pet ether as eluent to afford (S)-4-cyclopentylmethyl-2-hydroxymethyl-pyrrolidine-1-carboxylic acid tert-butyl ester (1.1 g, 46.8%) as a green liquid.

AnalpH2_MeCN_UPLC_4.0 min: Rt: 2.49 & 2.54 min, m/z 284.4 [M+H]+

Step 6: To a solution of (S)-4-cyclopentylmethyl-2-hydroxymethyl-pyrrolidine-1-carboxylic acid tert-butyl ester (1.1 g, 3.88 mmol) in acetonitrile (10 ml) and water (10 ml) at 0° C. were added TEMPO (182 mg, 1.16 mmol) and iodobenzene diacetate (2.75 g, 8.54 mmol). The mixture was stirred at RT for 16 h and then extracted with ethyl acetate (2×100 mL). The combined organic layer was washed with brine (100 mL), dried over $Na_2SO_4$ and concentrated under reduced pressure to afford the crude product, which was purified by column chromatography on silica gel (100-200 mesh) using 40% EA/Pet ether as an eluent to afford (S)-4-cyclopentylmethyl-pyrrolidine-1,2-dicarboxylic acid 1-tert-butyl ester (1.0 g, 86.9%) as an off-white solid.

AnalpH2_MeCN_UPLC_6.1 min: Rt: 2.04 min, no mass reported

Step 7: To a stirred solution of (S)-4-cyclopentylmethyl-pyrrolidine-1,2-dicarboxylic acid 1-tert-butyl ester (780 mg, 2.62 mmol) in DMF (15 ml) were added caesium carbonate (1.28 g, 3.93 mmol) and benzyl bromide (0.3 ml, 2.88 mmol) at 0° C. The mixture was stirred at RT under $N_2$ for 2 h and then diluted with water (50 ml) and extracted with ethyl acetate (2×100 ml). The combined organic layers were washed with water and brine (50 ml), dried over anhydrous $Na_2SO_4$ and concentrated under reduced pressure to afford the crude product, which was purified by column chromatography on silica gel (100-200 mesh) using 5% EA/Pet ether as eluent to afford the title compound as a mixture of diastereomers (1.0 g). The product was further purified by SFC to separate the diastereomers. to give (2S,4R)-4-cyclopentylmethyl-pyrrolidine-1,2-dicarboxylic acid 2-benzyl ester 1-tert-butyl ester (820 mg, 79%) as a white solid.

AnalpH2_MeCN_UPLC_5.0 min: Rt: 2.99 min, m/z 388.5 [M+H]+

Step 8: To a solution of (2S,4R)-4-cyclopentylmethyl-pyrrolidine-1,2-dicarboxylic acid 2-benzyl ester 1-tert-butyl ester (820 mg, 2.11 mmol) in methanol, in a Parr shaker was added 10% palladium carbon (811 mg) under nitrogen atmosphere. The reaction mixture was hydrogenated for 3 h at 60 psi. The mixture was filtered through celite, the residue washed with hot methanol and the filtrate was concentrated under reduced pressure to afford (2S,4R)-4-cyclopentylmethyl-pyrrolidine-1,2-dicarboxylic acid 1-tert-butyl ester (480 mg, 75.5%) as an off-white solid.

AnalpH2_MeCN_UPLC_5.0 min: Rt: 1.48 min, m/z 242.4 [M+H]+

Scheme. Synthesis of (2S,4S)-4-(Tetrahydro-pyran-4-yl-methyl)-pyrrolidine-1,2-dicarboxylic acid 1-tert-butyl ester

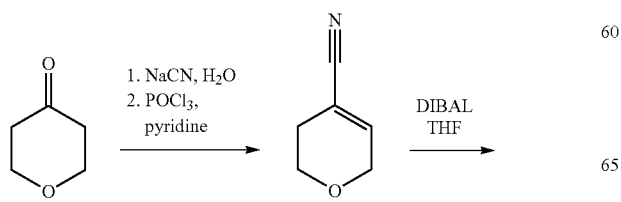

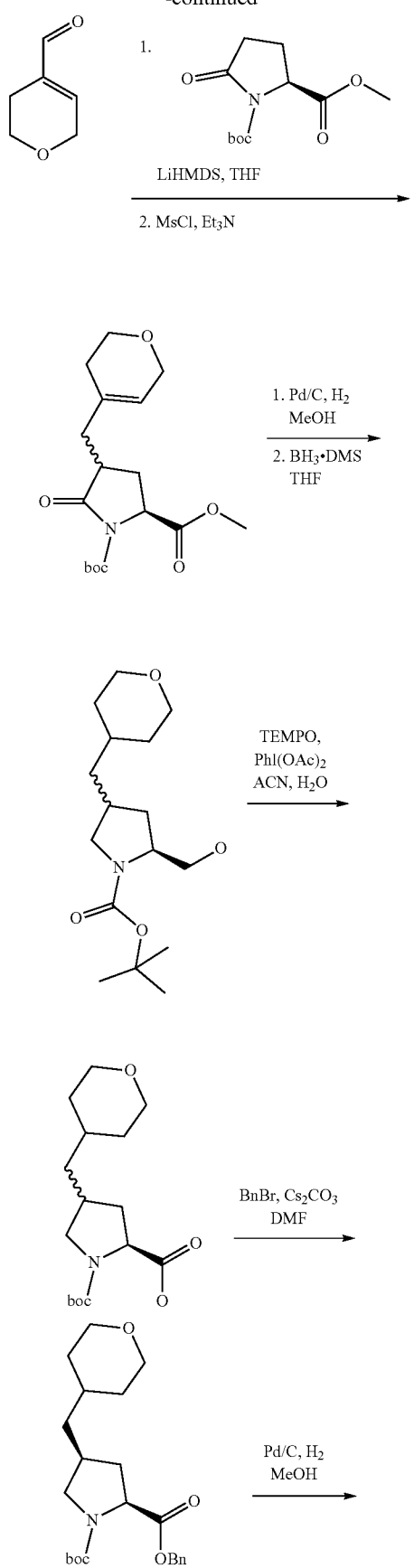

-continued

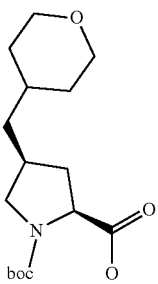

Step 1 & 2: To a stirred mixture of tetrahydro-pyran-4-one (25.0 g, 250 mmol) and water (250 ml) at 0° C. was added sodium cyanide (12.2 g, 250 mmol) followed by sodium bisulfate until a pH of 4.3 to 5 was reached. The reaction mixture was stirred for 1 h at 10° C. The organic layer was separated and the aqueous layer was extracted twice with ethyl acetate. The combined organic layers were washed with a small portion of water (50 ml) and then concentrated under reduced pressure. The resulting product was re-dissolved in toluene (100 ml), heated to 65° C. and pyridine (50.0 ml, 614 mmol) was added, followed by a slow addition of $POCl_3$ (27.0 ml, 288 mmol). The reaction mixture was stirred for 2 h at 65° C. and then cooled to 35° C., followed by slow addition of water (200 ml). The layers were separated and the aqueous layer was extracted with toluene (200 ml). The combined organic layers were washed with water (300 ml) and concentrated under reduced pressure to obtain 3,6-dihydro-2H-pyran-4-carbonitrile (28 g crude) as a white solid which was used directly in the next step without purification.

Step 3: To a solution of crude 3,6-dihydro-2H-pyran-4-carbonitrile (28.0 g, 256 mmol) in THF (40 ml), under nitrogen atmosphere, cooled to −5° C., was added DIBAL (1M in THF, 256 ml, 256 mmol) drop-wise. The reaction mixture was stirred for 3 hours, quenched with sat. aq. ammonium chloride (200 mL) and extracted with diethyl ether (3×300 mL). The combined extract was dried over $MgSO_4$ and concentrated in vacuo to obtain a yellow oil. The crude product was purified by column chromatography on silica gel (100-200 mesh) using 15% EA/Pet ether as an eluent to afford 3,6-dihydro-2H-pyran-4-carbaldehyde (3 g, 11%) as a yellow oil.

AnalpH2_MeCN_UPLC_3.8 min: Rt: 1.28 min, m/z 113.1 [M+H]+

Step 4: A stirred solution of (S)-5-oxo-pyrrolidine-1,2-dicarboxylic acid 1-tert-butyl ester 2-methyl ester (12.0 g, 49.3 mmol) in dry THF (120 mL), under nitrogen atmosphere was cooled to −78° C. LiHMDS (1M in THF, 54 ml, 54 mmol) was added dropwise to the reaction mixture. The mixture was stirred at −78° C. for 2 h and then a solution of 3,6-dihydro-2H-pyran-4-carbaldehyde (6.0 g, 54.3 mmol) was added slowly. The mixture was further stirred at −78° C. for 2 h, then the reaction was quenched with saturated ammonium chloride (200 ml) solution. The crude product was extracted with EtOAc (3×300 mL) and the combined extract was dried over anhydrous magnesium sulphate and concentrated in vacuo. The crude material was purified by flash column (0-5% EtOAc/is hexane) chromatography to obtain (S)-4-[(3,6-dihydro-2H-pyran-4-yl)-hydroxy-methyl]-5-oxo-pyrrolidine-1,2-dicarboxylic acid 1-tert-butyl ester 2-methyl ester (7.0 g, 40%) as a white solid.

AnalpH2_MeCN_UPLC_3.8 min: Rt: 1.45 & 1.50 min, mass ion not observed

Step 5: To a solution of (S)-4-[(3,6-dihydro-2H-pyran-4-yl)-hydroxy-methyl]-5-oxo-pyrrolidine-1,2-dicarboxylic acid 1-tert-butyl ester 2-methyl ester (7.00 g, 19.6 mmol) in DCM (70 ml) at 0° C. was added TEA (27.4, 196 mmol) and MsCl (4.5 ml, 58.7 mmol). The reaction mixture was stirred at RT for 4 h then concentrated under reduced pressure. The crude product was dissolved in water and extracted with ethyl acetate (2×300 mL). The combined organic extracts were dried over anhydrous $Na_2SO_4$, concentrated under reduced pressure to afford (S)-4-(3,6-dihydro-2H-pyran-4-ylmethyl)-5-oxo-pyrrolidine-1,2-dicarboxylic acid 1-tert-butyl ester 2-methyl ester (1.7 g, 26%) as yellow liquid.

AnalpH2_MeCN_UPLC_5.0 min: Rt: 2.39 min, m/z 338.4 [M+Na]+

Step 6: To a solution of (S)-4-(3,6-dihydro-2H-pyran-4-ylmethyl)-5-oxo-pyrrolidine-1,2-dicarboxylic acid 1-tert-butyl ester 2-methyl ester (1.7 g, 5.0 mmol) in methanol (50 ml), and 10% palladium carbon (644 mg, 6.05 mmol) was added under nitrogen atmosphere. The mixture was hydrogenated at 60 psi for 2 h. The reaction mixture was filtered through celite, the residue washed with hot methanol and the combined filtrate and washings concentrated under reduced pressure to afford crude (S)-5-oxo-4-(tetrahydro-pyran-4-ylmethyl)-pyrrolidine-1,2-dicarboxylic acid 1-tert-butyl ester 2-methyl ester (1.4 g, 81%) as an off white solid which was used in the subsequent reaction without further purification.

Step 7: To a stirred solution of (S)-5-oxo-4-(tetrahydro-pyran-4-ylmethyl)-pyrrolidine-1,2-dicarboxylic acid 1-tert-butyl ester 2-methyl ester (1.4 g, 4.1 mmol) in THF (60 ml) under argon was added $BH_3 \cdot DMS$ (1.2 ml, 12 mmol) solution to reaction mixture at 0° C. The mixture was stirred at 90° C. for 12 h, and then quenched with methanol, and the reaction mixture extracted with ethyl acetate (50 ml). The combined organic fractions were washed with brine, dried over $MgSO_4$ and concentrated under reduced pressure. The crude product was purified by column chromatography on silica gel (100-200 mesh) using 30% EA/Pet ether as eluent to afford (S)-2-hydroxymethyl-4-(tetrahydro-pyran-4-ylmethyl)-pyrrolidine-1-carboxylic acid tert-butyl ester (400 mg, 33%) as a yellow liquid.

AnalpH2_MeCN_UPLC_3.8 min: Rt: 1.86 min, m/z 300.6 [M+H]+

Step 8: To a solution of (S)-2-hydroxymethyl-4-(tetrahydro-pyran-4-ylmethyl)-pyrrolidine-1-carboxylic acid tert-butyl ester (400 mg, 1.33 mmol) in acetonitrile (10 ml) and water (10 ml) at 0° C. were added TEMPO (250 mg, 1.59 mmol) and iodobenzene diacetate (945 mg, 2.93 mmol). The mixture was stirred at room temperature for 16 h. The reaction mixture was extracted with ethyl acetate (2×100 mL) and the combined organic layers were washed with brine (100 mL), dried over $Na_2SO_4$ and concentrated under reduced pressure to afford crude product, which was purified by column chromatography on silica gel (100-200 mesh) using 40% EA/Pet ether as an eluent to afford (S)-4-(tetrahydro-pyran-4-ylmethyl)-pyrrolidine-1,2-dicarboxylic acid 1-tert-butyl ester (150 mg, 36%) as an off-white solid.

AnalpH2_MeCN_UPLC_4.0 min: Rt: 2.24 min, m/z 314.4 [M+H]+

Step 9: To a solution of (S)-4-(tetrahydro-pyran-4-ylmethyl)-pyrrolidine-1,2-dicarboxylic acid 1-tert-butyl ester (150 mg, 0.479 mmol) in DMF (15 ml) were added cesium carbonate (234 mg, 0.718 mmol), benzyl bromide (0.060 ml, 0.53 mmol) at 0° C. The mixture was stirred at RT for 2 h, and then diluted with water (10 ml) and extracted with ethyl acetate (2×25 ml). The combined organic layers were washed with water, brine (10 ml) and dried over anhydrous Na₂SO₄ and concentrated under reduced pressure. The crude product was purified by column chromatography on silica gel (100-200 mesh) using 15% EA/Pet ether as an eluent, followed by SFC purification to give (2S,4S)-4-(tetrahydro-pyran-4-ylmethyl)-pyrrolidine-1,2-dicarboxylic acid 2-benzyl ester 1-tert-butyl ester (40 mg, 79%) as a white solid.

AnalpH2_MeCN_UPLC_4.0 min: Rt: 2.39 min, m/z 404.5 [M+H]+

Step 10: To a solution of (2S,4S)-4-(tetrahydro-pyran-4-ylmethyl)-pyrrolidine-1,2-dicarboxylic acid 2-benzyl ester 1-tert-butyl ester (40 mg, 0.10 mmol) in methanol, in a Parr shaker was added 10% palladium carbon (40 mg) under nitrogen atmosphere. The reaction mixture was hydrogenated for 2 h at 60 psi. The mixture was filtered through celite, the residue washed with methanol and concentrated under reduced pressure to afford (2S,4S)-4-(tetrahydro-pyran-4-ylmethyl)-pyrrolidine-1,2-dicarboxylic acid 1-tert-butyl ester (28 mg, 90%) as an off-white semi solid.

AnalpH2_MeCN_UPLC_3.8 min: Rt: 1.66 min, m/z 312.3 [M−H]−

0° C. for 1 h. Water and EtOAc were added, the reaction filtered through celite and the layers separated. The aqueous layer was extracted with EtOAc and the combined organics dried (MgSO₄) and the solvent removed to give a crude sample of (2S,4R)-4-(3,4-difluoro-phenyl)-4-hydroxy-pyrrolidine-1,2-dicarboxylic acid 1-tert-butyl ester 2-methyl ester as an orange oil, which was used directly in the subsequent reaction.

(2S,4R)-4-(3,4-Difluoro-phenyl)-4-hydroxy-pyrrolidine-1,2-dicarboxylic acid 1-tert-butyl ester 2-methyl ester was hydrolysed following General Method 4B using 6 mL of 1M NaOH/MeOH/THF and stirred at rt for 1 h. The solvent was removed and the residue acidified to pH5 using 1 M HCl. The aqueous layer was extracted with EtOAc, the combined organic layers dried (MgSO₄) and the solvent removed to give (2S,4R)-4-(3,4-difluoro-phenyl)-4-hydroxy-pyrrolidine-1,2-dicarboxylic acid 1-tert-butyl ester (310 mg, 73% over 2 steps) as an orange solid.

AnalpH2_MeOH_4MIN: Rt: 3.07 min, m/z 366.3 [M+Na]+

The following compound was made by analogous methods:

| Structure | Analytical Data | Mass, yield, state |
|---|---|---|
| 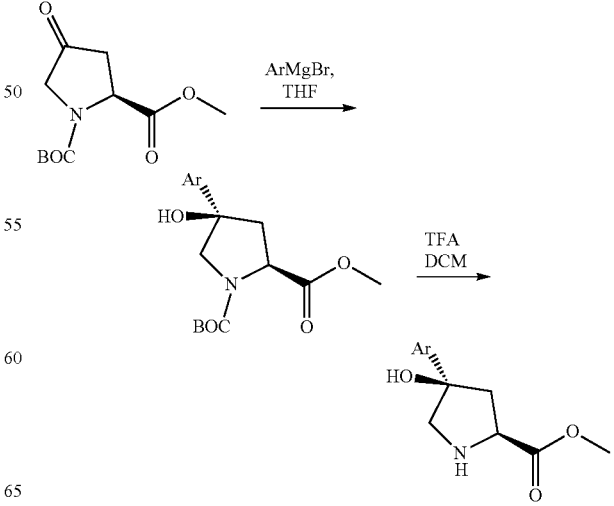 M05125-int & M05126-int | AnalpH2_MeOH_4MIN: Rt: 2.95 min, m/z 308.2 [M + H]+ | 195 mg, 77%, orange oil |

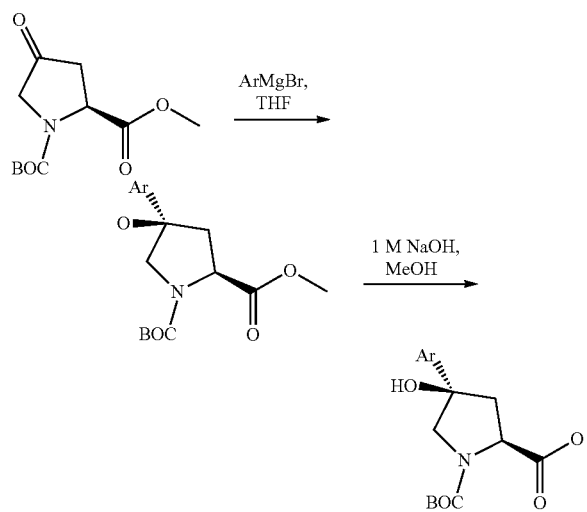

Scheme: Synthesis of (2S,4R)-4-(3,4-Difluoro-phenyl)-4-hydroxy-pyrrolidine-1,2-dicarboxylic acid 1-tert-butyl ester (M05128-int)

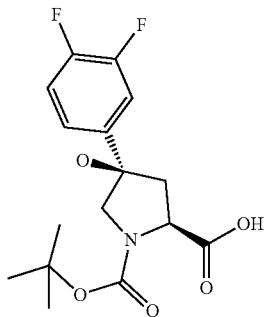 [SMILES: CC(C)(C)OC(=O)N1C[C@](O)(c2ccc(F)c(F)c2)C[C@H]1C(=O)O]

N-boc-4-Oxo-L-proline-methyl ester (300 mg, 1.23 mmol) was dissolved in THF and cooled to 0° C. 3,4-Difluorophenyl magnesium bromide (0.5 M in THF, 4.93 mL, 2.47 mmol) was added slowly and the mixture stirred at

Scheme. Synthesis of (2S,4R)-4-(3,4-Difluoro-phenyl)-4-hydroxy-pyrrolidine-2-carboxylic acid methyl ester (M05128-int)

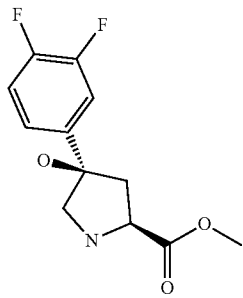 [SMILES: COC(=O)[C@@H]1C[C@@](O)(c2ccc(F)c(F)c2)CN1]

N-boc-4-Oxo-L-proline-methyl ester (300 g, 1.23 mmol) was dissolved in THF and cooled to 0° C. 3,4-Difluorophenyl magnesium bromide (0.5 M in THF, 4.93 mL, 2.47 mmol) was added slowly and the reaction mixture stirred at 0° C. for 1 h. Water and EtOAc were added, the reaction mixture filtered through celite and the layers separated. The aqueous layer was extracted with EtOAc and the combined organics were dried (MgSO₄) and the solvent removed to give (2S,4R)-4-(3,4-difluoro-phenyl)-4-hydroxy-pyrrolidine-1,2-dicarboxylic acid 1-tert-butyl ester 2-methyl ester as an orange oil, which was used directly in the subsequent reaction.

(2S,4R)-4-(3,4-Difluoro-phenyl)-4-hydroxy-pyrrolidine-1,2-dicarboxylic acid 1-tert-butyl ester 2-methyl ester was Boc-deprotected following General Method 2a, stirring at rt for 1 h. The solvent was removed and the residue azeotroped with toluene to give (2S,4R)-4-(3,4-difluoro-phenyl)-4-hydroxy-pyrrolidine-2-carboxylic acid methyl ester which was used crude in the next step.

Scheme. Synthesis of (2S,4S)-4-(3-Fluoro-benzyl)-pyrrolidine-1,2-dicarboxylic acid 1-tert-butyl ester

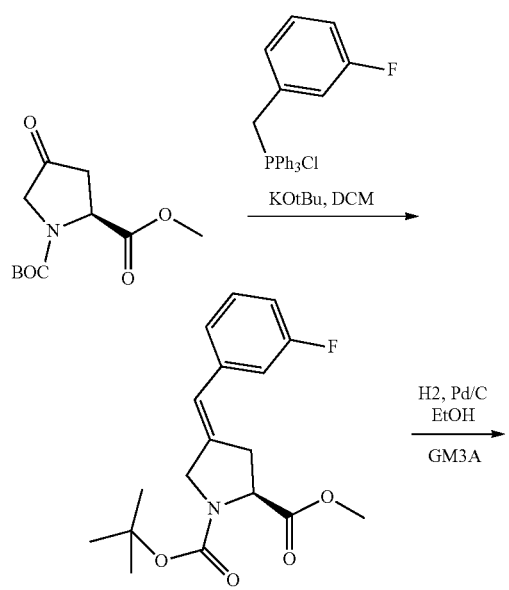

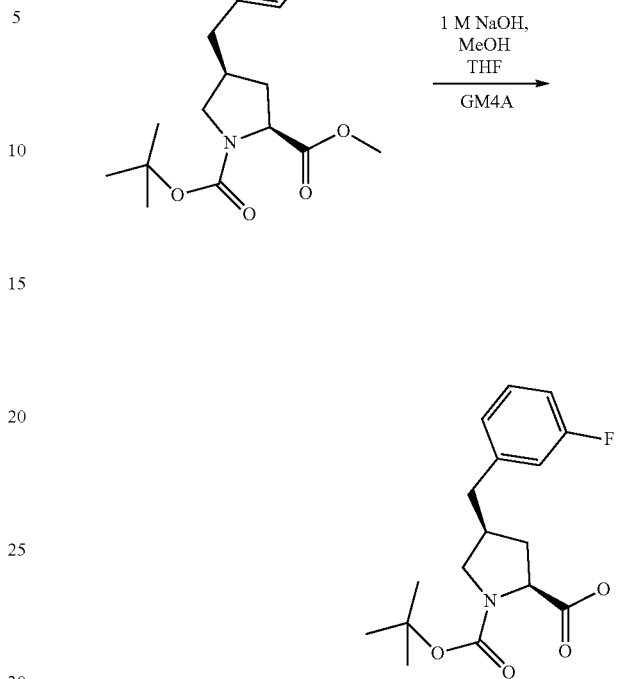

Step 1: To a stirred solution of (3-fluorobenzyl)(triphenyl)phosphonium chloride (250 mg, 1.03 mmol) in DCM (5 mL) was added KOtBu (1M in THF, 1.54 mL, 1.54 mmol). After 45 minutes, N-boc-4-oxo-L-proline methyl ester (250 mg, 1.03 mmol) was added and the reaction mixture stirred at room temperature for 1 hour. Water (20 mL) was added and the mixture extracted with DCM (2×20 mL). The combined organic extracts were dried (MgSO₄), the solvent removed and the residue purified by column chromatography (Biotage, 25 g SNAP, 0-50% EtOAc/ihexane) to give (S)-4-[1-(3-fluoro-phenyl)-meth-ylidene]-pyrrolidine-1,2-dicarboxylic acid 1-tert-butyl ester 2-methyl ester (206 mg, 60%) as a yellow oil.

AnalpH2_MeOH_4MIN: Rt: 3.40 min, m/z 358.3 [M+Na]+

Step 2: (S)-4-[1-(3-Fluoro-phenyl)-meth-(E)-ylidene]-pyrrolidine-1,2-dicarboxylic acid 1-tert-butyl ester 2-methyl ester (206 mg, 0.61 mmol) underwent hydrogenation using general method 3A for 2 hours to give (2S,4S)-4-(3-fluoro-benzyl)-pyrrolidine-1,2-dicarboxylic acid 1-tert-butyl ester 2-methyl ester (180 mg, 87%) as a colourless oil.

AnalpH2_MeOH_4MIN: Rt: 3.29 min, m/z 360.3 [M+Na]+

Step 3: (2S,4S)-4-(3-Fluoro-benzyl)-pyrrolidine-1,2-dicarboxylic acid 1-tert-butyl ester 2-methyl ester was hydrolysed according to general method 4B for 3 hours and isolated with purification method b to give (2S,4S)-4-(3-fluoro-benzyl)-pyrrolidine-1,2-dicarboxylic acid 1-tert-butyl ester (175 mg, 100%) as a colourless oil.

AnalpH2_MeOH_4MIN: Rt: 3.23 min, m/z 324.2 [M+H]+

Scheme. Synthesis of (2S,4S)-4-(Pyrazin-2-ylamino)-pyrrolidine-1,2-dicarboxylic acid 1-tert-butyl ester M05243-int

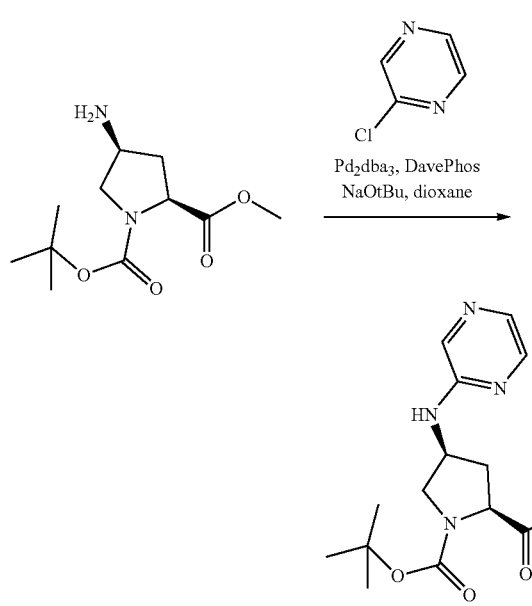

cis-4-Amino-B-boc-L-proline methyl ester hydrochloride (250 mg, 0.89 mmol), DavePhos (35 mg, 0.089 mmol), Pd₂dba₃ (41 mg, 0.044 mmol), 2-chloropyrazine (80 µL, 0.89 mmol) and NaOtBu (215 mg, 2.23 mmol) were suspended in dioxane (5 mL) and the reaction mixture degassed for 10 minutes. The reaction mixture was heated at 120° C. for 30 minutes in the microwave, filtered through celite and the filtrate extracted with basic aqueous solution. The basic aqueous extract was acidified and extracted with DCM (3×30 mL); the organic extracts dried (MgSO₄) and the solvent removed to give (2S,4S)-4-(pyrazin-2-ylamino)-pyrrolidine-1,2-dicarboxylic acid 1-tert-butyl ester as a brown oil (59 mg, 21%).

AnalpH2_MeOH_4MIN: Rt: 2.56 min, m/z 309.3 [M+H]+

Scheme

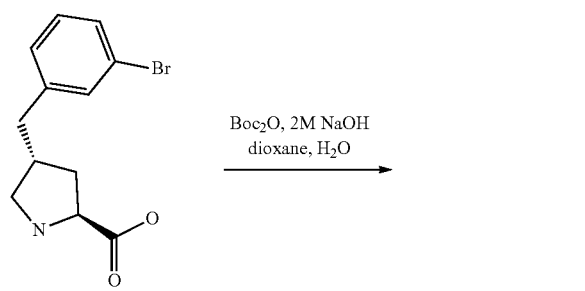

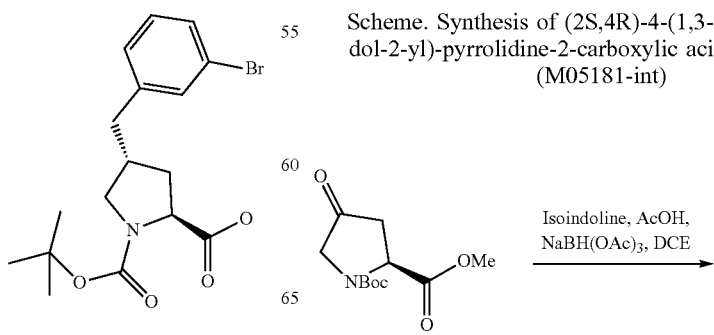

Synthesis of (2S,4R)-4-(3-Bromo-benzyl)-pyrrolidine-1,2-dicarboxylic acid 1-tert-butyl ester (M05366)

3-Bromobenzyl-L-proline (500 mg, 1.56 mmol) was dissolved in 1,4-dioxane (15 mL) and aqueous NaOH (2M, 1.6 mL, 3.12 mmol), and a solution of Boc₂O (511 mg, 2.34 mmol) in dioxane was added dropwise. The reaction mixture was stirred at room temperature overnight, then diluted with DCM and water, and the layers separated. The organic layer was washed with water, brine, then passed through a phase separator and the solvent removed to give (2S,4R)-4-(3-bromo-benzyl)-pyrrolidine-1,2-dicarboxylic acid 1-tert-butyl ester (313 mg, 52%) as a colourless oil which solidified on standing.

AnalpH2_MeOH_4MIN: Rt: 3.28 min, m/z 384.3/386.2 [M+H]+

The following compounds were made by analogous methods:

| Structure | Analytical data | Mass, yield, state |
|---|---|---|
| (3,4-dichlorobenzyl pyrrolidine structure) | With 3,4-dichloropyrrolidine, carboxylic acid, using EtOAc for extraction solvent. AnalpH2_MeOH_4MIN: Rt: 3.44 min, m/z 374.2/376.2 [M + H]+ | 447 mg, quant. |
| (4-bromobenzyl pyrrolidine structure) | With trans-4-(4-bromobenzyl)-L-proline, using Boc₂O and Et₃N in DCM AnalpH2_MeOH_4MIN: Rt: 3.25 min, m/z 406.1/408.1 [M + H]+ | 745 mg, quant |

Scheme. Synthesis of (2S,4R)-4-(1,3-Dihydro-isoindol-2-yl)-pyrrolidine-2-carboxylic acid methyl ester (M05181-int)

-continued

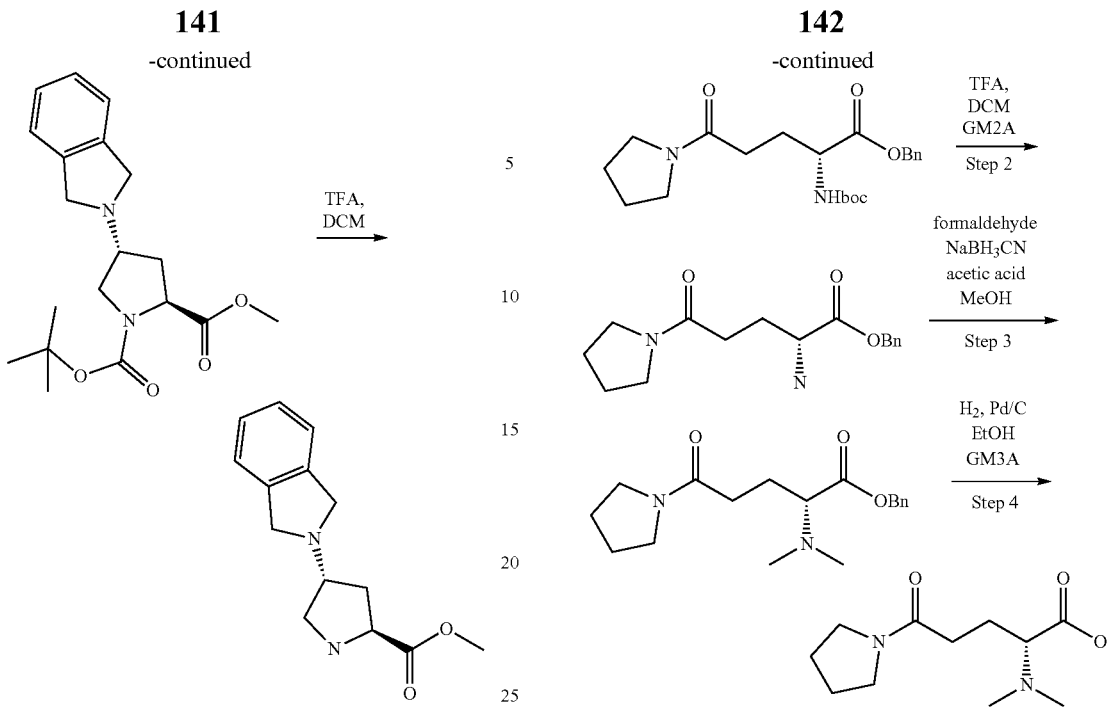

Step 1: Boc-4-Oxo-proline methyl ester (100 mg, 0.41 mmol) and isoindoline (51 µL, 0.43 mmol) were dissolved in DCE (1.5 mL) and acetic acid (25 µL, 0.41 mmol) added. After 1 hour, NaBH(OAc)$_3$ (261 mg, 1.23 mmol) was added and the reaction mixture stirred at room temperature overnight. The reaction mixture was diluted with sat. aq. NaHCO$_3$ and extracted with DCM. The combined organics were passed through a phase separator and the solvent removed to give a crude product which was purified by column chromatography (Biotage, 10 g SNAP, 0-80% EtOAc/ihexane) to give (2S,4R)-4-(1,3-dihydro-isoindol-2-yl)-pyrrolidine-1,2-dicarboxylic acid 1-tert-butyl ester 2-methyl ester (0.13 g, 92%) as a brown oil.

AnalpH2_MeOH_4MIN: Rt: 1.99 min, m/z 347.3 [M+H]+

Step 2: (2S,4R)-4-(1,3-Dihydro-isoindol-2-yl)-pyrrolidine-1,2-dicarboxylic acid 1-tert-butyl ester 2-methyl ester (110 mg, 0.32 mmol) underwent boc deprotection following General Method 2A for 1 hour. The solvent was removed in vacuo to give (2S,4R)-4-(1,3-dihydro-isoindol-2-yl)-pyrrolidine-2-carboxylic acid methyl ester which was used crude in the subsequent reaction.

AnalpH9_MeOH_4MIN: Rt: 2.41 min. m/z 247.4 [M+H]+

Synthesis of RgD

Scheme. Synthesis of (R)-2-Dimethylamino-5-oxo-5-pyrrolidin-1-yl-pentanoic acid

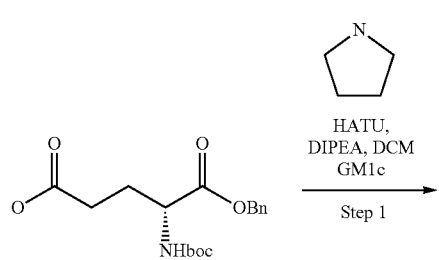

Step 1: Amide coupling of Boc-D-Glu-OBzl (2.0 g, 5.9 mmol) with pyrrolidine (0.6 mL, 7.1 mmol) using HATU and DIPEA in DCM followed General Method 1c. The product was purified using column chromatography (Biotage, 25 g SNAP, 20-80% EtOAc/ihexane) to give (R)-2-tert-butoxycarbonylamino-5-oxo-5-pyrrolidin-1-yl-pentanoic acid benzyl ester as a colourless oil, which was used directly in the subsequent reaction.

ANALPH2_MEOH_4 min, Rt: 3.04 min, m/z 391.5 [M+H]+

Step 2: Boc deprotection of (R)-2-tert-butoxycarbonylamino-5-oxo-5-pyrrolidin-1-yl-pentanoic acid benzyl ester using General Method 2A for 1.5 h followed by purification by SCX-2 then drying under vacuum gave (R)-2-amino-5-oxo-5-pyrrolidin-1-yl-pentanoic acid benzyl ester (1.4 g, 82% over 2 steps) which was used crude in the subsequent reaction.

ANALPH2_MEOH_4 min, Rt: 1.68 min, m/z 291.3 [M+H]+

Step 3: Formaldehyde (37% in water, 1 mL), acetic acid (0.5 mL) and NaBH$_3$CN (0.6 g, 9.4 mmol) were added to a solution of (R)-2-amino-5-oxo-5-pyrrolidin-1-yl-pentanoic acid benzyl ester (1.37 g, 4.7 mmol) in methanol (30 mL). The reaction mixture was stirred at room temperature for 2 hours, then the solvent removed in vacuo. The residue was partitioned between DCM and 10% K$_2$CO$_3$ (aq), the aqueous layer extracted with DCM and the combined organic layers dried (MgSO$_4$), and the solvent removed in vacuo to give (R)-2-dimethylamino-5-oxo-5-pyrrolidin-1-yl-pentanoic acid benzyl ester (1.7 g, quant.) as an opaque oil.

ANALPH2_MEOH_4 min, Rt: 2.99 min, m/z 319.4 [M+H]+

Step 4: Hydrogenation of (R)-2-dimethylamino-5-oxo-5-pyrrolidin-1-yl-pentanoic acid benzyl ester using General Method 3A for 36 hours. The product was dried in vacuo to give (R)-2-dimethylamino-5-oxo-5-pyrrolidin-1-yl-pentanoic acid (1.1 g, 100%) as a white solid.

ANALPH2_MEOH_4 min. Rt: 0.75 min. m/z 229.3 [M+H]+

Scheme. Synthesis of (2R,4R)-4-(Pyrrolidine-1-carbonyl)-pyrrolidine-1,2-dicarboxylic acid 1-tert-butyl ester

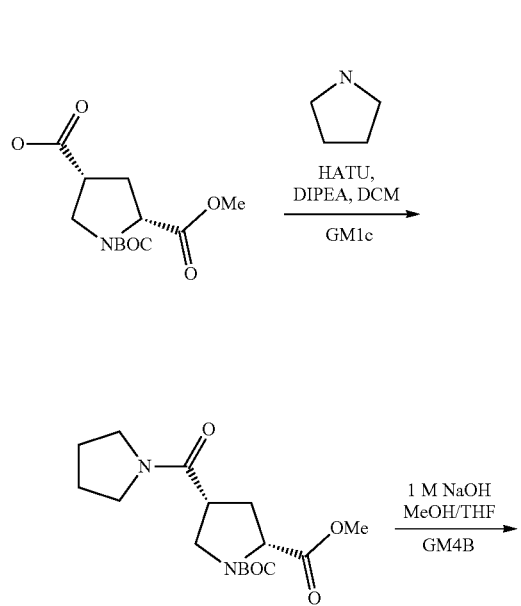

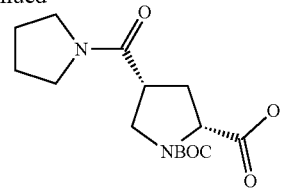

Step 1: Amide coupling of (2R,4R)-pyrrolidine-1,2,4-tricarboxylic acid 1-tert-butyl ester 2-methyl ester (172 mg, 0.63 mmol) with pyrrolidine (52 μL, 0.63 mmol) using HBTU (239 mg, 0.63 mmol) and DIPEA (329 μL, 1.89 mmol) in DCM (5 mL) following General Method 1c to give (2R,4R)-4-(pyrrolidine-1-carbonyl)-pyrrolidine-1,2-dicarboxylic acid 1-tert-butyl ester 2-methyl ester (380 mg, quant.) which was used crude in the next step.

ANALPH2_MEOH_4 min, Rt: 2.75 min, m/z 327.4 [M+H]+

Step 2: (2R,4R)-4-(Pyrrolidine-1-carbonyl)-pyrrolidine-1,2-dicarboxylic acid 1-tert-butyl ester 2-methyl ester was hydrolysed using General Method 4B (and isolation method c), to give (2R,4R)-4-(pyrrolidine-1-carbonyl)-pyrrolidine-1,2-dicarboxylic acid 1-tert-butyl ester (159 mg, 81% over two steps) as a colourless oil.

ANALPH2_MEOH_4 min, Rt: 2.57 min, m/z 313.3 [M+H]+

The following analogues were made by analogous methods:

| Structure | Method | Analytical data | Mass, state |
|---|---|---|---|
| 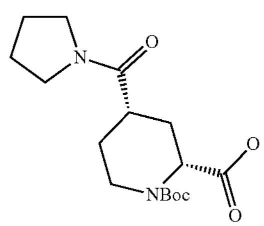 [SMILES: CC(C)(C)OC(=O)N1CC[C@H](C(=O)N2CCCC2)C[C@@H]1C(=O)O] | Amide coupling with (2R,4S)-1-(t-butoxycarbonyl)-2-(methoxycarbonyl)piperidine-4-carboxylic acid and pyrrolidine following GM1c with HATU followed by hydrolysis following method 4a | AnalpH2_MeOH_4MIN: Rt: 2.87 min, m/z 327.2 [M + H]+ | 343 mg, yellow oil |
| 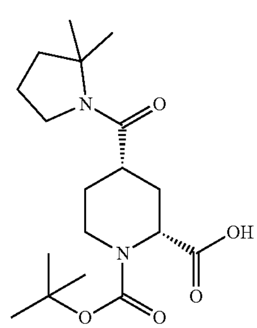 [SMILES: CC(C)(C)OC(=O)N1CC[C@H](C(=O)N2CCCC2(C)C)C[C@@H]1C(=O)O] | Amide coupling with (2R,4S)-1-(t-butoxycarbonyl)-2-(methoxycarbonyl)piperidine-4-carboxylic acid and pyrrolidine following GM1c with HCTU and Et3N followed by hydrolysis following method 4a | Thermo_MeOH_UHPLC_1.2 min LCMS: R$_t$ = 0.6 min m/z = 355.28 [M + H]+ | 20 mg, colourless oil |

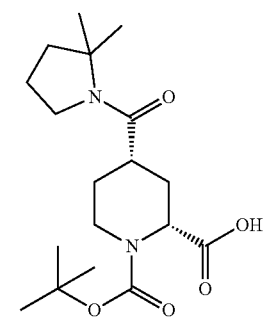

Scheme

Synthesis of 2-Amino-4-methyl-4-phenyl-pentanoic acid

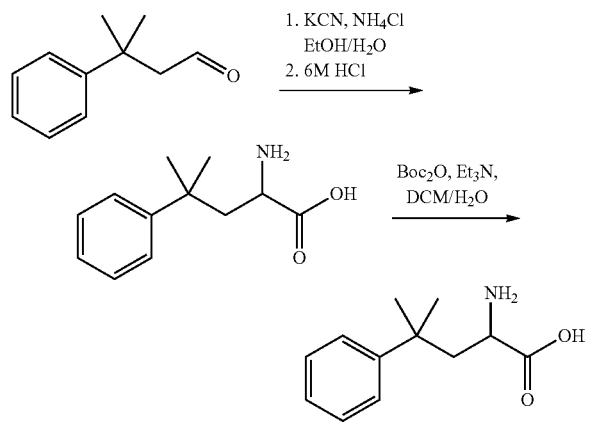

Step 1: 3-Methyl-3-phenylbutanal (500 mg, 3.08 mmol) was dissolved in EtOH (10 mL) and H₂O(10 mL), KCN (400 mg, 6.16 mmol) and NH₄Cl (489 mg, 9.24 mmol) were added and the reaction mixture heated at 60° C. overnight. After cooling to room temperature, water (20 mL) was added and the mixture extracted with EtOAc (2×30 mL). The combined organic layers were extracted with 1M HCl (3×20 mL), and the combined aqueous layer basified to pH9, and then product extracted into EtOAc (3×20 mL). These combined organic extracts were dried (MgSO₄) and the solvent removed to give 2-amino-4-methyl-4-phenyl-pentanenitrile (125 mg, 22%) as an orange oil, which was used directly in the subsequent reaction.

ANALPH2_MEOH_4 min, Rt: 1.92 min, m/z 189.3 [M+H]+

Step 2: 2-Amino-4-methyl-4-phenyl-pentanenitrile (125 mg) was dissolved in 6M HCl (5 mL) and heated at reflux overnight. The reaction mixture was cooled to room temperature, the solvent removed under reduced pressure and the residue dissolved in H₂O(5 mL)/DCM (5 mL). Boc₂O (158 mg, 0.73 mmol) and Et₃N (137 µL, 0.99 mmol) were added and the reaction mixture was stirred at room temperature for 4 days. The layers were separated and the aqueous layer acidified to pH4, and extracted with DCM (2×20 mL). The combined organic extract was passed through a hydrophobic frit and the solvent removed to give 2-amino-4-methyl-4-phenyl-pentanoic acid (210 mg, quant.) as a colourless oil.

ANALPH2_MEOH_4 min, Rt: 3.31 min, m/z 308.3 [M+H]+

Synthesis of (R)-2-tert-Butoxycarbonylamino-4-oxo-4-phenyl-butyric acid

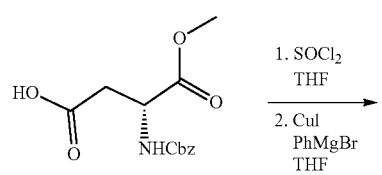

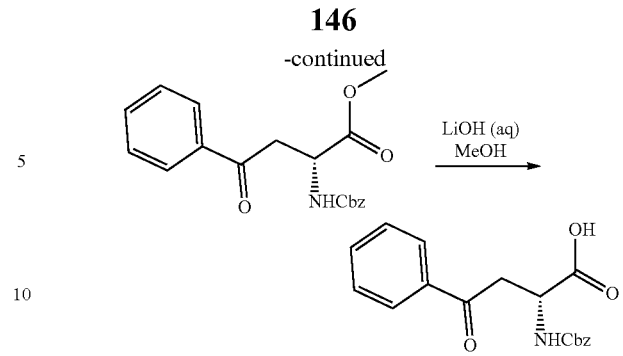

Step 1: Z-AspOMe (500 mg, 1.77 mmol) was dissolved in THF (5 mL) and SOCl₂ (200 µL) added. The reaction mixture was heated at 70° C. for 1 hour then cooled to room temperature and the solvent removed. The residue was dissolved in a minimum volume of DCM, cooled to 0° C. and isohexane added until a precipitate formed. The product was collected by filtration and dried to give (R)-2-Benzyloxycarbonylamino-3-chlorocarbonyl-propionic acid methyl ester (370 mg, 70%) as a white solid.

Step 2: (R)-2-Benzyloxycarbonylamino-3-chlorocarbonyl-propionic acid methyl ester (370 mg, 1.23 mmol) and CuI (22.8 mg, 0.12 mmol) were dissolved in THF (5 mL) and cooled to -78° C. Phenyl magnesium bromide (1M solution in THF, 1.2 mL, 1.2 mmol) was added and the reaction mixture allowed to warm to room temperature overnight. The mixture was partitioned between NH₄Cl (aq.) and EtOAc, the organic layer dried and the solvent removed. The residue was purified by column chromatography (Biotage, 10 g, EtOAc/hexane) to give (R)-2-Benzyloxycarbonylamino-4-oxo-4-phenyl-butyric acid methyl ester (50 mg, 0.15 mmol) as a yellow oil.

ANALPH2_MEOH_4 min, Rt: 2.98 min, m/z 342.3 [M+H]+

Step 3: (R)-2-Benzyloxycarbonylamino-4-oxo-4-phenyl-butyric acid methyl ester (50 mg, 0.15 mmol) was hydrolysed following General Method 4A to give (R)-2-Benzyloxycarbonylamino-4-oxo-4-phenyl-butyric acid which was used crude in subsequent reactions.

ANALPH2_MEOH_4 min, Rt: 2.88 min, m/z 328.3 [M+H]+

Synthesis of (R)-2-tert-Butoxycarbonylamino-3-(1,2,3,4-tetrahydro-naphthalen-1-yl)-propionic acid

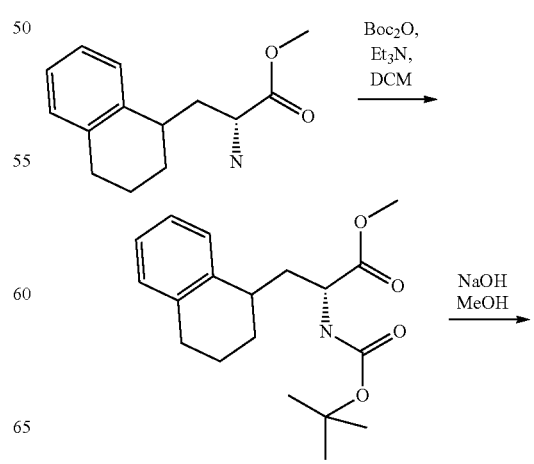

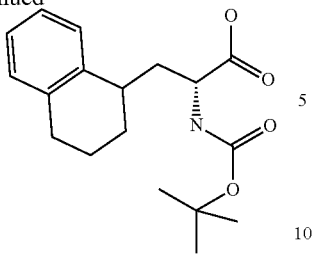

Step 1: (R)-2-Amino-3-(1,2,3,4-tetrahydro-naphthalen-1-yl)-propionic acid methyl ester (100 mg, 0.46 mmol) was dissolved in DCM (5 mL) and Et$_3$N (0.10 mL, 0.69 mmol), Boc$_2$O (110 mg, 0.51 mmol) was added and the reaction mixture stirred at room temperature overnight. The solvent was removed and the residue diluted with water and extracted with DCM. The combined organic extracts were dried and solvent removed to give (R)-2-tert-butoxycarbonylamino-3-(1,2,3,4-tetrahydro-naphthalen-1-yl)-propionic acid methyl ester (94 mg, 61%) as a colourless oil.

ANALPH2_MEOH_4 min, Rt: 3.51 min, m/z 334.3 [M+H]+

Step 2: (R)-2-tert-Butoxycarbonylamino-3-(1,2,3,4-tetrahydro-naphthalen-1-yl)-propionic acid methyl ester (94 mg 0.28 mmol) was dissolved in MeOH and 2M NaOH added (0.28 mL, 0.56 mmol) and stirred at room temperature for 2 hours. 2M HCl (aq) (0.28 mL, 0.56 mmol) was added, then the solvent removed and the residue partitioned between water and EtOAc. The aqueous layer was extracted with EtOAc, then the combined organic layers were washed with brine, dried and solvent removed to give (R)-2-tert-butoxycarbonylamino-3-(1,2,3,4-tetrahydro-naphthalen-1-yl)-propionic acid (60 mg, 41%) as a white solid.

ANALPH2_MEOH_4 min, Rt: 3.42 min, m/z 320.3 [M+H]+

Scheme 3 Constrained RgD & RgB Intermediates

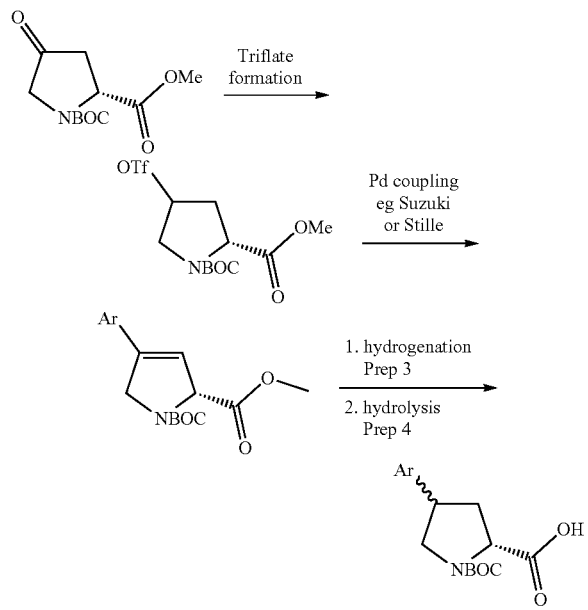

Example Procedure X: Synthesis of (R)-4-(1-Methyl-1H-pyrazol-4-yl)-pyrrolidine-1,2-dicarboxylic acid 1-tert-butyl ester

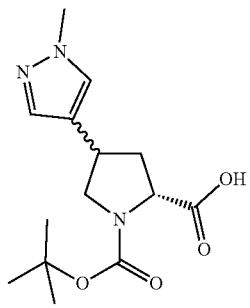 [SMILES: Cn1cc(C2C[C@H](C(=O)O)N(C(=O)OC(C)(C)C)C2)cn1]

Step 1: Triflate formation (R)-4-Trifluoromethanesulfonyloxy-2,5-dihydro-pyrrole-1,2-dicarboxylic acid 1-tert-butyl ester 2-methyl ester

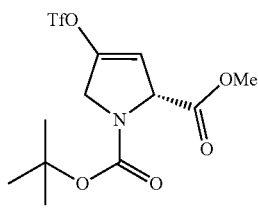 [SMILES: COC(=O)[C@H]1C=C(OS(=O)(=O)C(F)(F)F)CN1C(=O)OC(C)(C)C]

Lithium bis(trimethylsilyl)amide (1 M in THF, 44.0 mmol, 44.0 mL) was added dropwise over 20 minutes to a stirred solution of (R)-4-oxo-pyrrolidine-1,2-dicarboxylic acid 1-tert-butyl ester 2-methyl ester (40.0 mmol, 9.72 g) in anhydrous THF (50 mL) at −78° C. under an N$_2$ atmosphere. The resulting solution was stirred at −78° C. for 1 hour, then a solution of N-phenyl-bis(trifluoromethanesulfonamide) (44.0 mmol, 15.7 g) in anhydrous THF (40 mL) was added dropwise over 20 minutes. The resulting solution was stirred at −78° C. for 2 hour, and then allowed to warm to room temperature over 2 hours. Sat. aq. ammonium chloride (100 mL) was added to the reaction mixture, followed by DCM (100 mL) and water (100 mL). The layers were separated and the aqueous layer extracted with DCM (3×50 mL). The combined organic extracts were washed with water (100 mL) and brine (100 mL), passed through a hydrophobic frit and concentrated in vacuo. The crude material was partially-purified by column chromatography (Biotage Isolera, SNAP KP-Sil 340 g, dry loaded on celite, gradient i-hexane/EtOAc from 99:1 to 90:10) to give a sample of (R)-4-trifluoromethane sulfonyloxy-2,5-dihydro-pyrrole-1,2-dicarboxylic acid 1-tert-butyl ester 2-methyl ester (8.22 g, 30%) as a yellow oil, which was used 'as is' in subsequent reactions.

Step 2: Pd-Mediated Coupling

Example of Pd mediated coupling using Suzuki conditions: (R)-4-(1-Methyl-1H-pyrazol-4-yl)-2,5-dihydro-pyrrole-1,2-dicarboxylic acid 1-tert-butyl ester 2-methyl ester

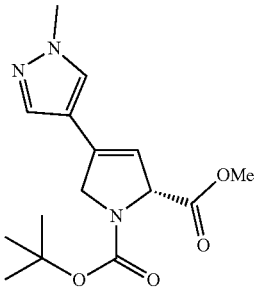 [SMILES: COC(=O)[C@H]1C=C(c2cnn(C)c2)CN1C(=O)OC(C)(C)C]

(R)-4-Trifluoromethane sulfonyloxy-2,5-dihydro-pyrrole-1,2-dicarboxylic acid 1-tert-butyl ester 2-methyl ester (2.67 mmol, 1.00 g); 1-methyl-pyrazole-4-boronic acid, pinacol ester (1.78 mmol, 1 equiv., 0.370 g); tetrakis(triphenylphosphine)palladium(0) (0.178 mmol, 0.206 g); and potassium carbonate (3.56 mmol, 0.492 g) were suspended in 1,4-dioxane/water (1:1 v/v, 16 mL) and sparged with nitrogen for 10 minutes. The resulting solution was heated at 100° C. in the microwave for 10 minutes. The reaction mixture was then diluted with DCM (20 mL) and water (20 mL). The organic phase was washed with water (2×20 mL), brine (20 mL) then passed through a hydrophobic frit and concentrated in vacuo. The crude product was purified by flash column chromatography (Biotage Isolera, SNAP KP-Sil 50 g, dry loaded on celite, gradient i-hexane/EtOAc from 70:30 to 50:50) to give (R)-4-(1-methyl-1H-pyrazol-4-yl)-2,5-dihydro-pyrrole-1,2-dicarboxylic acid 1-tert-butyl ester 2-methyl ester (0.425 g, 78%) as a colourless oil.

AnalpH2_MeOH_4MIN: Rt: 2.89 min, m/z 308.2 [M+H]+

Example of Pd Mediated Coupling Using Stille Conditions: (R)-4-Pyrimidin-4-yl-2,5-dihydro-pyrrole-1,2-dicarboxylic acid 1-tert-butyl ester 2-methyl ester

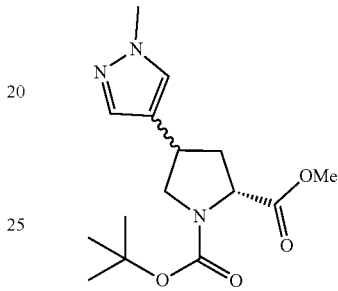

(R)-4-Trifluoromethane sulfonyloxy-2,5-dihydro-pyrrole-1,2-dicarboxylic acid 1-tert-butyl ester 2-methyl ester (0.799 mmol, 1.5 equiv., 0.300 g), 4-(tributylstannyl)pyrimidine (0.532 mmol, 1.0 equiv., 0.196 g), tetrakis(triphenylphosphine)palladium(0) (0.053 mmol, 0.1 equiv., 0.061 g) and copper(I) iodide (0.053 mmol, 0.1 equiv., 0.010 g) were suspended in 1,4-dioxane and sparged with nitrogen for 10 minutes. The resulting suspension was heated at 100° C. for 5 minutes in the microwave. The crude product was concentrated in vacuo, then purified by flash column chromatography (Biotage Isolera, SNAP KP-Sil 25 g, dry loaded on celite, gradient i-hexane/EtOAc from 70:60 to 50:50) to give (R)-4-pyrimidin-4-yl-2,5-dihydro-pyrrole-1,2-dicarboxylic acid 1-tert-butyl ester 2-methyl ester (0.157 g, 0.515 mmol, 97%) as yellow oil which was used without further purification.

AnalpH2_MeOH_4MIN: Rt: 2.96 min, m/z 306.3 [M+H]+

Step 3: Hydrogenation (R)-4-(1-Methyl-1H-pyrazol-4-yl)-pyrrolidine-1,2-dicarboxylic acid 1-tert-butyl ester 2-methyl ester (530-150-2-1)

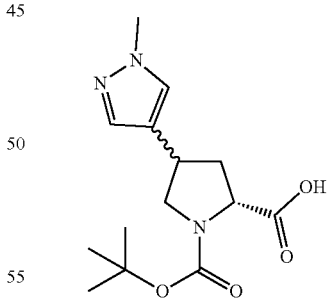

(R)-4-(1-Methyl-1H-pyrazol-4-yl)-2,5-dihydro-pyrrole-1,2-dicarboxylic acid 1-tert-butyl ester 2-methyl ester (1.38 mmol, 0.425 g), 10%-Palladium on carbon and hydrogen gas were reacted according to General Procedure 3A to give (R)-4-(1-methyl-1H-pyrazol-4-yl)-pyrrolidine-1,2-dicarboxylic acid 1-tert-butyl ester 2-methyl ester as a colourless oil (0.351 g, 1.13 mmol, 82%) which was used without further purification.

AnalpH2_MeOH_4MIN: Rt: 2.80 min, m/z 310.2 [M+H]+

Step 4: Ester hydrolysis (R)-4-(1-Methyl-1H-pyrazol-4-yl)-pyrrolidine-1,2-dicarboxylic acid 1-tert-butyl ester

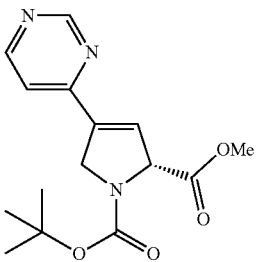 [SMILES: COC(=O)[C@H]1C=C(c2ccncn2)CN1C(=O)OC(C)(C)C]

(R)-4-(1-Methyl-1H-pyrazol-4-yl)-pyrrolidine-1,2-dicarboxylic acid 1-tert-butyl ester 2-methyl ester (1.13 mmol, 1.0 equiv., 0.351 g) and LiOH (1M in H₂O, 4.52 mmol, 4.0 equiv., 0.452 mL) were reacted according to General Procedure 4A and purified to give (R)-4-(1-methyl-1H-pyrazol-4-yl)-pyrrolidine-1,2-dicarboxylic acid 1-tert-butyl ester (0.333 g, 1.13 mmol, 100%) as a colourless gum which was used without further purification.

AnalpH2_MeOH_4MIN: Rt: 2.48 min, m/z 296.3 [M+H]+

The following compounds were synthesised by analogous methods:

| Structure | Method | Analytical data | Mass, state |
|---|---|---|---|
| 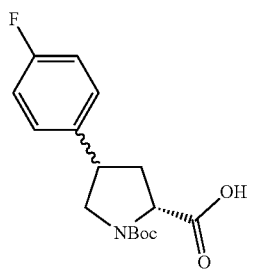 [SMILES: CC(C)(C)OC(=O)N1CC(c2ccc(F)cc2)C[C@@H]1C(=O)O] | Suzuki with 4-fluorobenzene boronic acid. Hydrogenation GM3A. Hydrolysis method GM4A | AnalpH2_MeOH_4MIN: Rt: 3.12 min, m/z 310.1 [M + H]+ | 95 mg, white solid |
| 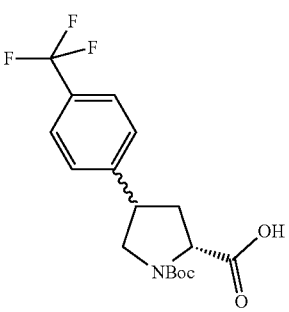 [SMILES: CC(C)(C)OC(=O)N1CC(c2ccc(C(F)(F)F)cc2)C[C@@H]1C(=O)O] | Suzuki with 4-trifluoromethylphenyl boronic acid, pinacol ester. Hydrogenation GM3A. Hydrolysis method GM4A. | AnalpH2_MeOH_4MIN: Rt: 3.22 min, m/z 360.2 [M + H]+ | 111 mg, white solid |
| 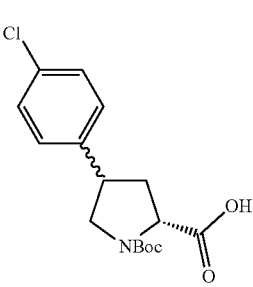 [SMILES: CC(C)(C)OC(=O)N1CC(c2ccc(Cl)cc2)C[C@@H]1C(=O)O] | Suzuki with 4-chlorophenyl boronic acid. Hydrogenation with PtO$_2$ and H$_2$ gas, in EtOH. Hydrolysis method GM4A | AnalpH2_MeOH_4MIN: Rt: 3.32 min, m/z 226.2 [M − Boc + H]+ | 225 mg, white solid |
| 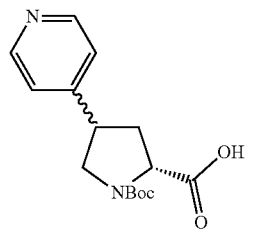 [SMILES: CC(C)(C)OC(=O)N1CC(c2ccncc2)C[C@@H]1C(=O)O] | Suzuki with pyridine-4-boronic acid, pinacol ester. Hydrogenation GM3B. Hydrolysis method GM4A | AnalpH2_MeOH_4MIN: Rt: 1.63 min, m/z 293.3 [M + H]+ | 72 mg, white solid |
| 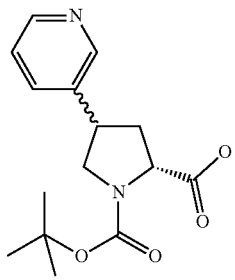 [SMILES: CC(C)(C)OC(=O)N1CC(c2cccnc2)C[C@@H]1C(=O)O] | Suzuki with pyridine-3-boronic acid, pinacol ester. Hydrogenation GM3A. Hydrolysis method GM4A | AnalpH2_MeOH_4MIN: Rt: 1.68 min, m/z 293.3 [M + H]+ | 94 mg, off-white solid |

-continued

| Structure | Method | Analytical data | Mass, state |
|---|---|---|---|
| (o-tolyl-substituted pyrrolidine with N-Boc and carboxylic acid) | Suzuki with o-tolylboronic acid. Hydrogenation GM3A. Hydrolysis method GM4A | AnalpH2_MeOH_4MIN: Rt:3.17 min, m/z 306.4 [M + H]+ | 27 mg, white solid |
| (1-methylpyrazol-5-yl-substituted pyrrolidine with N-Boc and carboxylic acid) | Suzuki with 1-methylpyrazole-5-boronic acid, pinacol ester. Hydrogenation GM3A. Hydrolysis method GM4A | AnalpH2_MeOH_4MIN: Rt: 2.41 min, m/z 296.3 [M + H]+ | White solid |
| (2-fluorophenyl-substituted pyrrolidine with N-Boc and carboxylic acid) | Suzuki with 2-fluorophenyl boronic acid. Hydrogenation GM3A. Hydrolysis method GM4A | AnalpH2_MeOH_4MIN: Rt: 3.24 min, m/z 332.3 [M + Na]+ | White solid |
| (2-methoxyphenyl-substituted pyrrolidine with N-Boc and carboxylic acid) | Suzuki with 2-methoxybenzene boronic acid. Hydrogenation GM3A, purified by flash column chromatography. Hydrolysis method GM4A | AnalpH2_MeOH_4MIN: Rt: 3.21 min, m/z 322.3 [M + H]+ | White solid |
| (2-pyridyl-substituted pyrrolidine with N-Boc and carboxylic acid) | Suzuki with 2-pyridylboronic acid MIDA ester. Hydrogenation GM3B. Hydrolysis method GM4A | AnalpH2_MeOH_4MIN: Rt: 2.12 min, m/z 293.3 [M + H]+ | Used crude in subsequent reaction |

| Structure | Method | Analytical data | Mass, state |
|---|---|---|---|
| 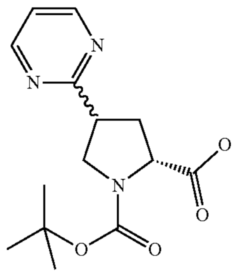 [SMILES: CC(C)(C)OC(=O)N1CC(c2ncccn2)C[C@@H]1C(=O)O] | Stille with 2-(tributylstannyl)pyrimidine. Hydrogenation GM3B. Hydrolysis method GM4A | AnalpH2_MeOH_4MIN: Rt: 2.41 min, m/z 294.3 [M + H]+ | 18 mg, off-white solid |
| 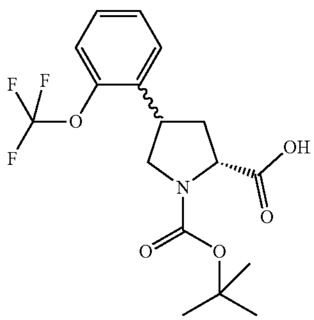 [SMILES: CC(C)(C)OC(=O)N1CC(c2ccccc2OC(F)(F)F)C[C@@H]1C(=O)O] | Suzuki with 2-(trifluoromethoxy)benzene boronic acid. Hydrogenation GM3A. Hydrolysis method GM4A. | AnalpH2_MeOH_4MIN: Rt: 3.46 min, m/z 398.2 [M + Na]+ | White solid |
| 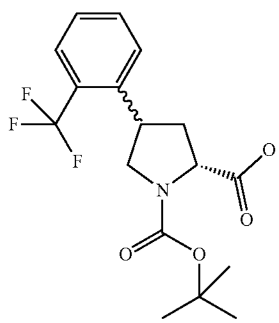 [SMILES: CC(C)(C)OC(=O)N1CC(c2ccccc2C(F)(F)F)C[C@@H]1C(=O)O] | Suzuki with 2-(trifluoromethyl)phenyl boronic acid. Hydrogenation GM3A. Hydrolysis method GM4A | AnalpH2_MeOH_4MIN: Rt: 3.40 min, m/z 382.3 [M + Na]+ | White solid |
| 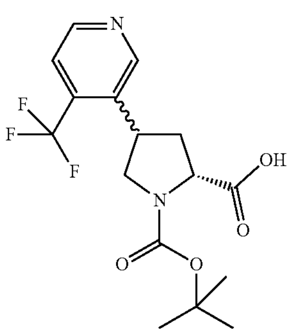 [SMILES: CC(C)(C)OC(=O)N1CC(c2cnccc2C(F)(F)F)C[C@@H]1C(=O)O] | Suzuki with 4-(trifluoromethyl)pyridine-3-boronic acid, pinacol ester. Hydrogenation GM3A. Hydrolysis method GM4A | AnalpH2_MeOH_4MIN: Rt:3.13 min, m/z 361.3 [M + H]+ | White solid |
| 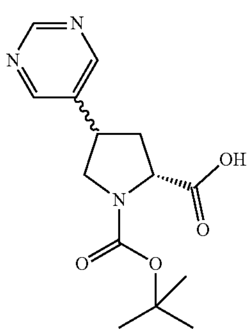 [SMILES: CC(C)(C)OC(=O)N1CC(c2cncnc2)C[C@@H]1C(=O)O] | Suzuki with pyrimidine-5-boronic acid, pinacol ester. Hydrogenation GM3A. Hydrolysis method GM4B | AnalpH2_MeOH_4MIN: Rt: 2.37 min, m/z 294 [M + H]+ | 20 mg. |

| Structure | Method | Analytical data | Mass, state |
|---|---|---|---|
| 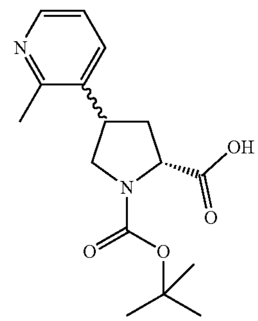 [SMILES: Cc1ncccc1C1C[C@H](C(=O)O)N(C(=O)OC(C)(C)C)C1] | Suzuki with 2-methylpyridine-3-boronic acid, pinacol ester. Hydrogenation GM3A. Hydrolysis method GM4A | AnalpH2_MeOH_4MIN: Rt: 1.61 min, m/z 307.3 [M + H]+ | White solid |
| 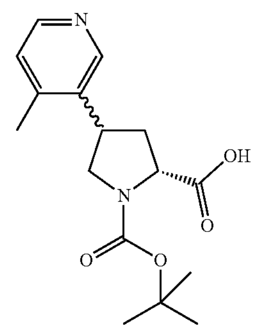 [SMILES: Cc1ccncc1C1C[C@H](C(=O)O)N(C(=O)OC(C)(C)C)C1] | Suzuki with 4-methylpyridine-3-boronic acid. Hydrogenation GM3A. Hydrolysis method GM4A | AnalpH2_MeOH_4MIN: Rt: 1.75 min, m/z 307.3 [M + H]+ | White solid |
| 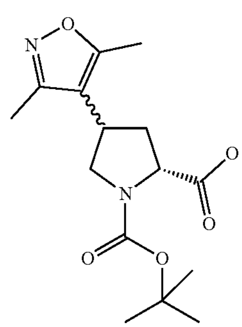 [SMILES: Cc1noc(C)c1C1C[C@H](C(=O)O)N(C(=O)OC(C)(C)C)C1] | Suzuki with 3,5-dimethylisoxazol-4-yl-4-boronic acid. Hydrogenation GM3A. Hydrolysis method GM4A. | AnalpH2_MeOH_4MIN: Rt: 2.65 (major) and 2.75 (minor) min, m/z 311.3 [M + H]+ | Yellow oil |
| 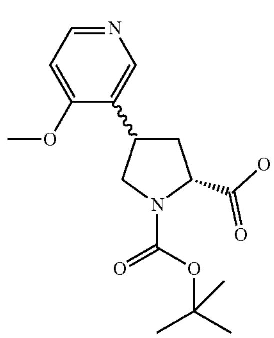 [SMILES: COc1ccncc1C1C[C@H](C(=O)O)N(C(=O)OC(C)(C)C)C1] | Suzuki with 4-methoxy-3-pyridine boronic acid, hydrochloride. Hydrogenation GM3A. Hydrolysis method GM4A. | AnalpH2_MeOH_4MIN: Rt: 1.66 (minor) and 1.76 (major) min, m/z 323.2 [M + H]+ | White solid |

-continued

| Structure | Method | Analytical data | Mass, state |
|---|---|---|---|
| 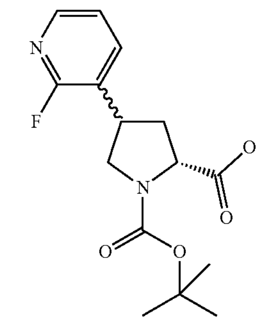 [SMILES: CC(C)(C)OC(=O)N1CC(c2cccnc2F)C[C@@H]1C(=O)O] | Suzuki with 2-fluoropyridine-3-boronic acid. Hydrogenation GM3A. Hydrolysis method GM4A | AnalpH2_MeOH_4MIN: Rt: 2.79 min, m/z 311.3 [M + H]+ | White solid |
| 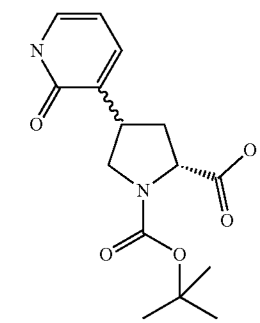 [SMILES: CC(C)(C)OC(=O)N1CC(c2ccc[nH]c2=O)C[C@@H]1C(=O)O] | Suzuki with 2-benzyloxypyridine-3-boronic acid. Hydrogenation GM3A. Hydrolysis method GM4A | AnalpH2_MeOH_4MIN: Rt: 2.37 min, m/z 309.2 [M + H]+ | White solid |
| 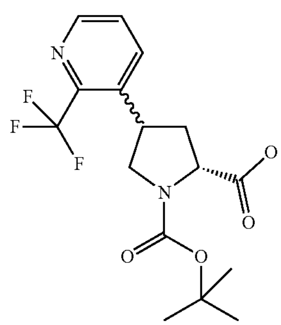 [SMILES: CC(C)(C)OC(=O)N1CC(c2cccnc2C(F)(F)F)C[C@@H]1C(=O)O] | Suzuki with 2-(trifluoromethyl)pyridine-3-boronic acid. Hydrogenation GM3A. Hydrolysis method GM4A. | AnalpH2_MeOH_4MIN: Rt: 3.11 min, m/z 361.2 [M + H]+ | White solid |
| 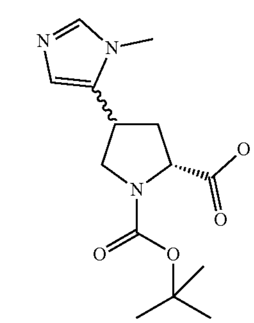 [SMILES: Cn1cncc1C1C[C@H](C(=O)O)N(C(=O)OC(C)(C)C)C1] | Suzuki with (3-methylimidazol-4-yl)boronic acid, pinacol ester. Methyl ester hydrolysed under reaction conditions. Hydrogenation GM3A. | AnalpH2_MeOH_4MIN: Rt: 1.41 min, m/z 296.2 [M + H]+ | White solid |
| 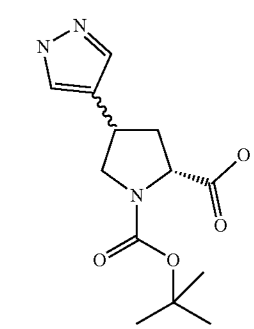 [SMILES: CC(C)(C)OC(=O)N1CC(c2cn[nH]c2)C[C@@H]1C(=O)O] | Suzuki with 4-pyrazole boronic acid, pinacol ester. Hydrogenation GM3B. Hydrolysis method GM4A, | AnalpH2_MeOH_4MIN: Rt: 2.38 min, m/z 282.3 [M + H]+ | White solid |

-continued

| Structure | Method | Analytical data | Mass, state |
|---|---|---|---|
| (pyrazinyl pyrrolidine Boc structure) | Stille with 2-(tributylstannyl)pyrazine. Hydrogenation GM3B. Hydrolysis method GM4A | AnalpH2_MeOH_4MIN: Rt: 2.44/2.56 min, m/z 294.2 [M + H]+ | White solid |
| (trityl imidazole pyrrolidine Boc structure) | Stille with 4-(tributylstannyl)-1-tritylimidazole. Hydrogenation GM3A. Hydrolysis method GM4A, | AnalpH2_MeOH_4MIN: Rt: 3.16 min, m/z 524.2 [M + H]+ | White solid |
| (M05174-int) (phenoxyphenyl pyrrolidine Boc structure) | Suzuki with 2-phenoxybenzene boronic acid. Hydrolysis method GM4B, | AnalpH2_MeOH_4MIN: Rt: 3.49 min, m/z 406.2 [M + Na]+ | 190 mg, colourless oil |
| (M05157-int) (4-fluorophenyl pyrrolidine Boc structure) | Suzuki with 4-fluorophenyl boronic acid. Hydrolysis method GM4B | AnalpH2_MeOH_4MIN: Rt: 3.14 min, m/z 332.2 [M + Na]+ | 50 mg |

Scheme 4 Carboxamide Library

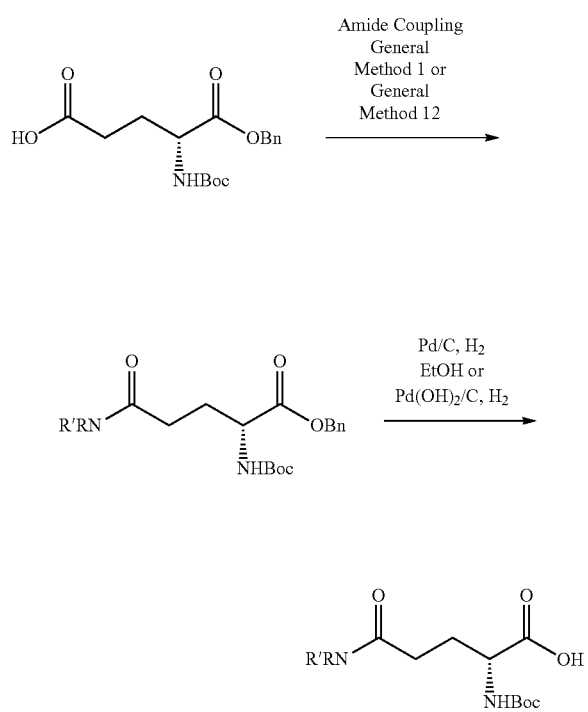

Synthesis of (R)-2-tert-Butoxycarbonylamino-5-oxo-5-pyrrolidin-1-yl-pentanoic acid

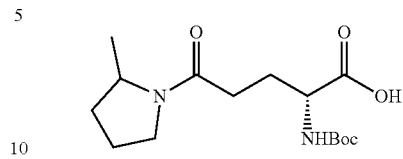

Step 1: Boc-D-Glu-OBzl (400 mg, 1.19 mmol) was dissolved in DCM (20 mL) and HATU (498 mg, 1.31 mmol) and DIPEA (0.62 mL, 3.57 mmol) were added. 2-Methylpyrrolidine (0.15 mL, 1.42 mmol) was added and the reaction mixture stirred at room temperature overnight. The reaction mixture was washed with water (3×40 mL), the organic layer dried (MgSO$_4$) and the solvent removed in vacuo. The residue was purified by column chromatography to give (R)-2-tert-butoxycarbonylamino-5-(2-methyl-pyrrolidin-1-yl)-5-oxo-pentanoic acid benzyl ester (0.37 g, 77%) as a colourless oil.

Step 2: (R)-2-tert-Butoxycarbonylamino-5-(2-methyl-pyrrolidin-1-yl)-5-oxo-pentanoic acid benzyl ester (0.37 g, 0.91 mmol) was dissolved in EtOH (10 mL), placed under N$_2$ atmosphere, and Pd/C (37 mg) added. A H$_2$ atmosphere was introduced and the reaction mixture stirred at room temperature for 72 h. The reaction mixture was filtered through celite and the solvent removed in vacuo to give (R)-2-tert-butoxycarbonylamino-5-(2-methyl-pyrrolidin-1-yl)-5-oxo-pentanoic acid (273 mg, 95%) as a colourless oil.

AnalpH2_MeOH_4MIN: Rt: 2.75 min. m/z 315.2 [M+H]+

The following compounds were synthesised by analogous methods:

| Structure | Method | Analytical Data | Mass, state |
|---|---|---|---|
| ![structure] | GM1 using 2-(trifluoromethyl) Pyrrolidine, GM3A using Pd/C, H$_2$, EtOH | AnalpH2_MeOH_4 MIN: Rt: 2.92 min, m/z 369.3 [M + H]+ | 501 mg, yellow oil |
| ![structure] | GM1 using 1-boc-piperazine, , GM3A using Pd/C, H$_2$, EtOH | AnalpH2_MeOH_4 MIN: Rt: 3.00 min, m/z 416.3 [M + H]+ | 331 mg, white solid |
| ![structure] | GM1 using 7-azabicyclo[2,2,1]heptanehydrochloride, , GM3A using Pd/C, H$_2$, EtOH | AnalpH2_MeOH_4 MIN: Rt: 2.78 min, m/z 327.3 [M + H]+ | 587 mg, colourless oil |

-continued

| Structure | Method | Analytical Data | Mass, state |
|---|---|---|---|
| (structure) | GM1 using 2,5-dimethylpyrroline, GM3A using Pd/C, H₂, EtOH | AnalpH2_MeOH_4 MIN: Rt: 2.91 and 2.95 min, m/z 329.3 [M + H]+ | 373 mg, colourless oil |
| (structure) | GM1 using (S)-3-fluoropyrrolidine hydrochloride, GM3A using Pd/C, H₂, EtOH | AnalpH2_MeOH_4 MIN: Rt: 2.43 min, m/z 319.2 [M + H]+ | 2.18 g, yellow oil |
| (structure) | GM1 using (S)-pyrrolidine-2-carbonitrile. TFA salt. Hydrogenation using H-cube, 30° C., atm pressure, 10% Pd/C CatCart. | AnalpH2_MeOH_4 MIN: Rt: 2.36 min, m/z 326.3 [M + H]+ | 120 mg, colourless oil |
| (structure) | GM1 using (2S)-2-isopropyl pyrrolidine, GM3A using Pd/C, H₂, EtOH | AnalpH2_MeOH_4 MIN: Rt: 3.10 min, m/z 343.4 [M + H]+ | 652 mg, colourless oil |
| (structure) | GM1 using 3-Oxa-8-aza-bicyclo[3.2.1]octane, GM3A using Pd/C, H₂, EtOH | AnalpH2_MeOH_4 MIN: Rt: 2.48 min, m/z 343.2 [M + H]+ | 601 mg, colourless oil |
| (structure) | GM1 using (2R)-2-isopropyl pyrrolidine, GM3A using Pd/C, H₂, EtOH | AnalpH2_MeOH_4 MIN: Rt: 3.10 min, m/z 343.4 [M + H]+ | 591 mg, colourless oil |
| (structure) | GM1 with pyrrolidine and HBTU, GM3A using Pd/C, H₂, EtOH | AnalpH2_MeOH_4 MIN: Rt: 2.48 min, m/z 301.3 [M + H]+ | 780 mg, white solid |

Scheme 5 Synthesis of (2R)-2-{[(tert-butoxy)carbonyl]amino}-4-(4-fluorophenyl)butanoic acid

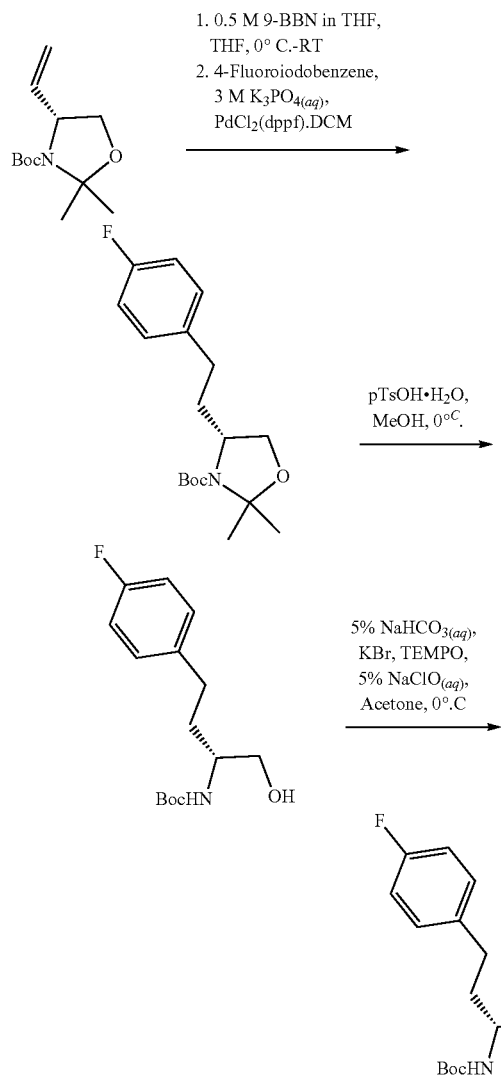

Step i: To (R)—N-boc-2,2-dimethyl-4-vinyloxazolidine (95 mg, 0.43 mmol) in anhydrous THF (1.5 mL) under $N_2$ at 0° C. was added dropwise 9-BBN (0.5M in THF, 1.7 mL, 0.84 mmol). The flask was wrapped in foil and stirred at RT for 2 h. 3M $K_3PO_{4(aq)}$ (0.28 mL, 0.84 mmol) was then added dropwise, followed by 4-fluoroiodobenzene (0.5 mL, 0.46 mmol) in anhydrous degassed DMF (1.5 mL) and $PdCl_2$ (dppf).DCM (17 mg, 0.02 mmol). The reaction was then stirred for 19 h before concentrating the reaction mixture in vacuo. The crude mixture was suspended in $Et_2O$ (30 mL) and washed with sat. $NaHCO_{3(aq)}$ solution (40 mL). The aqueous phase was washed with further $Et_2O$ (30 mL). The combined organic phases were washed with brine (30 mL) and dried over $Na_2SO_4$ and concentrated in vacuo. Column chromatography (0-20% EtOAc in petrol) isolated tert-butyl (4R)-4-[2-(4-fluorophenyl)ethyl]-2,2-dimethyl-1,3-oxazolidine-3-carboxylate as a colourless oil (55 mg, 0.17 mmol, 40%). LCMS: Rt=46.3 sec m/z 224.36 [M-Boc+H]$^+$ Step ii: To a solution of tert-butyl (4R)-4-[2-(4-fluorophenyl)ethyl]-2,2-dimethyl-1,3-oxazolidine-3-carboxylate (22 mg, 0.069 mmol) in methanol (2 mL) at 0° C. was added para-toluenesulfonic acid monohydrate (1 mg, 0.007 mmol). The reaction was stirred at 0° C. for 1 h then warmed to RT and stirred for a further 20 h. The reaction mixture was concentrated in vacuo, then partitioned between DCM (20 mL) and sat. $NaHCO_3$ solution (20 mL). The aqueous phase was extracted further with DCM (2×20 mL). The combined organic phase was dried over $Na_2SO_4$ and concentrated in vacuo. Column chromatography (20-60% EtOAc in petrol) isolated tert-butyl N-[(2R)-4-(4-fluorophenyl)-1-hydroxybutan-2-yl]carbamate as a colourless gum which solidified on standing to a white solid (10 mg, 0.035 mmol, 51%). LCMS: Rt=0.6 min m/z 589.57 [2M+Na]$^+$ Step iii: To a solution of tert-butyl N-[(2R)-4-(4-fluorophenyl)-1-hydroxybutan-2-yl]carbamate (36 mg, 0.13 mmol) in acetone (0.6 mL) was added 5% solution $NaHCO_3$ (0.3 mL) and the reaction mixture was cooled to 0° C. Potassium bromide (2 mg, 0.013 mmol) and TEMPO (24 mg, 0.15 mmol) were added, then 5% sodium hypochlorite solution (0.32 mL, 0.24 mmol) was added dropwise. The reaction temperature was maintained below 5° C. for 1 h. The reaction mixture was then diluted with water (3 mL) and extracted with EtOAc (2×7 mL). The combined organic phase was washed with brine (10 mL), dried over $Na_2SO_4$ and concentrated in vacuo. (2R)-2-{[(tert-butoxy)carbonyl]amino}-4-(4-fluorophenyl)butanoic acid was used without further purification (8 mg, 0.027 mmol, 21%). LCMS: Rt=0.6 min m/z 617.51 [2M+Na]$^+$ Synthesis of Homophenylalanine Library (A)

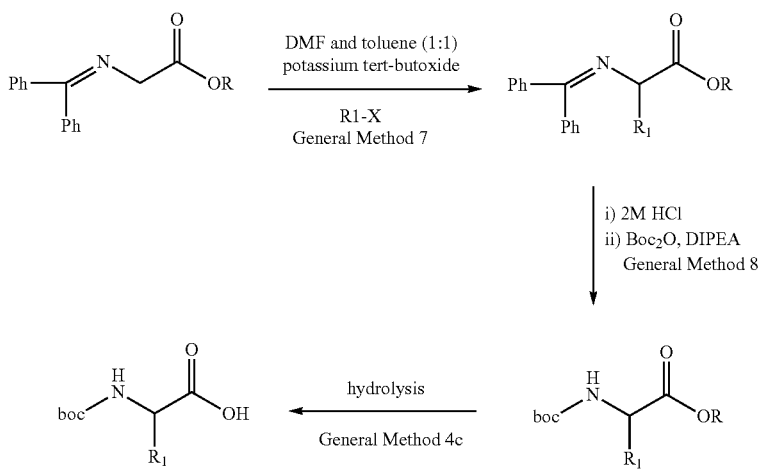

This general methodology was used to prepare the following intermediates:

| Example No. | Structure & Conditions | Analytical Data | Mass, % yield, state |
|---|---|---|---|
| GS7-int760 | 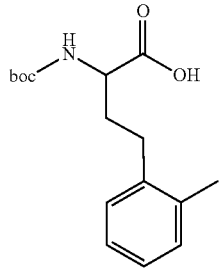<br>Step 1 with N-(diphenylmethylene)glycinate and 2-methylphenethyl bromide<br>GM7 Step 2 GM8<br>Step 3 GM4C | Agilent_MeCN_HPLC_3 min<br>LCMS: $R_t$ = 1.96 min<br>m/z = 194.1<br>[M − Boc + H]$^+$ | 144 mg, colourless oil |
| GS7-int762 | 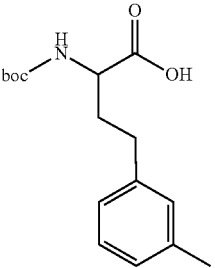<br>Step 1 with methyl N-(diphenylmethylene) glycinate and 3-methylphenethyl bromide<br>GM7 Step 2 GM8<br>Step 3 GM4C | Agilent_MeCN_HPLC_3 min<br>LCMS: $R_t$ = 1.98 min<br>m/z = 316.1<br>[M + Na]$^+$ | 67 mg, colourless oil |

Synthesis of Homophenylalanine Library (B)

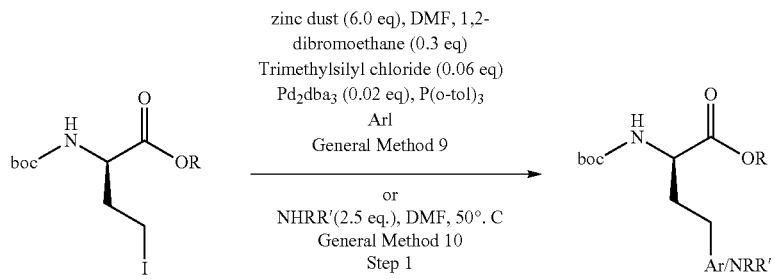

zinc dust (6.0 eq), DMF, 1,2-dibromoethane (0.3 eq)
Trimethylsilyl chloride (0.06 eq)
Pd$_2$dba$_3$ (0.02 eq), P(o-tol)$_3$
ArI
General Method 9 or
NHRR'(2.5 eq.), DMF, 50° C
General Method 10
Step 1

Step 2 | hydrolysis General method 4C or 4A

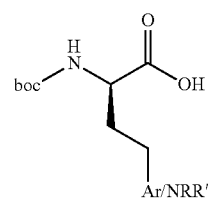

(or lithium salt)

| Example No. | Structure & Conditions | Analytical Data | Mass, % yield, state |
|---|---|---|---|
| GS7-int787 | 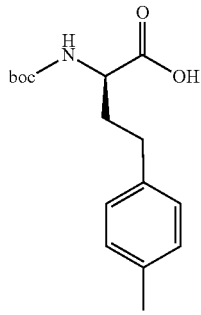<br>Step 1: benzyl (2R)-2-{[(tert-butoxy)carbonyl]amino}-4-iodobutanoate (synthesised as described by Jackson R. F. W. et al J. Org. Chem. 1998, 63, 7875-7884) and 4-iodotoluene, GM9<br>Step 2 GM4C | Agilent_MeCN_HPLC_3 min LCMS: $R_t$ = 1.97 min m/z = 316.1 $[M + Na]^+$ | 84 mg, colourless gum |
| GS7-int789 | 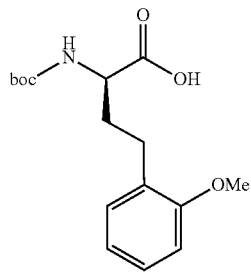<br>Step 1: benzyl (2R)-2-{[(tert-butoxy)carbonyl]amino}-4-iodobutanoate (synthesised as described by Jackson R. F. W. et al J. Org. Chem. 1998, 63, 7875-7884) and 4-iodoanisole, GM9<br>Step 2 GM4C | Agilent_MeCN_HPLC_3 min LCMS: $R_t$ = 1.89 min m/z = 332.0 $[M + Na]^+$ | 32 mg, colourless gum |
| GS7-int801 | 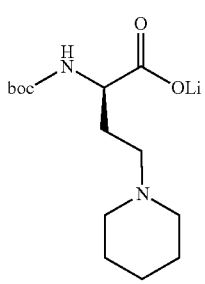<br>Step 1: piperidine and benzyl (2R)-2-{[(tert-butoxy)carbonyl]amino}-4-iodobutanoate (synthesised as described by Jackson R. F. W. et al J. Org. Chem. 1998, 63, 7875-7884), GM10<br>Step 2 GM4A | Agilent_MeCN_HPLC_3 min LCMS: $R_t$ = 1.22 min m/z = 287.5 $[M + H]^+$ | 28 mg, colourless gum |

-continued

| Example No. | Structure & Conditions | Analytical Data | Mass, % yield, state |
|---|---|---|---|
| GS7-int805 | 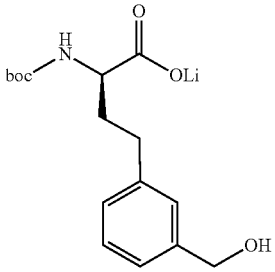<br>Step 1: benzyl (2R)-2-{[(tert-butoxy)carbonyl]amino}-4-iodobutanoate (synthesised as described by Jackson R. F. W. et al J. Org. Chem. 1998, 63, 7875-7884) and 3-iodobenzyl alcohol, GM9<br>Step 2 GM4A | Agilent_MeCN_HPLC_3 min LCMS: $R_t$ = 1.66 min m/z = 287.5 $[M + Na]^+$ | 42 mg, colourless gum |
| GS7-int808 | 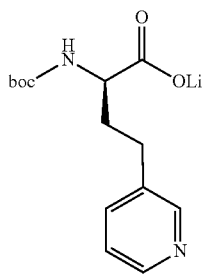<br>Step 1: benzyl (2R)-2-{[(tert-butoxy)carbonyl]amino}-4-iodobutanoate (synthesised as described by Jackson R. F. W. et al J. Org. Chem. 1998, 63, 7875-7884) and 3-iodopyridine, GM9<br>Step 2 GM4A | Agilent_MeCN_HPLC_3 min LCMS: $R_t$ = 1.20 min m/z = 281.5 $[M + H]^+$ | 27 mg, colourless gum |

Synthesis of 1-tert-butyl 2-lithio (2R,4R)-4-(piperidin-1-yl)pyrrolidine-12-dicarboxylate

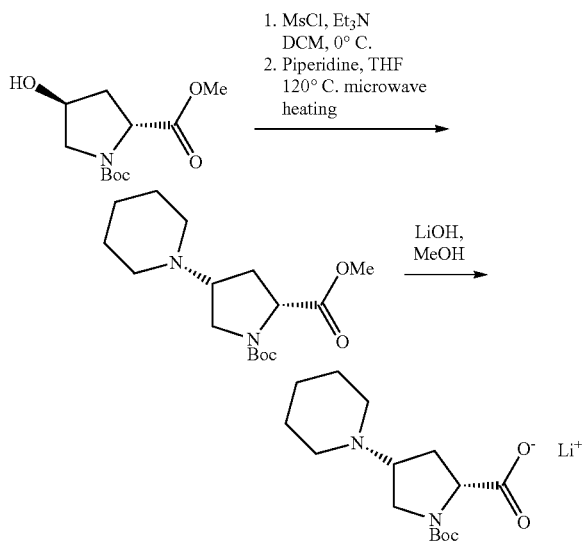

Step 1: To a solution of (2R,4S)-1-tert-butyl-2-methyl-4-hydroxypyrrolidine-1,2-dicarboxylate (267 mg, 1.09 mmol) and $Et_3N$ (0.18 mL, 1.31 mmol) in anhydrous DCM (5 mL), under $N_2$ at 0° C. was added mesyl chloride (0.10 mL, 1.31 mmol). The temperature maintained below 5° C. for 1 h, then the reaction was diluted with DCM (20 mL) and washed sequentially with 1 M HCl (30 mL), sat. $NaHCO_3$ (aq) and brine (30 mL) before drying over $Na_2CO_3$ and concentrated in vacuo. The crude mesylate was then dissolved in THF (1 mL) and piperidine (1 mL) and heated at 120° C. with microwave heating. After 110 min the reaction was diluted with water (30 mL) and extracted with EtOAc (3×30 mL). The combined organic phases were washed with brine (40 mL), dried over $Na_2CO_3$ and concentrated in vacuo. The crude product purified using SCX-2 to give 1-tert-butyl 2-methyl (2R,4R)-4-(piperidin-1-yl)pyrrolidine-1,2-dicarboxylate (137 mg, 40%)

Thermo_MeOH_UHPLC_1.2 min LCMS: Rt=0.6 min m/z 313.44 $[M+H]^+$

Step 2: To a solution of 1-tert-butyl 2-methyl (2R,4R)-4-(piperidin-1-yl)pyrrolidine-1,2-dicarboxylate (137 mg, 0.44 mmol) in MeOH (5 mL) was added $LiOH·H_2O$ (18 mg, 0.44 mmol). The reaction was stirred at RT for 48 h, then further $LiOH·H_2O$ (18 mg, 0.44 mmol) was added. After stirring for a further 2.5 h at RT the reaction was heated to 60° C. for 3 h. Further $LiOH·H_2O$ (18 mg, 0.44 mmol) was added and the reaction heated to 60° C. for a further 1 h before LCMS indicated complete consumption of starting material. The reaction mixture was cooled to RT before concentrating in vacuo and using 1-tert-butyl 2-lithio (2R,4R)-4-(piperidin-1-yl)pyrrolidine-1,2-dicarboxylate without further purification (148 mg, 95%).

Thermo_MeOH_UHPLC_1.2 min LCMS: Rt=27.8 sec m/z 299.40 [M+H]+

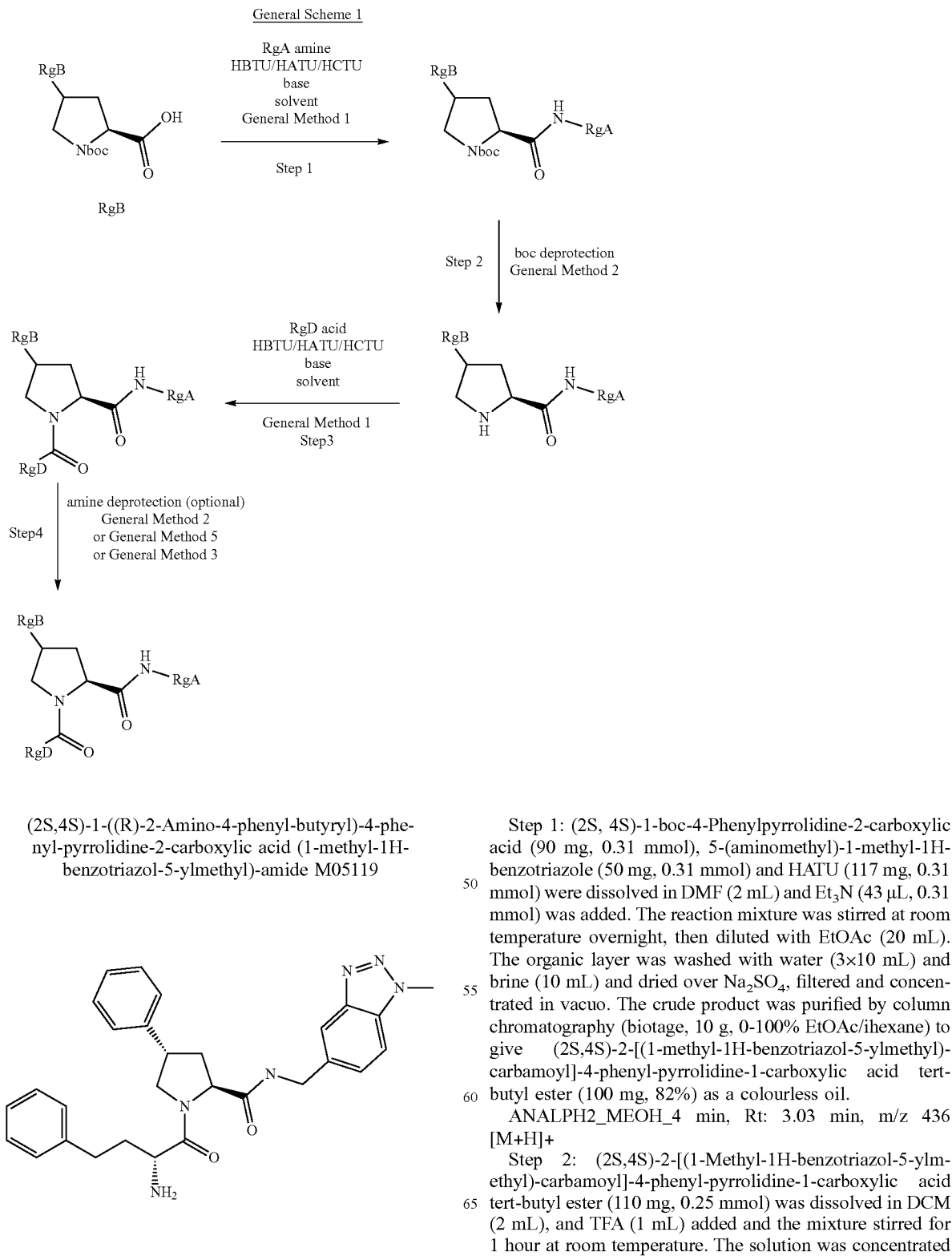

(2S,4S)-1-((R)-2-Amino-4-phenyl-butyryl)-4-phenyl-pyrrolidine-2-carboxylic acid (1-methyl-1H-benzotriazol-5-ylmethyl)-amide M05119

Step 1: (2S, 4S)-1-boc-4-Phenylpyrrolidine-2-carboxylic acid (90 mg, 0.31 mmol), 5-(aminomethyl)-1-methyl-1H-benzotriazole (50 mg, 0.31 mmol) and HATU (117 mg, 0.31 mmol) were dissolved in DMF (2 mL) and Et₃N (43 µL, 0.31 mmol) was added. The reaction mixture was stirred at room temperature overnight, then diluted with EtOAc (20 mL). The organic layer was washed with water (3×10 mL) and brine (10 mL) and dried over Na₂SO₄, filtered and concentrated in vacuo. The crude product was purified by column chromatography (biotage, 10 g, 0-100% EtOAc/ihexane) to give (2S,4S)-2-[(1-methyl-1H-benzotriazol-5-ylmethyl)-carbamoyl]-4-phenyl-pyrrolidine-1-carboxylic acid tert-butyl ester (100 mg, 82%) as a colourless oil.

ANALPH2_MEOH_4 min, Rt: 3.03 min, m/z 436 [M+H]+

Step 2: (2S,4S)-2-[(1-Methyl-1H-benzotriazol-5-ylmethyl)-carbamoyl]-4-phenyl-pyrrolidine-1-carboxylic acid tert-butyl ester (110 mg, 0.25 mmol) was dissolved in DCM (2 mL), and TFA (1 mL) added and the mixture stirred for 1 hour at room temperature. The solution was concentrated in vacuo to give (2S,4S)-2-[(1-methyl-1H-benzotriazol-5-ylmethyl)-carbamoyl]-4-phenyl-pyrrolidine as a clear oil which was used in the subsequent reaction without further purification.

ANALPH2_MEOH_4 min, Rt: 1.71 min, m/z 336 [M+H]+

Step 3: (2S,4S)-2-[(1-Methyl-1H-benzotriazol-5-ylmethyl)-carbamoyl]-4-phenyl-pyrrolidine (85 mg, 0.25 mmol), Boc-D-homophenylalanine (71 mg, 0.25 mmol) and HATU (96 mg, 0.25 mmol) were combined in DMF (2 mL) then Et₃N (60 µL, 0.25 mmol) added and the mixture stirred at room temperature overnight. The reaction mixture was diluted with EtOAc. The organic layer was washed with water (2×10 mL), sat. aq. NH₄Cl solution (2×10 mL), sat. aq. NaHCO₃ solution (2×10 mL), brine, dried over Na₂SO₄, filtered and concentrated in vacuo to give ((R)-1-{(2S,4S)-2-[(1-methyl-1H-benzotriazol-5-ylmethyl)-carbamoyl]-4-phenyl-pyrrolidine-1-carbonyl}-3-phenyl-propyl)-carbamic acid tert-butyl ester (110 mg, 74%) as a colourless oil which was used in the subsequent reaction without further purification.

ANALPH2_MEOH_4 min, Rt: 3.40 min, m/z 597.4 [M+H]+

Step 4: ((R)-1-{(2S,4S)-2-[(1-Methyl-1H-benzotriazol-5-ylmethyl)-carbamoyl]-4-phenyl-pyrrolidine-1-carbonyl}-3-phenyl-propyl)-carbamic acid tert-butyl ester (110 mg, 0.19 mmol) was dissolved in DCM (2 mL), TFA (1 mL) was added and the reaction mixture stirred at room temperature overnight. The reaction mixture was purified by SCX-2 (2 g), washing with MeOH and eluting with NH₃/MeOH to give a yellow oil which was lyophilised from MeCN/H₂O to give (2S,4S)-1-((R)-2-amino-4-phenyl-butyryl)-4-phenyl-pyrrolidine-2-carboxylic acid (1-methyl-1H-benzotriazol-5-ylmethyl)-amide (65 mg, 71%) as a white solid.

ANALPH9_MEOH_QC_v1, Rt: 7.58 min, m/z 497.33 [M+H]+

ANALPH2_MEOH_QC_v1, Rt: 5.70 min, m/z 497.26 [M+H]+

1H NMR (400 MHz, DMSO-D6) δ 8.86 (t, J=5.9 Hz, 0.2H), 8.51 (t, J=6.0 Hz, 0.8H), 7.90 (s, 0.2H), 7.89 (s, 0.8H), 7.80 (d, J=8.6 Hz, 0.8H), 7.74 (d, J=8.5 Hz, 0.2H), 7.48 (dd, J=8.6, 1.5 Hz, 1H), 7.39-7.09 (m, 9.5H), 6.97-6.91 (m, 0.5H), 4.55-4.37 (m, 3H), 4.29 (s, 3H), 4.22 (s, 1H), 3.95 (dd, J=9.5, 7.6 Hz, 1H), 3.50 (d, J=9.6 Hz, 1H), 3.22 (t, J=9.8 Hz, 1H), 2.88-2.56 (m, 2H), 2.46-2.13 (m, 2H), 2.08 (s, 2H), 1.86-1.71 (m, 1H), 1.63-1.43 (m, 1H).

The following compounds were made by analogous methods

| Example No. | Structure & Conditions | Analytical Data | Mass, % yield, state |
|---|---|---|---|
| M00760 | RgA: 1-(N-Boc-aminomethyl)-4-(aminomethyl)benzene<br>RgB: Z-Pro-OH<br>RgD: 2-{[(tert-Butoxy)carbonyl]amino}-4-(2-methylphenyl)butanoic acidadd<br>Step 1 & 3 GM1 with HCTU and Et₃N<br>Step 2 GM3A with Pd/C<br>Step 4 GM2A | Agilent_MeCN_HPLC_3 min LCMS: R$_t$ = 1.33 min m/z = 409.3 [M + H]⁺ | 20 mg white crystalline solid |
| M00762 | RgA: 1-(N-Boc-aminomethyl)-4-(aminomethyl)benzene<br>RgB: Z-Pro-OH<br>RgD: 2-{[(tert-Butoxy)carbonyl]amino}-4-(3-methylphenyl)butanoic acid | Agilent_MeCN_HPLC_3 min LCMS: R$_t$ = 1.37 min m/z = 409.3 [M + H]⁺ | 31 mg off-white solid |

-continued

| Example No. | Structure & Conditions | Analytical Data | Mass, % yield, state |
|---|---|---|---|
| | Step 1 & 3 GM1 with HCTU and Et₃N<br>Step 2 GM3A with Pd/C<br>Step 4 GM2A | | |
| M00787 | [Structure of compound with 4-methylphenyl group, H₂N, pyrrolidine amide, benzyl-CH₂NH₂]<br><br>RgA: 1-(N-Boc-aminomethyl)-4-(aminomethyl)benzene<br>RgB: Z-Pro-OH<br>RgD: (2R)-2-{[(tert-Butoxy)carbonyl]amino}-4-(4-methylphenyl)butanoic acid<br>Step 1 & 3 GM1 with HCTU and Et₃N<br>Step 2 GM3A with Pd/C<br>Step 4 GM2A | Agilent_MeCN_HPLC_3 min<br>LCMS: $R_t$ = 1.35 min m/z = 409.1 [M + H]⁺ | 19 mg<br>white<br>powder |
| M00789 | [Structure of compound with 2-methoxyphenyl (OMe) group, H₂N, pyrrolidine amide, benzyl-CH₂NH₂]<br><br>RgA: 1-(N-Boc-aminomethyl)-4-(aminomethyl)benzene<br>RgB: Z-Pro-OH<br>RgD: (2R)-2-{[(tert-Butoxy)carbonyl]amino}-4-(2-methoxyphenyl)butanoic acid<br>Step 1 & 3 GM1 with HCTU and Et₃N<br>Step 2 GM3A with Pd/C<br>Step 4 GM2A | Agilent_MeCN_HPLC_3 min<br>LCMS: $R_t$ = 1.33 min m/z = 425.2 [M + H]⁺ | 25 mg<br>white<br>powder |
| M00801 | [Structure of compound with piperidine group, H₂N, pyrrolidine amide, benzyl-CH₂NH₂]<br><br>RgA: 1-(N-Boc-aminomethyl)-4-(aminomethyl)benzene<br>RgB: Z-Pro-OH<br>RgD: Lithio (2S)-2-{[(tert- | Agilent_MeCN_HPLC_3 min<br>LCMS: $R_t$ = 0.26 min m/z = 402.2 [M + H]⁺ | 20 mg<br>light<br>brown<br>solid |

| Example No. | Structure & Conditions | Analytical Data | Mass, % yield, state |
|---|---|---|---|
| | butoxy)carbonyl]amino}-4-(piperidin-1-yl)butanoate<br>Step 1 & 3 GM1 with HCTU and Et$_3$N<br>Step 2 GM3A with Pd/C<br>Step 4 GM2A | | |
| M00805 | 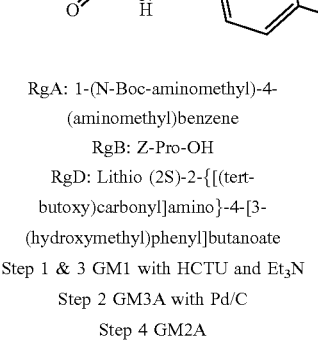<br>RgA: 1-(N-Boc-aminomethyl)-4-(aminomethyl)benzene<br>RgB: Z-Pro-OH<br>RgD: Lithio (2S)-2-{[(tert-butoxy)carbonyl]amino}-4-[3-(hydroxymethyl)phenyl]butanoate<br>Step 1 & 3 GM1 with HCTU and Et$_3$N<br>Step 2 GM3A with Pd/C<br>Step 4 GM2A | Agilent_MeCN_HPLC_3 min<br>LCMS: R$_t$ = 1.00 min m/z =<br>425.6 [M + H]$^+$ | 16 mg<br>colourless<br>glass |
| M00808 | <br>RgA: 1-(N-Boc-aminomethyl)-4-(aminomethyl)benzene<br>RgB: Z-Pro-OH<br>RgD: Lithio (2S)-2-{[(tert-butoxy)carbonyl]amino}-4-(pyridin-3-yl)butanoate<br>Step 1 & 3 GM1 with HCTU and Et$_3$N (step 3 additional purification SCX cartridge, eluting the desired product with 2M NH$_3$ in MeOH)<br>Step 2 GM3A with Pd/C<br>Step 4 GM2A | Agilent_MeCN_HPLC_3 min<br>LCMS: R$_t$ = 0.27 min m/z =<br>396.6 [M + H]$^+$ | 16 mg,<br>brown<br>gum |

| Example No. | Structure & Conditions | Analytical Data | Mass, % yield, state |
|---|---|---|---|
| M00948 | 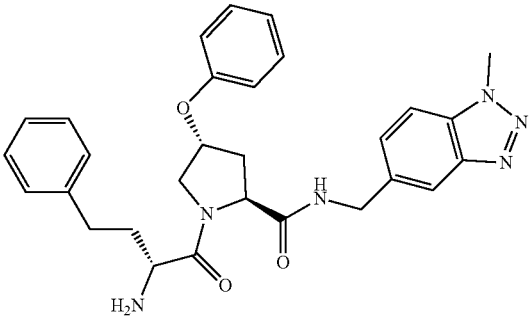 [SMILES: Cn1nnc2cc(CNC(=O)[C@@H]3C[C@@H](Oc4ccccc4)CN3C(=O)[C@H](N)CCc3ccccc3)ccc21]<br>RgA: C-(1-Methyl-1H-benzotriazol-5-yl)-methylamine<br>RgB: (2S,4R)-Boc-4-phenoxy-pyrrolidine-2-carboxylic acid<br>RgD: N-Boc-D-homophenylalanine<br>Step 1 & 3 GM1 with HCTU and Et₃N<br>Step 2 & 4 GM2B | Thermo_MeOH_UHPLC_1.2 min<br>LCMS: $R_t$ = 0.5 min m/z 513.56 $[M + H]^+$ | 22 mg pale yellow powder (60%) |
| M00949 | 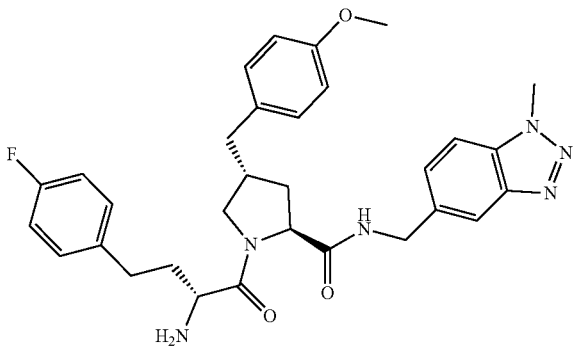 [SMILES: COc1ccc(C[C@@H]2C[C@@H](C(=O)NCc3ccc4c(c3)nnn4C)N(C(=O)[C@H](N)CCc3ccc(F)cc3)C2)cc1]<br>RgA: C-(1-Methyl-1H-benzotriazol-5-yl)-methylamine<br>RgB: boc-(R)-γ-(4-methoxybenzyl)-L-proline<br>RgD: (2R)-2-{[(tert-butoxy)carbonyl]amino}-4-(4-fluorophenyl)butanoic acid<br>Step 1 & 3 GM1 with HCTU and Et₃N<br>Step 2, 4 GM2B | Thermo_MeOH_UHPLC_1.2 min<br>LCMS: $R_t$ = 0.6 min m/z 559.58 $[M + H]^+$ | 7 mg, yellow gum |
| M00952 | 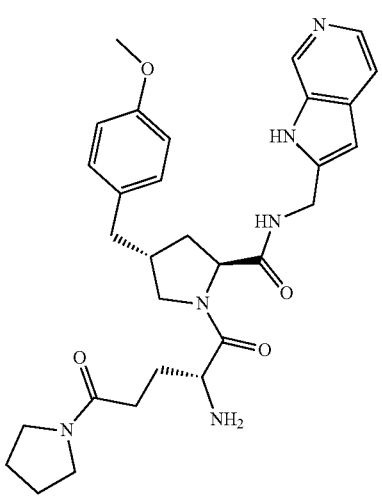 [SMILES: COc1ccc(C[C@@H]2C[C@@H](C(=O)NCc3cc4ccncc4[nH]3)N(C(=O)[C@H](N)CCC(=O)N3CCCC3)C2)cc1]<br>RgA: {1H-pyrrolo[2,3-c]pyridine-2-yl}methanamine<br>RgB: boc-(R)-γ-(4-methoxybenzyl)-L-proline | Thermo_MeOH_UHPLC_1.2 min<br>LCMS: $R_t$ = 0.5 min m/z 547.65 $[M + H]^+$ | 42 mg, yellow gum |

| Example No. | Structure & Conditions | Analytical Data | Mass, % yield, state |
|---|---|---|---|
| | RgD: (R)-2-tert-Butoxycarbonylamino-5-oxo-5-pyrrolidin-1-yl-pentanoic acid<br>Step 1 & 3 GM1 with HCTU and Et₃N<br>Step 2 & 4 GM2B | | |
| M00953 | 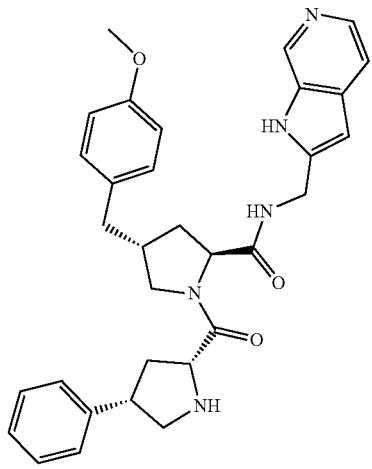 [SMILES: COc1ccc(C[C@@H]2C[C@@H](C(=O)NCc3cc4ccncc4[nH]3)N(C(=O)[C@H]3C[C@@H](c4ccccc4)CN3)C2)cc1]<br><br>RgA: {1H-pyrrolo[2,3-c]pyridine-2-yl}methanamine<br>RgB: boc-(R)-γ-(4-methoxybenzyl)-L-proline<br>RgD: (2R,4R)-Boc-4-phenyl-pyrrolidine-2-carboxylic acid<br>Step 1 & 3 GM1 with HCTU and Et₃N<br>Step 2 & 4 GM2B | Thermo_MeOH_UHPLC_1.2 min<br>LCMS: $R_t$ = 0.5 min m/z = 538.58 [M + H]⁺ | 35 mg, yellow gum |
| M00954 | 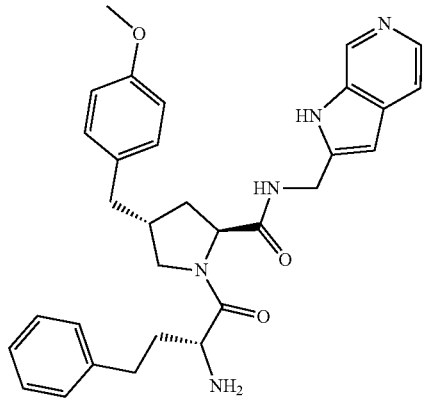 [SMILES: COc1ccc(C[C@@H]2C[C@@H](C(=O)NCc3cc4ccncc4[nH]3)N(C(=O)[C@H](N)CCc3ccccc3)C2)cc1]<br><br>RgA: {1H-pyrrolo[2,3-c]pyridine-2-yl}methanamine<br>RgB: boc-(R)-γ-(4-methoxybenzyl)-L-proline<br>RgD: N-Boc-D-homophenylalanine<br>Step 1 & 3 GM1 with HCTU and Et₃N<br>Step 2 & 4 GM2B | Thermo_MeOH_UHPLC_1.2 min<br>LCMS: $R_t$ = 0.5 min m/z = 526.61 [M + H]⁺ | 55 mg, yellow gum |

-continued

| Example No. | Structure & Conditions | Analytical Data | Mass, % yield, state |
|---|---|---|---|
| M00957 | 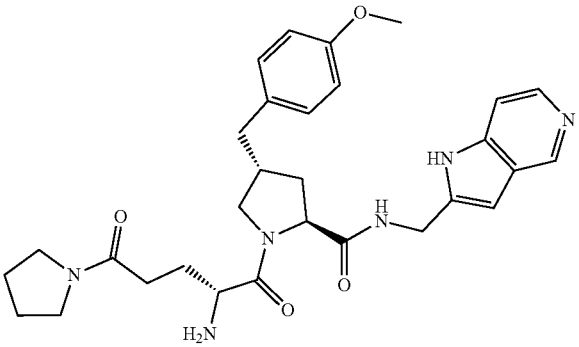 [SMILES: COc1ccc(C[C@@H]2C[C@@H](C(=O)NCc3cc4cnccc4[nH]3)N(C(=O)[C@H](N)CCC(=O)N3CCCC3)C2)cc1]<br>RgA: {1H-pyrrolo[3,2-c]pyridin-2-yl}methanamine<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3 GM1 with HCTU and Et₃N<br>Step 2 & 4 GM2B | Thermo_MeOH_UHPLC_1.2 min<br>LCMS: $R_t$ = 0.5 min m/z = 547.66 [M + H]⁺ | 15 mg, yellow powder |
| M00959 | 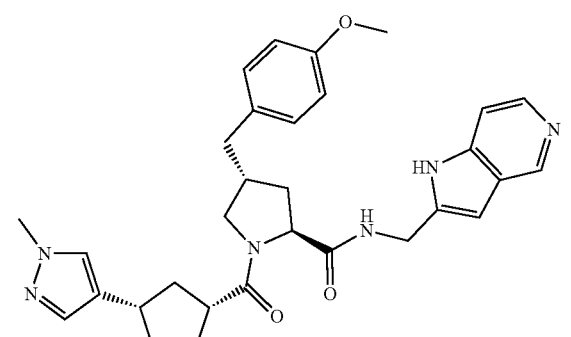<br>RgA: {1H-pyrrolo[3,2-c]pyridin-2-yl}methanamine<br>RgB: boc-(R)-γ-(4-methoxybenzyl)-L-proline<br>RgD: (R)-4-(1-Methyl-1H-pyrazol-4-yl)-pyrrolidine-1,2-dicarboxylic acid 1-tert-butyl ester<br>Step 1 & 3 GM1 with HCTU and Et₃N<br>Step 2 & 4 GM2B | Thermo_MeOH_UHPLC_1.2 min<br>LCMS: $R_t$ = 0.5 min m/z = 542.69 [M + H]⁺ | 10 mg, yellow gummy solid |
| M00960 | 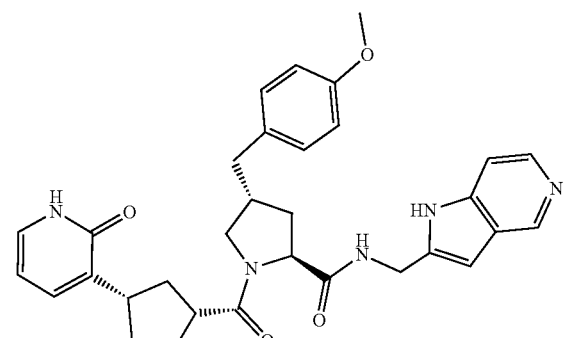<br>RgA: {1H-pyrrolo[3,2-c]pyridin-2-yl}methanamine<br>RgB: boc-(R)-γ-(4-methoxybenzyl)-L-proline<br>RgD: : (R)-4-(2-Oxo-1,2-dihydro-pyridin-3-yl)-pyrrolidine-1,2-dicarboxylic acid 1-tert-butyl ester<br>Step 1 & 3 GM1 with HCTU and Et₃N | Thermo_MeOH_UHPLC_1.2 min<br>LCMS: $R_t$ = 0.6 min m/z = 554.64 [M + H]⁺ | 16 mg, cream powder |

| Example No. | Structure & Conditions | Analytical Data | Mass, % yield, state |
|---|---|---|---|
| | Step 2 & 4 GM2B | | |
| M00961 | 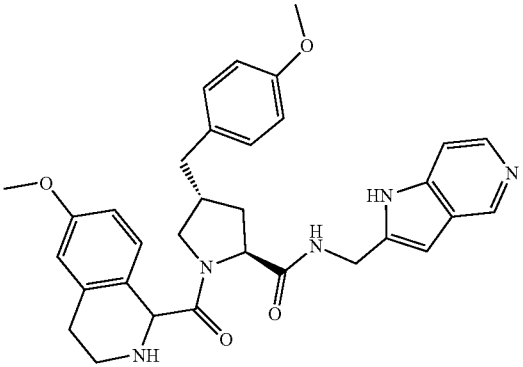 [SMILES: COc1ccc(C[C@@H]2C[C@@H](C(=O)NCc3cc4cnccc4[nH]3)N(C(=O)C3NCCc4cc(OC)ccc43)C2)cc1]<br>Stereoisomer A<br>RgA: {1H-pyrrolo[3,2-c]pyridin-2-yl}methanamine<br>RgB: boc-(R)-γ-(4-methoxybenzyl)-L-proline<br>RgD: 2-Boc-6-methoxy-3,4-dihydro-1H-isoquinoline-1-carboxylic acid<br>Step 1 & 3 GM1 with HCTU and Et$_3$N<br>Step 2 & 4 GM2B | Thermo_MeOH_UHPLC_1.2 min<br>LCMS: R$_t$ = 35.6 sec m/z = 554.57 [M + H]$^+$ | 16 mg, pale yellow powder |
| M00963 | 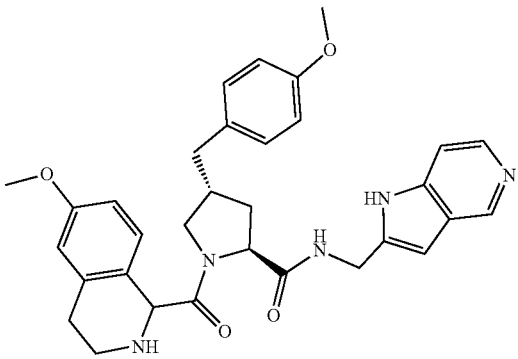 [SMILES: COc1ccc(C[C@@H]2C[C@@H](C(=O)NCc3cc4cnccc4[nH]3)N(C(=O)C3NCCc4cc(OC)ccc43)C2)cc1]<br>Stereoisomer B<br>RgA: {1H-pyrrolo[3,2-c]pyridin-2-yl}methanamine<br>RgB: boc-(R)-γ-(4-methoxybenzyl)-L-proline<br>RgD: 2-Boc-6-methoxy-3,4-dihydro-1H-isoquinoline-1-carboxylic acid<br>Step 1 & 3 GM1 with HCTU and Et$_3$N<br>Step 2 & 4 GM2B | Thermo_MeOH_UHPLC_ 1.2 min<br>LCMS: R$_t$ = 0.5 min m/z = 554.52 [M + H]$^+$ | 7 mg, pale yellow powder |
| M00964 | 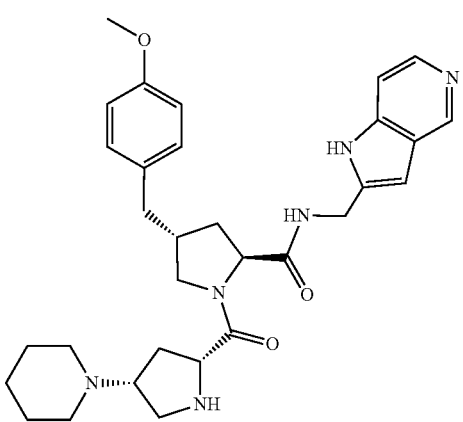 [SMILES: COc1ccc(C[C@@H]2C[C@@H](C(=O)NCc3cc4cnccc4[nH]3)N(C(=O)[C@H]3C[C@@H](N4CCCCC4)CN3)C2)cc1] | Thermo_MeOH_UHPLC_1.2 min<br>LCMS: R$_t$ = 0.4 min m/z = 545.51 [M + H]$^+$ | 65 mg, pale yellow solid |

| Example No. | Structure & Conditions | Analytical Data | Mass, % yield, state |
|---|---|---|---|
| | RgA: {1H-pyrrolo[3,2-c]pyridin-2-yl}methanamine<br>RgB: boc-(R)-γ-(4-methoxybenzyl)-L-proline<br>RgD: 1-tert-butyl 2-lithio (2R,4R)-4-(piperidin-1-yl)pyrrolidine-1,2-dicarboxylate<br>Step 1 & 3 GM1 with HCTU and Et₃N<br>Step 2 & 4 GM2B | | |
| M00965 | 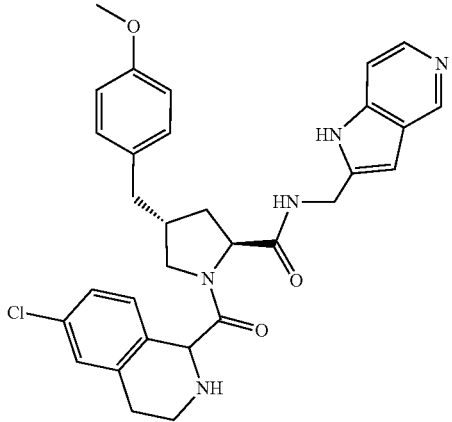 [SMILES: COc1ccc(C[C@@H]2C[C@@H](C(=O)NCc3cc4cnccc4[nH]3)N(C(=O)C3NCCc4cc(Cl)ccc43)C2)cc1]<br>RgA: {1H-pyrrolo[3,2-c]pyridin-2-yl}methanamine<br>RgB: boc-(R)-γ-(4-methoxybenzyl)-L-proline<br>RgD: 2-boc-6-chloro-3,4-dihydro-1H-isoquinoline-1-carboxylic acid<br>Step 1 & 3 GM1 with HCTU and Et₃N<br>Step 2 & 4 GM2B | Thermo_MeOH_UHPLC_1.2 min<br>LCMS: R$_t$ = 0.4 min m/z = 558.51 [M + H]⁺ | 38 mg, pale yellow powder |
| M00966 | 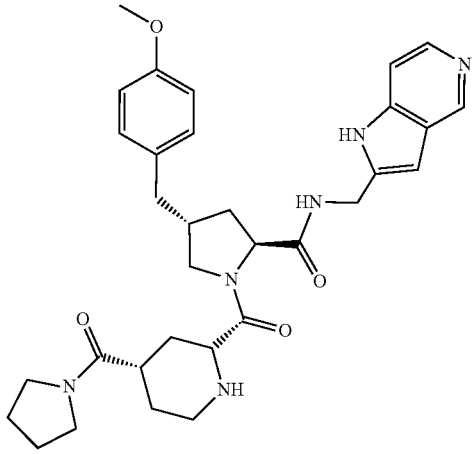<br>RgA: {1H-pyrrolo[3,2-c]pyridin-2-yl}methanamine<br>RgB: boc-(R)-γ-(4-methoxybenzyl)-L-proline<br>RgD: (2R,4S)-1-[(tert-butoxy)carbonyl]-4-(pyrrolidine-1-carbonyl)piperidine-2-carboxylic acid<br>Step 1 & 3 GM1 with HCTU and Et₃N<br>Step 2 & 4 GM2B | Thermo_MeOH_UHPLC_1.2 min<br>LCMS: R$_t$ = 0.4 min m/z = 573.47 [M + H]⁺ | 16 mg, yellow, gummy solid |

| Example No. | Structure & Conditions | Analytical Data | Mass, % yield, state |
|---|---|---|---|
| M00967 | 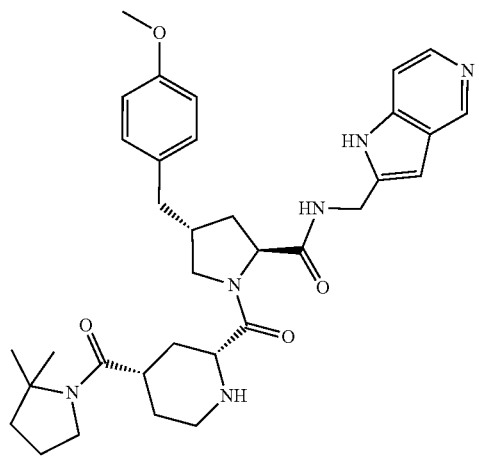 [SMILES: COc1ccc(C[C@@H]2C[C@@H](C(=O)NCc3cc4cnccc4[nH]3)N(C(=O)[C@H]3C[C@@H](C(=O)N4CCCC4(C)C)CCN3)C2)cc1]<br>RgA: {1H-pyrrolo[3,2-c]pyridin-2-yl}methanamine<br>RgB: boc-(R)-γ-(4-methoxybenzyl)-L-proline<br>RgD: (2R,4S)-1-[(tert-butoxy)carbonyl]-4-(2,2-dimethylpyrrolidine-1-carbonyl)piperidine-2-carboxylic acid<br>Step 1 & 3 GM1 with HCTU and Et$_3$N<br>Step 2 & 4 GM2B | Thermo_MeOH_UHPLC_1.2 min<br>LCMS: R$_t$ = 0.5 min m/z = 601.50 [M + H]$^+$ | 16 mg, cream powder |
| M00968 | 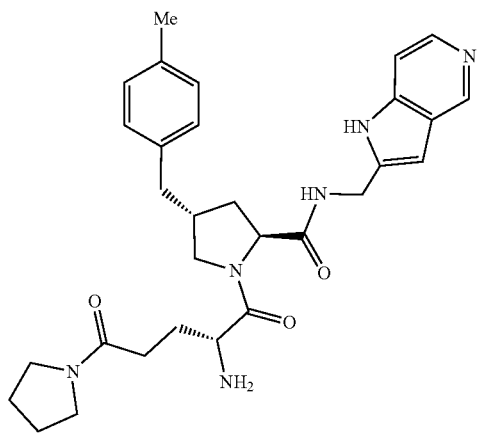 [SMILES: Cc1ccc(C[C@@H]2C[C@@H](C(=O)NCc3cc4cnccc4[nH]3)N(C(=O)[C@H](N)CCC(=O)N3CCCC3)C2)cc1]<br>RgA: {1H-pyrrolo[3,2-c]pyridin-2-yl}methanamine<br>RgB: Boc-(R)-γ-(4-methylbenzyl)-L-proline<br>RgD: (R)-2-tert-Butoxycarbonylamino-5-oxo-5-pyrrolidin-1-yl-pentanoic acid<br>Step 1 & 3 GM1 with HCTU and Et$_3$N<br>Step 2 & 4 GM2B | Thermo_MeOH_UHPLC_1.2 min<br>LCMS: R$_t$ = 0.5 min m/z = 531.46 [M + H]$^+$ | 35 mg, yellow gummy solid |

| Example No. | Structure & Conditions | Analytical Data | Mass, % yield, state |
|---|---|---|---|
| M00969 | 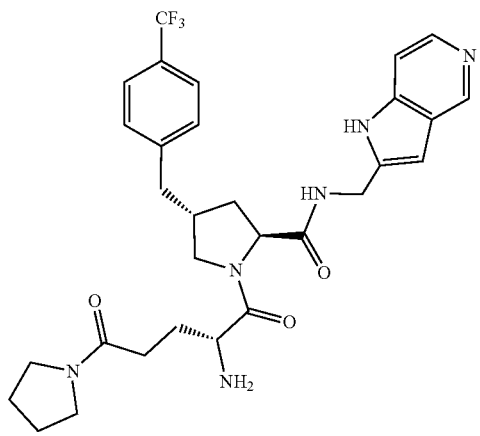 [SMILES: N[C@H](CCC(=O)N1CCCC1)C(=O)N1C[C@H](Cc2ccc(C(F)(F)F)cc2)C[C@H]1C(=O)NCc1cc2cnccc2[nH]1]<br>RgA: {1H-pyrrolo[3,2-c]pyridin-2-yl}methanamine<br>RgB: boc-(R)-4-[4-trifluoromethylbenzyl]-L-proline<br>RgD: (R)-2-tert-Butoxycarbonylamino-5-oxo-5-pyrrolidin-1-yl-pentanoic acid<br>Step 1 & 3 GM1 with HCTU and Et$_3$N<br>Step 2 & 4 GM2B | Thermo_MeOH_UHPLC_1.2 min<br>LCMS: R$_t$ = 0.5 min m/z = 585.49 [M + H]$^+$ | 35 mg, white solid |
| M00970 | 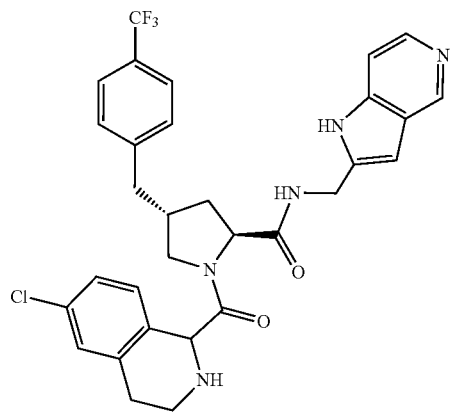 [SMILES: O=C(NCc1cc2cnccc2[nH]1)[C@@H]1C[C@@H](Cc2ccc(C(F)(F)F)cc2)CN1C(=O)C1NCCc2cc(Cl)ccc21]<br>RgA: {1H-pyrrolo[3,2-c]pyridin-2-yl}methanamine<br>RgB: boc-(R)-4-[4-trifluoromethylbenzyl]-L-proline<br>RgD: 2-boc-6-chloro-3,4-dihydro-1H-isoquinoline-1-carboxylic acid<br>Step 1 & 3 GM1 with HCTU and Et$_3$N<br>Step 2 & 4 GM2B | Thermo_MeOH_UHPLC_1.2 min<br>LCMS: R$_t$ = 0.5 min m/z = 596.42 [M + H]$^+$ | 57 mg, cream solid |

-continued

| Example No. | Structure & Conditions | Analytical Data | Mass, % yield, state |
|---|---|---|---|
| M00972 | 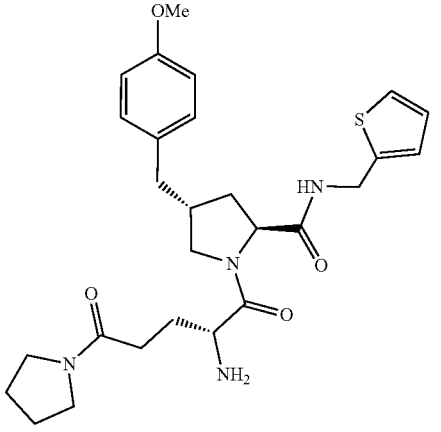 [SMILES: COc1ccc(C[C@@H]2C[C@@H](C(=O)NCc3cccs3)N(C(=O)[C@H](N)CCC(=O)N3CCCC3)C2)cc1]<br>RgA: (thiophen-2-yl)methanamine<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3 GM1 with HCTU and Et₃N<br>Step 2 & 4 GM2B | Thermo_MeOH_UHPLC_1.2 min<br>LCMS: $R_t$ = 0.5 min m/z = 513.39 [M + H]⁺ | 25 mg, yellow solid |
| M00973 | 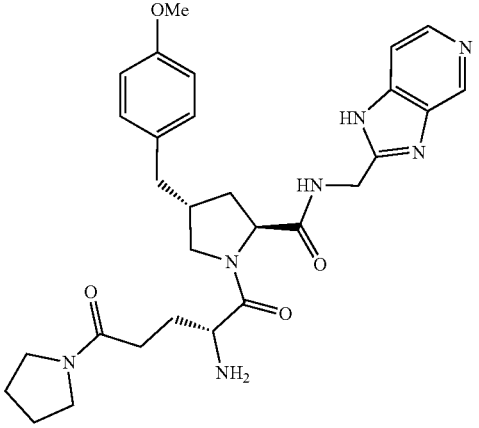 [SMILES: COc1ccc(C[C@@H]2C[C@@H](C(=O)NCc3nc4cnccc4[nH]3)N(C(=O)[C@H](N)CCC(=O)N3CCCC3)C2)cc1]<br>RgA: {1H-imidazo[4,5-c]pyridin-2-yl}methanamine<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3 GM1 with HCTU and Et₃N<br>Step 2 & 4 GM2B | Thermo_MeOH_UHPLC_1.2 min<br>LCMS: $R_t$ = 0.4 min m/z = 548.21 [M + H]⁺ | 32 mg, yellow gummy solid |
| M05102 | 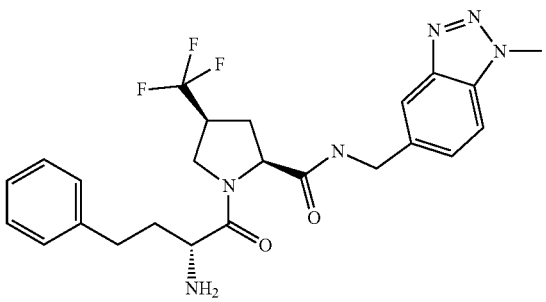<br>RgA: C-(1-Methyl-1H-benzotriazol-5-yl)-methylamine<br>RgB: (2S,4S)-1-boc-4- | ANALPH2_MEOH_QC_v 1, Rt: 5.23 min, m/z 489.3 [M + H]+<br>ANALPH9_MEOH_QC_v 1, Rt: 7.17 min, m/z 489.3 [M + H]+ | 15 mg, white solid |

| Example No. | Structure & Conditions | Analytical Data | Mass, % yield, state |
|---|---|---|---|
| | trifluoromethylpyrrolidine-2-carboxylic acid<br>RgD: Boc-D-homophenylalanine<br>Step 1 & 3: GM1 with HATU & Et₃N in DMF;<br>Step 2 & 4: GM2B | | |
| M05125 | 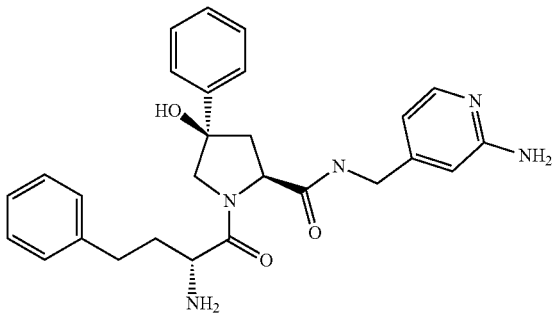<br>RgA: 4-aminomethylpyridin-2-ylamine<br>RgB: (2S,4R)-4-Hydroxy-4-phenyl-pyrrolidine-1,2-dicarboxylic acid 1-tert-butyl ester<br>RgD: Fmoc-D-homophenylalanine<br>Step 1: GM1 with HBTU & DIPEA; Step 2: GM2B, Step 3: GM1 with HBTU & DIPEA; Step 4: GM5 | ANALPH2_MEOH_QC_v 1, Rt: 3.64 min, m/z 474.2 [M + H]+<br>ANALPH9_MEOH_QC_v 1, Rt: 7.12 min, m/z 474.3 [M + H]+ | 15.1 mg, white solid |
| M05126 | 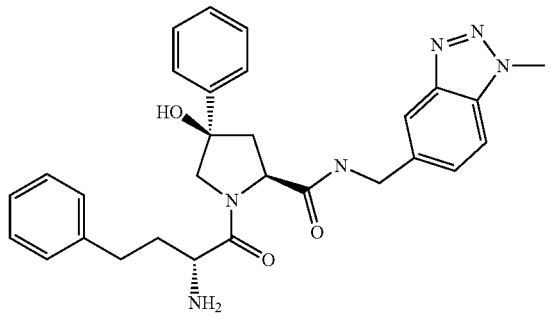<br>RgA: C-(1-Methyl-1H-benzotriazol-5-yl)-methylamine<br>RgB: (2S,4R)-4-Hydroxy-4-phenyl-pyrrolidine-1,2-dicarboxylic acid 1-tert-butyl ester<br>RgD: Fmoc-D-homophenylalanine<br>Step 1: GM1 with HBTU & DIPEA; Step 2: GM2B, Step 3: GM1 with HBTU & DIPEA; Step 4: GM5 | ANALPH2_MEOH_QC_v 1, Rt: 5.31 min, m/z 513.4 [M + H]+<br>ANALPH9_MEOH_QC_v 1, Rt: 7.22 min, m/z 513.4 [M + H]+ | 9.1 mg, white solid |
| M05128 | 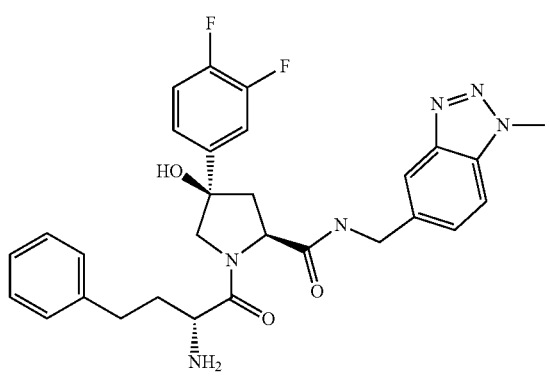<br>RgA: C-(1-Methyl-1H-benzotriazol-5-yl)-methylamine<br>RgB: (2S,4R)-4-(3,4-Difluoro-phenyl)-4-hydroxy-pyrrolidine-1,2-dicarboxylic acid 1- | ANALPH9_MEOH_QC_v 1, Rt: 7.44 min, m/z 549.3 [M + H]+<br>ANALPH2_MEOH_QC_v 1, Rt: 5.59 min, m/z 549.3 [M + H]+ | 25 mg, white solid |

| Example No. | Structure & Conditions | Analytical Data | Mass, % yield, state |
|---|---|---|---|
| | tert-butyl ester<br>RgD: boc-D-homophenylalanine<br>Step 1 & 3: GM1 with HBTU & DIPEA;<br>Step 2 & 4: GM2A | | |
| M05139 | 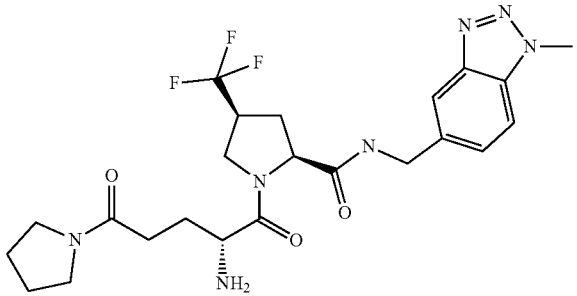<br>RgA: C-(1-Methyl-1H-benzotriazol-5-yl)-methylamine<br>RgB: (2S,4S)-1-boc-4-trifluoromethylpyrrolidine-2-carboxylic acid<br>RgD: (R)-2-tert-Butoxycarbonylamino-5-oxo-5-pyrrolidin-1-yl-pentanoic acid<br>Step 1: GM1 with HBTU & DIPEA in DCM;<br>Step 3: GM1 with HBTU & DIPEA in DCM;<br>Step 2 & 4: GM2B | ANALPH9_MEOH_QC_v 1, Rt: 6.24 min, m/z 510.3 [M + H]+<br>ANALPH2_MEOH_QC_v 1, Rt: 4.46 min, m/z 510.3 [M + H]+<br>$^1$H NMR (400 MHz, CDCl$_3$) δ 7.92 (d, J = 1.8 Hz, 1H), 7.49 (d, J = 12.5 Hz, 3H), 4.93-4.54 (m, 2H), 4.47 (s, 1H), 4.30 (s, 3H), 3.74 (dd, J = 9.4, 3.5 Hz, 1H), 3.60 (t, J = 10.4 Hz, 1H), 3.51-3.20 (m, 5H), 3.14-2.96 (m, 1H), 2.74-2.55 (m, 2H), 2.52-2.32 (m, 2H), 2.03-1.92 (m, 2H), 1.91-1.79 (m, 2H), 1.73-1.58 (m, 1H). | 62 mg, white solid |
| M05155 | 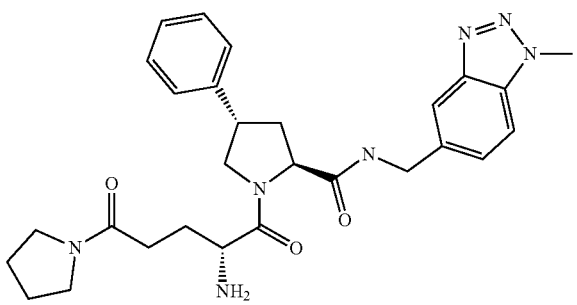<br>RgA: C-(1-Methyl-1H-benzotriazol-5-yl)-methylamine<br>RgB: (2S,4S)-1-boc-4-phenylpyrrolidine-2-carboxylic acid<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2B | ANALPH2_MEOH_QC_v 1, Rt: 5.12 min, m/z 518.3 [M + H]+<br>ANALPH9_MEOH_QC_v 1, Rt: 6.82 min, m/z 518.3 [M + H]+ | 21.2 mg, white solid |
| M05157 | 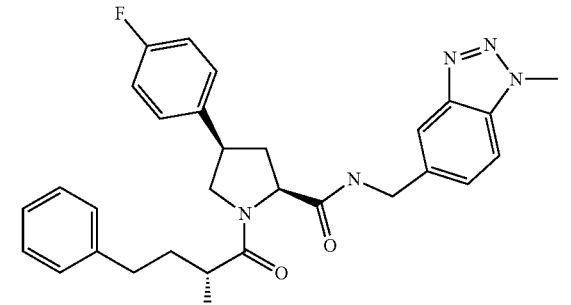 | ANALPH9_MEOH_QC_v 1, Rt: 7.54 min, m/z 515.3 [M + H]+<br>ANALPH2_MEOH_QC_v 1, Rt: 5.66 min, m/z 515.3 [M + H]+ | 11 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: (2S,4R)-4-(4-Fluoro-phenyl)-pyrrolidine-1,2-dicarboxylic acid 1-tert-butyl ester<br>RgD: boc-D-homophenylalanine<br>Step 1 & 3: GM1 with HBTU & DIPEA<br>Step 2 & 4: GM2A | | |
| M05163 | | ANALPH2_MEOH_QC_v 1, Rt: 5.25 min, m/z 497.2 [M + H]+<br>ANALPH9_MEOH_QC_v 1, Rt: 6.92 min, m/z 497.2 [M + H]+ | 78.5 mg, white solid |
| | RgA: C-(1-Methyl-1H-benzotriazol-5-yl)-methylamine<br>RgB: (2S,4R)-boc-4-phenylpyrrolidine-4-carboxylic acid<br>RgD: boc-D-homophenylalanine<br>Step 1 & 3: GM1 with HBTU & DIPEA in DMF; Step 2 & 4 GM2A | | |
| M05174 | | ANALPH9_MEOH_QC_v 1, Rt: 8.22 min, m/z 589.3 [M + H]+<br>ANALPH2_MEOH_QC_v 1, Rt: 6.37 min, m/z 589.3 [M + H]+ | 58 mg, white solid |
| | RgA: C-(1-Methyl-1H-benzotriazol-5-yl)-methylamine<br>RgB: (2S,4R)-4-(2-Phenoxy-phenyl)-pyrrolidine-1,2-dicarboxylic acid 1-tert-butyl ester<br>RgD: boc-D-homophenylalanine<br>Step 1 & 3: GM1 with HBTU & DIPEA<br>Step 2 & 4: GM2A | | |
| M05188 | | ANALPH9_MEOH_QC_v 1, Rt: 7.76 min, m/z 496.3 [M + H]+<br>ANALPH2_MEOH_QC_v 1, Rt: 5.86 min, m/z 496.3 [M + H]+ | 7 mg, white solid |

| Example No. | Structure & Conditions | Analytical Data | Mass, % yield, state |
|---|---|---|---|
| | RgA: 5-(aminomethyl)-1-methyl-1H indazole<br>RgB: (2S,4S)-1-boc-4-phenylpyrrolidine-2-carboxylic acid<br>RgD: boc-D-homophenyl alanine<br>Step 1 & 3: GM1 with HBTU & DIPEA in DCM; Step 2 & 4: GM2B | | |
| M05189 | 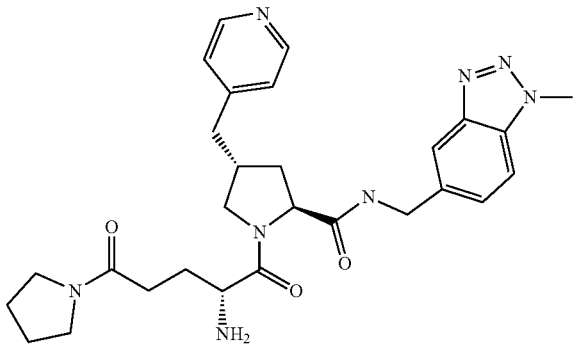<br>RgA: C-(1-Methyl-1H-benzotriazol-5-yl)-methylamine<br>RgB: boc-(R)-γ-(4-pyridylmethyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2B | ANALPH9_MEOH_QC_v 1, Rt: 6.10 min, m/z 533.4 [M + H]+<br>ANALPH2_MEOH_QC_v 1, Rt: 3.04 min, m/z 533.3 [M + H]+<br>$^1$H NMR (400 MHz, CDCl$_3$) δ 8.56-8.48 (m, 2H), 7.93-7.87 (m, 2H), 7.44 (dd, J = 2.3, 1.2 Hz, 2H), 7.22-7.16 (m, 1H), 7.13-7.04 (m, 1H), 4.67 (dd, J = 8.3, 1.5 Hz, 1H), 4.60-4.43 (m, 2H), 4.33-4.25 (m, 3H), 3.80 (dd, J = 10.1, 7.4 Hz, 1H), 3.72 (dd, J = 9.5, 3.1 Hz, 1H), 3.57-3.20 (m, 5H), 2.77 (d, J = 7.4 Hz, 2H), 2.72-2.57 (m, 1H), 2.54-2.34 (m, 2H), 2.01-1.94 (m, 2H), 1.93-1.82 (m, 2H), 1.75-1.63 (m, 2H). | 24 mg, white solid |
| M05190 | 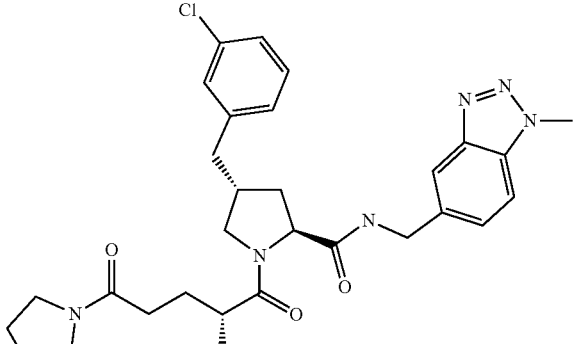<br>RgA: C-(1-Methyl-1H-benzotriazol-5-yl)-methylamine<br>RgB: boc-(R)-γ-(3-chlorobenzyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2B | ANALPH2_MEOH_QC_v 1, Rt: 5.60 min, m/z 566.4 [M + H]+<br>ANALPH9_MEOH_QC_v 1, Rt: 7.33 min, m/z 566.4 [M + H]+ | 86 mg, white solid |

| Example No. | Structure & Conditions | Analytical Data | Mass, % yield, state |
|---|---|---|---|
| M05218 | 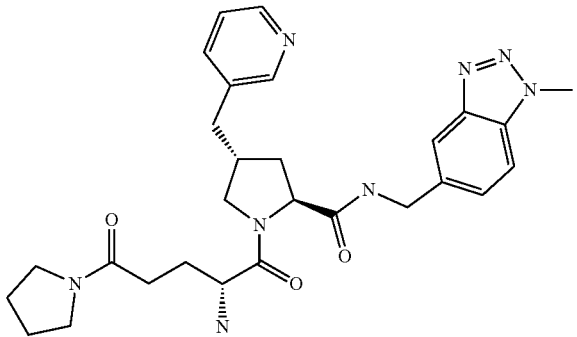<br>RgA: C-(1-Methyl-1H-benzotriazol-5-yl)-methylamine<br>RgB: boc-(R)-γ-(3-pyridylmethyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4: GM2A | ANALPH9_MEOH_QC_v 1, Rt: 6.15 min, m/z 533.5 [M + H]+<br>ANALPH2_MEOH_QC_v 1, Rt: 3.31 min, m/z 533.4 [M + H]+ | 23 mg, white solid |
| M05219 | 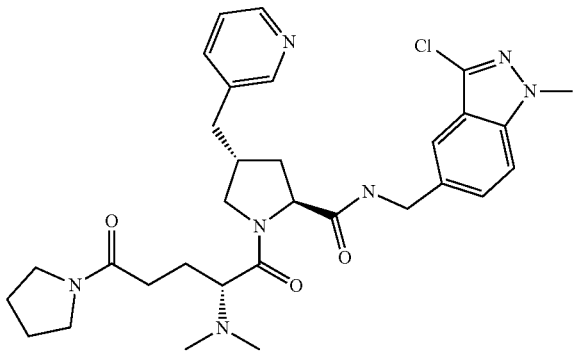<br>RgA: C-(3-chloro-1-methyl-1H-indazol-5-yl)-methylamine. HCl<br>RgB: boc-(R)-γ-(3-pyridylmethyl)-L-proline<br>RgD: (R)-2-Dimethylamino-5-oxo-5-pyrrolidin-1-yl-pentanoic acid<br>Step 1 & 3: GM1 with HATU & DIPEA in DMF; Step 2 GM2A; step 4 omitted | ANALPH2_MEOH_QC_v 1, Rt: 4.08 min, m/z 594.4 [M + H]+<br>ANALPH9_MEOH_QC_v 1, Rt: 7.24 min, m/z 594.4 [M + H]+ | 52 mg, white solid |
| M05220 | 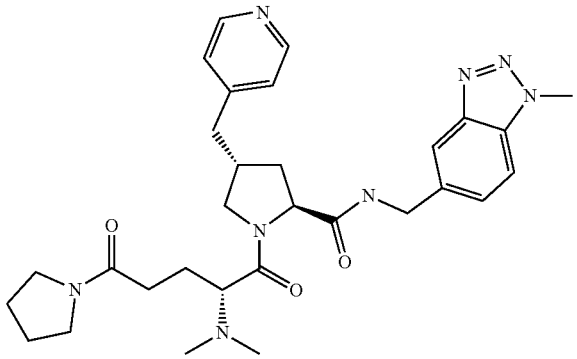<br>RgA: C-(1-Methyl-1H-benzotriazol-5-yl)-methylamine<br>RgB: boc-(R)-γ-(4-pyridylmethyl)-L-proline<br>RgD: (R)-2-Dimethylamino-5-oxo-5-pyrrolidin-1-yl-pentanoic acid<br>Step 1 & 3: GM1 with HBTU & DIPEA in DCM; Step 2: GM2B; step 4 omitted | ANALPH2_MEOH_QC_v 1, Rt: 3.09 min, m/z 561.4 [M + H]+<br>ANALPH9_MEOH_QC_v 1, Rt: 6.45 min, m/z 561.4 [M + H]+ | 29.8 mg, white solid |

| Example No. | Structure & Conditions | Analytical Data | Mass, % yield, state |
|---|---|---|---|
| M05222 | 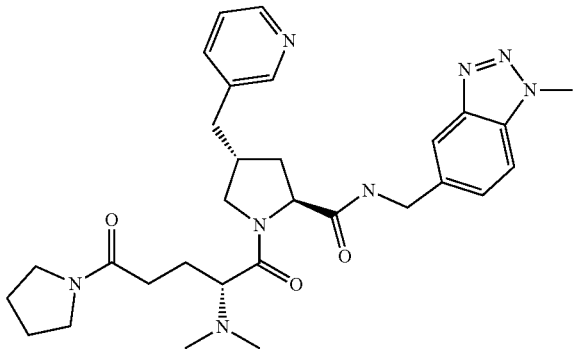<br>RgA: C-(1-Methyl-1H-benzotriazol-5-yl)-methylamine<br>RgB: boc-(R)-γ-(3-pyridylmethyl)-L-proline<br>RgD: (R)-2-Dimethylamino-5-oxo-5-pyrrolidin-1-yl-pentanoic acid<br>Step 1 & 3: GM1 with HATU & DIPEA in DMF; Step 2 GM2A; step 4 omitted | ANALPH9_MEOH_QC_v 1, Rt: 6.51 min, m/z 561.5 [M + H]+<br>ANALPH2_MEOH_QC_v 1, Rt: 3.32 min, m/z 561.5 [M + H]+ | 11 mg, white solid |
| M05223 | 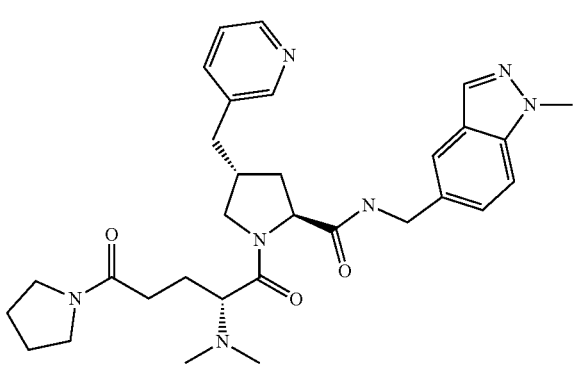<br>RgA: 5-(aminomethyl)-1-methyl-1H-indazole<br>RgB: boc-(R)-γ-(3-pyridylmethyl)-L-proline<br>RgD: (R)-2-Dimethylamino-5-oxo-5-pyrrolidin-1-yl-pentanoic acid<br>Step 1 & 3: GM1 with HATU & DIPEA in DMF; Step 2 GM2A; step 4 omitted | ANALPH2_MEOH_QC_v 1, Rt: 3.61 min, m/z 560.6 [M + H]+<br>ANALPH9_MEOH_QC_v 1, Rt: 6.81 min, m/z 560.5 [M + H]+ | 8 mg, white solid |
| M05224 | 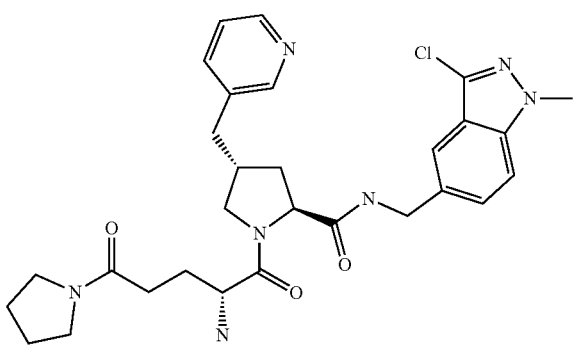<br>RgA: C-(3-chloro-1-methyl-1H-indazol-5-yl)-methylamine hydrochloride<br>RgB: boc-(R)-γ-(3-pyridylmethyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4 GM2A | ANALPH2_MEOH_QC_v 1, Rt: 4.17 min, m/z 566.5 [M + H]+<br>ANALPH9_MEOH_QC_v 1, Rt: 6.93 min, m/z 566.5 [M + H]+ | 50 mg, white solid |

| Example No. | Structure & Conditions | Analytical Data | Mass, % yield, state |
|---|---|---|---|
| M05228 | 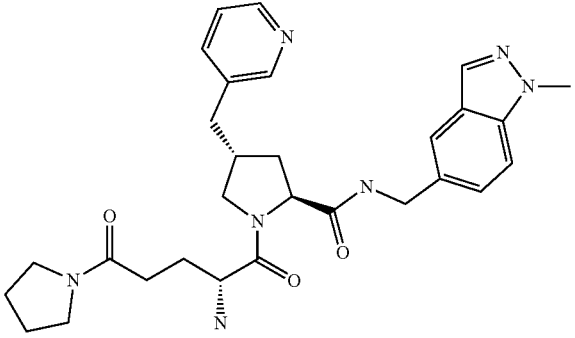<br>RgA: 5-(aminomethyl)-1-methyl-1H-indazole<br>RgB: boc-(R)-γ-(3-pyridylmethyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 GM2A | ANALPH2_MEOH_QC_v 1, Rt: 3.58 min, m/z 532.5 [M + H]+<br>ANALPH9_MEOH_QC_v 1, Rt: 6.46 min, m/z 532.5 [M + H]+ | 11 mg, white solid |
| M05232 | 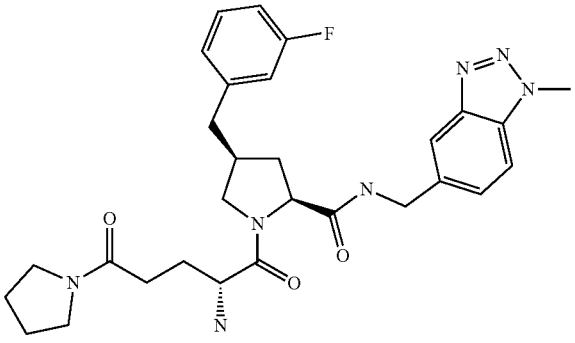<br>RgA: C-(1-Methyl-1H-benzotriazol-5-yl)-methylamine<br>RgB: (2S,4S)-4-(3-Fluoro-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 GM2B | ANALPH9_MEOH_QC_v 1, Rt: 7.02 min, m/z 550.5 [M + H]+<br>ANALPH2_MEOH_QC_v 1, Rt: 5.28 min, m/z 550.5 [M + H]+ | 14.8 mg, white solid |
| M05235 | 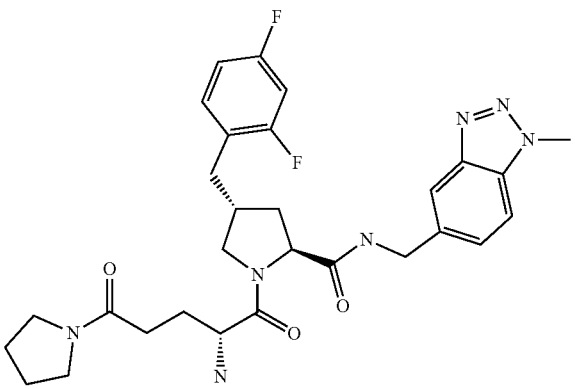<br>RgA: C-(1-Methyl-1H-benzotriazol-5-yl)-methylamine<br>RgB: (S)-4-(2,4-Difluoro-benzyl)-pyrrolidine-1,2-dicarboxylic acid 1-tert-butyl ester | ANALPH9_MEOH_QC_v 1, Rt: 7.12 min, m/z 568.5 [M + H]+<br>ANALPH2_MEOH_QC_v 1, Rt: 5.47 min, m/z 568.4 [M + H]+ | 41 mg, white solid |

| Example No. | Structure & Conditions | Analytical Data | Mass, % yield, state |
|---|---|---|---|
| | RgD: (R)-2-tert-Butoxycarbonylamino-5-oxo-5-pyrrolidin-1-yl-pentanoic acid<br>Step 1 & 3: GM1 with HATU & DIPEA in DCM; Step 2 GM2A | | |
| M05241 | 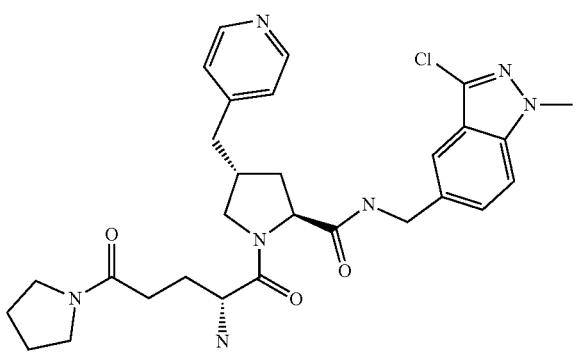<br>RgA: C-(3-chloromethyl-1H-indazol-5-yl)-methylamine hydrochloride<br>RgB: boc-(R)-γ-(4-pyridylmethyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | ANALPH2_MEOH_QC_v 1, Rt: 3.72 min, m/z 566.4 [M + H]+<br>ANALPH9_MEOH_QC_v 1, Rt: 6.75 min, m/z 566.4 [M + H]+ | 65 mg, off-white solid |
| M05243 | 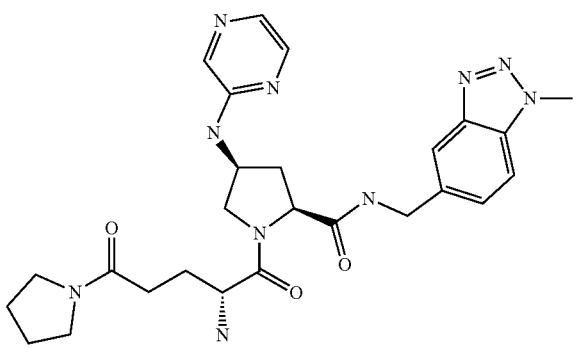<br>RgA: C-(1-Methyl-1H-benzotriazol-5-yl)-methylamine<br>RgB: (2S,4S)-4-(Pyrazin-2-ylamino)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 4.12 min, m/z 535.5 [M + H]+<br>ANALPH9_MEOH_QC_v 1, Rt: 5.75 min, m/z 535.5 [M + H]+ | 6.4 mg, off-white solid |
| M05244 | 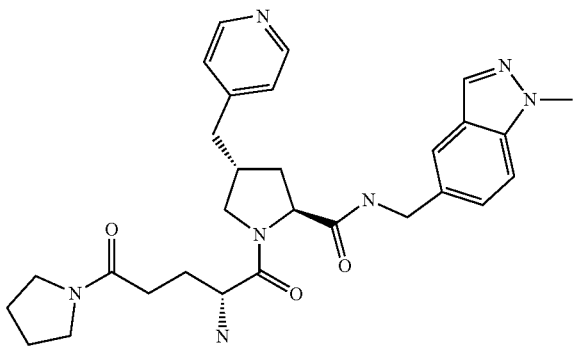 | ANALPH9_MEOH_QC_v 1, Rt: 6.30 min, m/z 532.5 [M + H]+<br>ANALPH2_MEOH_QC_v 1, Rt: 3.20 min, m/z 532.4 [M + H]+ | 24 mg, white solid |

| Example No. | Structure & Conditions | Analytical Data | Mass, % yield, state |
|---|---|---|---|
| | RgA: 5-(aminomethyl)-1-methyl-1H-indazole<br>RgB: boc-(R)-γ-(4-pyridylmethyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4 GM2A | | |
| M05265 | 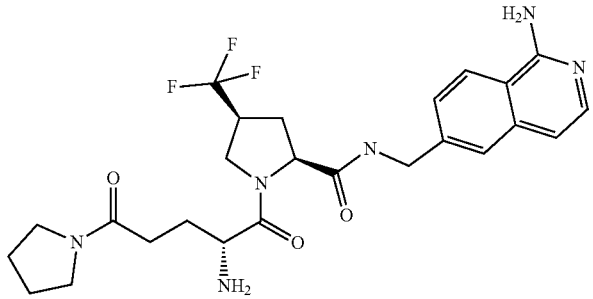<br>RgA: 6-Aminomethyl-isoquinolin-1-ylamine<br>RgB: (2S,4S)-1-(tertbutoxycarbonyl)-4-trifluoromethyl)pyrrolidine-2-carboxylic acid<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 3.21 min, m/z 521.3 [M + H]+<br>ANALPH9_MEOH_QC_v 1, Rt: 6.50 min, m/z 521.3 [M + H]+ | 0.6 mg, white solid |
| M05266 | 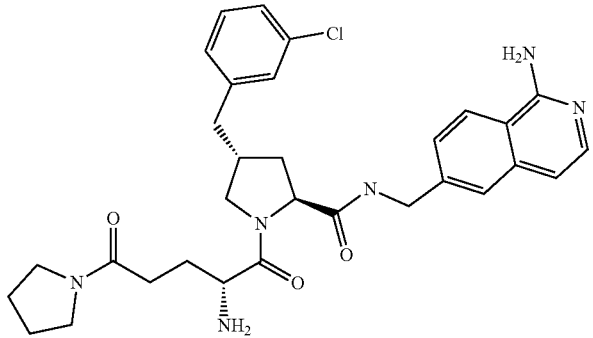<br>RgA: 6-Aminomethyl-isoquinolin-1-ylamine<br>RgB: boc-(R)-γ-(4-chlorobenzyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 4.35 min, m/z 577.3 [M + H]+<br>ANALPH9_MEOH_QC_v 1, Rt: 7.49 min, m/z 577.3 [M + H]+ | White solid |
| M05272 | 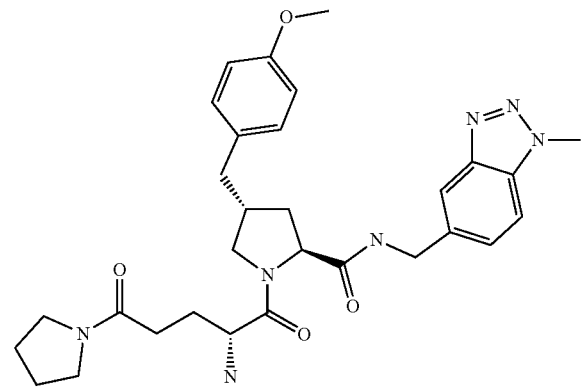 | ANALPH9_MEOH_QC_v 1, Rt: 7.03 min, m/z 562.5 [M + H]+<br>ANALPH2_MEOH_QC_v 1, Rt: 5.56 min, m/z 562.5 [M + H]+<br>1H NMR (400 MHz, CDCl3) δ 7.87 (d, J = 7.2 Hz, 1H), 7.74 (s, 1H), 7.41 (s, 2H), 7.13-7.00 (m, 2H), 6.85-6.76 (m, 2H), 4.69-4.57 (m, 1H), 4.61-4.47 (m, 2H), 4.29-4.22 (m, 3H), 3.77 (s, 3H), 3.75-3.65 (m, 1H), 3.50-3.32 (m, 4H), 3.33-3.19 (m, 1H), 2.74 (s, 1H), 2.66 (d, J = 7.4 Hz, 2H), 2.63-2.48 (m, 1H), 2.46-2.32 (m, 2H), 2.06- | 21 mg, white solid |

| Example No. | Structure & Conditions | Analytical Data | Mass, % yield, state |
|---|---|---|---|
| | | 1.89 (m, 3H), 1.90-1.79 (m, 2H), 1.67 (ddd, J = 12.5, 10.4, 8.2 Hz, 1H). | |
| | RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4 GM2A | | |
| M05274 | 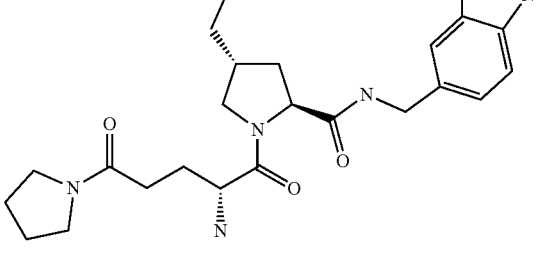 | ANALPH9_MEOH_QC_v 1, Rt: 7.05 min, m/z 568.4 [M + H]+<br>ANALPH2_MEOH_QC_v 1, Rt: 5.36 min, m/z 568.4 [M + H]+ | 19 mg, off-white solid |
| | RgA: C-(1-Methyl-1H-benzotriazol-5-yl)-methylamine<br>RgB: S)-4-(3,5-Difluoro-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4 GM2A | | |
| M05278 | 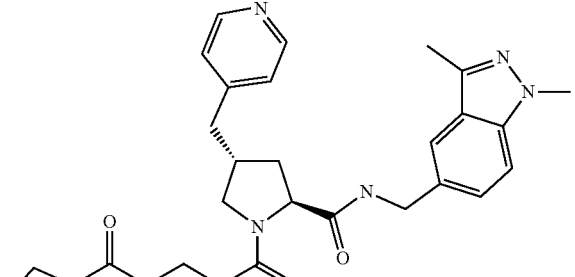 | ANALPH9_MEOH_QC_v 1, Rt: 6.46 min, m/z 546.4 [M + H]+<br>ANALPH2_MEOH_QC_v 1, Rt: 3.54 min, m/z 546.4 [M + H]+ | 47 mg, white solid |
| | RgA: C-(1,3-Dimethyl-1H-indazol-5-yl)-methylamine hydrochloride<br>RgB: boc-(R)-γ-(4-pyridylmethyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4 GM2A | | |

| Example No. | Structure & Conditions | Analytical Data | Mass, % yield, state |
|---|---|---|---|
| M05280 | 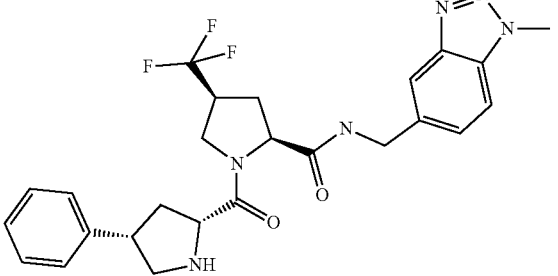<br>RgA: C-(1-Methyl-1H-benzotriazol-5-yl)-methylamine<br>RgB: (2S,4S)-1-boc-4-trifluoromethylpyrrolidine-2-carboxylic acid<br>RgD: (2R, 4S)-boc-4-phenylpyrrolidine-2-carboxylic acid<br>Step 1 & 3: GM1 with HATU & DIPEA in DMF; Step 2 & 4 GM2A | ANALPH9_MEOH_QC_v 1, Rt: 6.89 min, m/z 501.3 [M + H]+<br>ANALPH2_MEOH_QC_v 1, Rt: 4.90 min, m/z 501.3 [M + H]+ | 21 mg, white solid |
| M05281 | 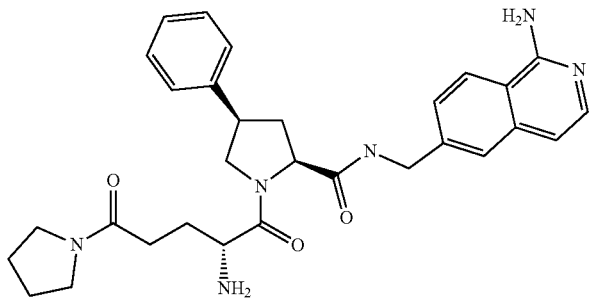<br>RgA: 6-Aminomethyl-isoquinolin-1-ylamine<br>RgB: (2S,4R)-boc-4-phenylpyrrolidine-2-carboxylic acid<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH9_MEOH_QC_v 1, Rt: 6.92 min, m/z 529.4 [M + H]+<br>ANALPH2_MEOH_QC_v 1, Rt: 3.82 min, m/z 529.4 [M + H]+ | 27 mg, white solid |
| M05282 | 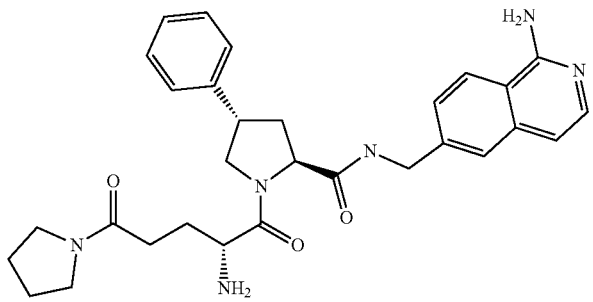<br>RgA: 6-Aminomethyl-isoquinolin-1-ylamine<br>RgB: (2S,4S)-boc-4-phenylpyrrolidine-2-carboxylic acid<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 3.87 min, m/z 529.4 [M + H]+<br>ANALPH9_MEOH_QC_v 1, Rt: 6.91 min, m/z 529.3 [M + H]+ | 48 mg, white solid |

| Example No. | Structure & Conditions | Analytical Data | Mass, % yield, state |
|---|---|---|---|
| M05288 | 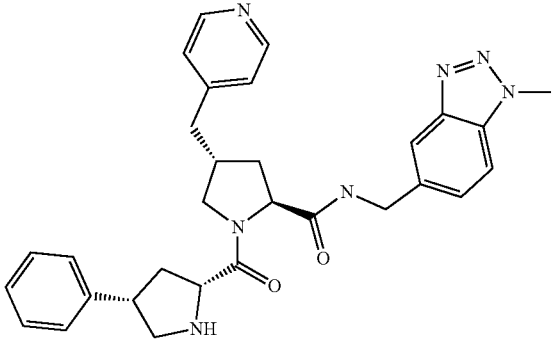<br><br>RgA: C-(1-Methyl-1H-benzotriazol-5-yl)-methylamine<br>RgB: boc-(R)-γ-(4-pyridylmethyl)-L-proline<br>RgD: (2R,4S)-boc-4-phenylpyrrolidine-2-carboxylic acid<br>Step 1 & 3: GM1 with HATU & DIPEA in DMF; Step 2 & 4 GM2A | ANALPH9_MEOH_QC_v1, Rt: 6.69 min, m/z 524.2 [M + H]+<br>ANALPH2_MEOH_QC_v1, Rt: 3.41 min, m/z 524.2 [M + H]+ | 35 mg, white solid |
| M05289 | 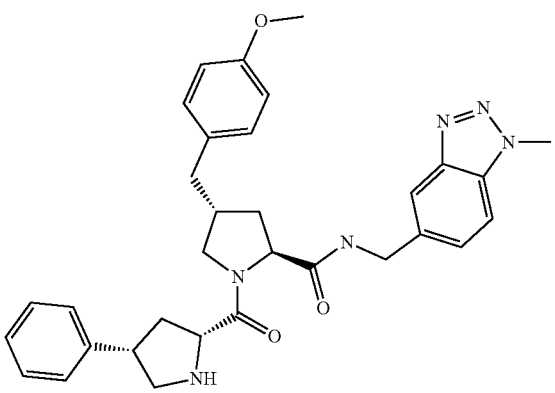<br><br>RgA: C-(1-Methyl-1H-benzotriazol-5-yl)-methylamine<br>RgB: boc-(R)-γ-(4-methoxybenzyl)-L-proline<br>RgD: (2R,4S)-boc-4-phenylpyrrolidine-2-carboxylic acid<br>Step 1 & 3: GM1 with HBTU & DIPEA in DMF; Step 2 & 4 GM2A | ANALPH9_MEOH_QC_v1, Rt: 7.81 min, m/z 553.2 [M + H]+<br>ANALPH2_MEOH_QC_v1, Rt: 5.62 min, m/z 553.3 [M + H]+<br>1H-NMR (400 MHz, DMSO-D6) δ 8.67 (t, J = 6.2 Hz, 0.3H), 8.41 (t, J = 6.0 Hz, 0.7H), 7.80 (s, 1H), 7.71 (d, J = 9.2 Hz, 0.7H), 7.63 (d, J = 7.8 Hz, 0.3H), 7.39-7.36 (m, 1H), 7.29-7.11 (m, 4.5H), 7.10-7.03 (m, 2.5H), 6.94-6.71 (m, 2H), 4.74-4.57 (m, 0.3H), 4.44-4.31 (m, 2.7H), 4.26 (d, J = 15.1 Hz, 2H), 4.19 (s, 1H), 3.96 (t, J = 8.0 Hz, 1H), 3.76 (dd, J = 9.4, 6.6 Hz, 1H), 3.72-3.61 (m, 3H), 3.20-3.01 (m, 2H), 2.88 (dt, J = 29.3, 9.4 Hz, 1H), 2.69-2.49 (m, 2H), 1.92 (t, J = 7.6 Hz, 0.5H), 1.87-1.75 (m, 1.5H), 1.75-1.57 (m, 1H) | 65 mg, white solid |

-continued

| Example No. | Structure & Conditions | Analytical Data | Mass, % yield, state |
|---|---|---|---|
| M05291 | 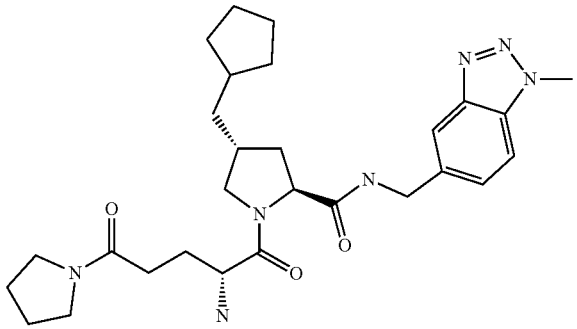<br>RgA: C-(1-Methyl-1H-benzotriazol-5-yl)-methylamine<br>RgB: (2S,4R)-4-Cyclopentylmethyl-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4 GM2A | ANALPH9_MEOH_QC_v 1, Rt: 7.38 min, m/z 524.4 [M + H]+<br>ANALPH2_MEOH_QC_v 1, Rt: 5.63 min, m/z 524.4 [M + H]+ | 30 mg, white solid |
| M05293 | 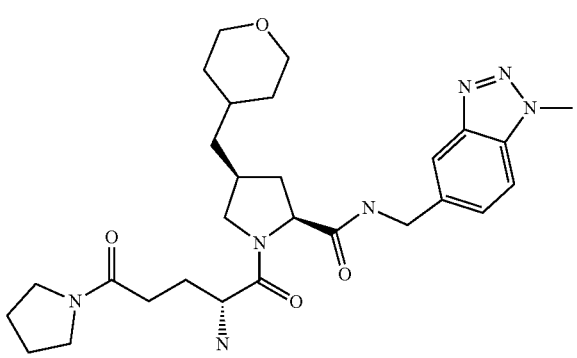<br>RgA: C-(1-Methyl-1H-benzotriazol-5-yl)-methylamine<br>RgB: (2S,4S)-4-(Tetrahydro-pyran-4-ylmethyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 4.59 min, m/z 540.4 [M + H]+<br>ANALPH9_MEOH_QC_v 1, Rt: 6.12 min, m/z 540.4 [M + H]+ | 5 mg, Yellow solid |
| M05294 | 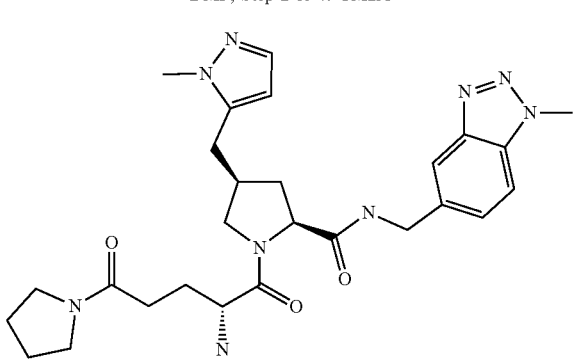<br>RgA: C-(1-Methyl-1H-benzotriazol-5-yl)-methylamine<br>RgB: (2S,4R)-4-(2-Methyl-2H-pyrazol-3-ylmethyl)-pyrrolidine-1,2-dicarboxylic acid 1-tert-butyl ester | ANALPH9_MEOH_QC_v 1, Rt: 5.69 min, m/z 536.3 [M + H]+<br>ANALPH2_MEOH_QC_v 1, Rt: 4.24 min, m/z 536.3 [M + H]+ | 9 mg, white solid |

| Example No. | Structure & Conditions | Analytical Data | Mass, % yield, state |
|---|---|---|---|
| | RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | | |
| M05296 | 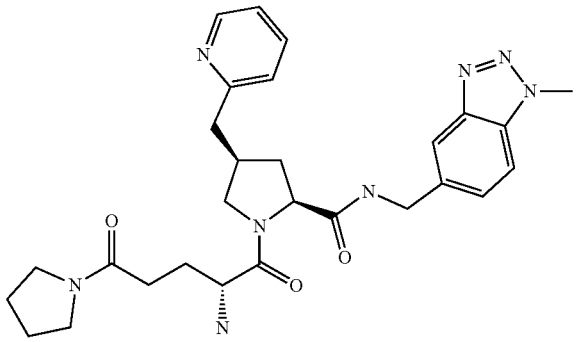<br>RgA: C-(1-Methyl-1H-benzotriazol-5-yl)-methylamine<br>RgB: (2S,4R)-4-Pyridin-2-ylmethyl-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | ANALPH2_MEOH_QC_v 1, Rt: 3.70 min, m/z 533.4 [M + H]+<br>ANALPH9_MEOH_QC_v 1, Rt: 6.09 min, m/z 533.4 [M + H]+ | 45 mg, white solid |
| M05302 | 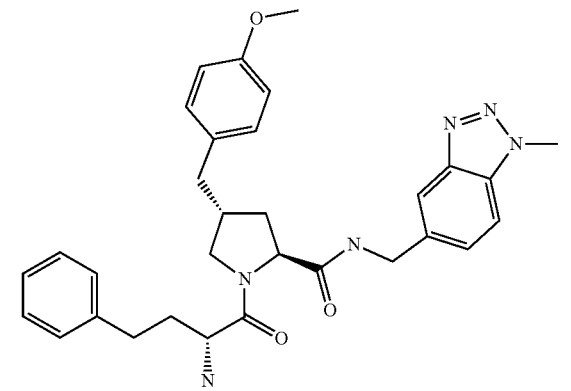<br>RgA: C-(1-Methyl-1H-benzotriazol-5-yl)-methylamine<br>RgB: boc-(R)-γ-(4-methoxybenzyl)-L-proline<br>RgD: boc-homophenylalanine<br>Step 1 & 3: GM1 with HATU & DIPEA in DMF; Step 2 & 4: GM2A | ANALPH9_MEOH_QC_v 1, Rt: 7.85 min, m/z 541.3 [M + H]+<br>ANALPH2_MEOH_QC_v 1, Rt: 6.17 min, m/z 541.3 [M + H]+ | 23 mg, white solid |
| M05303 | 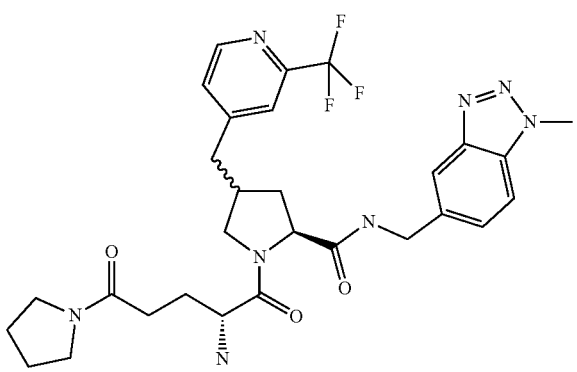 | ANALPH9_MEOH_QC_v 1, Rt: 6.72 min, m/z 601.3 [M + H]+<br>ANALPH2_MEOH_QC_v 1, Rt: 5.28 & 5.42 min, m/z 601.3 [M + H]+ | 11 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: (S)-4-(2-Trifluoromethyl-pyridin-4-ylmethyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HATU & Et₃N in DMF;<br>Step 2 & 4: GM2A | | |
| M05308 | 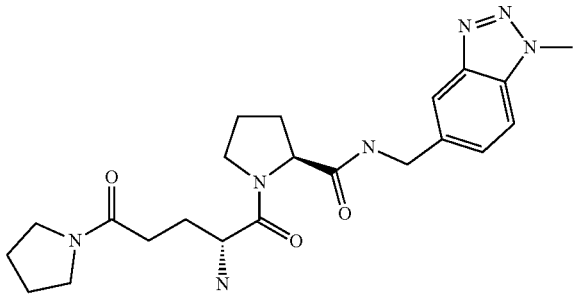<br>RgA: C-(1-Methyl-1H-benzotriazol-5-yl)-methylamine<br>RgB: boc-L-Proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4: GM2A | ANALPH9_MEOH_QC_v 1, Rt: 5.47 min, m/z 442.2 [M + H]+<br>ANALPH2_MEOH_QC_v 1, Rt: 4.04 min, m/z 442.2 [M + H]+ | 85 mg, white solid |
| M05317 | 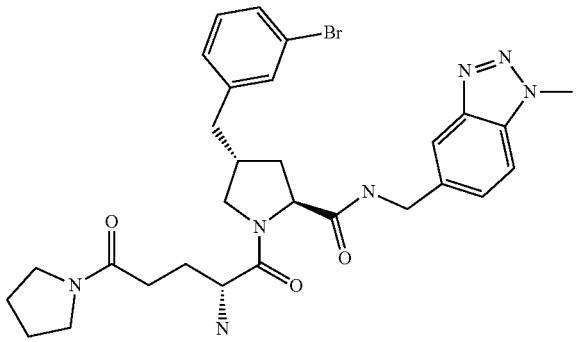<br>RgA: C-(1-Methyl-1H-benzotriazol-5-yl)-methylamine<br>RgB: (2S,4R)-4-(3-Bromo-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | ANALPH2_MEOH_QC_v 1, Rt: 5.87 min, m/z 610.1 [M + H]+<br>ANALPH9_MEOH_QC_v 1, Rt: 7.55 min, m/z 610.1 [M + H]+ | 50 mg, white solid |
| M05318 | 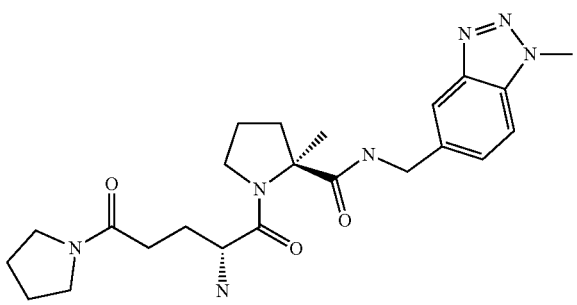<br>RgA: C-(1-Methyl-1H-benzotriazol-5-yl)-methylamine | ANALPH9_MEOH_QC_v 1, Rt: 5.73 min, m/z 456.2 [M + H]+<br>ANALPH2_MEOH_QC_v 1, Rt: 4.18 min, m/z 456.2 [M + H]+ | 75 mg, white solid |

| Example No. | Structure & Conditions | Analytical Data | Mass, % yield, state |
|---|---|---|---|
| | RgB: 1-boc-2-methyl-L-proline<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4: GM2A | | |
| M05319 | 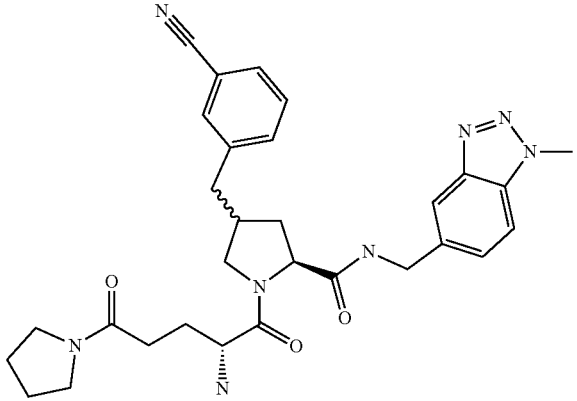<br>RgA: C-(1-Methyl-1H-benzotriazol-5-yl)-methylamine<br>RgB: (S)-4-(3-Cyano-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4: GM2A | ANALPH9_MEOH_QC_v 1, Rt: 6.65 min, m/z 557.3 [M + H]+<br>ANALPH2_MEOH_QC_v 1, Rt: 5.14 min, m/z 557.2 [M + H]+<br>1H-NMR (400 MHz, CHLOROFORM-D) δ 7.91-7.80 (m, 1.4H), 7.57-7.35 (m, 5.6H), 4.73-4.51 (m, 2H), 4.33-4.21 (m, 3H), 3.84-3.61 (m, 1.5H), 3.63-3.17 (m, 4.5H), 3.33 (assumed 2H buried), 2.88-2.56 (m, 3H), 2.51-2.32 (m, 2H), 2.21-1.58 (m, 12H) | 20 mg, white solid |
| M05320 | 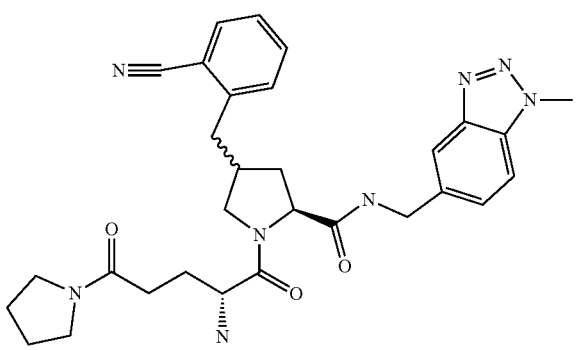<br>RgA: C-(1-Methyl-1H-benzotriazol-5-yl)-methylamine<br>RgB: (S)-4-(2-Cyano-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HATU & DIPEA in DMF; Step 2 & 4: GM2A | ANALPH2_MEOH_QC_v 1, Rt: 5.22 min, m/z 557.3 [M + H]+<br>ANALPH9_MEOH_QC_v 1, Rt: 6.69 min, m/z 557.3 [M + H]+ | 20 mg, white solid |

| Example No. | Structure & Conditions | Analytical Data | Mass, % yield, state |
|---|---|---|---|
| M05324 | 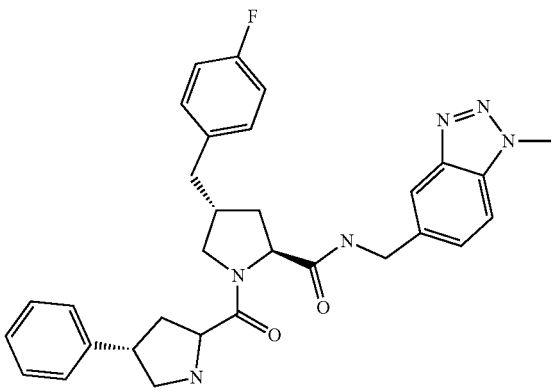<br><br>RgA: C-(1-Methyl-1H-benzotriazol-5-yl)-methylamine<br>RgB: Boc-(R)-γ-(4-fluorobenzyl)-L-proline<br>RgD: (2S,2R)-Boc-4-phenyl-pyrrolidine-2-carboxylic acid<br>Step 1 & 3: GM1 with HATU & DIPEA in DMF; Step 2 & 4: GM2A | ANALPH9_MEOH_QC_v 1, Rt: 7.87 min, m/z 541.1 [M + H]+<br>ANALPH2_MEOH_QC_v 1, Rt: 5.89 min, m/z 541.2 [M + H]+<br>1H NMR (400 MHz, DMSO-D6) δ 8.68 (t, J = 6.1 Hz, 0.3H), 8.39 (t, J = 6.0 Hz, 0.7H), 7.80 (d, J = 3.5 Hz, 1H), 7.71 (d, J = 8.6 Hz, 0.7H), 7.64 (d, J = 8.6 Hz, 0.3H), 7.37 (ddd, J = 8.7, 3.1, 1.5 Hz, 1H), 7.29-7.11 (m, 6H), 7.11-7.01 (m, 3H), 4.66 (s, 0.2H), 4.42-4.33 (m, 2.8H), 4.24 (s, 2H), 4.19 (s, 1H), 3.89 (t, J = 7.9 Hz, 0.7H), 3.76 (dd, J = 9.6, 7.1 Hz, 0.7H), 3.61 (t, J = 7.7 Hz, 0.3H), 3.49 (dd, J = 11.5, 7.6 Hz, 0.3H), 3.37-3.13 (m, 1H), 3.05 (ddd, J = 23.6, 9.8, 7.3 Hz, 2H), 2.85 (dt, J = 35.0, 9.1 Hz, 1H), 2.72-2.47 (m, 3H), 1.98-1.76 (m, 2H), 1.77-1.61 (m, 1H). | 28 mg, white solid |
| M05325 | 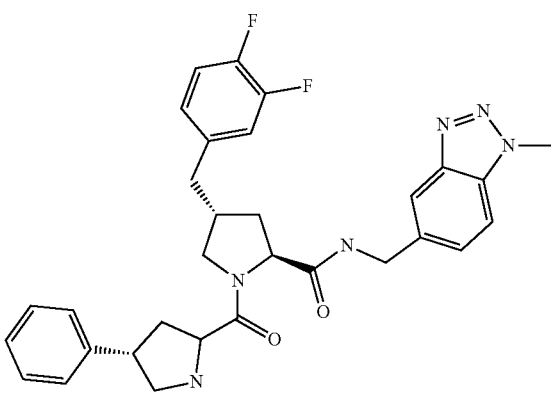<br><br>RgA: C-(1-Methyl-1H-benzotriazol-5-yl)-methylamine<br>RgB: Boc-(R)-γ-(3,4-difluorobenzyl)-L-proline<br>RgD: (2S,2R)-Boc-4-phenyl-pyrrolidine-2-carboxylic acid<br>Step 1 & 3: GM1 with HATU & DIPEA in DMF; Step 2 & 4: GM2A | ANALPH2_MEOH_QC_v 1, Rt: 5.97 min, m/z 559.2 [M + H]+<br>ANALPH9_MEOH_QC_v 1, Rt: 7.92 min, m/z 559.1 [M + H]+ | 20 mg, white solid |

| Example No. | Structure & Conditions | Analytical Data | Mass, % yield, state |
|---|---|---|---|
| M05326) | 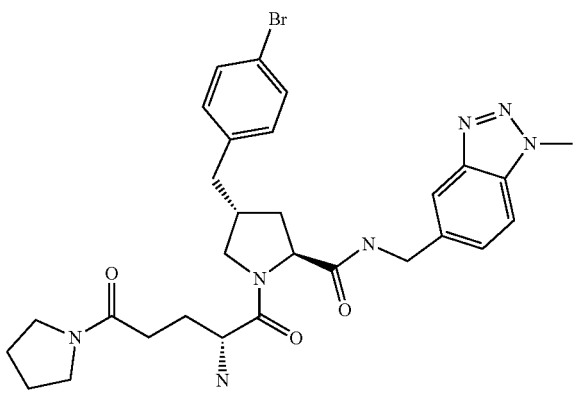<br>RgA: C-(1-Methyl-1H-benzotriazol-5-yl)-methylamine<br>RgB: (2S,4R)-4-(4-Bromo-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | ANALPH9_MEOH_QC_v 1, Rt: 7.62 min, m/z 612.2 [M + H]+<br>ANALPH2_MEOH_QC_v 1, Rt: 5.91 min, m/z 612.2 [M + H]+ | 2.5 mg, white solid |
| M05327 | 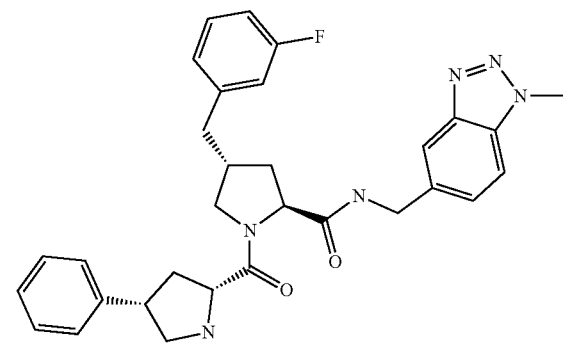<br>RgA: C-(1-Methyl-1H-benzotriazol-5-yl)-methylamine<br>RgB: Boc-(R)-γ-(3-fluorobenzyl)-L-proline<br>RgD: (2S,2R)-Boc-4-phenyl-pyrrolidine-2-carboxylic acid<br>Step 1 & 3: GM1 with HATU & DIPEA in DMF; Step 2 & 4: GM2A | ANALPH9_MEOH_QC_v 1, Rt: 7.86 min, m/z 541.1 [M + H]+<br>ANALPH2_MEOH_QC_v 1, Rt: 5.93 min, m/z 541.1 [M + H]+ | 35 mg, white solid |
| M05328 | 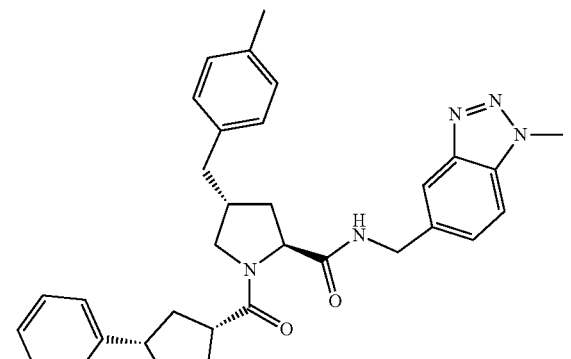<br>RgA: C-(1-Methyl-1H-benzotriazol-5-yl)-methylamine | ANALPH2_MEOH_QC_v 1, Rt: 6.19 min, m/z 537.1 [M + H]+<br>ANALPH9_MEOH_QC_v 1, Rt: 8.16 min, m/z 537.1 [M + H]+ | 45 mg, white solid |

| Example No. | Structure & Conditions | Analytical Data | Mass, % yield, state |
|---|---|---|---|
| | RgB: Boc-(R)-γ-(4-methylbenzyl)-L-proline<br>RgD: (2S,2R)-Boc-4-phenyl-pyrrolidine-2-carboxylic acid<br>Step 1 & 3: GM1 with HATU & DIPEA in DMF; Step 2 & 4: GM2A | | |
| M05329 | 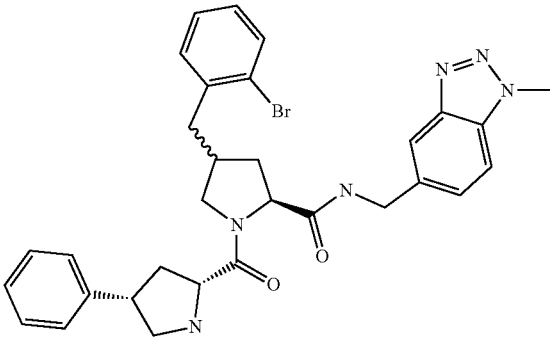<br>RgA: C-(1-Methyl-1H-benzotriazol-5-yl)-methylamine<br>RgB: (S)-4-(2-Bromo-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH9_MEOH_QC_v 1, Rt: 8.17 min, m/z 602.9 [M + H]+<br>ANALPH2_MEOH_QC_v 1, Rt: 6.21 min, m/z 602.9 [M + H]+ | 24 mg, white solid |
| M05332 | 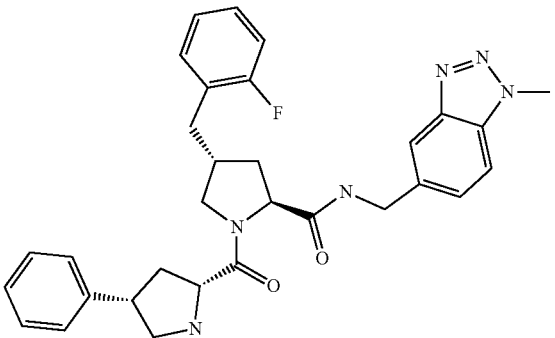<br>RgA: C-(1-Methyl-1H-benzotriazol-5-yl)-methylamine<br>RgB: Boc-(R)-γ-(2-fluorobenzyl)-L-proline<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH2_MEOH_QC_v 1, Rt: 5.95 min, m/z 541.3 [M + H]+<br>ANALPH9_MEOH_QC_v 1, Rt: 7.90 min, m/z 541.3 [M + H]+ | 56.5 mg, white solid |
| M05333 | 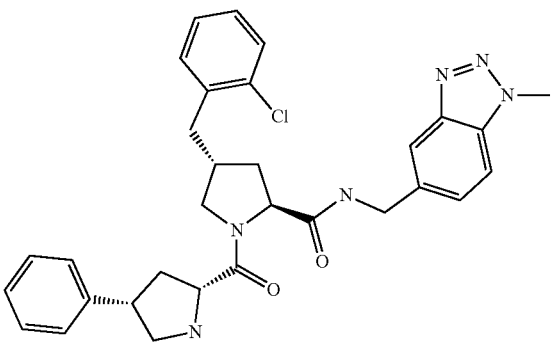<br>RgA: C-(1-Methyl-1H-benzotriazol-5-yl)-methylamine | ANALPH9_MEOH_QC_v 1, Rt: 8.11 min, m/z 557.2 [M + H]+<br>ANALPH2_MEOH_QC_v 1, Rt: 6.14 min, m/z 557.2 [M + H]+ | 47 mg, white solid |

| Example No. | Structure & Conditions | Analytical Data | Mass, % yield, state |
|---|---|---|---|
| | RgB: Boc-(R)-γ-(2-chlorobenzyl)-L-proline
RgD: (4S,2R)-Boc-4-phenyl-pyrrolidine-2-carboxylic acid
Step 1 & 3: GM1 with HBTU & DIPEA in DCM; Step 2 & 4: GM2A | | |
| M05334 | 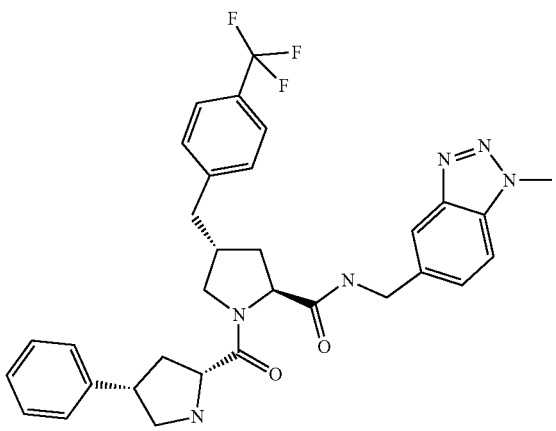

RgA: C-(1-Methyl-1H-benzotriazol-5-yl)-methylamine
RgB: boc-(R)-4-[4-trifluoromethylbenzyl]-L-proline
RgD: (2R,4S)-boc-4-phenylpyrrolidine-2-carboxylic acid
Step 1 & 3: GM1 with HATU & Et₃N in DCM;
Step 2 & 4: GM2A | ANALPH2_MEOH_QC_v 1, Rt: 6.34 min, m/z 591.1 [M + H]+
ANALPH9_MEOH_QC_v 1, Rt: 8.19 min, m/z 591.2 [M + H]+ | 5.7 mg, white solid |
| M05335 | 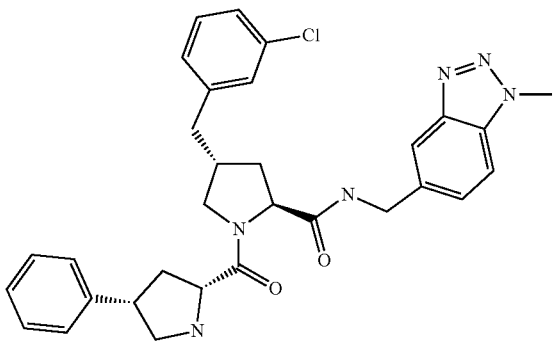

RgA: C-(1-Methyl-1H-benzotriazol-5-yl)-methylamine
RgB: boc-(R)-γ-(3-chlorobenzyl)-L-proline
RgD: (2R,4S)-boc-4-phenylpyrrolidine-2-carboxylic acid
Step 1 & 3: GM1 with HATU & Et₃N in DCM;
Step 2 & 4: GM2A | ANALPH9_MEOH_QC_v 1, Rt: 8.15 min, m/z 557.2 [M + H]+
ANALPH2_MEOH_QC_v 1, Rt: 6.19 min, m/z 557.2 [M + H]+ | 24 mg, white solid |

| Example No. | Structure & Conditions | Analytical Data | Mass, % yield, state |
|---|---|---|---|
| M05336 | 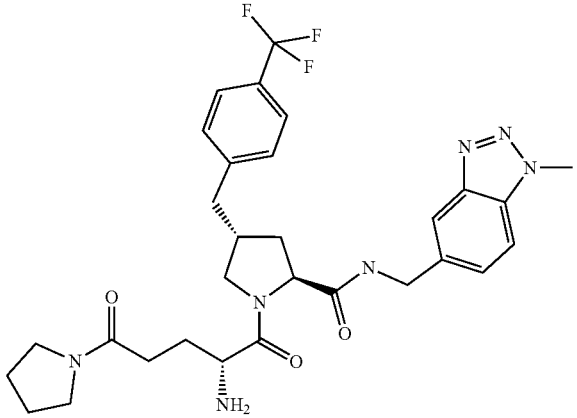<br>RgA: C-(1-Methyl-1H-benzotriazol-5-yl)-methylamine<br>RgB: boc-(R)-4-[4-trifluoromethylbenzyl]-L-proline<br>RgD: (R)-2-tert-Butoxycarbonylamino-5-oxo-5-pyrrolidin-1-yl-pentanoic acid<br>Step 1 & 3: GM1 with HATU & Et₃N in DCM;<br>Step 2 & 4: GM2A | ANALPH9_MEOH_QC_v 1, Rt: 7.66 min, m/z 600.2 [M + H]+<br>ANALPH2_MEOH_QC_v 1, Rt: 6.03 min, m/z 600.2 [M + H]+ | 27 mg, pink solid |
| M05337 | 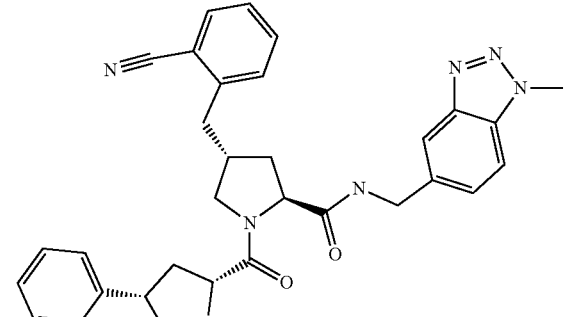<br>RgA: C-(1-Methyl-1H-benzotriazol-5-yl)-methylamine<br>RgB: (S)-4-(2-Cyano-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH9_MEOH_QC_v 1, Rt: 7.48 min, m/z 548.2 [M + H]+<br>ANALPH2_MEOH_QC_v 1, Rt: 5.59 min, m/z 548.2 [M + H]+ | 18 mg, white solid |
| M05338 | 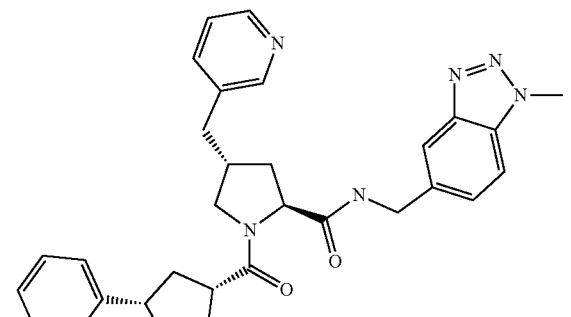<br>RgA: C-(1-Methyl-1H-benzotriazol-5-yl)-methylamine<br>RgB: boc-(R)-γ-(3-pyridylmethyl)-L-proline | ANALPH9_MEOH_QC_v 1, Rt: 6.98 min, m/z 524.4 [M + H]+<br>ANALPH2_MEOH_QC_v 1, Rt: 3.92 min, m/z 524.3 [M + H]+ | 43 mg, white solid |

| Example No. | Structure & Conditions | Analytical Data | Mass, % yield, state |
|---|---|---|---|
| | RgD: (4S,2R)-Boc-4-phenyl-pyrrolidine-2-carboxylic acid<br>Step 1 & 3: GM1 with HATU & DIPEA in DMF; Step 2 & 4: GM2A | | |
| M05339 | 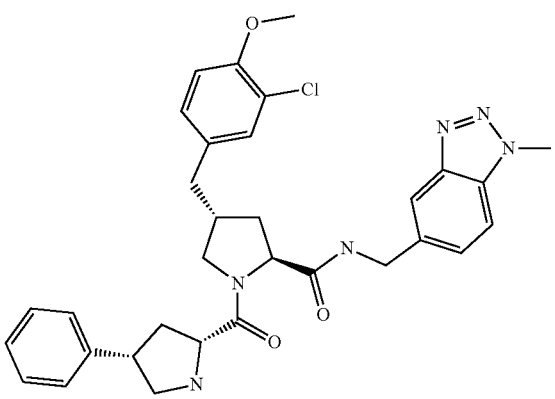<br>RgA: C-(1-Methyl-1H-benzotriazol-5-yl)-methylamine<br>RgB: (S)-4-(3-Chloro-4-methoxy-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HATU & DIPEA in DMF/DCM; Step 2 & 4: GM2A | ANALPH2_MEOH_QC_v 1, Rt: 6.10 min, m/z 587.3 [M + H]+<br>ANALPH9_MEOH_QC_v 1, Rt: 7.96 min, m/z 587.3 [M + H]+ | 35 mg, white solid |
| M05340 | 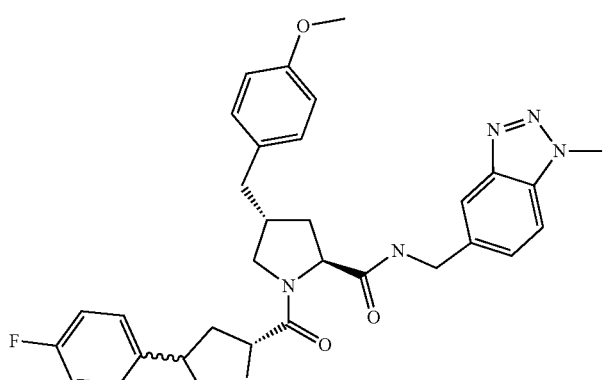<br>RgA: C-(1-Methyl-1H-benzotriazol-5-yl)-methylamine<br>RgB: boc-(R)-γ-(4-methoxybenzyl)-L-proline<br>RgD: (R)-4-(4-Fluoro-phenyl)-pyrrolidine-1,2-dicarboxylic acid 1-tert-butyl ester<br>Step 1 & 3: GM1 with HATU & DIPEA in DMF; Step 2 & 4: GM2A | ANALPH9_MEOH_QC_v 1, Rt: 7.86 min, m/z 571.4 [M + H]+<br>ANALPH2_MEOH_QC_v 1, Rt: 5.98 min, m/z 571.3 [M + H]+ | White solid |

-continued

| Example No. | Structure & Conditions | Analytical Data | Mass, % yield, state |
|---|---|---|---|
| M05342 | 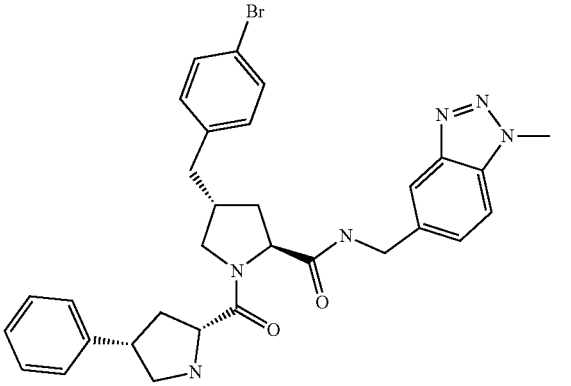<br>RgA: C-(1-Methyl-1H-benzotriazol-5-yl)-methylamine<br>RgB: (2S,4R)-4-(4-Bromo-benzyl)-pyrrolidine-1,2-dicarboxylic acid 1-tert-butyl ester<br>RgD: (2S, 2R)-Boc-4-phenyl-pyrrolidine-2-carboxylic acid<br>Step 1 & 3: GM1 with HBTU & DIPEA in DCM; Step 2 & 4: GM2A | ANALPH9_MEOH_QC_v 1, Rt: 8.25 min, m/z 601.1 [M + H]+<br>ANALPH2_MEOH_QC_v 1, Rt: 6.41 min, m/z 601.1 [M + H]+ | 135 mg, white solid |
| M05345 | 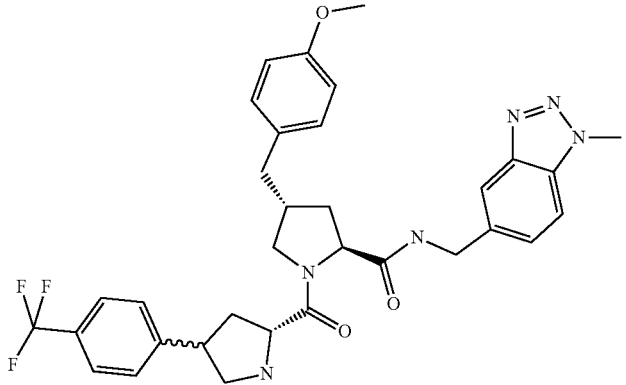<br>RgA: C-(1-Methyl-1H-benzotriazol-5-yl)-methylamine<br>RgB: boc-(R)-γ-(4-methoxybenzyl)-L-proline<br>RgD: (R)-4-(4-Trifluoromethyl-phenyl)-pyrrolidine-1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 6.43 min, m/z 621.2 [M + H]+<br>ANALPH9_MEOH_QC_v 1, Rt: 8.19 min, m/z 621.3 [M + H]+ | 7.9 mg, white solid |
| M05346 | 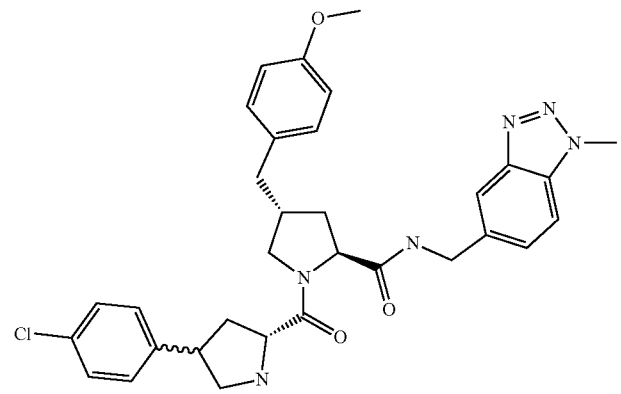 | ANALPH2_MEOH_QC_v 1, Rt: 6.22 min, m/z 587.4 [M + H]+<br>ANALPH9_MEOH_QC_v 1, Rt: 8.14 min, m/z 587.4 [M + H]+ | 7.4 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-4-(4-Chloro-phenyl)-pyrrolidine-1,2-dicarboxylic acid 1-tert-butyl ester<br>Step 1 & 3: GM1 with HATU & DIPEA in DMF; Step 2 & 4: GM2A | | |
| M05348 | 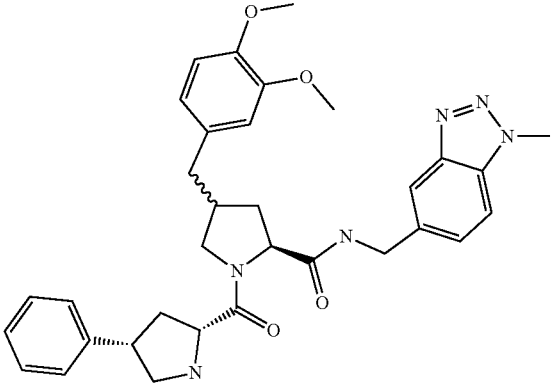<br>RgA: C-(1-Methyl-1H-benzotriazol-5-yl)-methylamine<br>RgB: (S)-4-(3,4-Dimethoxy-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH9_MEOH_QC_v 1, Rt: 7.44 min, m/z 583.5 [M + H]+<br>ANALPH2_MEOH_QC_v 1, Rt: 5.68 min, m/z 583.4 [M + H]+ | 12 mg, white solid |
| M05349 | 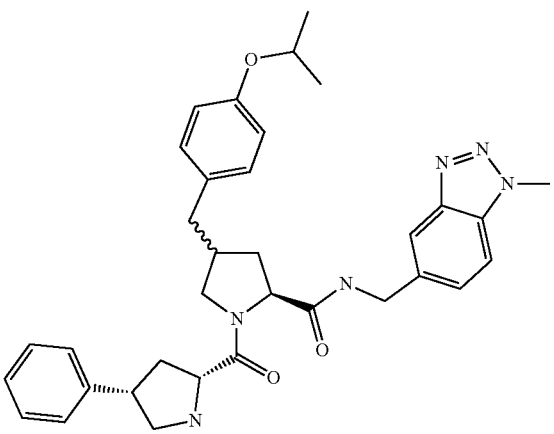<br>RgA: C-(1-Methyl-1H-benzotriazol-5-yl)-methylamine<br>RgB: (S)-4-(4-Isopropoxy-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH2_MEOH_QC_v 1, Rt: 6.27 min, m/z 581.4 [M + H]+<br>ANALPH9_MEOH_QC_v 1, Rt: 8.20 min, m/z 581.5 [M + H]+ | 45 mg, white solid |

| Example No. | Structure & Conditions | Analytical Data | Mass, % yield, state |
|---|---|---|---|
| M05351 | 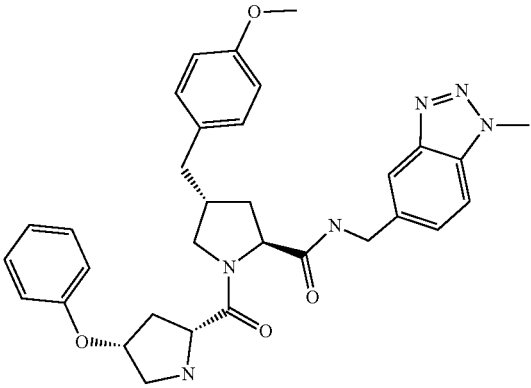 [SMILES: COc1ccc(C[C@@H]2C[C@@H](C(=O)NCc3ccc4c(c3)nnn4C)N(C(=O)[C@H]3C[C@@H](Oc4ccccc4)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R,R)-Boc-4-phenoxypyrrolidine carboxylic acid<br>Step 1 & 3: GM1 with HBTU & DIPEA in DCM; Step 2 & 4: GM2A | ANALPH2_MEOH_QC_v 1, Rt: 5.83 min, m/z 569.4 [M + H]+<br>ANALPH9_MEOH_QC_v 1, Rt: 7.75 min, m/z 569.4 [M + H]+ | 21 mg, white solid |
| M05352 | 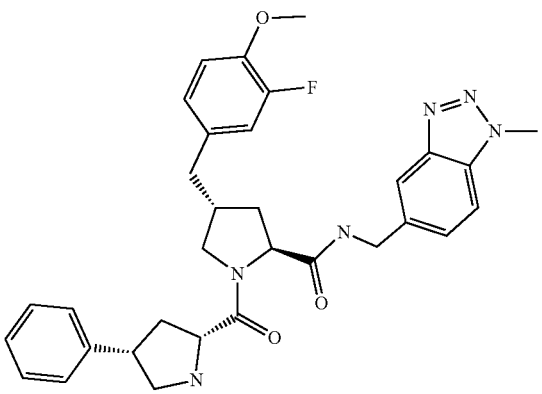 [SMILES: COc1ccc(C[C@@H]2C[C@@H](C(=O)NCc3ccc4c(c3)nnn4C)N(C(=O)[C@H]3C[C@@H](c4ccccc4)CN3)C2)cc1F]<br>RgA: C-(1-Methyl-1H-benzotriazol-5-yl)-methylamine<br>RgB: (S)-4-(3-Fluoro-4-methoxy-benzyl)-pyrro-lidine-1,2-dicarboxylic acid 1-tert-butyl ester<br>RgD: (R)-4-Pyridin-4-yl-pyrrolidine-1,2-dicarboxylic acid 1-tert-butyl ester<br>Step 1 & 3: GM1 with HBTU & DIPEA in DCM; Step 2 & 4: GM2A | ANALPH9_MEOH_QC_v 1, Rt: 7.71 min, m/z 571.4 [M + H]+<br>ANALPH2_MEOH_QC_v 1, Rt: 5.80 min, m/z 571.4 [M + H]+ | 23 mg, white solid |
| M05353 | 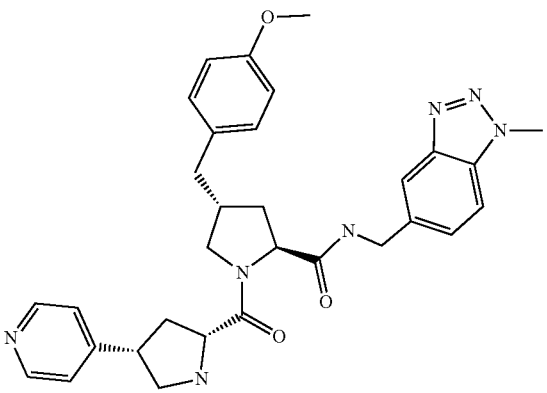 [SMILES: COc1ccc(C[C@@H]2C[C@@H](C(=O)NCc3ccc4c(c3)nnn4C)N(C(=O)[C@H]3C[C@@H](c4ccncc4)CN3)C2)cc1] | ANALPH2_MEOH_QC_v 1, Rt: 4.50 min, m/z 554.4 [M + H]+<br>ANALPH9_MEOH_QC_v 1, Rt: 7.09 min, m/z 554.4 [M + H]+ | 8 mg, white solid |

-continued

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-4-Pyridin-4-yl-pyrrolidine-1,2-dicarboxylic acid 1-tert-butyl ester<br>Step 1 & 3: GM1 with HATU & Et₃N in DCM;<br>Step 2 & 4: GM2A | | |
| M05354 | 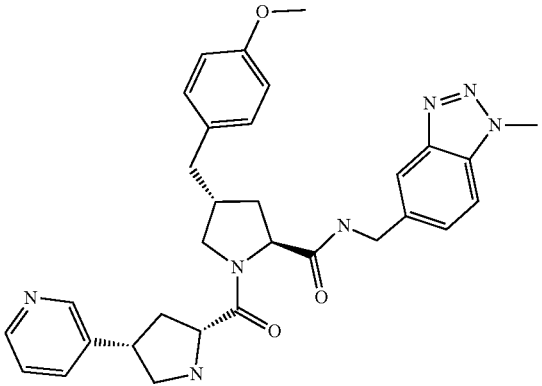 [SMILES: COc1ccc(C[C@@H]2C[C@@H](C(=O)NCc3ccc4c(c3)nnn4C)N(C(=O)[C@H]3C[C@@H](c4cccnc4)CN3)C2)cc1] | ANALPH2_MEOH_QC_v 1, Rt: 4.79 min, m/z 554.4 [M + H]+<br>ANALPH9_MEOH_QC_v 1, Rt: 7.12 min, m/z 554.4 [M + H]+ | 5 mg, white solid |
| | RgA: C-(1-Methyl-1H-benzotriazol-5-yl)-methylamine<br>RgB: boc-(R)-γ-(4-methoxybenzyl)-L-proline<br>RgD: (R)-4-Pyridin-3-yl-pyrrolidine-1,2-dicarboxylic acid 1-tert-butyl ester<br>Step 1 & 3: GM1 with HATU & Et₃N in DCM;<br>Step 2 & 4: GM2A | | |
| M05355 | 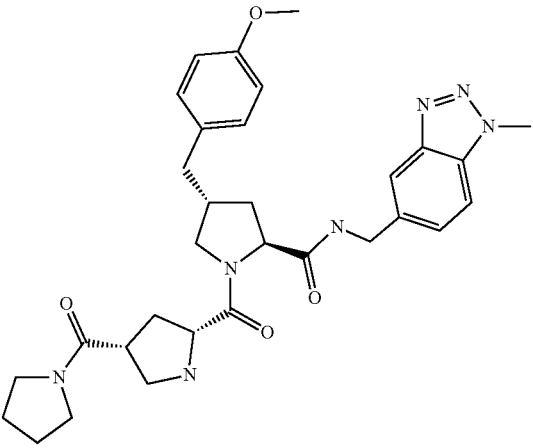 [SMILES: COc1ccc(C[C@@H]2C[C@@H](C(=O)NCc3ccc4c(c3)nnn4C)N(C(=O)[C@H]3C[C@@H](C(=O)N4CCCC4)CN3)C2)cc1] | ANALPH2_MEOH_QC_v 1, Rt: 5.33 min, m/z 574.4 [M + H]+<br>ANALPH9_MEOH_QC_v 1, Rt: 7.07 min, m/z 574.4 [M + H]+ | 2.5 mg, white solid |
| | RgA: C-(1-Methyl-1H-benzotriazol-5-yl)-methylamine<br>RgB: boc-(R)-γ-(4-methoxybenzyl)-L-proline<br>RgD: (2R,4R)-4-(Pyrrolidine-1-carbonyl)-pyrrolidine-1,2-dicarboxylic acid 1-tert-butyl ester<br>Step 1 & 3: GM1 with HATU & DIPEA in DMF; Step 2 & 4: GM2A | | |

| Example No. | Structure & Conditions | Analytical Data | Mass, % yield, state |
|---|---|---|---|
| M05356 | 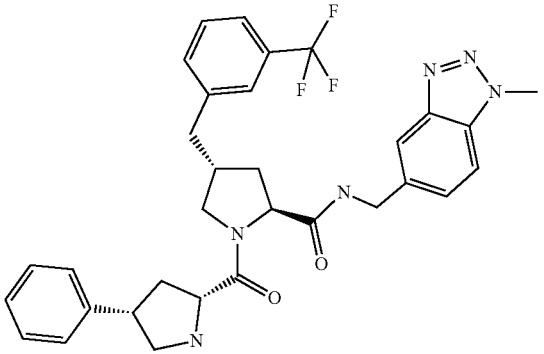 [SMILES: Cn1nnc2cc(CNC(=O)[C@@H]3C[C@@H](Cc4cccc(C(F)(F)F)c4)CN3C(=O)[C@H]3C[C@@H](c4ccccc4)CN3)ccc21]<br>RgA: C-(1-Methyl-1H-benzotriazol-5-yl)-methylamine<br>RgB: (2S,4R)-4-(3-(trifluoromethyl)benzyl) pyrrolidine-2-caboxylic acid<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH2_MEOH_QC_v 1, Rt: 6.27 min, m/z 591.3 [M + H]+<br>ANALPH9_MEOH_QC_v 1, Rt: 8.15 min, m/z 591.4 [M + H]+ | 35 mg, white solid |
| M05357 | 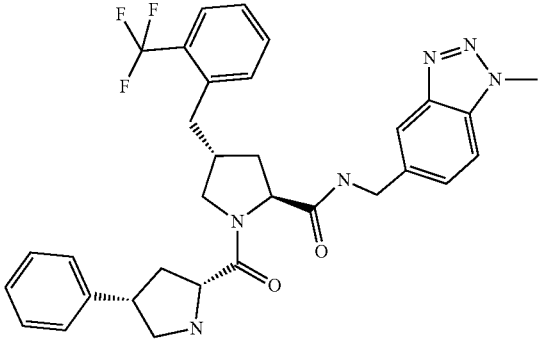 [SMILES: Cn1nnc2cc(CNC(=O)[C@@H]3C[C@@H](Cc4ccccc4C(F)(F)F)CN3C(=O)[C@H]3C[C@@H](c4ccccc4)CN3)ccc21]<br>RgA: C-(1-Methyl-1H-benzotriazol-5-yl)-methylamine<br>RgB: (2S,4R)-4-(2-(trifluoromethyl)benzyl) pyrrolidine-2-caboxylic acid<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH2_MEOH_QC_v 1, Rt: 6.24 min, m/z 591.3 [M + H]+<br>ANALPH9_MEOH_QC_v 1, Rt: 8.15 min, m/z 591.4 [M + H]+ | 30 mg, white solid |
| M05359 | 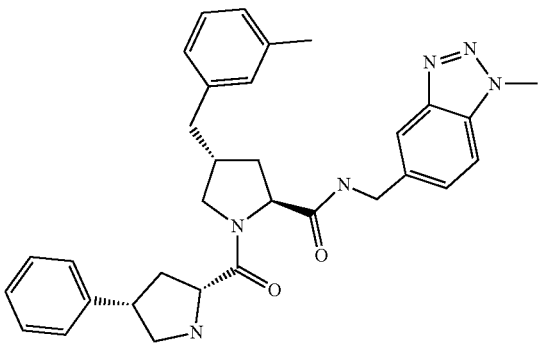 [SMILES: Cc1cccc(C[C@@H]2C[C@@H](C(=O)NCc3ccc4c(c3)nnn4C)N(C(=O)[C@H]3C[C@@H](c4ccccc4)CN3)C2)c1]<br>RgA: C-(1-Methyl-1H-benzotriazol-5-yl)-methylamine<br>RgB: (2S,4R)-4-(3-methylbenzyl)pyrrolidine-2-caboxylic acid<br>RgD: (4S,2R)-Boc-4-phenyl-pyrrolidine-2-carboxylic acid | ANALPH9_MEOH_QC_v 1, Rt: 8.14 min, m/z 537.3 [M + H]+<br>ANALPH2_MEOH_QC_v 1, Rt: 6.14 min, m/z 537.3 [M + H]+ | 22 mg, white solid |

| Example No. | Structure & Conditions | Analytical Data | Mass, % yield, state |
|---|---|---|---|
| | Step 1 & 3: GM1 with HATU & DIPEA in DMF; Step 2 & 4: GM2A | | |
| M05360 | 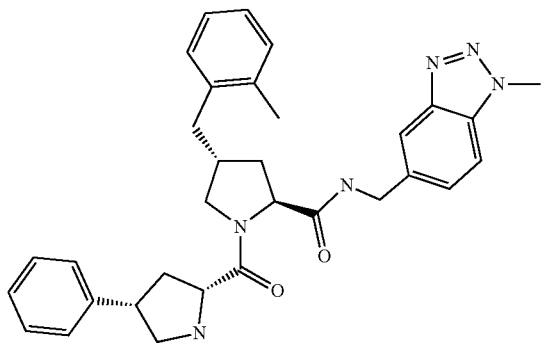 [SMILES: Cc1ccccc1C[C@@H]1C[C@@H](C(=O)NCc2ccc3c(c2)nnn3C)N(C(=O)[C@H]2C[C@@H](c3ccccc3)CN2)C1]<br>RgA: C-(1-Methyl-1H-benzotriazol-5-yl)-methylamine<br>RgB: (2S,4R)-4-(2-methylbenzyl)pyrrolidine-2-caboxylic acid<br>RgD: (4S,2R)-Boc-4-phenyl-pyrrolidine-2-carboxylic acid<br>Step 1 & 3: GM1 with HATU & DIPEA in DMF; Step 2 & 4: GM2A | ANALPH2_MEOH_QC_v 1, Rt: 6.06 min, m/z 537.3 [M + H]+<br>ANALPH9_MEOH_QC_v 1, Rt: 8.08 min, m/z 537.3 [M + H]+ | 32 mg, white solid |
| M05361 | 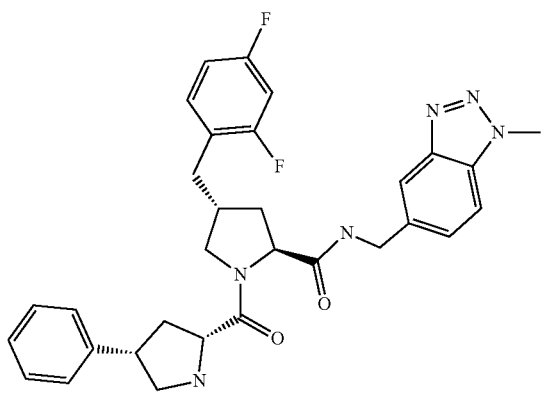 [SMILES: Cn1nnc2cc(CNC(=O)[C@@H]3C[C@@H](Cc4ccc(F)cc4F)CN3C(=O)[C@H]3C[C@@H](c4ccccc4)CN3)ccc21]<br>RgA: C-(1-Methyl-1H-benzotriazol-5-yl)-methylamine<br>RgB: (S)-4-(2,4-Difluoro-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH2_MEOH_QC_v 1, Rt: 6.07 min, m/z 559.4 [M + H]+<br>ANALPH9_MEOH_QC_v 1, Rt: 7.97 min, m/z 559.4 [M + H]+ | 48 mg, white solid |

| Example No. | Structure & Conditions | Analytical Data | Mass, % yield, state |
|---|---|---|---|
| M05362 | 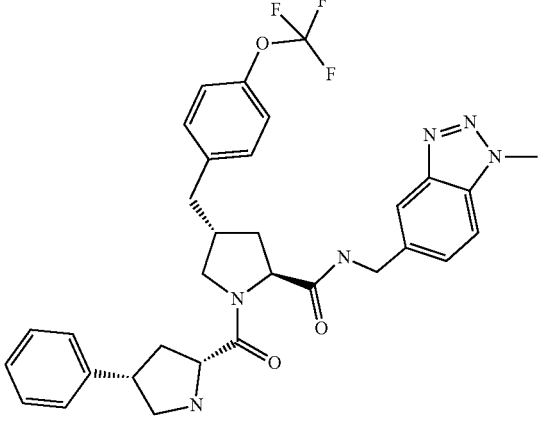 [SMILES: Cn1nnc2cc(CNC(=O)[C@@H]3C[C@@H](Cc4ccc(OC(F)(F)F)cc4)CN3C(=O)[C@H]3C[C@@H](c4ccccc4)CN3)ccc21]<br>RgA: C-(1-Methyl-1H-benzotriazol-5-yl)-methylamine<br>RgB: (S)-4-(4-Trifluoromethoxy-benzyl)-pyrroli-ine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH9_MEOH_QC_v 1, Rt: 8.28 min, m/z 607.3 [M + H]+<br>ANALPH2_MEOH_QC_v 1, Rt: 6.49 min, m/z 607.3 [M + H]+ | 14 mg, white solid |
| M05365 | 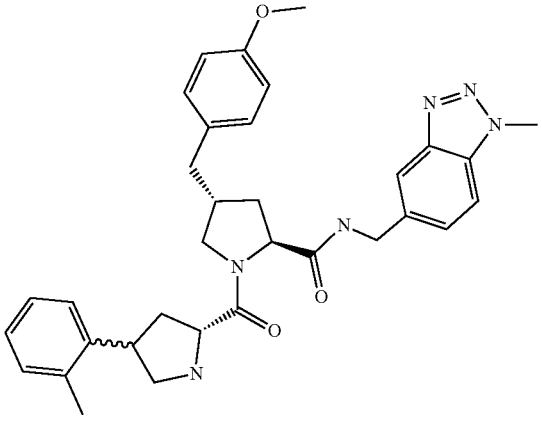 [SMILES: COc1ccc(C[C@@H]2C[C@@H](C(=O)NCc3ccc4c(c3)nnn4C)N(C(=O)[C@H]3CC(c4ccccc4C)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-o-Tolyl-pyrrolidine-1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 6.08 min, m/z 567.4 [M + H]+<br>ANALPH9_MEOH_QC_v 1, Rt: 8.01 min, m/z 567.4 [M + H]+ | 3.0 mg, white solid |
| M05366 | 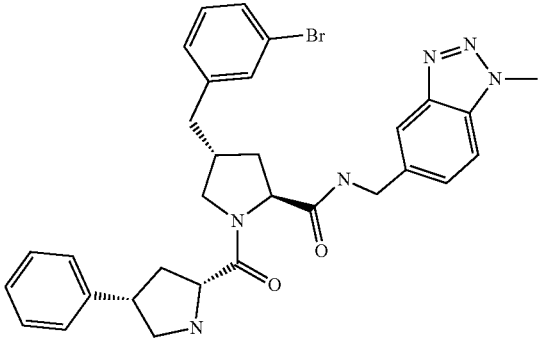 [SMILES: Cn1nnc2cc(CNC(=O)[C@@H]3C[C@@H](Cc4cccc(Br)c4)CN3C(=O)[C@H]3C[C@@H](c4ccccc4)CN3)ccc21] | ANALPH2_MEOH_QC_v 1, Rt: 6.26 min, m/z 601.3 [M + H]+<br>ANALPH9_MEOH_QC_v 1, Rt: 8.32 min, m/z 601.3 [M + H]+ | 154 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: (2S,4R)-4-(3-Bromo-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | | |
| M05368 | 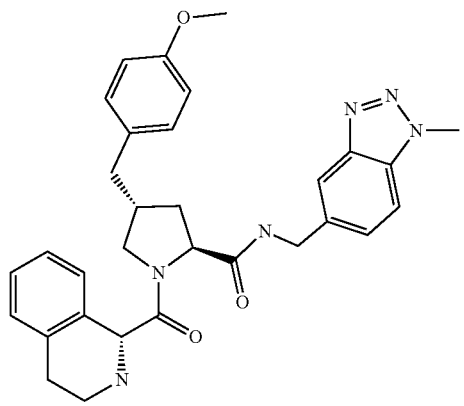 [SMILES: COc1ccc(C[C@@H]2C[C@@H](C(=O)NCc3ccc4c(c3)nnn4C)N(C(=O)[C@@H]3NCCc4ccccc43)C2)cc1]<br>RgA: C-(1-Methyl-1H-benzotriazol-5-yl)-methylamine<br>RgB: boc-(R)-γ-(4-methoxybenzyl)-L-proline<br>RgD: Boc-tetrahydroisoquinoline-2-carboxylic acid<br>Step 1 & 3: GM1 with HBTU & DIPEA in DCM; Step 2 Step 4: GM2A | ANALPH2_MEOH_QC_v 1, Rt: 5.6 min, m/z 539.4 [M + H]+<br>ANALPH9_MEOH_QC_v 1, Rt: 7.66 min, m/z 539.4 [M + H]+ | 19 mg, white solid |
| M05371 | 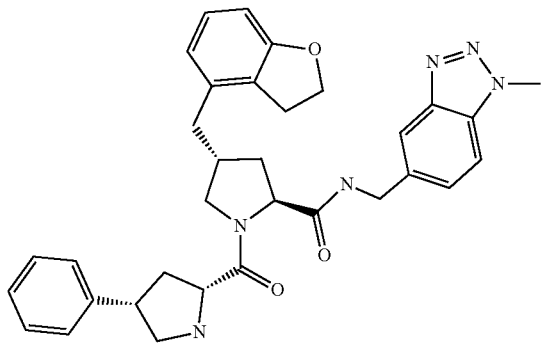 [SMILES: Cn1nnc2cc(CNC(=O)[C@@H]3C[C@@H](Cc4cccc5c4CCO5)CN3C(=O)[C@H]3C[C@@H](c4ccccc4)CN3)ccc21]<br>RgA: C-(1-Methyl-1H-benzotriazol-5-yl)-methylamine<br>RgB: (S)-4-(2,3-Dihydro-benzofuran-4-yl methyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH9_MEOH_QC_v 1, Rt: 7.81 min, m/z 565.4 [M + H]+<br>ANALPH2_MEOH_QC_v 1, Rt: 5.95 min, m/z 565.4 [M + H]+ | 15 mg, white solid |

| Example No. | Structure & Conditions | Analytical Data | Mass, % yield, state |
|---|---|---|---|
| M05372 | 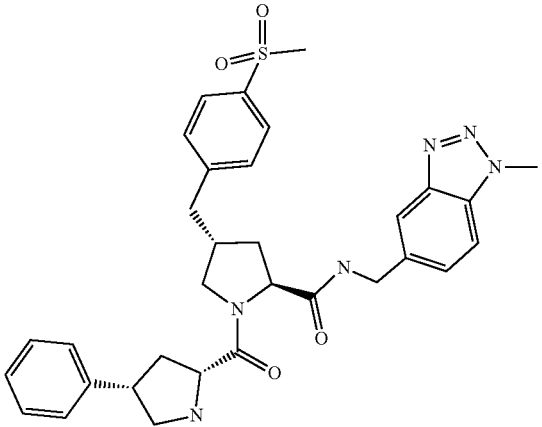 [SMILES: Cn1nnc2cc(CNC(=O)[C@@H]3C[C@@H](Cc4ccc(S(C)(=O)=O)cc4)CN3C(=O)[C@H]3C[C@@H](c4ccccc4)CN3)ccc21]<br>RgA: C-(1-Methyl-1H-benzotriazol-5-yl)-methylamine<br>RgB: (S)-4-(4-Methanesulfonyl-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH2_MEOH_QC_v 1, Rt: 5.17 min, m/z 601.4 [M + H]+<br>ANALPH9_MEOH_QC_v 1, Rt: 6.92 min, m/z 601.4 [M + H]+ | 24 mg, white solid |
| M05373 | 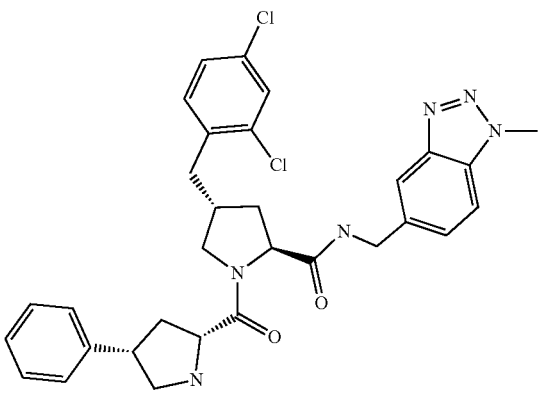 [SMILES: Cn1nnc2cc(CNC(=O)[C@@H]3C[C@@H](Cc4ccc(Cl)cc4Cl)CN3C(=O)[C@H]3C[C@@H](c4ccccc4)CN3)ccc21]<br>RgA: C-(1-Methyl-1H-benzotriazol-5-yl)-methylamine<br>RgB: (2S,4R)-4-(2,4-Dichloro-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH2_MEOH_QC_v 1, Rt: 6.63 min, m/z 591.3 [M + H]+<br>ANALPH9_MEOH_QC_v 1, Rt: 8.49 min, m/z 591.3 [M + H]+ | 7 mg, white solid |

-continued

| Example No. | Structure & Conditions | Analytical Data | Mass, % yield, state |
|---|---|---|---|
| M05374 | RgA: C-(1-Methyl-1H-benzotriazol-5-yl)-methylamine<br>RgB: boc-(R)-γ-(4-methoxybenzyl)-L-proline<br>RgD: (2R,4S)-1-(tert-butoxycarbonyl)-4-phenylpiperidine-2-carboxylic acid<br>Step 1 & 3: GM1 with HBTU & DIPEA in DCM; Step 2 & 4: GM2A | ANALPH2_MEOH_QC_v1, Rt: 6.10 min, m/z 567.4 [M + H]+<br>ANALPH9_MEOH_QC_v1, Rt: 7.97 min, m/z 567.4 [M + H]+ | 20 mg, white solid |
| M05376 | RgA: C-(1-Methyl-1H-benzotriazol-5-yl)-methylamine<br>RgB: boc-(R)-γ-(4-methoxybenzyl)-L-proline<br>RgD: (R)-4-(2-Methyl-2H-pyrazol-3-yl)-pyrrolidine-1,2-dicarboxylic acid 1-tert-butyl ester<br>Step 1 & 3: GM1 with HBTU & DIPEA in DCM; Step 2 & 4: GM2A | ANALPH2_MEOH_QC_v1, Rt: 5.35 min, m/z 557.4 [M + H]+<br>ANALPH9_MEOH_QC_v1, Rt: 7.05 min, m/z 557.4 [M + H]+ | 63 mg, white solid |
| M05377 | RgA: C-(1-Methyl-1H-benzotriazol-5-yl)-methylamine | ANALPH9_MEOH_QC_v1, Rt: 7.88 min, m/z 571.4 [M + H]+<br>ANALPH2_MEOH_QC_v1, Rt: 6.00 min, m/z 571.3 [M + H]+ | 46 mg, white solid |

| Example No. | Structure & Conditions | Analytical Data | Mass, % yield, state |
|---|---|---|---|
| | RgB: boc-(R)-γ-(4-methoxybenzyl)-L-proline<br>RgD: (R)-4-(2-Fluoro-phenyl)-pyrrolidine-1,2-dicarboxylic acid 1-tert-butyl ester<br>Step 1 & 3: GM1 with HATU & DIPEA in DMF; Step 2 & 4: GM2A | | |
| M05378 | 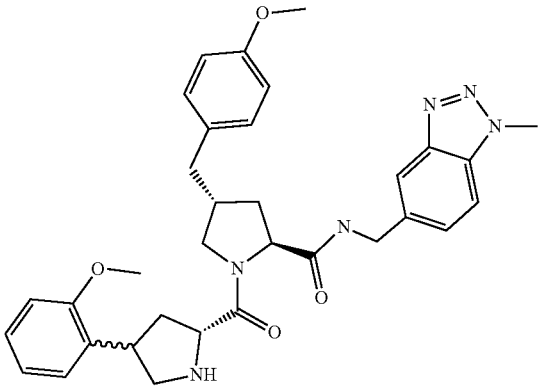 [SMILES: COc1ccc(C[C@@H]2C[C@@H](C(=O)NCc3ccc4c(c3)nnn4C)N(C(=O)[C@H]3CC(c4ccccc4OC)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(2-Methoxy-phenyl)pyrrolidine 1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 6.11 min, m/z 583.3 [M + H]+<br>ANALPH9_MEOH_QC_v 1, Rt: 7.90 min, m/z 583.4 [M + H]+ | 37 mg, white solid |
| M05379 | 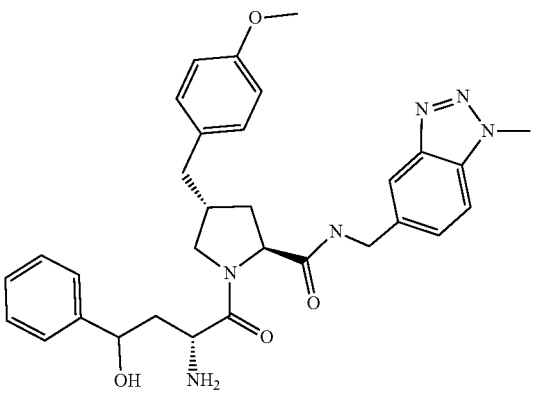 [SMILES: COc1ccc(C[C@@H]2C[C@@H](C(=O)NCc3ccc4c(c3)nnn4C)N(C(=O)[C@H](N)CC(O)c3ccccc3)C2)cc1]<br>RgA: C-(1-Methyl-1H-benzotriazol-5-yl)-methylamine<br>RgB: boc-(R)-γ-(4-methoxybenzyl)-L-proline<br>RgD(R)-2-Benzyloxycarbonylamino-4-oxo-4-phenyl-butyric acid<br>Step 1 & 3: GM1 with HBTU & DIPEA in DCM; Step 2 GM2A<br>Step 4: GM3A with Pd/C | ANALPH2_MEOH_QC_v 1, Rt: 5.89 min, m/z 557.3 [M + H]+<br>ANALPH9_MEOH_QC_v 1, Rt: 7.38 min, m/z 557.4 [M + H]+ | 13 mg, white solid |

-continued

| Example No. | Structure & Conditions | Analytical Data | Mass, % yield, state |
|---|---|---|---|
| M05380 | 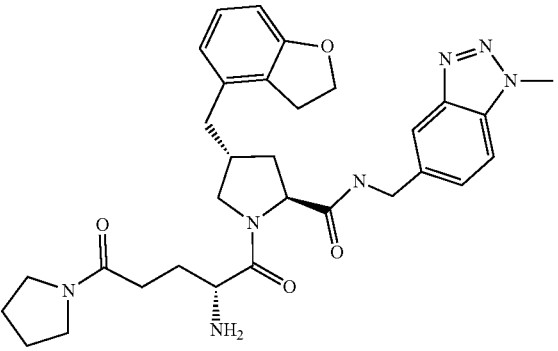 [SMILES: Cn1nnc2cc(CNC(=O)[C@@H]3C[C@@H](Cc4cccc5c4CCO5)CN3C(=O)[C@H](N)CCC(=O)N3CCCC3)ccc21]<br><br>RgA: C-(1-Methyl-1H-benzotriazol-5-yl)-methylamine<br>RgB: (S)-4-(2,3-Dihydro-benzofuran-4-yl methyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | ANALPH9_MEOH_QC_v 1, Rt: 7.04 min, m/z 574.4 [M + H]+<br>ANALPH2_MEOH_QC_v 1, Rt: 5.51 min, m/z 574.4 [M + H]+ | 31 mg, white solid |
| M05381 | 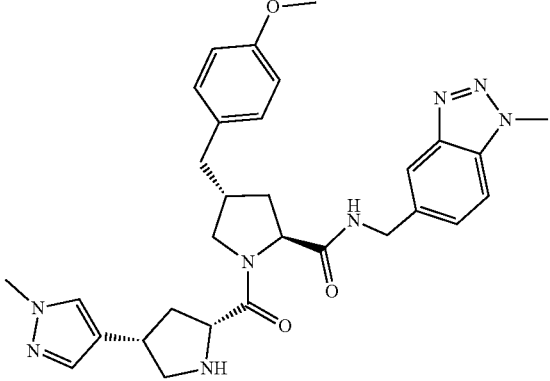<br><br>RgA: C-(1-Methyl-1H-benzotriazol-5-yl)-methylamine<br>RgB: boc-(R)-γ-(4-methoxybenzyl)-L-proline<br>RgD: (R)-4-(1-Methyl-1H-pyrazol-4-yl)-pyrrolidine-1,2-dicarboxylic acid 1-tert-butyl ester<br>Step 1 & 3: GM1 with HBTU & DIPEA in DCM; Step 2 & 4: GM2A | ANALPH9_MEOH_QC_v 1, Rt: 6.96 min, m/z 557.5 [M + H]+<br>ANALPH2_MEOH_QC_v 1, Rt: 5.14 min, m/z 557.5 [M + H]+<br>1H NMR (400 MHz, CDCl3) δ 8.12 (s, 1H), 7.89 (s, 1H), 7.42 (dd, J = 8.5, 1.5 Hz, 1H), 7.34 (d, J = 8.5 Hz, 1H), 7.29 (s, 1H), 7.22 (s, 1H), 7.11-7.00 (m, 2H), 6.89-6.76 (m, 2H), 4.67-4.52 (m, 2H), 4.44 (dd, J = 14.9, 5.6 Hz, 1H), 4.29 (t, J = 8.6 Hz, 1H), 4.21 (s, 3H), 3.83 (s, 3H), 3.78 (s, 3H), 3.40-3.27 (m, 2H), 3.04 (t, J = 9.4 Hz, 1H), 3.00-2.92 (m, 1H), 2.85-2.46 (m, 4H), 2.60 (s, 2H), 2.48-2.35 (m, 1H), 1.84-1.62 (m, 1H). | 35 mg, white solid |

-continued

| Example No. | Structure & Conditions | Analytical Data | Mass, % yield, state |
|---|---|---|---|
| M05382 | 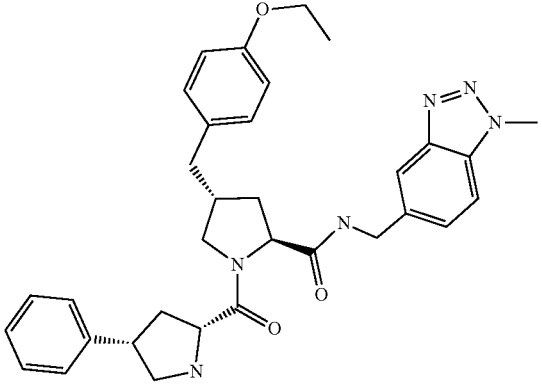 [SMILES: CCOc1ccc(C[C@@H]2C[C@@H](C(=O)NCc3ccc4c(c3)nnn4C)N(C(=O)[C@H]3C[C@@H](c4ccccc4)CN3)C2)cc1]<br>RgA: C-(1-Methyl-1H-benzotriazol-5-yl)-methylamine<br>RgB: (S)-4-(4-Ethoxy-benzyl)-pyrrolidine-1,2-dicarboxylic acid 1-tert-butyl ester<br>RgD: (4S,2R)-Boc-4-phenyl-pyrrolidine-2-carboxylic acid<br>Step 1 & 3: GM1 with HBTU & DIPEA in DCM; Step 2 & 4: GM2A | ANALPH9_MEOH_QC_v 1, Rt: 8.06 min, m/z 567.5 [M + H]+<br>ANALPH2_MEOH_QC_v 1, Rt: 6.02 min, m/z 567.5 [M + H]+ | 34 mg, white solid |
| M05383 | 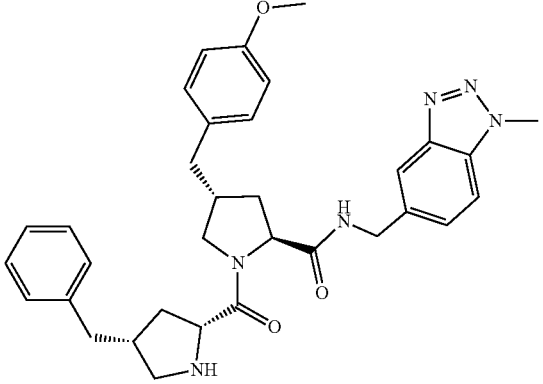 [SMILES: COc1ccc(C[C@@H]2C[C@@H](C(=O)NCc3ccc4c(c3)nnn4C)N(C(=O)[C@H]3C[C@@H](Cc4ccccc4)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: 4R-Boc-4-benzyl-D-proline<br>Step 1 & 3: GM1 with HBTU & DIPEA in DCM; Step 2 & 4: GM2A | ANALPH2_MEOH_QC_v 1, Rt: 6.00 min, m/z 567.5 [M + H]+<br>ANALPH9_MEOH_QC_v 1, Rt: 7.94 min, m/z 567.5 [M + H]+ | 48 mg, white solid |
| M05384 | 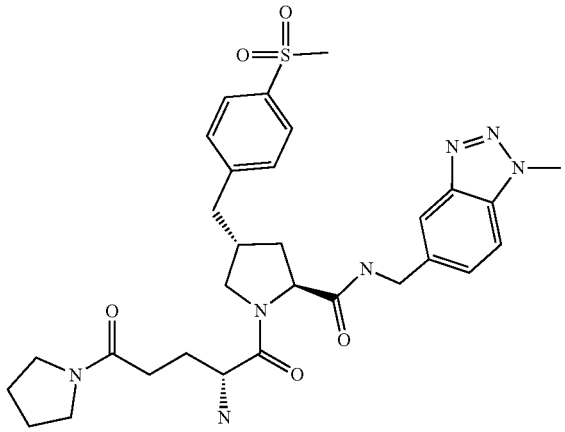 [SMILES: Cn1nnc2cc(CNC(=O)[C@@H]3C[C@@H](Cc4ccc(S(C)(=O)=O)cc4)CN3C(=O)[C@H](N)CCC(=O)N3CCCC3)ccc21] | ANALPH2_MEOH_QC_v 1, Rt: 4.63 min, m/z 610.5 [M + H]+<br>ANALPH9_MEOH_QC_v 1, Rt: 6.05 min, m/z 610.5 [M + H]+ | 25 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: (S)-4-(4-Methanesulfonyl-benzyl)-pyrrolidine-1,2-dicarboxylic acid 1-tert-butyl ester<br>RgD: (R)-2-tert-Butoxycarbonylamino-5-oxo-5-pyrrolidin-1-yl-pentanoic acid<br>Step 1 & 3: GM1 with HBTU & DIPEA in DCM; Step 2 & 4: GM2A | | |
| M05386 | 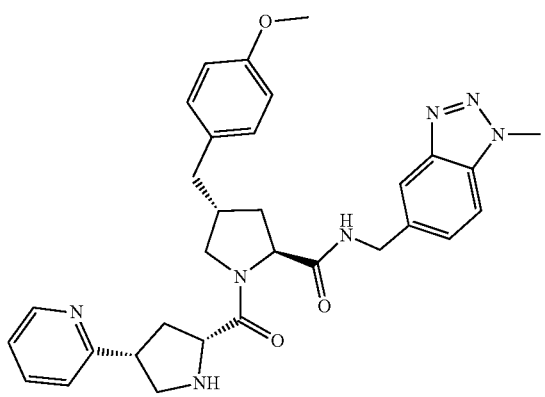<br>RgA: C-(1-Methyl-1H-benzotriazol-5-yl)-methylamine<br>RgB: boc-(R)-γ-(4-methoxybenzyl)-L-proline<br>RgD: (R)-4-Pyridin-2-yl-pyrrolidine-1,2-dicarboxylic acid 1-tert-butyl ester<br>Step 1 & 3: GM1 with HATU & Et₃N in DCM;<br>Step 2 & 4: GM2A | ANALPH2_MEOH_QC_v 1, Rt: 6.27 min, m/z 591.3 [M + H]+<br>ANALPH9_MEOH_QC_v 1, Rt: 8.15 min, m/z 591.4 [M + H]+ | 3 mg, pale yellow solid |
| M05387 | 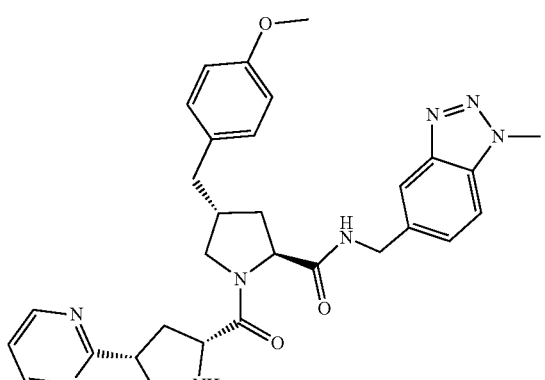<br>RgA: C-(1-Methyl-1H-benzotriazol-5-yl)-methylamine<br>RgB: boc-(R)-γ-(4-methoxybenzyl)-L-proline<br>RgD: (R)-4-Pyrimidin-2-yl-pyrrolidine-1,2-dicarboxylic acid 1-tert-butyl ester<br>Step 1 & 3: GM1 with HATU & Et₃N in DCM;<br>Step 2 & 4: GM2A | ANALPH9_MEOH_QC_v 1, Rt: 7.02 min, m/z 555.4 [M + H]+<br>ANALPH2_MEOH_QC_v 1, Rt: 5.43 min, m/z 555.4 [M + H]+ | 3 mg, white solid |

-continued

| Example No. | Structure & Conditions | Analytical Data | Mass, % yield, state |
|---|---|---|---|
| M05388 | 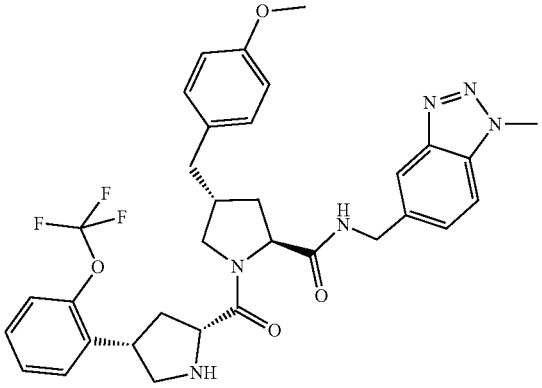 [SMILES: COc1ccc(C[C@@H]2C[C@@H](C(=O)NCc3ccc4c(c3)nnn4C)N(C(=O)[C@H]3C[C@@H](c4ccccc4OC(F)(F)F)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(2-Trifluoromethoxy-phenyl)-pyrro-lidine-1,2-dicarboxylic acid 1-tert-butyl ester<br>Step 1 & 3: GM1 with HATU & DIPEA in DMF; Step 2 & 4: GM2A | ANALPH9_MEOH_QC_v 1, Rt: 8.32 min, m/z 637.4 [M + H]+<br>ANALPH2_MEOH_QC_v 1, Rt: 6.41 min, m/z 637.4 [M + H]+ | 17 mg, white solid |
| M05390 | 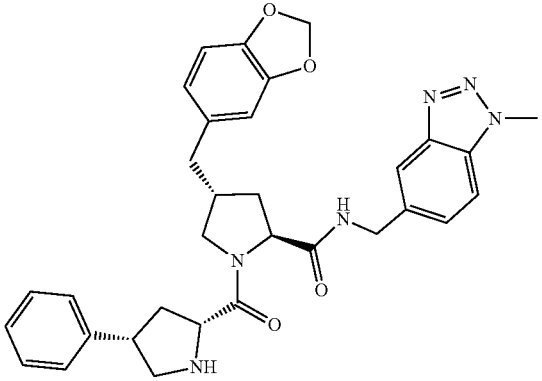 [SMILES: Cn1nnc2cc(CNC(=O)[C@@H]3C[C@@H](Cc4ccc5c(c4)OCO5)CN3C(=O)[C@H]3C[C@@H](c4ccccc4)CN3)ccc21]<br>RgA: C-(1-Methyl-1H-benzotriazol-5-yl)-methylamine<br>RgB: (2S,4R)-4-Benzo[1,3]dioxol-5-ylmethyl-pyrrolidine-1,2-dicarboxylic acid 1-tert-butyl ester<br>RgD: (2R,4S)-boc-4-phenylpyrrolidine-2-carboxylic acid<br>Step 1 & 3: GM1 with HATU & Et₃N in DCM; Step 2 & 4: GM2A | ANALPH9_MEOH_QC_v 1, Rt: 7.77 min, m/z 567.4 [M + H]+<br>ANALPH2_MEOH_QC_v 1, Rt: 5.81 min, m/z 567.4 [M + H]+ | 33 mg, white solid |
| M05391 | 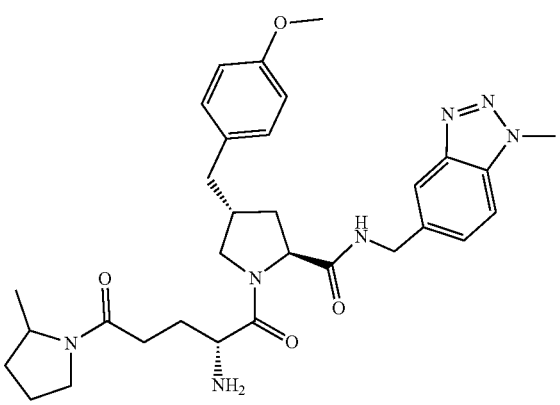 [SMILES: COc1ccc(C[C@@H]2C[C@@H](C(=O)NCc3ccc4c(c3)nnn4C)N(C(=O)[C@H](N)CCC(=O)N3CCCC3C)C2)cc1] | ANALPH9_MEOH_QC_v 1, Rt: 7.30 min, m/z 576.4 [M + H]+<br>ANALPH2_MEOH_QC_v 1, Rt: 5.62 min, m/z 576.5 [M + H]+ | 32 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-(2-methyl-pyrrolidin-1-yl)-5-oxo-pentanoic acid<br>Step 1 & 3: GM1 with HATU & DIPEA in DCM; Step 2 & 4: GM2A | | |
| M05392 | 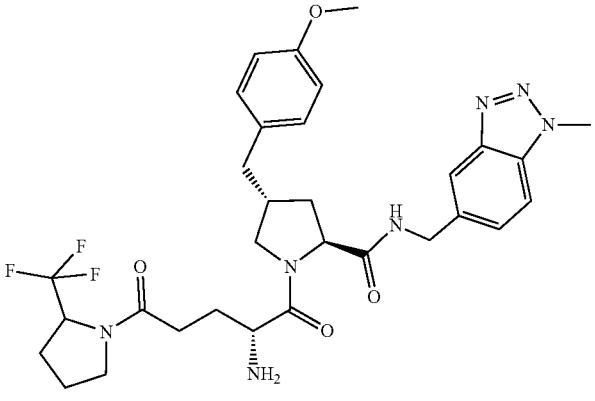 [SMILES: COc1ccc(C[C@@H]2C[C@@H](C(=O)NCc3ccc4c(c3)nnn4C)N(C(=O)[C@H](N)CCC(=O)N3CCCC3C(F)(F)F)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-oxo-5-(2-trifluoromethyl-pyrrolidin-1-yl)-pentanoic acid<br>Step 1 & 3: GM1 with HATU & DIPEA in DCM; Step 2 & 4: GM2A | ANALPH2_MEOH_QC_v 1, Rt: 5.95 min, m/z 630.4 [M + H]+<br>ANALPH9_MEOH_QC_v 1, Rt: 7.59 min, m/z 630.4 [M + H]+ | 18 mg, white solid |
| M05393 | 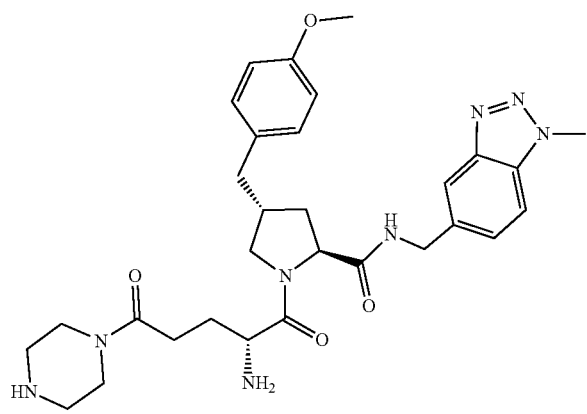 [SMILES: COc1ccc(C[C@@H]2C[C@@H](C(=O)NCc3ccc4c(c3)nnn4C)N(C(=O)[C@H](N)CCC(=O)N3CCNCC3)C2)cc1]<br>RgA: C-(1-Methyl-1H-benzotriazol-5-yl)-methylamine<br>RgB: boc-(R)-γ-(4-methoxybenzyl)-L-proline<br>RgD: 4-((R)-4-tert-Butoxycarbonylamino-4-carboxy-butyryl)-piperazine-1-carboxylic acid tert-butyl ester<br>Step 1 & 3: GM1 with HATU & DIPEA in DCM; Step 2 & 4: GM2A | ANALPH9_MEOH_QC_v 1, Rt: 6.48 min, m/z 577.4 [M + H]+<br>ANALPH2_MEOH_QC_v 1, Rt: 4.08 min, m/z 577.4 [M + H]+<br>1H-NMR (400 MHz, CDCl3) δ 7.93-7.80 (m, 1H), 7.72 (s, 1H), 7.55-7.33 (m, 2H), 7.14-6.97 (m, 2H), 6.87-6.71 (m, 2H), 4.71-4.47 (m, 3H), 4.26 (t, J = 3.9 Hz, 3H), 3.77 (d, J = 4.1 Hz, 3H), 3.73-3.53 (m, 2H), 3.47 (s, 2H), 3.37 (t, J = 9.6 Hz, 1H), 3.06-2.52 (m, 7H), 2.41 (d, J = 5.5 Hz, 1H), 2.32-1.78 (m, 6H), 1.69 (t, J = 9.6 Hz, 1H) | 12 mg, white solid |

| Example No. | Structure & Conditions | Analytical Data | Mass, % yield, state |
|---|---|---|---|
| M05394 | 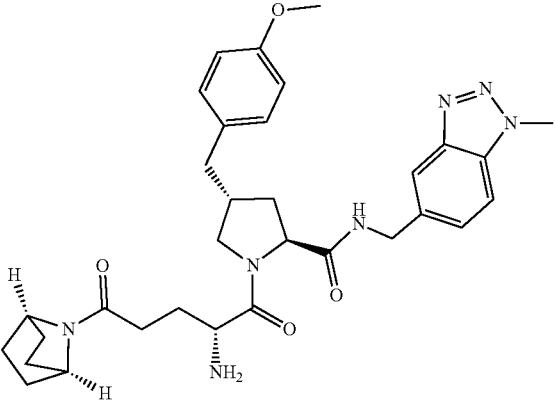 [SMILES: COc1ccc(C[C@@H]2C[C@@H](C(=O)NCc3ccc4c(c3)nnn4C)N(C(=O)[C@H](N)CCC(=O)N3[C@H]4CC[C@@H]3CC4)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-5-(7-Aza-bicyclo[2.2.1]hept-7-yl)-2-tert-butoxycarbonylamino-5-oxo-pentanoic acid<br>Step 1 & 3: GM1 with HATU & DIPEA in DCM; Step 2 & 4: GM2A | ANALPH2_MEOH_QC_v 1, Rt: 5.68 min, m/z 588.5 [M + H]+<br>ANALPH9_MEOH_QC_v 1, Rt: 7.33 min, m/z 588.4 [M + H]+ | 27 mg, white solid |
| M05397 | 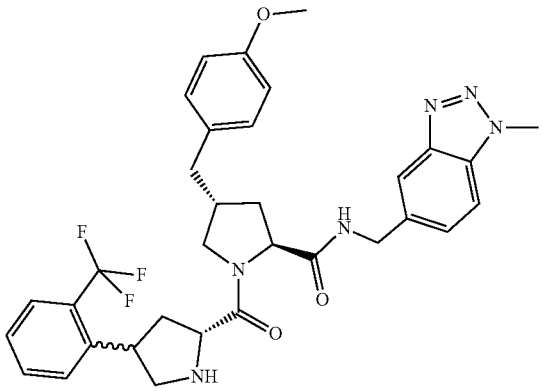 [SMILES: COc1ccc(C[C@@H]2C[C@@H](C(=O)NCc3ccc4c(c3)nnn4C)N(C(=O)[C@H]3CC(c4ccccc4C(F)(F)F)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(2-Trifluoromethyl-phenyl)-pyrrolidine-1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 6.18 min, m/z 621.4 [M + H]+<br>ANALPH9_MEOH_QC_v 1, Rt: 8.17 min, m/z 621.4 [M + H]+ | 10 mg, white solid |
| M05398 | 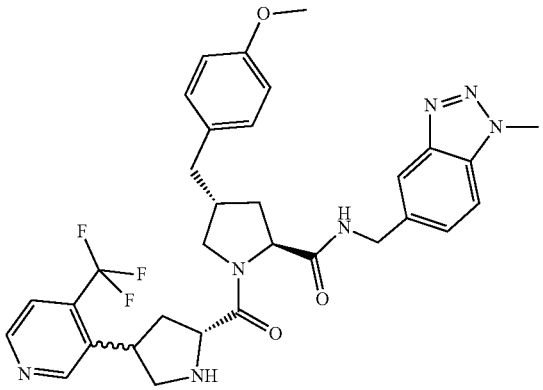 [SMILES: COc1ccc(C[C@@H]2C[C@@H](C(=O)NCc3ccc4c(c3)nnn4C)N(C(=O)[C@H]3CC(c4cnccc4C(F)(F)F)CN3)C2)cc1] | ANALPH9_MEOH_QC_v 1, Rt: 7.73 min, m/z 622.4 [M + H]+<br>ANALPH2_MEOH_QC_v 1, Rt: 5.65 min, m/z 622.3 [M + H]+ | 3 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-4-(4-Trifluoromethyl-pyridin-3-yl)-pyrrolidine-1,2-dicarboxylic acid 1-tert-butyl ester<br>Step 1 & 3: GM1 with HATU & DIPEA in DMF; Step 2 & 4: GM2A | | |
| M05399 | 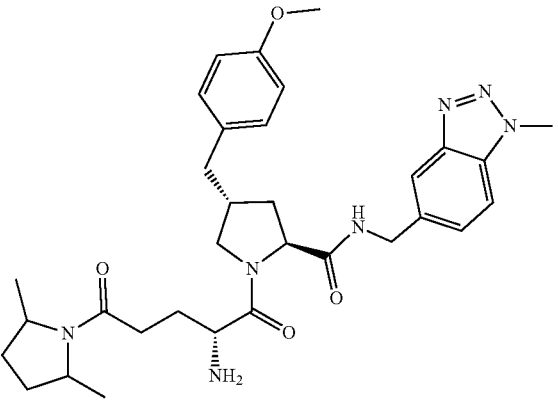 [SMILES: COc1ccc(C[C@@H]2C[C@@H](C(=O)NCc3ccc4c(c3)nnn4C)N(C(=O)[C@H](N)CCC(=O)N3C(C)CCC3C)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-(2,5-dimethyl-pyrrolidin-1-yl)-5-oxo-pentanoic acid<br>Step 1 & 3: GM1 with HATU & DIPEA in DCM; Step 2 & 4: GM2A | ANALPH9_MEOH_QC_v 1, Rt: 7.50 min, m/z 590.5 [M + H]+<br>ANALPH2_MEOH_QC_v 1, Rt: 5.84 min, m/z 590.4 [M + H]+ | 12 mg, white solid |
| M05400 | 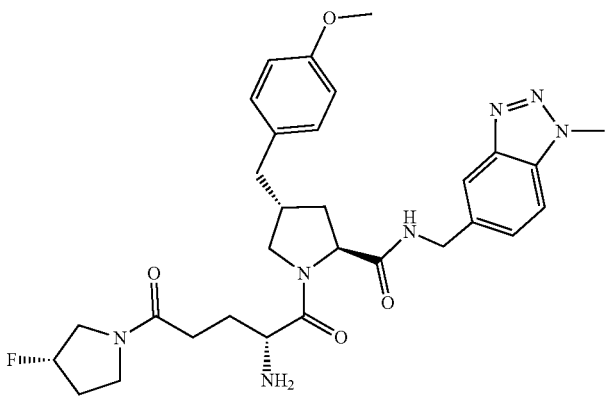 [SMILES: COc1ccc(C[C@@H]2C[C@@H](C(=O)NCc3ccc4c(c3)nnn4C)N(C(=O)[C@H](N)CCC(=O)N3CC[C@H](F)C3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-((S)-3-fluoro-pyrrolidin-1-yl)-5-oxo-pentanoic acid<br>Step 1 & 3: GM1 with HATU & DIPEA in DCM; Step 2 GM2A<br>Step 4: GM2A | ANALPH9_MEOH_QC_v 1, Rt: 6.89 min, m/z 580.4 [M + H]+<br>ANALPH2_MEOH_QC_v 1, Rt: 5.41 min, m/z 580.4 [M + H]+ | 50 mg, white solid |

| Example No. | Structure & Conditions | Analytical Data | Mass, % yield, state |
|---|---|---|---|
| M05401 | 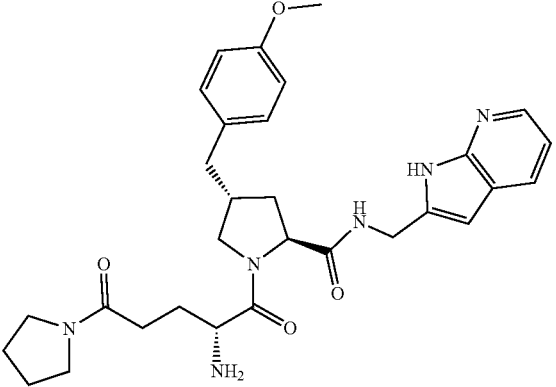 [SMILES: COc1ccc(C[C@@H]2C[C@@H](C(=O)NCc3cc4cccnc4[nH]3)N(C(=O)[C@H](N)CCC(=O)N3CCCC3)C2)cc1]<br>RgA: 1H-pyrrolo[2,3-B]pyridine-2-ylmethanamine<br>RgB: boc-(R)-γ-(4-methoxybenzyl)-L-proline<br>RgD: (R)-2-tert-Butoxycarbonylamino-5-((S)-2-cyano-pyrrolidin-1-yl)-5-oxo-pentanoic acid<br>Step 1 & 3: GM1 with HATU & DIPEA in DCM; Step 2 & 4: GM2A | ANALPH2_MEOH_QC_v 1, Rt: 5.48 min, m/z 547.5 [M + H]+<br>ANALPH9_MEOH_QC_v 1, Rt: 7.49 min, m/z 547.5 [M + H]+ | 46 mg, white solid |
| M05402 | 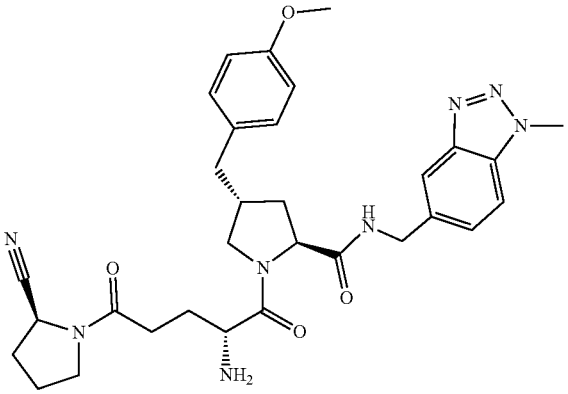 [SMILES: COc1ccc(C[C@@H]2C[C@@H](C(=O)NCc3ccc4c(c3)nnn4C)N(C(=O)[C@H](N)CCC(=O)N3CCC[C@H]3C#N)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-((S)-2-cyano-pyrrolidin-1-yl)-5-oxo-pentanoic acid<br>Step 1 & 3: GM1 with HATU & DIPEA in DCM; Step 2 & 4: GM2A | ANALPH9_MEOH_QC_v 1, Rt: 6.86 min, m/z 587.4 [M + H]+<br>ANALPH2_MEOH_QC_v 1, Rt: 5.41 min, m/z 587.4 [M + H]+ | 31 mg, white solid |
| M05404 | 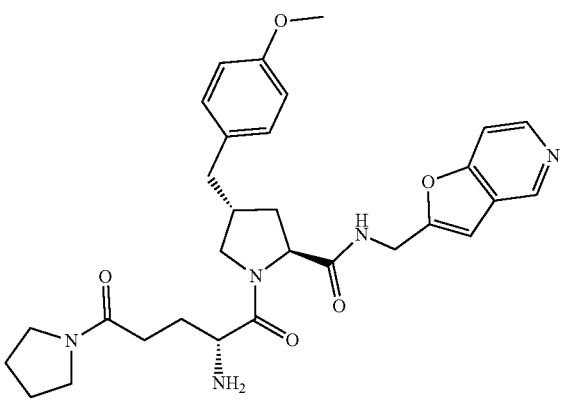 [SMILES: COc1ccc(C[C@@H]2C[C@@H](C(=O)NCc3cc4cnccc4o3)N(C(=O)[C@H](N)CCC(=O)N3CCCC3)C2)cc1] | ANALPH9_MEOH_QC_v 1, Rt: 7.19 min, m/z 548.4 [M + H]+<br>ANALPH2_MEOH_QC_v 1, Rt: 4.16 min, m/z 548.4 [M + H]+ | 31 mg, white solid |

| Example No. | Structure & Conditions | Analytical Data | Mass, % yield, state |
|---|---|---|---|
| | RgA: Furo[3,2-c]pyridine-2-ylmethylamine dihydrochloride<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | | |
| M05405 | 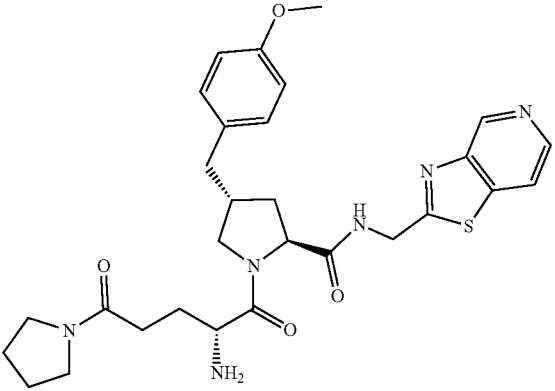 [SMILES: COc1ccc(C[C@@H]2C[C@@H](C(=O)NCc3nc4cnccc4s3)N(C(=O)[C@H](N)CCC(=O)N3CCCC3)C2)cc1]<br>RgA: {[1,3]thiazolo[4,5-c]pyridine-2-yl}methylamine dihydrochloride<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HBTU & DIPEA in DMF; Step 2 & 4: GM2A | ANALPH2_MEOH_QC_v 1, Rt: 5.07 min, m/z 564.4 [M + H]+<br>ANALPH9_MEOH_QC_v 1, Rt: 7.10 min, m/z 564.4 [M + H]+ | 15 mg, white solid |
| M05406 | 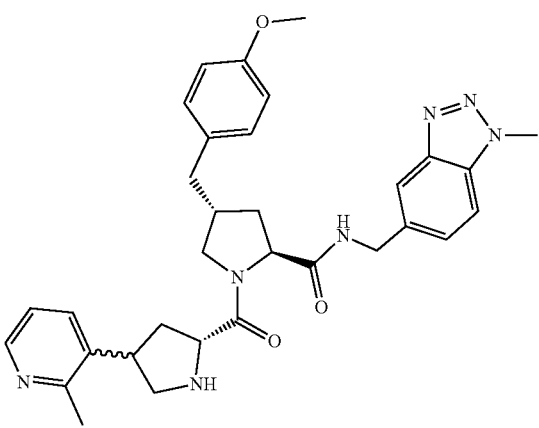 [SMILES: COc1ccc(C[C@@H]2C[C@@H](C(=O)NCc3ccc4c(c3)nnn4C)N(C(=O)[C@H]3CC(c4cccnc4C)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(2-Methyl-pyridin-3-yl)-pyrrolidine-1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 4.38 min, m/z 568.4 [M + H]+<br>ANALPH9_MEOH_QC_v 1, Rt: 7.24 min, m/z 568.5 [M + H]+ | 8 mg, white solid |

-continued

| Example No. | Structure & Conditions | Analytical Data | Mass, % yield, state |
|---|---|---|---|
| M05407 | 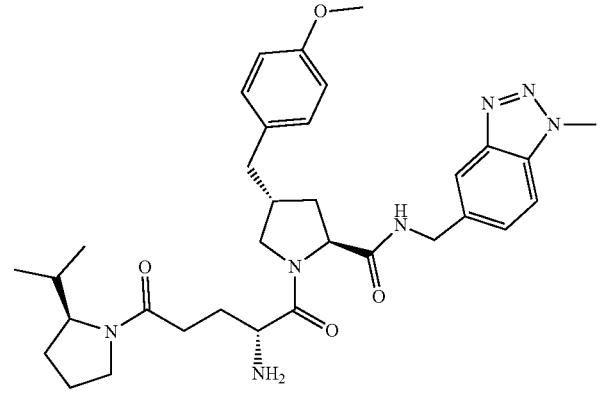 [SMILES: COc1ccc(C[C@@H]2C[C@@H](C(=O)NCc3ccc4c(c3)nnn4C)N(C(=O)[C@H](N)CCC(=O)N3CCC[C@H]3C(C)C)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-((S)-2-isopropyl-pyrrolidin-1-yl)-5-oxo-pentanoic acid<br>Step 1 & 3: GM1 with HATU & DIPEA in DCM; Step 2 & 4: GM2A | ANALPH2_MEOH_QC_v 1, Rt: 6.17 min, m/z 604.5 [M + H]+<br>ANALPH9_MEOH_QC_v 1, Rt: 7.81 min, m/z 604.5 [M + H]+ | 32 mg, white solid |
| M05408 | 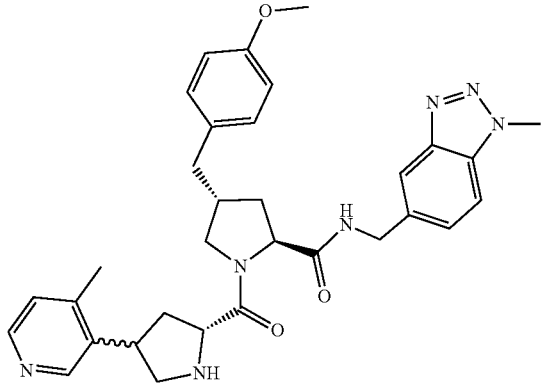 [SMILES: COc1ccc(C[C@@H]2C[C@@H](C(=O)NCc3ccc4c(c3)nnn4C)N(C(=O)[C@H]3CC(c4cnccc4C)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(4-Methyl-pyridin-3-yl)-pyrrolidine-1,2-dicarboxylic acid 1-tert-butyl ester<br>Step 1 & 3: GM1 with HATU & DIPEA in DMF; Step 2 & 4: GM2A | ANALPH2_MEOH_QC_v 1, Rt: 4.51 min, m/z 568.4 [M + H]+<br>ANALPH9_MEOH_QC_v 1, Rt: 7.30 min, m/z 568.4 [M + H]+ | 8 mg, white solid |
| M05409 | 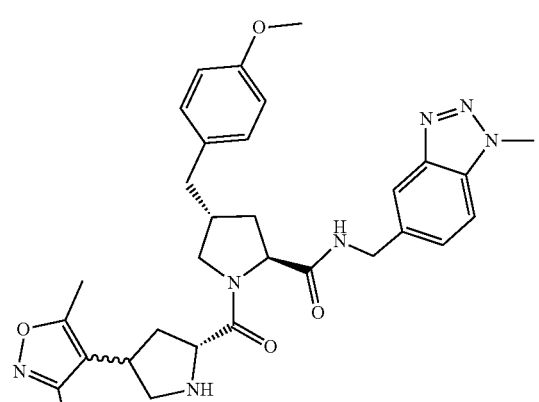 | ANALPH2_MEOH_QC_v 1, Rt: 5.38 min, m/z 572.4 [M + H]+<br>ANALPH9_MEOH_QC_v 1, Rt: 7.21 min, m/z 572.4 [M + H]+ | 20 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-4-(3,5-Dimethyl-isoxazol-4-yl)-pyrrolidine-1,2-dicarboxylic acid 1-tert-butyl ester<br>Step 1 & 3: GM1 with HATU & DIPEA in DMF; Step 2 & 4: GM2A | | |
| M05410 | 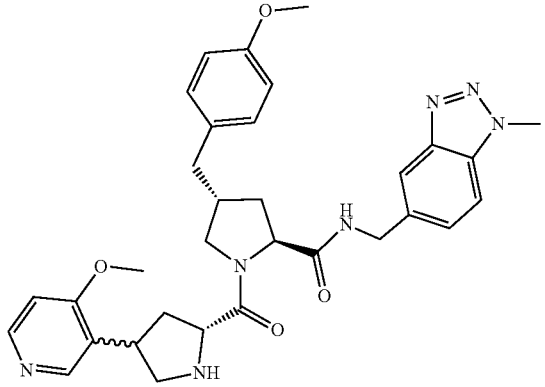 [SMILES: COc1ccc(C[C@@H]2C[C@@H](C(=O)NCc3ccc4c(c3)nnn4C)N(C(=O)[C@H]3CC(c4cnccc4OC)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(4-Methoxy-pyridin-3-yl)-pyrrolidine-1,2-dicarboxylic acid 1-tert-butyl ester<br>Step 1 & 3: GM1 with HATU & DIPEA in DMF; Step 2 and 4: GM2A | ANALPH2_MEOH_QC_v 1, Rt: 4.16 min, m/z 584.4 [M + H]+<br>ANALPH9_MEOH_QC_v 1, Rt: 7.20 min, m/z 584.4 [M + H]+ | 13 mg, white solid |
| M05411 | 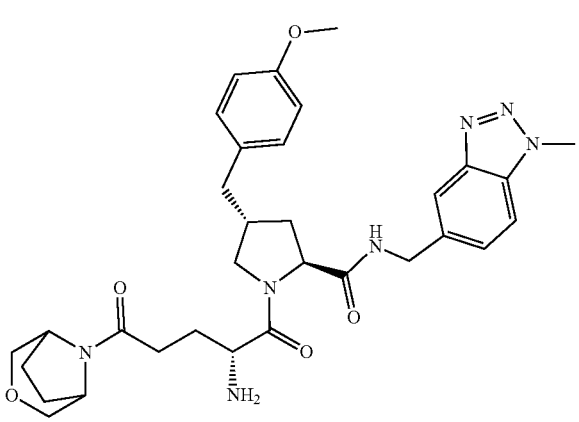 [SMILES: COc1ccc(C[C@@H]2C[C@@H](C(=O)NCc3ccc4c(c3)nnn4C)N(C(=O)[C@H](N)CCC(=O)N3C4CCC3COC4)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-(3-oxa-8-aza-bicyclo[3.2.1]oct-8-yl)-5-oxo-pentanoic acid<br>Step 1 & 3: GM1 with HATU & DIPEA in DCM; Step 2 & 4: GM2A | ANALPH9_MEOH_QC_v 1, Rt: 6.96 min, m/z 604.3 [M + H]+<br>ANALPH2_MEOH_QC_v 1, Rt: 5.40 min, m/z 604.4 [M + H]+ | 37 mg, white solid |

| Example No. | Structure & Conditions | Analytical Data | Mass, % yield, state |
|---|---|---|---|
| M05412 | 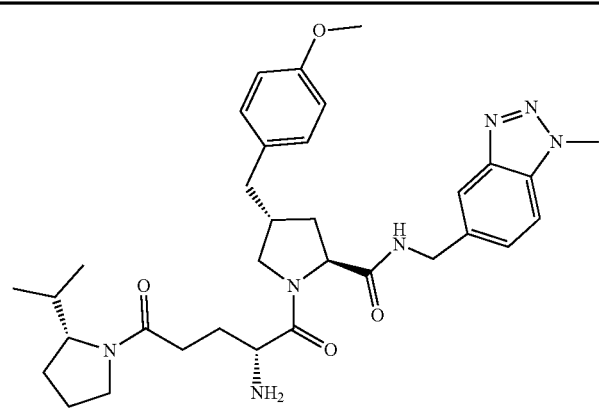<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-5-((R)-2-isopropyl-pyrrolidin-1-yl)-5-oxo-pentanoic acid<br>Step 1 & 3: GM1 with HATU & DIPEA in DCM; Step 2 GM2A<br>Step 4: GM2A | ANALPH9_MEOH_QC_v 1, Rt: 7.81 min, m/z 604.5 [M + H]+<br>ANALPH2_MEOH_QC_v 1, Rt: 6.18 min, m/z 604.5 [M + H]+ | 22 mg, white solid |
| M05413 | 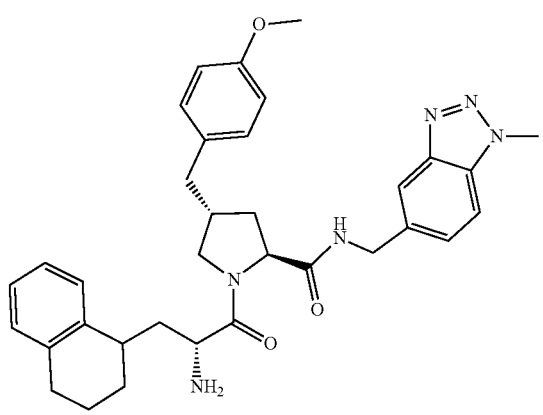 [SMILES: COc1ccc(C[C@@H]2C[C@@H](C(=O)NCc3ccc4c(c3)nnn4C)N(C(=O)[C@H](N)CC3CCCc4ccccc43)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-2-tert-Butoxycarbonylamino-3-(1,2,3,4-tetrahydro-naphthalen-1-yl)-propionic acid<br>Step 1 & 3: GM1 with HATU & DIPEA in DCM; Step 2 & 4: GM2A | ANALPH2_MEOH_QC_v 1, Rt: 6.45 min, m/z 581.4 [M + H]+<br>ANALPH9_MEOH_QC_v 1, Rt: 8.11 min, m/z 581.5 [M + H]+ | 30 mg, white solid |

| Example No. | Structure & Conditions | Analytical Data | Mass, % yield, state |
|---|---|---|---|
| M05415 | 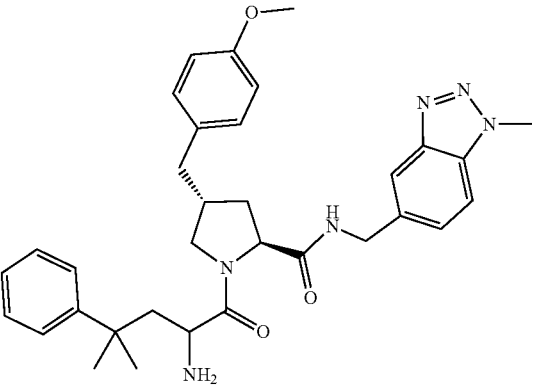 [SMILES: COc1ccc(C[C@@H]2C[C@@H](C(=O)NCc3ccc4c(c3)nnn4C)N(C(=O)C(N)CC(C)(C)c3ccccc3)C2)cc1]<br>RgA: C-(1-Methyl-1H-benzotriazol-5-yl)-methylamine<br>RgB: boc-(R)-γ-(4-methoxybenzyl)-L-proline<br>RgD: 2-Amino-4-methyl-4-phenyl-pentanoic acid<br>Step 1 & 3: GM1 with HBTU & DIPEA in DMF; Step 2 & 4: GM2A | ANALPH2_MEOH_QC_v 1, Rt: 6.40 min, m/z 569.4 [M + H]+<br>ANALPH9_MEOH_QC_v 1, Rt: 8.07 min, m/z 569.4 [M + H]+ | 4 mg, white solid |
| M05416 | 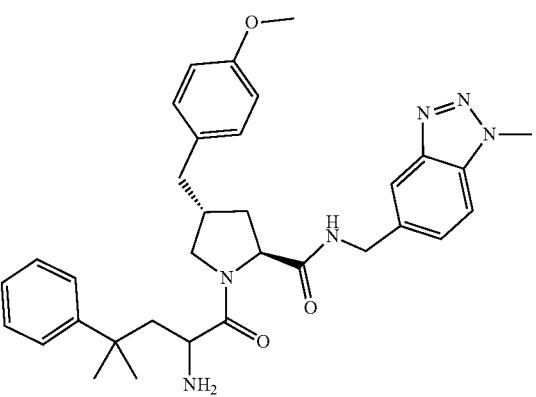 [SMILES: COc1ccc(C[C@@H]2C[C@@H](C(=O)NCc3ccc4c(c3)nnn4C)N(C(=O)C(N)CC(C)(C)c3ccccc3)C2)cc1]<br>RgA: C-(1-Methyl-1H-benzotriazol-5-yl)-methylamine<br>RgB: boc-(R)-γ-(4-methoxybenzyl)-L-proline<br>RgD: 2-Amino-4-methyl-4-phenyl-pentanoic acid<br>Step 1 & 3: GM1 with HBTU & DIPEA in DMF; Step 2 & 4: GM2A | ANALPH2_MEOH_QC_v 1, Rt: 6.31 min, m/z 569.4 [M + H]+<br>ANALPH9_MEOH_QC_v 1, Rt: 8.16 min, m/z 569.4 [M + H]+ | 6 mg, white solid |
| M05418 | 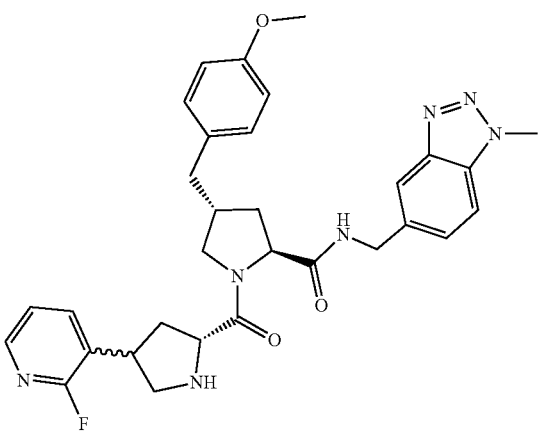 [SMILES: COc1ccc(C[C@@H]2C[C@@H](C(=O)NCc3ccc4c(c3)nnn4C)N(C(=O)[C@H]3CC(c4cccnc4F)CN3)C2)cc1] | ANALPH9_MEOH_QC_v 1, Rt: 7.21 min, m/z 572.4 [M + H]+<br>ANALPH2_MEOH_QC_v 1, Rt: 5.48 min, m/z 572.3 [M + H]+ | 10 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: (R)-4-(2-Fluoro-pyridin-3-yl)-pyrrolidine-1,2-dicarboxylic acid 1-tert-butyl ester<br>Step 1 & 3: GM1 with HATU & DIPEA in DMF; Step 2 & 4: GM2A | | |
| M05419 | 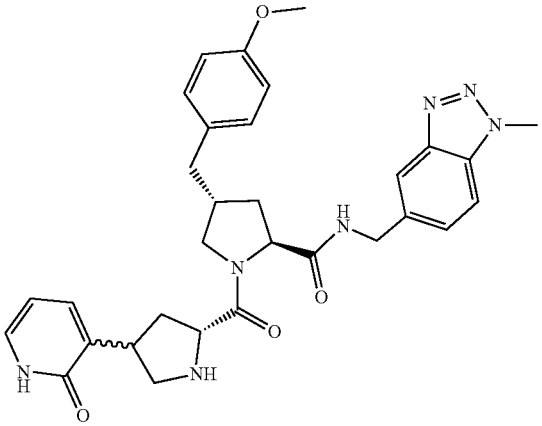 [SMILES: COc1ccc(C[C@@H]2C[C@@H](C(=O)NCc3ccc4c(c3)nnn4C)N(C(=O)[C@H]3CC(c4ccc[nH]c4=O)CN3)C2)cc1] | ANALPH9_MEOH_QC_v 1, Rt: 6.78 min, m/z 570.4 [M + H]+<br>ANALPH2_MEOH_QC_v 1, Rt: 5.29 min, m/z 570.3 [M + H]+<br>1H NMR (400 MHz, DMSO-D6) δ 11.47 (s, 1H), 8.65 (t, J = 6.0 Hz, 0.3H), 8.41 (t, J = 6.1 Hz, 0.7H), 7.79 (s, 1H), 7.70 (dd, J = 16.3, 8.5 Hz, 1H), 7.37 (dd, J = 8.7, 1.7 Hz, 1H), 7.25(dd, J = 6.9, 2.1 Hz, 1H), 7.18 (ddd, J = 14.1,6.6, 2.0 Hz, 1H), 7.11-7.03 (m, 2H), 6.85-6.77 (m, 2H), 6.08 (t, J = 6.6 Hz, 0.7H), 6.01 (t, J = 6.6 Hz, 0.3H), 4.36 (dd, J = 7.7, 4.8 Hz, 3H), 4.25 (s, 2.1H), 4.21 (s, 0.9H), 3.87 (t, J = 8.2 Hz, 1H), 3.75 (dd, J = 9.6, 6.6 Hz, 1H), 3.68 (d, J = 1.6 Hz, 3H), 3.59-3.42 (m, 1H), 3.17-2.89 (m, 2H), 2.81 (dd, J = 10.3, 7.7 Hz, 1H), 2.65-2.46 (m, 3H), 2.39 (dt, J = 12.3, 8.0 Hz, 1H), 1.95- 1.73 (m, 2H), 1.71-1.55 (m, 1H). | 10 mg, white solid |
| | RgA: C-(1-Methyl-1H-benzotriazol-5-yl)-methylamine<br>RgB: boc-(R)-γ-(4-methoxybenzyl)-L-proline<br>RgD: (R)-4-(2-Oxo-1,2-dihydro-pyridin-3-yl)-pyrrolidine-1,2-dicarboxylic acid 1-tert-butyl ester<br>Step 1 & 3: GM1 with HATU & DIPEA in DMF; Step 2 & 4: GM2A | | |
| M05421 | 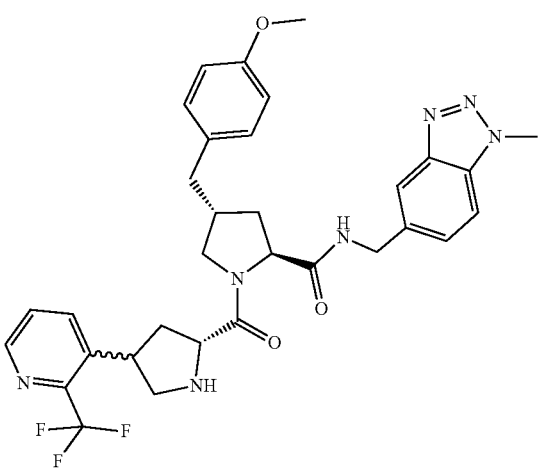 [SMILES: COc1ccc(C[C@@H]2C[C@@H](C(=O)NCc3ccc4c(c3)nnn4C)N(C(=O)[C@H]3CC(c4cccnc4C(F)(F)F)CN3)C2)cc1] | ANALPH9_MEOH_QC_v 1, Rt: 7.58 min, m/z 622.3 [M + H]+<br>ANALPH2_MEOH_QC_v 1, Rt: 5.63 min, m/z 622.3 [M + H]+ | 11 mg, white solid |
| | RgA: C-(1-Methyl-1H-benzotriazol-5-yl)-methylamine<br>RgB: boc-(R)-γ-(4-methoxybenzyl)-L-proline | | |

| Example No. | Structure & Conditions | Analytical Data | Mass, % yield, state |
|---|---|---|---|
| | RgD: (R)-4-(2-Trifluoromethyl-pyridin-3-yl)-pyrrolidine-1,2-dicarboxylic acid 1-tert-butyl ester<br>Step 1 & 3: GM1 with HATU & DIPEA in DMF; Step 2 & 4: GM2A | | |
| M05429 | 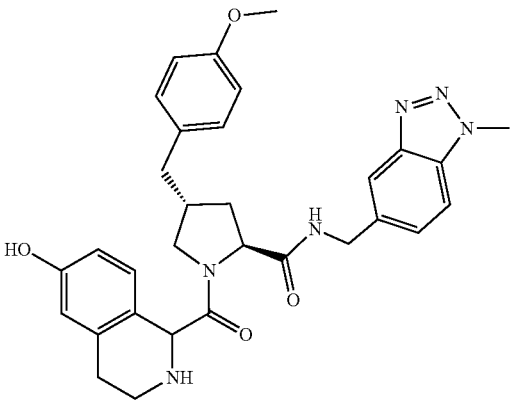 [SMILES: COc1ccc(C[C@@H]2C[C@@H](C(=O)NCc3ccc4c(c3)nnn4C)N(C(=O)C3NCCc4cc(O)ccc43)C2)cc1]<br>RgA: C-(1-Methyl-1H-benzotriazol-5-yl)-methylamine<br>RgB: boc-(R)-γ-(4-methoxybenzyl)-L-proline<br>RgD: 2-boc-6-hydroxy-1,2,3,4-tetrahydroisoquinoline-1-carboxylic acid<br>Step 1 & 3: GM1 with HATU & DIPEA in DCM; Step 2 & 4: GM2A | ANALPH9_MEOH_QC_v 1, Rt: 7.11 min, m/z 555.3 [M + H]+<br>ANALPH2_MEOH_QC_v 1, Rt: 5.38 min, m/z 555.3 [M + H]+ | 36 mg, white solid |
| M05430 | 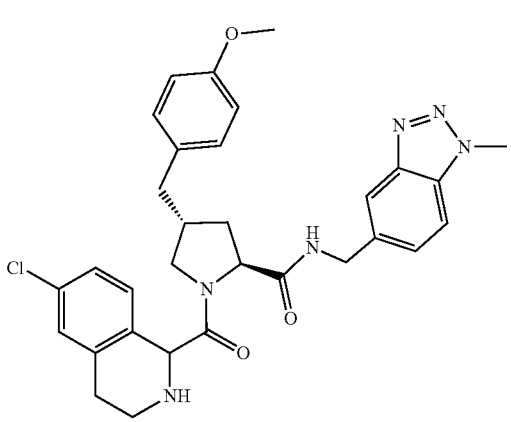 [SMILES: COc1ccc(C[C@@H]2C[C@@H](C(=O)NCc3ccc4c(c3)nnn4C)N(C(=O)C3NCCc4cc(Cl)ccc43)C2)cc1]<br>RgA: C-(1-Methyl-1H-benzotriazol-5-yl)-methylamine<br>RgB: boc-(R)-γ-(4-methoxybenzyl)-L-proline<br>RgD: 2-boc-6-chloro-3,4-dihydro-1H-isoquinoline-1-carboxylic acid<br>Step 1 & 3: GM1 with HATU & DIPEA in DCM; Step 2 & 4: GM2A | ANALPH2_MEOH_QC_v 1, Rt: 6.00 min, m/z 573.3 [M + H]+<br>ANALPH9_MEOH_QC_v 1, Rt: 7.93 min, m/z 573.3 [M + H]+ | 25 mg, white solid |

| Example No. | Structure & Conditions | Analytical Data | Mass, % yield, state |
|---|---|---|---|
| M05431 | 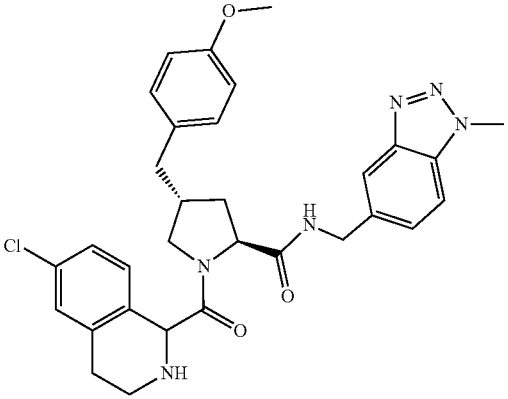 [SMILES: COc1ccc(C[C@@H]2C[C@@H](C(=O)NCc3ccc4c(c3)nnn4C)N(C(=O)C3NCCc4cc(Cl)ccc43)C2)cc1]<br>RgA: C-(1-Methyl-1H-benzotriazol-5-yl)-methylamine<br>RgB: boc-(R)-γ-(4-methoxybenzyl)-L-proline<br>RgD: 2-boc-6-chloro-3,4-dihydro-1H-isoquinoline-1-carboxylic acid<br>Step 1 & 3: GM1 with HATU & DIPEA in DCM; Step 2 & 4: GM2A | ANALPH9_MEOH_QC_v 1, Rt: 8.07 min, m/z 573.3 [M + H]+<br>ANALPH2_MEOH_QC_v 1, Rt: 6.16 min, m/z 573.3 [M + H]+ | 28 mg, white solid |
| M05441 | 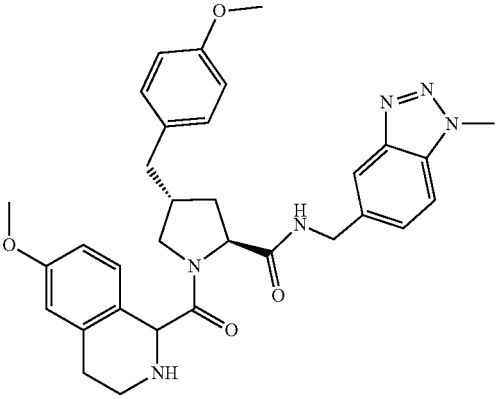 [SMILES: COc1ccc(C[C@@H]2C[C@@H](C(=O)NCc3ccc4c(c3)nnn4C)N(C(=O)C3NCCc4cc(OC)ccc43)C2)cc1]<br>RgA: C-(1-Methyl-1H-benzotriazol-5-yl)-methylamine<br>RgB: boc-(R)-γ-(4-methoxybenzyl)-L-proline<br>RgD: 2-boc-6-methoxy-3,4-dihydro-1H-isoquinoline-1-carboxylic acid<br>Step 1 & 3: GM1 with HATU & DIPEA in DCM; Step 2 & 4: GM2A | ANALPH2_MEOH_QC_v 1, Rt: 5.90 min, m/z 569.4 [M + H]+<br>ANALPH9_MEOH_QC_v 1, Rt: 7.59 min, m/z 569.4 [M + H]+ | 28 mg, white solid |
| M05442 | 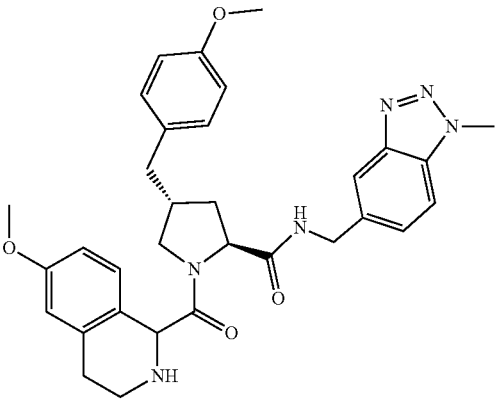 [SMILES: COc1ccc(C[C@@H]2C[C@@H](C(=O)NCc3ccc4c(c3)nnn4C)N(C(=O)C3NCCc4cc(OC)ccc43)C2)cc1] | ANALPH9_MEOH_QC_v 1, Rt: 7.71 min, m/z 569.4 [M + H]+<br>ANALPH2_MEOH_QC_v 1, Rt: 6.00 min, m/z 569.4 [M + H]+ | 31 mg, white solid |

| Example No. | Structure & Conditions | Analytical Data | Mass, % yield, state |
|---|---|---|---|
| | RgA: C-(1-Methyl-1H-benzotriazol-5-yl)-methylamine<br>RgB: boc-(R)-γ-(4-methoxybenzyl)-L-proline<br>RgD: 2-boc-6-methoxy-3,4-dihydro-1H-isoquinoline-1-carboxylic acid<br>Step 1 & 3: GM1 with HATU & DIPEA in DCM; Step 2 & 4: GM2A | | |
| M05446 | 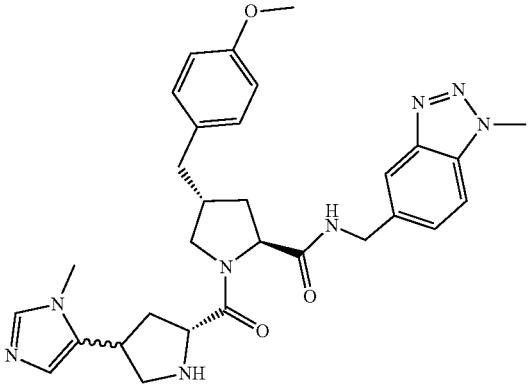 [SMILES: COc1ccc(C[C@@H]2C[C@@H](C(=O)NCc3ccc4c(c3)nnn4C)N(C(=O)[C@H]3CC(c4cncn4C)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(3-Methyl-3H-imidazol-4-yl) pyrolidine-1,2-dicarboxylic acid 1-tert-butyl ester<br>Step 1 & 3: GM1 with HATU & DIPEA in DMF; Step 2 & 4: GM2A | ANALPH9_MEOH_QC_v 1, Rt: 6.94 min, m/z 557.4 [M + H]+<br>ANALPH2_MEOH_QC_v 1, Rt: 4.16 min, m/z 557.4 [M + H]+ | 15 mg, white solid |
| M05447 | 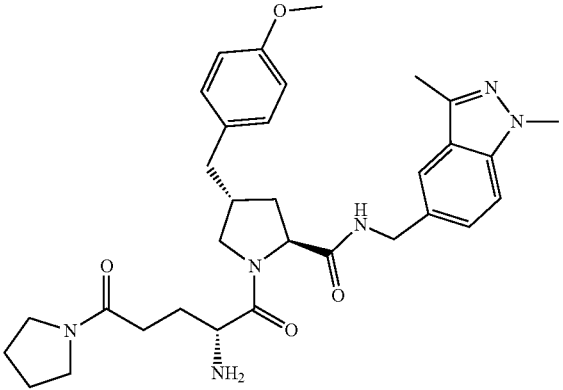 [SMILES: COc1ccc(C[C@@H]2C[C@@H](C(=O)NCc3ccc4c(c3)c(C)nn4C)N(C(=O)[C@H](N)CCC(=O)N3CCCC3)C2)cc1]<br>RgA: C-(1,3-Dimethyl-1H-indazol-5-yl)-methylamine hydrochloride<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DCM; Step 2 & 4: GM2A | ANALPH2_MEOH_QC_v 1, Rt: 6.02 min, m/z 575.5 [M + H]+<br>ANALPH9_MEOH_QC_v 1, Rt: 7.60 min, m/z 575.5 [M + H]+ | 64 mg, white solid |

| Example No. | Structure & Conditions | Analytical Data | Mass, % yield, state |
|---|---|---|---|
| M05448 | 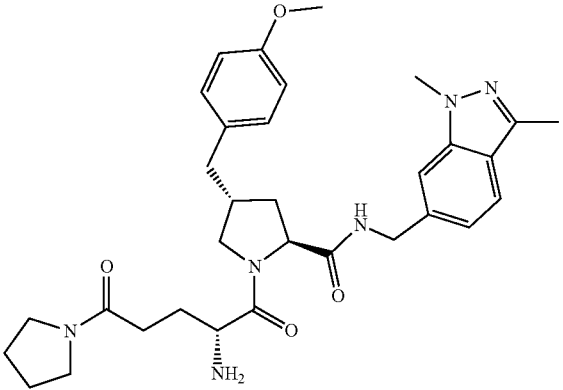 [SMILES: COc1ccc(C[C@@H]2C[C@@H](C(=O)NCc3ccc4c(C)nn(C)c4c3)N(C(=O)[C@H](N)CCC(=O)N3CCCC3)C2)cc1]<br>RgA: C-(1,3-Dimethyl-1H-indazol-6-yl)-methylamine hydrochloride<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DCM; Step 2 & 4: GM2A | ANALPH9_MEOH_QC_v 1, Rt: 7.71 min, m/z 575.4 [M + H]+<br>ANALPH2_MEOH_QC_v 1, Rt: 6.08 min, m/z 575.4 [M + H]+ | 12 mg, white solid |
| M05449 | 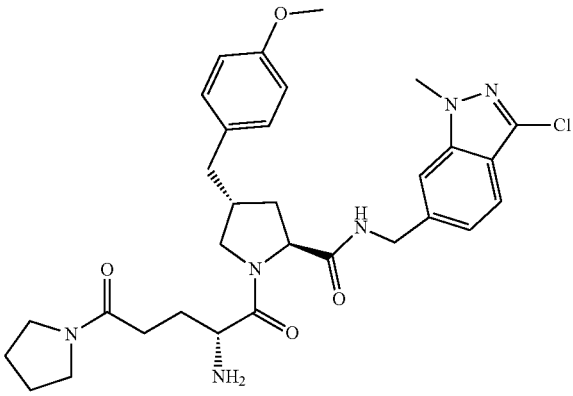 [SMILES: COc1ccc(C[C@@H]2C[C@@H](C(=O)NCc3ccc4c(Cl)nn(C)c4c3)N(C(=O)[C@H](N)CCC(=O)N3CCCC3)C2)cc1]<br>RgA: C-(3-Chloro-1-methyl-1H-indazol-6-yl)-methylamine hydrochloride<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DCM; Step 2 & 4: GM2A | ANALPH9_MEOH_QC_v 1, Rt: 7.99 min, m/z 595.4 [M + H]+<br>ANALPH2_MEOH_QC_v 1, Rt: 6.37 min, m/z 595.3 [M + H]+ | 62 mg, white solid |
| M05453 | 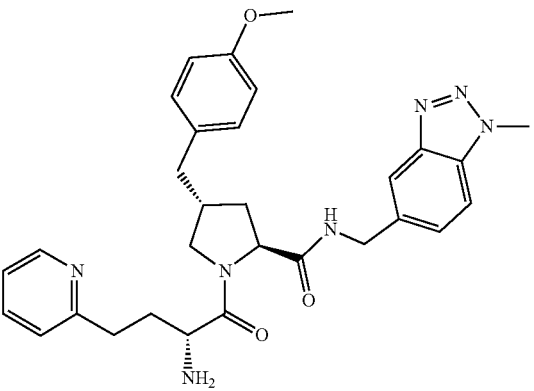 [SMILES: COc1ccc(C[C@@H]2C[C@@H](C(=O)NCc3ccc4c(c3)nnn4C)N(C(=O)[C@H](N)CCc3ccccn3)C2)cc1]<br>RgA: C-(1-Methyl-1H-benzotriazol-5-yl)-methylamine | ANALPH2_MEOH_QC_v 1, Rt: 5.18 min, m/z 542.4 [M + H]+<br>ANALPH9_MEOH_QC_v 1, Rt: 7.22 min, m/z 542.4 [M + H]+ | 20 mg, White solid |

| Example No. | Structure & Conditions | Analytical Data | Mass, % yield, state |
|---|---|---|---|
| | RgB: boc-(R)-γ-(4-methoxybenzyl)-L-proline<br>RgD: (R)-2-(tert-Butoxycarbonylamino)-4-(pyridin-2-yl)butanoic acid<br>Step 1 & 3: GM1 with HBTU & DIPEA in DCM; Step 2 & 4: GM2A | | |
| M05454 | 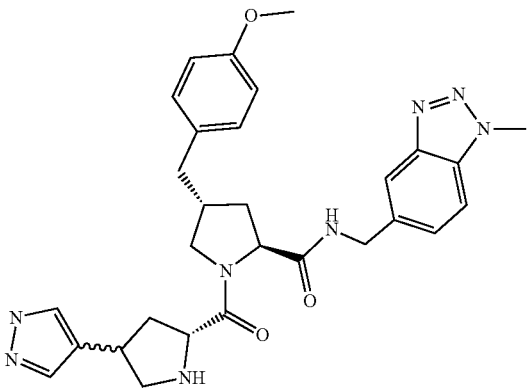 [SMILES: COc1ccc(C[C@@H]2C[C@@H](C(=O)NCc3ccc4c(c3)nnn4C)N(C(=O)[C@H]3CC(c4cn[nH]c4)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-(1H-Pyrazol-4-yl)-pyrrolidine-2-carboxylic acid<br>Step 1 & 3: GM1 with HATU & DIPEA in DMF; Step 2 & 4: GM2A | ANALPH9_MEOH_QC_v 1, Rt: 6.88 min, m/z 543.5 [M + H]+<br>ANALPH2_MEOH_QC_v 1, Rt: 5.16 min, m/z 543.5 [M + H]+ | 8 mg, white solid |
| M05459 | 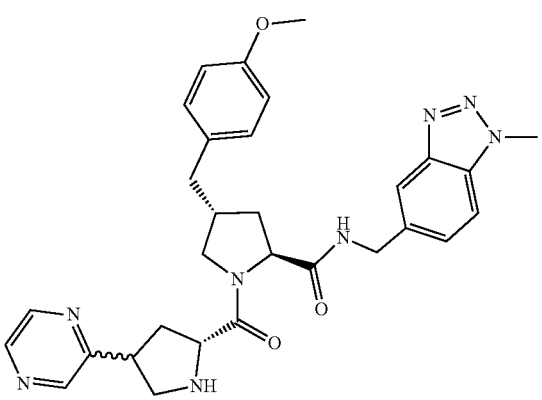 [SMILES: COc1ccc(C[C@@H]2C[C@@H](C(=O)NCc3ccc4c(c3)nnn4C)N(C(=O)[C@H]3CC(c4cnccn4)CN3)C2)cc1]<br>RgA: C-(1-Methyl-1H-benzotriazol-5-yl)-methylamine<br>RgB: boc-(R)-γ-(4-methoxybenzyl)-L-proline<br>RgD: (R)-4-Pyrazin-2-yl-pyrrolidine-2-carboxylic acid<br>Step 1 & 3: GM1 with HATU & DIPEA in DMF; Step 2 & 4: GM2A | ANALPH9_MEOH_QC_v 1, Rt: 6.98 min, m/z 555.3 [M + H]+<br>ANALPH2_MEOH_QC_v 1, Rt: 5.26 min, m/z 555.3 [M + H]+ | 30 mg, pale yellow solid |

| Example No. | Structure & Conditions | Analytical Data | Mass, % yield, state |
|---|---|---|---|
| M05462 | 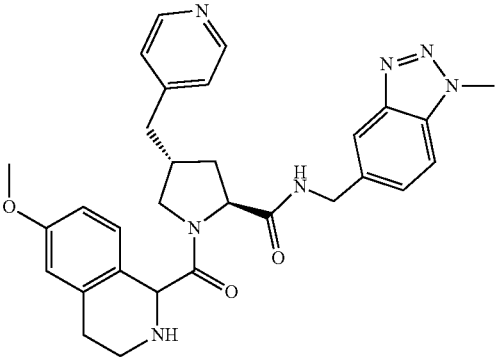 [SMILES: COc1ccc2c(c1)CCNC2C(=O)N1C[C@H](Cc2ccncc2)C[C@H]1C(=O)NCc1ccc2c(c1)nnn2C]<br>RgA: C-(1-Methyl-1H-benzotriazol-5-yl)-methylamine<br>RgB: boc-(R)-γ-(4-pyridylmethyl)-L-proline<br>RgD: 2-Boc-6-methoxy-3,4-dihydro-1H-isoquinoline-1-carboxylic acid<br>Step 1 & 3: GM1 with HBTU & DIPEA in DCM; Step 2 & 4: GM2A | ANALPH2_MEOH_QC_v 1, Rt: 3.53 min, m/z 540.4 [M + H]+<br>ANALPH9_MEOH_QC_v 1, Rt: 6.78 min, m/z 540.4 [M + H]+ | 4 mg, White solid |
| M05463 | 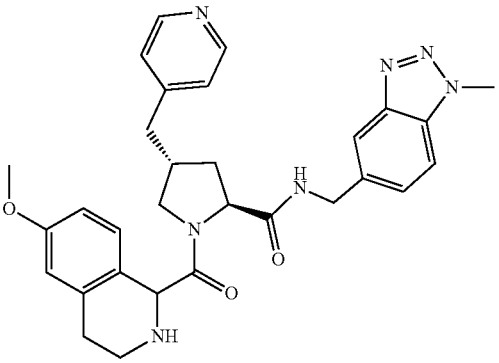 [SMILES: COc1ccc2c(c1)CCNC2C(=O)N1C[C@H](Cc2ccncc2)C[C@H]1C(=O)NCc1ccc2c(c1)nnn2C]<br>RgA: C-(1-Methyl-1H-benzotriazol-5-yl)-methylamine<br>RgB: boc-(R)-γ-(4-pyridylmethyl)-L-proline<br>RgD: 2-Boc-6-methoxy-3,4-dihydro-1H-isoquinoline-1-carboxylic acid<br>Step 1 & 3: GM1 with HBTU & DIPEA in DCM; Step 2 & 4: GM2A | ANALPH9_MEOH_QC_v 1, Rt: 6.95 min, m/z 540.4 [M + H]+<br>ANALPH2_MEOH_QC_v 1, Rt: 3.80 min, m/z 540.4 [M + H]+ | 6 mg, White solid |
| M05464 | 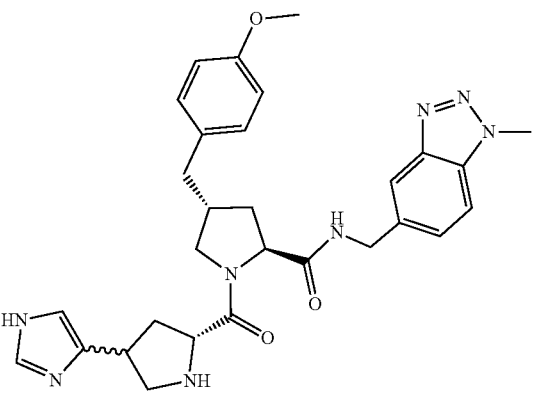 [SMILES: COc1ccc(C[C@@H]2C[C@@H](C(=O)NCc3ccc4c(c3)nnn4C)N(C(=O)[C@H]3CC(c4c[nH]cn4)CN3)C2)cc1]<br>RgA: C-(1-Methyl-1H-benzotriazol-5-yl)-methylamine | ANALPH2_MEOH_QC_v 1, Rt: 4.24 min, m/z 543.4 [M + H]+<br>ANALPH9_MEOH_QC_v 1, Rt: 6.84 min, m/z 543.4 [M + H]+ | 3 mg, off-White solid |

| Example No. | Structure & Conditions | Analytical Data | Mass, % yield, state |
|---|---|---|---|
| | RgB: boc-(R)-γ-(4-methoxybenzyl)-L-proline<br>RgD: (R)-4-(1-Trityl-1H-imidazol-4-yl)-pyrrolidine-1,2-dicarboxylic acid 1-tert-butyl ester<br>Step 1 & 3: GM1 with HATU & DIPEA in DMF; Step 2 & 4: GM2A | | |
| M05465 | 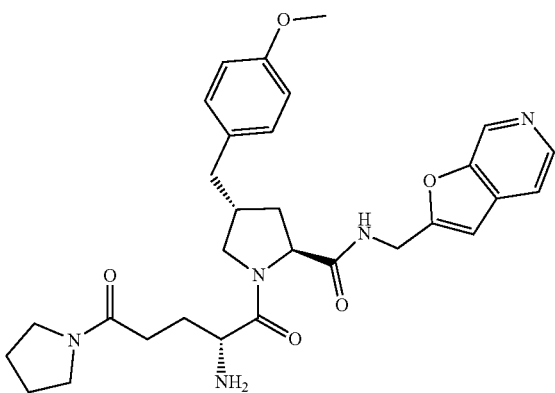 [SMILES: COc1ccc(C[C@@H]2C[C@@H](C(=O)NCc3cc4ccncc4o3)N(C(=O)[C@H](N)CCC(=O)N3CCCC3)C2)cc1]<br>RgA: C-Furo[2,3-c]pyridin-2-yl-methylamine<br>RgB: boc-(R)-γ-(4-methoxybenzyl)-L-proline<br>RgD: (R)-2-tert-Butoxycarbonylamino-5-oxo-5-pyrrolidin-1-yl-pentanoic acid<br>Step 1 & 3: GM1 with HATU & DIPEA in DCM; Step 2 & 4: GM2A | ANALPH9_MEOH_QC_v 1, Rt: 7.26 min, m/z 548.4 [M + H]+<br>ANALPH2_MEOH_QC_v 1, Rt: 4.28 min, m/z 548.4 [M + H]+ | 38 mg, off-white solid |
| M05470 | 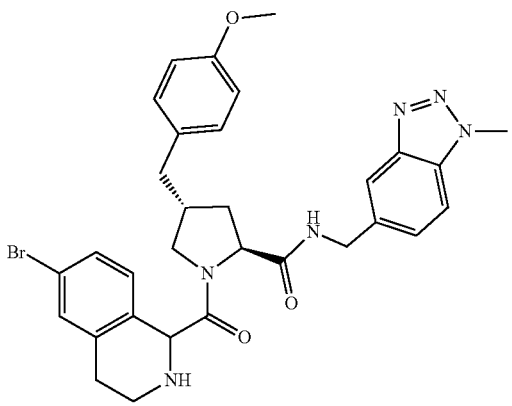 [SMILES: COc1ccc(C[C@@H]2C[C@@H](C(=O)NCc3ccc4c(c3)nnn4C)N(C(=O)C3NCCc4cc(Br)ccc43)C2)cc1]<br>RgA: C-(1-Methyl-1H-benzotriazol-5-yl)-methylamine<br>RgB: boc-(R)-γ-(4-methoxybenzyl)-L-proline<br>RgD: 2-Boc-6-Bromo-3,4-dihydro-1H-isoquinoline-1-carboxylic acid<br>Step 1 & 3: GM1 with HATU & DIPEA in DCM; Step 2 & 4: GM2A | ANALPH9_MEOH_QC_v 1, Rt: 8.05 min, m/z 617.2 [M + H]+<br>ANALPH2_MEOH_QC_v 1, Rt: 6.19 min, m/z 7.17 [M + H]+ | 11 mg. White solid |

| Example No. | Structure & Conditions | Analytical Data | Mass, % yield, state |
|---|---|---|---|
| M05471 | 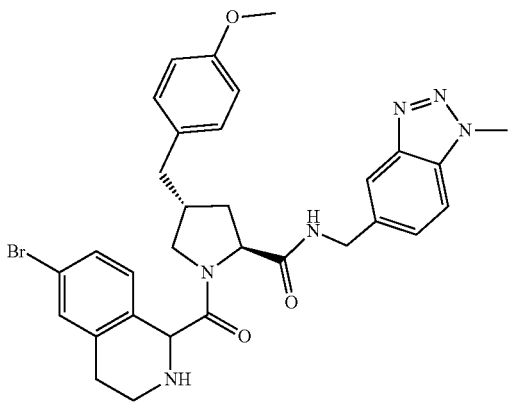<br>RgA: C-(1-Methyl-1H-benzotriazol-5-yl)-methylamine<br>RgB: boc-(R)-γ-(4-methoxybenzyl)-L-proline<br>RgD: 2-Boc-6-methoxy-3,4-dihydro-1H-isoquinoline-1-carboxylic acid<br>Step 1 & 3: GM1 with HATU & DIPEA in DCM; Step 2 & 4: GM2A | ANALPH9_MEOH_QC_v 1, Rt: 8.19 min, m/z 617.3 [M + H]+<br>ANALPH2_MEOH_QC_v 1, Rt: 6.34 min, m/z 617.2 [M + H]+ | 12 mg, White solid |
| M05490 | 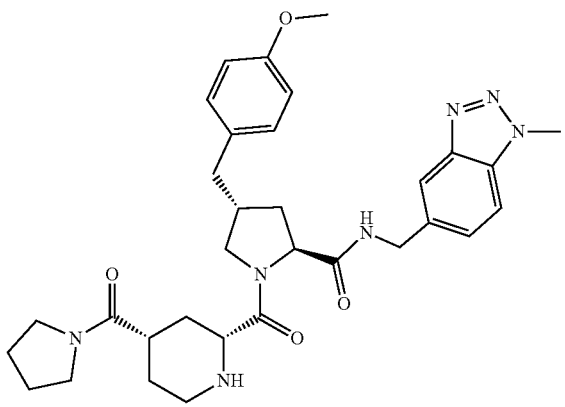 [SMILES: COc1ccc(C[C@@H]2C[C@@H](C(=O)NCc3ccc4c(c3)nnn4C)N(C(=O)[C@H]3C[C@@H](C(=O)N4CCCC4)CCN3)C2)cc1]<br>RgA: C-(1-Methyl-1H-benzotriazol-5-yl)-methylamine<br>RgB: boc-(R)-γ-(4-methoxybenzyl)-L-proline<br>RgD: (1R,3S)-3-(Pyrrolidine-1-carbonyl)-cyclohexanecarboxylic acid<br>Step 1 & 3: GM1 with HATU & DIPEA in DCM; Step 2 & 4: GM2A | ANALPH9_MEOH_QC_v 1, Rt: 7.29 min, m/z 588.4 [M + H]+<br>ANALPH2_MEOH_QC_v 1, Rt: 5.35 min, m/z 99.18 [M + H]+ | 25 mg, White solid |

The following compounds were made by analogous methods (General Scheme 1) omitting step 4:

| Example No. | Structure & Conditions | Analytical Data | Mass, state |
|---|---|---|---|
| GS3-int1 | RgA: C-(1-Methyl-1H-benzotriazol-5-yl)-methylamine<br>RgB: (2S, 4S)-Fmoc-4-amino-1-Boc-pyrrolidin-2-carboxylic acid<br>RgD: N-Boc-Homophenylalanine<br>Step 1 & 3: GM1 HBTU and DIPEA in DMF<br>Step 2: GM2A | ANALPH2_MEOH_4 min, Rt: 3.69 min, m/z 758.4 [M + H]+ | 1.02 g, cream foam |
| GS3-int2 | 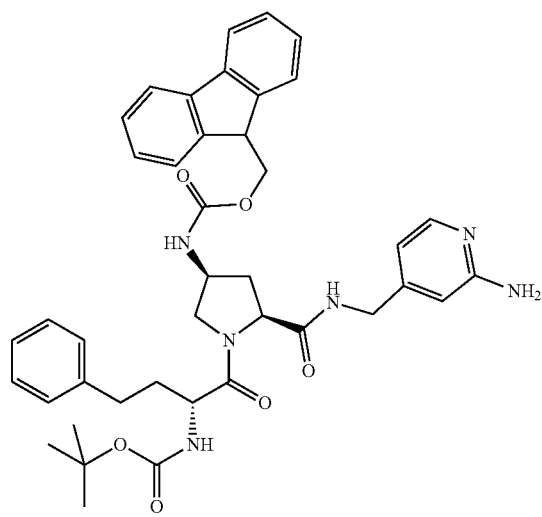<br>RgA: 4-aminomethyl pyridin-2-ylamine<br>RgB: (2S, 4S)-Fmoc-4-amino-1-Boc-pyrrolidin-2-carboxylic acid<br>RgD: N-Boc-Homophenylalanine<br>Step 1 & 3: GM1 HBTU and DIPEA in DMF<br>Step 2: GM2A | ANALPH2_MEOH_4 min, Rt: 2.98 min, m/z 719 [M + H]+ | 1.10 g, off-white solid |

| Example No. | Structure & Conditions | Analytical Data | Mass, state |
|---|---|---|---|
| GS3-int3 | 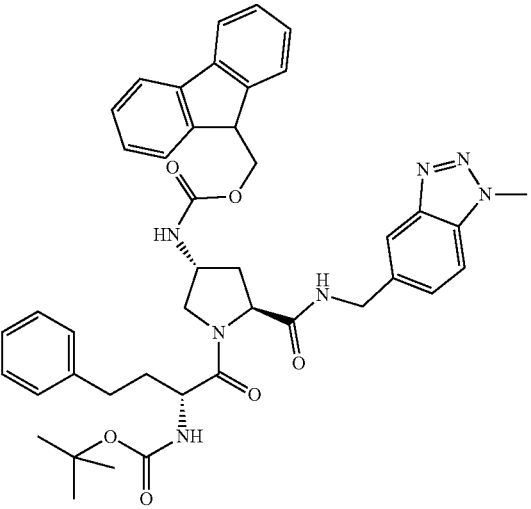<br>RgA: C-(1-Methyl-1H-benzotriazol-5-yl)-methylamine<br>RgB: (2S, 4S)-Fmoc-4-amino-1-Boc-pyrrolidin-2-carboxylic acid<br>RgD: N-Boc-Homophenylalanine<br>Step 1 & 3: GM1 HBTU in DMF<br>Step 2: GM2A | ANALPH2_MEOH_4 min, Rt: 3.56 min, m/z 758.5 [M + H]+ | 0.58 g, cream foam |
| GS6-int1 | 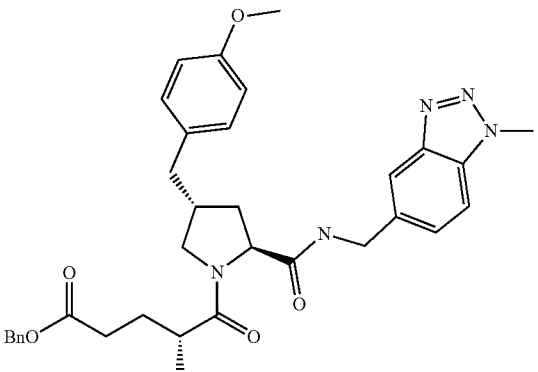<br>RgA: C-(1-Methyl-1H-benzotriazol-5-yl)-methylamine<br>RgB: boc-(R)-γ-(4-methoxybenzyl)-L-proline<br>RgD: N-boc-D-glutamic acid 5-benzyl ester<br>Step 1 & 3: GM1 with HATU and DIPEA in DCM;<br>Step2 GM2A | ANALPH2_MEOH_4 min, Rt: 3.43 min, m/z 699.4 [M + H]+ | 918 mg, brown oil |
| GS7-int1 | 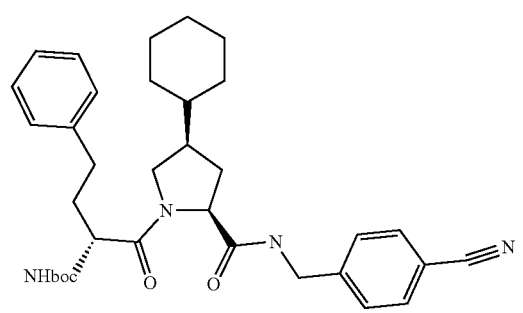<br>RgA: 4-(aminomethyl)benzonitrile hydrochloride<br>RgB: (2S, 4R)-Boc-4-cyclohexyl-pyrrolidine-2-carboxylic acid<br>RgD: Boc-D-homophenylalanine (Step 1 & 3: GM1 with HATU & DIPEA in DMF<br>Step 2: GM2A | ANALPH2_MEOH_4 min, Rt: 3.69 min, m/z 573.4 [M + H]+ | 140 mg, colourless oil |

| Example No. | Structure & Conditions | Analytical Data | Mass, state |
|---|---|---|---|
| GS7-int2 | 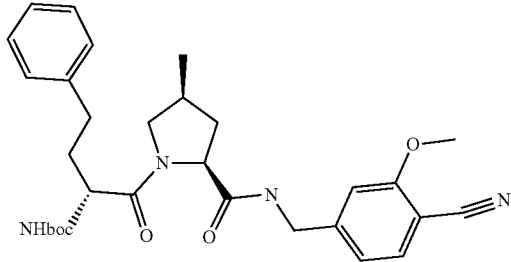<br>RgA: 4-(aminomethyl)-2-methoxybenzonitrile<br>RgB: (4S)-1-boc-4-methyl-L-proline<br>RgD: Boc-D-homophenylalanine<br>Step 1 & 3: GM1 with HATU and Et$_3$N in DMF<br>Step 2: GM2A | ANALPH2_MEOH_4 min, Rt: 3.35 min, m/z 535.3 [M + H]+ | 246 mg, white solid |
| GS7-int3 | 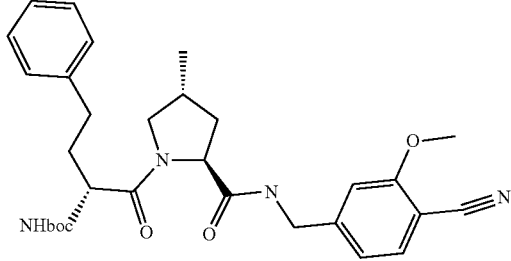<br>RgA: 4-(aminomethyl)-2-methoxybenzonitrile<br>RgB: (4R)-1-boc-4-methyl-L-proline<br>RgD: Boc-D-homophenylalanine<br>Step 1 & 3: GM1 with HATU & Et$_3$N in DMF<br>Step 2: GM2A | ANALPH2_MEOH_4 min, Rt: 3.35 min, m/z 535.3 [M + H]+ | 264 mg, white solid |
| GS7-int6 | 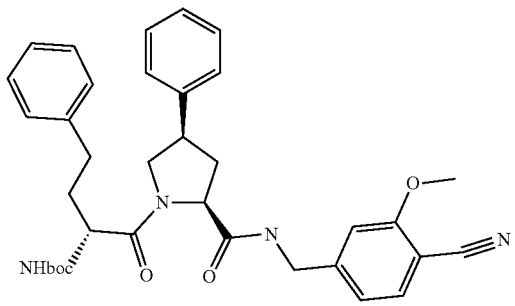<br>RgA: 4-(aminomethyl)-2-methoxybenzonitrile<br>RgB: (2S,4R)-Boc-4-phenylpyrrolidine-2-carboxylic acid<br>RgD: Boc-D-homophenylalanine<br>Step 1 & 3: GM1 with HATU & Et$_3$N in DMF<br>Step 2: GM2A | ANALPH2_MEOH_4 min, Rt: 3.50 min, m/z 597.3 [M + H]+ | 260 mg, white foam |

-continued

| Example No. | Structure & Conditions | Analytical Data | Mass, state |
|---|---|---|---|
| GS8-int1 | 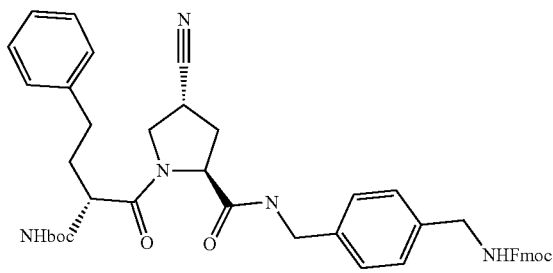<br>RgA: (4-Aminomethyl-benzyl)-carbamic acid 9H-fluoren-9-ylmethyl ester<br>RgB: (2S,4R)-4-Cyano-pyrrolidine-1,2-dicarboxylic acid 1-tert-butyl ester<br>RgD: Boc-D-homophenylalanine<br>Step 1 & 3: GM1 with HATU & Et$_3$N<br>Step 2: GM2A | ANALPH2_MEOH_4 min, Rt: 3.66 min, m/z 742.4 [M + H]+ | 207 mg, white solid |
| GS8-int2 | 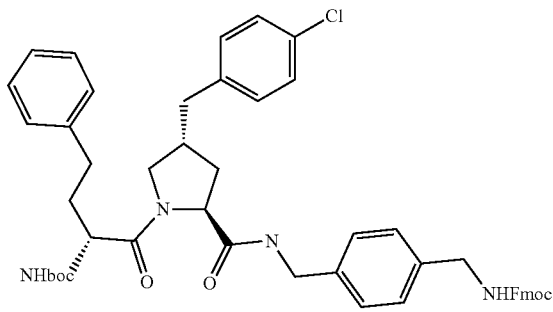<br>RgA: (4-Aminomethyl-benzyl)-carbamic acid 9H-fluoren-9-ylmethyl ester<br>RgB: Boc-(R)-gamma-(4-chlorobenzyl)L-proline<br>RgD: Boc-D-homophenylalanine<br>Step 1 & 3: GM1 with HATU & Et$_3$N<br>Step 2: GM2A | ANALPH2_MEOH_4 min, Rt: 3.82 min, m/z 841 [M + H]+ | 205 mg, yellow oil |
| GS8-int3 | 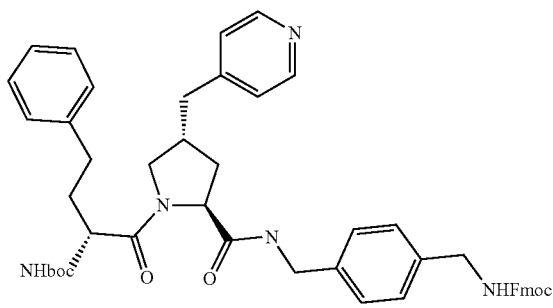<br>RgA: (4-Aminomethyl-benzyl)-carbamic acid 9H-fluoren-9-ylmethyl ester<br>RgB: Boc-(R)-gamma-(4-pyridylmethyl)-L-proline<br>RgD: Boc-D-homophenylalanine<br>Step 1 & 3: GM1 with HBTU & DIPEA<br>Step 2: GM2B | ANALPH2_MEOH_4 min, Rt: 3.35 min, m/z 808 [M + H]+ | 380 mg, white solid |

-continued

| Example No. | Structure & Conditions | Analytical Data | Mass, state |
|---|---|---|---|
| GS8-int4 | 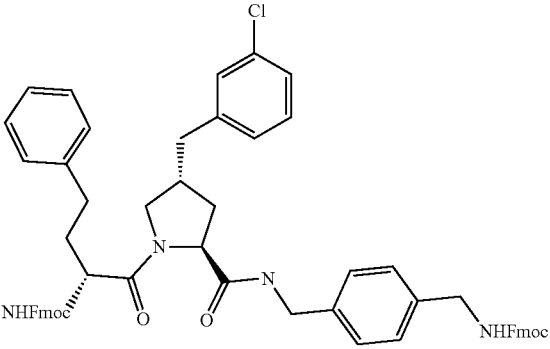<br>RgA: (4-Aminomethyl-benzyl)-carbamic acid 9H-fluoren-9-ylmethyl ester (<br>RgB: Boc-(R)-gamma-(3-chlorobenzyl)-L-proline<br>RgD: Fmoc-D-homophenylalanine (,<br>Step 1: GM1 with HATU & Et$_3$N in DMF<br>Step 2: GM2A<br>Step 3: GM1 with HBTU and DIPEA in DMF) | ANALPH2_50-95 MEOH_4 min, Rt: 2.54 min, m/z 963.5 [M + H]+ | 200 mg, colourless oil |
| GS9-int1 | 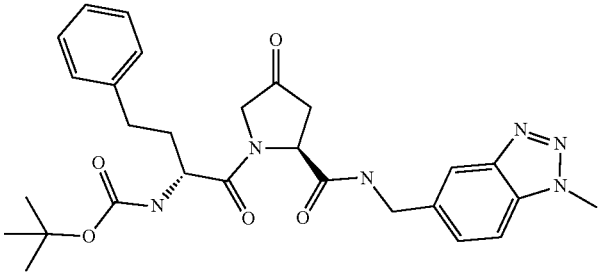<br>RgA: C-(1-Methyl-1H-benzotriazol-5-yl)-methylamine)<br>RgB: N-boc-4-oxo-L-proline<br>RgD: Boc-D-homophenylalanine<br>Step 1 & 3: GM1 with HBTU & DIPEA<br>Step 2: GM2A | ANALPH2_MEOH_4 min, Rt: 2.94 min, m/z 353.4 [M + H]+ | oil, used directly in subsequent reaction |
| GS13-int1 | 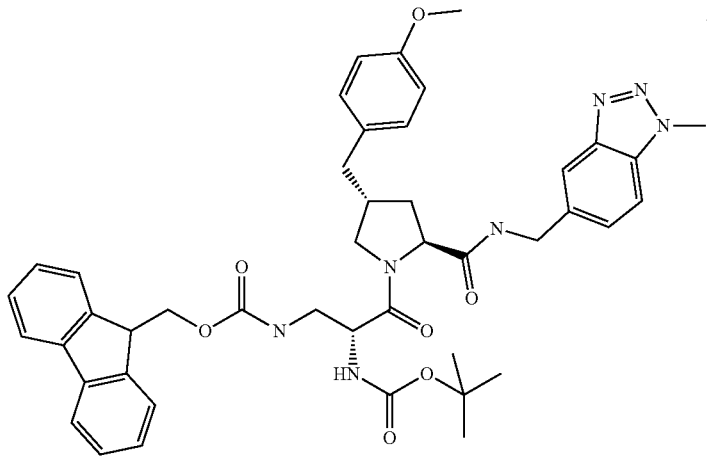<br>RgA: C-(1-Methyl-1H-benzotriazol-5-yl)-methylamine<br>RgB: boc-(R)-γ-(4-methoxybenzyl)-L-proline<br>RgD: Boc-D-diaminopropionic(Fmoc)-acid<br>Step 1 & 3: GM1 with HATU and DIPEA in DCM;<br>Step 2: GM2A | ANALPH2_MEOH_4 min, Rt: 3.60 min, m/z 788.6 [M + H]+ | 204 mg, orange oil |

General Scheme 2

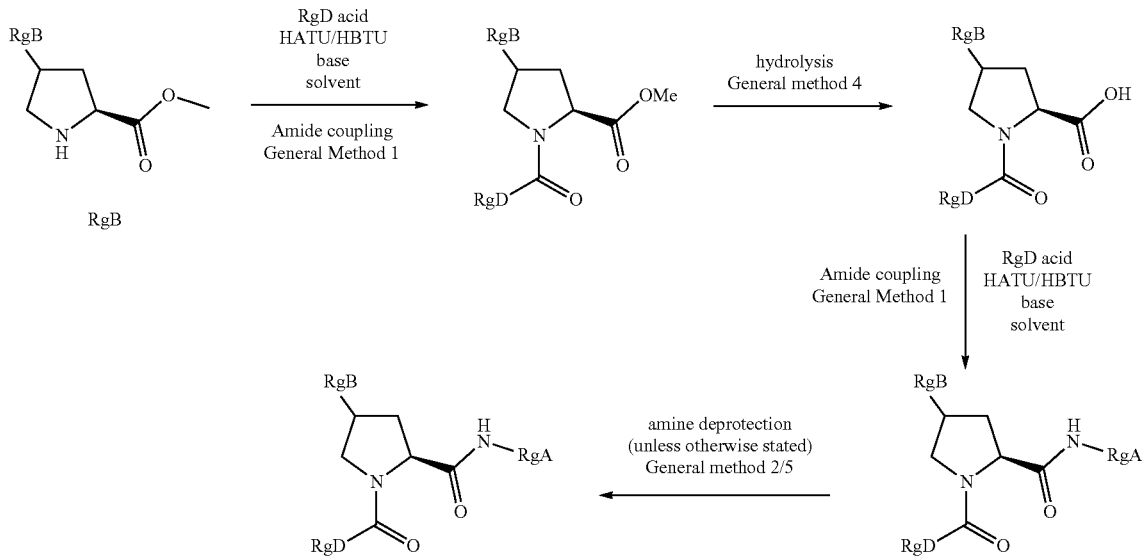

Synthesis of (S)-1-((R)-2-Amino-5-oxo-5-pyrrolidin-1-yl-pentanoyl)-4-(4-trifluoromethoxy-benzyl)-pyrrolidine-2-carboxylicacid (1-methyl-1H-benzotriazol-5-ylmethyl)-amide (M05306)

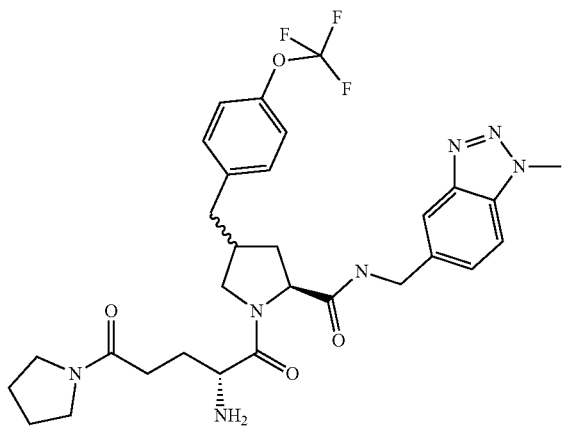 [SMILES: Cn1nnc2cc(CNC(=O)[C@@H]3CC(Cc4ccc(OC(F)(F)F)cc4)CN3C(=O)[C@H](N)CCC(=O)N3CCCC3)ccc21]

Step 1: (S)-4-(4-Trifluoromethoxy-benzyl)-pyrrolidine-2-carboxylic acid methyl ester (100 mg, 0.33 mmol), (R)-2-tert-butoxycarbonylamino-5-oxo-5-pyrrolidin-1-yl-pentanoic acid (109 mg, 0.36 mmol), HATU (125 mg, 0.33 mmol) and DIPEA (172 µL, 0.99 mmol) were dissolved in DMF (2 mL) and stirred at room temperature overnight. The reaction mixture was diluted with DCM, washed with water (20 mL) and brine (20 mL) then passed through a phase separator and solvent removed in vacuo. The residue was purified by column chromatography (biotage, 0-100% EtOAc/ihexane) to give (S)-1-((R)-2-tert-butoxycarbonylamino-5-oxo-5-pyrrolidin-1-yl-pentanoyl)-4-(4-trifluoromethoxy-benzyl)-pyrrolidine-2-carboxylic acid methyl ester as a yellow oil (79 mg, 41%).

ANALPH2_MEOH_4 min, Rt: 3.35 min, m/z 586 [M+H]+

Step 2: (S)-1-((R)-2-tert-Butoxycarbonylamino-5-oxo-5-pyrrolidin-1-yl-pentanoyl)-4-(4-trifluoromethoxy-benzyl)-pyrrolidine-2-carboxylic acid methyl ester 79 mg, 0.14 mmol) was dissolved in MeOH (1 mL) and aq. LiOH (1 M solution, 1 mL) and stirred at room temperature for 2 h. The solvent was removed under reduced pressure to give (S)-1-((R)-2-tert-butoxycarbonylamino-5-oxo-5-pyrrolidin-1-yl-pentanoyl)-4-(4-trifluoromethoxy-benzyl)-pyrrolidine-2-carboxylic acid (77 mg, 40%) which was used crude in the next step.

ANALPH2_MEOH_4 min, Rt: 3.32 min, m/z 572.2 [M+H]+

Step 3: (S)-1-((R)-2-tert-Butoxycarbonylamino-5-oxo-5-pyrrolidin-1-yl-pentanoyl)-4-(4-trifluoromethoxy-benzyl)-pyrrolidine-2-carboxylic acid (77 mg, 0.14 mmol), C-(1-methyl-1H-benzotriazol-5-yl)-methylamine (29 mg, 0.15 mmol), HATU (57 mg, 0.14 mmol) and DIPEA (94 µL, 0.54 mmol) were dissolved in DMF (2 mL) and stirred at room temperature overnight. Additional DIPEA (24 µL, 0.14 mmol), HATU (57 mg, 0.14 mmol) and C-(1-methyl-1H-benzotriazol-5-yl)-methylamine (29 mg, 0.15 mmol) were added and the reaction mixture stirred at room temperature for three days. The reaction mixture was diluted with DCM, washed with water (2×20 mL) then brine (20 mL). Organics were passed through a phase separator and solvent removed in vacuo to give {(R)-1-[(S)-2-[(1-methyl-1H-benzotriazol-5-ylmethyl)-carbamoyl]-4-(4-trifluoromethoxy-benzyl)-pyrrolidine-1-carbonyl]-4-oxo-4-pyrrolidin-1-yl-butyl}-carbamic acid tert-butyl ester which was used crude in the next step.

ANALPH2_MEOH_4 min, Rt: 3.26 min, m/z 716[M+H]+

Step 4: {(R)-1-[(S)-2-[(1-Methyl-1H-benzotriazol-5-ylmethyl)-carbamoyl]-4-(4-trifluoromethoxy-benzyl)-pyrrolidine-1-carbonyl]-4-oxo-4-pyrrolidin-1-yl-butyl}-carbamic acid tert-butyl ester was dissolved in 10% TFA/DCM and stirred at room temperature overnight. The reaction mixture was passed through an SCX-2 cartridge, eluting with 1M NH3/MeOH and solvent removed. The residue was purified by prep HPLC to give (S)-1-((R)-2-amino-5-oxo-5-pyrrolidin-1-yl-pentanoyl)-4-(4-trifluoromethoxy-benzyl)-pyrrolidine-2-carboxylicacid (1-methyl-1H-benzotriazol-5-ylmethyl)-amide as a white solid (4 mg, 5%).

ANALPH9_MEOH_QC_v1, Rt: 7.74 min, m/z 616.3 [M+H]+

ANALPH2_MEOH_QC_v1, Rt: 6.27 min, m/z 616.3 [M+H]+

The following compounds were made by analogous methods to those listed above, except where modifications were used, in which case the nature of the modified protocol is detailed:

| Example No. | Structure & Conditions | Analytical Data | Mass, state |
|---|---|---|---|
| M05099 | 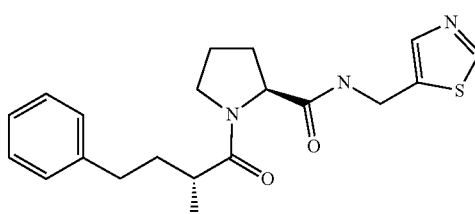<br>RgA: (5-Aminomethyl-thiazol-2-ylmethyl)-carbamic acid tert-butyl ester<br>RgB: L-Proline methyl ester hydrochloride<br>RgD: Boc-D-homophenyl alanine<br>Step 2 GM4B using 1M KOH;<br>Step 3 GM1 with Et3N | ANALPH2_MEOH_QC_v1, Rt: 2.15 min, m/z 402.3 [M + H]+<br>ANALPH9_MEOH_QC_v1, Rt: 6.23 min, m/z 402.3 [M + H]+ | 16.4 mg, white solid |
| M05127 | 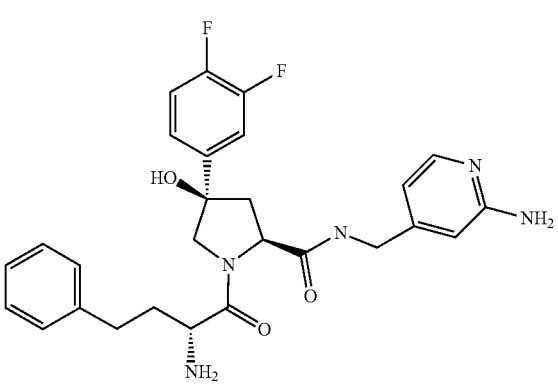<br>RgA: 4-aminomethylpyridin-2-ylamine<br>RgB: (2S,4R)-4-(3,4-Difluoro-phenyl)-4-hydroxy-pyrrolidine-2-carboxylic acid methyl ester<br>RgD: boc-D-homophenylalanine<br>Step 1: GM1 with HBTU & DIPEA;<br>Step 2: GM4B;<br>Step 3: GM1 with HBTU & DIPEA | ANALPH9_MEOH_QC_v1, Rt: 7.35 min, m/z 510.4 [M + H]+<br>ANALPH2_MEOH_QC_v1, Rt: 3.92 min, m/z 510.4 [M + H]+ | 9.0 mg, white solid |
| M05237 | 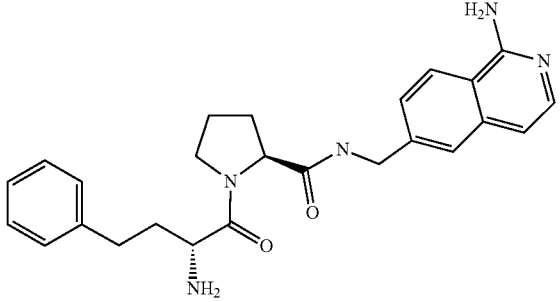<br>RgA: 6-Aminomethyl-isoquinolin-1-ylamine<br>RgB: L-proline-OtBu<br>RgD: Fmoc-homophenylalanine<br>Step 1: GM1 with HBTU & DIPEA in DCM;<br>Step 2 GM2A;<br>Step 3: GM1 with HATU & Et3N in DMF;<br>Step 4: GM5 | ANALPH2_MEOH_QC_v1, Rt: 3.21 min, m/z 432.4 [M + H]+<br>ANALPH9_MEOH_QC_v1, Rt: 6.73 min, m/z 432.4 [M + H]+ | 10 mg, white solid |

-continued

| Example No. | Structure & Conditions | Analytical Data | Mass, state |
|---|---|---|---|
| M05295 | 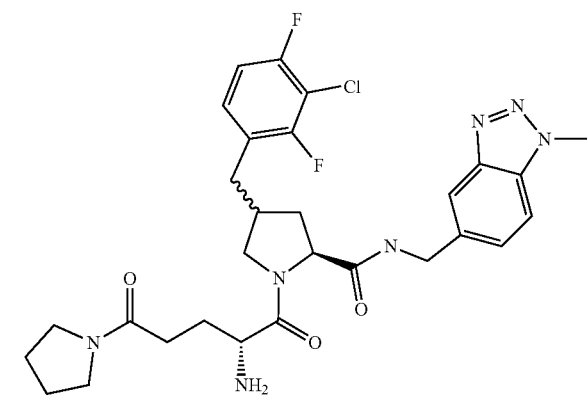<br>RgA: C-(1-Methyl-1H-benzotriazol-5-yl)-methylamine<br>RgB: (S)-4-(3-Chloro-2,4-difluoro-benzyl)-pyrrolidine-2-carboxylic acid methyl ester<br>RgD: (R)-2-tert-Butoxycarbonylamino-5-oxo-5-pyrrolidin-1-yl-pentanoic acid | ANALPH2_MEOH_QC_v1, Rt: 5.84 min, m/z 602.2 [M + H]+<br>ANALPH9_MEOH_QC_v1, Rt: 7.46 min, m/z 602.2 [M + H]+ | 15 mg, white solid |
| M05297 | 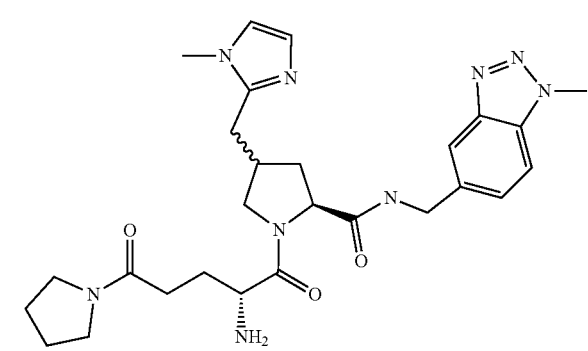<br>RgA: C-(1-Methyl-1H-benzotriazol-5-yl)-methylamine<br>RgB: (S)-4-(1-Methyl-1H-imidazol-2-ylmethyl)-pyrrolidine-2-carboxylic acid methyl ester<br>RgD: (R)-2-tert-Butoxycarbonylamino-5-oxo-5-pyrrolidin-1-yl-pentanoic acid<br>Step 1 & 3: GM1 with HBTU in DCM; | ANALPH9_MEOH_QC_v1, Rt: 5.62 min, m/z 536.3 [M + H]+<br>ANALPH2 MEOH_QC_v1, Rt: 1.52 min, m/z 536.3 [M + H]+ | 14 mg, off-white solid |
| M05300 | 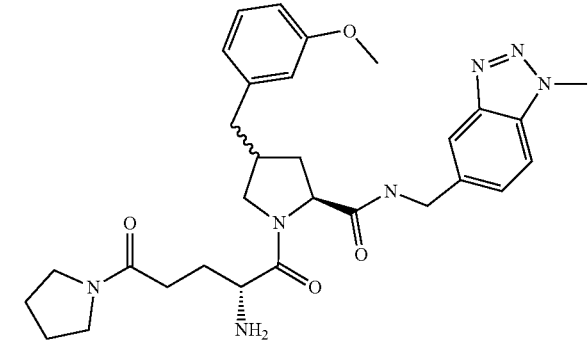<br>RgA: C-(1-Methyl-1H-benzotriazol-5-yl)-methylamine<br>RgB: (S)-4-(3-Methoxy-benzyl)-pyrrolidine-2-carboxylic acid methyl ester<br>RgD: (R)-2-tert-Butoxycarbonylamino-5-oxo-5-pyrrolidin-1-yl-pentanoic acid | ANALPH9_MEOH_QC_v1, Rt: 7.06 min, m/z 562.3 [M + H]+<br>ANALPH2_MEOH_QC_v1, Rt: 5.78 min, m/z 562.3 [M + H]+ | 9 mg, white solid |

325 326

-continued

| Example No. | Structure & Conditions | Analytical Data | Mass, state |
|---|---|---|---|
| M05298 | 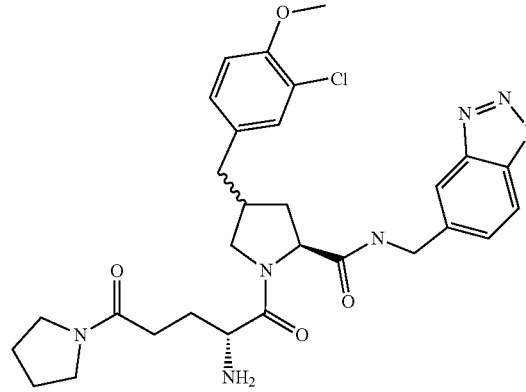<br>RgA: C-(1-Methyl-1H-benzotriazol-5-yl)-methylamine<br>RgB: (S)-4-(3-Chloro-4-methoxy-benzyl)-pyrrolidine-2-carboxylic acid methyl ester<br>RgD: (R)-2-tert-Butoxycarbonylamino-5-oxo-5-pyrrolidin-1-yl-pentanoic acid | ANALPH9_MEOH_QC_v1, Rt: 7.25 min, m/z 596.3 [M + H]+<br>ANALPH2_MEOH_QC_v1, Rt: 5.77 min, m/z 596.3 [M + H]+<br>1H-NMR (400 MHz, DMSO-D6) δ 8.64 (t, J = 6.0 Hz, 0.2H), 8.31 (t, J = 6.0 Hz, 0.8H), 7.82-7.77 (m, 1H), 7.74-7.67 (m, 1H), 7.38 (dt, J = 8.5, 1.5 Hz, 1H), 7.28-7.21 (m, 1H), 7.15-7.07 (m, 1H), 7.04-6.99 (m, 1H), 4.40-4.31 (m, 2H), 4.24 (s, 3H), 3.81-3.76 (m, 3.4H), 3.73-3.66 (m, 0.6H), 3.45-3.19 (m, 4H (estimated as obscured by solvent residual peak)), 3.16-2.95 (m, 1H), 2.41-2.18 (m, 2H), 1.93-1.60 (m, 9H), 1.44-1.38 (m, 1H) | 5 mg, colourless oil |
| M05309 | 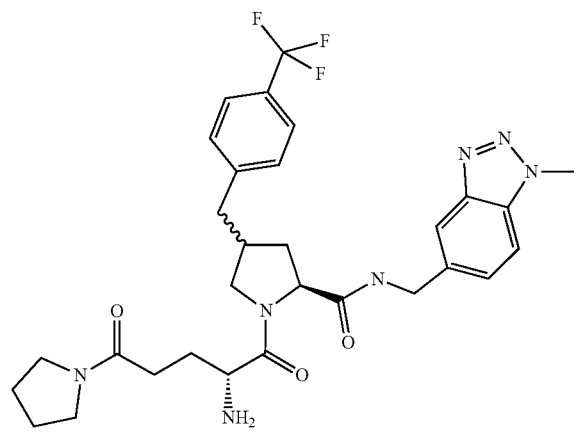<br>RgA: C-(1-Methyl-1H-benzotriazol-5-yl)-methylamine<br>RgB: (S)-4-(4-Trifluoromethyl-benzyl)-pyrrolidine-2-carboxylic acid methyl ester<br>RgD: (R)-2-tert-Butoxycarbonylamino-5-oxo-5-pyrrolidin-1-yl-pentanoic acid<br>Steps 1 and 3: GM1 with HATU & Et3N in DMF;<br>Step 4 GM2A | ANALPH2_MEOH_QC_v1, Rt: 5.97 min, m/z 600.2 [M + H]+<br>ANALPH9_MEOH_QC_v1, Rt: 7.60 min, m/z 600.3 [M + H]+<br>1H-NMR (400 MHz, DMSO-D6) δ 8.83-8.59 (m, 0.2H), 8.58-8.25 (m, 0.8H), 7.96-7.68 (m, 2H), 7.66-7.53 (m, 2H), 7.51-7.28 (m, 3H), 4.59-4.31 (m, 2H), 4.31-4.16 (m, 4H), 3.99-3.69 (m, 1H), 3.56-3.35 (m, 2H), 3.24-3.02 (m, 2H), 2.87-2.66 (m, 2H), 2.40-2.08 (m, 2H), 2.04-1.15 (m, 9H) | 57 mg, white solid |

| Example No. | Structure & Conditions | Analytical Data | Mass, state |
|---|---|---|---|
| M05304 | 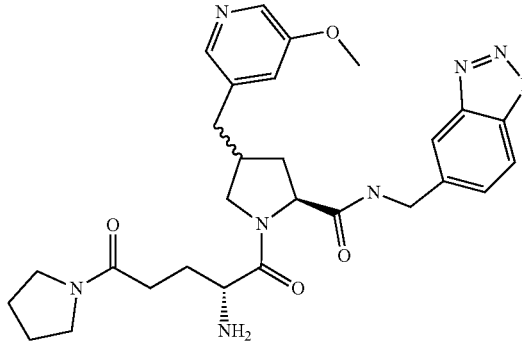<br>RgA: C-(1-Methyl-1 H-benzotriazol-5-yl)-methylamine<br>RgB: (S)-4-(5-Methoxy-pyridin-3-ylmethyl)-pyrrolidine-2-carboxylic acid methyl ester<br>RgD: (R)-2-tert-Butoxycarbonylamino-5-oxo-5-pyrrolidin-1-yl-pentanoic acid<br>Step 1 GM1 with HBTU in DCM/DMF;<br>Step 3 GM1 with HBTU in DCM/DMF | ANALPH2_MEOH_QC_v1, Rt: 5.03 min, m/z 563.3 [M + H]+<br>ANALPH9_MEOH_QC_v1, Rt: 6.60 min, m/z 563.3 [M + H]+ | 21.5 mg, off-white solid |
| M05021 | 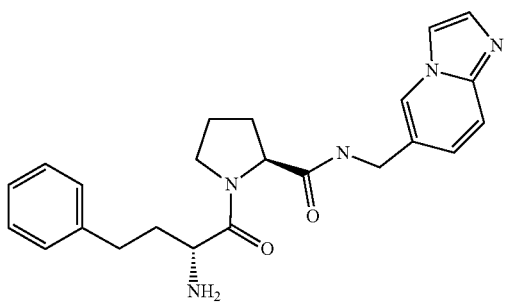<br>RgA: 6-(aminomethyl)imidazo[1,2-A]pyridine<br>RgB: L-Proline methyl ester hydrochloride<br>RgD: Boc-D-homophenyl alanine<br>Step 2 GM4C;<br>Step 3 GM1 with Et3N | ANALPH2_MEOH_QC_v1, Rt: 2.94 min, m/z 406.4 [M + H]+<br>ANALPH9_MEOH_QC_v1, Rt: 6.80 min, m/z 406.3 [M + M]+ | 25 mg, white solid |
| M05312 | 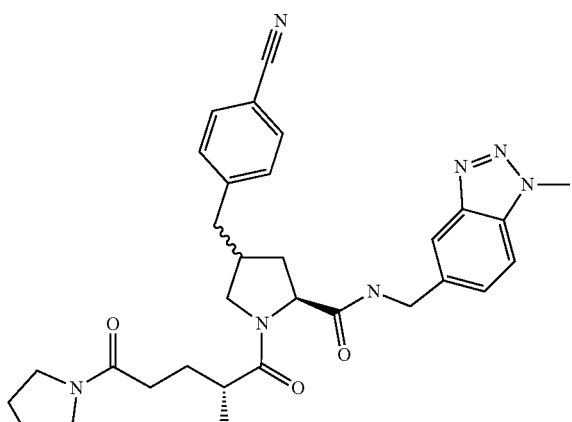<br>RgA: C-(1-Methyl-1H-benzotriazol-5-yl)-methylamine<br>RgB: (S)-4-(4-Cyano-benzyl)-pyrrolidine-2-carboxylic acid methyl ester<br>RgD: (R)-2-tert-Butoxycarbonylamino-5-oxo-5-pyrrolidin-1-yl-pentanoic acid<br>Step 1 & 3: GM1 with HBTU in DCM/DMF,; | ANALPH2_MEOH_QC_v1, Rt: 5.10 min, m/z 557.3 [M + H]+<br>ANALPH9_MEOH_QC_v1, Rt: 6.56 min, m/z 557.3 [M + H]+ | 23 mg, white solid |

| Example No. | Structure & Conditions | Analytical Data | Mass, state |
|---|---|---|---|
| M05314 | 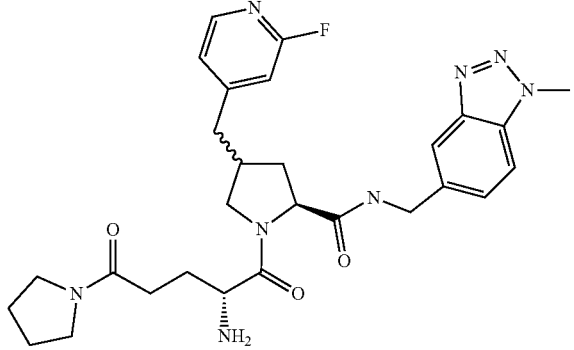<br>RgA: C-(1-Methyl-1H-benzotriazol-5-yl)-methylamine<br>RgB: (S)-4-(2-Fluoro-pyridin-4-ylmethyl)-pyrrolidine-2-carboxylic acid methyl ester<br>RgD: (R)-2-tert-Butoxycarbonylamino-5-oxo-5-pyrrolidin-1-yl-pentanoic acid | ANALPH2_MEOH_QC_v1, Rt: 4.70 min, m/z 551.3 [M + H]+<br>ANALPH9_MEOH_QC_v1, Rt: 6.16 min, m/z 551.3 [M + H]+ | 5 mg, white solid |
| M05315 | 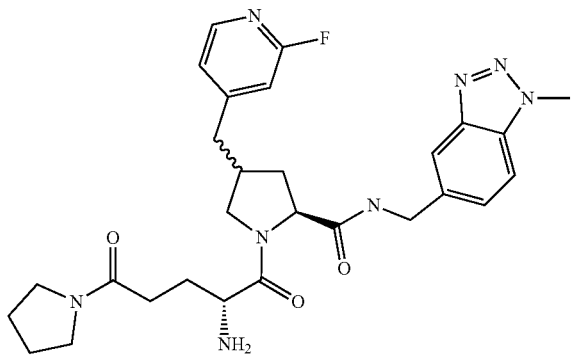<br>RgA: C-(1-Methyl-1H-benzotriazol-5-yl)-methylamine<br>RgB: (S)-4-(2-Fluoro-pyridin-4-ylmethyl)-pyrrolidine-2-carboxylic acid methyl ester<br>RgD: (R)-2-tert-Butoxycarbonylamino-5-oxo-5-pyrrolidin-1-yl-pentanoic acid | ANALPH2_MEOH_QC_v1, Rt: 4.98 min, m/z 551.3 [M + H]+<br>ANALPH9_MEOH_QC_v1, Rt: 6.21 min, m/z 551.3 [M + H]+ | 4 mg, white solid |
| M05181 | 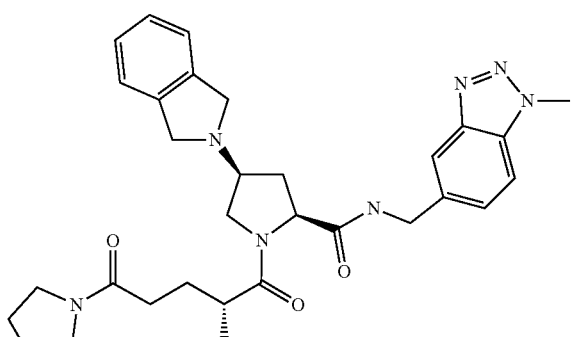<br>RgA: C-(1-Methyl-1H-benzotriazol-5-yl)-methylamine<br>RgB: (2S,4R)-4-(1,3-Dihydro-isoindol-2-yl)-pyrrolidine-2-carboxylic acid methyl ester<br>RgD: (R)-2-tert-Butoxycarbonylamino-5-oxo-5-pyrrolidin-1-yl-pentanoic acid<br>Step 1 & 3 GM1 with HBTU;<br>Step 2 GM4A in dioxane | ANALPH2_MEOH_QC_v1, Rt: 7.52 min, m/z 538.4 [M + H]+<br>ANALPH9_MEOH_QC_v1, Rt: 4.17 min, m/z 538.4 [M + H]+ | 14.3 mg, off-white solid |

| Example No. | Structure & Conditions | Analytical Data | Mass, state |
|---|---|---|---|
| GS7-int4 | 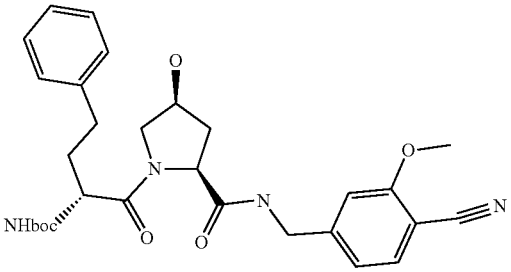<br>RgA: 4-(aminomethyl)-2-methoxybenzonitrile<br>RgB: (4S)-1-boc-4-hydroxy-L-proline<br>RgD: Boc-D-homophenylalanine<br>Step 1 & 3: GM1 with HATU and Et₃N in DMF<br>Step 2: GM4A using NaOH. No final deprotection | ANALPH2_MEOH_4 min, Rt: 3.02 min, m/z 537.3 [M + H]+ | 184 mg, white solid |
| GS7-int5 | 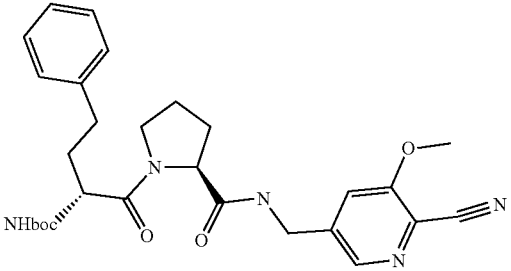<br>RgA: 5-Aminomethyl-3-methoxy-pyridine-2-carbonitrile<br>RgB L-Proline methyl ester hydrochloride<br>RgD: Boc-D-homophenylalanine<br>Step 1 & 3: GM1 with HATU and Et₃N in DMF<br>Step 2: GM4C,; No final deprotection | ANALPH2_MEOH_4 min, Rt: 3.19 min, m/z 522.3 [M + H]+ | 97 mg, white solid |
| GS7-int7 | 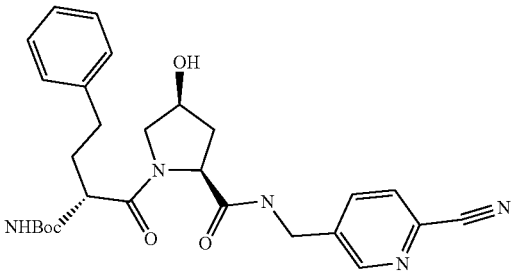<br>RgA: 5-Aminomethyl-picolinonitrile•2HCl ()<br>RgB: (4S)-1-boc-4-hydroxy-L-proline<br>RgD: Boc-D-homophenylalanine<br>Step 1 & 3: GM1 with HATU and Et₃N in DMF<br>Step 2: GM4C,; No final deprotection | ANALPH2_MEOH_4 min, Rt: 3.00 min, m/z 508.2 [M + H]+ | 191 mg, white solid |

| Example No. | Structure & Conditions | Analytical Data | Mass, state |
|---|---|---|---|

GS7-int8

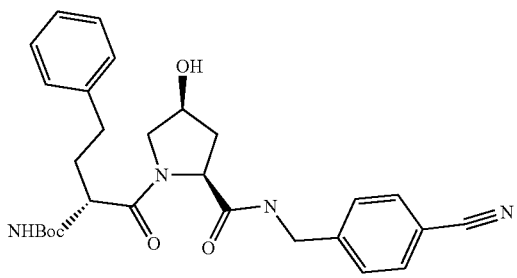

RgA: 4-(aminomethyl)benzonitrile hydrochloride
RgB: N-Boc-cis-4-hydroxy-L-proline
RgD: N-Boc-D-homophenylalanine
Step 1 & 3 GM1 with HATU and Et₃N
Step 2 GM2B. No final deprotection

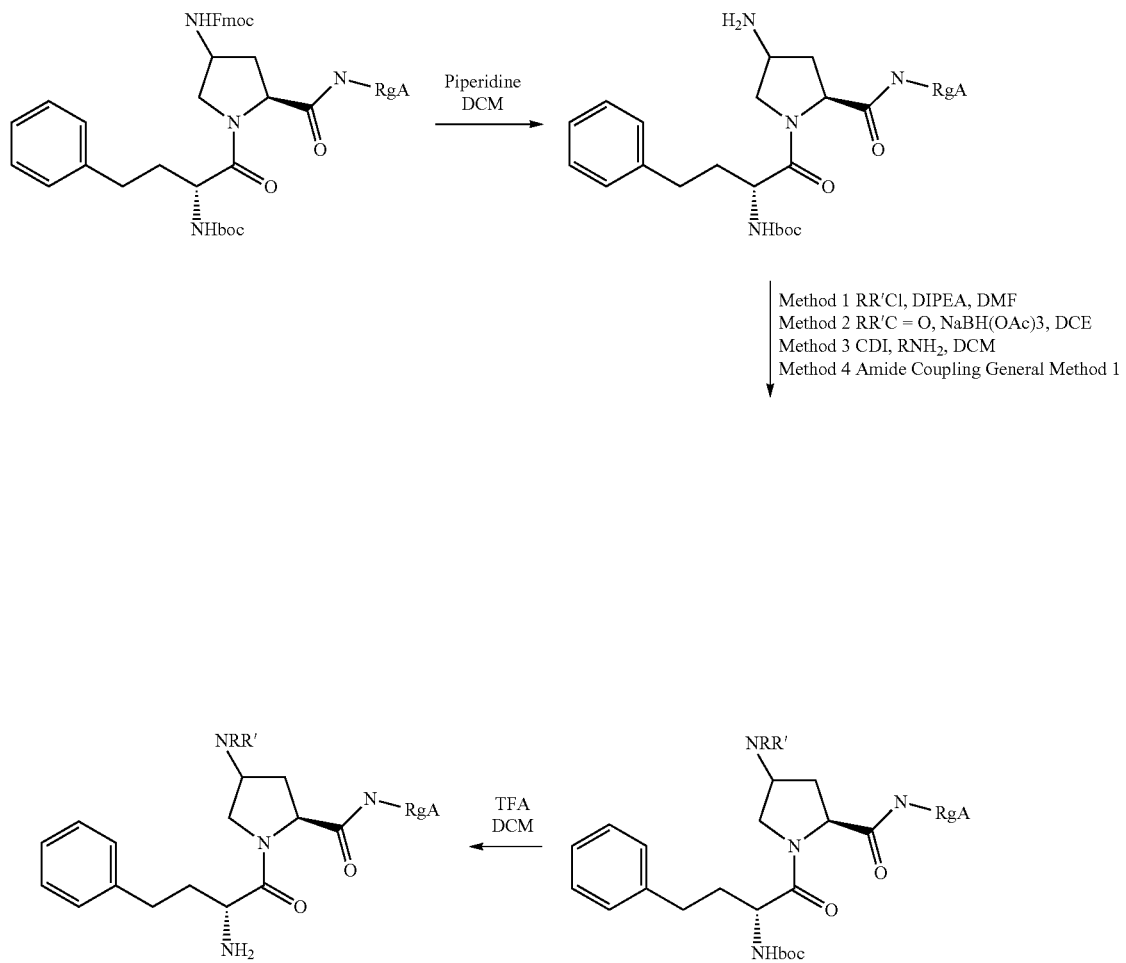

General Scheme 3 (amino RgB)

Method 1 RR'Cl, DIPEA, DMF
Method 2 RR'C = O, NaBH(OAc)3, DCE
Method 3 CDI, RNH₂, DCM
Method 4 Amide Coupling General Method 1

335
Synthesis of (2S,4S)-4-Acetylamino-1-((R)-2-amino-4-phenyl-butyryl)-pyrrolidine-2-carboxylic acid (1-methyl-1H-benzotriazol-5-ylmethyl)-amide (M05144)

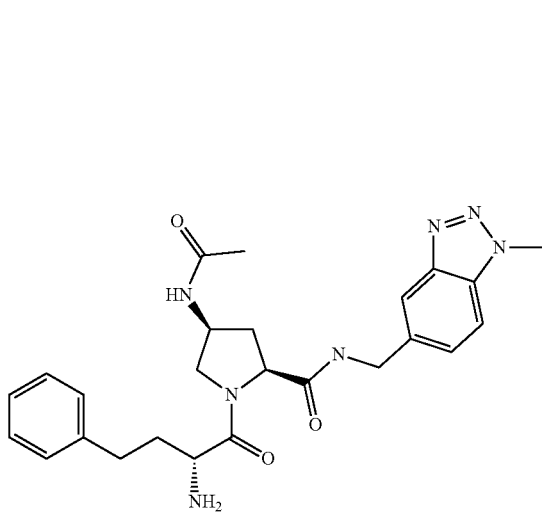 [SMILES: CC(=O)N[C@H]1C[C@@H](C(=O)NCc2ccc3c(c2)nnn3C)N(C(=O)[C@H](N)CCc2ccccc2)C1]

Step 1 Piperidine (1 mL) was slowly added to a solution of {(3S,5S)-1-((R)-2-amino-4-phenyl-butyryl)-5-[(1-methyl-1H-benzotriazol-5-ylmethyl)-carbamoyl]-pyrrolidin-3-yl}-carbamic acid 9H-fluoren-9-ylmethyl ester (1.42 g, 1.87 mmol) in DCM (10 mL) and the reaction mixture stirred for 4 hours at room temperature. The solvent was removed in vacuo and the product purified by column chromatography (Biotage, 100 g SNAP, (0-(1% Et₃N and 10% MeOH) in DCM) to give ((R)-1-{(S)-4-amino-2-[(1-methyl-1H-benzotriazol-5-ylmethyl)-carbamoyl]-pyrrolidine-1-carbonyl}-3-phenyl-propyl)-carbamic acid tert-butyl ester (878 mg, 88%) as an off-white solid.

ANALPH2_MEOH_4 min, Rt: 2.28 min, m/z 536.4 [M+H]+

Step 2: Amine Functionalisation

Example of amine functionalisation using Method 1 alkylation: ((R)-1-{(S)-4-Amino-2-[(1-methyl-1H-benzotriazol-5-ylmethyl)-carbamoyl]-pyrrolidine-1-carbonyl}-3-phenyl-propyl)-carbamic acid tert-butyl ester (50 mg, 0.093 mmol) was dissolved in DMF (3 mL) and DIPEA (49 µL, 0.14 mmol, 1.5 eq) was added followed by acetyl chloride (20 µL, 0.28 mmol, 3.0 eq). The reaction mixture was stirred at room temperature for 1.5 hours, then brine was added and the mixture extracted with EtOAc. The combined organics were washed with brine, dried (MgSO₄) and solvent removed in vacuo to give crude ((R)-1-{(S)-4-acetylamino-2-[(1-methyl-1H-benzotriazol-5-ylmethyl)-carbamoyl]-pyrrolidine-1-carbonyl}-3-phenyl-propyl)-carbamic acid tert-butyl ester (51 mg, 95%) which was used directly in subsequent reaction without further purification.

ANALPH2_MEOH_4 min, Rt: 3.05 min, m/z 600.4 [M+Na]+

336
Example of Amine Functionalisation Using Method 2 Reductive Amination

Synthesis of ((R)-1-{(2S,4S)-4-Benzylamino-2-[(1-methyl-1H-benzotriazol-5-ylmethyl)-carbamoyl]-pyrrolidine-1-carbonyl}-3-phenyl-propyl)-carbamic acid tert-butyl ester

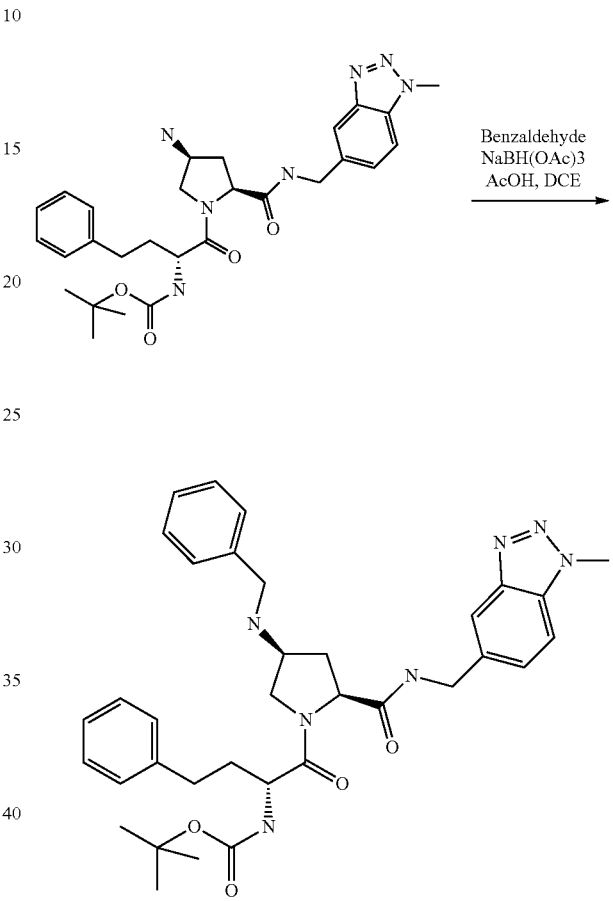

((R)-1-{(S)-4-Amino-2-[(1-methyl-1H-benzotriazol-5-ylmethyl)-carbamoyl]-pyrrolidine-1-carbonyl}-3-phenyl-propyl)-carbamic acid tert-butyl ester (100 mg, 0.19 mmol) was dissolved in DCE and AcOH (22 µL, 0.38 mmol) followed by benzaldehyde (21 µL, 0.21 mmol) and NaBH(OAc)₃ (61 mg, 0.29 mmol) were added. The reaction mixture was stirred at room temperature overnight followed by a further addition of NaBH(OAc)₃ (41 mg, 0.19 mol) and AcOH (11 µL, 0.19 mmol) and stirring for 1.5 hours. Na₂CO₃ solution (sat. aq.) was added and the mixture passed through a phase separator, then the aqueous layer further extracted with DCM. The combined organic extracts were purified by SCX-2, eluting with 0.5 M NH₃/MeOH. The solvent was removed under reduced pressure to give ((R)-1-{(2S,4S)-4-benzylamino-2-[(1-methyl-1H-benzotriazol-5-ylmethyl)-carbamoyl]-pyrrolidine-1-carbonyl}-3-phenyl-propyl)-carbamic acid tert-butyl ester (96 mg, 81%) which was used in the subsequent reaction without further purification.

ANALPH2_MEOH_4 min, Rt: 3.36 min, m/z 626.3 [M+H]+

Example of Amine Functionalisation Using Method 3 Urea Formation

Synthesis of {(R)-1-[(2S,4S)-2-[(1-Methyl-1H-benzotriazol-5-ylmethyl)-carbamoyl]-4-(3-methyl-ureido)-pyrrolidine-1-carbonyl]-3-phenyl-propyl}-carbamic acid tert-butyl ester

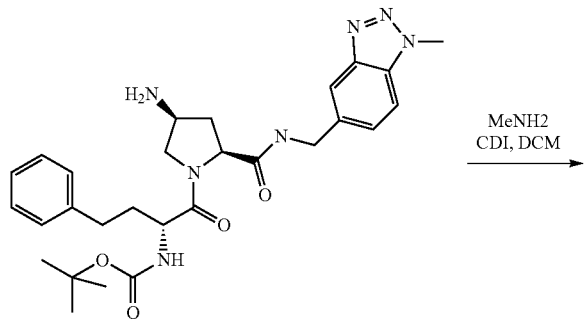

MeNH2
CDI, DCM

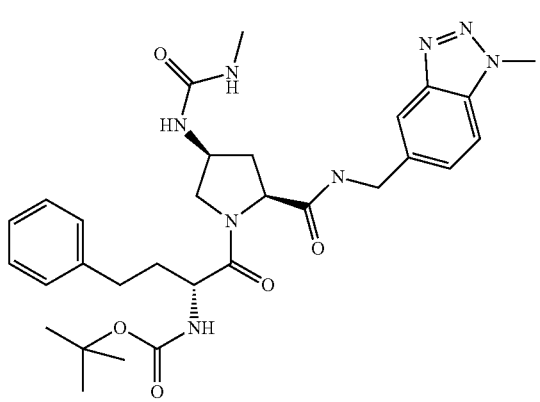

((R)-1-{(S)-4-Amino-2-[(1-methyl-1H-benzotriazol-5-ylmethyl)-carbamoyl]-pyrrolidine-1-carbonyl}-3-phenyl-propyl)-carbamic acid tert-butyl ester (75 mg, 0.14 mmol) was dissolved in DCM, and Et₃N (29 μL, 0.21 mmol) and CDI (24 mg, 0.15 mmol) were added and the reaction mixture stirred for 1.75 hours at room temperature. Methylamine (2 M in THF, 0.35 mL, 0.7 mmol) was added and the reaction mixture stirred for 30 minutes. A further aliquot of methylamine (2 M in THF, 0.21 mL, 0.42 mmol) was added and the mixture stirred at room temperature for 3 days. The reaction mixture was diluted with brine and DCM, then the aqueous layer was extracted with DCM and the combined organic layers were concentrated to give {(R)-1-[(2S,4S)-2-[(1-methyl-1H-benzotriazol-5-ylmethyl)-carbamoyl]-4-(3-methyl-ureido)-pyrrolidine-1-carbonyl]-3-phenyl-propyl}-carbamic acid tert-butyl ester (70 mg, 84%) as a colourless oil which was used directly in subsequent reactions without further purification.

ANALPH2_MEOH_4 min, Rt: 2.99 min, m/z 593 [M+H]+

Step 3: Final Deprotection

Acetylamino-2-[(1-methyl-1H-benzotriazol-5-ylmethyl)-carbamoyl]-pyrrolidine-1-carbonyl}-3-phenyl-propyl)-carbamic acid tert-butyl ester (50 mg, 0.090 mmol) was dissolved in DCM (4 mL) and TFA (2 mL) added. The reaction mixture was stirred at room temperature for 2 hours, then the solvent was removed under reduced pressure, and the crude material purified by prep HPLC to give (S)-4-acetylamino-1-((R)-2-amino-4-phenyl-butyryl)-pyrrolidine-2-carboxylic acid (1-methyl-1H-benzotriazol-5-ylmethyl)-amide (22.1 mg, 51%) as a white solid.

ANALPH2_MEOH_QC_v1, Rt: 4.21 min, m/z 478.3 [M+H]+

ANALPH9_MEOH_QC_v1, Rt: 6.18 min, m/z 478.4 [M+H]+

The following examples were made by analogous methods:

| Example No. | Structure & Method | Analytical Data | Mass, state |
|---|---|---|---|
| M05195 | | ANALPH2_MEOH_QC_v1, Rt: 5.42 min, m/z 568.4 [M + H]+ ANALPH9_MEOH_QC_v1, Rt: 7.31 min, m/z 568.4 [M + H]+ | 16.6 mg, white solid |

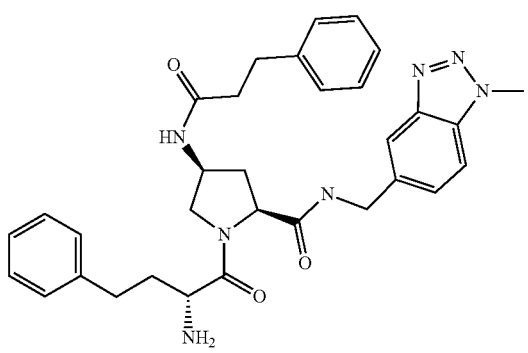

Method 4 (GM1 using HBTU and 3-Phenylpropionic acid in DMF)

| Example No. | Structure & Method | Analytical Data | Mass, state |
|---|---|---|---|
| M05196 | 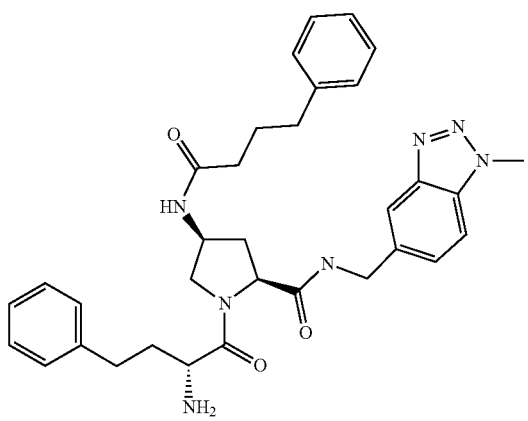<br>Method 4 (GM1 using HBTU and 4-phenylbutyric acid in DMF) | ANALPH9_MEOH_QC_v1, Rt: 7.55 min, m/z 582.4 [M + H]+<br>ANALPH2_MEOH_QC_v1, Rt: 5.68 min, m/z 582.4 [M + H]+ | 15.3 mg, white solid |
| M05141 | 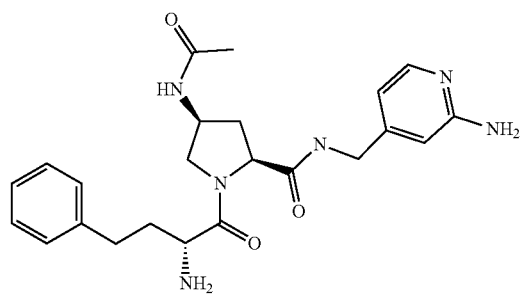<br>Starting material from GS1(GS3-int2)<br>Method 1 using Acetyl chloride | ANALPH9_MEOH_QC_v1, Rt: 5.84 min, m/z 439.3 [M + H]+<br>ANALPH2_MEOH_QC_v1, Rt: 1.31 min, m/z 439.3 [M + H]+<br>$^1$H NMR (400 MHz, CDCl$_3$) δ 7.95 – 7.87 (m, 1H), 7.76 (d, J = 5.4 Hz, 1H), 7.64 (d, J = 7.1 Hz, 1H), 7.12 (td, J = 8.4, 7.7, 2.0 Hz, 2H), 7.07 – 6.97 (m, 2H), 6.31 (dd, J = 5.4, 1.6 Hz, 1H), 6.19 (s, 1H), 4.77 (s, 2H), 4.55 (d, J = 8.8 Hz, 1H), 4.41 – 4.25 (m, 2H), 4.03 (dd, J = 16.3, 5.1 Hz, 1H), 3.42 – 3.16 (m, 3H), 2.64 (ddd, J = 14.4, 9.0, 6.0 Hz, 1H), 2.55 – 2.40 (m, 1H), 2.17 (d, J = 14.1 Hz, 1H), 2.00 – 1.87 (m, 1H), 1.87 – 1.77 (m, 1H), 1.74 (s, 3H), 1.70 – 1.60 (m, 1H). | 19.4 mg, off-white solid |
| M05142 | 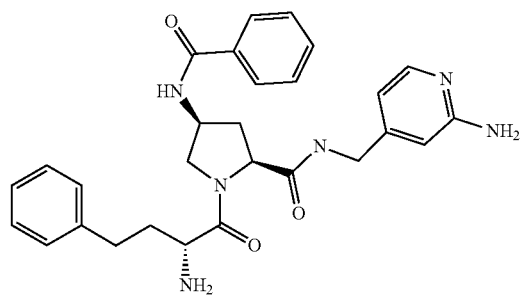<br>Starting material from GS1(GS3-int2)<br>Method 1 using benzoyl chloride | ANALPH2_MEOH_QC_v1, Rt: 3.34 min, m/z 501.3 [M + H]+<br>ANALPH9_MEOH_QC_v1, Rt: 6.92 min, m/z 501.3 [M + H]+ | 30.7 mg, off-white solid |

| Example No. | Structure & Method | Analytical Data | Mass, state |
| --- | --- | --- | --- |
| M05143 | 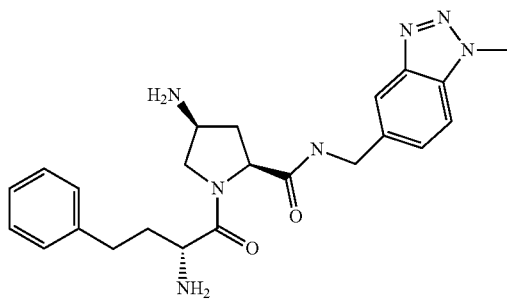<br>Step 2 omitted | ANALPH2_MEOH_QC_v1, Rt: 1.51 min, m/z 436.3 [M + H]+<br>ANALPH9_MEOH_QC_v1, Rt: 6.07 min, m/z 436.3 [M + H]+ | 17.9 mg, white solid |
| M05158 | 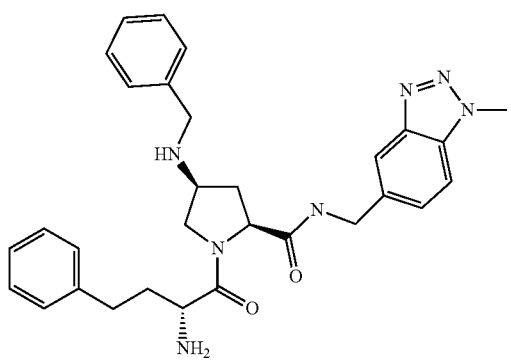<br>Method 2: using benzaldehyde | ANALPH2_MEOH_QC_v1, Rt: 3.88 min, m/z 526.3 [M + H]+<br>ANALPH9_MEOH_QC_v1, Rt: 7.30 min, m/z 526.3 [M + H]+<br>1H NMR (400 MHz, CDCl3) δ 7.91 (dd, J = 1.6, 0.8 Hz, 0.8H), 7.74 (s, 0.2H), 7.58 (t, J = 6.0 Hz, 1H), 7.44 (qd, J = 8.6, 1.1 Hz, 2H), 7.35 – 7.13 (m, 9H), 7.13 – 7.00 (m, 1H), 4.69 – 4.57 (m, 2H), 4.57 – 4.45 (m, 1H), 4.28 (s, 2.4H), 4.17 (s, 0.6H), 3.83 – 3.56 (m, 3H), 3.42 (dd, J = 8.3, 4.6 Hz, 1H), 3.40 – 3.33 (m, 1H), 3.31 (m, J = 4.4, 2.4 Hz, 1H), 2.88 – 2.57 (m, 2H), 2.54 – 2.27 (m, 1H), 2.17 (ddd, J = 13.6, 9.3, 5.9 Hz, 1H), 1.95 – 1.73 (m, 2H). | 32.9 mg, White solid |
| M05160 (449-042-03) | 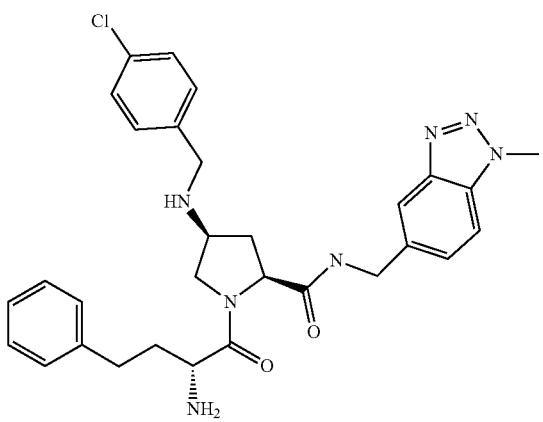<br>Method 2 using4-chlorobenzaldehyde | ANALPH9_MEOH_QC_v1, Rt: 7.66 min, m/z 560.2 [M + H]+<br>ANALPH2_MEOH_QC_v1, Rt: 4.28 min, m/z 560.3 [M + H]+ | 57.2 mg, white solid |

| Example No. | Structure & Method | Analytical Data | Mass, state |
|---|---|---|---|
| M05161 | 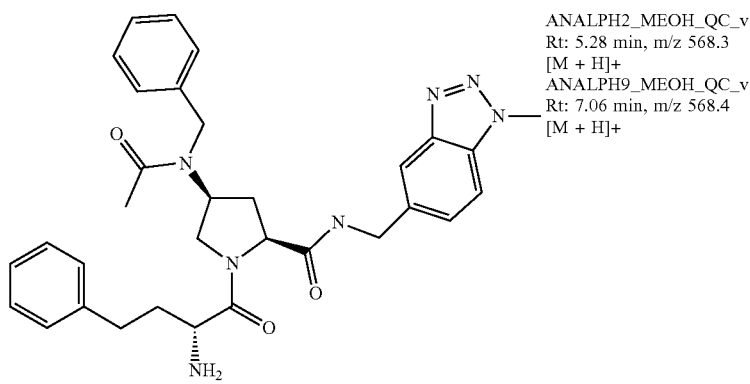<br>Method 2 using benzaldehyde followed by Method 1 using acetyl chloride | ANALPH2_MEOH_QC_v1, Rt: 5.28 min, m/z 568.3 [M + H]+<br>ANALPH9_MEOH_QC_v1, Rt: 7.06 min, m/z 568.4 [M + H]+ | 22.5 mg, white solid |
| M05162 | 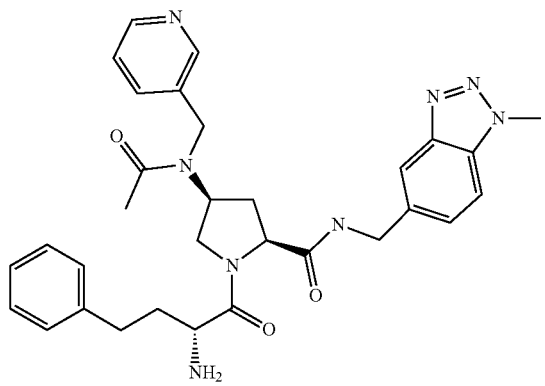<br>Method 2 using 3-pyridinecarboxaldehyde followed by Method 1 using acetyl chloride | ANALPH2_MEOH_QC_v1, Rt: 3.74 min, m/z 569.3 [M + H]+<br>ANALPH9_MEOH_QC_v1, Rt: 6.37 min, m/z 569.3 [M + H]+ | 22.2 mg, white solid |
| M05179 | 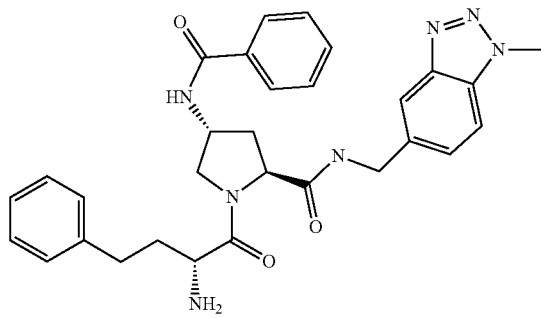<br>Method 1 using benzoyl chloride | ANALPH2_MEOH_QC_v1, Rt: 5.12 min, m/z 540.3 [M + H]+<br>ANALPH9_MEOH_QC_v1, Rt: 6.95 min, m/z 540.3 [M + H]+ | 34.6, white solid |

| Example No. | Structure & Method | Analytical Data | Mass, state |
|---|---|---|---|
| M05205 | 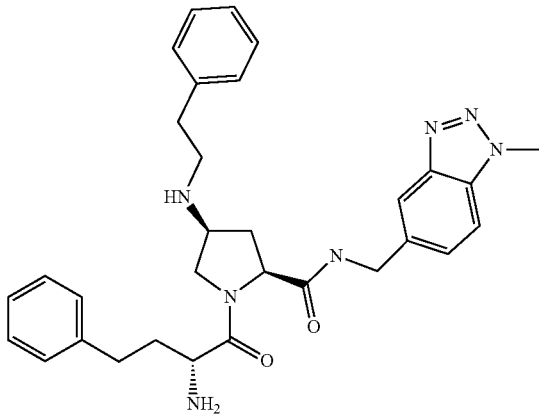<br>Method 2 using phenylacetaldehyde | ANALPH9_MEOH_QC_v1, Rt: 7.50 min, m/z 540.4 [M + H]+<br>ANALPH2_MEOH_QC_v1, Rt: 4.11 min, m/z 540.4 [M + H]+ | 3.0 mg, colourless gum |
| M05206 | 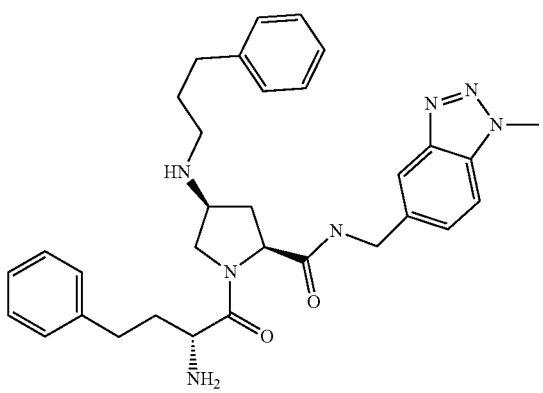<br>Method 2 using 3-phenylpropionaldehyde | ANALPH2_MEOH_QC_v1, Rt: 4.37 min, m/z 554.4 [M + H]+<br>ANALPH9_MEOH_QC_v1, Rt: 7.68 min, m/z 554.4 [M + H]+ | 7.9 mg, colourless gum |
| M05207 | 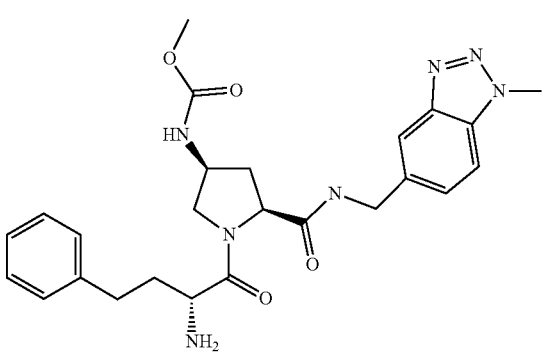<br>Method 1 using methyl chloroformate, Et$_3$N and DCM | ANALPH2_MEOH_QC_v1, Rt: 4.53 min, m/z 494.3 [M + H]+<br>ANALPH9_MEOH_QC_v1, Rt: 6.45 min, m/z 494.3 [M + H]+ | 25 mg, off-white solid |

-continued

| Example No. | Structure & Method | Analytical Data | Mass, state |
|---|---|---|---|
| M05208 | 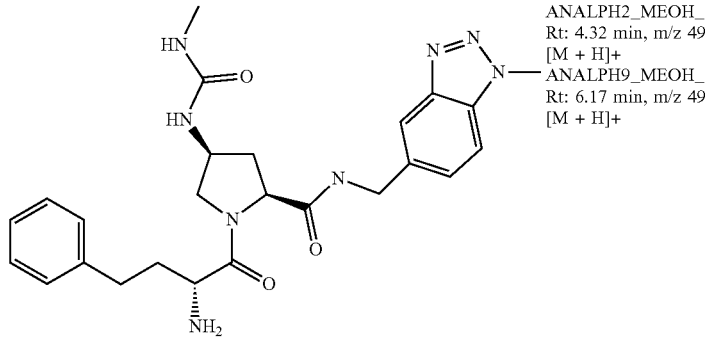<br>Method 3 using methylamine | ANALPH2_MEOH_QC_v1, Rt: 4.32 min, m/z 493.3 [M + H]+<br>ANALPH9_MEOH_QC_v1, Rt: 6.17 min, m/z 493.3 [M + H]+ | 17 mg, off-white solid |
| M05216 | 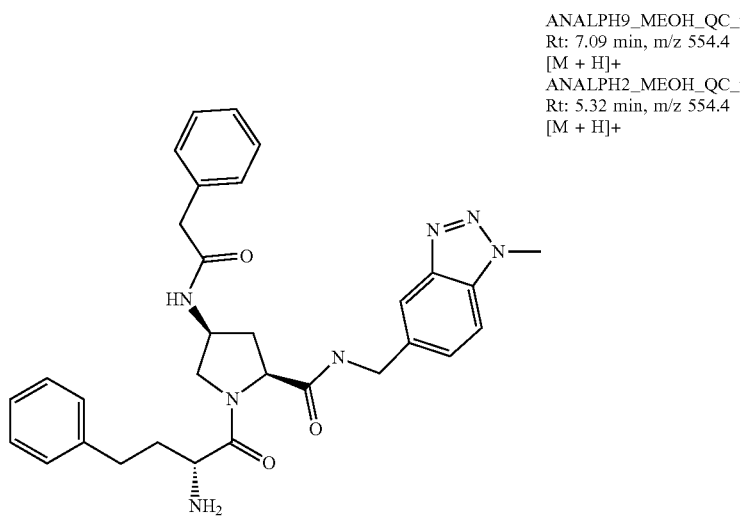<br>Method 1 using phenyl acetyl chloride and DCM | ANALPH9_MEOH_QC_v1, Rt: 7.09 min, m/z 554.4 [M + H]+<br>ANALPH2_MEOH_QC_v1, Rt: 5.32 min, m/z 554.4 [M + H]+ | 23 mg, white solid |
| M05159 | 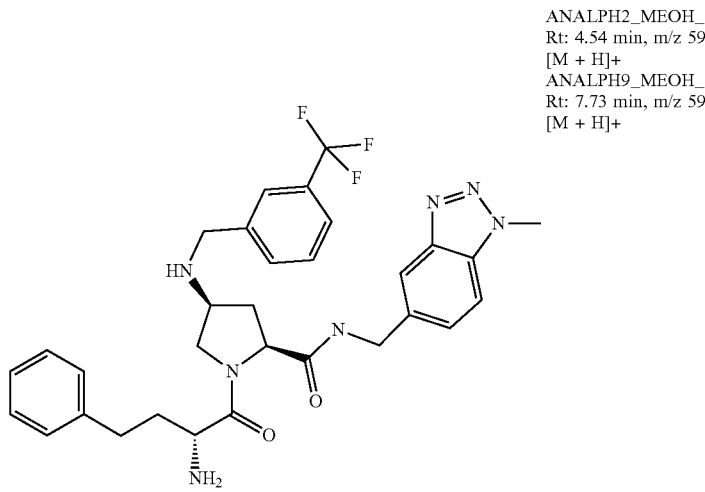<br>Method 2 using 3-trifluoromethyl benzaldehyde | ANALPH2_MEOH_QC_v1, Rt: 4.54 min, m/z 594.3 [M + H]+<br>ANALPH9_MEOH_QC_v1, Rt: 7.73 min, m/z 594.3 [M + H]+ | 55.3 mg, white solid |

General Scheme 4

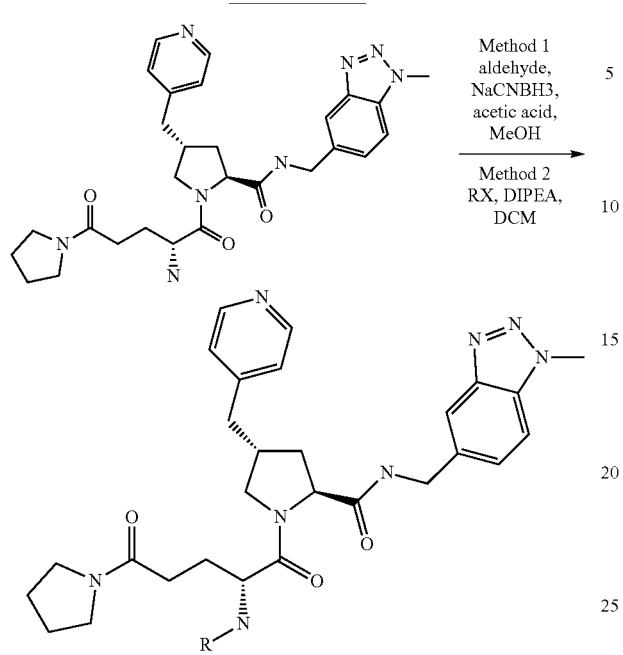

(Method 1): Synthesis of (2S,4R)-1-((R)-2-Benzylamino-5-oxo-5-pyrrolidin-1-yl-pentanoyl)-4-pyridin-4-ylmethyl-pyrrolidine-2-carboxylic acid (1-methyl-1H-benzotriazol-5-ylmethyl)-amide (M05261)

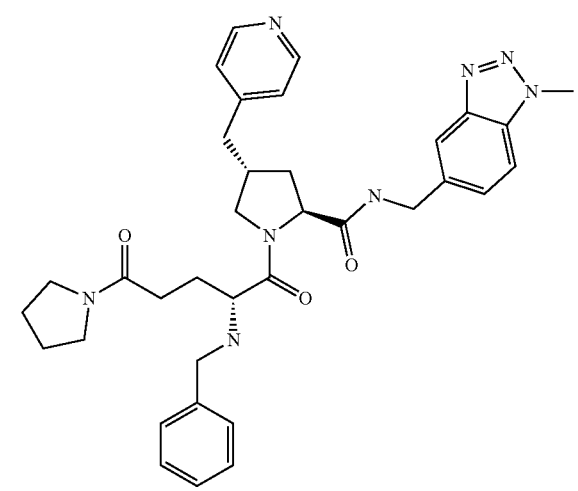 [SMILES: Cn1nnc2cc(CNC(=O)[C@@H]3C[C@@H](Cc4ccncc4)CN3C(=O)[C@@H](CCC(=O)N3CCCC3)NCc3ccccc3)ccc21]

Benzaldehyde (2.0 mg, 0.020 mmol, 1.05 equiv.,), sodium cyanoborohydride (11 mg, 0.180 mmol, 10 equiv.,) and acetic acid (0.1 mL) were added to a solution (2S,4R)-1-((R)-2-amino-5-oxo-5-pyrrolidin-1-yl-pentanoyl)-4-pyridin-4-ylmethyl-pyrrolidine-2-carboxylic acid (1-methyl-1H-benzotriazol-5-ylmethyl)-amide (10 mg, 0.019 mmol, 1.0 equiv.) in methanol (1 mL). The resulting solution was stirred at room temperature for 2 hours, then concentrated under reduced pressure. The resulting product was then purified by reverse phase preparative LCMS to give (2S, 4R)-1-((R)-2-benzylamino-5-oxo-5-pyrrolidin-1-yl-pentanoyl)-4-pyridin-4-ylmethyl-pyrrolidine-2-carboxylic acid (1-methyl-1H-benzotriazol-5-ylmethyl)-amide (6 mg, 53%) as a white solid.

ANALPH2_MEOH_QC_v1, Rt: 3.91 min, m/z 623.3 [M+H]+

ANALPH9_MEOH_QC_v1, Rt: 6.95 min, m/z 623.3 [M+H]+

(Method 2) Synthesis of (2S,4R)-1-((R)-5-Oxo-2-phenylacetylamino-5-pyrrolidin-1-yl-pentanoyl)-4-pyridin-4-ylmethyl-pyrrolidine-2-carboxylic acid (1-methyl-1H-benzotriazol-5-ylmethyl)-amide (M05267)

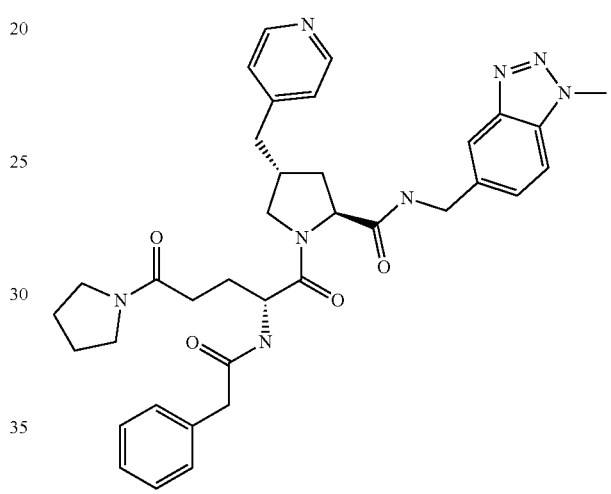

N,N-Diisopropylethylamine (15.0 mg, 0.113 mmol, 1.2 equiv.) and phenylacetyl chloride (17 mg, 0.113 mmol, 1.2 equiv.) were added to a solution of (2S,4R)-1-((R)-2-amino-5-oxo-5-pyrrolidin-1-yl-pentanoyl)-4-pyridin-4-ylmethyl-pyrrolidine-2-carboxylic acid (1-methyl-1H-benzotriazol-5-ylmethyl)-amide (10 mg, 0.019 mmol, 1.0 equiv.) in dichloromethane (1 mL). The resulting solution was stirred at room temperature for 1 hour, then concentrated under reduced pressure. The resulting product was purified by reverse phase preparative LCMS to give (2S,4R)-1-((R)-5-oxo-2-phenylacetylamino-5-pyrrolidin-1-yl-pentanoyl)-4-pyridin-4-ylmethyl-pyrrolidine-2-carboxylic acid (1-methyl-1H-benzotriazol-5-ylmethyl)-amide (12 mg, 95%) as a yellow oil.

ANALPH2_MEOH_QC_v1, Rt: 5.19 min, m/z 651.3 [M+H]+

ANALPH9_MEOH_QC_v1, Rt: 6.90 min, m/z 651.3 [M+H]+

1H NMR (400 MHz, DMSO-d6) δ 8.79 (d, J=6.0 Hz, 0.3H), 8.55 (dd, J=12.4, 7.1 Hz, 1H), 8.46 (td, J=3.9, 1.5 Hz, 2H), 8.16 (t, J=6.1 Hz, 0.7H), 7.84-7.69 (m, 2H), 7.48-7.34 (m, 1H), 7.32-7.21 (m, 3H), 7.21-7.12 (m, 4H), 5.01-4.90 (m, 0.5H), 4.48-4.34 (m, 2H), 4.34-4.23 (m, 5H), 4.12 (q, J=7.7 Hz, 0.5H), 3.80 (dd, J=10.1, 7.5 Hz, 1H), 3.54-3.37 (m, 2H), 3.30-3.08 (m, 5H), 3.00 (t, J=6.6 Hz, 1H), 2.75-2.59 (m, 2H), 2.47-2.20 (m, 2H), 1.98-1.64 (m, 7H).

The following examples were made by analogous methods:

| Example No. | Structure and Method | Analytical Data | Mass, State, Yield |
|---|---|---|---|
| M05262 | 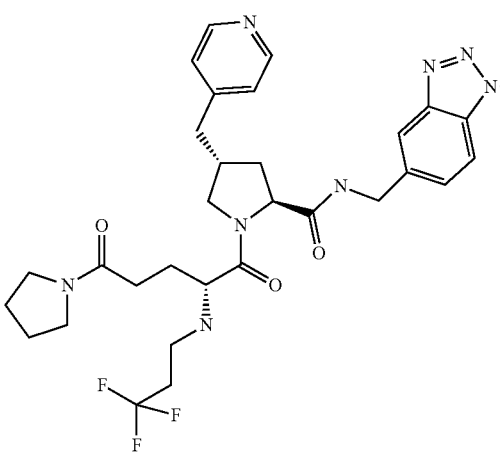<br>Synthesised by Method 1 from 3,3,3-trifluoropropanal. | ANALPH9_MEOH_QC_v1, Rt: 6.82 min, m/z 629.4 [M + H]+<br>ANALPH2_MEOH_QC_v1, Rt: 3.57 min, m/z 629.3 [M + H]+<br>1H NMR (400 MHz, DMSO-d6) δ 8.74 (s, 0.2H), 8.52 – 8.45 (m, 2H), 8.42 (t, J = 6.0 Hz, 0.7H), 7.84 (d, J = 1.4 Hz, 1H), 7.73 (dd, J = 8.6, 0.8 Hz, 1H), 7.43 (ddd, J = 14.1, 8.6, 1.5 Hz, 1H), 7.26 (ddd, J = 23.7, 4.3, 1.6 Hz, 2H), 4.49 – 4.33 (m, 3H), 4.31 – 4.23 (m, 4H), 3.83 (dd, J = 10.0, 6.5 Hz, 1H), 3.47 – 3.24 (m, 3H), 3.24 – 3.04 (m, 2H), 2.78 – 2.53 (m, 5H), 2.49 – 2.35 (m, 2H), 2.36 – 2.21 (m, 2H), 2.13 – 1.94 (m, 1H), 1.96 – 1.65 (m, 5H), 1.64 – 1.41 (m, 2H). | 8.0 mg, 27%, white solid |
| M05268 | 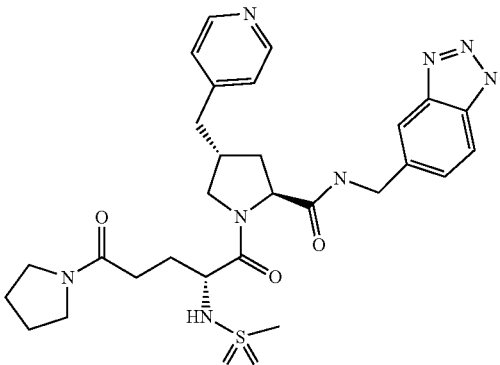<br>Synthesised by Method 2 from methanesulfonyl chloride | ANALPH9_MEOH_QC_v1, Rt: 6.10 min, m/z 611.3 [M + H]+<br>ANALPH2_MEOH_QC_v1, Rt: 4.13 min, m/z 611.3 [M + H]+ | 0.008 g, 14%, yellow oil |
| M05269 | 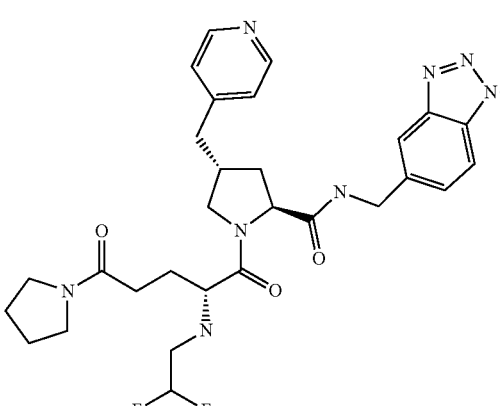<br>Synthesised by Method 2 from 2,2-difluoroethyl trifluoromethanesulfonate | ANALPH9_MEOH_QC_v1, Rt: 6.42 min, m/z 597.4 [M + H]+<br>ANALPH2_MEOH_QC_v1, Rt: 3.62 min, m/z 597.4 [M + H]+ | 5.0 mg, 9%, yellow oil |

-continued
| Example No. | Structure and Method | Analytical Data | Mass, State, Yield |
|---|---|---|---|
| M05271 | 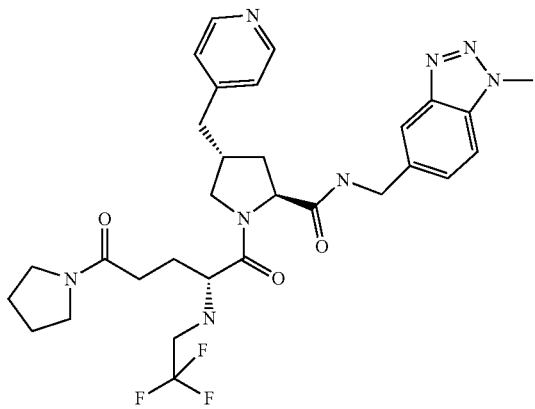<br>Synthesised by Method 2 from 2,2,2-trifluoromethanesulfonate | ANALPH9_MEOH_QC_v1, Rt: 6.79 min, m/z 615.3 [M + H]+ ANALPH2_MEOH_QC_v1, Rt: 4.93 min, m/z 615.3 [M + H]+ | 13 mg, 23%, colourless oil |
| M05290 | 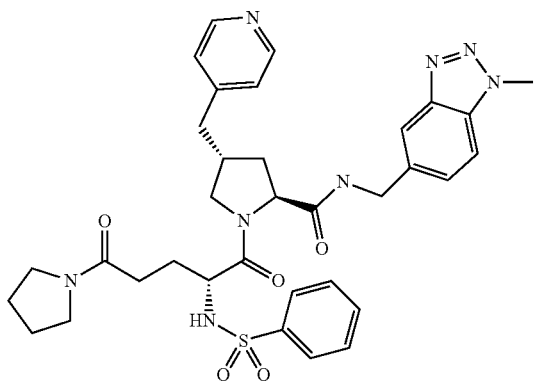<br>Synthesised by Method 2 from benzenesulfonyl chloride | ANALPH9_MEOH_QC_v1, Rt: 6.57 min, m/z 673.2 [M + H]+ ANALPH2_MEOH_QC_v1, Rt: 4.95 min, m/z 673.2 [M + H]+ | 8.0 mg, 13%, white solid |

General Scheme 5: Final Step Suzuki

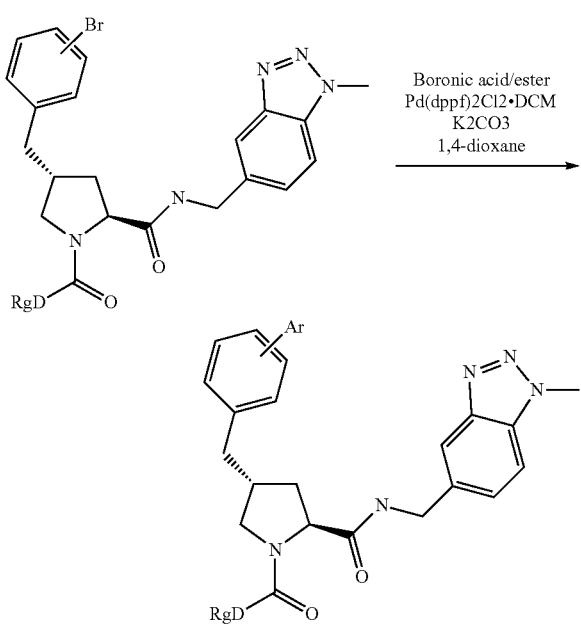

Synthesis of (2S,4R)-1-((R)-2-Amino-5-oxo-5-pyrrolidin-1-yl-pentanoyl)-4-[3-(2-methyl-2H-pyrazol-3-yl)-benzyl]-pyrrolidine-2-carboxylic acid (1-methyl-1H-benzotriazol-5-ylmethyl)-amide (M05350)

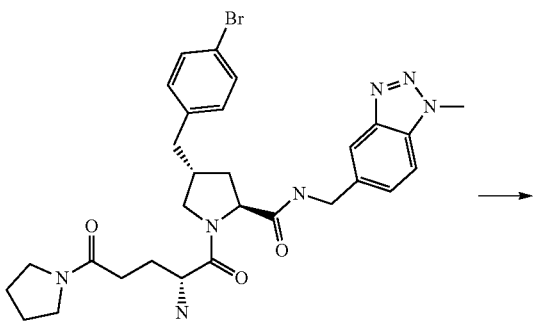

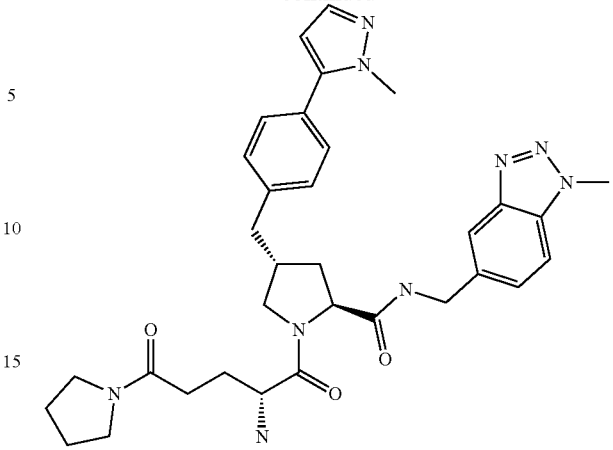

(2S,4R)-1-((R)-2-Amino-5-oxo-5-pyrrolidin-1-yl-pentanoyl)-4-(4-bromo-benzyl)-pyrrolidine-2-carboxylic acid (1-methyl-1H-benzotriazol-5-ylmethyl)-amide (37 mg, 0.061 mmol), 1-methyl-5-(4,4,5,5-tetramethyl-1,3,2-dioxaborolan-2-yl)pyrazole (15 mg, 0.072 mmol), Pd(dppf)$_2$Cl$_2$·DCM (2.5 mg, 0.0031 mmol) and K$_2$CO$_3$ (16 mg, 0.12 mmol) were dissolved in 1,4-dioxane (1.8 mL) and H$_2$O (0.2 mL). The reaction mixture was degassed with N$_2$ for 5 minutes. The stirred mixture was then heated at 90° C. for 45 minutes in the microwave. The mixture was filtered through celite, and the residue washed with DCM. The filtrate was washed twice with H$_2$O then evaporated in vacuo. The crude product was purified by reversed phase HPLC, the product-containing fractions were passed through a catch-release cartridge (Biotage SCX-2; 5 g) eluting with NH$_3$-MeOH to yield the title compound (14 mg, 38%) as a white solid;

ANALPH2_MEOH_QC_v1, Rt: 5.49 min, m/z 612.5 [M+H]+

ANALPH9_MEOH_QC_v1, Rt: 6.98 min, m/z 612.5 [M+H]+

Optionally the work-up procedure may also involve an additional wash with sat. brine (aq) and a catch-release purification (Biotage SCX-2)eluting with 0.5M NH$_3$-MeOH.

The following examples were synthesised by analogous methods:

| Example No. | Structure & Method | Analytical data | Mass, yield, state |
|---|---|---|---|
| M05363 | Using 3-pyridinylboronic acid and (2S,4R)-1-((R)-2-amino-5-oxo-5-pyrrolidin-1-yl- | ANALPH2_MEOH_QC_v1, Rt: 5.22 min, m/z 600.3 [M + H]+ ANALPH9_MEOH_QC_v1, Rt: 7.80 min, m/z 600.3 [M + H]+ | 14 mg, 28%, white solid |

| Example No. | Structure & Method | Analytical data | Mass, yield, state |
|---|---|---|---|
| | pentanoyl)-4-(4-bromo-benzyl)-pyrrolidine-2-carboxylic acid (1-methyl-1H-benzotriazol-5-ylmethyl)-amide | | |
| M05323 | 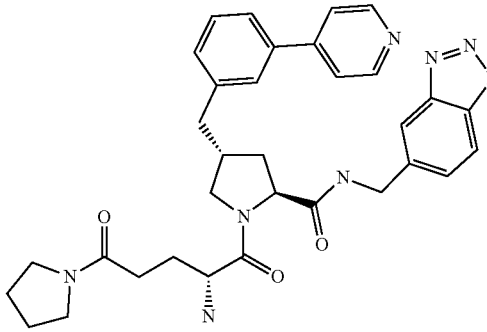<br>Using 4-pyridinylboronic acid and (2S,4R)-1-((R)-2-amino-5-oxo-5-pyrrolidin-1-yl-pentanoyl)-4-(3-bromo-benzyl)-pyrrolidine-2-carboxylic acid (1-methyl-1H-benzotriazol-5-ylmethyl)-amide | ANALPH2_MEOH_QC_v1, Rt: 4.42 min, m/z 609.2 [M + H]+<br>ANALPH9_MEOH_QC_v1, Rt: 7.10 min, m/z 609.2 [M + H]+<br>1H-NMR (400 MHz, DMSO-D6) δ 8.67 (t, J = 5.7 Hz, 0.2H), 8.63 – 8.53 (m, 2H), 8.42 (t, J = 6.0 Hz, 0.8H), 8.31 – 8.21 (1.6H) (stoichiometry of formate salt), 7.79 (s, 1H), 7.72 – 7.55 (m, 5H), 7.52 – 7.18 (m, 3H), 4.67 (t, J = 5.0 Hz, 0.2H), 4.45 – 4.29 (m, 2.8H), 4.27 – 4.15 (m, 3H), 3.82 – 3.67 (m, 1H), 3.62 – 3.42 (m, 1H), 3.42 – 3.24 (m, 2H), 3.24 – 3.01 (m, 3H), 2.83 – 2.67 (m, 2H), 2.66 – 2.52 (m, 1H), 2.40 – 2.17 (m, 1H), 2.02 – 1.33 (9H) | 13 mg, 46%, white solid |
| M05330 | 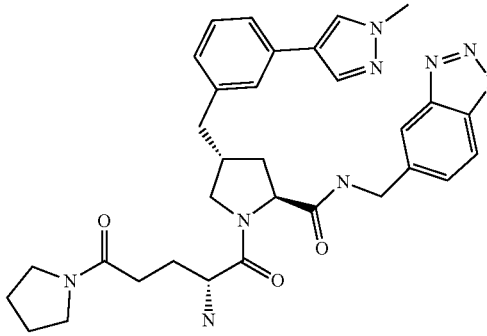<br>Using 1-methylpyrazole-4-boronic acid pinacol ester and (2S,4R)-1-((R)-2-amino-5-oxo-5-pyrrolidin-1-yl-pentanoyl)-4-(3-bromo-benzyl)-pyrrolidine-2-carboxylic acid (1-methyl-1H-benzotriazol-5-ylmethyl)-amide | ANALPH9_MEOH_QC_v1, Rt: 6.95 min, m/z 612.1 [M + H]+<br>ANALPH2_MEOH_QC_v1, Rt: 5.53 min, m/z 612.1 [M + H]+ | 2 mg, 10%, white solid |
| M05341 | 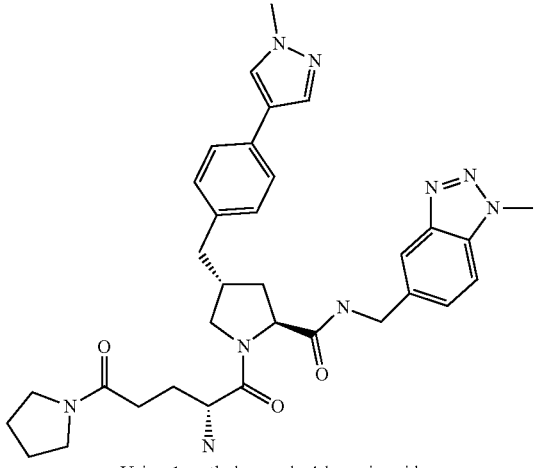<br>Using 1-methylpyrazole-4-boronic acid pinacol ester and (2S,4R)-1-((R)-2-amino-5-oxo-5-pyrrolidin-1-yl-pentanoyl)-4-(4- | ANALPH9_MEOH_QC_v1, Rt: 6.82 min, m/z 612.3 [M + H]+<br>ANALPH2_MEOH_QC_v1, Rt: 5.39 min, m/z 612.3 [M + H]+ | 15.5 mg, 50%, white solid |

| Example No. | Structure & Method | Analytical data | Mass, yield, state |
|---|---|---|---|
| | bromo-benzyl)-pyrrolidine-2-carboxylic acid (1-methyl-1H-benzotriazol-5-ylmethyl)-amide | | |
| M05364 | 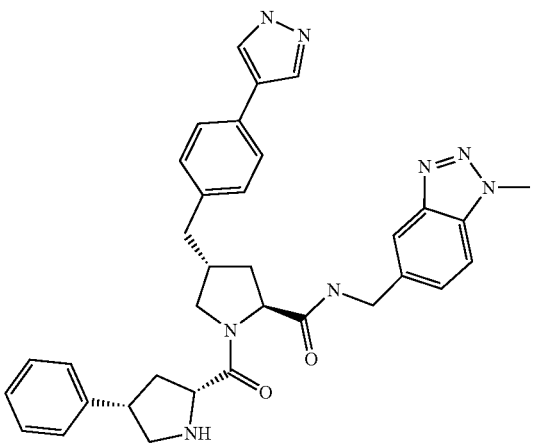<br>Using 4-pyrazole-4-boronic acid pinacol ester and (2S,4R)-4-(4-bromo-benzyl)-1-((2R,4S)-4-phenyl-pyrrolidine-2-carbonyl)-pyrrolidine-2-carboxylic acid (1-methyl-1H-benzotriazol-5-ylmethyl)-amide | ANALPH2_MEOH_QC_v1, Rt: 5.59 min, m/z 589.3 [M + H]+<br>ANALPH9_MEOH_QC_v1, Rt: 7.45 min, m/z 589.3 [M + H]+ | 8 mg, 16%, white solid |
| M05367 | 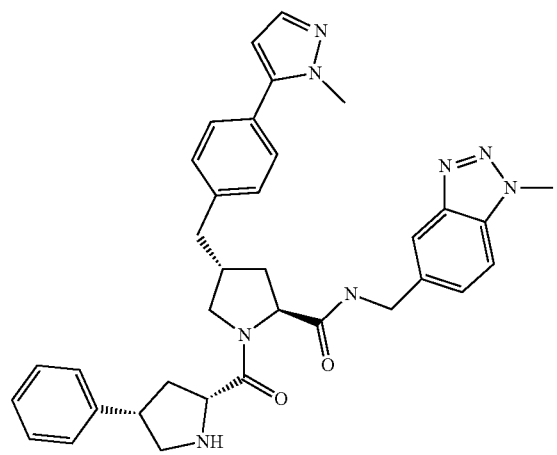<br>Using 1-methyl-1H-pyrazole-5-boronic acid pinacol ester and (2S,4R)-4-(4-bromo-benzyl)-1-((2R,4S)-4-phenyl-pyrrolidine-2-carbonyl)-pyrrolidine-2-carboxylic acid (1-methyl-1H-benzotriazol-5-ylmethyl)-amide | ANALPH9_MEOH_QC_v1, Rt: 7.71 min, m/z 603.4 [M + H]+<br>ANALPH2_MEOH_QC_v1, Rt: 5.89 min, m/z 603.4 [M + H]+ | 11.5 mg, 23%, white solid |

General Scheme 6 Late stage carboxamide synthesis

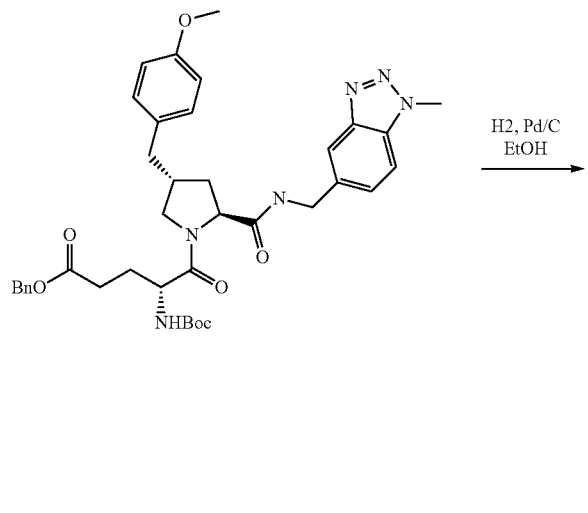

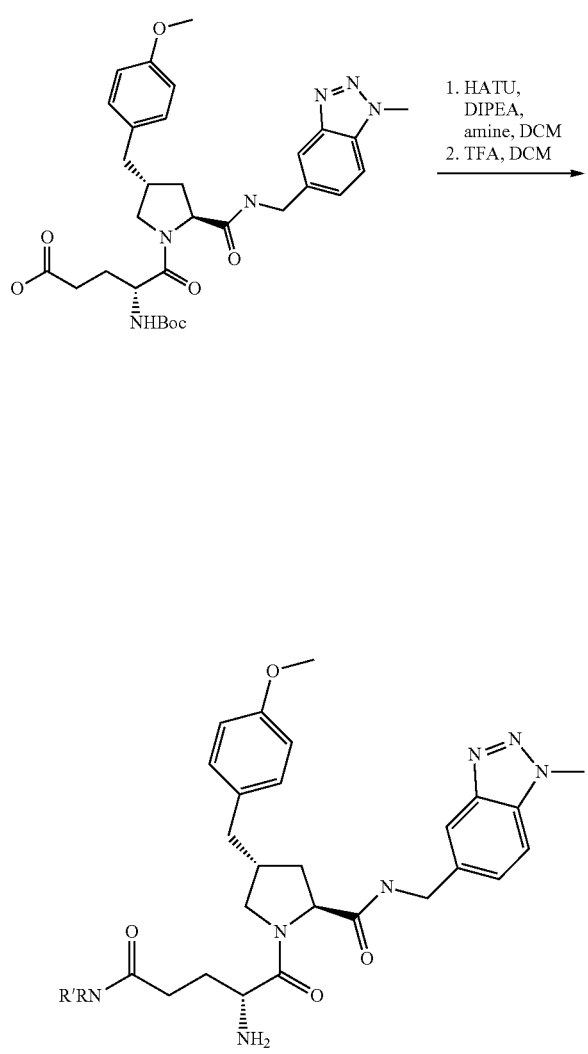

Synthesis of (2S,4R)-1-[(R)-2-amino-5-((S)-2-methyl-piperazin-1-yl)-5-oxo-pentanoyl]-4-(4-methoxy-benzyl)-pyrrolidine-2-carboxylic acid (1-methyl-1H-benzotriazol-5-ylmethyl)-amide (M05417)

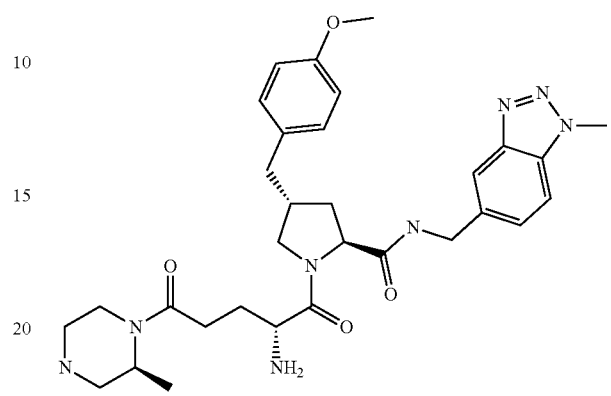

Step 1: (R)-4-tert-Butoxycarbonylamino-5-{(2S,4R)-4-(4-methoxy-benzyl)-2-[(1-methyl-1H-benzotriazol-5-ylmethyl)-carbamoyl]-pyrrolidin-1-yl}-5-oxo-pentoic acid benzyl ester (GS6-int1) (918 mg, 1.32 mmol) was dissolved in ethanol (10 mL) and hydrogenated by cycling through the H-cube using a 10% Pd/C CatCart at 60° C. for 5 hours. The reaction mixture was dried in vacuo to give (R)-4-tert-butoxycarbonylamino-5-{(2S,4R)-4-(4-methoxy-benzyl)-2-[(1-methyl-1H-benzotriazol-5-ylmethyl)-carbamoyl]-pyrrolidin-1-yl}-5-oxo-pentoic acid (775 mg, 96%) as a colourless oil.

ANALPH2_MEOH_4 min, Rt: 3.03 min, m/z 609.8 [M+H]+

Step 2: Amide coupling of (R)-4-tert-butoxycarbonylamino-5-{(2S,4R)-4-(4-methoxy-benzyl)-2-[(1-methyl-1H-benzotriazol-5-ylmethyl)-carbamoyl]-pyrrolidin-1-yl}-5-oxo-pentoic acid with (3S)-3-methyl-piperazine-1-carboxylic acid tert-butyl ester, was carried out using HATU, DIPEA in DCM and general method 1 isolation method c for 1 hour to give (S)-4-((R)-4-tert-butoxycarbonylamino-5-{(2S,4R)-4-(4-methoxy-benzyl)-2-[(1-methyl-1H-benzotriazol-5-ylmethyl)-carbamoyl]-pyrrolidin-1-yl}-5-oxo-pentanoyl)-3-methyl-piperazine-1-carboxylic acid tert-butyl ester (117 mg, 94%) as a colourless oil.

ANALPH2_MEOH_4 min, Rt: 3.40 min, m/z 791.8 [M+H]+

Step 3: Boc deprotection of (S)-4-((R)-4-tert-butoxycarbonylamino-5-{(2S,4R)-4-(4-methoxy-benzyl)-2-[(1-methyl-1H-benzotriazol-5-ylmethyl)-carbamoyl]-pyrrolidin-1-yl}-5-oxo-pentanoyl)-3-methyl-piperazine-1-carboxylic acid tert-butyl ester was carried out using TFA in DCM using General Method 2A for 1.5 hours. The reaction mixture was concentrated in vacuo and the residue purified using an SCX-2 cartridge (5 g) and eluted with 4M ammonia in methanol. The product-containing fractions were dried in vacuo and purified using prep-HPLC to afford (2S,4R)-1-[(R)-2-amino-5-((S)-2-methyl-piperazin-1-yl)-5-oxo-pentanoyl]-4-(4-methoxy-benzyl)-pyrrolidine-2-carboxylic acid (1-methyl-1H-benzotriazol-5-ylmethyl)-amide (15 mg, 16%) as a white solid.

ANALPH2_MEOH_QC_v1, RT: 4.33 min, m/z 591.4 [M+H]+

ANALPH9_MEOH_QC_v1, RT: 6.63 min, m/z 591.4 [M+H]+

The following examples were synthesised by analogous methods:

| Example No. | Structure | Analytical Data | Mass, state |
|---|---|---|---|
| M05420 | 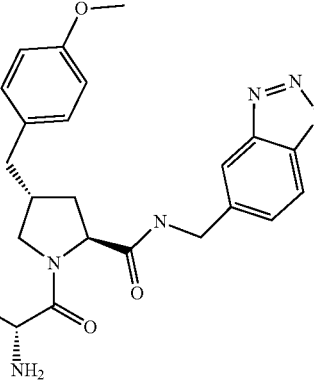<br>Step 2 using 3-Boc-3,8-diazabicyclo[3.2.1]octane | ANALPH2_MEOH_QC_v1, RT: 4.31 min, m/z 603.4 [M + H]+<br>ANALPH9_MEOH_QC_v1, RT: 6.65 min, m/z 603.4 [M + H]+ | 17 mg, white solid |
| M05443 | 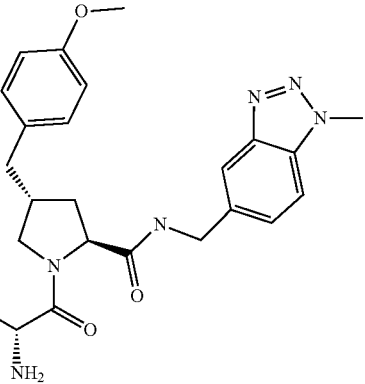<br>Step 2 using (3R)-3-methylpiperazine | ANALPH2_MEOH_QC_v1, RT: 4.17 min, m/z 591.4 [M + H]+<br>ANALPH9_MEOH_QC_v1, RT: 6.63 min, m/z 591.4 [M + H]+ | 12 mg, white solid |
| M05450 | 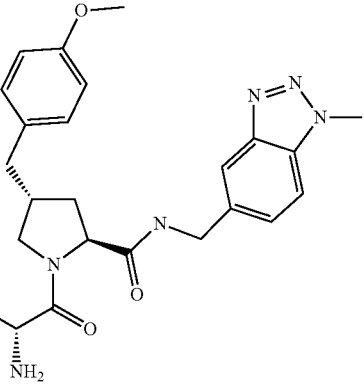<br>Step 2 using 2,2-Dimethylpyrrolidine | ANALPH2_MEOH_QC_v1, RT: 6.06 min, m/z 590.2 [M + H]+<br>ANALPH9_MEOH_QC_v1, RT: 7.69 min, m/z 590.4 [M + H]+ | 15.5 mg, white solid |

-continued

| Example No. | Structure | Analytical Data | Mass, state |
|---|---|---|---|
| M05451 | Step 2 using piperazin-2-one | ANALPH2_MEOH_QC_v1, RT: 5.11 min, m/z 591.4 [M + H]+ ANALPH9_MEOH_QC_v1, RT: 6.51 min, m/z 591.4 [M + H]+ | 15.3 mg, white solid |
| M05458 | Step 2 using (2)-2-cyanopyrrolidine | ANALPH2_MEOH_QC_v1, RT: 5.53 min, m/z 587.4 [M + H]+ ANALPH9_MEOH_QC_v1, RT: 6.97 min, m/z 587.4 [M + H]+ | 12.5 mg, white solid |
| M05460 | Step 2 using 3,8-diazabycyclo[3.2.1]octan-2-one | ANALPH2_MEOH_QC_v1, RT: 5.31 min, m/z 617.4 [M + H]+ ANALPH9_MEOH_QC_v1, RT: 6.65 min, m/z 617.3 [M + H]+ 1H NMR (400 MHz, DMSO-d6) δ 8.73 – 8.61 (m, 0.3H), 8.34 (t, J = 5.9 Hz, 0.7H), 7.87 – 7.68 (m, 2H), 7.51 – 7.37 (m, 2H), 7.11 (dd, J = 14.2, 8.5 Hz, 2H), 6.85 (dd, J = 8.4, 1.8 Hz, 2H), 4.76 – 4.45 (m, 2H), 4.43 – 4.26 (m, 3H), 4.29 (s, 3H), 3.80 – 3.67 (m, 4H), 3.40 (s, 2H), 3.10 – 2.83 (m, 1H), 2.70 – 2.52 (m, 3H), 2.47 – 2.29 (m, 1H), 2.29 – 1.54 (m, 11H), 1.45 (s, 1H). | 8 mg, white solid |

| Example No. | Structure | Analytical Data | Mass, state |
|---|---|---|---|
| M05461 | 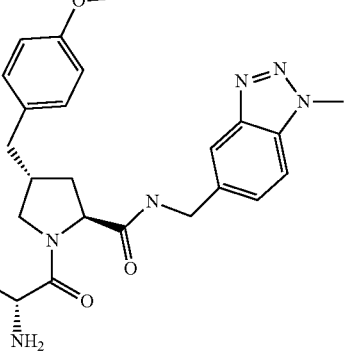Step 2 using t-Butylhomopiperazine carboxylate | ANALPH2_MEOH_QC_v1, RT: 4.25 min, m/z 591.4 [M + H]+ ANALPH9_MEOH_QC_v1, RT: 6.58 min, m/z 591.4 [M + H]+ | 10 mg, white solid |
General Scheme 7
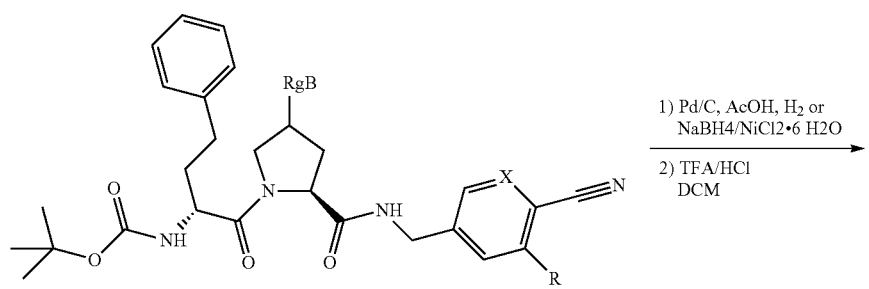
1) Pd/C, AcOH, H$_2$ or NaBH4/NiCl2·6 H2O
2) TFA/HCl DCM
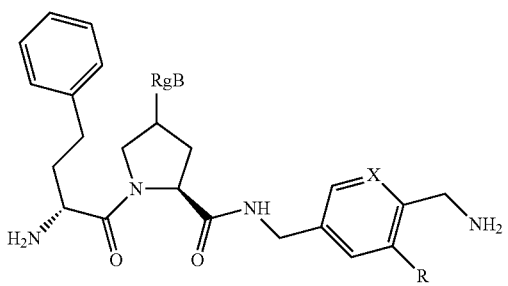

Synthesis of (2S,4R)-1-((R)-2-Amino-4-phenyl-butyryl)-4-cyclohexyl-pyrrolidine-2-carboxylic acid 4-aminomethyl-benzylamide (M05076)

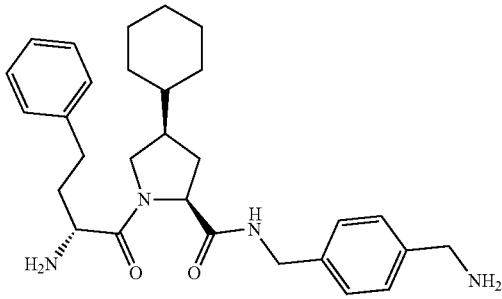

{(R)-1-[(2S,4R)-2-(4-Cyano-benzylcarbamoyl)-4-cyclohexyl-pyrrolidine-1-carbonyl]-3-phenyl-propyl}-carbamic acid tert-butyl ester (GS7-int 1, 140 mg, 0.24 mmol) was dissolved in AcOH (15 mL) and 10% Pd/C (50 mg) was added. The mixture was stirred under a $H_2$ atmosphere at 55° C. for 4 hours. The reaction mixture was filtered through celite then purified by SCX-2, eluting with 2M $NH_3$/MeOH. The solvent was removed and the residue was dissolved in TFA/DCM and stirred at room temperature for 1 hour. The solvent was removed and residue purified by SCX-2 cartridge followed by prep HPLC to give (2S,4R)-1-((R)-2-amino-4-phenyl-butyryl)-4-cyclohexyl-pyrrolidine-2-carboxylic acid 4-aminomethyl-benzylamide (60 mg, 53%) as a white solid.

ANALPH2_MEOH_QC_v1, Rt: 5.25 min, m/z 477.3 [M+H]+

ANALPH9_MEOH_QC_v1, Rt: 8.21 min, m/z 477.3 [M+H]+

1H NMR (400 MHz, $CDCl_3$) δ 7.36-7.26 (m, 2H), 7.30-7.11 (m, 7H), 6.91 (t, J=5.8 Hz, 1H), 4.49 (dd, J=14.9, 6.0 Hz, 1H), 4.42-4.29 (m, 2H), 3.86 (s, 2H), 3.43-3.27 (m, 2H), 2.89 (t, J=10.7 Hz, 1H), 2.80 (m, 2H), 2.26 (dt, J=12.7, 7.6 Hz, 1H), 1.93 (ddd, J=12.8, 11.4, 8.6 Hz, 1H), 1.87-1.64 (m 7H), 1.45 (d, J=12.3 Hz, 1H), 1.30-1.11 (m 4H), 0.99-0.81 (m 2H).

The following examples were synthesised by analogous methods:

| Example No. | Structure and Method | Analytical Data | Mass, state |
|---|---|---|---|
| M05073 | Using {(R)-1-[(2S,4S)-2-(4-Cyano-3-methoxy-benzylcarbamoyl)-4-methyl-pyrrolidine-1-carbonyl]-3-phenyl-propyl}-carbamic acid tert-butyl ester and Pd/C, $H_2$, AcOH and deprotection with TFA heating at 60° C. for reduction and additional aliquot Pd/C added during reaction | ANALPH2_MEOH_QC_v1, Rt: 3.66 min, m/z 439.3 [M + H]+ ANALPH9_MEOH_QC_v1, Rt: 6.76 min, m/z 439.3 [M + H]+ | 32.8 mg, white solid |
| M05074 | Using {(R)-1-[(2S,4R)-2-(4-Cyano-3-methoxy-benzylcarbamoyl)-4-methyl-pyrrolidine-1-carbonyl]-3-phenyl-propyl}-carbamic acid tert-butyl ester and Pd/C, $H_2$, AcOH and deprotection with TFA | ANALPH2_MEOH_QC_v1, Rt: 3.67 min, m/z 439.3 [M + H]+ ANALPH9_MEOH_QC_v1, Rt: 6.88 min, m/z 439.3 [M + H]+ | 9.1 mg, white solid |

| Example No. | Structure and Method | Analytical Data | Mass, state |
|---|---|---|---|
| M05056 | 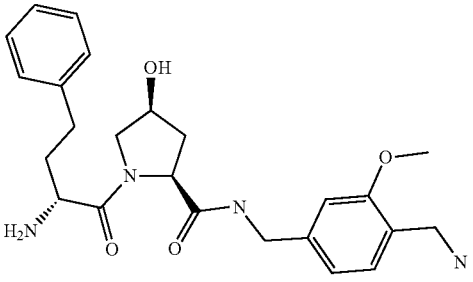<br>Using {(R)-1-[(2S,4S)-2-(4-Cyano-3-methoxy-benzyl carbamoyl)-4-hydroxy-pyrrolidine-1-carbonyl]-3-phenyl-propyl}-carbamic acid tert-butyl ester and Pd/C, $H_2$, AcOH and deprotection with TFA | ANALPH2_MEOH_QC_v1, Rt: 2.68 min, m/z 441.3 [M + H]+<br>ANALPH9_MEOH_QC_v1, Rt: 5.84 min, m/z 441.3 [M + H]+<br>$^1$H NMR (400 MHz, DMSO-d6) δ 8.40 (t, J = 5.9 Hz, 1H), 7.28 (d, J = 7.4 Hz, 2H), 7.24 – 7.13 (m, 2H), 7.12 – 6.96 (m, 1H), 6.94 – 6.84 (m, 1H), 6.80 (dd, J = 7.5, 1.6 Hz, 1H), 5.33 (s, 1H), 4.36 – 4.26 (m, 1H), 4.25 – 4.15 (m, 3H), 4.13 – 4.03 (m, 1H), 3.80 (d, J = 2.1 Hz, 3H), 3.73 (s, 1H), 3.61 (d, J = 10.7 Hz, 2H), 3.49 (dd, J = 10.5, 4.9 Hz, 1H), 2.79 – 2.69 (m, 1H), 2.69 – 2.57 (m, 1H), 2.32 – 2.20 (m, 1H), 1.86 – 1.70 (m, 3H), 1.59 – 1.44 (m, 1H). | 28.3 mg, white solid |
| M05053 | 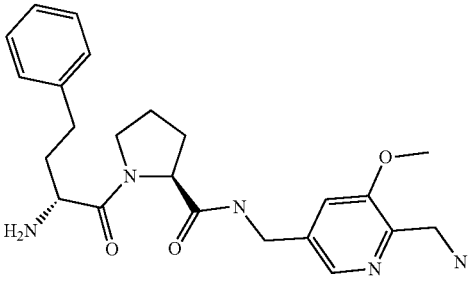<br>Using ((R)-1-{(S)-2-[(6-Cyano-5-methoxy-pyridin-3-ylmethyl)-carbamoyl]-pyrrolidine-1-carbonyl}-3-phenyl-propyl)-carbamic acid tert-butyl ester and Pd/C, $H_2$, AcOH and deprotection with TFA | ANALPH2_MEOH_QC_v1, Rt: 3.03 min, m/z 426.2 [M + H]+<br>ANALPH9_MEOH_QC_v1, Rt: 6.36 min, m/z 426.3 [M + H]+ | 21.2 mg, white solid |
| M05068 | 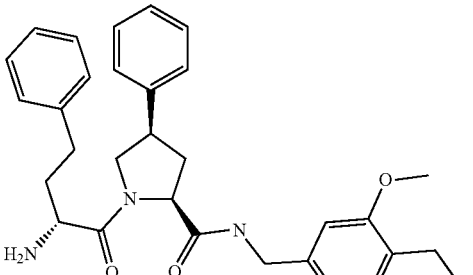<br>Using {(R)-1-[(2S,4R)-2-(4-Cyano-3-methoxy-benzyl carbamoyl)-4-phenyl-pyrrolidine-1-carbonyl]-3-phenyl-propyl}-carbamic acid tert-butyl ester and Pd/C, $H_2$, AcOH and deprotection with TFA. Additional purification of the boc-protected intermediate was carried out using column chromatography on silica | ANALPH2_MEOH_QC_v1, Rt: 4.49 min, m/z 501.3 [M + H]+<br>ANALPH9_MEOH_QC_v1, Rt: 7.51 min, m/z 501.3 [M + H]+ | 43 mg, white solid |

-continued

| Example No. | Structure and Method | Analytical Data | Mass, state |
|---|---|---|---|
| M05054 | 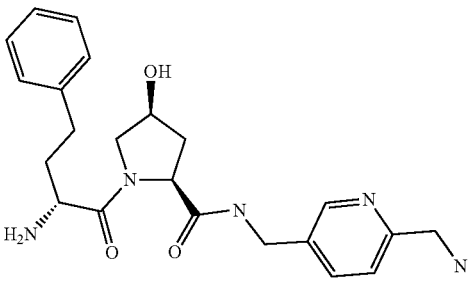<br>Using ((R)-1-{(2S,4S)-2-[(6-Cyano-pyridin-3-ylmethyl)-carbamoyl]-4-hydroxy-pyrrolidine-1-carbonyl}-3-phenyl-propyl)-carbamic acid tert-butyl ester and Pd/C, H$_2$, AcOH and deprotection with TFA | ANALPH2_MEOH_QC_v1, Rt: 1.35 min, m/z 412.2 [M + H]+<br>ANALPH9_MEOH_QC_v1, Rt: 5.59 min, m/z 412.2 [M + H]+ | 32.9 mg, white solid |
| M00626 | 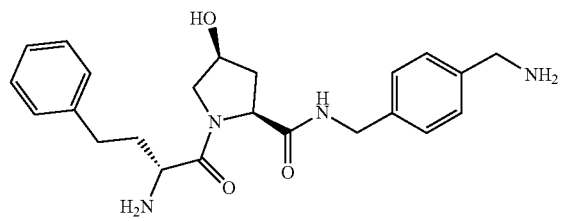 [SMILES: NCc1ccc(CNC(=O)[C@@H]2C[C@H](O)CN2C(=O)[C@H](N)CCc2ccccc2)cc1]<br>Using tert-Butyl N-[(2R)-1-[(4S)-2-{[(4-cyanophenyl)methyl]carbamoyl}-4-hydroxypyrrolidin-1-yl]-1-oxo-4-phenylbutan-2-yl]carbamateIUPAC and NiCl2, NaBH4 (GM6A) and deprotection using GM2A | Agilent_MeCN_HPLC_3 min LCMS: R$_t$ = 0.29 min m/z = 433.2 [M + Na]$^+$ | 56 mg white foamy solid |

General Scheme 8 (Fmoc deprotection followed by boc deprotection)

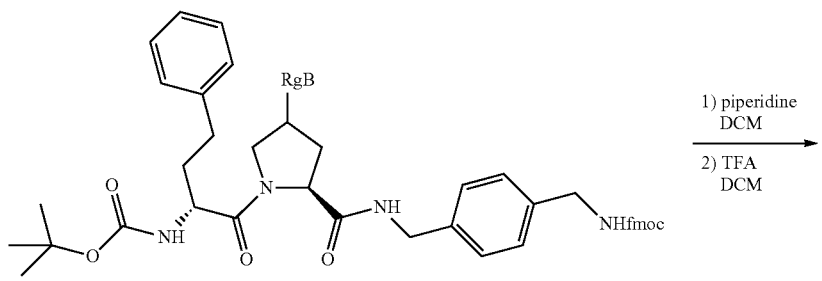

1) piperidine DCM
2) TFA DCM

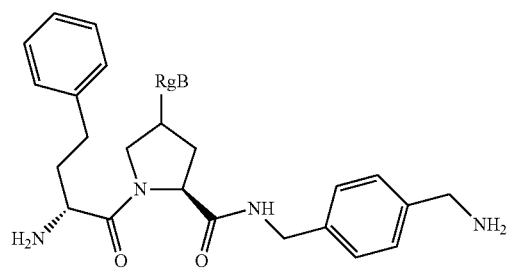

Synthesis of (2S,4R)-1-((R)-2-Amino-4-phenyl-butyryl)-4-cyano-pyrrolidine-2-carboxylic acid 4-aminomethyl-benzylamide (M05091)

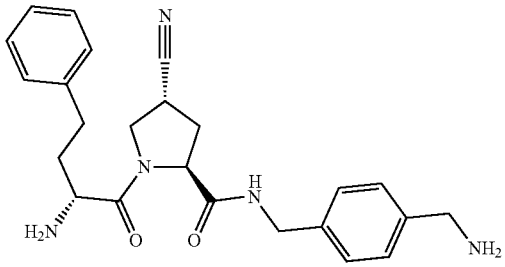

Step 1: [(R)-1-((2S,4R)-4-Cyano-2-{4-[(9H-fluoren-9-ylmethoxycarbonylamino)-methyl]-benzylcarbamoyl}-pyrrolidine-1-carbonyl)-3-phenyl-propyl]-carbamic acid tert-butyl ester (GS8-int1, 207 mg, 0.28 mmol) was dissolved in DCM (2 mL) and piperidine (0.2 mL) added. The reaction mixture was stirred at room temperature for 2 hours, then the solvent removed and the residue purified by prep LCMS to give {(R)-1-[(2S,4R)-2-(4-aminomethyl-benzylcarbamoyl)-4-cyano-pyrrolidine-1-carbonyl]-3-phenyl-propyl}-carbamic acid tert-butyl ester (133 mg, 93%) as a clear oil.

AnalpH2_MeOH_4MIN: Rt: 2.27 min, m/z 520.4 [M+H]$^+$

Step 2: {(R)-1-[(2S,4R)-2-(4-Aminomethyl-benzylcarbamoyl)-4-cyano-pyrrolidine-1-carbonyl]-3-phenyl-propyl}-carbamic acid tert-butyl ester (133 mg, 0.226 mmol) underwent BOC deprotection using General Method 2A and was purified by prep LCMS to give (2S,4R)-1-((R)-2-amino-4-phenyl-butyryl)-4-cyano-pyrrolidine-2-carboxylic acid 4-aminomethyl-benzylamide (81.4 mg, 62%) as a white solid.

ANALPH9_MEOH_QC_v1, Rt: 5.95 min, m/z 420.4 [M+H]+
ANALPH2_MEOH_QC_v1, Rt: 2.76 min, m/z 420.3 [M+H]+

$^1$H NMR (400 MHz, DMSO-d6) δ 8.66 (t, J=6.0 Hz, 1H), 7.42-7.36 (m, 2H), 7.36-7.27 (m, 5H), 7.28-7.17 (m, 3H), 4.45 (dd, J=8.6, 3.7 Hz, 1H), 4.30 (d, J=5.9 Hz, 2H), 4.21 (t, J=6.0 Hz, 1H), 4.02 (s, 2H), 3.99-3.88 (m, 1H), 3.76 (dd, J=10.3, 7.2 Hz, 1H), 3.63-3.42 (m, 1H), 2.77-2.59 (m, 2H), 2.49-2.41 (m, 1H), 2.23 (ddd, J=12.7, 6.7, 3.8 Hz, 1H), 2.02 (m, 2H).

The following examples were synthesised by analogous methods:

| Example No. | Structure and Method | Analytical Data | Mass, state |
|---|---|---|---|
| M05117 | Using [(R)-1-((2S,4R)-4-(4-Chloro-benzyl)-2-{4-[(9H-fluoren-9-ylmethoxycarbonylamino)-methyl]-benzylcarbamoyl}-pyrrolidine-1-carbonyl)-3-phenyl-propyl]-carbamic acid tert-butyl ester | ANALPH9_MEOH_QC_v1, Rt: 7.92 min, m/z 519.3 [M + H]+ ANALPH2_MEOH_QC_v1, Rt: 4.85 min, m/z 519.3 [M + H]+ | 9.5 mg, colourless oil |
| M05156 | Using [(R)-1-((2S,4R)-2-{4-[(9H-Fluoren-9-ylmethoxycarbonylamino)-methyl]-benzylcarbamoyl}-4-pyridin-4-ylmethyl-pyrrolidine-1-carbonyl)-3-phenyl-propyl]-carbamic acid tert-butyl ester | ANALPH2_MEOH_QC_v1, Rt: 1.22 min, m/z 486.3 [M + H]+ ANALPH9_MEOH_QC_v1, Rt: 6.83 min, m/z 486.3 [M + H]+ 1H NMR (400 MHz, CDCl$_3$) δ 8.59 – 8.50 (m, 2H), 7.52 (s, 1H), 7.32 (dd, J = 6.9, 1.5 Hz, 1H), 7.26 (t, J = 7.4 Hz, 5H), 7.23 – 7.17 (m, 5H), 7.11 – 7.01 (m, 2H), 4.60 (d, J = 7.9 Hz, 1H), 4.43 (dd, J = 14.9, 5.9 Hz, 1H), 4.33 (dd, J = 14.9, 5.7 Hz, 1H), 3.85 (s, 1H), 3.47 – 3.34 (m, 2H), 2.85 – 2.77 (m, 1H), 2.80 – 2.65 (m, 3H), 2.64 (s, 2H), 2.51 (ddd, J = 24.2, 13.0, 6.7 Hz, 2H), 1.96 – 1.76 (m, 2H), 1.54 (td, J = 11.7, 8.0 Hz, 1H). | 35.2 mg, white solid |

-continued

| Example No. | Structure and Method | Analytical Data | Mass, state |
|---|---|---|---|
| M05130 | 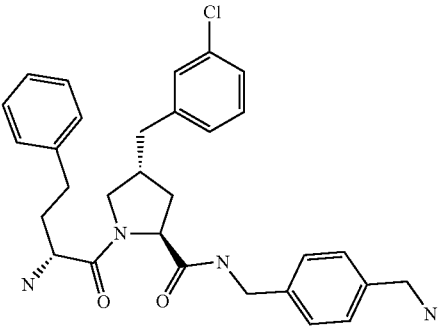  Using [(R)-1-((2S,4R)-4-(3-Chloro-benzyl)-2-{4-[(9H-fluoren-9-ylmethoxycarbonylamino)-methyl]-benzylcarbamoyl}-pyrrolidine-1-carbonyl)-3-phenyl-propyl]-carbamic acid 9H-fluoren-9-ylmethyl ester; Step 2 omitted | ANALPH9_MEOH_QC_v1, Rt: 8.04 min, m/z 519.3 [M + H]+ ANALPH2_MEOH_QC_v1, Rt: 4.73 min, m/z 519.3 [M + H]+ | Brown gum |

General Scheme 9:

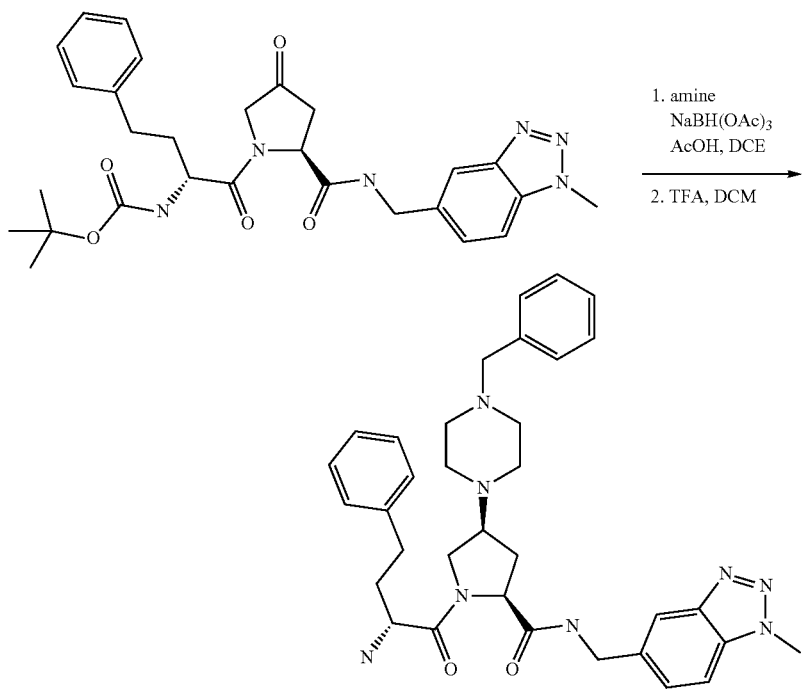

Synthesis of (2S,4S)-1-((R)-2-Amino-4-phenyl-butyryl)-4-(4-benzyl-piperazin-1-yl)-pyrrolidine-2-carboxylic acid (1-methyl-1H-benzotriazol-5-ylmethyl)-amide M05200

Step 1: ((R)-1-{(S)-2-[(1-Methyl-1H-benzotriazol-5-ylmethyl)-carbamoyl]-4-oxo-pyrrolidine-1-carbonyl}-3-phenyl-propyl)-carbamic acid tert-butyl ester (70 mg, 0.13 mmol), 1-benzylpiperazine (25 µL, 0.13 mmol) and AcOH (7.0 µL, 0.13 mmol) were stirred in DCE (1 mL) for 1 hour. NaBH(OAc)$_3$ (83 mg, 0.39 mmol) was added and the reaction stirred at room temperature overnight. The reaction was monitored by LCMS. Additional aliquots of amine, AcOH and NaBH(OAc)$_3$ (0.13 mmol each) were added followed by stirring for 1 hour. Further aliquots of amine and AcOH (0.13 mmol each) were added and the reaction mixture stirred overnight. The reaction was washed with sat. aq. NaHCO$_3$, dried over MgSO$_4$ and solvent removed. The residue was purified by SCX-2 cartridge (2 g), loading with MeOH and eluting with 0.5 M NH$_3$/MeOH. The product-containing fractions were concentrated to give ((R)-1-{(2S, 4S)-4-(4-benzyl-piperazin-1-yl)-2-[(1-methyl-1H-benzotriazol-5-ylmethyl)-carbamoyl]-pyrrolidine-1-carbonyl}-3-phenyl-propyl)-carbamic acid tert-butyl ester (61 mg, 68%) as a brown oil.

AnalpH2_MeOH_4MIN: Rt: 3.44 min, m/z 695.5[M+H]$^+$

Step 2: ((R)-1-{(2S,4S)-4-(4-Benzyl-piperazin-1-yl)-2-[(1-methyl-1H-benzotriazol-5-ylmethyl)-carbamoyl]-pyrrolidine-1-carbonyl}-3-phenyl-propyl)-carbamic acid tert-butyl ester (61 mg, 0.090 mmol) was dissolved in DCM (3 mL) and TFA (3 mL) added. The mixture was stirred at room temperature for 1 hour, then the solvent removed and residue purified by prep LCMS to give (2S,4S)-1-((R)-2-amino-4-phenyl-butyryl)-4-(4-benzyl-piperazin-1-yl)-pyrrolidine-2-carboxylic acid (1-methyl-1H-benzotriazol-5-ylmethyl)-amide (24.7 mg, 47%) as a white solid.

ANALPH9_MEOH_QC_v1, Rt: 7.65 min, m/z 595.5 [M+H]+

ANALPH2_MEOH_QC_v1, Rt: 3.7 min, m/z 595.5 [M+H]+

The following examples were synthesised by analogous methods:

| Example No. | Structure and Method | Analytical Data | Mass, state |
|---|---|---|---|
| M05203 | 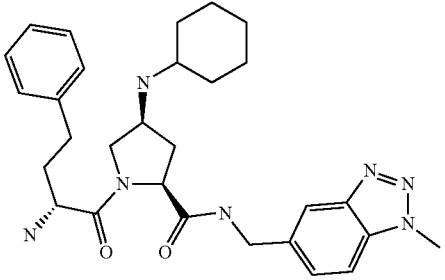<br>Using Cyclohexylamine; no additional aliquots of reagent necessary | ANALPH2_MEOH_QC_v1, Rt: 3.77 min, m/z 518.4 [M + H]+<br>ANALPH9_MEOH_QC_v1, Rt: 7.55 min, m/z 518.4 [M + H]+<br>$^1$H NMR (400 MHz, CDCl$_3$) δ 7.91 (d, J = 1.3 Hz, 0.7H), 7.85 (s, 0.3H), 7.65 (t, J = 5.7 Hz, 1H), 7.52 – 7.43 (m, 2H), 7.35 – 7.29 (m, 1H), 7.26 – 7.06 (m, 4H), 4.60 (ddd, J = 10.0, 9.6, 5.0 Hz, 2H), 4.49 (dd, J = 8.9, 4.0 Hz, 0.7H), 4.41 (dd, J = 14.7, 5.6 Hz, 0.3H), 4.29 (d, J = 0.9 Hz, 3H), 4.19 (s, 1H), 3.76 (dd, J = 7.9, 5.2 Hz, 0.3H), 3.73 – 3.56 (m, 0.7H), 3.48 (ddt, J = 12.9, 8.2, 4.5 Hz, 2H), 3.38 (dd, J = 10.6, 5.7 Hz, 1H), 3.24 (dd, J = 10.5, 4.1 Hz, 1H), 2.88 – 2.67 (m, 2H), 2.63 (d, J = 0.9 Hz, 2H), 2.55 – 2.29 (m, 1H), 2.29 – 2.11 (m, 2H), 1.98 – 1.85 (m, 1H), 1.64 – 1.42 (m, 1H), 1.31 – 1.05 (m, 3H), 0.97 (d, J = 11.5 Hz, 2.6H), 0.73 (m, 0.4H). | 6 mg, brown solid |
| M05204 | 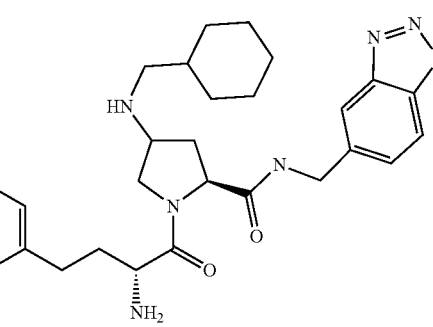<br>Using cyclohexane methyl amine, no additional aliquots of reagent necessary | ANALPH2_MEOH_QC_v1, Rt: 4.18 min, m/z 532.4 [M + H]+<br>ANALPH9_MEOH_QC_v1, Rt: 7.88 min, m/z 532.4 [M + H]+ | 7.6 mg, brown solid |

| Example No. | Structure and Method | Analytical Data | Mass, state |
|---|---|---|---|
| M05242 | 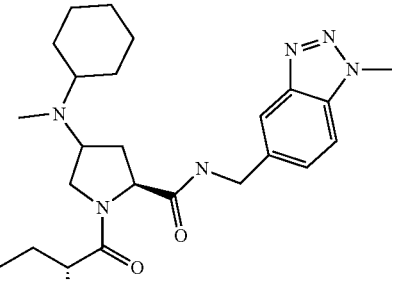  Using N-methylcyclohexylamine | ANALPH9_MEOH_QC_v1, Rt: 7.74 min, m/z 532.5 [M + H]+ ANALPH2_MEOH_QC_v1, Rt: 3.52 min, m/z 532.5 [M + H]+ | 7.4 mg, Off-white solid |

General Scheme 10: Synthesis of (S)-1-((R)-2-Methylamino-4-phenyl-butyryl)-pyrrolidine-2-carboxylic acid 4-aminomethyl-benzylamide

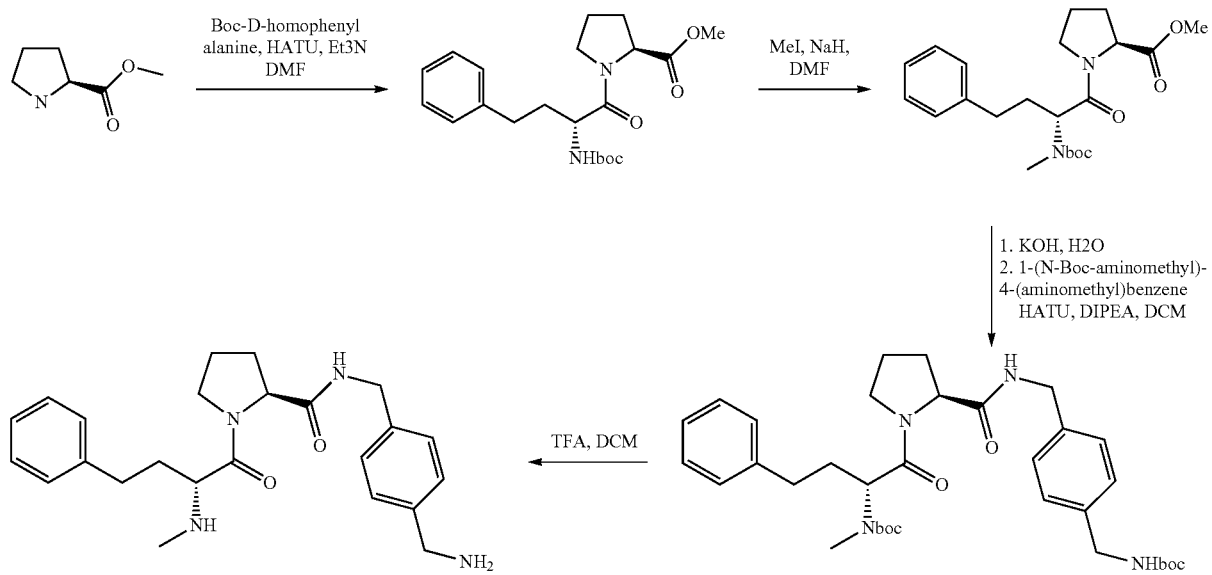

Step 1: The amide coupling of (S)-pyrrolidine-2-carboxylic acid methyl ester hydrochloride (3.00 g, 18.1 mmol) and Boc-D-homophenylalanine (5.00 g, 17.9 mmol) was carried out following General Method 1 using HATU (7.0 g, 18.4 mmol) and Et₃N (6 mL, 26.7 mmol) in DMF (100 mL). Purification by column chromatography (Biotage, 0-50% EtOAc/ihexane) gave (S)-1-((R)-2-tert-butoxycarbonylamino-4-phenyl-butyryl)-pyrrolidine-2-carboxylic acid methyl ester (6.1 g, 87%) as a clear oil.

AnalpH2_MeOH_4MIN: Rt: 3.21 min, m/z 291.3 [M+H-boc]+

Step 2: (S)-1-((R)-2-tert-Butoxycarbonylamino-4-phenyl-butyryl)-pyrrolidine-2-carboxylic acid methyl ester (500 mg, 1.3 mmol) was dissolved in DMF (20 mL) and NaH (60% dispersion in mineral oil, 76 mg, 1.9 mmol) added. The reaction mixture was stirred for 10 minutes, then methyl iodide (0.12 mL, 1.9 mmol) was added and the mixture stirred for 1 hour at room temperature. The reaction mixture was cooled to 0° C., quenched with H₂O and partitioned between EtOAc and H₂O. The organics were washed with brine and the solvent removed. The crude product was purified by column chromatography (Biotage, 0-50% EtOAc/ihexane) to give (S)-1-[(R)-2-(tert-butoxycarbonyl-methyl-amino)-4-phenyl-butyryl]-pyrrolidine-2-carboxylic acid methyl ester (690 mg, 70%) as a colourless oil.

AnalpH2_MeOH_4MIN: Rt: 3.30 min, m/z 405 [M+H]+

Step 3: (S)-1-[(R)-2-(tert-Butoxycarbonyl-methyl-amino)-4-phenyl-butyryl]-pyrrolidine-2-carboxylic acid methyl ester (690 mg, 1.7 mmol) was dissolved in aq. KOH (5M, 6 mL, 12 mmol), MeOH (20 mL) and THF (20 mL) and heated at 50° C. for 1 hour. The reaction mixture was cooled in an ice-bath, water added and the pH adjusted to pH 2 with addition of 2M aq. HCl. The mixture was extracted with EtOAc, the organics washed with brine, dried (MgSO₄)

and the solvent removed to give (S)-1-[(R)-2-(tert-butoxy-carbonyl-methyl-amino)-4-phenyl-butyryl]-pyrrolidine-2-carboxylic acid (450 mg, 68%) as a colourless oil which was used crude in the next step.

AnalpH2_MeOH_4MIN: Rt: 3.27 min, m/z 391.4 [M+H]$^+$

Step 4: Amide coupling of (S)-1-[(R)-2-(tert-Butoxycarbonyl-methyl-amino)-4-phenyl-butyryl]-pyrrolidine-2-carboxylic acid (280 mg, 0.72 mmol) with 1-(N-boc-aminomethyl)-4-(aminomethyl)benzene (170 mg, 0.72 mmol) was carried out following General Method 1 using HATU (330 mg, 0.86 mmol) and DIPEA (0.30 mL, 1.7 mmol) in DCM (50 mL). Purification by column chromatography (biotage, 0-80% EtOAc/petrol) gave ((R)-1-{(S)-2-[4-(tert-butoxycarbonylamino-methyl)-benzylcarbamoyl]-pyrrolidine-1-carbonyl}-3-phenyl-propyl)-methyl-carbamic acid tert-butyl ester (230 mg, 51%) as a colourless oil.

AnalpH2_MeOH_4MIN: Rt: 3.51 min, m/z 609 [M+H]$^+$

Step 5: ((R)-1-{(S)-2-[4-(tert-Butoxycarbonylamino-methyl)-benzylcarbamoyl]-pyrrolidine-1-carbonyl}-3-phenyl-propyl)-methyl-carbamic acid tert-butyl ester (230 mg, 0.34 mmol) was deprotected following General Method 2A using 5:1 DCM:TFA (12 mL) and stirred at room temperature for 1 h, followed by purification to give (S)-1-((R)-2-methylamino-4-phenyl-butyryl)-pyrrolidine-2-carboxylic acid 4-aminomethyl-benzylamide (59 mg, 38%) as a white foam.

ANALPH9_MEOH_QC_v1, Rt: 6.61 min, m/z 409.3 [M+H]+

ANALPH2_MEOH_QC_v1, Rt: 2.81 min, m/z 409.3 [M+H]+

Scheme 12 (Methylation of final compounds)

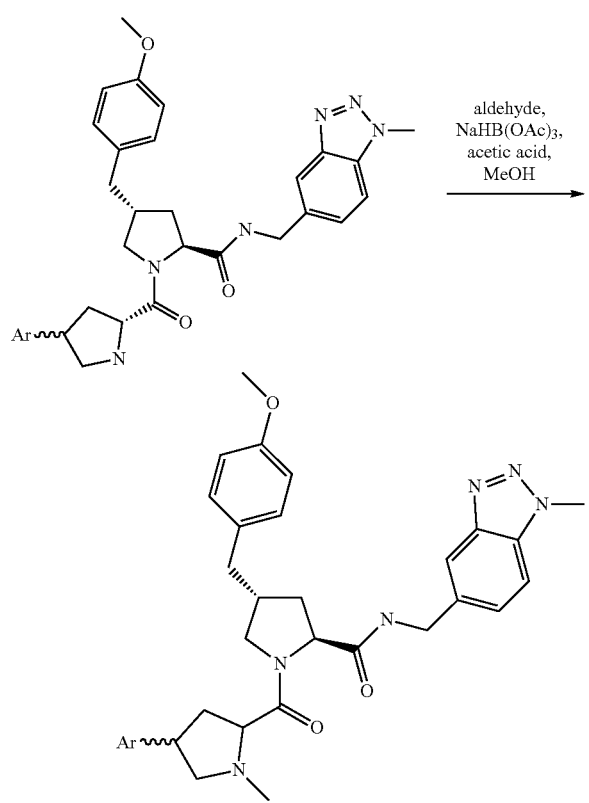

Synthesis of (2S,4R)-4-(4-Methoxy-benzyl)-1-[(2R,4S)-1-methyl-4-(1-methyl-1H-pyrazol-4-yl)-pyrrolidine-2-carbonyl]-pyrrolidine-2-carboxylic acid (1-methyl-1H-benzotriazol-5-ylmethyl)-amide (M05474)

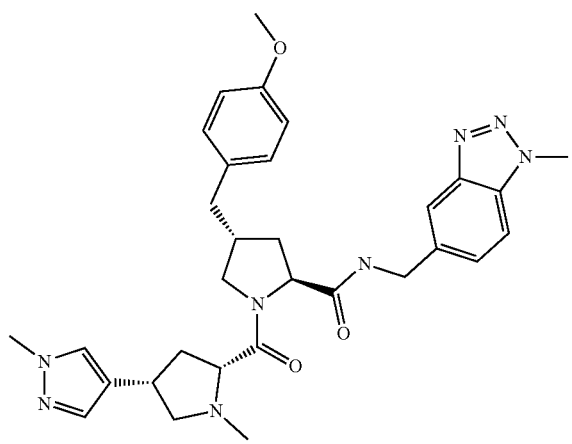

Formaldehyde (37% wt in water, 22 mg, 0.27 mmol, 3.0 equiv.,) and sodium triacetoxyborohydride (57 mg, 0.27 mmol, 3.0 equiv.), followed by acetic acid (5.0 mg, 0.081 mmol, 0.9 equiv.,), were added to a solution of ((2S,4R)-4-(4-methoxy-benzyl)-1-[(2R,4S)-4-(1-methyl-1H-pyrazol-4-yl)-pyrrolidine-2-carbonyl]-pyrrolidine-2-carboxylic acid (1-methyl-1H-benzotriazol-5-ylmethyl)-amide (50 mg, 0.090 mmol, 1.0 equiv.) in DCM (10 mL). The resulting solution was stirred at room temperature overnight. The reaction mixture was diluted with saturated aqueous NaHCO$_3$ (10 mL), then extracted with dichloromethane (3×10 mL). The combined organic phases were washed with brine, passed through a hydrophobic membrane and concentrated under vacuum. The crude product was purified by SCX-2 (2.5 g) to give (2S,4R)-4-(4-methoxy-benzyl)-1-[(2R,4S)-1-methyl-4-(1-methyl-1H-pyrazol-4-yl)-pyrrolidine-2-carbonyl]-pyrrolidine-2-carboxylic acid (1-methyl-1H-benzotriazol-5-ylmethyl)-amide (0.045 g, 0.078 mmol, 87%) as a white solid.

ANALPH2_MEOH_QC_v1, Rt: 5.28 min, m/z 571.4 [M+H]+

ANALPH9_MEOH_QC_v1, Rt: 7.32 min, m/z 571.4 [M+H]+

1H-NMR (400 MHz, DMSO-d6) δ 8.64 (t, J=6.2 Hz, 0.3H), 8.37 (t, J=6.2 Hz, 0.7H), 7.81 (s, 1H), 7.72 (t, J=9.2 Hz, 1H), 7.47 (s, 1H), 7.39 (dd, J=8.0, 4.8 Hz, 1H), 7.33 (s, 0.3H), 7.22 (d, J=8.2 Hz, 0.7H), 7.13-7.02 (m, 2H), 6.92-6.77 (2H), 4.60-4.27 (m, 3H), 4.27-4.18 (3H), 3.77-3.64 (m, 7H), 3.52-3.40 (0.3H), 3.22 (dd, J=18.3, 7.8 Hz, 1H), 3.12-3.00 (m, 0.7H), 2.91-2.67 (m, 1H), 2.65-2.49 (m, 4H), 2.39-2.26 (m, 1H), 2.27-2.09 (m, 3H), 2.05-1.85 (1H), 1.84-1.70 (m, 2H), 1.69-1.49 (1H)

The following examples were made by analogous methods:

| Example No. | Structure and Method | Analytical Data | Mass, State, Yield |
|---|---|---|---|
| M05389 | 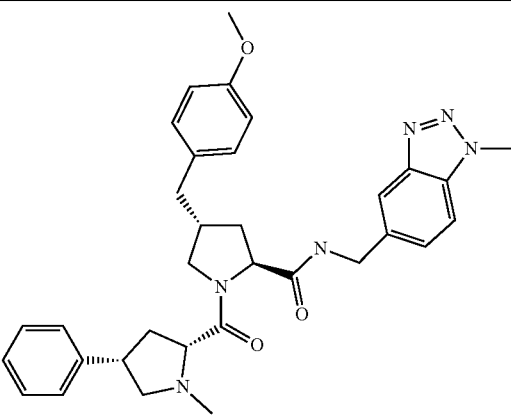<br>(2S,4R)-4-(4-Methoxy-benzyl)-1-((2R,4S)-1-methyl-4-phenyl-pyrrolidine-2-carbonyl)-pyrrolidine-2-carboxylic acid (1-methyl-1H-benzotriazol-5-ylmethyl)-amide<br>Using (2S,4R)-4-(4-Methoxy-benzyl)-1-((2R,4S)-4-phenyl-pyrrolidine-2-carbonyl)-pyrrolidine-2-carboxylic acid (1-methyl-1H-benzotriazol-5-ylmethyl)-amide | ANALPH2_MEOH_QC_v1, Rt: 5.90 min, m/z 567.4 [M + H]+<br>ANALPH9_MEOH_QC_v1, Rt: 8.05 min, m/z 567.4 [M + H]+ | 11 mg, white solid, 36% |

General Scheme 13: Synthesis of (2S, 4R)-1-{(R)-2-Amino-3-[pyrrolidine-1-carbonyl)-amino]-propionyl}-4-(4-methoxy-benzyl)-pyrrolidine-2-carboxylic acid (1-methyl-1H-benzotriazole-5-ylmethyl)-amide (M05414)

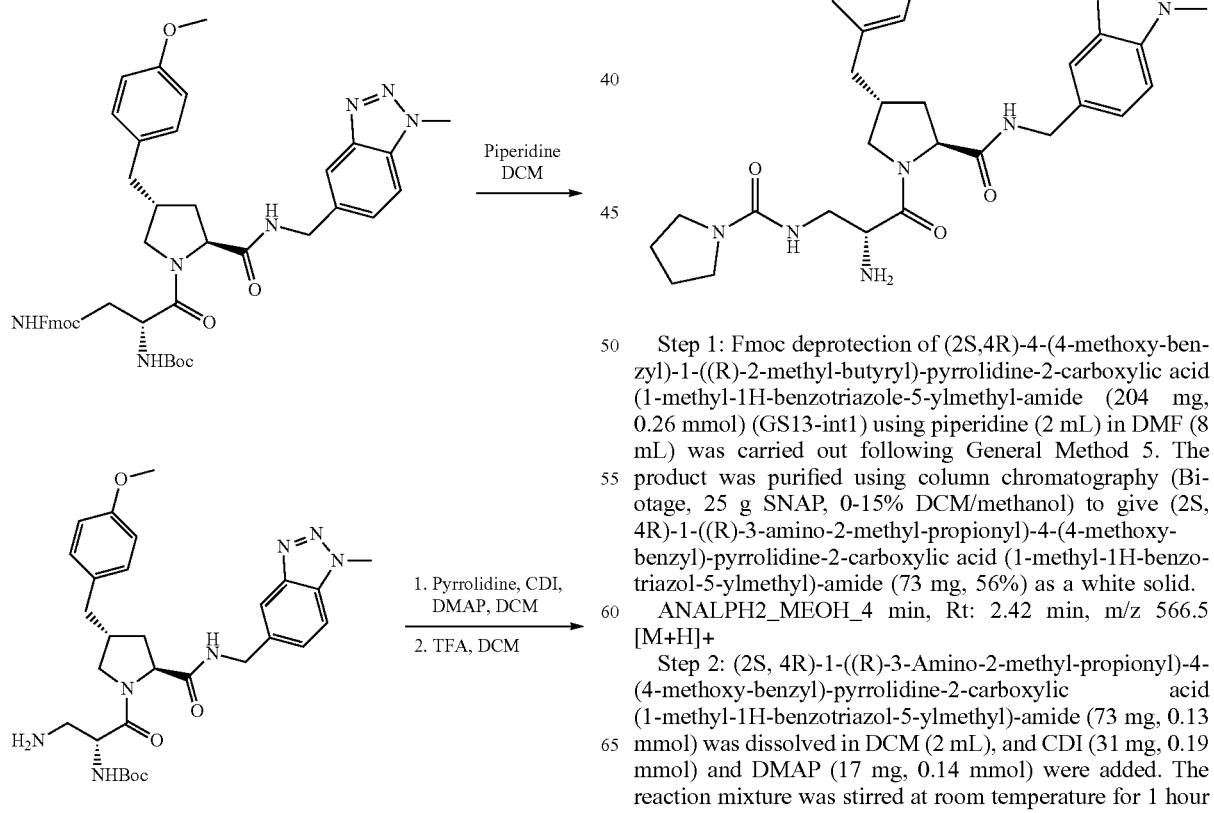

Step 1: Fmoc deprotection of (2S,4R)-4-(4-methoxy-benzyl)-1-((R)-2-methyl-butyryl)-pyrrolidine-2-carboxylic acid (1-methyl-1H-benzotriazole-5-ylmethyl-amide (204 mg, 0.26 mmol) (GS13-int1) using piperidine (2 mL) in DMF (8 mL) was carried out following General Method 5. The product was purified using column chromatography (Biotage, 25 g SNAP, 0-15% DCM/methanol) to give (2S, 4R)-1-((R)-3-amino-2-methyl-propionyl)-4-(4-methoxy-benzyl)-pyrrolidine-2-carboxylic acid (1-methyl-1H-benzotriazol-5-ylmethyl)-amide (73 mg, 56%) as a white solid.

ANALPH2_MEOH_4 min, Rt: 2.42 min, m/z 566.5 [M+H]+

Step 2: (2S, 4R)-1-((R)-3-Amino-2-methyl-propionyl)-4-(4-methoxy-benzyl)-pyrrolidine-2-carboxylic acid (1-methyl-1H-benzotriazol-5-ylmethyl)-amide (73 mg, 0.13 mmol) was dissolved in DCM (2 mL), and CDI (31 mg, 0.19 mmol) and DMAP (17 mg, 0.14 mmol) were added. The reaction mixture was stirred at room temperature for 1 hour before addition of pyrrolidine (16 μL, 0.19 mmol). The reaction mixture was stirred for a further 24 hours before quenching with water. The layers were separated and the aqueous layer was extracted with DCM (×3). The combined organic layers were washed with brine, dried (MgSO₄), and the solvent removed in vacuo to give ((R)-2-{(2S,4R)-4-(4-methoxy-benzyl)-2-[1-methyl-1H-benzotriazol-5-ylmethyl)-carbamoyl]-pyrrolidin-1-yl}-2-oxo-1-{[pyrrolidine-1-carbonyl)-amino]-methyl}-ethyl)-carbamic acid tert-butyl ester (57 mg, 66%) as a colourless oil.

ANALPH2_MEOH_4 min, Rt: 3.16 min, m/z 663.4 [M+H]+

Step 3: Boc deprotection of ((R)-2-{(2S,4R)-4-(4-methoxy-benzyl)-2-[1-methyl-1H-benzotriazol-5-ylmethyl)-carbamoyl]-pyrrolidin-1-yl}-2-oxo-1-{[pyrrolidine-1-carbonyl)-amino]-methyl}-ethyl)-carbamic acid tert-butyl ester (57 mg, 0.086 mmol) was carried out using TFA in DCM following General Method 2A for 1 hour. Solvent was removed in vacuo and the residue purified using SCX-2 and eluted with 4M NH₃ in methanol. The product-containing fractions were concentrated in vacuo and purified using prep-HPLC to afford (2S, 4R)-1-{(R)-2-amino-3-[pyrrolidine-1-carbonyl)-amino]-propionyl}-4-(4-methoxy-benzyl)-pyrrolidine-2-carboxylic acid (1-methyl-1H-benzotriazole-5-ylmethyl)-amide (13 mg, 27%) as a white solid.

ANALPH2_MEOH_QC_v1, RT: 5.49 min, m/z 563.4 [M+H]+

ANALPH9_MEOH_QC_v1, RT: 7.05 min, m/z 563.4 [M+H]+

¹H NMR (400 MHz, DMSO-d₆) δ 8.41 (s, 1H), 7.79 (d, J=7.2 Hz, 1H), 7.71 (d, J=8.6 Hz, 1H), 7.38 (dd, J=8.7, 1.4 Hz, 1H), 7.09-7.01 (m, 2H), 6.83-6.77 (m, 2H), 6.32 (s, 1H), 4.44-4.27 (m, 3H), 4.24 (s, 3H), 3.84 (s, 1H), 3.75 (s, 1H), 3.67 (s, 3H), 3.29-3.09 (m, 6H), 2.62-2.46 (m, 2H), 1.79-1.69 (m, J=6.2 Hz, 8H).

General Scheme 14 Synthesis of cis benzyl RgB compounds (M05210 and M05211)

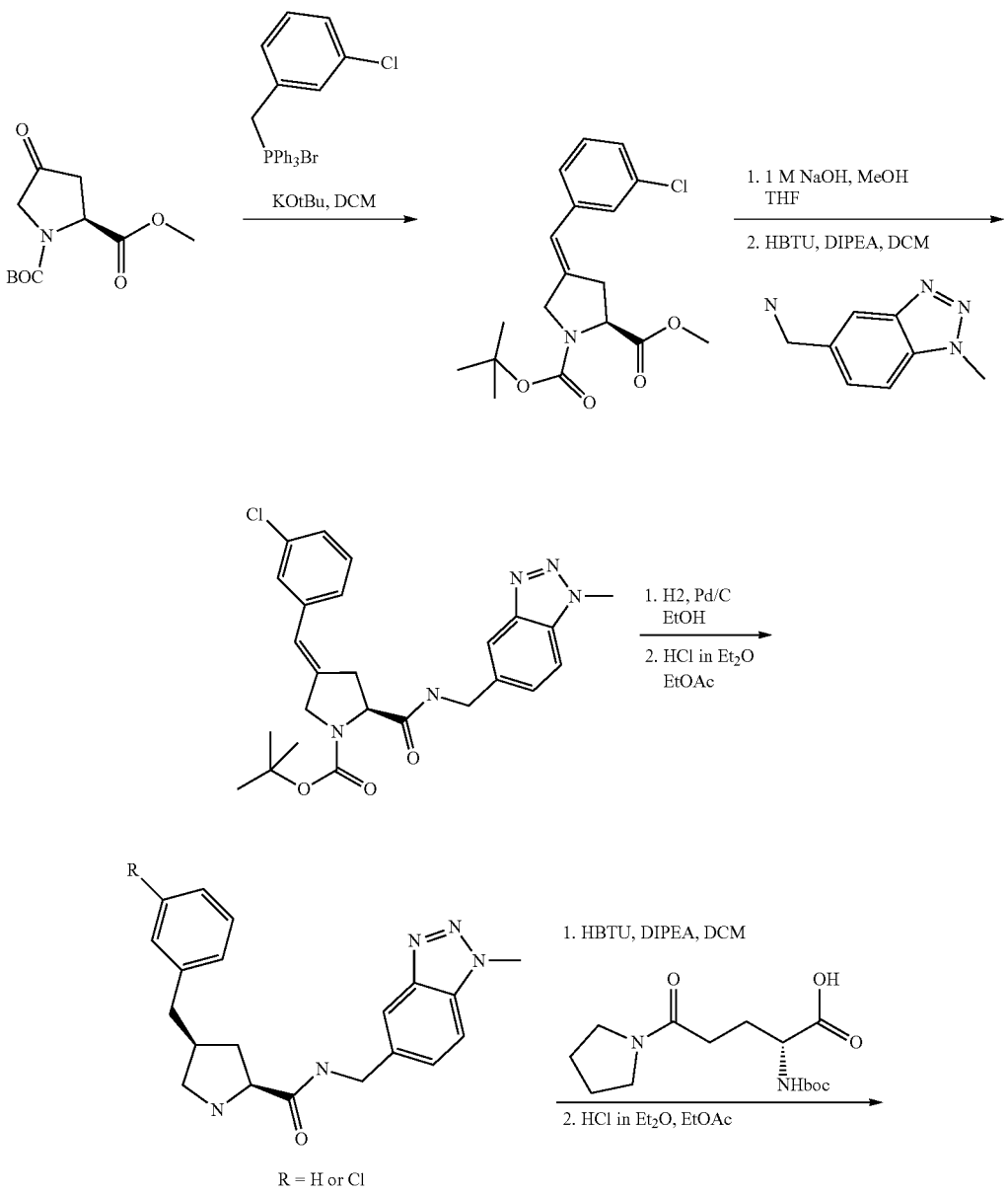

R = H or Cl

-continued

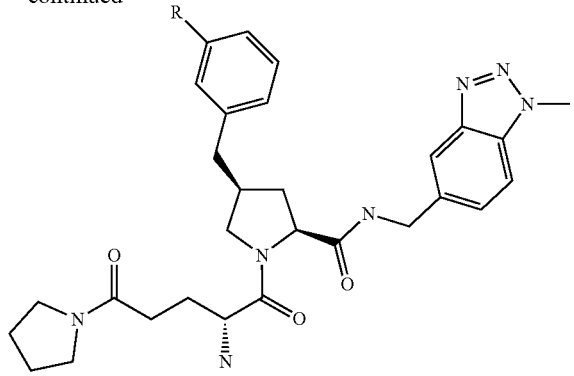

R = H or Cl

Step 1: (3-Chlorobenzyl)(triphenyl) phosphonium bromide (400 mg, 0.86 mmol) was dissolved in DCM (10 mL) and KOtBu (1M in THF, 0.86 mL, 0.86 mmol) was added. After 45 minutes N-boc-4-oxo-L-proline methyl ester (180 mg, 0.74 mmol) was added and the reaction mixture was stirred at room temperature for 1 hour. Water (20 mL) was added and the mixture extracted with DCM (2×20 mL). The combined organic layers were dried (MgSO₄), the solvent removed and the residue purified by column chromatography (Biotage, 25 g SNAP, 0-50% EtOAc/ihexane) to give (S)-4-[1-(3-chloro-phenyl)-meth-(E)-ylidene]-pyrrolidine-1,2-dicarboxylic acid 1-tert-butyl ester 2-methyl ester (148 mg, 57%) as a colourless oil.

ANALPH2_MEOH_4 min, Rt: 3.44 min, m/z 352 [M+H]+

Step 2: (S)-4-[1-(3-Chloro-phenyl)-meth-(E)-ylidene]-pyrrolidine-1,2-dicarboxylic acid 1-tert-butyl ester 2-methyl ester (150 mg, 0.42 mmol) was dissolved in THF (1 mL) and MeOH (1 mL) and NaOH (1M aq, 1 mL) were added, and the reaction mixture stirred at room temperature for 1 hour. The solvent was removed and sat. aq. NH₄Cl (5 mL) and 1M HCl aq. added to acidify to pH5. The aqueous layer was extracted with EtOAc, and the combined organic extracts dried over MgSO₄. The solvent was removed to give (S)-4-[1-(3-chloro-phenyl)-meth-(E)-ylidene]-pyrrolidine-1,2-dicarboxylic acid 1-tert-butyl ester (120 mg) as a pale yellow oil which was used directly in the subsequent reaction without further purification.

ANALPH2_MEOH_4 min, Rt: 3.43 min, m/z 338 [M+H]+

Step 3: (S)-4-[1-(3-Chloro-phenyl)-meth-(E)-ylidene]-pyrrolidine-1,2-dicarboxylic acid 1-tert-butyl ester (120 mg, 0.36 mmol) was dissolved in DCM (5 mL) and HBTU (159 mg, 0.42 mmol), C-(1-methyl-1H-benzotriazol-5-yl)-methylamine (68 mg, 0.42 mmol) and DIPEA (217 µL, 1.26 mmol) added. The reaction mixture was stirred at room temperature for 1 hour, then water (20 mL) added and the aqueous layer extracted with DCM. The combined organic extracts were dried (MgSO₄) and the solvent removed. The residue was purified by column chromatography (Biotage, 10 g SNAP, 0-100% EtOAc/ihex) to give (S)-4-[1-(3-Chloro-phenyl)-meth-(E)-ylidene]-2-[(1-methyl-1H-benzotriazol-5-ylmethyl)-carbamoyl]-pyrrolidine-1-carboxylic acid tert-butyl ester as a colourless oil (174 mg, 86% over 2 steps).

ANALPH2_MEOH_4 min, Rt: 3.19 min, m/z 482 [M+H]+

Step 4: (S)-4-[1-(3-Chloro-phenyl)-meth-(E)-ylidene]-2-[(1-methyl-1H-benzotriazol-5-ylmethyl)-carbamoyl]-pyrrolidine-1-carboxylic acid tert-butyl ester (174 mg, 0.36 mmol) was dissolved in EtOH (5 mL) under N₂ and Pd/C (20 mg) added. A H₂ atmosphere was introduced and the reaction mixture stirred at room temperature for 7 hours. Additional Pd/C (20 mg) was added and the reaction mixture stirred overnight, then heated to 45° C. for 2 hours. The mixture was cooled to room temperature then filtered through celite, the residue washed with EtOH and the combined filtrate and washings concentrated to give a combination of (2S,4S)-4-(3-chloro-benzyl)-2-[(1-methyl-1H-benzotriazol-5-ylmethyl)-carbamoyl]-pyrrolidine-1-carboxylic acid tert-butyl ester and (2S,4S)-4-benzyl-2-[(1-methyl-1H-benzotriazol-5-ylmethyl)-carbamoyl]-pyrrolidine-1-carboxylic acid tert-butyl ester (140 mg, 80%) as a colourless oil.

ANALPH2_MEOH_4 min, Rt: 3.23 min, m/z 484 [M+H]+(Cl); Rt: 3.09 min, m/z 450 [M+H]+(H)

Step 5: A combination of (2S,4S)-4-(3-Chloro-benzyl)-2-[(1-methyl-1H-benzotriazol-5-ylmethyl)-carbamoyl]-pyrrolidine-1-carboxylic acid tert-butyl ester and (2S,4S)-4-benzyl-2-[(1-methyl-1H-benzotriazol-5-ylmethyl)-carbamoyl]-pyrrolidine-1-carboxylic acid tert-butyl ester (140 mg, 0.29 mmol) were dissolved in EtOAc (3 mL) and HCl (1M in Et₂O, 3 mL) added and stirred at room temperature for 1 hour. The solvent was removed to give a combination of (2S,4S)-4-(3-chloro-benzyl)-2-[(1-methyl-1H-benzotriazol-5-ylmethyl)-carbamoyl]-pyrrolidine and (2S,4S)-4-benzyl-2-[(1-methyl-1H-benzotriazol-5-ylmethyl)-carbamoyl]-pyrrolidine as a white solid which were used crude in the next step.

Step 6: The crude mixture of (2S,4S)-4-(3-chloro-benzyl)-2-[(1-methyl-1H-benzotriazol-5-ylmethyl)-carbamoyl]-pyrrolidine and (2S,4S)-4-benzyl-2-[(1-methyl-1H-benzotriazol-5-ylmethyl)-carbamoyl]-pyrrolidine were dissolved in DCM (5 mL), and HBTU (110 mg, 0.29 mmol), (R)-2-tert-butoxycarbonylamino-5-oxo-5-pyrrolidin-1-yl-pentanoic acid (87 mg, 0.29 mmol) and DIPEA (300 µL, 1.74 mmol) added. The mixture was stirred at room temperature overnight, then water (20 mL) added and the aqueous layer extracted with DCM. The combined organic layers were dried (MgSO₄) and solvent removed. The residue was purified by column chromatography (Biotage, 10 g SNAP, 0-100% EtOAc/ihex followed by 0-20% MeOH/EtOAc) to afford a mixture of ((R)-1-{(2S,4S)-4-(3-chloro-benzyl)-2-[(1-methyl-1H-benzotriazol-5-ylmethyl)-carbamoyl]-pyrrolidine-1-carbonyl}-4-oxo-4-pyrrolidin-1-yl-butyl)-carbamic acid tert-butyl ester and ((R)-1-{(2S,4S)-4-benzyl-2-[(1-methyl-1H-benzotriazol-5-ylmethyl)-carbamoyl]-pyrrolidine-1-carbonyl}-4-oxo-4-pyrrolidin-1-yl-butyl)-carbamic acid tert-butyl ester as a colourless oil (119 mg, 62% over 2 steps).

ANALPH2_MEOH_4 min. Rt: 3.29 min. m/z 666 [M+H]+(Cl); Rt: 3.17 min. m/z 632 [M+H]+(H)

Step 7: ((R)-1-{(2S,4S)-4-(3-Chloro-benzyl)-2-[(1-methyl-1H-benzotriazol-5-ylmethyl)-carbamoyl]-pyrrolidine-1-carbonyl}-4-oxo-4-pyrrolidin-1-yl-butyl)-carbamic acid tert-butyl ester (119 mg, 0.18 mmol) was dissolved in EtOAc (5 mL) and HCl (1M in Et₂O, 3 mL) was added. The reaction mixture was stirred at room temperature for 2 hours. The solvent was removed, 1M NH₃ in MeOH (10 mL) added and the solvent removed and residue purified by prep HPLC to give (2S,4S)-1-((R)-2-amino-5-oxo-5-pyrrolidin-1-yl-pentanoyl)-4-(3-chloro-benzyl)-pyrrolidine-2-carboxylic acid (1-methyl-1H-benzotriazol-5-ylmethyl)-amide and (2S,4S)-1-((R)-2-Amino-5-oxo-5-pyrrolidin-1-yl-pentanoyl)-4-benzyl-pyrrolidine-2-carboxylic acid (1-methyl-1H-benzotriazol-5-ylmethyl)-amide as white solids.

M05210 (2S,4S)-1-((R)-2-amino-5-oxo-5-pyrrolidin-1-yl-pentanoyl)-4-(3-chloro-benzyl)-pyrrolidine-2-carboxylic acid (1-methyl-1H-benzotriazol-5-ylmethyl)-amide (9 mg, 9%)

ANALPH9_MEOH_QC_v1, Rt: 7.34 min, m/z 566.3 [M+H]+

ANALPH2_MEOH_QC_v1, Rt: 5.57 min, m/z 566.2 [M+H]+

M05211 (2S,4S)-1-((R)-2-Amino-5-oxo-5-pyrrolidin-1-yl-pentanoyl)-4-benzyl-pyrrolidine-2-carboxylic acid (1-methyl-1H-benzotriazol-5-ylmethyl)-amide (33 mg, 33%)

ANALPH9_MEOH_QC_v1, Rt: 6.97 min, m/z 532.3 [M+H]+

ANALPH2_MEOH_QC_v1, Rt: 5.2 min, m/z 532.2 [M+H]+

General Scheme 15. Late stage N-alkykation:

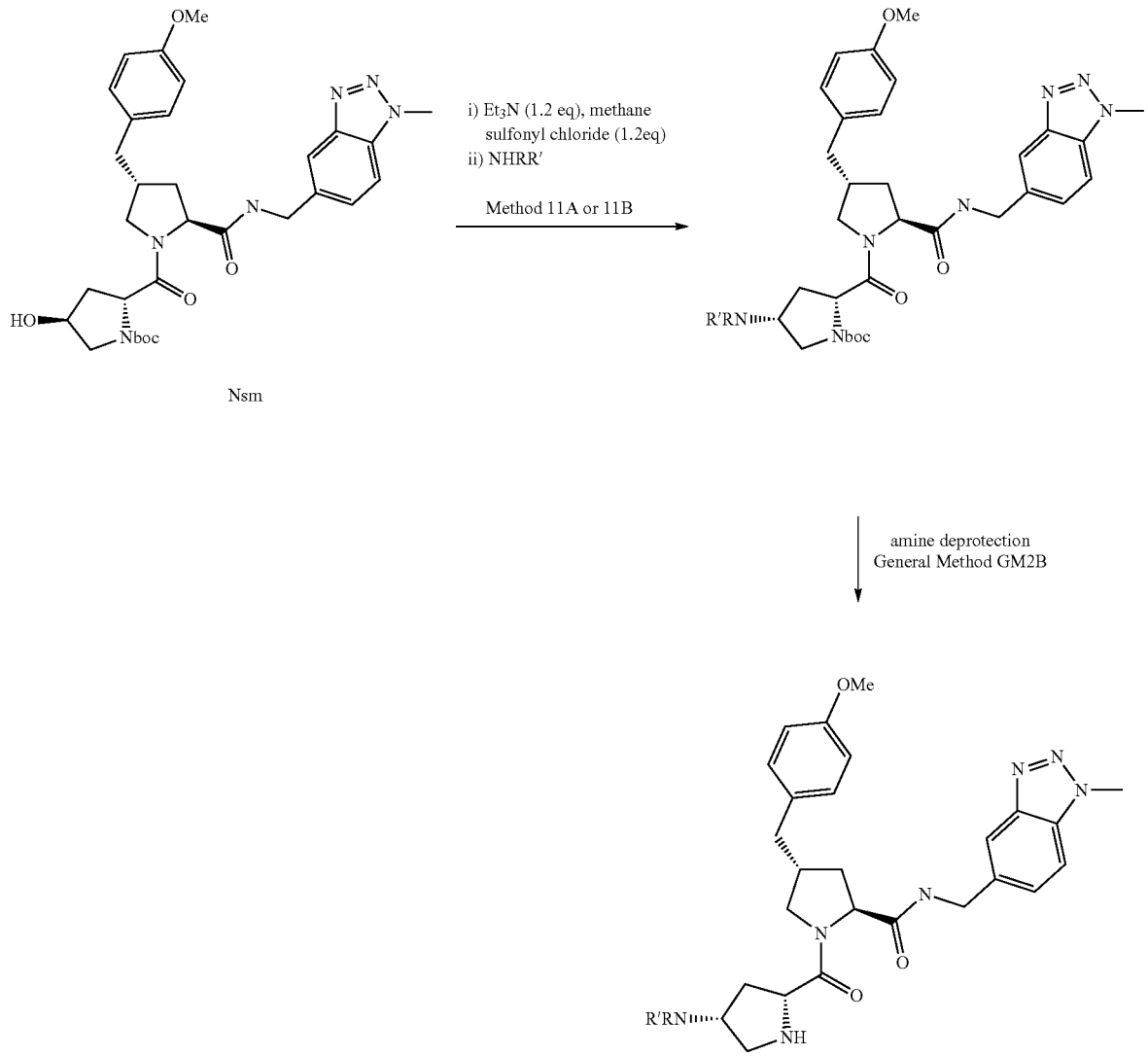

The general method was used to synthesise the following compounds:

| | | | |
|---|---|---|---|
| M00958 | 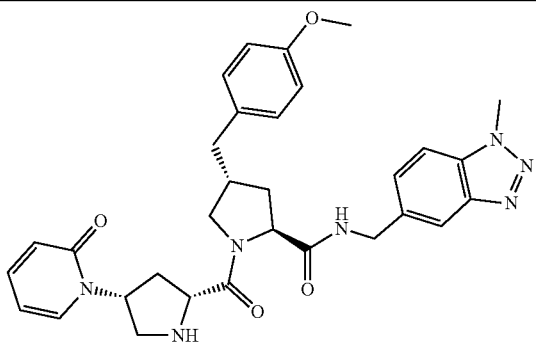 | Thermo_MeOH_UHPLC_1.2 min<br>LCMS: Rt = 0.6 min m/z = 570.67 [M + H]+ | 9 mg, yellow gummy solid |
| | Synthesis of starting material (Nsm) using C-(1-Methyl-1H-benzotriazol-5-yl)-methylamine and boc-(R)-γ-(4-methoxybenzyl)-L-proline using GM1 with HCTU and Et3N followed by amine deprotection using GM2B followed by amide coupling with N-Boc-trans-4-hydroxy-D-proline using HCTU and Et3N<br>Step 1: N-alkylation with 2-pyridone using GM11B<br>Step 2 GM2B | | |
| M00955 | 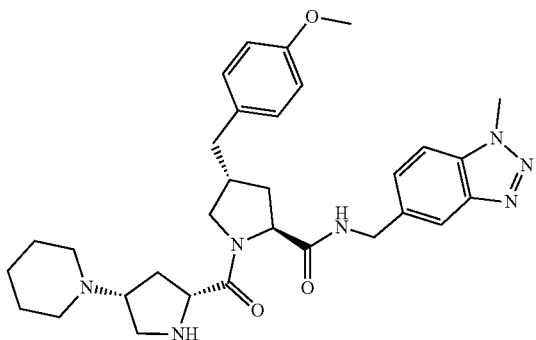 [SMILES: COc1ccc(C[C@@H]2C[C@@H](C(=O)NCc3ccc4c(c3)nnn4C)N(C(=O)[C@H]3C[C@@H](N4CCCCC4)CN3)C2)cc1] | Thermo_MeOH_UHPLC_1.2 min<br>LCMS: R$_t$ = 0.5 min m/z = 560.71 [M + H]$^+$ | 11 mg, brown gum |
| | Synthesis of starting material as for above (pyridinone analogue)<br>Step 1: N-alkylation with piperidine using GM11A<br>Step 2: GM2B | | |

General Scheme 16. Synthesis of RgD Glutamic acid derivatives

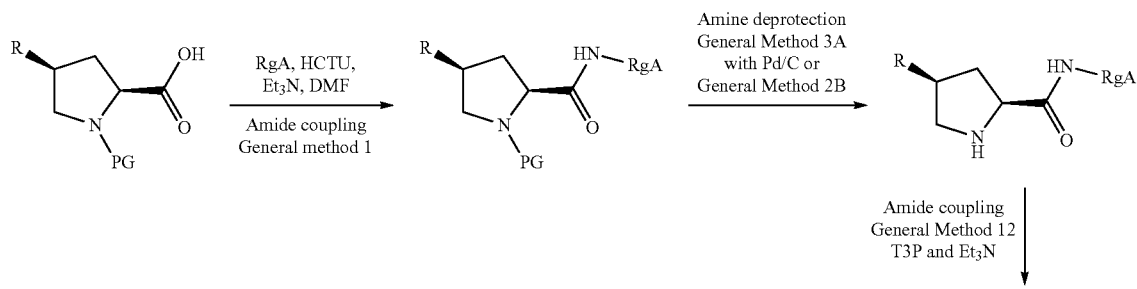

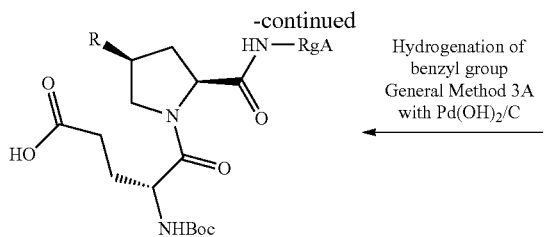 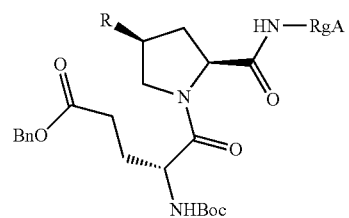

Hydrogenation of benzyl group General Method 3A with Pd(OH)₂/C

The general method was used to synthesise the following compounds

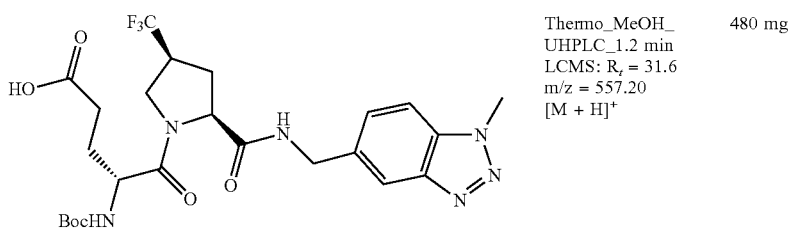

| | |
|---|---|
| Thermo_MeOH_UHPLC_1.2 min LCMS: R$_t$ = 31.6 min m/z = 557.20 [M + H]⁺ | 480 mg |

RgA: C-(1-Methyl-1H-benzotriazol-5-yl)-methylamine
RgB: (2S,4S)-1-boc-4-trifluoromethylpyrrolidine-2-carboxylic acid
RgD: (2R)-5-(benzyloxy)-2-{[(tert-butoxy)carbonyl]amino}-5-oxopentanoic acid
Step 1: GM1 with HCTU and Et₃N
Step 2: GM2B
Step 3: GM12
Step 4: GM3A with Pd(OH)₂/C

| | |
|---|---|
| Thermo_MeOH_UHPLC_1.2 min LCMS: R$_t$ = 0.6 min m/z = 563.37 [M + H]⁺ | 1.67 g, white powder |

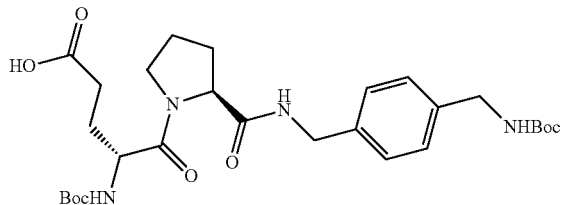 [SMILES: CC(C)(C)OC(=O)NCc1ccc(CNC(=O)[C@@H]2CCCN2C(=O)[C@@H](CCC(=O)O)NC(=O)OC(C)(C)C)cc1]

RgA: 1-(N-Boc-aminomethyl)-4-(aminomethyl)benzene
RgB: Z-Pro-OH
RgD: (2R)-5-(benzyloxy)-2-{[(tert-butoxy)carbonyl]amino}-5-oxopentanoic acid
Step 1: GM1 with HCTU and Et₃N
Step 2 & 4: GM3A with Pd/C
Step 3: GM12

General Scheme 17 Synthesis of late stage functionalised RgD caboxamides

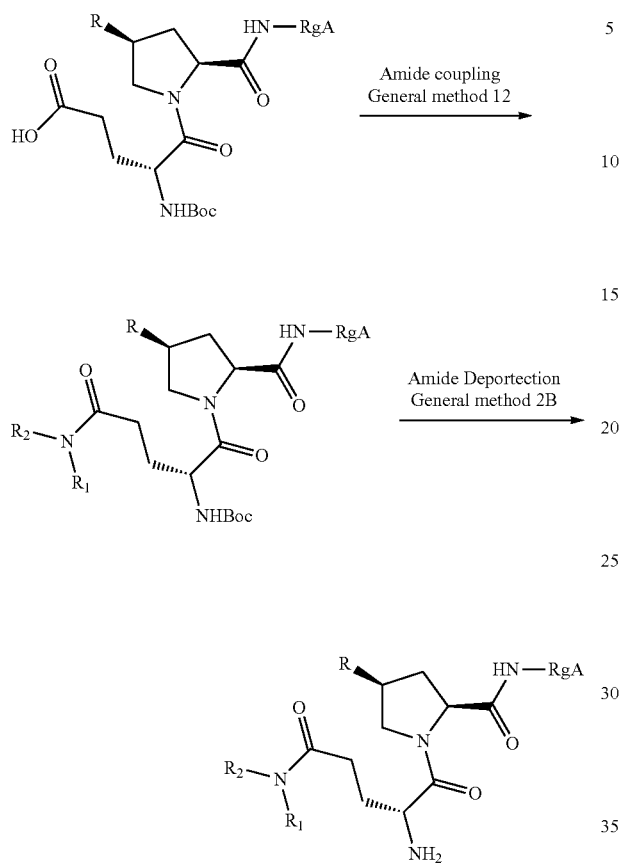

The general method was used to synthesis the following compounds:

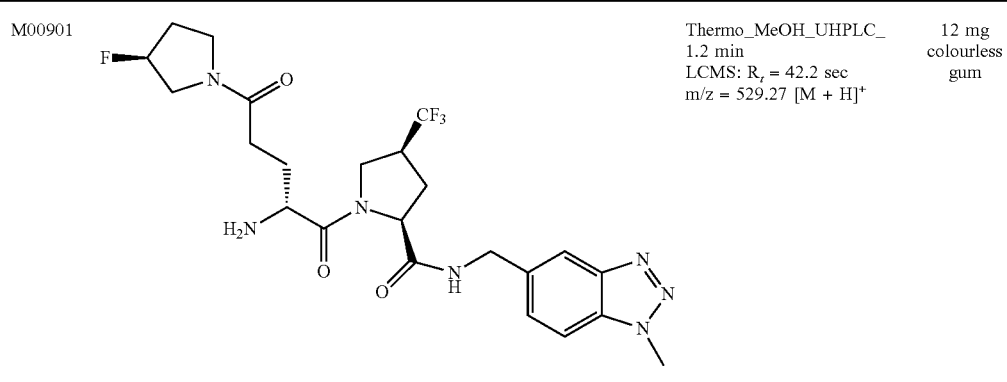

M00901

Step 1: GM12 from (4R)-4-{[(tert-butoxy)carbonyl]amino}-5-[(2S,4S)-2-{[(1-methyl-1H-1,2,3-benzotriazol-5-yl)methyl]carbamoyl}-4-(trifluoromethyl)pyrrolidin-1-yl]-5-oxopentanoic acid and (R)-3-fluoropyrrolidine hydrochloride
Step 2: GM2B Thermo_MeOH_UHPLC_1.2 min
LCMS: $R_t$ = 42.2 sec
m/z = 529.27 [M + H]⁺

12 mg
colourless gum

| | | | |
|---|---|---|---|
| M00915 | 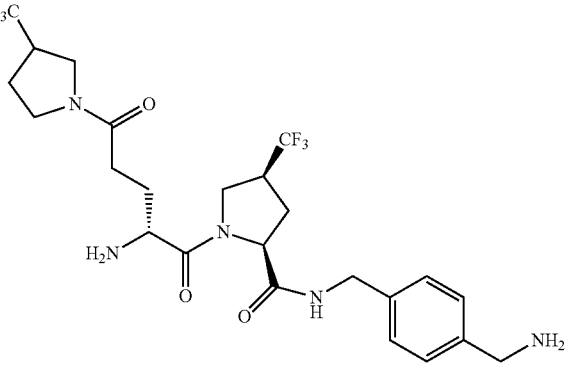 Step 1: GM12 from (4R)-4-{[(tert-butoxy)carbonyl]amino}-5-[(2S)-2-({[4-({[(tert-butoxy)carbonyl]amino}methyl)phenyl]methyl}carbamoyl)pyrrolidin-1-yl]-5-oxopentanoic acid and 3-(trifluoromethyl)pyrrolidine hydrochloride Step 2: GM2B | Thermo_MeOH_UHPLC_1.2 min LCMS: $R_t$ = 7.1 sec m/z = 484.31 $[M + H]^+$ | 21 mg off-white solid |
| M00922 | 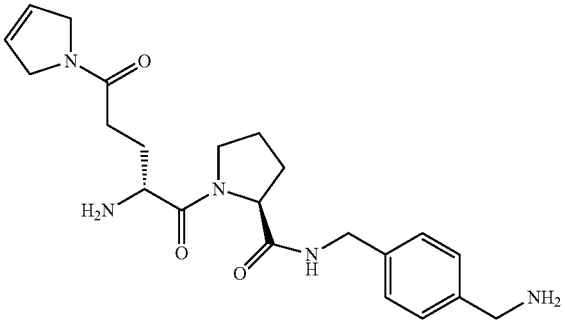 [SMILES: NCc1ccc(CNC(=O)[C@@H]2CCCN2C(=O)[C@H](N)CCC(=O)N2CC=CC2)cc1] Step 1: GM12 from (4R)-4-{[(tert-butoxy)carbonyl]amino}-5-[(2S)-2-({[4-({[(tert-butoxy)carbonyl]amino}methyl)phenyl]methyl}carbamoyl)pyrrolidin-1-yl]-5-oxopentanoic acid and 2,5-dihydro-1H-pyrrole Step 2: GM2B | Thermo_MeOH_UHPLC_1.2 min LCMS: $R_t$ = 21.1 sec m/z = 414.30 $[M + H]^+$ | 12 mg black solid |
| M00929 | 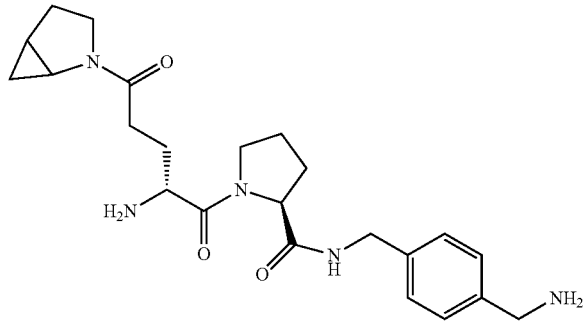 [SMILES: NCc1ccc(CNC(=O)[C@@H]2CCCN2C(=O)[C@H](N)CCC(=O)N2CCC3CC32)cc1] Step 1: GM12 from (4R)-4-{[(tert-butoxy)carbonyl]amino}-5-[(2S)-2-({[4-({[(tert-butoxy)carbonyl]amino}methyl)phenyl]methyl}carbamoyl)pyrrolidin-1-yl]-5-oxopentanoic acid and 2-azabicyclo[3.1.0]hexane hydrochloride Step 2: GM2B | Thermo_MeOH_UHPLC_1.2 min LCMS: $R_t$ = 0.1 min m/z = 428.36 $[M + H]^+$ | 14 mg off-white solid |

General Test Methods

The activities of the compounds of the invention have been determined in vitro using the following assays protocols for the screening of activity of FXIIa and other proteases. Each of these assays were performed in a purified system employing the use of chromogenic assays in microplate plate wells. Chromogenic peptide substrates mimicking natural protein substrates are attached via an amide bond to a chromogenic group. Paranitroaniline (pNA) is released from the peptide following catalyses by the proteolytic enzyme; the absorbance increases and can be monitored at 405 nm.

All compounds were dissolved in 100% (v/v) DMSO to a stock concentration of 10 mM, the highest concentration of compound used in each assay is 500 µM. The final concentrations of DMSO were 5% (v/v) in 50 mM Tris 137 mM NaC pH 7.4. Where no test compound was added a final concentration of 5% DMSO was employed.

Determination of Factor XIa Inhibition

Factor XIa activity was measured using a chromogenic substrate S-2302 (Chromogenix). Various concentrations of compound were incubated with 10 nM of FXIIa and incubated at 37° C. for 10 minutes in 50 mM Tris, 137 mM NaCl, pH 7.4, prior to the addition of a final concentration of 450 M S-2302 chromogenic substrate. Kinetic readings at 405 nm were monitored every 12 secs for a total duration of 3 hours at 37° C. Gradients of initial rates were determined and employed to calculate $IC_{50}$ values. Values of $IC_{50}$ were converted to $K_i$ values based on the formula:

$$K_i = IC_{50}/(1+[Substrate]/Km).$$

The $K_i$ data obtained in the above manner is shown in Table 1 below. The activity of the compounds of the invention has been categorised based on the $K_i$ values, the categories being "*", "" and "*". The category "*" refers to compounds with a $K_i$ value of greater than 2 µM. The category "" refers to compounds with a $K_i$ value of 0.2 µM to 2 µM. The category "*" refers to compounds with a $K_i$ value of less than 0.2 µM.

Determination of Selectivity

To determine selectivity of test compounds, these test compounds were assayed for inhibitory activity against other serine proteases including FXa and thrombin. Essentially compounds at increasing concentrations were incubated with each enzyme: FXa (5 nM) and thrombin (5 nM), for 10 mins at 37° C. followed the appropriate chromogenic substrate, S2765 (350 M), and GPR (250 M) respectively in 50 mM Tris, 137 mM NaCl, pH 7.4. Chromogenic substrates S2765 was from Chromogenix, and GPR from Bachem. Kinetic readings at 405 nm were monitored every 12 secs for a total duration of 3 hours at 37° C. Gradients of initial rates were determined and employed to calculate $IC_{50}$ values. Values of $IC_{50}$ were converted to $K_i$ values based on the formula:

$$K_i = IC_{50}/(1+[Substrate]/Km)$$

Where [Substrate] denotes the concentration of substrate used in the assay and Km is the determined value of each enzyme with its own substrate. Compounds of this chemical series demonstrate competitive inhibition.

The fold selectivity for thrombin and FXa are also shown in Table 1 below. The fold selectivity demonstrates a preferential inhibition of FXIIa over FXa and thrombin. The fold selectivity for FXIIa over thrombin for the compounds of the invention has been categorised based on the fold selectivity values, the categories being "+", "++" and "+++". The category "+" refers to fold selectivity values less than 10. The category "++" refers to a fold selectivity value of 10 to 100. The category "+++" refers to fold selectivity values greater than 100.

The fold selectivity for FXIIa over FXa for the compounds of the invention has been categorised based on the fold selectivity values, the categories being "o", "oo" and "ooo". The category "o" refers to fold selectivity values less than 10. The category "oo" refers to a fold selectivity value of 10 to 100. The category "ooo" refers to fold selectivity values greater than 100.

Determination of In Vivo Anticoagulant Efficacy

Reagents

AlexaFluor 488 conjugate fibrinogen was purchased from Invitrogen (Paisley, UK).

Animals

C57BL/6 male mice weighing between 20 and 30 g were used for all experiments. All procedures were approved by the University of Sheffield ethics committee and performed in accordance with the Home Office Animals (Scientific Procedures) Act 1985 of the United Kingdom.

Intravital Microscopy for Real Time Assessment of Fibrin Formation In Vivo

Microscopic observation of thrombus formation following ferric chloride ($FeCl_3$)induced injury in vivo were made using an upright microscope (Nikon eclipse E600-FN, Nikon UK, Kingston upon Thames, United Kingdom) equipped for bright field and fluorescence microscopy and with a water immersion objective (40/0.80 W).

Mice were anaesthetised with an i.p. injection of 125 mg/kg ketamine hydrochloride (Ketaset; Willows Francis Veterinary, Crawley, UK), 12.5 mg/kg xylazine hydrochloride (Bayer Suffolk, UK) and 0.025 mg/kg Atropine sulphate (phoenix Pharmaceuticals Ltd, UK). Cannulation of the trachea (to aid breathing) and carotid artery (for maintenance of anaesthesia and substance administration) were performed and the femoral vein was exposed. 100 µl of AlexaFluor488 conjugate fibrinogen (2 mg/ml) and 100 µl of compound (diluted in 10% DMSO and 90% saline in the 100 µl) or vehicle (10% DMSO in saline in 100 µl) were administered via the carotid artery 5 min prior to application of a 3 mm×2 mm filter paper saturated with 10% (v/v) $FeCl_3$ being placed directly on the femoral vein for 3 minutes.

Real-time, Alexa488 nm (green channel) images using Slidebook imaging software (Version 5.0; Intelligent Imaging Innovations, 3i, Denver, USA) were taken to monitor thrombus formation in vivo at regular intervals for 1 h. The area was flushed with warm PBS following $FeCl_3$ exposure and throughout the experiment.

Data Analyses Slidebook to Determine Fibrin Clot Formation in Real Time

Real time images of thrombus formation were analysed using Slidebook image analysis software by setting a background region outside the thrombus area and measuring Alexa680 nm signal intensities above background over entire area of injury. Setting individual background intensities for the green channel in this way allows selection of pixels that only show signal above background for both probes at each time frame. The resulting selection of pixels or "masked" region (defined as region used for data analyses) is then determined for the pixel's signal intensity for FITC 488 nm (encompassing intensity and area of signal). The Slidebook software allows for the calculation of background for each image file representing different time points in an automated manner, therefore allowing for background subtraction at each time point. Thrombus area is determined by quantifying pixel intensities above background (at each time point) in the FITC 488 nm channel and expressing the masked pixels as total pixel area. When establishing the background region, all time frames within the background are run as a movie to ensure that the region selected as background does not develop any clot growth over the duration of experiment. Background signal prior to ferric chloride injury is determined and subtracted from readings post ferric chloride injury. This is important for analyses with Slidebook because the same region of background is employed for signal determination at each time frame. Data generated is reflective of area intensity of each pixel and as background subtraction takes place with the same image/time frame this data provides an accurate assessment of FITC area with intensity. Data is plotted as relative fluorescence units (RFU) overtime.

The percentage inhibition of clot formation is calculated relative to mice administered vehicle only for the 60 minute time point. The results are shown in FIG. 1.

TABLE 1

| Compound code | FXIIa alpha (Human) Ki | Thrombin (human)/ FXIIa alpha (human) | FXa (human)/ FXIIa alpha (human) |
|---|---|---|---|
| M00626 | * | ++ | oo |
| M00760 | * | + | oo |
| M00762 | * | + | oo |
| M00787 | * | + | oo |
| M00801 | * | ++ | oo |
| M00805 | * | + | oo |
| M00808 | * | + | oo |
| M00901 | * | ++ | oo |
| M00915 | * | + | oo |
| M00922 | * | + | oo |
| M00929 | * | + | oo |
| M00948 | * | ND | ND |
| M00949 | ** | +++ | oo |
| M00952 | *** | +++ | ooo |
| M00953 | *** | ++ | ooo |
| M00954 | *** | + | ooo |
| M00955 | ** | +++ | ooo |
| M00957 | *** | +++ | ooo |
| M00958 | ** | +++ | ooo |
| M00959 | *** | +++ | ooo |
| M00960 | *** | +++ | ooo |
| M00961 | *** | +++ | ooo |
| M00963 | *** | +++ | ooo |
| M00964 | *** | +++ | ooo |
| M00965 | *** | +++ | ooo |
| M00966 | *** | +++ | ooo |
| M00967 | *** | +++ | ooo |
| M00968 | *** | +++ | ooo |
| M00969 | *** | +++ | ooo |
| M00970 | ** | ++ | ooo |
| M00972 | ** | ++ | oo |
| M00973 | * | +++ | ooo |
| M05021 | * | + | oo |
| M05051 | * | + | oo |
| M05053 | * | + | oo |
| M05054 | * | ++ | oo |
| M05056 | ** | +++ | ooo |
| M05068 | ** | ++ | ooo |
| M05073 | ** | + | oo |
| M05074 | ** | + | ooo |
| M05076 | * | ++ | oo |
| M05091 | * | + | oo |
| M05099 | * | + | oo |
| M05102 | * | ++ | oo |
| M05117 | ** | ++ | ooo |
| M05119 | * | ++ | oo |
| M05125 | ** | ++ | oo |
| M05126 | * | ++ | oo |
| M05127 | ** | ++ | oo |
| M05128 | * | ++ | oo |
| M05130 | ** | ++ | ooo |

TABLE 1-continued

| Compound code | FXIIa alpha (Human) Ki | Thrombin (human)/ FXIIa alpha (human) | FXa (human)/ FXIIa alpha (human) |
|---|---|---|---|
| M05139 | * | +++ | ooo |
| M05141 | * | + | o |
| M05142 | ** | + | oo |
| M05143 | * | ++ | oo |
| M05144 | * | ++ | oo |
| M05155 | ** | +++ | ooo |
| M05156 | ** | + | ooo |
| M05157 | * | ++ | oo |
| M05158 | * | ++ | oo |
| M05159 | * | ++ | oo |
| M05160 | * | ++ | oo |
| M05161 | * | ++ | oo |
| M05162 | * | ++ | oo |
| M05163 | * | ++ | oo |
| M05174 | * | ++ | oo |
| M05179 | * | ++ | oo |
| M05181 | * | ++ | oo |
| M05188 | * | ++ | oo |
| M05189 | ** | +++ | ooo |
| M05190 | *** | +++ | ooo |
| M05195 | * | ++ | oo |
| M05196 | * | ++ | oo |
| M05200 | * | ++ | oo |
| M05203 | * | ++ | oo |
| M05204 | * | ++ | oo |
| M05205 | * | ++ | oo |
| M05206 | * | ++ | oo |
| M05207 | * | ++ | oo |
| M05208 | * | ++ | oo |
| M05210 | ** | +++ | ooo |
| M05211 | ** | +++ | ooo |
| M05216 | * | ++ | oo |
| M05218 | ** | +++ | ooo |
| M05219 | *** | +++ | ooo |
| M05220 | ** | +++ | ooo |
| M05222 | ** | +++ | ooo |
| M05223 | ** | +++ | ooo |
| M05224 | *** | +++ | ooo |
| M05228 | ** | +++ | ooo |
| M05232 | ** | +++ | ooo |
| M05235 | *** | +++ | ooo |
| M05237 | ** | + | oo |
| M05241 | *** | ++ | ooo |
| M05242 | * | ++ | oo |
| M05243 | * | ++ | oo |
| M05244 | *** | +++ | ooo |
| M05262 | * | ++ | oo |
| M05265 | ** | + | o |
| M05266 | ** | + | oo |
| M05267 | * | ++ | oo |
| M05268 | * | +++ | ooo |
| M05269 | * | ++ | oo |
| M05271 | * | ++ | oo |
| M05272 | *** | +++ | ooo |
| M05274 | ** | +++ | ooo |
| M05278 | ** | ++ | ooo |
| M05280 | * | ++ | oo |
| M05281 | ** | ++ | o |
| M05282 | ** | ++ | o |
| M05288 | * | ++ | ooo |
| M05289 | ** | +++ | ooo |
| M05290 | * | +++ | oo |
| M05291 | ** | +++ | ooo |
| M05293 | * | ++ | oo |
| M05294 | ** | ++ | ooo |
| M05295 | ** | +++ | ooo |
| M05296 | ** | +++ | ooo |
| M05297 | ** | +++ | ooo |
| M05298 | *** | +++ | ooo |
| M05300 | ** | +++ | ooo |
| M05302 | ** | +++ | ooo |
| M05303 | ** | ++ | ooo |
| M05304 | ** | +++ | ooo |
| M05306 | *** | +++ | ooo |

TABLE 1-continued

| Compound code | FXIIa alpha (Human) Ki | Thrombin (human)/ FXIIa alpha (human) | FXa (human)/ FXIIa alpha (human) |
|---|---|---|---|
| M05308 | * | ++ | oo |
| M05309 | ** | +++ | ooo |
| M05312 | ** | +++ | ooo |
| M05314 | ** | ++ | ooo |
| M05315 | * | ++ | oo |
| M05317 | *** | +++ | ooo |
| M05318 | * | + | oo |
| M05319 | ** | +++ | ooo |
| M05320 | *** | +++ | ooo |
| M05323 | *** | +++ | ooo |
| M05324 | * | ++ | oo |
| M05325 | * | ++ | oo |
| M05326 | *** | +++ | ooo |
| M05327 | * | ++ | o |
| M05328 | ** | ++ | ooo |
| M05329 | * | ++ | oo |
| M05330 | ** | +++ | ooo |
| M05332 | * | ++ | oo |
| M05333 | * | ++ | o |
| M05334 | ** | ++ | oo |
| M05335 | * | ++ | oo |
| M05336 | *** | +++ | ooo |
| M05337 | * | ++ | oo |
| M05338 | * | ++ | oo |
| M05339 | ** | +++ | ooo |
| M05340 | ** | ++ | oo |
| M05341 | ** | +++ | ooo |
| M05342 | ** | ++ | ooo |
| M05345 | * | ++ | oo |
| M05346 | * | ++ | oo |
| M05348 | ** | +++ | ooo |
| M05349 | ** | ++ | oo |
| M05350 | ** | +++ | ooo |
| M05351 | * | ++ | oo |
| M05352 | ** | +++ | ooo |
| M05353 | * | ++ | oo |
| M05354 | ** | +++ | ooo |
| M05354 | ** | +++ | ooo |
| M05355 | * | ++ | oo |
| M05355 | ** | +++ | ooo |
| M05356 | * | ++ | oo |
| M05357 | * | ++ | oo |
| M05359 | ** | ++ | oo |
| M05360 | ** | ++ | oo |
| M05361 | ** | ++ | oo |
| M05362 | ** | ++ | oo |
| M05363 | * | ++ | oo |
| M05364 | * | ++ | oo |
| M05365 | ** | +++ | ooo |
| M05366 | ** | ++ | oo |
| M05367 | ** | +++ | ooo |
| M05368 | * | ++ | oo |
| M05371 | * | ++ | oo |
| M05372 | ** | ++ | ooo |
| M05373 | ** | ++ | oo |
| M05374 | * | ++ | oo |
| M05376 | * | ++ | oo |
| M05377 | ** | +++ | ooo |
| M05378 | ** | ++ | ooo |
| M05379 | ** | +++ | ooo |
| M05380 | ** | +++ | ooo |
| M05381 | ** | +++ | ooo |
| M05382 | ** | +++ | ooo |
| M05383 | ** | ++ | ooo |
| M05384 | ** | +++ | ooo |
| M05386 | ** | ++ | oo |
| M05387 | ** | +++ | ooo |
| M05388 | ** | +++ | ooo |
| M05389 | ** | +++ | ooo |
| M05390 | ** | ++ | ooo |
| M05391 | *** | +++ | ooo |
| M05392 | *** | +++ | ooo |
| M05393 | ** | +++ | ooo |
| M05394 | ** | +++ | ooo |
| M05397 | ** | +++ | ooo |
| M05398 | * | ND | ND |
| M05399 | *** | +++ | ooo |
| M05400 | *** | +++ | ooo |
| M05401 | * | ++ | oo |
| M05402 | *** | +++ | ooo |
| M05404 | *** | +++ | ooo |
| M05405 | * | ++ | oo |
| M05406 | ** | +++ | ooo |
| M05407 | *** | +++ | ooo |
| M05408 | * | ND | ND |
| M05409 | * | + | oo |
| M05410 | * | + | oo |
| M05411 | ** | +++ | ooo |
| M05412 | *** | +++ | ooo |
| M05413 | ** | ++ | ooo |
| M05414 | ** | +++ | ooo |
| M05415 | * | ND | ND |
| M05416 | * | ND | ND |
| M05417 | ** | +++ | ooo |
| M05418 | ** | +++ | ooo |
| M05419 | *** | +++ | ooo |
| M05420 | *** | +++ | ooo |
| M05421 | ** | +++ | ooo |
| M05429 | * | ++ | oo |
| M05430 | ** | +++ | ooo |
| M05431 | * | ++ | oo |
| M05441 | *** | +++ | ooo |
| M05442 | ** | +++ | ooo |
| M05443 | ** | +++ | ooo |
| M05446 | * | ++ | oo |
| M05447 | ** | +++ | ooo |
| M05448 | ** | +++ | ooo |
| M05449 | *** | +++ | ooo |
| M05450 | *** | +++ | ooo |
| M05451 | *** | +++ | ooo |
| M05453 | *** | +++ | ooo |
| M05454 | * | ++ | oo |
| M05458 | *** | +++ | ooo |
| M05459 | ** | +++ | ooo |
| M05460 | ** | +++ | ooo |
| M05461 | *** | +++ | ooo |
| M05462 | ** | +++ | ooo |
| M05463 | * | ++ | oo |
| M05464 | * | ++ | oo |
| M05465 | ** | +++ | ooo |
| M05470 | *** | +++ | ooo |
| M05471 | * | ++ | oo |
| M05474 | ** | +++ | ooo |
| M05490 | *** | +++ | ooo |

ND refers to entries where test data has not been obtained.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound of formula (Ia) or a pharmaceutically acceptable salt thereof:

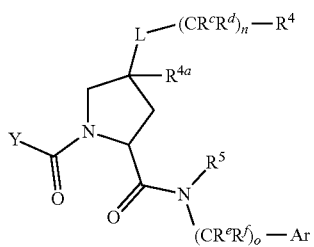

(Ia)

wherein

Y is selected from the group consisting of:

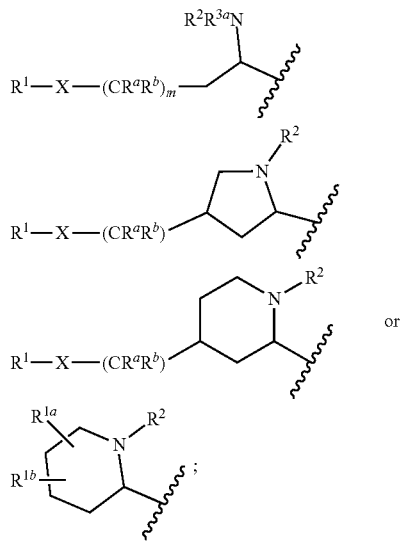

X is a bond, —C(O)NH—, —C(O)O— or —C(O)—;
L-(CR$^c$R$^d$)$_n$— is selected from the group consisting of: a bond, CH$_2$, —NH—, —NHCH$_2$—, —NH(CH$_2$)$_2$—, —NH(CH$_2$)$_3$—, —N(Me)—, —N(C(O)Me)CH$_2$—, —NHC(O)—, —NHC(O)CH$_2$—, —NHC(O)(CH$_2$)$_2$—, or NHC(O)(CH$_2$)$_3$;
Ar is a substituted or unsubstituted 9 to 10 membered bicyclic heteroaromatic ring, wherein the bicyclic heteroaromatic ring is an aromatic hydrocarbon ring with at least one heteroatom within the ring selected from the group consisting of O, N and S or a bicyclic ring which is not completely aromatic but contains an aromatic ring, wherein the at least one heteroatom is present within the aromatic ring or the non-aromatic ring, and wherein, when substituted, the Ar is substituted with 1, 2, or 3 substituents selected from the group consisting of: halo, C$_{1-6}$ alkyl, —OR$^g$, —NR$^g$R$^h$ or C$_{1-4}$ alkyl substituted by —NR$^g$R$^h$; m is selected from the group consisting of 1, 2, or 3;
n is 0, 1, 2, 3, or 4;
o is 1 or 2;
R$^1$ is selected from the group consisting of substituted or unsubstituted: —NR$^8$R$^9$, 5 to 10 membered carbocyclic ring or a 5 to 10 membered heterocyclic ring;
wherein when substituted R$^1$ is substituted with 1, 2, or 3 groups selected from the group consisting of: =O, CN, —OH, or —O—C$_{1-6}$ alkyl, halo, C$_{1-6}$ alkyl or C$_{1-6}$ haloalkyl;
R$^{1a}$ and R$^{1b}$ taken together form a substituted or unsubstituted: 5 or 6 membered heteroaromatic ring or a phenyl ring;
wherein, when the ring formed from R$^{1a}$ and R$^{1b}$ is substituted, it is substituted with 1, 2, or 3 R$^z$ groups, wherein R$^z$ is independently selected at each occurrence from: =O, CN, —OH, —O—C$_{1-6}$ alkyl, halo and C$_{1-6}$ alkyl;
R$^2$ is H, C$_{1-6}$ alkyl, C$_{1-6}$ haloalkyl, phenyl, benzyl, —C(O)R$^{2a}$, and S(O)$_2$R$^{2a}$; and
wherein R$^{2a}$ is selected from the group consisting of: C$_{1-6}$ alkyl, phenyl, or benzyl;
R$^{3a}$ is H or C$_{1-6}$ alkyl; and
R$^4$ is =CH$_2$, —CN, halo, C$_{1-4}$ alkyl, C$_{1-4}$ haloalkyl, —OR$^{10}$, —NR$^{10}$R$^{11}$, 6 to 10 membered aryl, C$_{3-8}$ cycloalkyl, 3 to 6 membered heterocycloalkyl, or 5 to 10 membered heteroaryl, wherein the C3.8 cycloalkyl, 3 to 6 membered heterocycloalkyl, 6 to 10 membered aryl, or 5 to 10 membered heteroaryl group is unsubstituted or substituted with 1, 2 or 3 R$^{12}$;
R$^{4a}$ is H, —OH, halo or C$_{1-4}$ alkyl;
R$^5$ is H or C$_{1-6}$ alkyl;
R$^8$ and R$^9$ are independently selected from the group consisting of: H, C$_{1-6}$ alkyl, C$_{3-6}$ cycloalkyl, phenyl, C$_{1-4}$ alkyl substituted with —OR$^i$, or C$_{1-4}$ alkyl substituted with phenyl, or R$^8$ and R$^9$ taken together with the atom to which they are attached form 3 to 8 membered heterocycloalkyl ring, which is unsubstituted or substituted with: CN, halo, C$_{1-6}$ alkyl or —OR$^i$;
R$^{12}$ is independently at each occurrence selected from the group consisting of: halo, C$_{1-4}$ alkyl, C$_{1-4}$ haloalkyl, —OR$^{13}$, —CN, —C(O)R$^{10}$, =O, SO$_2$R$^{10}$, benzyl, phenyl, unsubstituted 5 or 6 membered heteroaryl, or methyl substituted 5 or 6 membered heteroaryl;
R$^{10}$ and R$^{11}$ are independently at each occurrence selected from the group consisting of: H or C$_{1-4}$ alkyl;
R$^{13}$ is H, C$_{1-4}$ alkyl, C$_{1-4}$ haloalkyl, phenyl or benzyl;
R$^a$ and R$^b$ are independently at each occurrence selected from the group consisting of: H, C$_{1-4}$ alkyl, and —OR$^j$; and
R$^e$, R$^f$, R$^g$, R$^h$, R$^i$ and R$^j$ are independently at each occurrence selected from the group consisting of: H or C$_{1-4}$ alkyl.

2. The compound of claim 1, wherein X is a bond, —C(O)NH—, or —C(O)—.

3. The compound of claim 1, wherein $R^z$ is H, OH, Cl or OMe.

4. The compound of claim 1, wherein o is 1 and/or $R^e$ and $R^f$ are H.

5. The compound of claim 1, wherein $R^2$ is H.

6. The compound of claim 1, wherein $R^3$ is H.

7. The compound of claim 1, wherein $R^5$ is H.

8. The compound of claim 1, wherein $R^a$ and $R^b$ are each H.

9. The compound of claim 1, wherein $R^{4a}$ is H, OH or F.

10. The compound of claim 1, wherein $R^g$ and $R^h$ is independently at each occurrence selected from the group consisting of: H and methyl.

11. The compound of claim 1, wherein Ar is benzotriazole, imidazopyridine, pyridofuran, azaindole, benzopyrazole, pyridoazathiophene, benzoxazole, quinoline, or isoquinoline; and wherein Ar is unsubstituted or substituted with methyl, chloro, —OMe, —NH$_2$ or —CH$_2$NH$_2$.

12. The compound of claim 1, wherein Ar is:

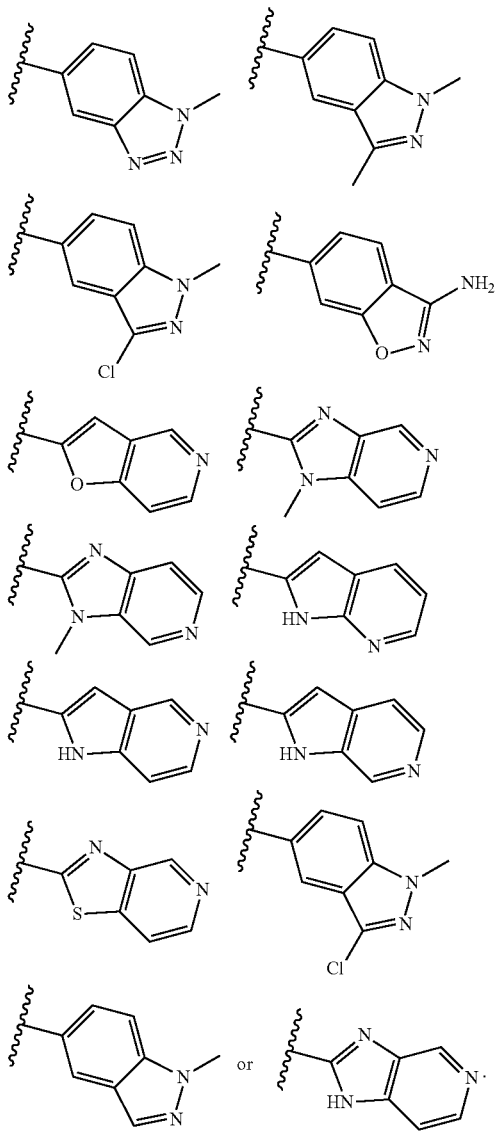

13. The compound of claim 11, wherein Ar is azaindole, benzotriazole or N-methyl benzotriazole.

14. The compound of claim 1, wherein $R^{4a}$ is H, OH or F; and wherein -L-(CR$^c$R$^d$)$_n$—R$^4$ is —CF$_3$, —OH, —NH$_2$, =CH$_2$, —CN, —NHC(O)Me, —NHC(O)Ph, —NHC(O)Bn, —NHC(O)CH$_2$CH$_2$Ph, —NHC(O)(CH$_2$)$_3$Ph, —NHC(O)OMe, —NHC(O)NHMe, —N(C(O)Me)benzyl, —N(C(O)Me)CH$_2$pyridinyl, —N(Me)cyclohexyl, phenyl, isoindoline, piperazine, benzyl, —CH$_2$phenyl, —CH$_2$pyridinyl, —CH$_2$cyclopentyl, —CH$_2$tetrahydropyranyl, —CH$_2$pyrazolyl, —CH$_2$dihydrobenzofuran, —CH$_2$imidazolyl, —CH$_2$benzodioxolanyl, —NHcyclohexane, —NHpyrazinyl, —NHCH$_2$Ph, —NHCH$_2$cyclohexane, —NHCH$_2$CH$_2$Ph, and —NHCH$_2$CH$_2$CH$_2$Ph;

wherein any of the above cyclic groups is unsubstituted or substituted with 1, 2 or 3 groups selected from the group consisting of: Cl, Br, F, CF$_3$, OMe, OEt, —O-phenyl, —O-benzyl, CN, SO$_2$Me, methyl, pyridinyl, or methylpyrazole.

15. The compound of claim 1, wherein $R^1$ is selected from the group consisting of substituted or unsubstituted: —NR$^8$R$^9$, 6 or 10 membered aryl, 5, 6 or 9 membered heteroaryl, or 3 to 7 membered heterocycloalkyl; wherein when substituted, $R^1$ is substituted with 1, 2, or 3 groups selected from the group consisting of: =O, CN, —OH, or —O—C$_{1-6}$ alkyl, halo, C$_{1-6}$ alkyl or C$_{1-6}$ haloalkyl.

16. The compound of claim 15, wherein $R^1$ is NMe$_2$, —N(Me)i-Pr, —NH-cyclopropyl, cyclopropyl, phenyl, pyridinyl, pyridinonyl, pyrimidinyl, imidazolyl, oxazolyl, pyrollidinyl, methylpyrollidinyl, fluoropyrollidinyl, azetidinyl, piperidinyl, piperazinyl, azepanyl, indoline, tetrahydronapthalenyl, or

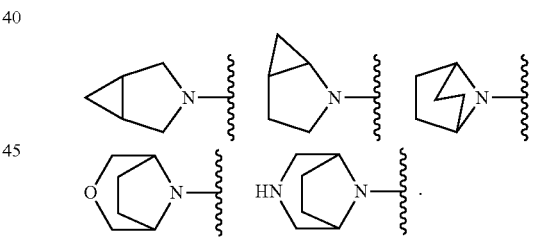

17. The compound of claim 15, wherein $R^1$ is substituted with a group selected from the group consisting of: F, CN, =O, —OH, —OCF$_3$, —OMe, Me, i-Pr, or —CF$_3$.

18. The compound of claim 1, wherein the compound is:

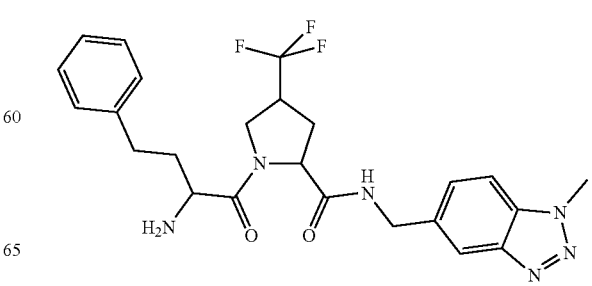

411
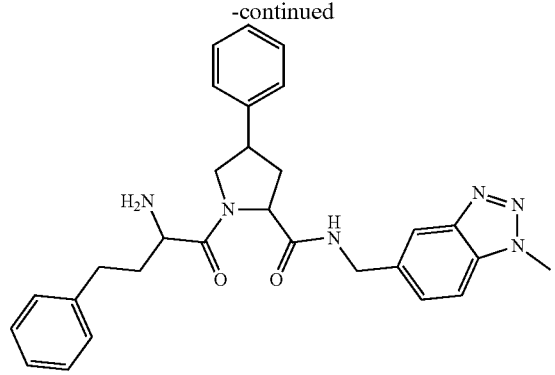
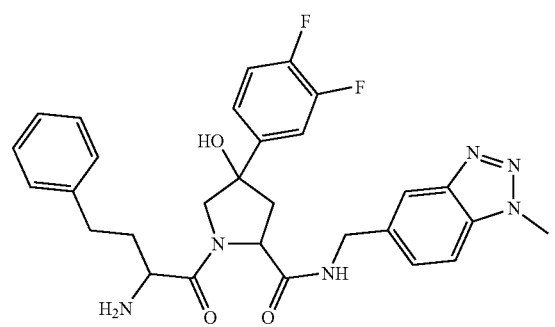
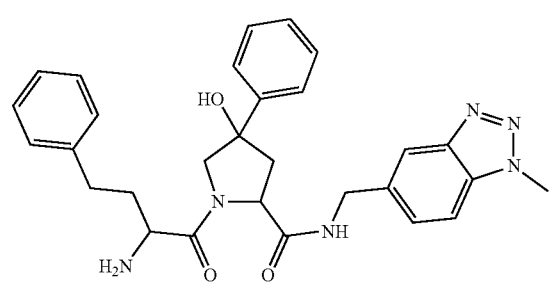
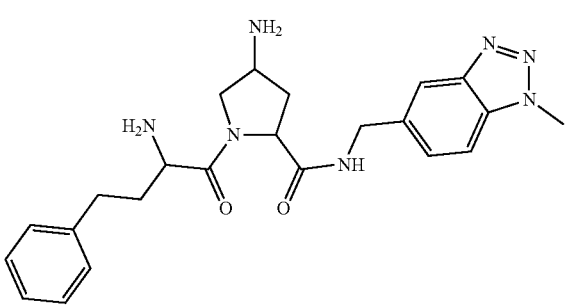
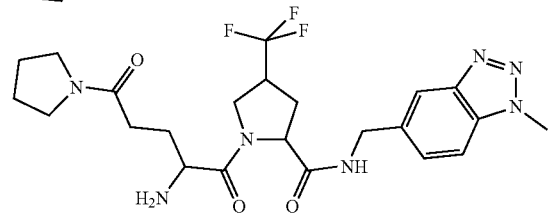
412
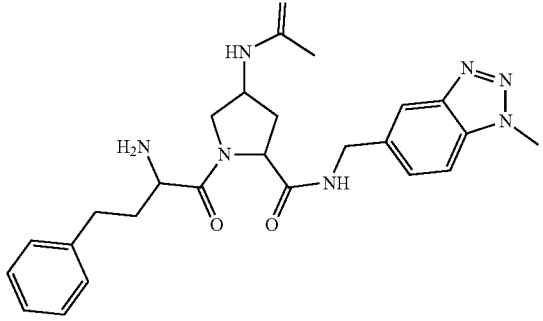
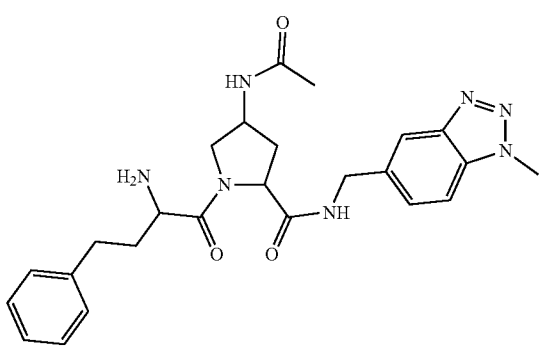
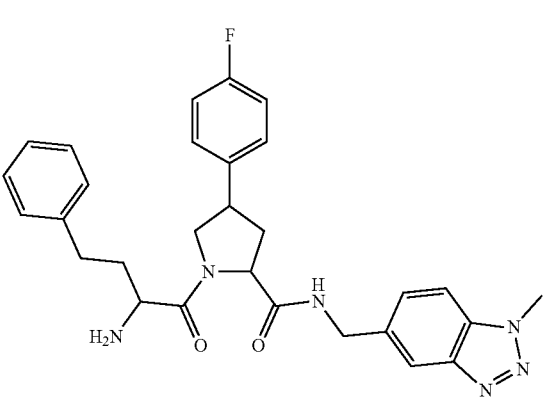
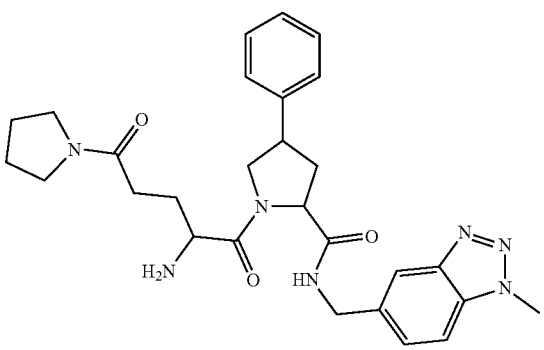

413
-continued
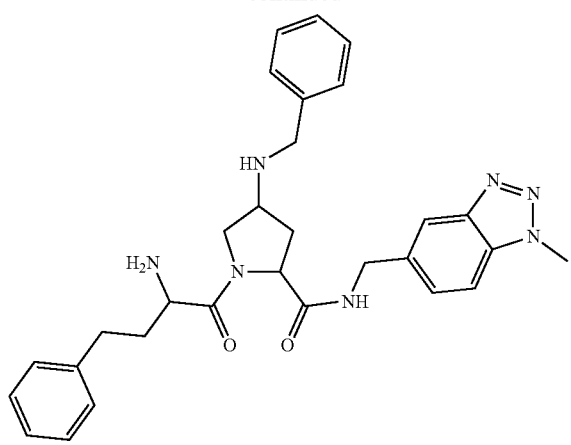
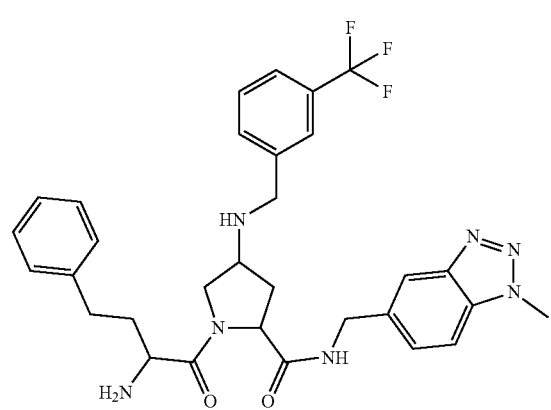
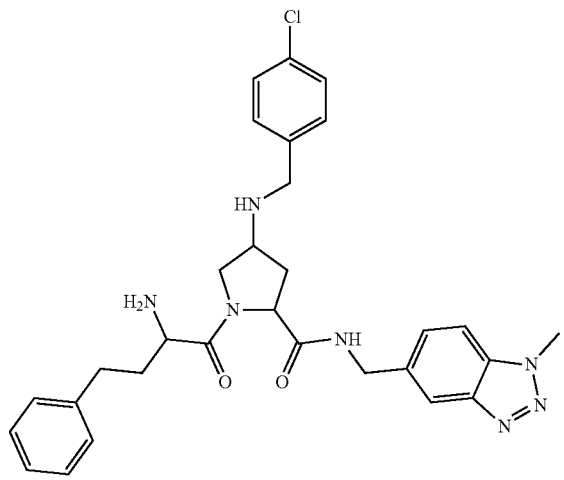
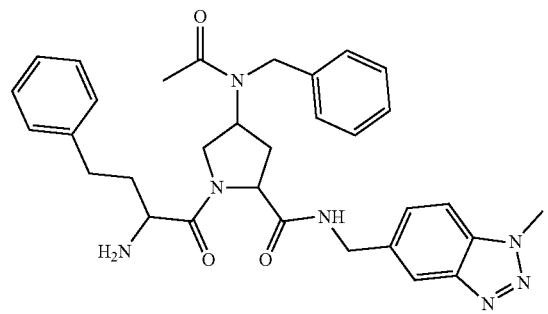
414
-continued
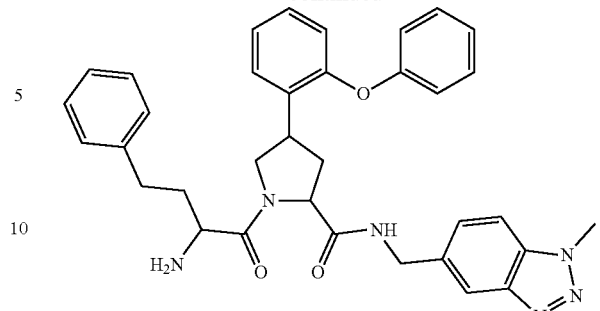
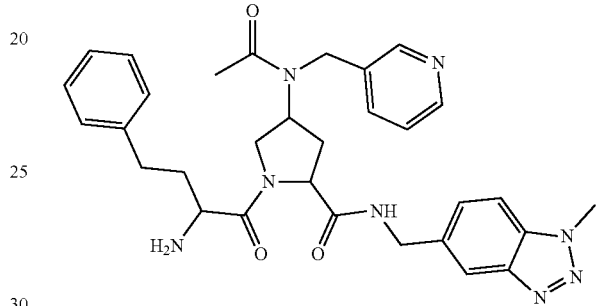
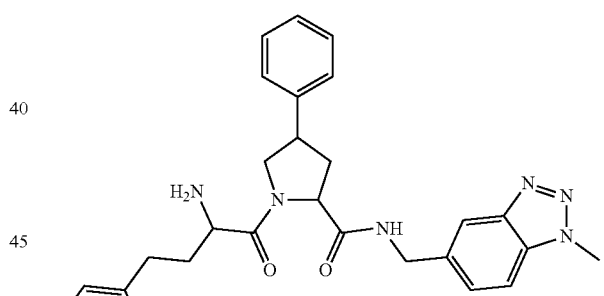
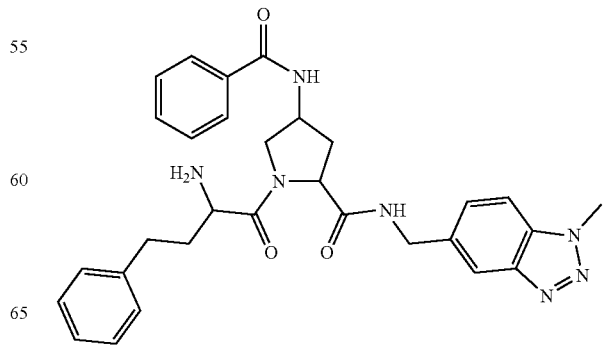

415
-continued
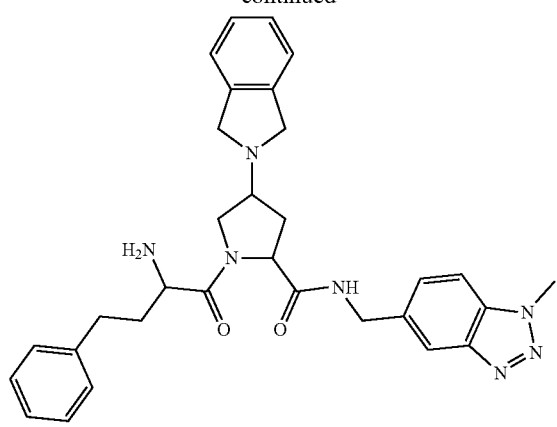
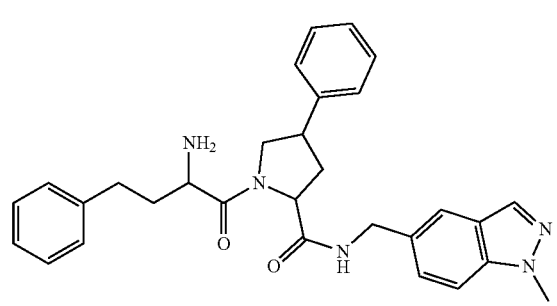
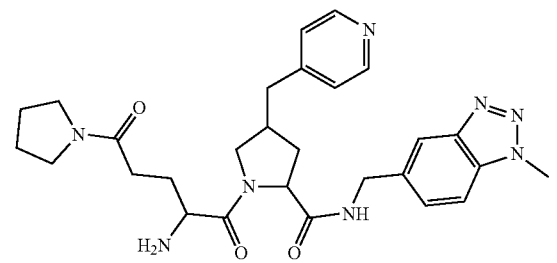
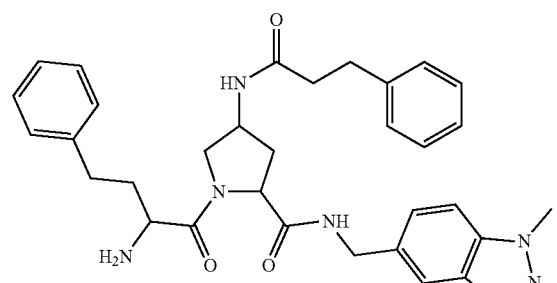
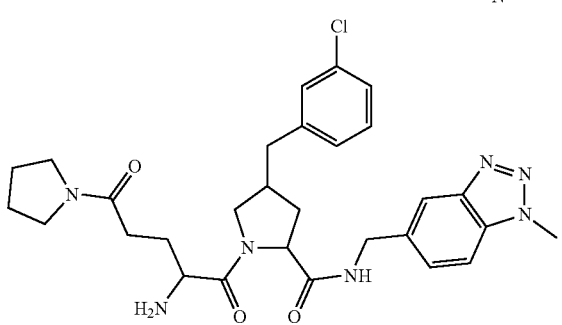
416
-continued
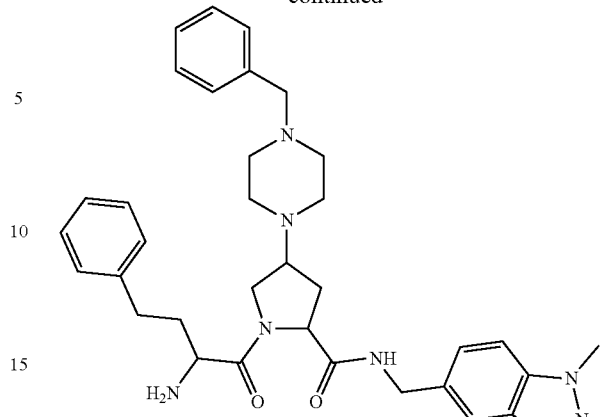
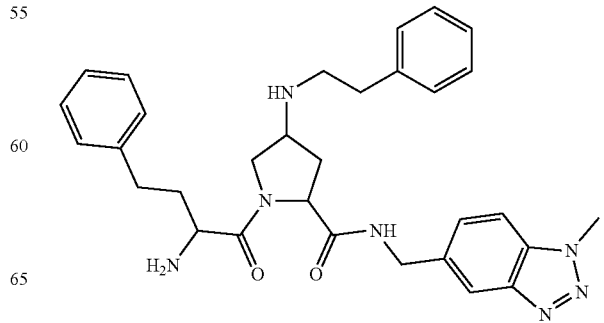

417
-continued
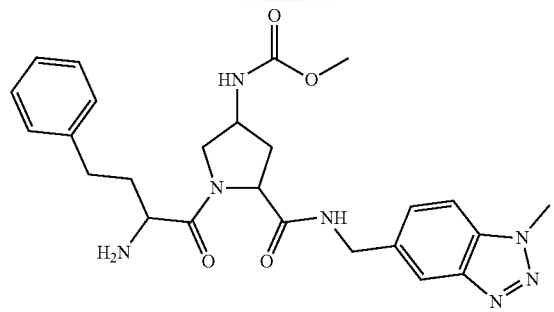
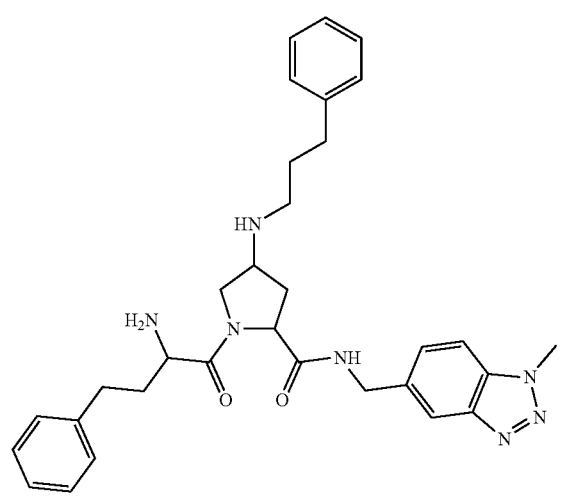
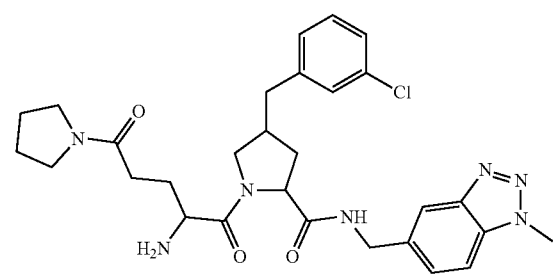
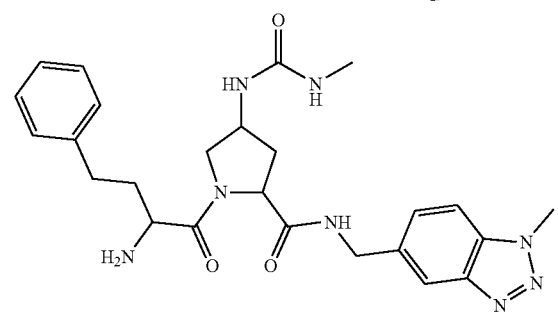
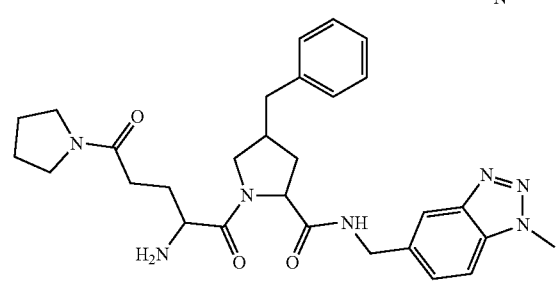
418
-continued
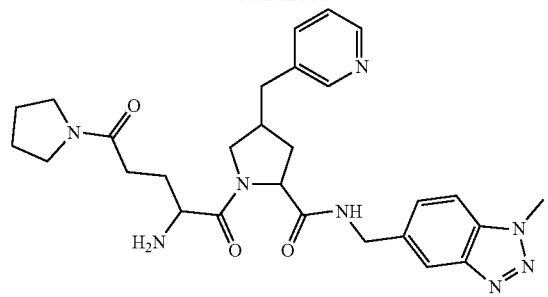
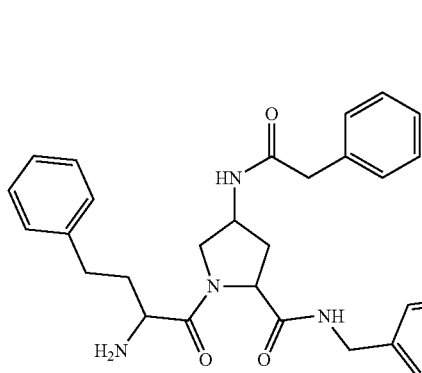
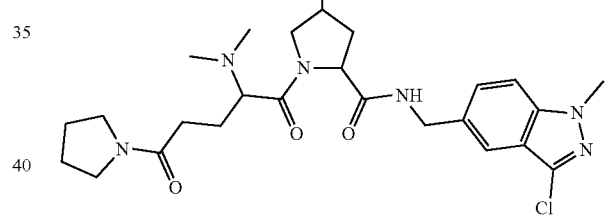
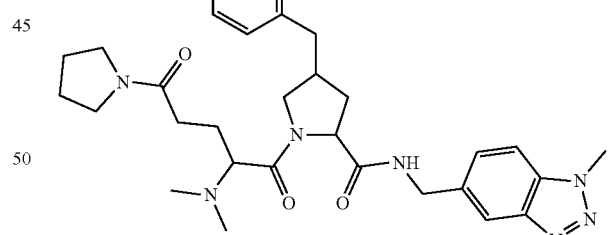
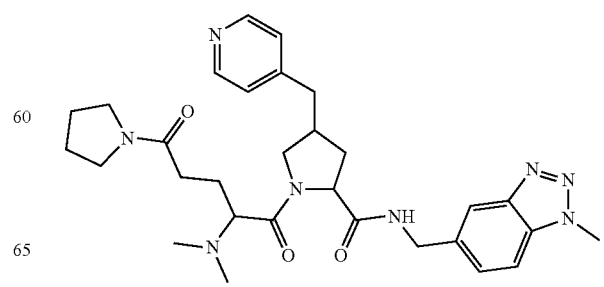

419
-continued
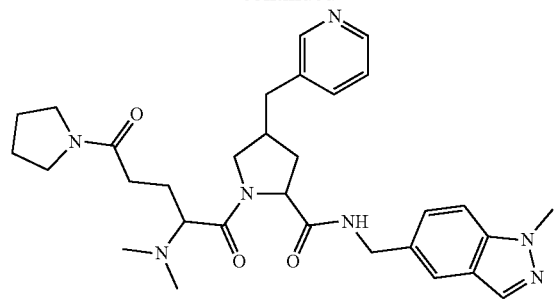
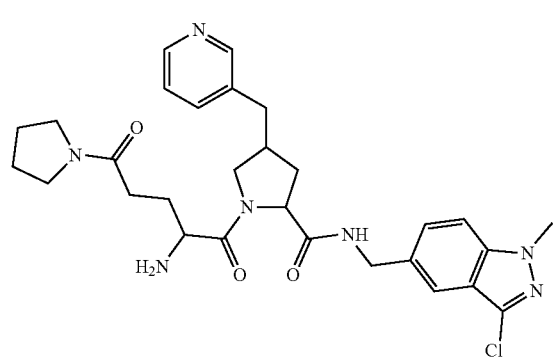
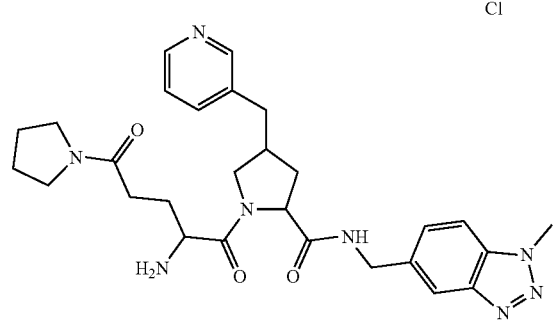
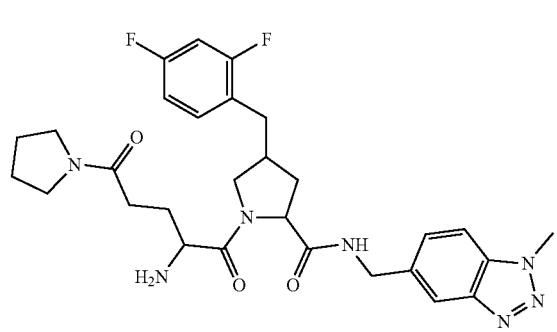
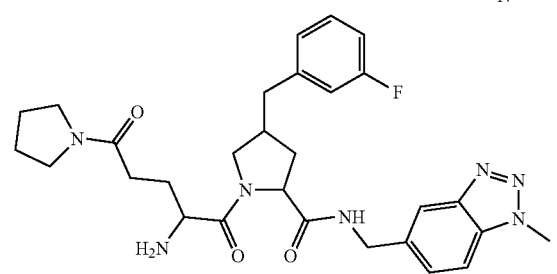
420
-continued
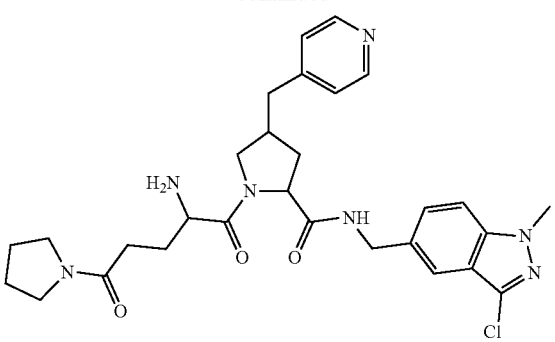
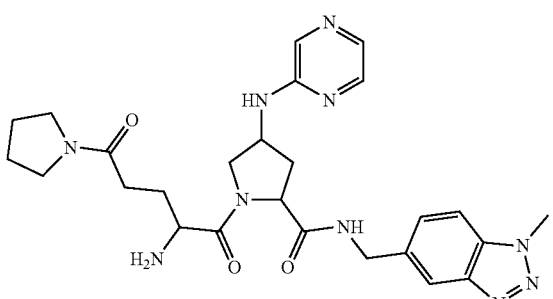
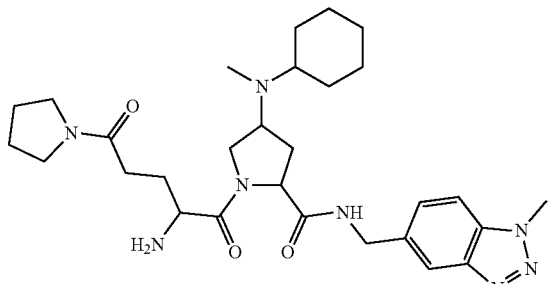
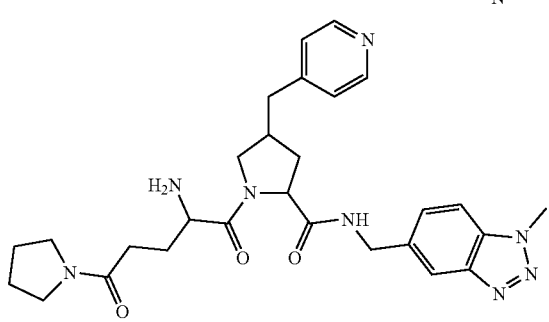
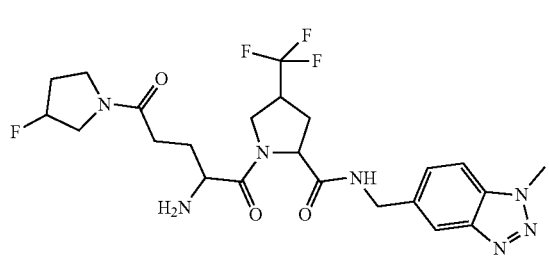

-continued
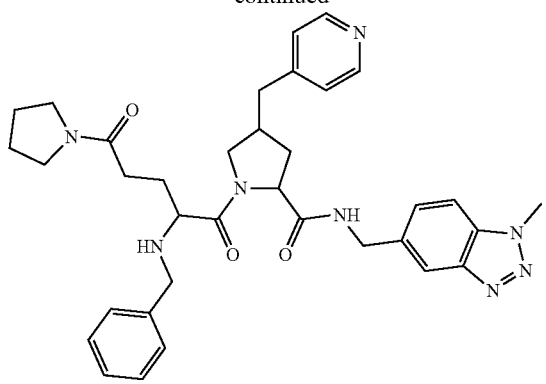
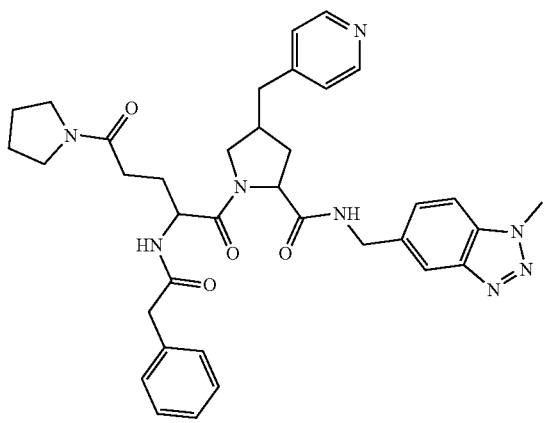
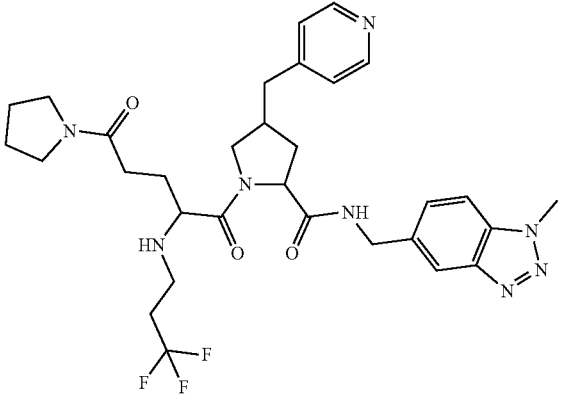
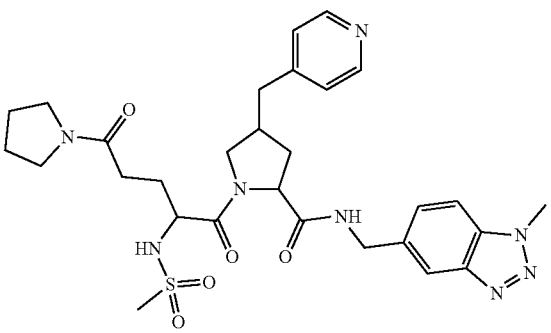
-continued
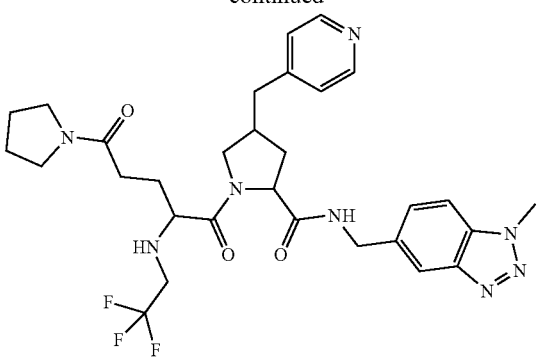
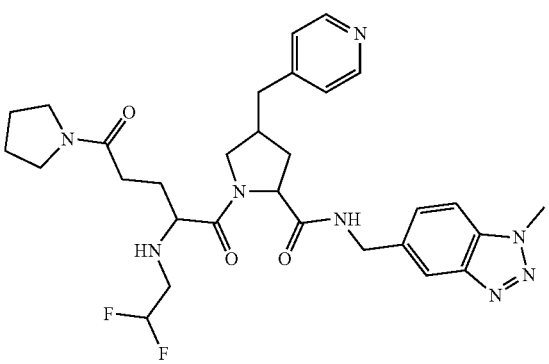
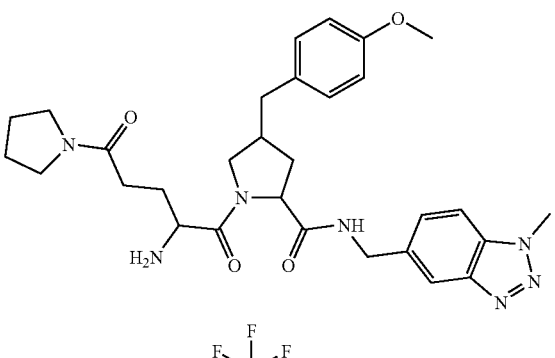
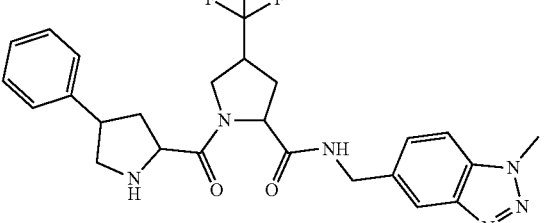
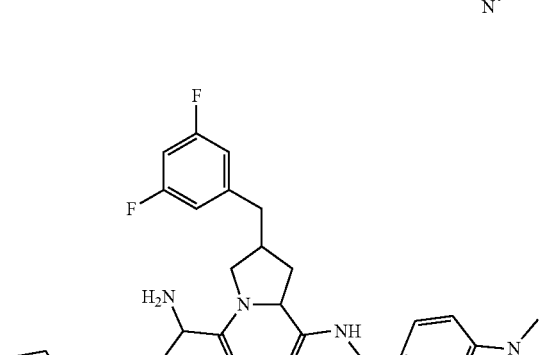

423
-continued
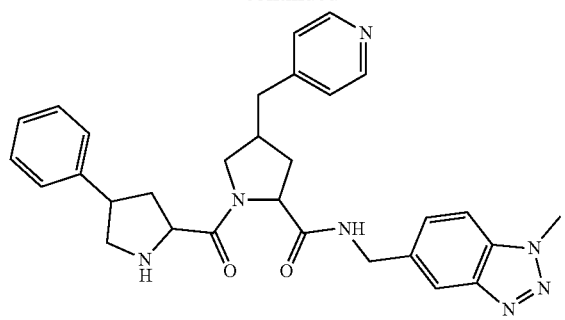
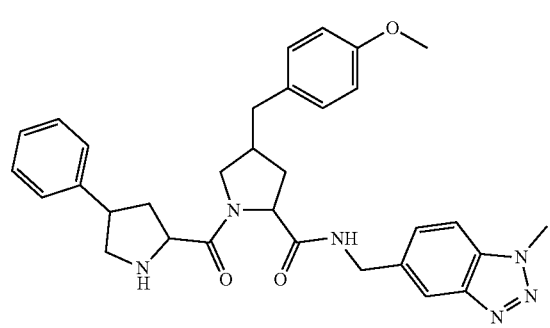
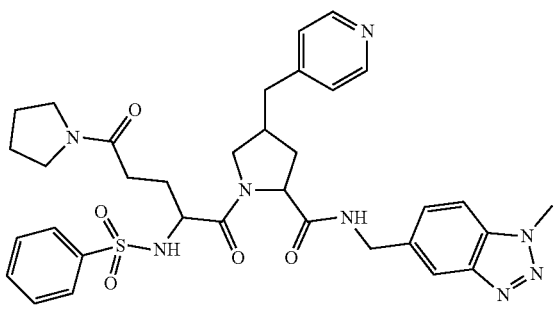
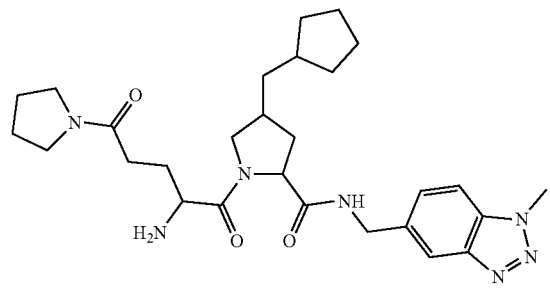
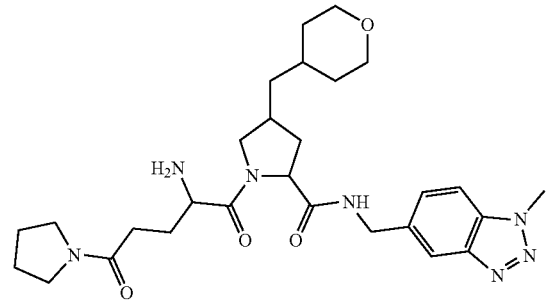
424
-continued
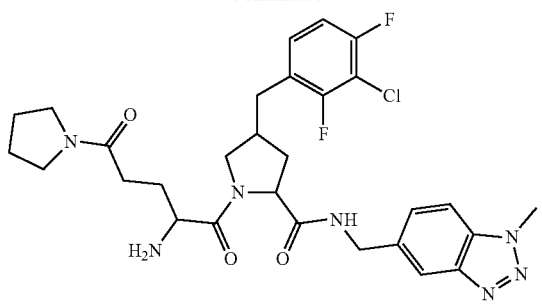
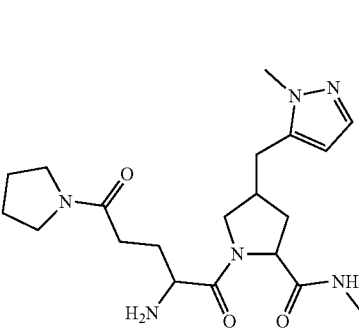
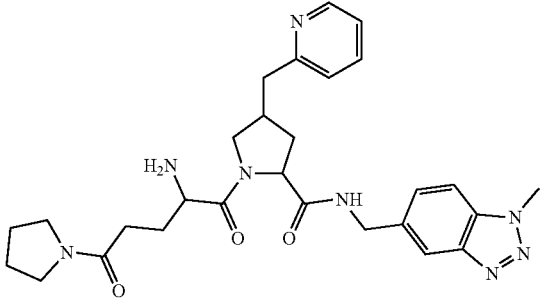
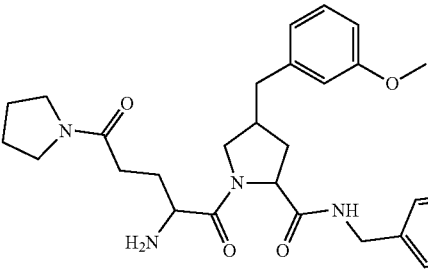
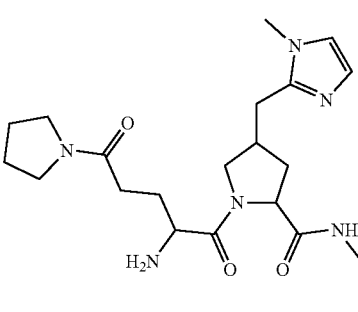

425
-continued
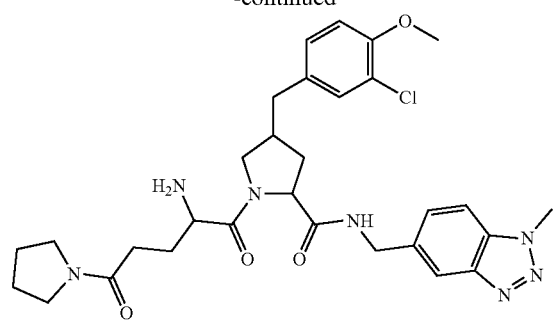
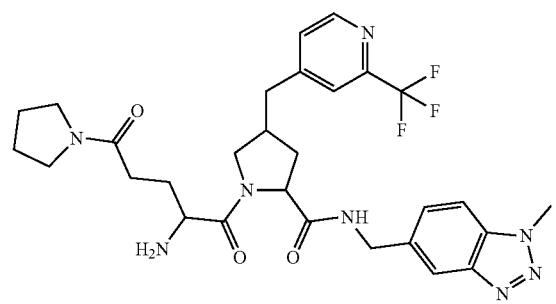
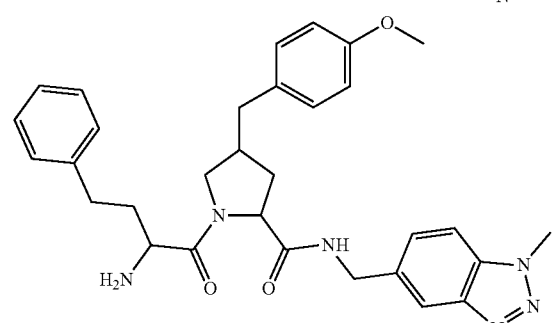
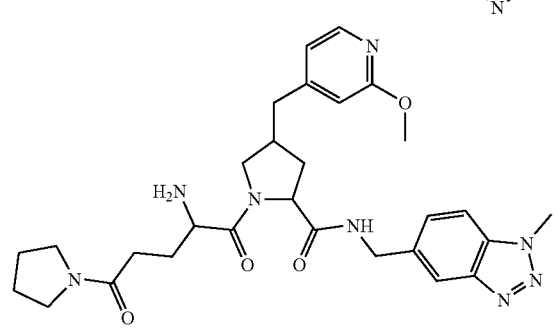
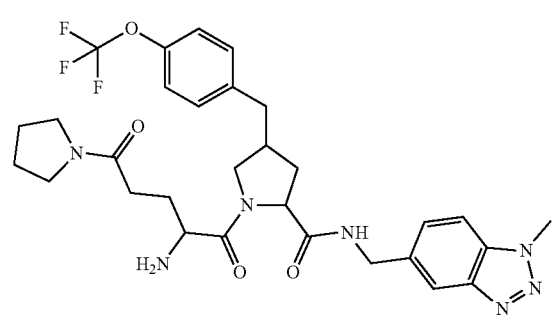
426
-continued
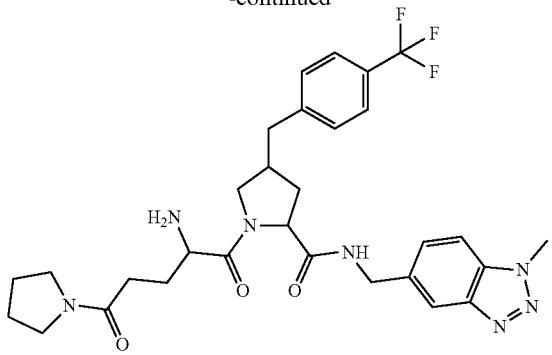
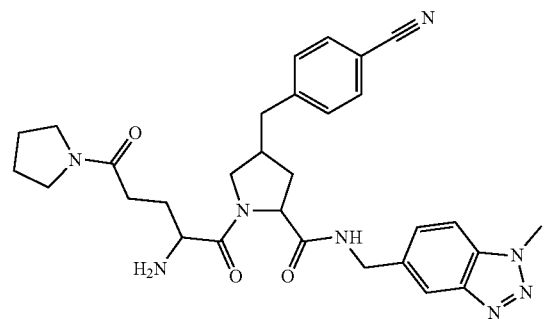
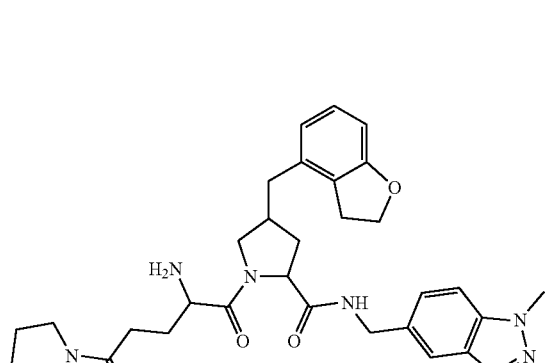
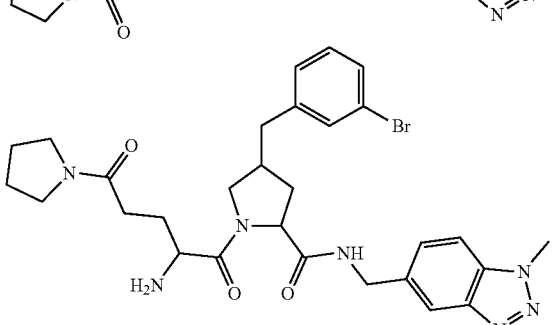
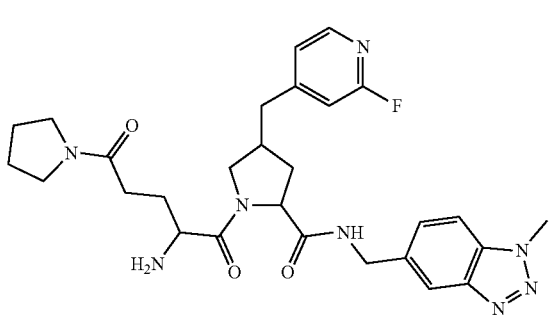

427
-continued
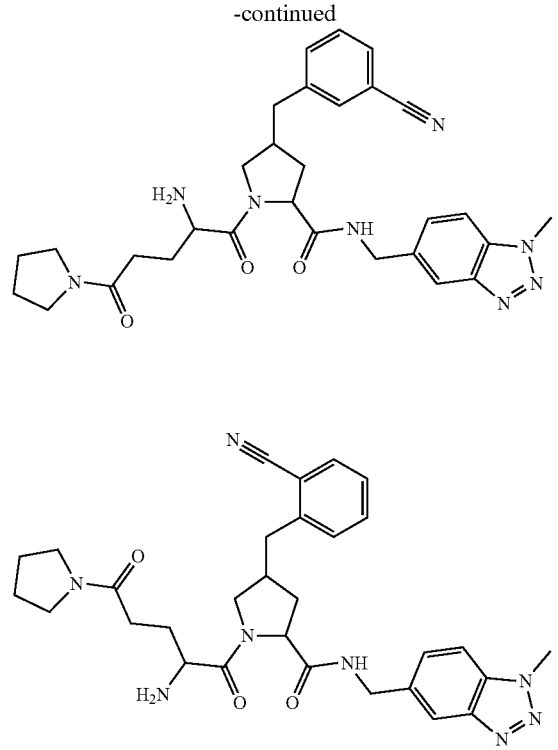
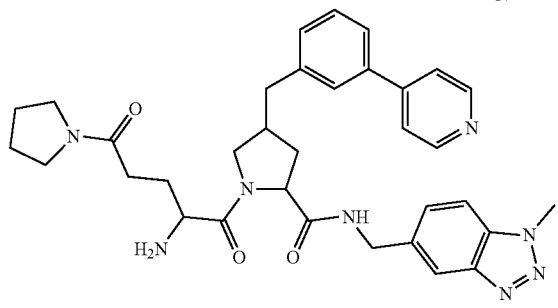
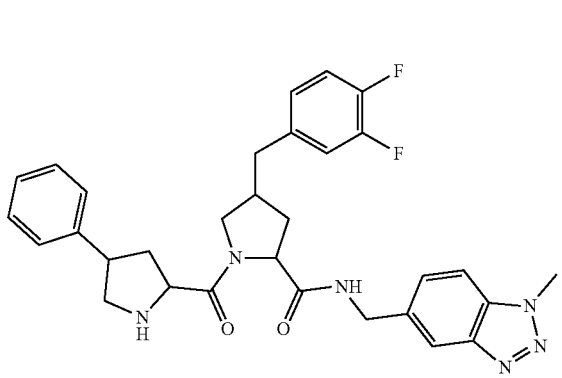
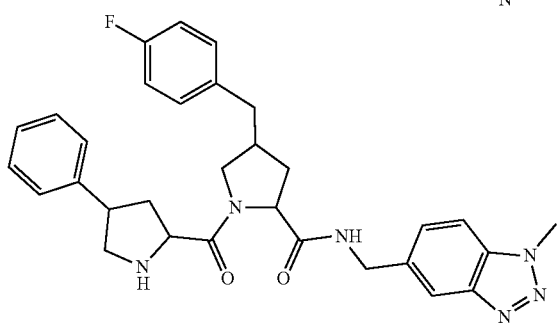
428
-continued
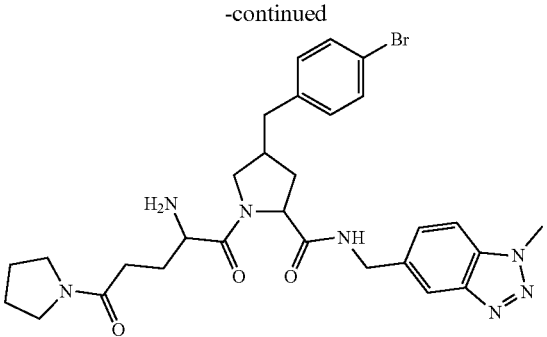
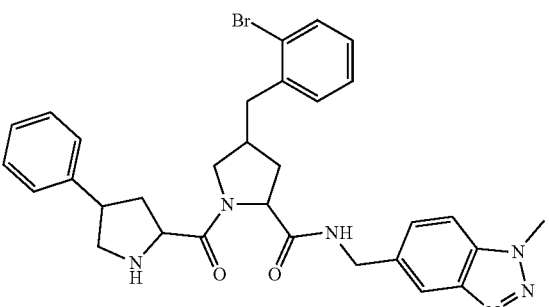
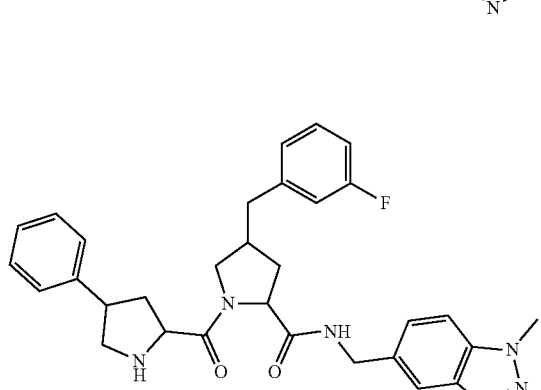
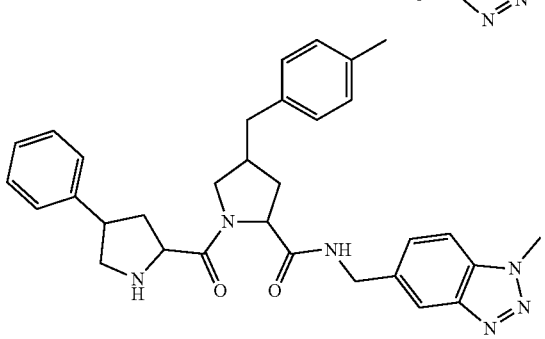
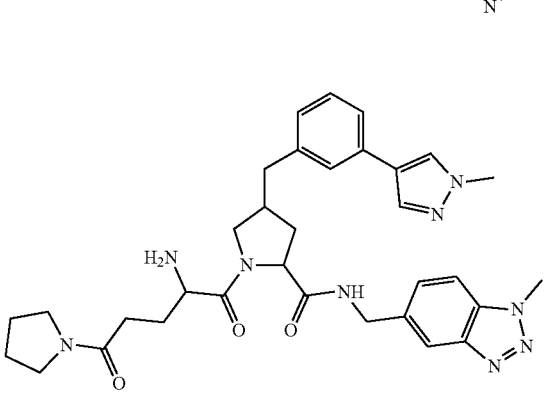

429
-continued
430
-continued
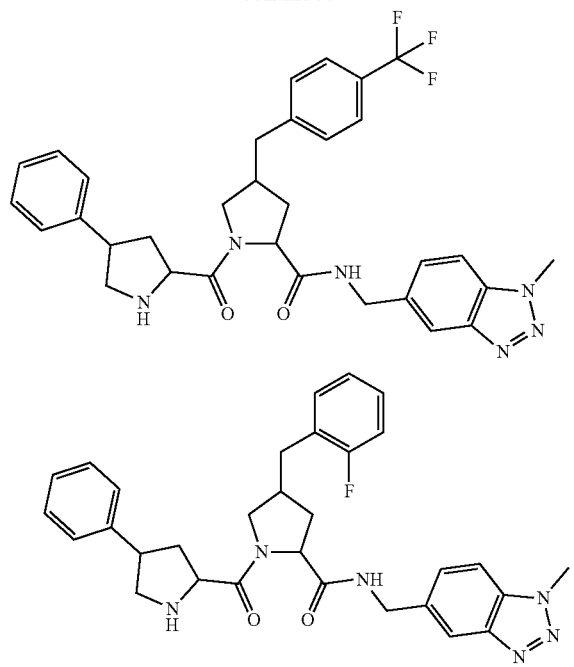
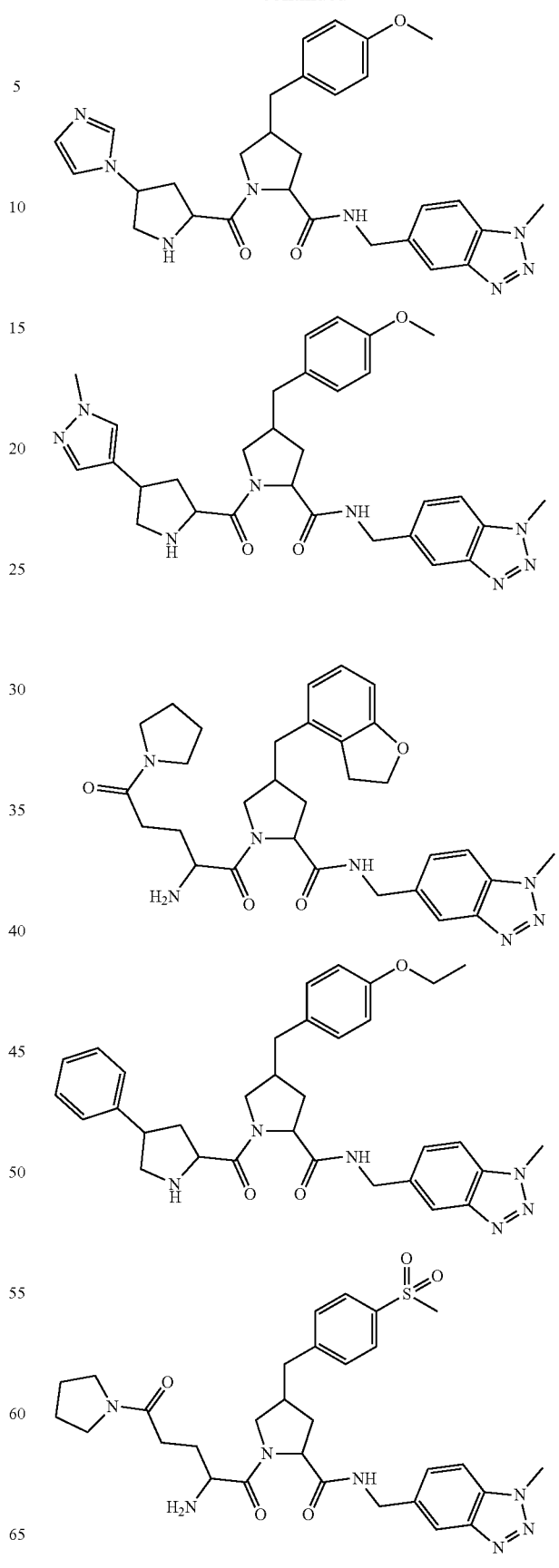

431
-continued
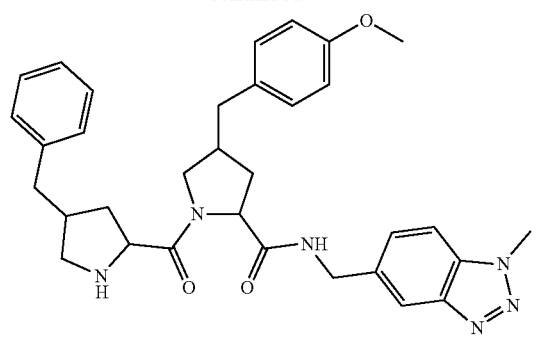
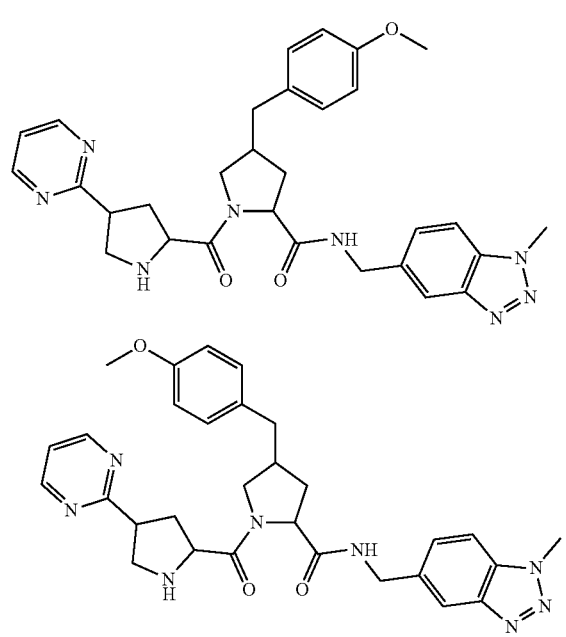
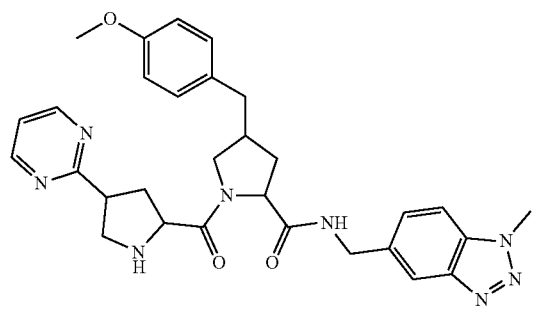
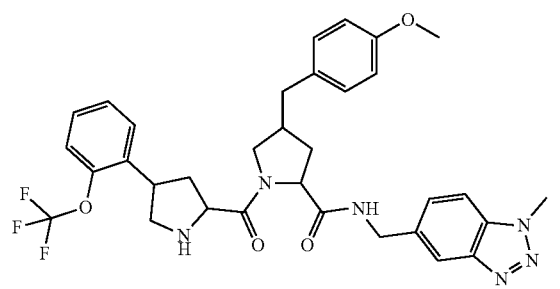
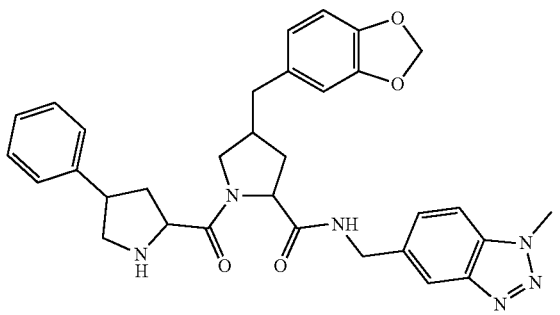
432
-continued
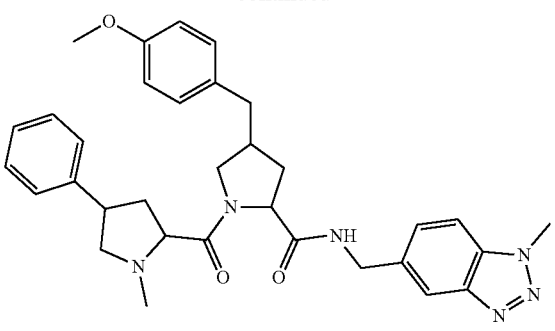
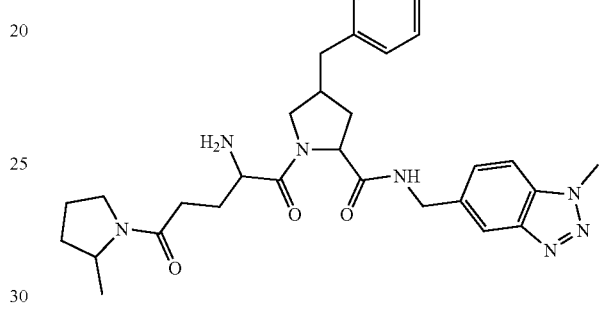
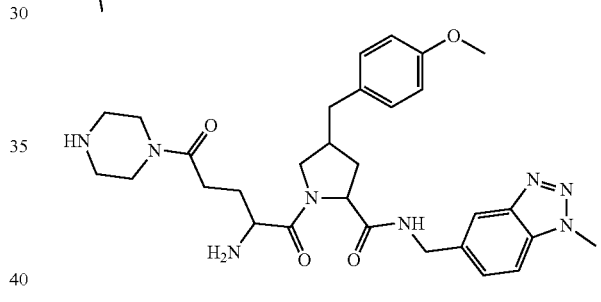
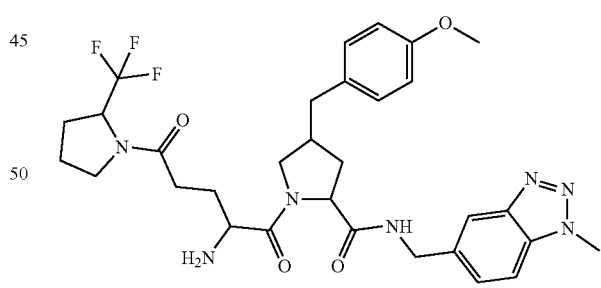
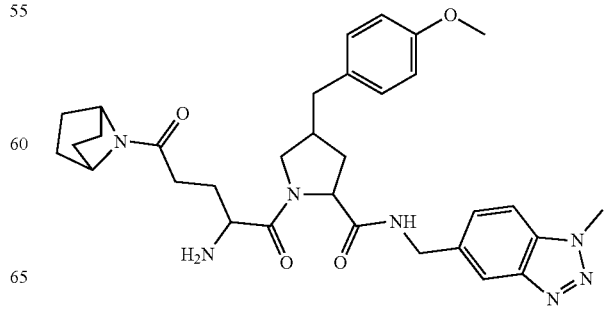

433
-continued
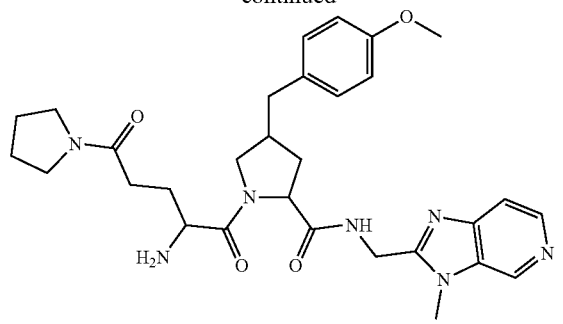
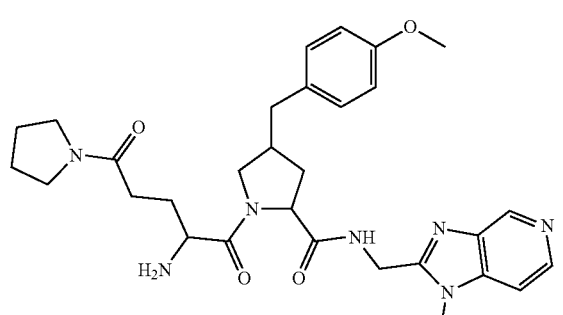
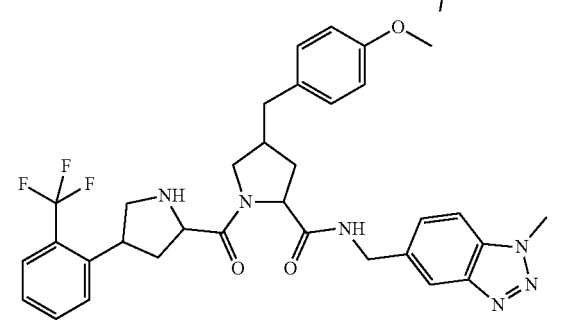
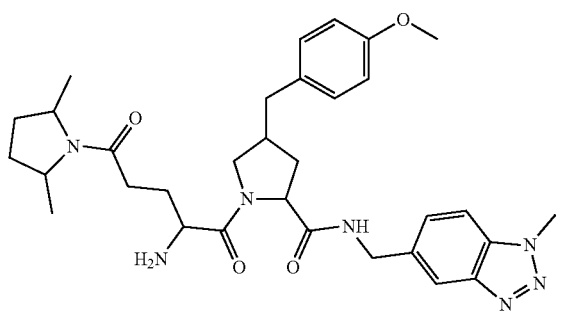
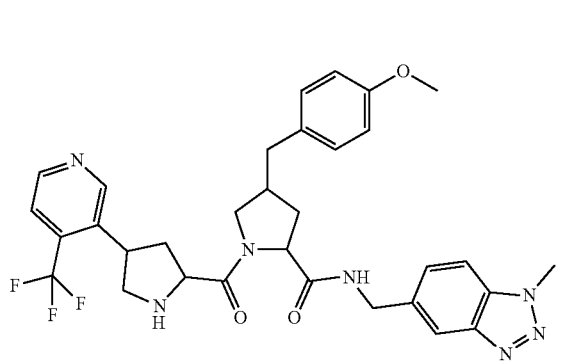
434
-continued
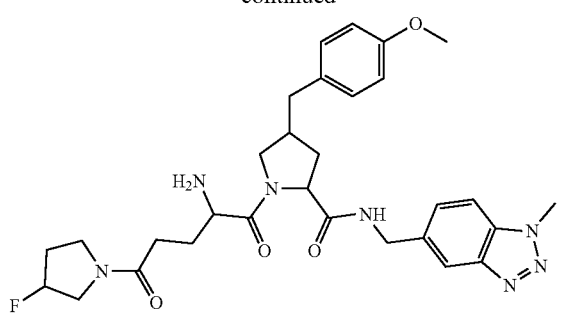
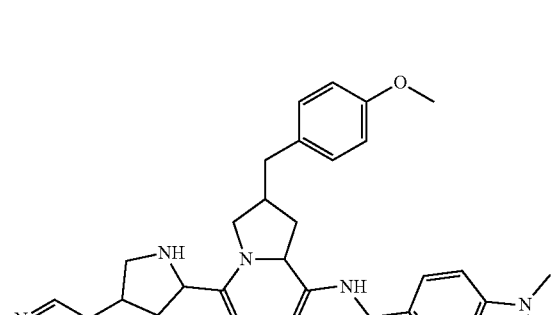
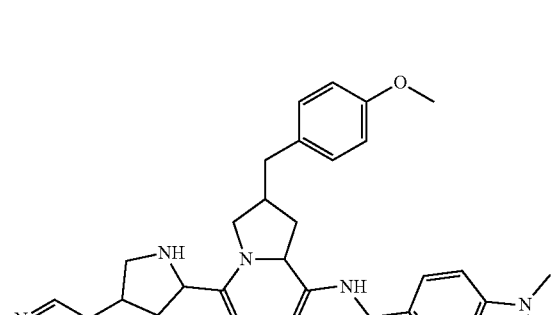
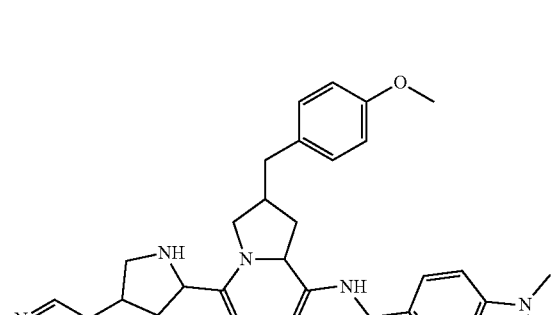
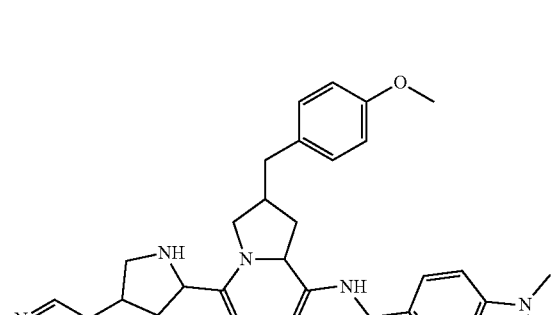

435
-continued
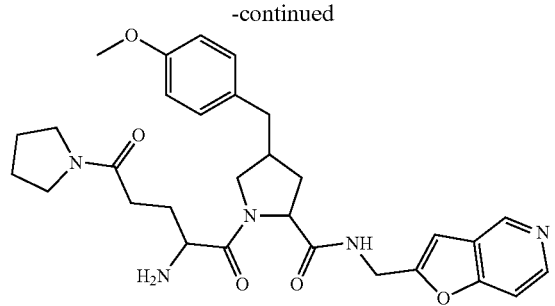
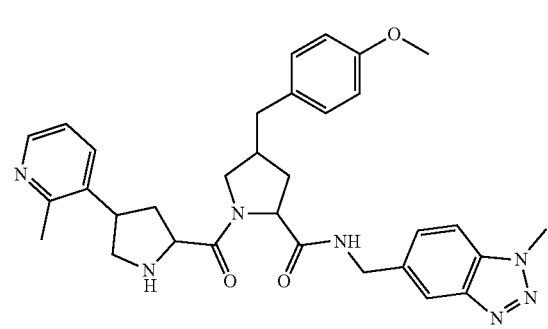
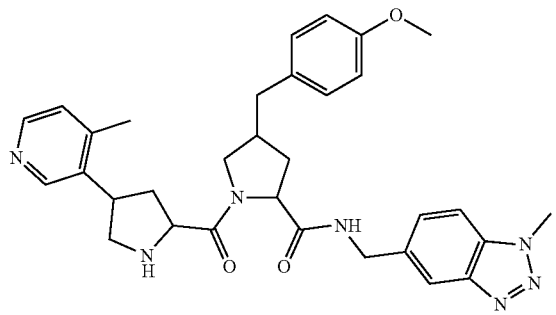
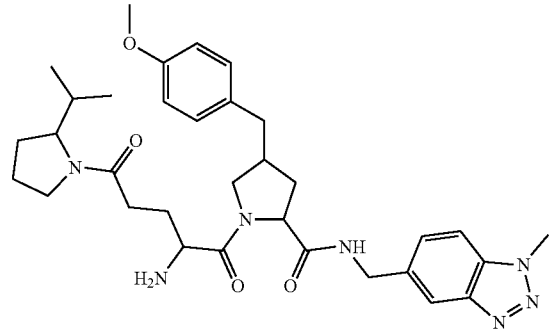
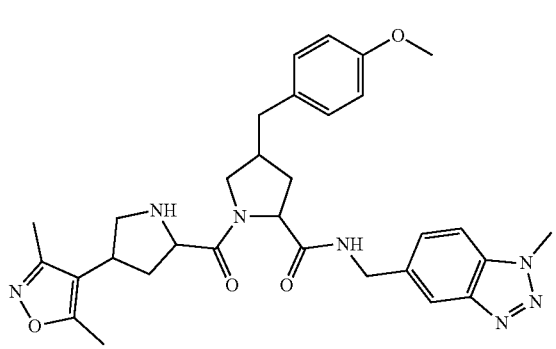
436
-continued
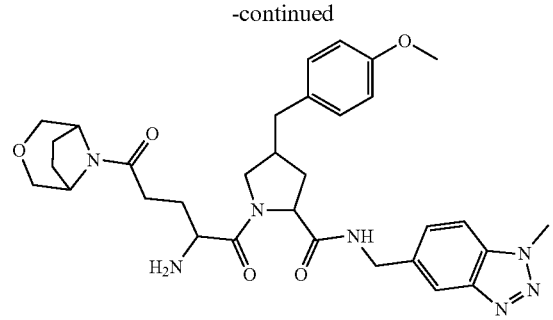
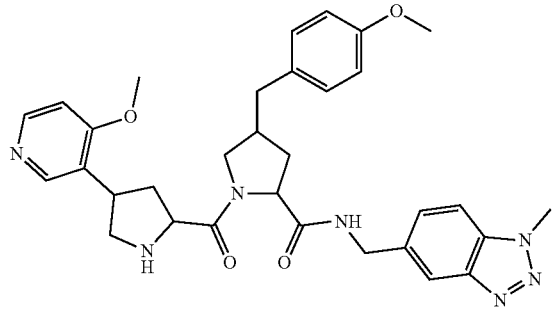
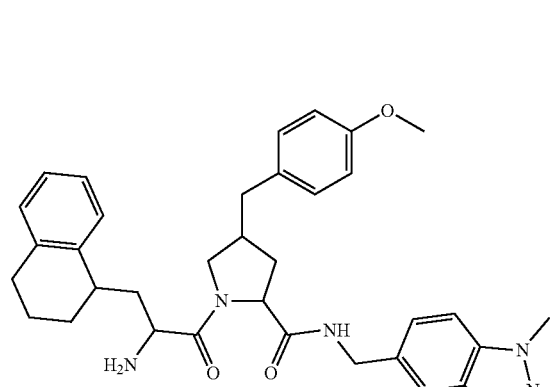
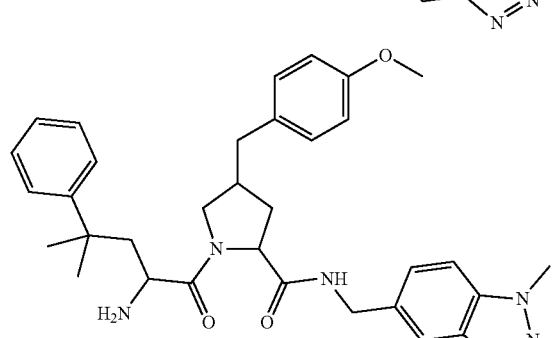
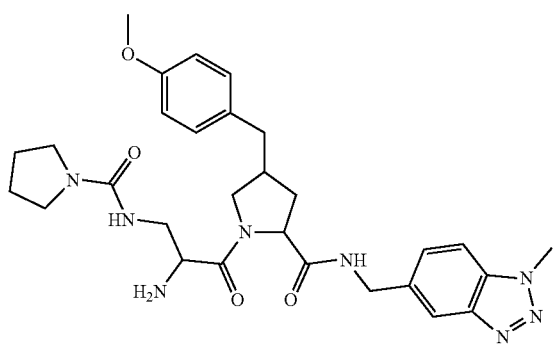

437
-continued
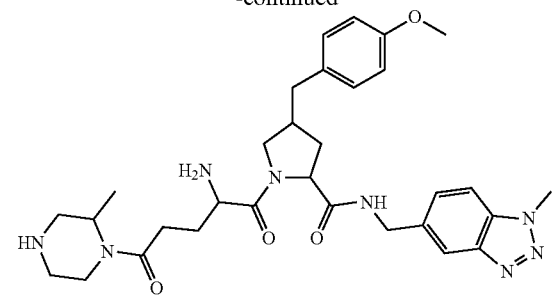
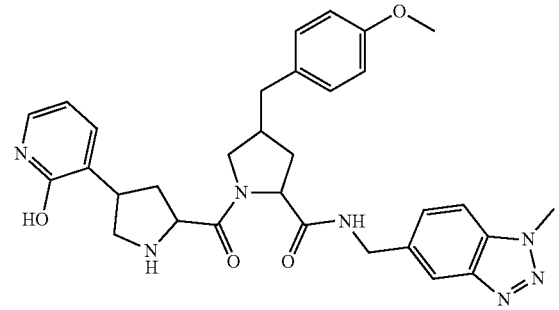
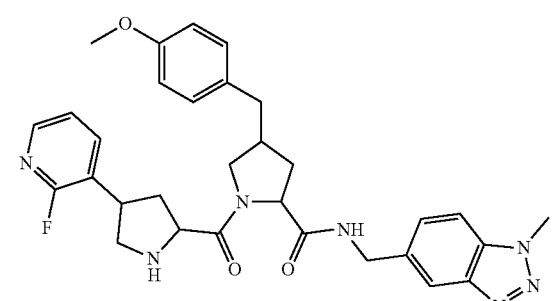
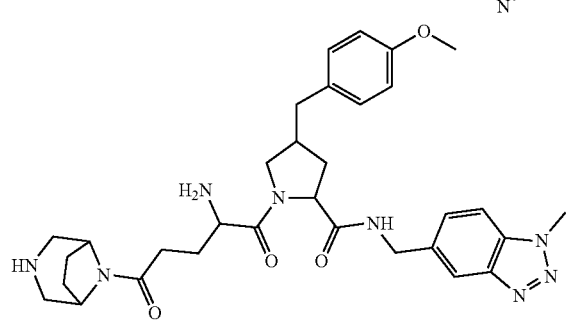
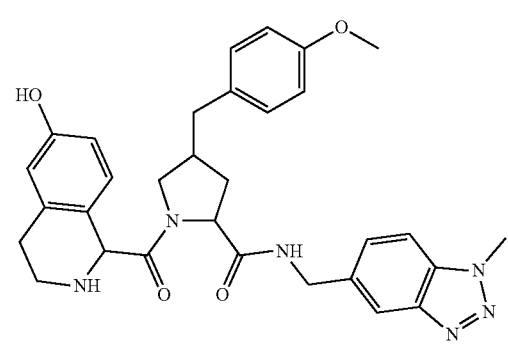
438
-continued
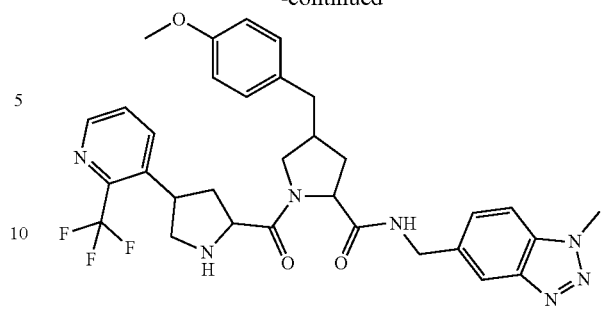
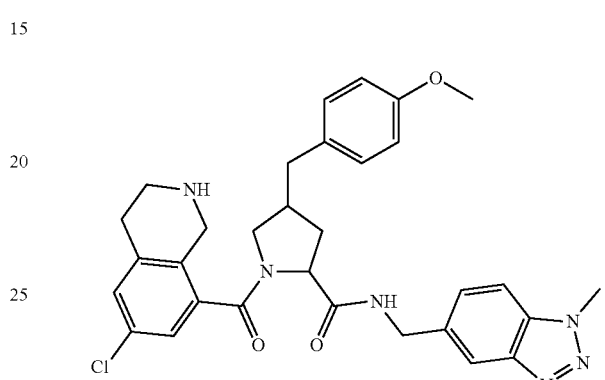
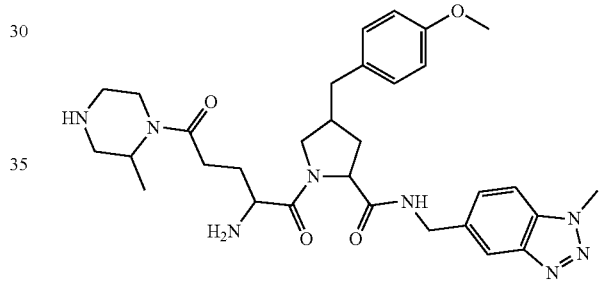
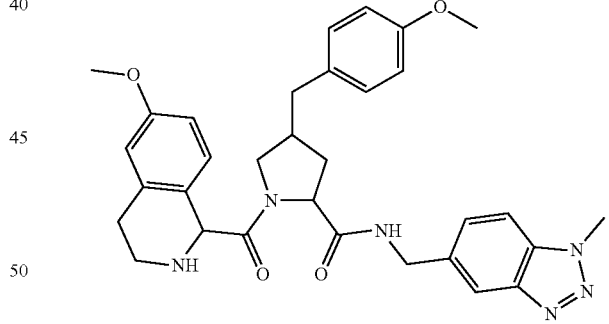
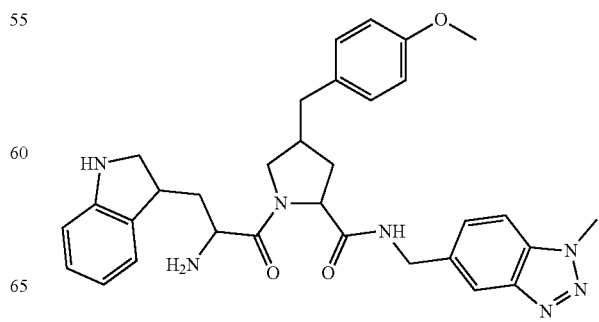

439
-continued
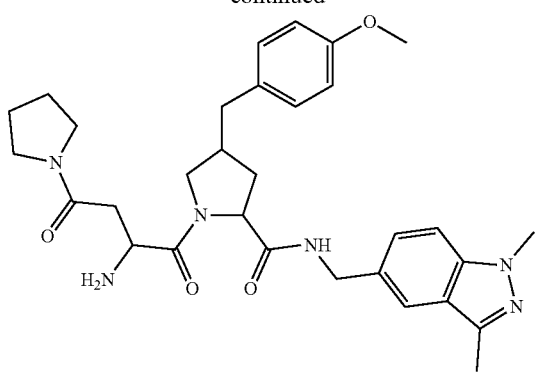
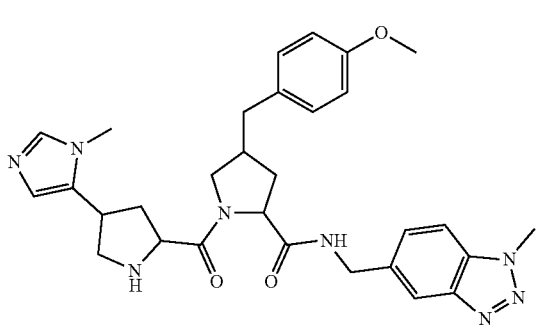
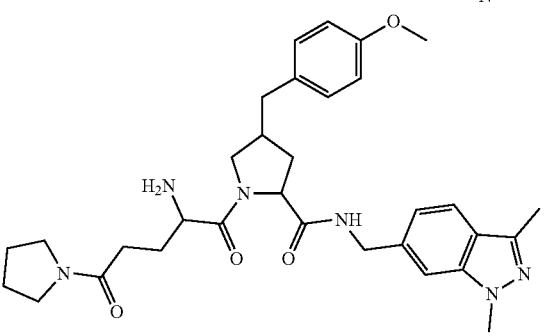
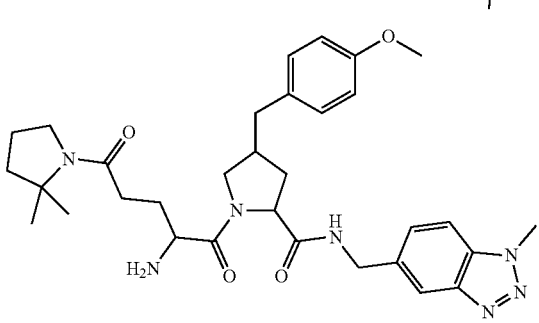
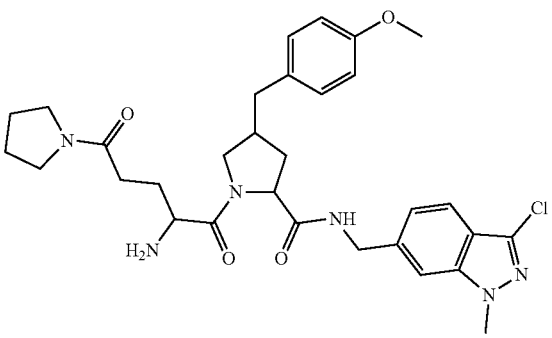
440
-continued
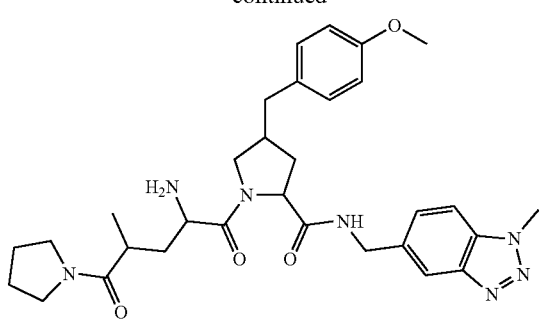
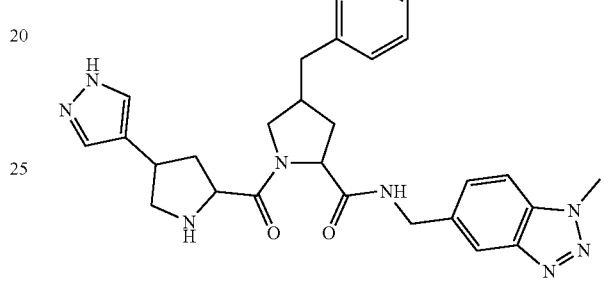
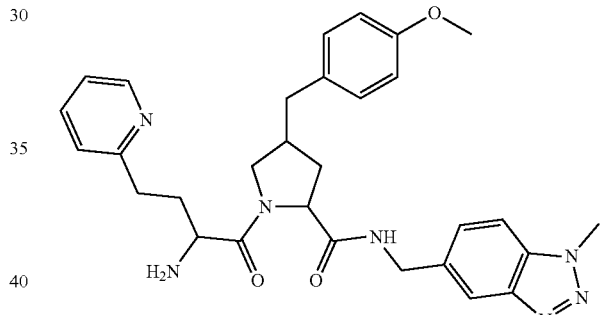
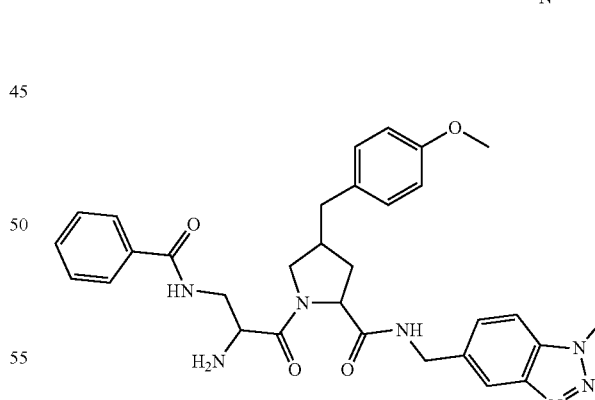
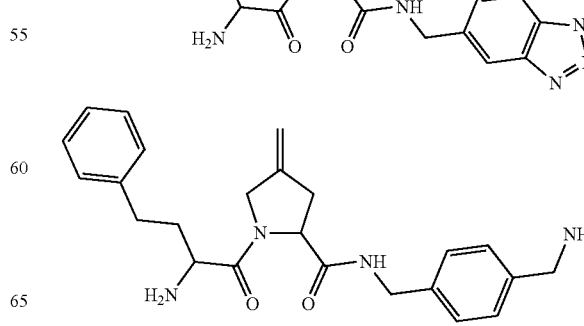

441
-continued
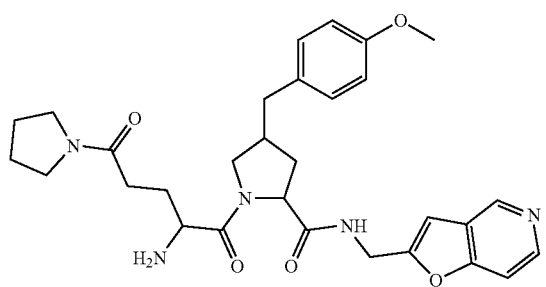
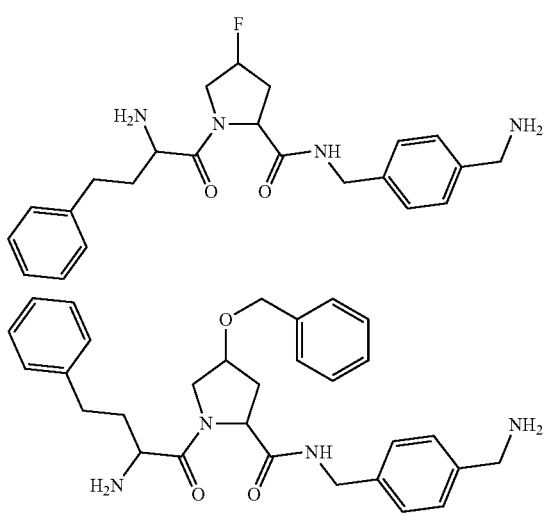
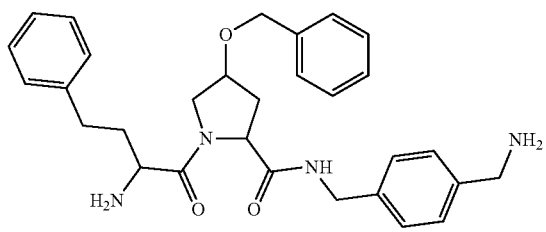
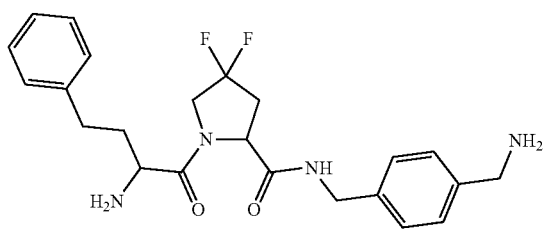
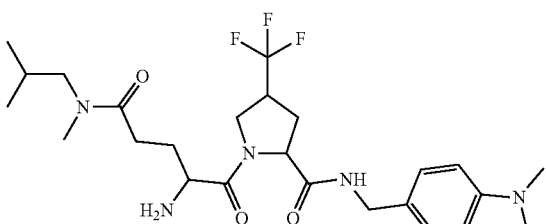
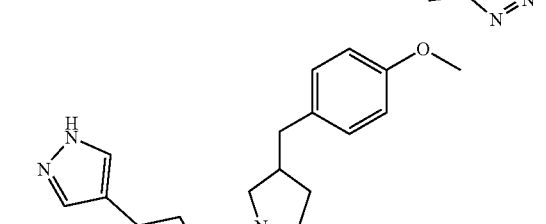
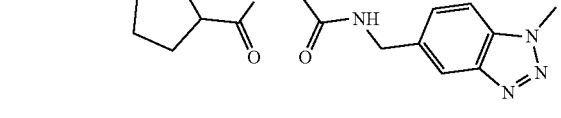
442
-continued
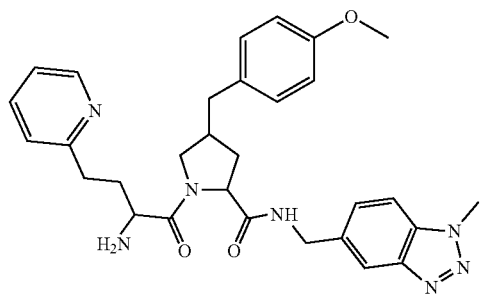
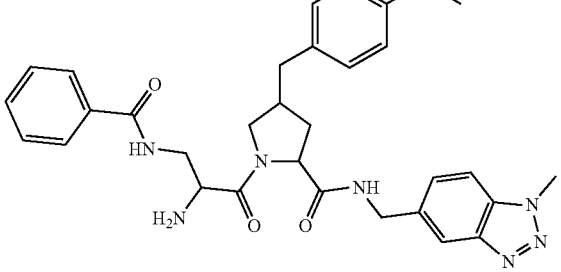
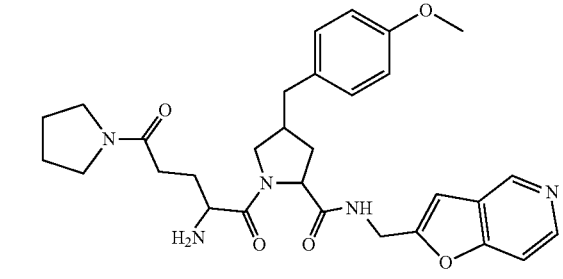
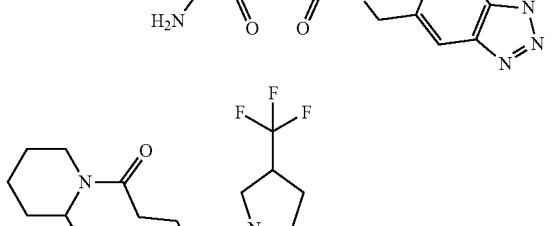
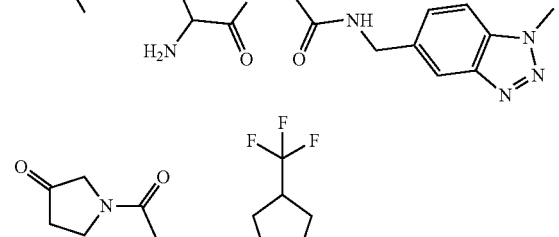
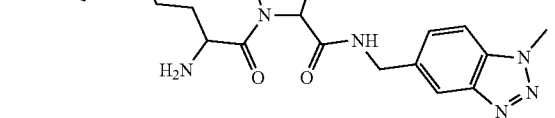

443
-continued
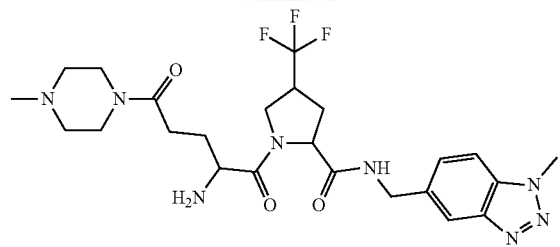
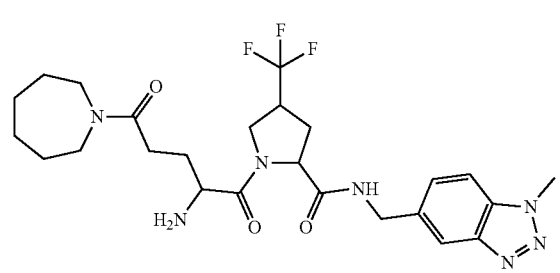
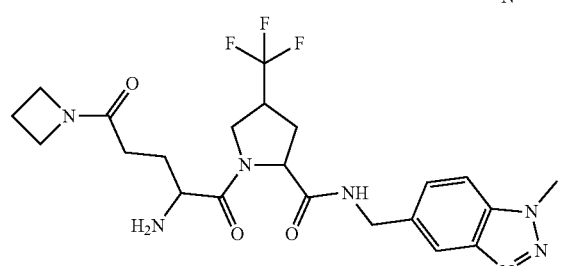
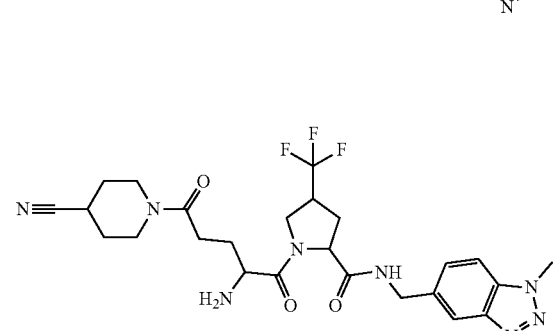
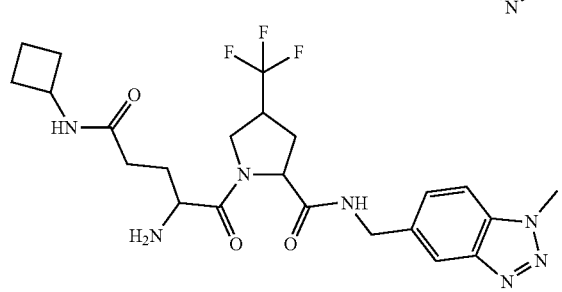
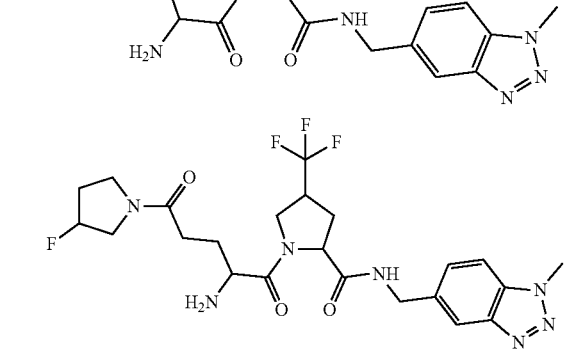
444
-continued
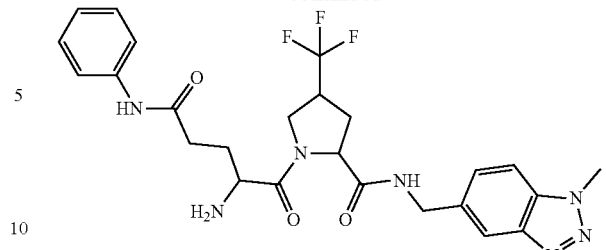
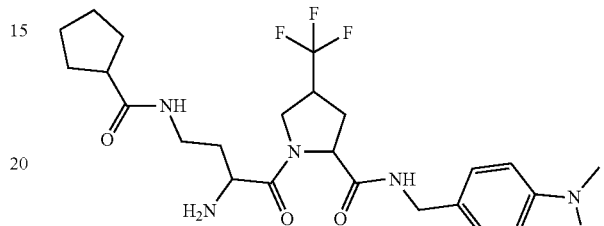
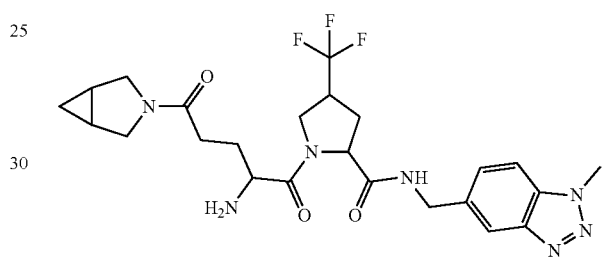
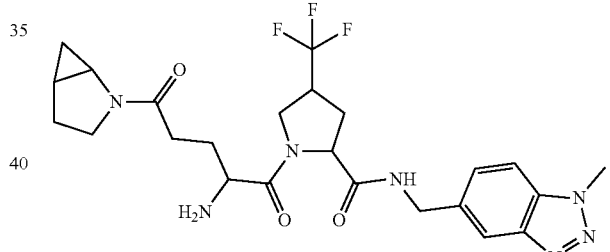
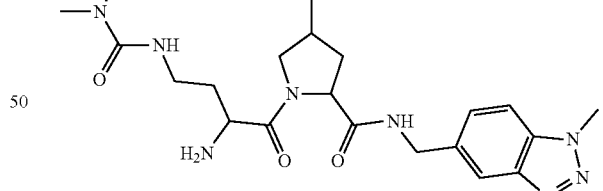
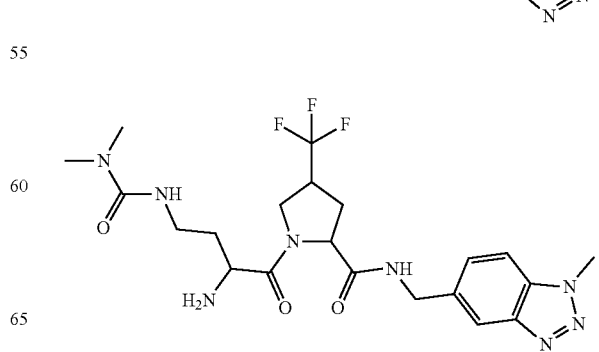

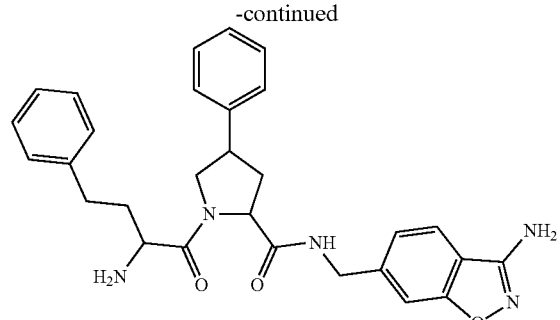
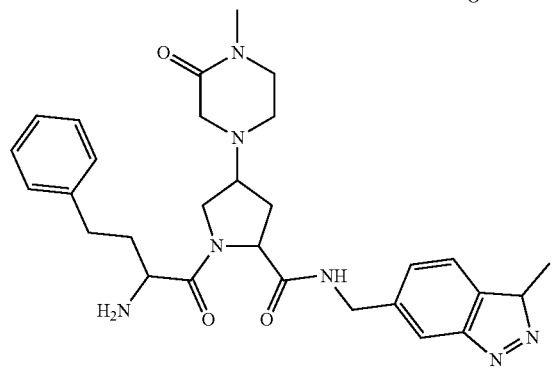
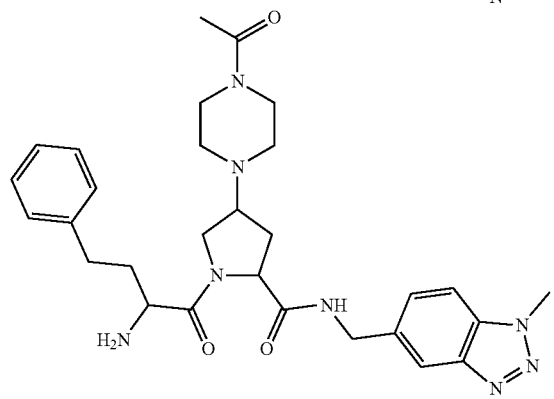
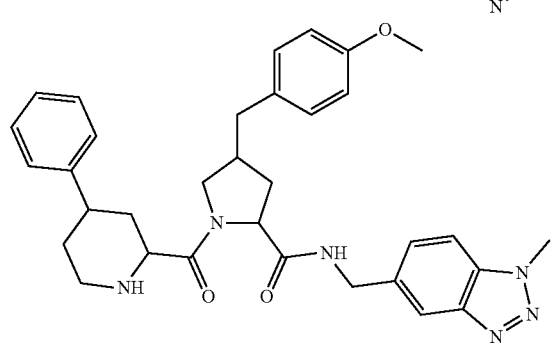
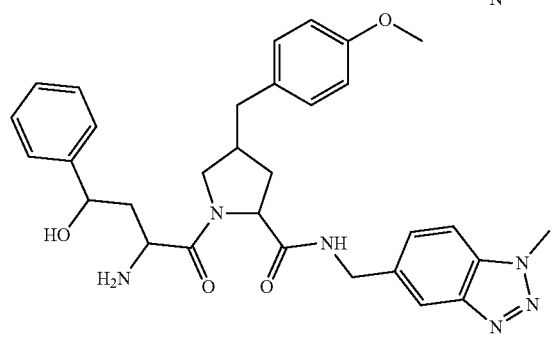
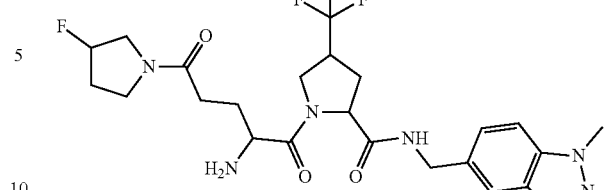
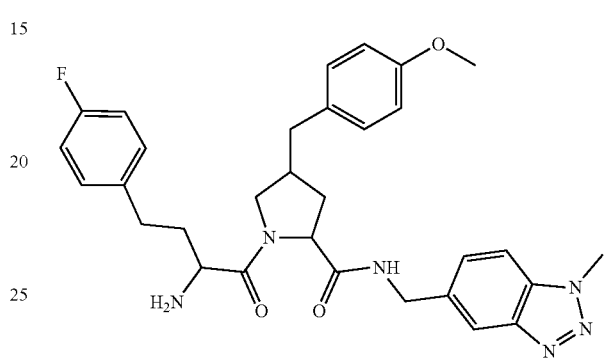
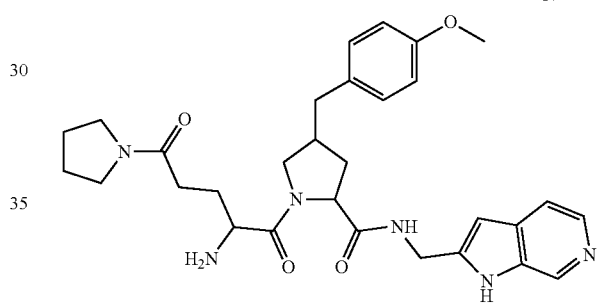
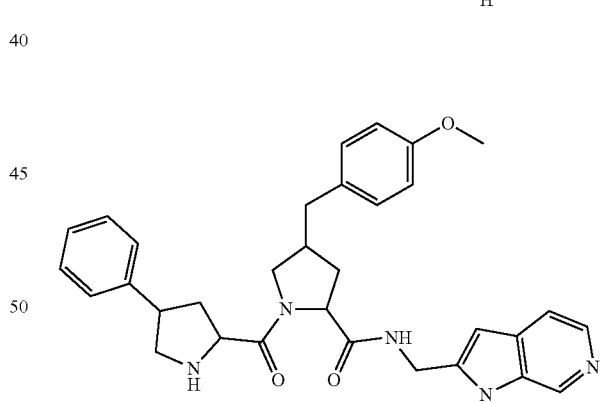
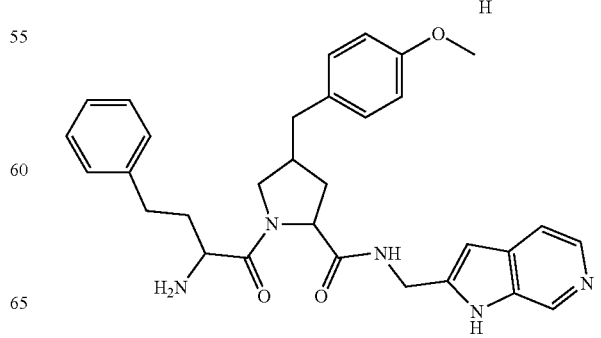

447
-continued
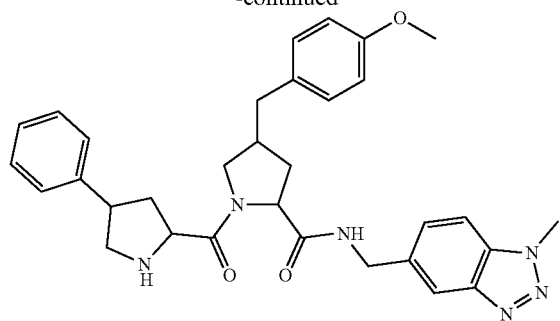
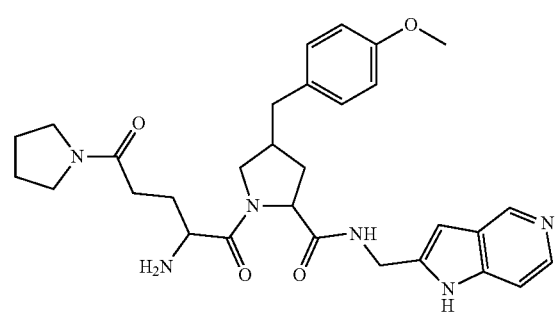
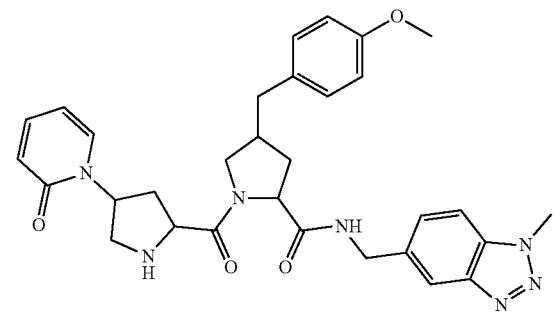
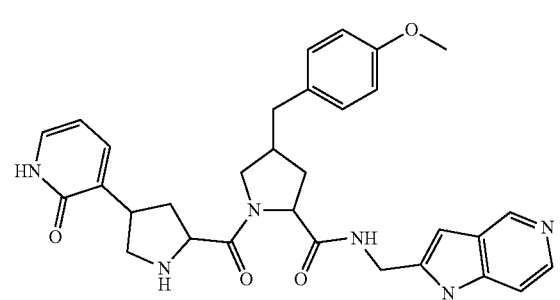
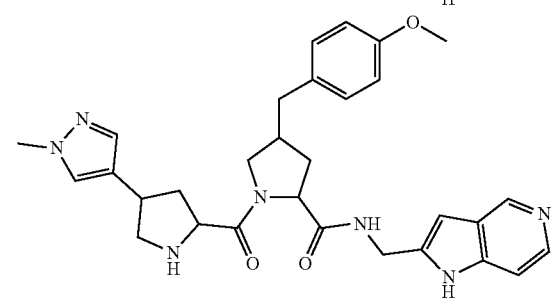
448
-continued
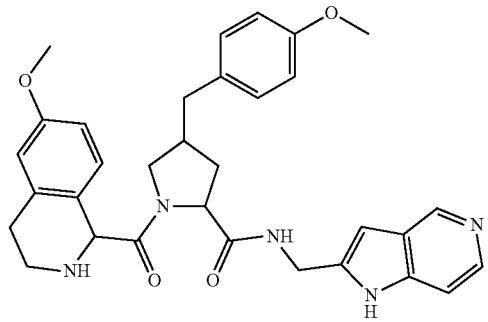
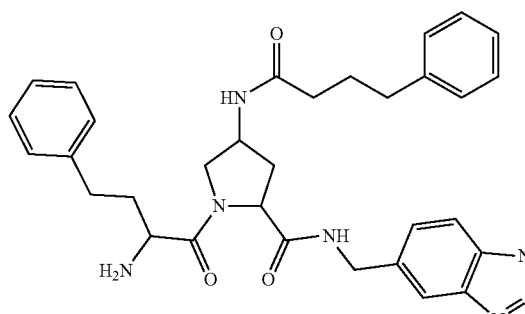
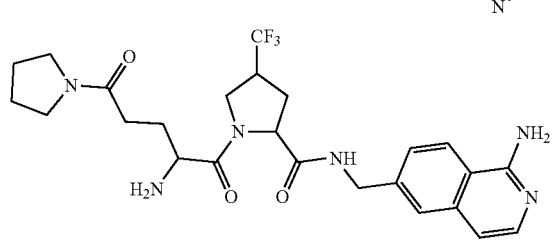
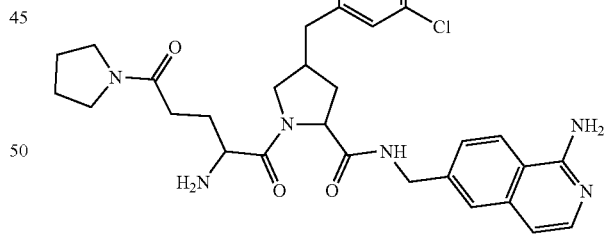
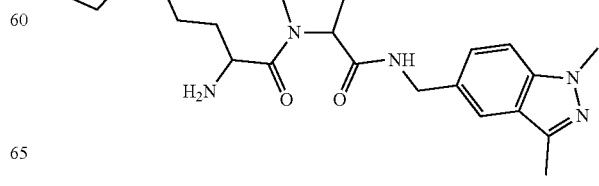

449
-continued
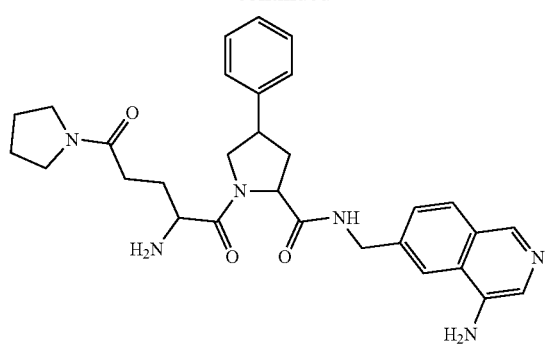
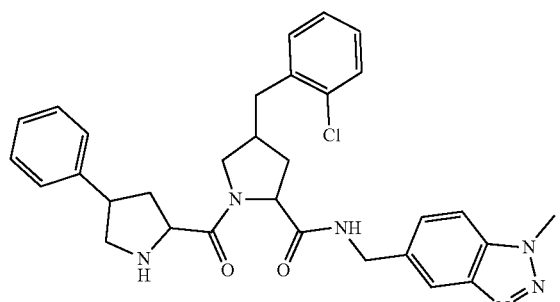
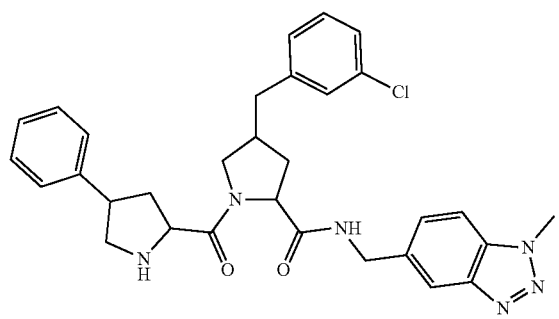
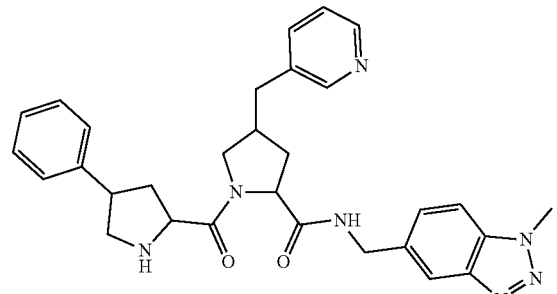
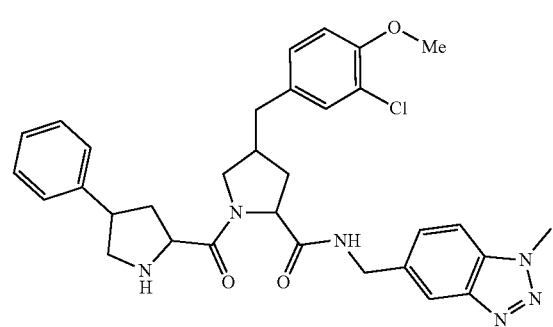
450
-continued
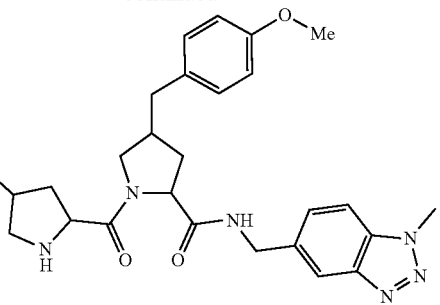
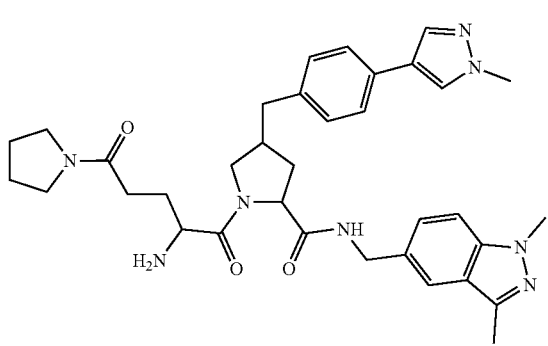
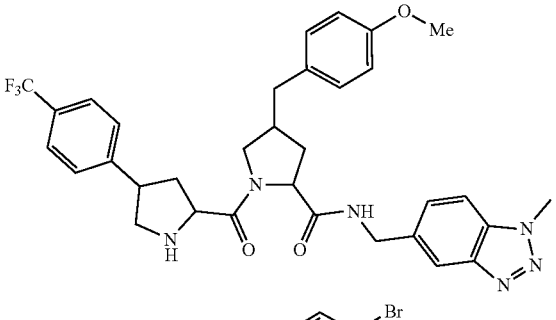
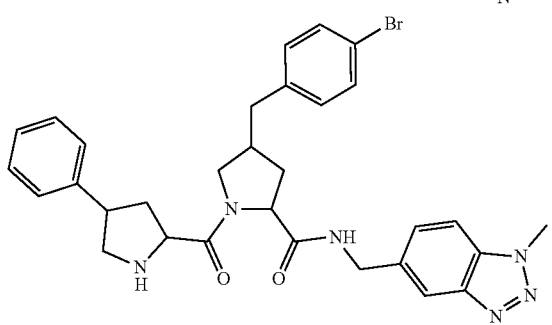
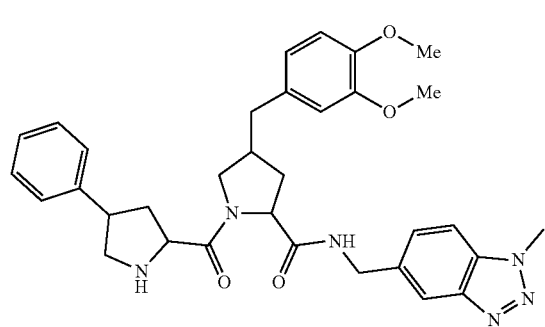

451
-continued
452
-continued
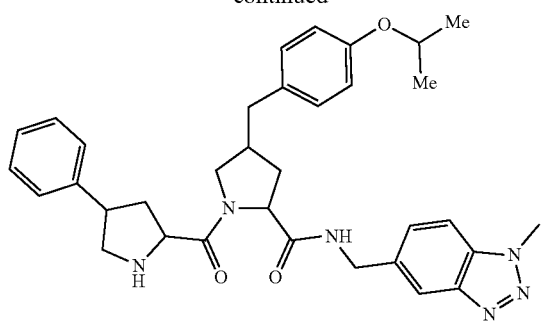
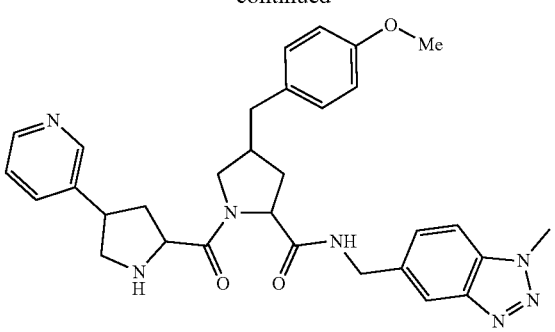

453
-continued
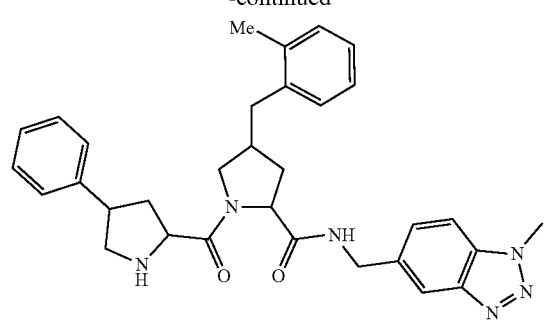
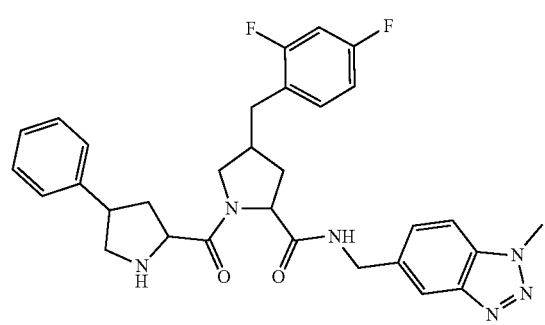
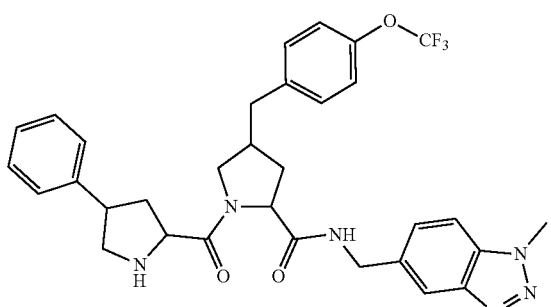
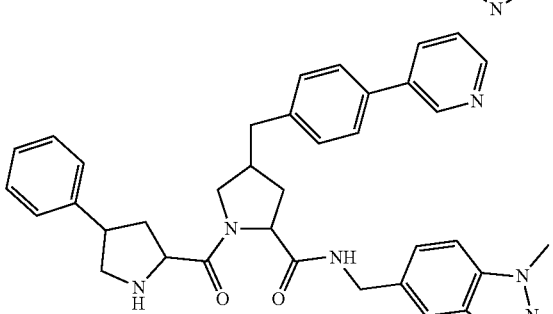
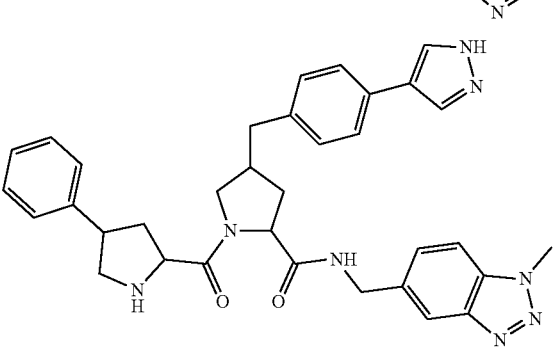
454
-continued
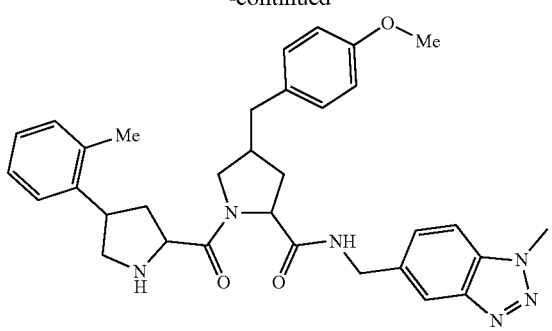
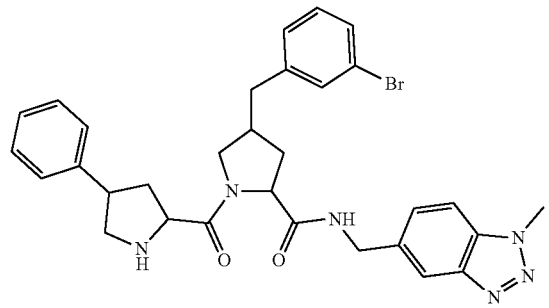
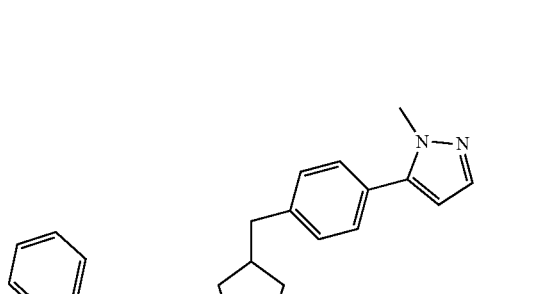
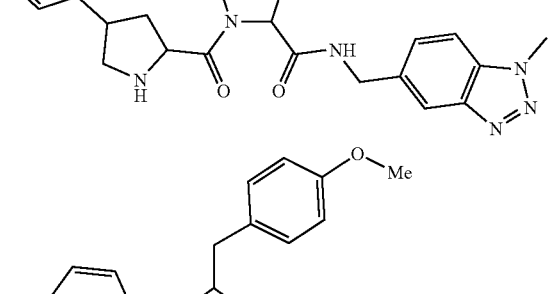
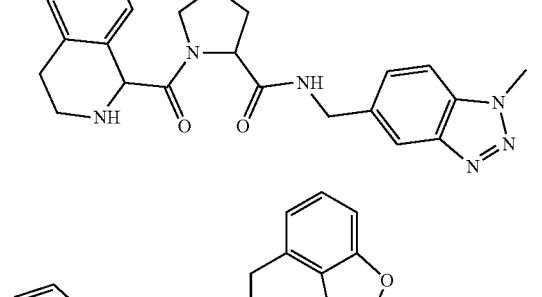
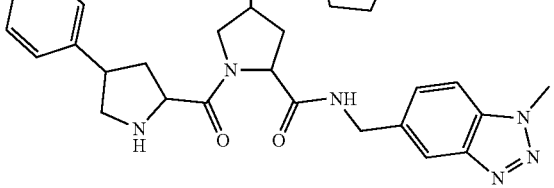

455
-continued
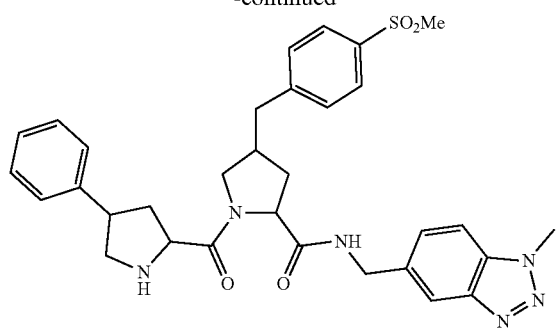
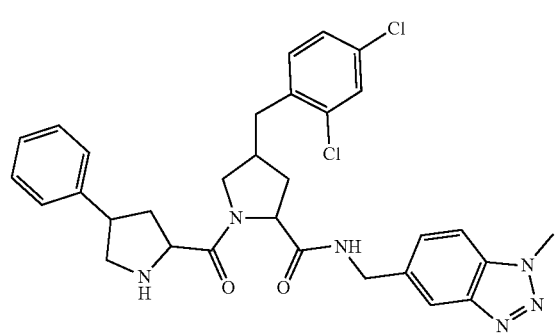
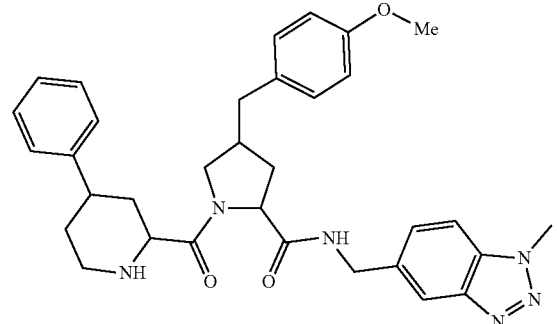
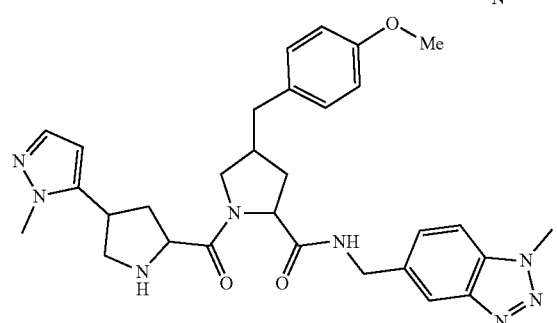
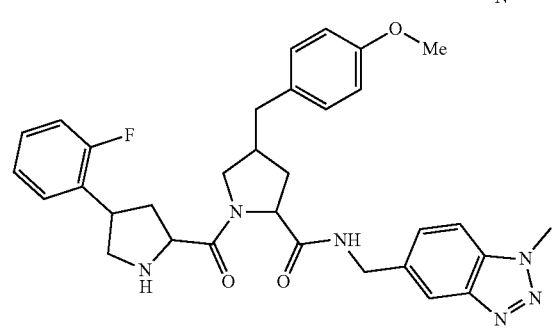
456
-continued
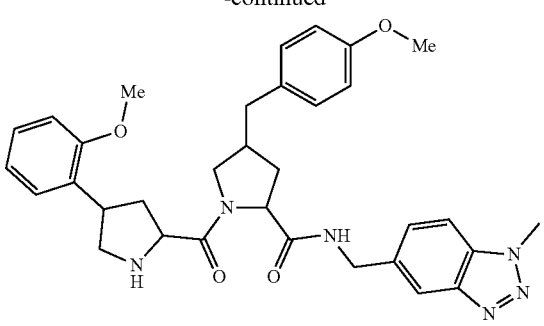
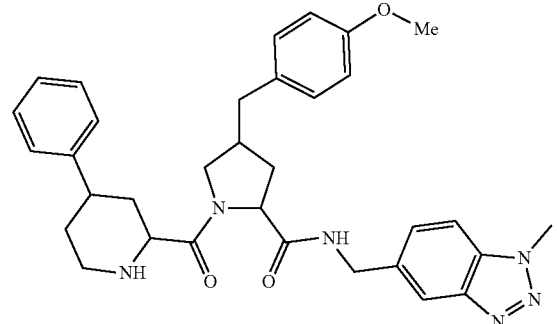
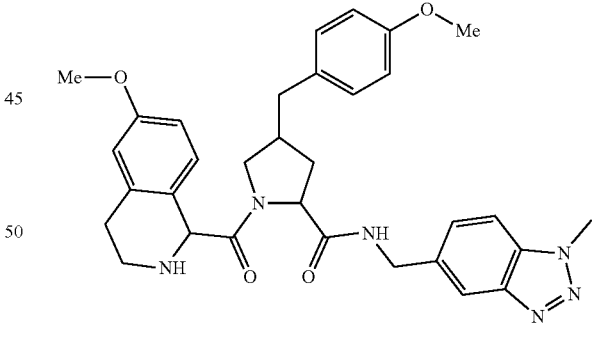
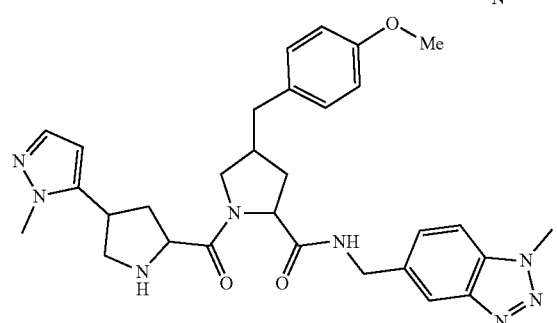
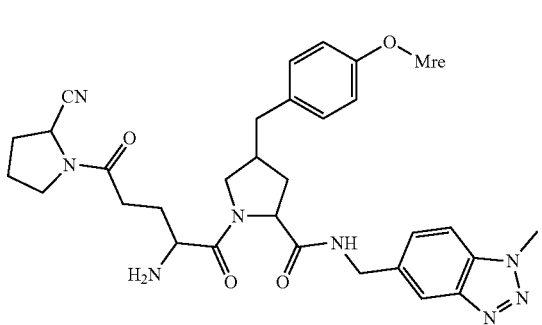

457
-continued
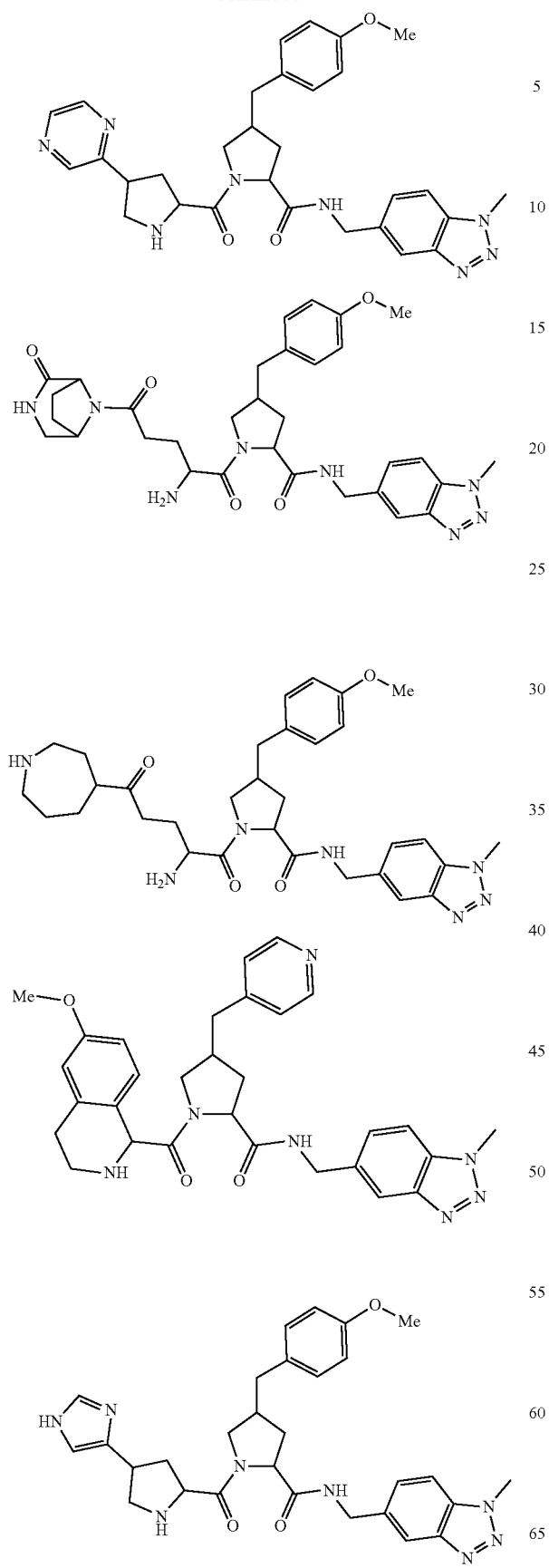
458
-continued
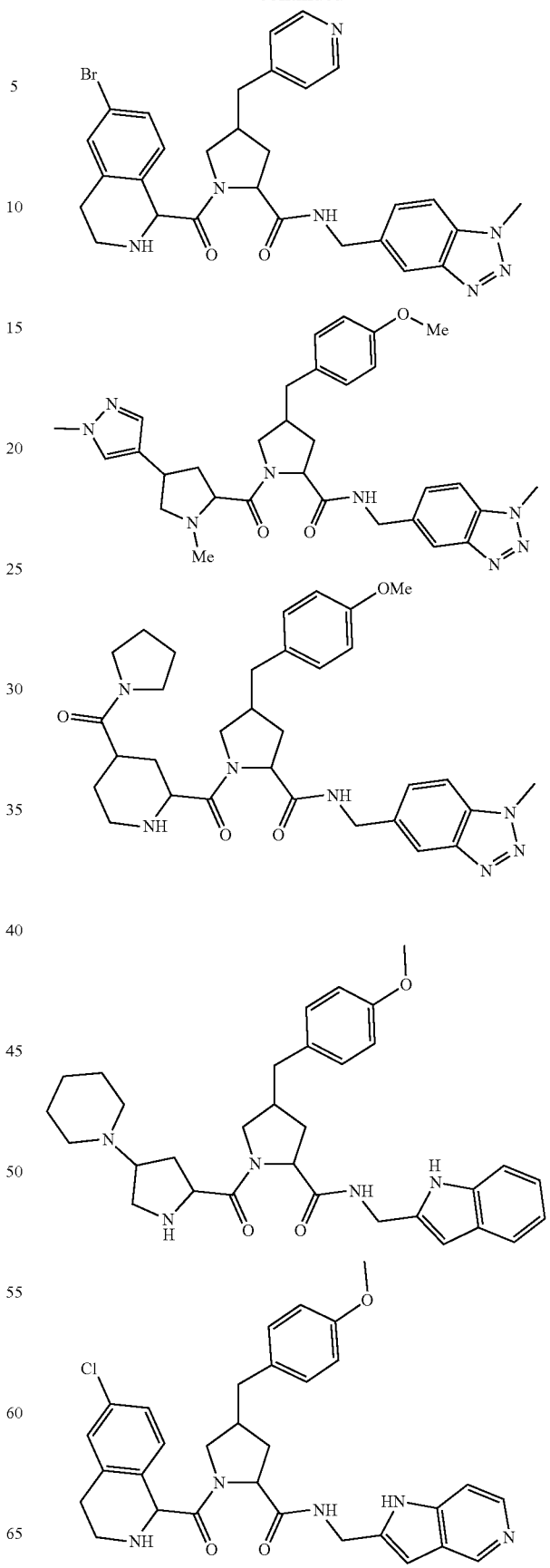

-continued
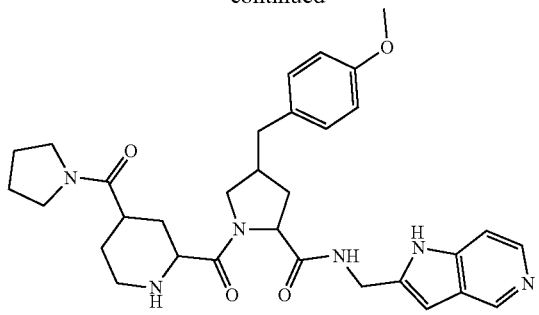
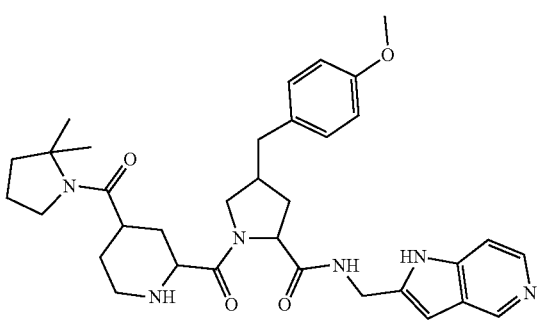
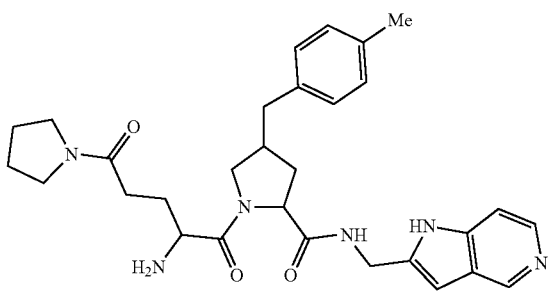
-continued
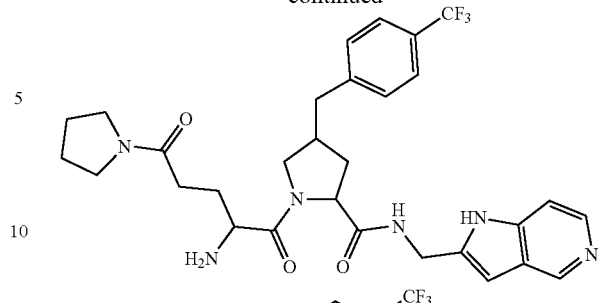
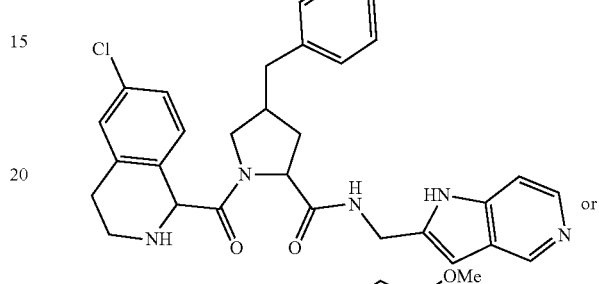
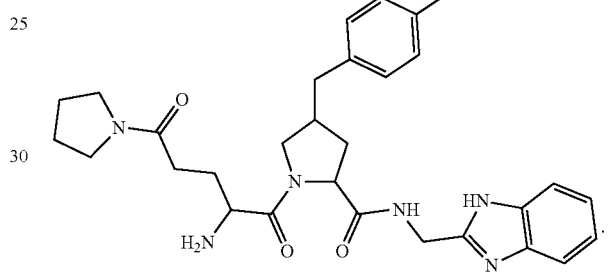
19. A pharmaceutical formulation comprising a compound of claim 1 and a pharmaceutically acceptable excipient.
20. The pharmaceutical composition of claim 19, wherein the composition is a combination product comprising an additional pharmaceutically active agent.
* * * * *